(12) United States Patent
Pakola et al.

(10) Patent No.: US 11,986,515 B2
(45) Date of Patent: May 21, 2024

(54) TREATMENT OF MUCOPOLYSACCHARIDOSIS II WITH RECOMBINANT HUMAN IDURONATE-2-SULFATASE (IDS)

(71) Applicant: REGENXBIO Inc., Rockville, MD (US)

(72) Inventors: Stephen Joseph Pakola, Irvington, NY (US); Paulo Falabella, Potomac, MD (US); Marie-Laure Nevoret, Virginia Beach, VA (US)

(73) Assignee: REGENXBIO Inc., Rockville, MD (US)

( * ) Notice: Subject to any disclaimer, the term of this patent is extended or adjusted under 35 U.S.C. 154(b) by 0 days.

(21) Appl. No.: 18/356,961

(22) Filed: Jul. 21, 2023

(65) Prior Publication Data

US 2024/0058426 A1    Feb. 22, 2024

Related U.S. Application Data

(63) Continuation of application No. PCT/US2022/014526, filed on Jan. 31, 2022.

(60) Provisional application No. 63/256,805, filed on Oct. 18, 2021, provisional application No. 63/242,250, filed on Sep. 9, 2021, provisional application No. 63/210,610, filed on Jun. 15, 2021, provisional application No. 63/180,361, filed on Apr. 27, 2021, provisional application No. 63/148,093, filed on Feb. 10, 2021.

(51) Int. Cl.
| | | |
|---|---|---|
| A61P 25/28 | (2006.01) | |
| A61K 38/46 | (2006.01) | |
| C12N 15/86 | (2006.01) | |
| G01N 33/53 | (2006.01) | |

(52) U.S. Cl.
CPC ............ A61K 38/465 (2013.01); A61P 25/28 (2018.01); C12N 15/86 (2013.01); C12Y 301/06013 (2013.01); G01N 33/5308 (2013.01); C12N 2750/14143 (2013.01); C12N 2750/14171 (2013.01); G01N 2400/00 (2013.01); G01N 2800/04 (2013.01)

(58) Field of Classification Search
CPC ....... A61K 38/465; A61P 25/28; C12N 15/86; C12Y 301/06013; G01N 33/5308
See application file for complete search history.

(56) References Cited

U.S. PATENT DOCUMENTS

| | | | |
|---|---|---|---|
| 6,596,535 B1 | 7/2003 | Carter et al. | |
| 7,125,717 B2 | 10/2006 | Carter et al. | |
| 7,282,199 B2 | 10/2007 | Gao et al. | |
| 7,456,683 B2 | 11/2008 | Takano et al. | |
| 7,790,449 B2 | 9/2010 | Gao et al. | |
| 7,906,111 B2 | 3/2011 | Wilson et al. | |
| 8,318,480 B2 | 11/2012 | Gao et al. | |
| 8,524,446 B2 | 9/2013 | Gao et al. | |
| 8,628,966 B2 | 1/2014 | Chatterjee et al. | |
| 8,734,809 B2 | 5/2014 | Gao et al. | |
| 8,927,514 B2 | 1/2015 | Chatterjee et al. | |
| 8,962,332 B2 | 2/2015 | Gao et al. | |
| 8,999,678 B2 | 4/2015 | Weiler et al. | |
| 9,169,299 B2 | 10/2015 | Lisowski et al. | |
| 9,193,956 B2 | 11/2015 | Schaffer et al. | |
| 9,284,357 B2 | 3/2016 | Gao et al. | |
| 9,409,953 B2 | 8/2016 | Asokan et al. | |
| 9,458,517 B2 | 10/2016 | Schaffer et al. | |
| 9,585,971 B2 | 3/2017 | Deverman et al. | |
| 9,587,282 B2 | 3/2017 | Schaffer | |
| 11,613,739 B2 | 3/2023 | Yoo et al. | |
| 2013/0224836 A1 | 8/2013 | Muramatsu et al. | |
| 2014/0242059 A1 | 8/2014 | Thong-Gyu et al. | |
| 2015/0126588 A1 | 5/2015 | Nakai et al. | |
| 2015/0374803 A1 | 12/2015 | Wolfe et al. | |
| 2016/0215024 A1 | 7/2016 | Vandenberghe et al. | |
| 2016/0376323 A1 | 12/2016 | Schaffer et al. | |
| 2017/0051257 A1 | 2/2017 | Vandenberghe et al. | |
| 2017/0067908 A1 | 3/2017 | Nakai et al. | |
| 2019/0070311 A1 | 3/2019 | Hinderer et al. | |
| 2020/0149019 A1* | 5/2020 | Arguello | A61P 3/00 |
| 2020/0246439 A1 | 8/2020 | Hinderer et al. | |

FOREIGN PATENT DOCUMENTS

| | | |
|---|---|---|
| WO | WO 2011/163649 | 12/2011 |
| WO | WO 2012/177020 | 12/2012 |
| WO | WO 2015/082570 | 6/2015 |
| WO | WO 2015/121501 | 8/2015 |
| WO | WO 2016/126729 | 8/2015 |
| WO | WO 2015/191508 | 12/2015 |
| WO | WO 2016/007909 | 1/2016 |

(Continued)

OTHER PUBLICATIONS

Boulos et al. Identification of a biomarker that differentiates neuronopathic forms of MPS I and MPS II. Molecular Genetics and Metabolism, Feb. 2022, vol. 135, No. 2, pp. S24. Abstract only. (Year: 2022).*

Castro et al. Gene Therapy for Neuronopathic Mucopolysaccharidoses: State of the Art. International Journal of Molecular Sciences . Sep. 2021. vol. 22, No. 9200, p. 1-17. (Year: 2021).*

D' Avanzo et al. Mucopolysaccharidosis Type II: One Hundred Years of Research, Diagnosis, and Treatment. Int. J. Mol. Sci. Feb. 2020. vol. 21, No. 4, 1-38. (Year: 2020).*

(Continued)

*Primary Examiner* — Channing S Mahatan
(74) *Attorney, Agent, or Firm* — Jones Day

(57) ABSTRACT

Compositions and methods are described for the delivery of recombinant human iduronate-2-sulfatase (IDS) produced by human neuronal or glial cells to the cerebrospinal fluid of the central nervous system (CNS) of a human subject diagnosed with mucopolysaccharidosis II (MPS II).

30 Claims, 56 Drawing Sheets

Figure 4:
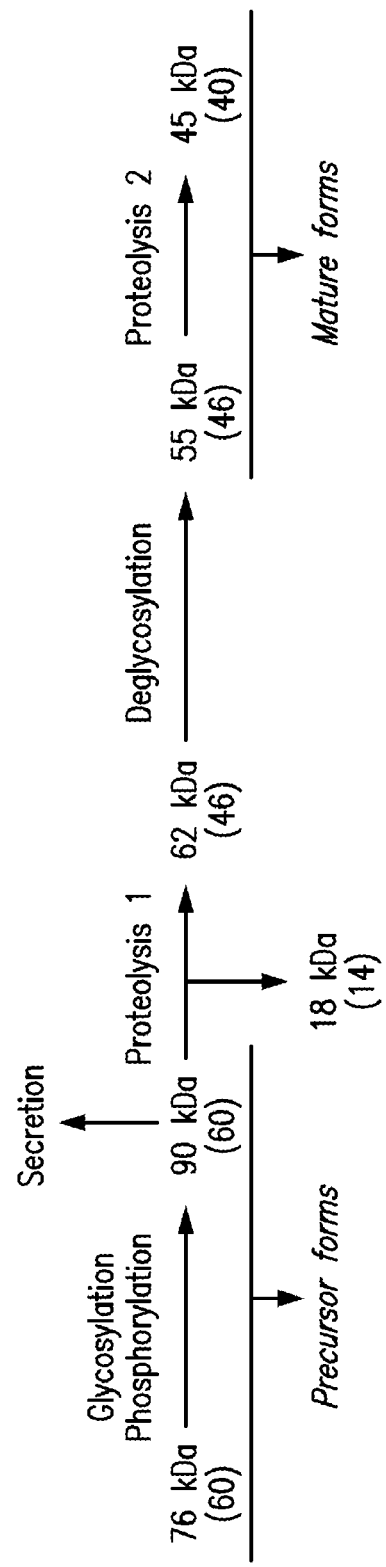

Specification includes a Sequence Listing.

(56) References Cited

FOREIGN PATENT DOCUMENTS

| WO | WO 2016/077356 | 5/2016 |
|---|---|---|
| WO | WO 2016/100603 | 6/2016 |
| WO | WO 2016/187017 | 11/2016 |
| WO | WO 2016/193431 | 12/2016 |
| WO | WO 2017/181113 | 10/2017 |
| WO | WO 2018/191666 | 10/2018 |
| WO | WO 2021/154963 | 8/2021 |

OTHER PUBLICATIONS

Lawrence et al. Glycan-based biomarkers for mucopolysaccharidoses. Mol. Genet. Metab. Feb. 2014. vol. 111, No. 2, p. 73-83. (Year: 2014).*

Muenzer et al. A phase II/III clinical study of enzyme replacement therapy with idursulfase in mucopolysaccharidosis II (Hunter syndrome). Genetics in Medicine. Aug. 2006. vol. 8, No. 8, p. 465-473. (Year: 2006).*

International Search Report and Written Opinion dated Jul. 16, 2018 for PCT/US2018/027568 (17 pages).

Bielicki et al., 1993, "Recombinant human iduronate-2-sulphatase: correction of mucopolysaccharidosis-type II fibroblasts and characterization of the purified enzyme", Biochem J, 289(1):241-246.

Daniele et al., 2002, "Uptake of recombinant iduronate-2-sulfatase into neuronal and glial cells in vitro," Biochim Biophys Acta., 1588(3):203-209.

Genbank, 2016, NM_010498: Mus musculus iduronate 2-sulfatase (ids), mRNA, 5 pages, retrieved from the internet: <https://www.ncbi.nlm.nih.gov/nuccore/262205477>.

Ghaderi et al., 2013, "Production platforms for biotherapeutic glycoproteins. Occurrence, impact, and challenges of non-human sialylation", Biotechnol. Genet. Eng. Rev., 28:147-175.

Hinderer et al., 2016, "Delivery of an Adeno-Associated Virus Vector into Cerebrospinal Fluid Attenuates Central Nervous System Disease in Mucopolysaccharidosis Type II Mice", Hum Gene Ther, 27(11):906-915.

Motas et al., 2016, "CNS-directed gene therapy for the treatment of neurologic and somatic mucopolysaccharidosis type II (Hunter syndrome)", JCI Insight, 1(9): e86696:1-18.

Zuber et al., 2014, "The effect of recombinant human iduronate-2-sulfatase (idursulfase) on growth in young patients with Mucopolysaccharidosis Type II", PLoS One, 9(1):1-5.

Alba et al., 2005, "Gutless adenovirus: last-generation adenovirus for gene therapy", Gene Therapy, 12:S18-S27.

Ausubel et al., 2012, "Production of CGMP-Grade Lentiviral Vectors," BioProcess International, 10(2):32-43.

Ayoub et al., 2013, "Correct primary structure assessment and extensive glyco-profiling of cetuximab by a combination of intact, middle-up, middle-down and bottom-up ESI and MALDI mass spectrometry techniques", Landes Bioscience, 5(5):699-710.

Bonuccelli et al., 2001, "The effect of four mutations on the expression of iduronate-2-sulfatase in mucopolysaccharidosis type II," Biochimica et Biophysica Acta (BBA)—Molecular Basis of Disease, 1537(3):233-238.

Bosques et al., 2010, "Chinese hamster ovary cells can produce galactose-α-1,3-galactose antigens on proteins", Nature Biotechnology, 28:1153-1156.

Bundgaard et al., 1995, "Tyrosine O-sulfation promotes proteolytic processing of progastrin," The EMBO Journal, 14(13):3073-3079.

Chung et al., 2014, "A biochemical and physicochemical comparison of two recombinant enzymes used for enzyme replacement therapies of hunter syndrome," Glycoconjugate Journal, 31:309-315.

Clarke, L, 2008, "Idursulfase for the treatment of mucopolysaccharidosis II," Expert Opinion on Pharmacotherapy, 9(2):311-317.

Cohen-Pfeffer et al., 2017, "Intracerebroventricular Delivery as a Safe, Long-Term Route of Drug Administration," Pediatric Neurology, 67:23-25.

D'Avanzo et al., 2020, "Mucopolysaccharidosis Type II: One Hundred Years of Research, Diagnosis, and Treatment," International Journal of Molecular Sciences, 21(4):1258; Retrieved from the Internet: URL:https://www.ncbi.nlm.nih.gov/pmc/articles/PMC7072947/pdf/ijms-21-01258.pdf> see p. 13.

Dean et al., 2006, "Detection of Mucopolysaccharidosis Type II by Measurement of Iduronate-2-Sulfatase in Dried Blood Spots and Plasma Samples," Clinical Chemistry, 52(4):643-649.

Dekaban, AS, 1978, "Changes in brain weights during the span of human life: relation of brain weights to body heights and body weights," Annals of Neurology, 4(4):345-356.

Dinculescu et al., 2005, "Adeno-associated virus-vectored gene therapy for retinal disease", Human Gene Therapy, 16(6):649-663.

Drake et al., 2000, "CSF shunts 50 years on—past, present and future," Child's Nervous System, 16:800-804.

Dumont et al., 2015, "Human cell lines for biopharmaceutical manufacturing: history, status, and future perspectives," Critical Reviews in Biotechnology, Early Online: 1-13.

Elaprase (idursulfase) injection [package insert] Lexington, MA: Shire Human Genetic Therapies, Inc; 2013, available at http://pi.shirecontent.com/PI/PDFs/Elaprase_USA_ENG.pdf.

Ferreira et al., 2009, "Sleep Disturbance Scale for Children: Translation, cultural adaptation, and validation," Sleep Medicine, 10(4):457-463.

Froissart et al., 1995, "Processing of iduronate 2-sulphatase in human fibroblasts," Biochemical Journal, 309(2):425-430.

Galili et al., 1998, "A sensitive assay for measuring alpha-Gal epitope expression on cells by a monoclonal anti-Gal antibody", Transplantaion, 65(8):1129-1132.

Garcia et al., 2007, "The characterization of a murine model of mucopolysaccharidosis II (Hunter syndrome)," Journal of Inherited Metabolic Disease, 30:924-934.

Hague et al., 1998, "Structural determination of oligosaccharides from recombinant iduronidase released with peptide N-glycanase F using fluorophore-assisted carbohydrate electrophoresis," Electrophoresis, 19(15):2612-2620.

Hara et al., 1989, "Highly sensitive determination of N-acetyl- and N-glycolylneuraminic acids in human serum and urine and rat serum by reversed-phase liquid chromatography with fluorescence detection," Journal of Chromatography B: Biomedical Sciences and Applications, 377:111-119.

Hocquemiller et al., 2016, "Adeno-Associated Virus-Based Gene Therapy for CNS Diseases," Human Gene Therapy, 27(7):478-496.

International Search Report and Written Opinion dated May 10, 2021 for PCT/US2021/015446.

Kanan et al., 2015, "Role of tyrosine-sulfated proteins in retinal structure and function," Experimental Eye Research, 133:126-131.

Kato et al., 2007, "Evaluation of ADL in patients with Hunter disease using FIM score," Brain and Development, 29(5):298-305.

Kratzer et al., 2003, "Factors Affecting Liver Size A Sonographic Survey of 2080 Subjects," Journal of Ultrasound Medicine, 22(11):1155-1161.

Lee et al., 2015, "Direct assay of iduronate-2-sulfatase for Hunter disease using UPLC-tandem mass spectrometry and fluorogenic substrate," Clinical Biochemistry, 48(18):1350-1353.

Lesch et al., 2011, "Production and purification of lentiviral vectors generated in 293T suspension cells with baculoviral vectors", Gene Therapy, 18(6):531-538.

Martin et al., 2008, "Recognition and Diagnosis of Mucopolysaccharidosis II (Hunter Syndrome), " Pediatrics, 121(2):e377-e386.

McCarty et al., 2001, "Self-complementary recombinant adeno-associated virus (scAAV) vectors promote efficient transduction independently of DNA synthesis", Gene Therapy, 8(16):1248-1254.

Mikkelsen and Ezban, 1991, "Heterogeneity in the tyrosine sulfation of Chinese hamster ovary cell produced recombinant FVIII", Biochemistry, 30(6):1533-1537.

Millat et al., 1997, "Characterization of iduronate sulphatase mutants affecting N-glycosylation sites and the cysteine-84 residue," Biochemical Journal, 326(1):243-247.

Millat et al., 1998, "COS cell expression studies of P86L, P86R, P480L and P480Q Hunter's disease-causing mutations," Biochimica et Biophysica Acta (BBA)—Molecular Basis of Disease, 1406(2):214-218.

(56) References Cited

OTHER PUBLICATIONS

Millat et al., 1997, "IDS Transfer from Overexpressing Cells to IDS-Deficient Cells," Experimental Cell Research, 230(2):362-367.
Miyazaki et al., 1989, "Expression vector system based on the chicken beta-actin promoter directs efficient production of interleukin-5," Gene, 79(2):269-277.
Moore et al., 2003, "The biology and enzymology of protein tyrosine O-sulfation", Journal of Biological Chemistry, 278(27):24243-24246.
Muenzer et al., 2016, "A phase I/II study of intrathecal idursulfase-IT in children with severe mucopolysaccharidosis II," Genetics in Medicine, 18:73-81.
Muenzer et al., 2002, "Enzyme replacement therapy in mucopolysaccharidosis type II (Hunter syndrome): a preliminary report," Acta Paediatrica Supplement, 91(439):98-99.
Muenzer et al., 2009, "Mucopolysaccharidosis I: Management and Treatment Guidelines," Pediatrics, 123(1):19-29.
Niwa et al., 1991, "Efficient selection for high-expression transfectants with a novel eukaryotic vector," Gene, 108(2):193-199.
Platts-Mills et al., 2015, "Anaphylaxis to the carbohydrate side chain alpha-gal," Immunology and Allergy Clinics of North America, 35(2):247-260.
Polito and Cosma, 2009, "IDS Crossing of the Blood-Brain Barrier Corrects CNS Defects in MPSII Mice," The American Jounral of Human Genetics, 85(2):296-301.
Quax et al., 2015, "Codon Bias as a Means to Fine-Tune Gene Expression", Molecular Cell, 59(2):149-161.
REGENXBIO Press Release; 2018, "REGENXBIO Announces Interim Data From Phase I/II Trial of RGX-121 for the Treatment of Mucopolysaccharidosis Type II (MPS II)", 8 pages, Retrieved from the internet at: <http://ir.regenxbio.com/news-releases/news-release-details/regenxbio-announces-interim-data-phase-iii-trial-rgx-121> on Feb. 3, 2020.
Royle et al., 2002, "An analytical and structural database provides a strategy for sequencing O-glycans from microgram quantities of glycoproteins", Analytical Biochemistry, 304(1):70-90.
Schmidt et al., 1995, "A novel amino acid modification in sulfatases that is defective in multiple sulfatase deficiency," Cell, 82(2):271-278.
Search Report dated Dec. 16, 2020 for European Pat. App. No. 18783760.4.
Slavc et al., 2018, "Best practices for the use of intracerebroventricular drug delivery devices," Molecular Genetics and Metabolism, 124:184-188.
Sleat et al., 2006, "Identification of Sites of Mannose 6-Phosphorylation on Lysosomal Proteins," Molecular & Cellular Proteomics, 5(4):686-701.
Sleat et al., 1996, "Rat brain contains high levels of mannose-6-phosphorylated glycoproteins including lysosomal enzymes and palmitoyl-protein thioesterase, an enzyme implicated in infantile neuronal lipofuscinosis," Journal of Biological Chemistry, 271(32):19191-19198.
Sleat et al., 2005, "The human brain mannose 6-phosphate glycoproteome: a complex mixture composed of multiple isoforms of many soluble lysosomal proteins," Proteomics, 5(6):1520-1532.
Smith et al., 2014, "Gene transfer properties and structural modeling of human stem cell-derived AAV," Molecular Therapy, 22(9):1625-1634.
Stroncek et al., 1999, "Retroviral transduction and expansion of peripheral blood lymphocytes for the treatment of mucopolysaccharidosis type II, Hunter's syndrome," Transfusion, 39(4):343-350.
Sukegawa-Hayasaka et al., 2006, "Effect of Hunter disease (mucopolysaccharidosis type II) mutations on molecular phenotypes of iduronate-2-sulfatase: Enzymatic activity, protein processing and structural analysis," Journal of Inherited Hetabolic Disease, 29(6):755-761.
Tanjuakio et al., 2015, "Activities of daily living in patients with Hunter syndrome: Impact of enzyme replacement therapy and hematopoietic stem cell transplantation," Molecular Genetics and Metabolism, 114(2):161-169.
Wraith et al., 2007, "Enzyme replacement therapy in patients who have mucopolysaccharidosis I and are younger than 5 years: results of a multinational study of recombinant human alpha-L-iduronidase (laronidase)," Pediatrics, 120(1):e37-e46.
Wu et al., 2007, "Self-complementary recombinant adeno-associated viral vectors: packaging capacity and the role of rep proteins in vector purity", Human Gene Therapy, 18(2):171-182.
Yan et al., 2005, "Inverted terminal repeat sequences are important for intermolecular recombination and circularization of adeno-associated virus genomes", Journal of Virology, 79(1):364-379.
Yang et al., 2015, "Tyrosine sulfation as a protein post-translational modification", Molecules, 20(2):2138-2164.
Young et al., 1982, A clinical and genetic study of Hunter's syndrome. 2 Differences between the mild and severe forms, Journal of Medicical Genetics, 19(6):408-411.
Zinn et al., 2015, "In Silico Reconstruction of the Viral Evolutionary Lineage Yields a Potent Gene Therapy Vector," Cell Reports, 12(6):1056-1068.
Sestito et al., 2018, "Genetics and Gene Therapy in Hunter Disease," Current Gene Therapy, 18(2):90-95.
Jung et al., 2010, "Characterization of a novel mucopolysaccharidosis type II mouse model and recombinant AAV2/8 vector-mediated gene therapy," Molecules and Cells, 30(1):13-18.
Watanabe et al., "Transgenic Expression of a Novel Immunosuppressive Signal Converter on T Cells", May 1, 2013 (May 1, 2013), p. S153-S153.
Lamanna et al, 2012, "A Genetic Model of Substrate Reduction Therapy for Mucopolysaccharidosis", Journal of Biological Chemistry, 287(43):36283-36290.
Névoret et al, 2020, "RGX-121 Gene Therapy for Severe Mucopolysaccharidosis Type II (MPS II): Interim Results of an Ongoing First in Human Trial," Abstracts / Molecular Genetics and Metabolism, 132:S13-S116.
Vollebregt et al, 2017, "Genotype-phenotype relationship in mucopolysaccharidosis II: predictive power of IDS variants for the neuronopathic phenotype", Developmental Medicine & Child Neurolory, Heinemann William Medical Books, London, GB, 59(10):1063-1070,.
International Search Report and Written Opinion dated Aug. 24, 2022 for PCT/US2022/014526 (31 pages).
Kanan et al, 2009, "Protein tyrosine-O-sulfation in the retina," Exp. Eye Res. 89:559-567.

* cited by examiner

Amino Acid Sequence of Human IDS (SEQ ID NO:1)

Iduronate-2-sulfatase (IDS)

→ Signal →  Mature 42kD

```
         10         20         30         40         50
MPPPRTGRGL LWLGLVLSSV CVALGSETQA NSTTDALNVL LIIVDDLRPS
         60         70         80         90        100
LGCYGDKLVR SPNIDQLASH SLLFQNAFAQ QAVCAPSRVS FLTGRRPDTT
        110        120        130        140        150
RLYDFNSYWR VHAGNFSTIP QYFKENGYVT MSVGKVFHPG ISSNHTDDSP
        160        170        180        190        200
YSWSFPPYHP SSEKYENTKT CRGPDGELHA NLLCPVDVLD VPEGTLPDKQ
        210        220        230        240        250
STEQAIQLLE KMKTSASPFF LAVGYHKPHI PFRYPKEFQK LYPLENITLA
        260        270        280        290        300
PDPEVPDGLP PVAYNPWMDI RQREDVQALN ISVPYGPIPV DFQRKIRQSY
        310        320        330        340        350
FASVSYLDTQ VGRLLSALDD LQLANSTIIA FTSDHGWALG EHGEWAKYSN
        360        370        380        390        400
FDVATHVPLI FYVPGRTASL PEAGEKLFPY LDPFDSASQL MEPGRQSMDL
        410        420        430        440        450
VELVSLFPTL AGLAGLQVPP RCPVPSFHVE LCREGKNLLK HFRFRDLEED
```

→ Mature 14kD

```
        460        470        480        490        500
PYLPGNPREL IAYSQYPRPS DIPQWNSDKP SLKDIKIMGY SIRTIDYRYT
        510        520        530        540        550
VWVGFNPDEF LANFSDIHAG ELYFVDSDPL QDHNMYNDSQ GGDLFQLLMP
```

*Italics* = signal sequence (*MPPPRTGRGL LWLGLVLSSV CVALG*) (SEQ ID NO:46)

N = N-linked glycosylation sites (GlcNac...)

Boxed = Y-sulfation site (PSSEKYENTKTCRGPD) (SEQ ID NO:47)

Underscore = amino-terminal sequence of 42kD and 14kD peptides (Sleat 2005)

$C^{84}$ = formylglycine modification $N^{280}$ = M-6-P residue(s)

FIG. 1

CLUSTAL O(1.2.4) multiple sequence alignment of hIDS to orthologs

```
SP|P22304|IDS_HUMAN                    MPPPRTGRGLLWLGLVLSSVCVALGSETQANSTTDALNVLLIIVDDLRPSLGCYGDKLVR    60
TR|K6ZGI9|K6ZGI9_PANTR                 MPPPRTGRGLPWLGLVLSSVCVALGSETQANSTTDALNVLLIIVDDLRPSLGCYGDKLVR    60
TR|K7BKV4|K7BKV4_PANTR                 MPPPRTGRGLPWLGLVLSSVCVALGSETQANSTTDALNVLLIIVDDLRPSLGCYGDKLVR    60
TR|H9FTX2|H9FTX2_MACMU                 MPTPGSGRGFLWLGLVLSSVCVALGCETQANSTTDALNVLLIIVDDLRPSLGCYGDKLVR    60
TR|F7EJG2|F7EJG2_CALJA                 MPPPRTSRCLLLLGLVLGSVCVTLGSQAQASSTTDALNVLLIIVDDLRPSLGCYGDKLVR    60
TR|U3DTL8|U3DTL8_CALJA                 MPPPRPSRCLLLLGLVLGSVCVTLGSQAQASSTTDALNVLLIIVDDLRPSLGCYGDKLVR    60
TR|G7NRX7|G7NRX7_MACMU                 MPTPGSGRGFLWLGLVLSSVCVALGCETQANSTTDALNILLIIVDDLRPSLGCYGDKLVR    60
TR|G7Q1V9|G7Q1V9_MACFA                 MPTPGSGRGFLWLGLVLSSVCVALGSETQADSTTDGLNVLLIIVDDLRPSLGCYGDKLVR    60
TR|H2PX10|H2PX10_PONAB                 MPTPGSGRGFLWLGLVLSSVCVALGSETQANSTTDALNVLLIIVDDLRPSLGCYGDKLVR    60
TR|A0A0D9R4D1|A0A0D9R4D1_CHLSB         MPTPGSGRGFLWLGVLLSSVCVAXVTSPKPPSFVDALNVLLIIVDDLRPSLGCYGDKLVR    60
TR|G1RST8|G1RST8_NOMLE                 MSPPRTGQGLLWLGVLLSSVCVALGCETQANSTTDALNILLIIVDDLRPSLGCYGDKLVR    60
UPI00000D9F625                         MPTPGSGRGFLWLGLVLGLLLGLVLGSVCVTLGSQAQANSTTDALNILLIIVDDLRPSLGCYGDKLVR    60
UPI000274358B                          MPTPGSGRGFLWLGLVLSSVCVALGCEMQANSTTDALNILLIIVDDLRPSLGCYGDKLVR    60
UPI00027F6FC5                          MPPPGSGRGFLWLGLVLGSVCVTLGSQAQANSTTDALNILLIIVDDLRPSLGCYGDKLVR    60
UPI00027FAE03                          MPPPRTGLCLLLLGLVLGSVCVTLGSQAQANSTTDALNILLIIVDDLRPSLGCYGDKLVR    60
UPI0003ABBF28                          MPPPGSGRGFLWLGLVLSSVCVALGSETQANSTTDALNILLIIVDDLRPSLGCYGDKLVR    60
UPI000533297F                          MPTPASGRGFLWLGLVLRSVCVALGSETQANSTTDALNILLIIVDDLRPSLGCYGDKLVR    60
UPI0005F40BD2                          MPTPASGRGFLWLGLVLSSVCVALGSETQANSTTDALNILLIIVDDLRPSLGCYGDKLVR    60
                                       *  :** ****: :. :*:***:********** *:*****************

SP|P22304|IDS_HUMAN                    SPNIDQLASHSLLFQNAFAQQAVCAPSRVSFLTGRRPDTTRLYDFNSYWRVHAGNFSTIP   120
TR|K6ZGI9|K6ZGI9_PANTR                 SPNIDQLASHSLLFQNAFAQQAVCAPSRVSFLTGRRPDTTRLYDFNSYWRVHAGNFSTIP   120
TR|K7BKV4|K7BKV4_PANTR                 SPNIDQLASHSLLFQNAFAQQAVCAPSRVSFLTGRRPDTTRLYDFNSYWRVHAGNFSTIP   120
TR|H9FTX2|H9FTX2_MACMU                 SPNIDQLASHSLLFQNAFAQQAVCAPSRVSFLTGRRPDTTRLYDFNSYWRVHAGNFSTIP   120
TR|F7EJG2|F7EJG2_CALJA                 SPNIDQLASHSLLFQNAFAQQAVCAPSRVSFLTGRRPDTTRLYDFNSYWRVHAGNFSTIP   120
TR|U3DTL8|U3DTL8_CALJA                 SPNIDQLASHSLLFQNAFAQQAVCAPSRVSFLTGRRPDTTRLYDFNSYWRVHAGNFSTIP   120
TR|G7NRX7|G7NRX7_MACMU                 SPNIDQLASHSLLFQNAFAQQAVCAPSRVSFLTGRRPDTTRLYDFNSYWRVHAGNFSTIP   120
TR|G7Q1V9|G7Q1V9_MACFA                 SPNIDQLASHSLLFQNAFAQQAVCAPSRVSFLTGRRPDPTRLYDFNSYWRVHAGNFSTIP   120
TR|H2PX10|H2PX10_PONAB                 SPNIDQLASHSLLFQNAFAQQAVCAPSRVSFLTGRRPDTTRLYDFNSYWRVHAGNFSTIP   120
TR|A0A0D9R4D1|A0A0D9R4D1_CHLSB         SPNIDQLASHSLLFQNAFAQQAVCAPSRVSFLTGRRPDTTRLYDFNSYWRVHAGNFSTIP   120
TR|G1RST8|G1RST8_NOMLE                 SPNIDQLASHSLLFQNAFAQQAVCAPSRVSFLTGRRPDTTRLYDFNSYWRVHAGNFSTIP   120
```

FIG. 2

| | |
|---|---|
| TR\|A0A0D9R4D1\|A0A0D9R4D1_CHLSB | SPNIDQLASHSLLFQNAFAQQAVCAPSRVSFLTGRRPDTTRLHNFNSYWRVHAGNFSTIP 120 |
| TR\|G1RST8\|G1RST8_NOMLE | SPNIDQLASHSLLFQNAFAQQAVCAPSRVSFLTGRRPDTTRLYDFNSYWRVHAGNFSTIP 120 |
| UPI000D9F625 | SPNIDQLASHSLLFQNAFAQQAVCAPSRVSFLTGRRPDTTRLYDFNSYWRVHAGNFSTIP 120 |
| UPI0002743588 | SPNIDQLASHSLLFQNAFAQQAVCAPSRVSFLTGRRPDTTRLYDFNSYWRVHAGNFSTIP 120 |
| UPI00027F6FC5 | SPNIDQLASHSLLFQNAFAQQAVCAPSRVSFLTGRRPDTTRLYDFNSYWRVHAGNFSTIP 120 |
| UPI00027FAE03 | SPNIDQLASHSLLFQNAFVQQAVCAPSRVSFLTGRRPDTTRLYDFNSYWRVHAGNFSTIP 120 |
| UPI0003ABBF28 | SPNIDQLASHSLLFQNAFAQEAVCAPSRVSFLTGRRPDTTRLYDFNSYWRVHAGNFSTIP 120 |
| UPI00053297F | SPNIDQLASHSLLFQNAFAQQAVCAPSRVSFLTGRRPDTTRLYDFNSYWRVHAGNFSTIP 120 |
| UPI0005F40BD2 | SPNIDQLASHSLLFQNAFAQQAVCTPSHVSFLTGRRPDTTRLYDFNSYWRVHAGNFSTIP 120 |
| | ******************:*:*::***************************** |
| SP\|P22304\|IDS_HUMAN | QYFKENGYVTMSVGKVFHPGISSNHTDDSPYSWSFPPYHPSSEKYENTKTCRGPDGELHA 180 |
| TR\|K6ZGI9\|K6ZGI9_PANTR | QYFKENGYVTMSVGKVFHPGISSNHTDDSPYSWSFPPYHPSSEKYENTKTCRGPDGELHA 180 |
| TR\|K7BKV4\|K7BKV4_PANTR | QYFKENGYVTMSVGKVFHPGISSNHTDDSPYSWSFPPYHPSSEKYENTKTCRGPDGELHA 180 |
| TR\|H9FTX2\|H9FTX2_MACMU | QYFKENGYVTMSVGKVFHPGITSNHTDDSPYSWSFPPYHPSSEKYENTKTCRGPDGELHA 180 |
| TR\|F7EJG2\|F7EJG2_CALJA | QYFKDNGYVTMSVGKVFHPGISSNHSDDSPYSWSFPPYHPSSEKYENTKTCRGPDGELHA 180 |
| TR\|U3DTL8\|U3DTL8_CALJA | QYFKENGYVTMSVGKVFHPGISSNHSDDSPYSWSFPPYHPSSEKYENTKTCRGPDGELHA 180 |
| TR\|G7NRX7\|G7NRX7_MACMU | QYFKENGYVTMSVGKVFHPGITSNHTDDSPYSWSFPPYHPSSEKYENTKTCRGPDGELHA 180 |
| TR\|G7Q1V9\|G7Q1V9_MACFA | QYFKENGYVTMSVGKVFHPGITSNHTDDSPYSWSFPPYHPSSEKYENTKTCRGPDGELHA 180 |
| TR\|H2PX10\|H2PX10_PONAB | QYFKENGYVTMSVGKVFHPGISSNHTDDSPYSWSFPPYHPSSEKYENTKTCRGPDGELHA 180 |
| TR\|A0A0D9R4D1\|A0A0D9R4D1_CHLSB | QYFKENGYVTMSVGKVFHPGITSNHTDDSPYSWSFPPYHPSSEKYENTKTCRGPDGELHA 180 |
| TR\|G1RST8\|G1RST8_NOMLE | QYFKENGYVTMSVGKVFHPGITSNHTDDSPYSWSFPPYHPSSEKYENTKTCRGPDGELHA 180 |
| UPI000D9F625 | QYFKENGYVTMSVGKVFHPGITSNHTDDSPYSWSFPPYHPSSXXXXXXKTCRGPDGELHA 180 |
| UPI0002743588 | QYFKENGYVTMSVGKVFHPGITSNHTDDSPYSWSFPPYHPSSEKYENTKTCRGPDGELHA 180 |
| UPI00027F6FC5 | QYFKENGYVTMSVGKVFHPGITSNHTDDSPYSWSFPPYHPSSEKYENTKTCRGPDGELHA 180 |
| UPI00027FAE03 | QYFKENGYVTMSVGKVFHPGITSNHTDDSPYSWSFPPYHPSSEKYENTKTCRGPDGELHA 180 |
| UPI0003ABBF28 | QYFKENGYVTMSVGKVFHPGITSNHTDDSPYSWSFPPYHPSSEKYENTKTCRGPDGELHA 180 |
| UPI00053297F | QYFKENGYVTMSVGKVFHPGITSNHTDDSPYSWSFPPYHPSSEKYENTKTCRGPDGELHA 180 |
| UPI0005F40BD2 | QYFKENGYVTMSVGKVFHPGITSNHTDDSPYSWSFPPYHPSSEKYENTKTCRGPDGELHA 180 |
| | **:***********:***:************* ********* |

FIG. 2 continued

| | |
|---|---|
| SP\|P22304\|IDS_HUMAN | NLLCPVDVLDVPEGTLPDKQSTEQAIQLLEKMKTSASPFFLAVGYHKPHIPFRYPKEFQK 240 |
| TR\|K6ZGI9\|K6ZGI9_PANTR | NLLCPVDVLDVPEGTLPDKQSTEQAIQLLEKMKTSASPFFLAVGYHKPHIPFRYPKEFQK 240 |
| TR\|K7BKV4\|K7BKV4_PANTR | NLLCPVDVLDVPEGTLPDKQSTEQAIQLLEKMKTSASPFFLAVGYHKPHIPFRYPKEFQK 240 |
| TR\|H9FTX2\|H9FTX2_MACMU | NLLCPVDVVDVPEGTLPDKQSTEQAIQLLEKMKTSASPFFLAVGYHKPHIPFRYPKEFQK 240 |
| TR\|F7EJG2\|F7EJG2_CALJA | NLLCPVDVVDVPEGTLPDKQSTEEAIRLLEKMKTSASPFFLAVGYHKPHIPFRYPKEFQK 240 |
| TR\|U3DTL8\|U3DTL8_CALJA | NLLCPVDVVDVPEGTLPDKQSTEEAIRLLEKMKTSASPFFLAVGYHKPHIPFRYPKEFQK 240 |
| TR\|G7NRX7\|G7NRX7_MACMU | NLLCPVDVVDVPEGTLPDKQSTEQAIQLLEKMKTSASPFFLAVGYHKPHIPFRYPKEFQK 240 |
| TR\|G7Q1V9\|G7Q1V9_MACFA | NLLCPVDVVDVPEGTLPDKQSTEQAIQLLEKMKTSASPFFLAVGYHKPHIPFRYPKEFQK 240 |
| TR\|H2PX10\|H2PX10_PONAB | NLIAKKMCWMFPRAPCCDKQSTEQAIQLLEKMKTSASPFFLAVGYHKPHIPFRYPKEFQK 240 |
| TR\|A0A0D9R4D1\|A0A0D9R4D1_CHLSB | NLLCPVDVVDVPEGTLPDKQSTEQAIQLLEKMKTSASPFFLAVGYHKPHIPFRYPKEFQK 240 |
| TR\|G1RST8\|G1RST8_NOMLE | NLLCPVDVLDVPEGTLPDKQSTEQAIQLLEKMKTSASPFFLAVGYHKPHIPFRYPKEFQK 240 |
| UPI0000D9F625 | NLLCPVDVLDVPEGTLPDKQSTEQAIRLLEKMKTSASPFFLAVGYHKPHIPFRYPKEFQK 240 |
| UPI00274358B | NLLCPVDVLDVPEGTLPDKQSTEQAIRLLKKMKTSASPFFLAVGYHKPHIPFRYPKEFQK 240 |
| UPI00027F6FC5 | NLLCPVDVVDVPEGTLPDKQSTEQAVQLLEKMKTSASPFFLAVGYHKPHIPFRYPKEFQK 240 |
| UPI00027FAE03 | NLLCPVDVVDVPEGTLPDKQSTEQAIQLLEKMKTSASPFFLAVGYHKPHIPFRYPKEFQK 240 |
| UPI0003ABBF28 | NLLCPVDVVDVPEGTLPDKQSTEQAIQLLEKMKTSASPFFLAVGYHKPHIPFRYPKEFQK 240 |
| UPI000533297F | NLLCPVDVVDVPEGTLPDKQSTEQAIQLLEKMKTSASPFFLAVGYHKPHIPFRYPKEFQK 240 |
| UPI0005F40BD2 | NLLCPVDVVDVPEGTLPDKQSTEQAIQLLEKMKTSASPFFLAVGYHKPHIPFRYPKEFQK 240 |
| | : .: :.****:*******************:*************** |

| | |
|---|---|
| SP\|P22304\|IDS_HUMAN | LYPLENITLAPDPEVPDGLPPVAYNPWMDIRQREDVQALNISVPYGPIPVDFQRKIRQSY 300 |
| TR\|K6ZGI9\|K6ZGI9_PANTR | LYPLENITLAPDPEVPDGLPPVAYNPWMDIRQREDVQALNISVPYGPIPVDFQRKIRQSY 300 |
| TR\|K7BKV4\|K7BKV4_PANTR | LYPLENITLAPDPEVPDGLPPVAYNPWMDIRQREDVQALNISVPYGPIPVDFQRKIRQSY 300 |
| TR\|H9FTX2\|H9FTX2_MACMU | LYPLENITLAPDPEVPDGLPPVAYNPWMDIRQREDVQALNISVPYGPIPVDFQRKIRQSY 300 |
| TR\|F7EJG2\|F7EJG2_CALJA | LYPLENITLAPDSEVPDGLPPVAYNPWMDIRQREDVQALNISVPYGPIPVEFQRKIRQSY 300 |
| TR\|U3DTL8\|U3DTL8_CALJA | LYPLENITLAPDSEVPDGLPPVAYNPWMDIRQREDVQALNISVPYGPIPVEFQRKIRQSY 300 |
| TR\|G7NRX7\|G7NRX7_MACMU | LYPLENITLAPDPEVPDGLPPVAYNPWMDIRQREDVQALNISVPYGPIPVDFQRKIRQSY 300 |
| TR\|G7Q1V9\|G7Q1V9_MACFA | LYPLENITLAPDPEVPDGLPPVAYNPWMDIRQREDVQALNISVPYGPIPVDFQRKIRQSY 300 |
| TR\|H2PX10\|H2PX10_PONAB | LYPLENITLAPDPEVPDGLPPVAYNPWMDIRQREDVQALNISVPYGPIPVDFQQKIRQSY 300 |

FIG. 2 continued

| | | |
|---|---|---|
| TR\|A0A0D9R4D1\|A0A0D9R4D1_CHLSB | LYPLENITLAPDSEVPDGLPPPVAYNPWMDIRQREDVQALNISVPYGPIPVEFQRKIRQSY | 300 |
| TR\|G1RST8\|G1RST8_NOMLE | LYPLENITLAPDSEVPDGLPPPVAYNPWMDIRQREDVQALNISVPYGPIPVDFQRKIRQSY | 300 |
| UPI000D9F625 | LYPLENITLAPDPEVPDGLPPPVAYNPWMDIRQREDVQALNISVPYGPIPVDFQRKIRQSY | 300 |
| UPI00027435B8 | LYPLENITLAPDSEVPDGLPPPVAYNPWMDIRQREDVQALNISVPYGPIPVDFQRKIRQSY | 300 |
| UPI00027F6FC5 | LYPLENITLAPDSEVPDGLPPPVAYNPWMDIRQREDVQALNISVPYGPIPVEFQRKIRQSY | 300 |
| UPI00027FAE03 | LYPLENITLAPDSEVPDGLPPPVAYNPWMDIRQREDVQALNISVPYGPIPVEFQRKIRQSY | 300 |
| UPI0003ABBF28 | LYPLENITLAPDSEVPDGLPPPVAYNPWMDIRQREDVQALNISVPYGPIPVEFQRKIRQSY | 300 |
| UPI000533297F | LYPLENITLAPDSEVPDGLPPPVAYNPWMDIRQREDVQALNISVPYGPIPVDFQRKIRQSY | 300 |
| UPI0005F40BD2 | LYPLENITLAPDSEVPDGLPPPVAYNPWMDIRQREDVQALNISVPYGPIPVDFQRKIRQSY | 300 |
| | ********:**.*****************:***:* | |

| | | |
|---|---|---|
| SP\|P22304\|IDS_HUMAN | FASVSYLDTQVGRLLSALDDLQLANSTIIAFTSDHGWALGEHGEWAKYSNFDVATHVPLI | 360 |
| TR\|K6ZGI9\|K6ZGI9_PANTR | FASVSYLDTQVGRLLSALDDLQLANSTIIAFTSDHGWALGEHGEWAKYSNFDVATHVPLM | 360 |
| TR\|K7BKV4\|K7BKV4_PANTR | FASVSYLDTQVGRLLSALDDLQLANSTIVAFTSDHGWALGEHGEWAKYSNFDVATHVPLM | 360 |
| TR\|H9FTX2\|H9FTX2_MACMU | FASVSYLDTQVGRLLSALDDLQLANSTIVAFTSDHGWALGEHGEWAKYSNFDVATHVPLM | 360 |
| TR\|F7EJG2\|F7EJG2_CALJA | FASVSYLDTQVGHLLSALDDLQLANSTIVAFTSDHGWALGEHGEWAKYSNFDVATHVPLM | 360 |
| TR\|U3DTL8\|U3DTL8_CALJA | FASVSYLDTQVGHLLSALDDLHLANSTIVAFTSDHGWALGEHGEWAKYSNFDVATHVPLM | 360 |
| TR\|G7NRX7\|G7NRX7_MACMU | FASVSYLDTQVGRLLSALDDLQLANSTIVAFTSDHGWALGEHGEWAKYSNFDVATRVPLM | 360 |
| TR\|G7Q1V9\|G7Q1V9_MACFA | FASVSYLDTQVGRLLSALDDLQLANSTIVAFTSDHGWALGEHGEWAKYSNFDVATRVPLM | 360 |
| TR\|H2PX10\|H2PX10_PONAB | FASVSYLDTQVGRLLSTLDDLQLANSTIIAFTSDHGWALGEHGEWAKYSNFDVATHVPLM | 360 |
| TR\|A0A0D9R4D1\|A0A0D9R4D1_CHLSB | FASVSYLDTQVGRLLSALDDLQLANSTIVAFTSDHGWALGEHGEWAKYSNFDVATHVPLM | 360 |
| TR\|G1RST8\|G1RST8_NOMLE | FASVSYLDTQVGHLLSALDDLQLANSTIVAFTSDHGWALGEHGEWAKYSNFDVATHVPLM | 360 |
| UPI000D9F625 | FASVSYLDTQVGHLLSALDDLQLANSTIVAFTSDHGWALGEHGEWAKYSNFDVATHVPLM | 360 |
| UPI00027435B8 | FASVSYLDTQVGHLLSALDDLQLANSTIVAFTSDHGWALGEHGEWAKYSNFDVATHVPLM | 360 |
| UPI00027F6FC5 | FASVSYLDTQVGHLLSALDDLQLANSTIVAFTSDHGWALGEHGEWAKYSNFDVATHVPLM | 360 |
| UPI00027FAE03 | FASVSYLDTQVGHLLSALDDLQLANSTIVAFTSDHGWALGEHGEWAKYSNFDVATHVPLM | 360 |
| UPI0003ABBF28 | FASVSYLDTQVGHLLSALDDLQLANSTIVAFTSDHGWALGEHGEWAKYSNFDVATHVPLM | 360 |
| UPI000533297F | FASVSYLDTQVGHLLSALDDLQLANSTIVAFTSDHGWALGEHGEWAKYSNFDVATHVPLM | 360 |
| UPI0005F40BD2 | FASVSYLDTQVGHLLSALDDLQLANSTIVAFTSDHGWALGEHGEWAKYSNFDVATHVPLM | 360 |
| | **********:*:**:**:*******************:*: | |

FIG. 2 continued

| | | |
|---|---|---|
| SP\|P22304\|IDS_HUMAN | FYVPGRTASLPEAGEKLFPYLDPFDSASQLMEPGRQSMDLVELVSLFPTLAGLAGLQVPP | 420 |
| TR\|K6ZGI9\|K6ZGI9_PANTR | FYVPGRTASLPEAGEKLFPYLDPFDSASQLMEPGRQSMDLVELVSLFPTLAGLAGLQAPP | 420 |
| TR\|K7BKV4\|K7BKV4_PANTR | FYVPGRTASLPEAGEKLFPYLDPFDSASQLMEPGRQSMDLVELVSLFPTLAGLAGLQAPP | 420 |
| TR\|H9FTX2\|H9FTX2_MACMU | FYVPGRTASLPEAGEKLFPYLDPFDSASQLMEPGRQSMDLVELVSLFPTLAGLAGLQVPP | 420 |
| TR\|F7EJG2\|F7EJG2_CALJA | FYVPGRTASLPEADEKLFPYVDPFDSASQLMEPGRQSMDLVELVSLFPTLAGLAGLQVPP | 420 |
| TR\|U3DTL8\|U3DTL8_CALJA | FYVPGRTASLPEADEKLFPYVDPFDSASQLMEPGRQSMDLVELVSLFPTLAGLAGLQVPP | 420 |
| TR\|G7NRX7\|G7NRX7_MACMU | FYVPGRTASLPEAGEKLFPYLDPFHSASELMEPGRQSMDLVELVSLFPTLAGLAGLQVPP | 420 |
| TR\|G7Q1V9\|G7Q1V9_MACFA | FYVPGRTASLPEAGEKLFPYLDPFHSASELMEPGRQSMDLVELVSLFPTLAGLAGLQVPP | 420 |
| TR\|H2PX10\|H2PX10_PONAB | FYVPGRTASLPEAGEKLFPYLDPFDSASELMEPGRQSMDLVELVSLFPTLAGLAGLQVPP | 420 |
| TR\|A0A0D9R4D1\|A0A0D9R4D1_CHLSB | FYVPGRTASLPEAGEKLFPYLDPFDSASELMEPGRQSMDLVELVSLFPTLAGLAGLQVPP | 420 |
| TR\|G1RST8\|G1RST8_NOMLE | FYVPGRTASLPEAGEKLFPYLDPFDSASELMEPGRQSMDLVELVSLFPTLAGLAGLQVPP | 420 |
| UPI0000D9F625 | FYVPGRTASLPEAGEKLFPYLDPFDSASQLMEPGRQSMDLVELVSLFPTLAGLAGLQVPP | 420 |
| UPI00027435B8 | FYVPGRTASLPETGEKLFPYLDPFHSASELMEPGRQSTDLVELVSLFPTLAGLAGLQVPP | 420 |
| UPI00027F6FC5 | FYVPGRTASLPEAGEKLFPYLDPFHSASELMEPGRQSMDLVELVSLFPTLAGLAGLQVPP | 420 |
| UPI00027FAE03 | FYVPGRTASLPEAGEKLFPYLDPFHSASELMEPGRQSMDLVELVSLFPTLAGLAGLQVPP | 420 |
| UPI0003ABBF28 | FYVPGRTASLPEAGEKLFPYLDPFDSASELMEPGRQSMDLVELVSLFPTLAGLAGLQVPP | 420 |
| UPI000533297F | FYVPGRTASLPEAGEKLFPYLDPFDSASELMEPGRQSMDLVELVSLFPTLAGLAGLQVPP | 420 |
| UPI0005F40BD2 | FYVPGRTASLPEAGEKLFPYLDPFDSASELMEPGRQSMDLVELVSLFPTLAGLAGLQVPP | 420 |
| | ******:.:*..*::******************:  | |

| | | |
|---|---|---|
| SP\|P22304\|IDS_HUMAN | RCPVPSFHVELCREGKNLLKHFRFRDLEEDPYLPGNPRELIAYSQYPRPSDIPQWNSDKP | 480 |
| TR\|K6ZGI9\|K6ZGI9_PANTR | RCPVPSFHVELCREGKNLLKHFRFRDLEEDPYLPGNPRELIAYSQYPRPSDIPQWNSDKP | 480 |
| TR\|K7BKV4\|K7BKV4_PANTR | RCPVPSFHVELCREGKNLLKHFRFRDLEEDPYLPGNPRELIAYSQYPRPSDIPQWNSDKP | 480 |
| TR\|H9FTX2\|H9FTX2_MACMU | RCPVPSFHVELCREGKNLLKHFRFRDLEEDPYLPGNPRELIAYSQYPRPSDIPQWNSDKP | 480 |
| TR\|F7EJG2\|F7EJG2_CALJA | RCPVPSFHVELCREGKSLLKHFRFRDLEEDPYLPGNPRELIAYSQYPRPADFPQWNSDKP | 480 |
| TR\|U3DTL8\|U3DTL8_CALJA | RCPVPSFHVELCREGKSLLKHFRFRDLEEDPYLPGNPRELIAYSQYPRPADFPQWNSDKP | 480 |
| TR\|G7NRX7\|G7NRX7_MACMU | RCPVPSFHVELCREGKNLLKHFRFHGLEEDPYLPGNPRELIAYSQYPRPADFPQWNSDKP | 480 |
| TR\|G7Q1V9\|G7Q1V9_MACFA | RCPVPSFHVELCREGKNLLKHFRFHGLEEDPYLPGNPRELIAYSQYPRPADFPQWNSDKP | 480 |
| TR\|H2PX10\|H2PX10_PONAB | RCPVPSFHVELCREGKNLLKHFRFRDLEEDPYLPGNPRELIAYSQYPRPADFPQWNSDKP | 480 |

FIG. 2 continued

```
TR|A0A0D9R4D1|A0A0D9R4D1_CHLSB    RCPVPSFHVELCREGKNLLKHFRFRDLEEDPYLPGNPRELIAYSQYPRPADFPQWNSDKP  480
TR|G1RST8|G1RST8_NOMLE            RCPVPSFHVELCREGKNLLKHFRFRDLEEDPYLPGNPRELIAYSQYPRPADFPQWNSDKP  480
UPI000009F625                     RCPVPSFHVELCREGKNLLKHFRFRDLEEDPYLPGNPRELIAYSQYPRPADFPQWNSDKP  480
UPI000027435B8                    RCPVPSFHVELCREGKNLLKHFRFRDLEEDPYLPGNPRELIAYSQYPRPSDIPQWNSDKP  480
UPI00027F6FC5                     RCPVPSFHVELCREGKNLLKHFRFRDLEEDPYLPGNPRELIAYSQYPRPADFPQWNSDKP  480
UPI00027FAE03                     RCPVPSFHVELCREGKNLLKHFRFRDLEEDPYLPGNPRELIAYSQYPRPADFPQWNSDKP  480
UPI0003ABBF28                     RCPVPSFHVELCREGKNLLKHFRFHGLEEDPYLPGNPRELIAYSQYPRPADFPQQNSDKP  480
UPI0005332976F                    RCPVPSFHVELCREGKNLLKHFRFRDLEEDPYLPGNPRELIAYSQYPRPADFPQWNSDKP  480
UPI0005F40BD2                     RCPVPSFHVELCREGKNLLKHFRFRDLEEDPYLPGNPRELIAYSQYPRPADFPQWNSDKP  480
                                  ****************.*.********.*******************:**:*****

SP|P22304|IDS_HUMAN               SLKDIKIMGYSIRTIDYRYTVWVGFNPDEFLANFSDIHAGELYFVDSDPLQDHNMYNDSQ  540
TR|K6ZGI9|K6ZGI9_PANTR            SLKDIKIMGYSIRTIDYRYTVWVGFNPDEFLANFSDIHAGELYFVDSDPLQDHNMYNDSQ  540
TR|K7BKV4|K7BKV4_PANTR            SLKDIKIMGYSIRTIDYRYTVWIGFNPDEFLANFSDIHAGELYFVDSDPLQDHNMYNDSQ  540
TR|H9FTX2|H9FTX2_MACMU            SLKDIKIMGYSIRTIDYRYTVWVGFNPDEFLANFSDIHAGELYFVDSDPLQDHNMYNDSQ  540
TR|F7EJG2|F7EJG2_CALJA            SLKYIKIMGYSIRTIDYRYTVWVGFSPDEFLANFSDIHAGELYFVDSDPLQDHNMYNDSQ  540
TR|U3DTL8|U3DTL8_CALJA            SLKYIKIMGYSIRTVDYRYTVWVGFNPDEFLANFSDIHAGELYFVDSDPLQDHNMYNDSQ  540
TR|G7NRX7|G7NRX7_MACMU            SLKDIKIMGYSIRTIDYRYTVWVGFNPDEFLANFSDIHAGELYFVDSDPLQDHNMYNDSQ  540
TR|G7Q1V9|G7Q1V9_MACFA            SLKDIKIMGYSIRTIDYRYTVWVGFNPDEFLANFSDIHAGELYFVDSDPLQDHNMYNDSQ  540
TR|H2PX10|H2PX10_PONAB            NLKDIKIMGYSIRTIDYRYTVWVGFNPDEFLANFSDIHAGELYFVDSDPLQDHNMYNDSQ  540
TR|A0A0D9R4D1|A0A0D9R4D1_CHLSB    SLKDIKIMGYSIRTIDYRYTVWVGFNPDEFLANFSDIHAGELYFVDSDPLQDHNMYNDSQ  540
TR|G1RST8|G1RST8_NOMLE            SLKDIKIMGYSIRTIDYRYTVWVGFNPDEFLANFSDIHAGELYFVDSDPLQDHNMYNDSQ  540
UPI000009F625                     SLKDIKIMGYSIRTIDYRYTVWVGFNPDEFLANFSDIHAGELYFVDSDPLQDHNMYNDSQ  540
UPI000027435B8                    SLKDIKIMGYSIRTIDYRYTVWVGFNPDEFLANFSDIHAGELYFVDSDPLQDHNMYNDSQ  540
UPI00027F6FC5                     SLKYIKIMGYSIRTIDYRYTVWVGFNPDEFLANFSDIHAGELYFVDSDPLQDHNMYNDSQ  540
UPI00027FAE03                     SLKDIKIMGYSIRTIDYRYTVWVGFNPDEFLANFSDIHAGELYFVDSDPLQDHNMYNDSQ  540
UPI0003ABBF28                     SLKDIKIMGYSIRTIDYRYTVWVGFNPDEFLANFSDIHAGELYFVDSDPLQDHNMYNDSQ  540
UPI0005332976F                    SLKDIKIMGYSIRTIDYRYTVWVGFNPDEFLANFSDIHAGELYFVDSDPFQDHNMYNDSQ  540
UPI0005F40BD2                     SLKDIKIMGYSIRTIDYRYTVWVGFNPDEFLANFSDIHAGELYFVDSDPLQDHNMYNDSQ  540
                                  .**:*************:*********:*********************:*********
```

FIG. 2 continued

```
SP|P22304|IDS_HUMAN              GGDLFQLLMP 550 (SEQ ID NO:27)
TR|K6ZGI9|K6ZGI9_PANTR           GGDLFQLLMP 550 (SEQ ID NO:28)
TR|K7BKV4|K7BKV4_PANTR           GGDLFQLLMP 550 (SEQ ID NO:29)
TR|H9FTX2|H9FTX2_MACMU           GGDLFQLLMP 550 (SEQ ID NO:30)
TR|F7EJG2|F7EJG2_CALJA           GGELFQSLMP 550 (SEQ ID NO:31)
TR|U3DTL8|U3DTL8_CALJA           GGELFQSLMP 550 (SEQ ID NO:32)
TR|G7NRX7|G7NRX7_MACMU           GGDLLQLLMP 550 (SEQ ID NO:33)
TR|G7Q1V9|G7Q1V9_MACFA           GGDLFQLLMP 550 (SEQ ID NO:34)
TR|H2PX10|H2PX10_PONAB           GGDLFQLLMP 550 (SEQ ID NO:35)
TR|A0A0D9R4D1|A0A0D9R4D1_CHLSB   GGDLFQLLMP 550 (SEQ ID NO:36)
TR|G1RST8|G1RST8_NOMLE           GGDLFQLLMP 550 (SEQ ID NO:37)
UPI0000D9F625                    GGDLFQLLMP 550 (SEQ ID NO:38)
UPI00027435BB                    GGDLFQLLMP 550 (SEQ ID NO:39)
UPI00027F6FC5                    GGDLFQLLMP 550 (SEQ ID NO:40)
UPI00027FAE03                    GGDLFQLLMP 550 (SEQ ID NO:41)
UPI0003ABBF28                    GGELFQSLMP 550 (SEQ ID NO:42)
UPI0005332297F                   GGDLFQLLMP 550 (SEQ ID NO:43)
UPI0005F40BD2                    GGDLFQLLMP 550 (SEQ ID NO:44)
                                 **:*:* ***

Species Legend:
SP|P22304|IDS_HUMAN              [Homo sapiens]
TR|K6ZGI9|K6ZGI9_PANTR           [Pan troglodytes (Chimpanzee)]
TR|K7BKV4|K7BKV4_PANTR           [Pan troglodytes (Chimpanzee)]
TR|H9FTX2|H9FTX2_MACMU           [Macaca mulatta (Rhesus macaque)]
TR|F7EJG2|F7EJG2_CALJA           [Callithrix jacchus (White-tufted-ear marmoset)]
TR|U3DTL8|U3DTL8_CALJA           [Callithrix jacchus (White-tufted-ear marmoset)]
TR|G7NRX7|G7NRX7_MACMU           [Macaca mulatta (Rhesus macaque)]
TR|G7Q1V9|G7Q1V9_MACFA           [Macaca fascicularis (Crab-eating macaque; Cynomologous monkey)]
```

FIG. 2 continued

| Accession | Species |
|---|---|
| TR\|H2PX10\|H2PX10_PONAB | Pongo abelii (Sumatran orangutan) |
| TR\|A0A0D9R4D1_CHLSB | Chlorocebus sabaeus (Green monkey) |
| TR\|G1RST8\|G1RST8_NOMLE | Nomascus leucogenys (Northern white-cheeked gibbon) |
| UPI0000D9F625 | Macaca mulatta (Rhesus macaque) |
| UPI00027435B8 | Pan paniscus (Pygmy chimpanzee; Bonobo) |
| UPI00027F6FC5 | Papio Anubis (Olive baboon) |
| UPI00027FAE03 | Saimiri boliviensis (Bolivian squirrel monkey) |
| UPI0003ABBF28 | Macaca fascicularis (Crab-eating macaque; Cynomologous monkey) |
| UPI000533297F | Rhinopithecus roxellana (Golden snub-nosed monkey; Pygathrix roxellana) |
| UPI0005F40BD2 | Colobus angolensis palliates (Peters' Angolan colobus) |

FIG. 2 continued hIDS MPS II Variants

L41P (mild);
41X (intermediate);
D45N (MPS2);
R48P (mild);
Y54D (severe);
N63D (mild/intermediate);
A68E (severe);
S71N (mild);
S71R (severe);
L73F (severe);
A79E (mild);
A82E (MPS2);
A82V (no significant enzyme activity);
A85S (severe);
A85T (mild to severe forms);
P86L (intermediate to severe forms);
P86Q (MPS2);
P86R (severe);
S87N (mild);
R88C (severe);

E125V (mild);
S132W (severe);
G134R (severe);
K135N (intermediate);
K135R (intermediate);
H138D (mild/intermediate);
G140V (MPS2; no significant enzyme activity);
S143F (MPS2);
D148H (intermediate);
H159P (severe);
159X (missing in MPS2; intermediate form;
P160R (MPS2);
N181I (mild);
L182P (intermediate);
C184F (mild/intermediate);
C184W (MPS2);
L196S (mild/intermediate);
D198G (mild);
A205P (intermediate);
L221P (intermediate);

D334G (severe);
D334N (mild);
H335R (intermediate);
G336E (severe);
G336R (severe);
W337R (intermediate);
L339R (severe);
G340D (mild);
E341K (severe);
H342Y (mild);
W345C (mild/severe);
A346D (mild/severe);
A346V (mild/severe);
K347I (MPS2);
K347Q (severe);
K347T (severe);
Y348H (MPS2);
S349I (severe);
P358R (severe);
L403R (intermediate);
L410P (MPS2);
C422G (mild);

FIG. 3

R88G (severe);
R88H (intermediate/severe form);
R88L (severe);
R88P (severe—total absence of residual activity);
V89F (MPS2);
L92P (severe);
G94D (mild);
R95G (intermediate);
R95T (mild);
95X (severe);
L102R (mild);
Y108C (mild);
Y108S (mild);
N115Y (MPS2);
S117Y (severe);
117X (missing in MPS2; severe form; deleterious mutation);
T118I (mild to severe; greatly reduced activity);
118X (missing in MPS2; severe form);
P120H (mild);
P120R (severe);
Q121H (severe);
Q121R (severe);

G224E (severe);
Y225D (intermediate);
K227M (intermediate);
K227Q (severe);
P228L (MPS2);
P228T (severe);
H229R (intermediate/severe);
H229Y (severe);
P231L (mild);
D252N (MPS2);
L259P (severe);
Y264N (MPS2);
N265I (intermediate; deleterious mutation);
P266H (mild);
P266R (MPS2);
D269V (MPS2);
Q293H (mild);
S299I (mild);
D308E (mild);
D308N (intermediate);
T309A (severe);
R313C (MPS2; unknown pathological significance);
L314P (severe);
S333L (severe);

C422R (severe);
C432Y (severe);
E434K (MPS2);
Q465P (severe);
P467L (severe);
R468G (mild/severe);
R468L (mild/severe);
R468Q (severe/intermediate; greatly reduced activity);
R468W (mild/severe);
P469H (mild);
D478G (mild);
D478Y (severe);
P480L (mild);
P480Q (mild);
P480R (severe);
I485K (MPS2);
I485R (severe);
MG488-489IA (intermediate);
Y490S (intermediate);
S491F (mild);
W502C (severe);
W502S (MPS2);
E521K (severe);
E521V (severe);
Y523C (mild).

FIG. 3 continued

Figure 7:
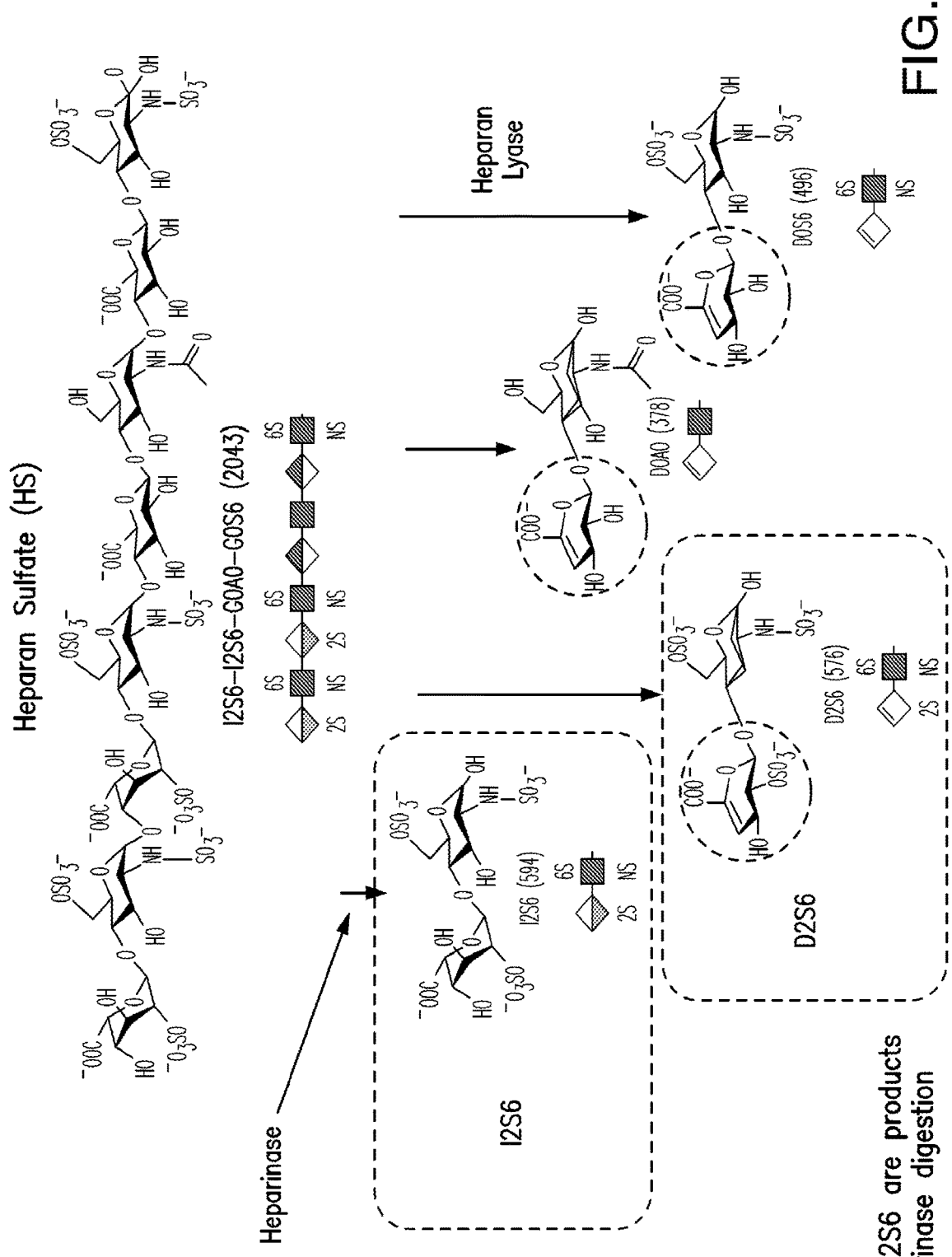

FIG. 7. IDS processing. Molecular mass of deglycosylated polypeptides is indicated in parentheses.

(From, Millat et al., 1997, Exp. Cell. Res. 230: 362–367 ("Millat 1997") Fig. 7).

```
                VP11-736 →
AAV1    MAADGYLPDWLEDNLSEGIREWWDLKPGAPKPKANQQKQDDGRGLVLPGYKYLGPFNGLD 60
AAV2    MAADGYLPDWLEDTLSEGIRQWWKLKPGPPPPKPAERHKDDSRGLVLPGYKYLGPFNGLD 60
AAV3-3  MAADGYLPDWLEDNLSEGIREWWALKPGVPQPKANQQHQDNRRGLVLPGYKYLGPGNGLD 60
AAV4-4  --MTDGYLPDWLEDNLSEGVREWWALQPGAPKPKANQQHQDNARGLVLPGYKYLGPGNGLD 59
AV5     MSFVDHPPDWLEE-VGEGLREFLGLEAGPPKPKPNQQHQDQARGLVLPGYNYLGPGNGLD 59
AAV6    MAADGYLPDWLEDNLSEGIREWWDLKPGAPKPKANQQKQDDGRGLVLPGYKYLGPFNGLD 60
AAV7    MAADGYLPDWLEDNLSEGIREWWDLKPGAPKPKANQQKQDNGRGLVLPGYKYLGPFNGLD 60
AAV8    MAADGYLPDWLEDNLSEGIREWWALKPGAPKPKANQQKQDDGRGLVLPGYKYLGPFNGLD 60
hu31    MAADGYLPDWLEDTLSEGIRQWWKLKPGPPPPKPAERHKDDSRGLVLPGYKYLGPGNGLD 60
hu32    MAADGYLPDWLEDTLSEGIRQWWKLKPGPPPPKPAERHKDDSRGLVLPGYKYLGPGNGLD 60
AAV9    MAADGYLPDWLEDNLSEGIREWWALKPGAPQPKANQQHQDNARGLVLPGYKYLGPGNGLD 60
SUBS    -STVDHP----ETVG---V-QFLK-QA-P-K---PAERKK-DG--------N----F-----
         MF            L    D E V P         QS                 
                           G     Q         R

AAV1    KGEPVNAADAAALEHDKAYDQQLKAGDNPYLRYNHADAEFQERLQEDTSFGGNLGRAVFQ 120
AAV2    KGEPVNEADAAALEHDKAYDRQLDSGDNPYLKYNHADAEFQERLKEDTSFGGNLGRAVFQ 120
AAV3-3  KGEPVNEADAAALEHDKAYDQQLKAGDNPYLKYNHADAEFQERLQEDTSFGGNLGRAVFQ 120
AAV4-4  KGEPVNAADAAALEHDKAYDQQLKAGDNPYLKYNHADAEFQQRLQGDTSFGGNLGRAVFQ 119
AV5     RGEPVNRADEVAREHDISYNEQLEAGDNPYLKYNHADAEFQEKLADDTSFGGNLGKAVFQ 119
AAV6    KGEPVNAADAAALEHDKAYDQQLKAGDNPYLRYNHADAEFQERLQEDTSFGGNLGRAVFQ 120
AAV7    KGEPVNAADAAALEHDKAYDQQLKAGDNPYLRYNHADAEFQERLQEDTSFGGNLGRAVFQ 120
AAV8    KGEPVNAADAAALEHDKAYDQQLQAGDNPYLRYNHADAEFQERLQEDTSFGGNLGRAVFQ 120
hu31    KGEPVNAADAAALEHDKAYDQQLKAGDNPYLKYNHADAEFQERLKEDTSFGGNLGRAVFQ 120
hu32    KGEPVNAADAAALEHDKAYDQQLKAGDNPYLKYNHADAEFQERLKEDTSFGGNLGRAVFQ 120
AAV9    KGEPVNAADAAALEHDKAYDQQLKAGDNPYLKYNHADAEFQERLKEDTSFGGNLGRAVFQ 120
SUBS    R-------E---EV-R----IS-NE--DS-------R----------QK-QD--------K-----
                R         R E             AG
                              Q
```

FIG. 6

```
         VP2-138→  ┌─HVR1─┐
AAV1    AKKRVLEPLGLVEEGAKTAPGKKRPVEQSPQ-EPDSSSGIGKTGQQPAKKRLNFGQTGDS 179
AAV2    AKKRVLEPLGLVEEPVKTAPGKKRPVEHSPV-EPDSSSGTGKAGQQPARKRLNFGQTGDA 179
AAV3-3  AKKRILEPLGLVEEAAKTAPGKKGAVDQSPQ-EPDSSSGVGKSGKQPARKRLNFGQTGDS 179
AAV4-4  AKKRVLEPLGLVEQAGETAPGKKRPLIESPQ-QPDSSTGIGKKGKQPAKKKLVFEDETGA 178
AV5     AKKRVLEPFGLVEEGAKTAPTGKRIDDHFP-------------KRKKARTEEDSKPSTSSDA 168
AAV6    AKKRVLEPFGLVEEGAKTAPGKKRPVEQSPQ-EPDSSSGIGKTGQQPAKKRLNFGQTGDS 179
AAV7    AKKRVLEPLGLVEEGAKTAPAKKRPVEPSPQRSPDSSTGIGKKGQQPARKRLNFGQTGDS 180
AAV8    AKKRVLEPLGLVEEGAKTAPGKKRPVEPSPQRSPDSSTGIGKKGQQPARKRLNFGQTGDS 180
hu31    AKKRLLEPLGLVEEAAKTAPGKKRPVEQSPQ-EPDSSAGIGKSGSQPAKKKLNFGQTGDT 179
hu32    AKKRLLEPLGLVEEAAKTAPGKKRPVEQSPQ-EPDSSAGIGKSGSQPAKKKLNFGQTGDT 179
AAV9    AKKRLLEPLGLVEEAAKTAPGKKRPVEQSPQ-EPDSSAGIGKSGAQPAKKRLNFGQTGDT 179
SUBS    ----V----F----QGGE----TG-GIDDHF-V-S-------S-T---KKQARTREKSVPEDETGA
             I       PV   A   ALIP    Q    T V   T K    E D K STSS S
                          E                       A S
                                                  R A
```

FIG. 6 continued

```
                    VP3203→
AAV1    ESVPD-PQPLGEPPATPAAVGPTTMASGGGAPMADNNEGADGVGNASGNWHCDSTWLGDR 238
AAV2    DSVPD-PQPLGQPPAAPSGLGTNTMATGSGAPMADNNEGADGVGNSSGNWHCDSTWMGDR 238
AAV3-3  ESVPD-PQPLGEPPAAPTSLGSNTMASGGGAPMADNNEGADGVGNSSGNWHCDSQWLGDR 238
AAV4-4  GDGP-----PEGSTSGAMS---DDSEMRAAACGAAVEGGQGADGVGNASGDWHCDSTWSEGH 232
AV5     EAGPSGSQQLQIPAQPASSLGADTMSAGGGGPLGDNNQGADGVGNASGDWHCDSTWMGDR 228
AAV6    ESVPD-PQPLGEPPATPAAVGPTTMASGGGAPMADNNEGADGVGNASGNWHCDSTWLGDR 238
AAV7    ESVPD-PQPLGEPPAAPSSVGSGTVAAGGGAPMADNNEGADGVGNASGNWHCDSTWLGDR 239
AAV8    ESVPD-PQPLGEPPAAPSGVGPNTMAAGGGAPMADNNEGADGVGSSSGNWHCDSTWLGDR 239
hu31    ESVPD-PQPIGEPPAAPSGVGSLTMASGGGAPVADNNEGADGVGSSSGNWHCDSQWLGDR 238
hu32    ESVPD-PQPIGEPPAAPSGVGSLTMASGGGAPVADNNEGADGVGSSSGNWHCDSQWLGDR 238
AAV9    ESVPD-PQPIGEPPAAPSGVGSLTMASGGGAPVADNNEGADGVGSSSGNWHCDSQWLGDR 238
SUBS    GDG-S-S-QLQQTSGTMASLDPNEVRAAA-GAMGEGGQ--------NA--D------T-MEGH
        DA      E S AQPATA  AG  ST S   LV                   S
                 I     —  DT         A
                          TD
                          S

HVR3
AAV1    VITTSTRTWALPTYNNHLYKQIS-SASTGASNDNHYFGYSTPWGYFDFNRFHCHFSPRDW 297
AAV2    VITTSTRTWALPTYNNHLYKQIS--SQSGASNDNHYFGYSTPWGYFDFNRFHCHFSPRDW 296
AAV3-3  VITTSTRTWALPTYNNHLYKQIS--SQSGASNDNHYFGYSTPWGYFDFNRFHCHFSPRDW 296
AAV4-4  VTTTSTRTWVLPTYNNHLYKRLG-----ESLQSNTYNGFSTPWGYFDFNRFHCHFSPRDW 287
AV5     VVTKSTRTWVLPSYNNHQYREIKS-GSVDGSNANAYFGYSTPWGYFDFNRFHSHWSPRDW 287
AAV6    VITTSTRTWALPTYNNHLYKQISSAST-GASNDNHYFGYSTPWGYFDFNRFHCHFSPRDW 297
AAV7    VITTSTRTWALPTYNNHLYKQISS-ETAGSTNDNTYFGYSTPWGYFDFNRFHCHFSPRDW 298
AAV8    VITTSTRTWALPTYNNHLYKQISNGTSGGATNDNTYFGYSTPWGYFDFNRFHCHFSPRDW 299
hu31    VITTSTRTWALPTYNNHLYKQISNSTSGGSSNDNAYFGYSTPWGYFDFNRFHCHFSPRDW 298
hu32    VITTSTRTWALPTYNNHLYKQISNSTSGGSSNDNAYFGYSTPWGYFDFNRFHCHFSPRDW 298
AAV9    VITTSTRTWALPTYNNHLYKQISNSTSGGSSNDNAYFGYSTPWGYFDFNRFHCHFSPRDW 298
SUBS    -T-K------V--S-----Q-RRLGSGSQSDATQA-T-----------S-W-----
         V              E K AATTEGL S H
                         G V
                         E A
```

FIG. 6 continued

```
AAV1     QRLINNNWGFRPKRLNFKLFNIQVKEVTTNDGVTTIANNLTSTVQVFSDSEYQLPYVLGS 357
AAV2     QRLINNNWGFRPKRLNFKLFNIQVKEVTQNDGTTTIANNLTSTVQVFTDSEYQLPYVLGS 356
AAV3-3   QRLINNNWGFRPKKLSFKLFNIQVRGVTQNDGTTTIANNLTSTVQVFTDSEYQLPYVLGS 356
AAV4-4   QRLINNNWGMRPKAMRVKIFNIQVKEVTTSNCETTVANNLTSTVQIFADSSYELPYVMDA 347
AV5      QRLINNYWGFRPRSLRVKIFNIQVKEVTVQDSTTTIANNLTSTVQVFTDDDYQLPYVVGN 347
AAV6     QRLINNNWGFRPKRLNFKLFNIQVKEVTTNDGVTTIANNLTSTVQVFSDSEYQLPYVLGS 357
AAV7     QRLINNNWGFRPKKLRFKLFNIQVKEVTTNDGVTTIANNLTSTIQVFSDSEYQLPYVLGS 358
AAV8     QRLINNNWGFRPKRLSFKLFNIQVKEVTQNEGTKTIANNLTSTIQVFTDSEYQLPYVLGS 359
hu31     QRLINNNWGFRPKRLNFKLFNIQVKEVTDNNGVKTIANNLTSTVQVFTDSDYQLPYVLGS 358
hu32     QRLINNNWGFRPKRLNFKLFNIQVKEVTDNNGVKTIANNLTSTVQVFTDSDYQLPYVLGS 358
AAV9     QRLINNNWGFRPKRLNFKLFNIQVKEVTDNNGVKTIANNLTSTVQVFTDSDYQLPYVLGS 358
SUBS     ————M—RAMRV-I————————VQDSTT————I-I-S-DE-E————MDA
              K S           QSE E         A  S
              S
```

FIG. 6 continued

```
                                          HVR4
AAV1     AHQGCLPPFPADVFMIPQYGYLTLNNG----SQAVGRSSFYCLEYFPSQMLRTGNNFTFSY 414
AAV2     AHQGCLPPFPADVFMVPQYGYLTLNNC----SQAVGRSSFYCLEYFPSQMLRTGNNFTFSY 413
AAV3-3   AHQGCLPPFPADVFMVPQYGYLTLNNG----SQAVGRSSFYCLEYFPSQMLRTGNNFQFSY 413
AAV4-4   GQEGSLPPFPNDVFMVPQYGYCGLVTGNTSQQQTDRNAFYCLEYFPSQMLRTGNNFEITY 407
AV5      GTEGCLPAFPPQVFTLPQYGYATLNRD-NTENPTERSSFFCLEYFPSKMLRTGNNFEFTY 406
AAV6     AHQGCLPPFPADVFMIPQYGYLTLNNG----SQAVGRSSFYCLEYFPSQMLRTGNNFTFSY 414
AAV7     AHQGCLPPFPADVFMIPQYGYLTLNNG----SQSVGRSSFYCLEYFPSQMLRTGNNFEFSY 415
AAV8     AHQGCLPPFPADVFMIPQYGYLTLNNG----SQAVGRSSFYCLEYFPSQMLRTGNNFQFTY 416
hu31     AHEGCLPPFPADVFMIPQYGYLTLNDG----GQAVGRSSFYCLEYFPSQMLRTGNNFQFSY 415
hu32     AHEGCLPPFPADVFMIPQYGYLTLNDG----SQAVGRSSFYCLEYFPSQMLRTGNNFQFSY 415
AAV9     AHEGCLPPFPADVFMIPQYGYLTLNDG----SQAVGRSSFYCLEYFPSQMLRTGNNFQFSY 415
SUBS     GQQ-S--A--PQ--TL----CG-VND--GNPTD-NA-F----------EIT-
           T       N   V    A    Q Q E                    T
                                R    E S

,----------HVR5----------,
AAV1     TFEEVPFHSSYAHSQSLDRLMNPLIDQYLYYLNRTQ-NQSGSAQNKDLLFSRGSPAGMSV 473
AAV2     TFEDVPFHSSYAHSQSLDRLMNPLIDQYLYYLSRTN-TPSGTTTQSRLQFSQAGASDIRD 472
AAV3-3   TFEDVPFHSSYAHSQSLDRLMNPLIDQYLYYLNRTQGTTSGTTNQSRLLFSQAGPQSMSL 473
AAV4-4   SFEKVPFHSMYAHSQSLDRLMNPLIDQYLWGLQSTTTGTTLNAGTATTNFTKLRPTNFSN 467
AV5      NFEEVPFHSSFAPSQNLFKLANPLVDQYLYRFVSTN---------NTGGVQFNKNLAGRYAN 459
AAV6     TFEDVPFHSSYAHSQSLDRLMNPLIDQYLYYLNRTQ-NQSGSAQNKDLLFSRGSPAGMSV 473
AAV7     SFEDVPFHSSYAHSQSLDRLMNPLIDQYLYYLARTQSNPGGTAGNRELQFYQGGPSTMAE 475
AAV8     TFEDVPFHSSYAHSQSLDRLMNPLIDQYLYYLSRTQT-TGGTANTQTLGFSQGGPNTMAN 475
hu31     EFENVPFHSSYAHSQSLDRLMNPLIDQYLYYLSKTINGSG--QNQQTLKFSVAGPSNMAV 473
hu32     EFENVPFHSSYAHSQSLDRLMNPLIDQYLYYLSKTINGSG--QNQQTLKFSVAGPSNMAV 473
AAV9     EFENVPFHSSYAHSQSLDRLMNPLIDQYLYYLSKTINGSG--QNQQTLKFSVAGPSNMAV 473
SUBS     T--D----MF--------A---V------WGFNR-QTNTS--AGTKRTQ-TQGSAATFSN
           S  E                         QS  NSTPT  TQNSDVN NKNL QGYRD
           N  K                         V   TG Q   T AE L  YRLR TRI L
                                         A         RG G          GS  E
                                                                  ND
```

FIG. 6 continued

```
              ┌─┐     ┌─HVR6─┐              ┌─HVR7─┐            ┌──HVR8──┐
AAV1     QPKNWLPGPCYRQQRVSKTKTDN------NNSNFTWTGASKYNLNGRESIINPGTAMASHK 528
AAV2     QSRNWLPGPCYRQQRVSKTSADN------NNSEYSWTGATKYHLNGRDSLVNPGPAMASHK 527
AAV3-3   QARNWLPGPCYRQQRLSKTANDN------NNSNFPWTAASKYHLNGRDSLVNPGPAMASHK 528
AAV4-4   FKKNWLPGPSIKQQGFSKTANQNYKIPATGSDSLIKYETHSTLDGRWSALTPGPPMATAG 527
AV5      TYKNWFPCPMGRTQGWNLGSGVN------RASVSAFATTNRMELEGASYQVPPQPNGMTNN 514
AAV6     QPKNWLPGPCYRQQRVSKTKTDN------NNSNFTWTGASKYNLNGRESIINPGTAMASHK 528
AAV7     QAKNWLPGPCFRQQRVSKTLDQN------NNSNFAWTGATKYHLNGRNSLVNPGVAMATHK 530
AAV8     QAKNWLPGPCYRQQRVSTTTGQN------NNSNFAWTAGTKYHLNGRNSLANPGIAMATHK 530
hu31     QGRNYIPGPSYRQQRVSTTVTQN------NNSEFAWPGASSWALNGRNSLMNPGPAMASHK 528
hu32     QGRNYIPGPSYRQQRVSTTVTQN------NNSEFAWPGASSWALNGRNSLMNPGPAMASHK 528
AAV9     QGRNYIPGPSYRQQRVSTTVTQN------NNSEFAWPGASSWALNGRNSLMNPGPAMASHK 528
SUBS     FAK-WL----CIKT-GWNLGSGV------TG-DSLIKYETHST-D-ASYQVP-QTPGMTAG
         TP   F    MG   F K AND       RA NYTFATTNRME E  D ALT  VN  NN
         K         F    L KA          V P TAG KYN    W II   I
         Y                 LD           S       H    E  A
         S                 T
```

FIG. 6 continued

```
                    ┌─────────────HVR9─────────────┐                          ┌──┐
AAV1    DDEDKFFPMSGVMIFGKESA---GASNTALD-NVMITDEEEIKATNPVATERFGTVAVNFQ 585
AAV2    DDEEKFFPQSGVLIFGKQGS---EKTNVDIE-KVMITDEEEIRTTNPVATEQYGSVSTNLQ 584
AAV3-3  DDEEKFFPMHGNLIFGKEGT---TASNAELD-NVMITDEEEIRTTNPVATEQYGTVANNLQ 585
AAV4-4  PADSKFS-NSQLIFAGPKQN---GNTATVPC-TLIFTSEEELAATNATDTDMWCNLPGGDQ 583
AV5     LQGSNTYALENTMIFNSQPANPGTTATYLEGNMLITSESETQPVNRVAYNVGGQMATNNQ  574
AAV6    DDKDKFFPMSGVMIFGKESA---GASNTALD-NVMITDEEEIKATNPVATERFGTVAVNLQ 585
AAV7    DDEDRFFPSSGVLIFGKTGA---TN-KTTLE-NVLMTNEEEIRPTNPVATEEYGIVSSNLQ 586
AAV8    DDEERFFPSNGILIFGKQNA---ARDNADYS-DVMLTSEEEIKTTNPVATEEYGIVADNLQ 587
hu31    EGEDRFFPLSGSLIFGKQGT---GRDNVDAD-KVMITNEEEIKTTNPVATESYGQVATNHQ 585
hu32    EGEDRFFPLSGSLIFGKQGT---GRDNVDAD-KVMITNEEEIKTTNPVATESYGQVATNHQ 585
AAV9    EGEDRFFPLSGSLIFGKQGT---GRDNVDAD-KVMITNEEEIKTTNPVATESYGQVATNHQ 585
SUBS    LQGSNTYAMENTMFANPKQN---TNTATVPG-TLIF-S-S-TQPV-ATDYDMW-NLPGGD-
        PADEK S QHQLI   SESA    EASKAALE-NMLM D    RA  R   NVF TMSN L
        DDK    NN V    TPS     AK  KTY       L     A       QG  I  V N
               S I     N           EI                      E   S  S F
               N                    Y                      R      D

┌─HVR10──┐
AAV1    SSSTDPATGDVHAMGALPGMVWQDRDVYLQGPIWAKIPHTDGHFHPSPLMGGFGLKNPPP 645
AAV2    RGNRQAATADVNTQGVLPGMVWQDRDVYLQGPIWAKIPHTDGHFHPSPLMGGFGLKHPPP 644
AAV3-3  SSNTAPTTGTVNHQGALPGMVWQDRDVYLQGPIWAKIPHTDGHFHPSPLMGGFGLKHPPP 645
AAV4-4  SNSNLPTVDRLTALGAVPGMVWQNRDIYYQGPIWAKIPHTDGHFHPSPLIGGFGLKHPPP 643
AV5     SSTTAPATGTYNLQEIVPGSVWMERDVYLQGPIWAKIPETGAHFHPSPAMGGFGLKHPPP 634
AAV6    SSSTDPATGDVHVMGALPGMVWQDRDVYLQGPIWAKIPHTDGHFHPSPLMGGFGLKHPPP 645
AAV7    AANTAAQTQVVNNQGALPGMVWQNRDVYLQGPIWAKIPHTDGNFHPSPLMGGFGLKHPPP 646
AAV8    QQNTAPQIGTVNSQGALPGMVWQNRDVYLQGPIWAKIPHTDGNFHPSPLMGGFGLKHPPP 647
hu31    SAQAQAQTGWVQNQGILPGMVWQDRDVYLQGPIWAKIPHTDGNFHPSPLMGGFGMKHPPP 645
hu32    SAQAQAQTGWVQNQGILPGMVWQDRDVYLQGPIWAKIPHTDGNFHPSPLMGGFGMKHPPP 645
AAV9    SAQAQAQTGWVQNQGILPGMVWQDRDVYLQGPIWAKIPHTDGNFHPSPLMGGFGMKHPPP 645
SUBS    RNSNLPTVDRLTALEAV---S--ME--I----------E-GAH-------AI----L-N--
        ASNTA AIADYHTM V      N
        QGTRD QT NH
        Q     V  L
                 V
                 S
```

FIG. 6 continued

```
                    ┌──HVR11──┐
AAV1    QILIKNTPVPANPPAEFSATKFASFITQYSTGQVSVEIEWELQKENSKRWNPEVQYTSNY 705
AAV2    QILIKNTPVPANPSTTFSAAKFASFITQYSTGQVSVEIEWELQKENSKRWNPEIQYTSNY 704
AAV3-3  QIMIKNTPVPANPPTTFSPAKFASFITQYSTGQVSVEIEWELQKENSKRWNPEIQYTSNY 705
AAV4-4  QIFIKNTPVPANPATTFSSTPVNSFITQYSTGQVSVQIDWEIQKERSKRWNPEVQFTSNY 703
AV5     MMLIKNTPVPGNI-TSFSDVPVSSFITQYSTGQVTVEMEWELKKENSKRWNPEIQYTNNY 693
AAV6    QILIKNTPVPANPPAEFSATKFASFITQYSTGQVSVEIEWELQKENSKRWNPEVQYTSNY 705
AAV7    QILIKNTPVPANPPEVFTPAKFASFITQYSTGQVSVEIEWELQKENSKRWNPEIQYTSNF 706
AAV8    QILIKNTPVPADPPTTFNQSKLNSFITQYSTGQVSVEIEWELQKENSKRWNPEIQYTSNY 707
hu31    QILIKNTPVPADPPTAFNKDKLNSFITQYSTGQVSVEIEWELQKENSKRWNPEIQYTSNY 705
hu32    QILIKNTPVPADPPTAFNKDKLNSFITQYSTGQVSVEIEWELQKENSKRWNPEIQYTSNY 705
AAV9    QILIKNTPVPADPPTAFNKDKLNSFITQYSTGQVSVEIEWELQKENSKRWNPEIQYTSNY 705
SUBS    MMM-----G-IAAE-SDVPVS----------QMD---IK--R-------V---------
          F        SET TAA FA
                   S   PT
                   V   QS
                       S
```

FIG. 6 continued

```
          ┌─────HVR12─────┐
AAV1    AKSANVDFTVDNNGLYTEPRPIGTRYLTRPL 736 (SEQ ID NO. 16)
AAV2    NKSVNVDFTVDTNGVYSEPRPIGTRYLTRNL 735 (SEQ ID NO. 17)
AAV3-3  NKSVNVDFTVDTNGVYSEPRPIGTRYLTRNL 736 (SEQ ID NO. 18)
AAV4-4  GQQNSLLWAPDAAGKYTEPRAIGTRYLTHHL 734 (SEQ ID NO. 19)
AV5     NDPQFVDFAPDSTGEYRTTRPIGTRYLTRPL 724 (SEQ ID NO. 20)
AAV6    AKSANVDFTVDNNGLYTEPRPIGTRYLTRPL 736 (SEQ ID NO. 21)
AAV7    EKQTGVDFAVDSQGVYSEPRPIGTRYLTRNL 737 (SEQ ID NO. 22)
AAV8    YKSTSVDFAVNTEGVYSEPRPIGTRYLTRNL 738 (SEQ ID NO. 23)
hu31    YKSNNVEFAVSTEGVYSEPRPIGTRYLTRNL 736 (SEQ ID NO. 24)
hu32    YKSNNVEFAVNTEGVYSEPRPIGTRYLTRNL 736 (SEQ ID NO. 25)
AAV9    YKSNNVEFAVNTEGVYSEPRPIGTRYLTRNL 736 (SEQ ID NO. 26)
SUBS    GQQVSLLWTPDAA-K-RTT-A------HP-     (SEQ ID NO:48)
        NDPQF D  SSN E T         H          (SEQ ID NO:49)
        A  TG    NQ  L                      (SEQ ID NO:50)
        E  A     T                          (SEQ ID NO:51)
                                            (SEQ ID NO:52)
                                            (SEQ ID NO:53)
```

FIG. 6 continued

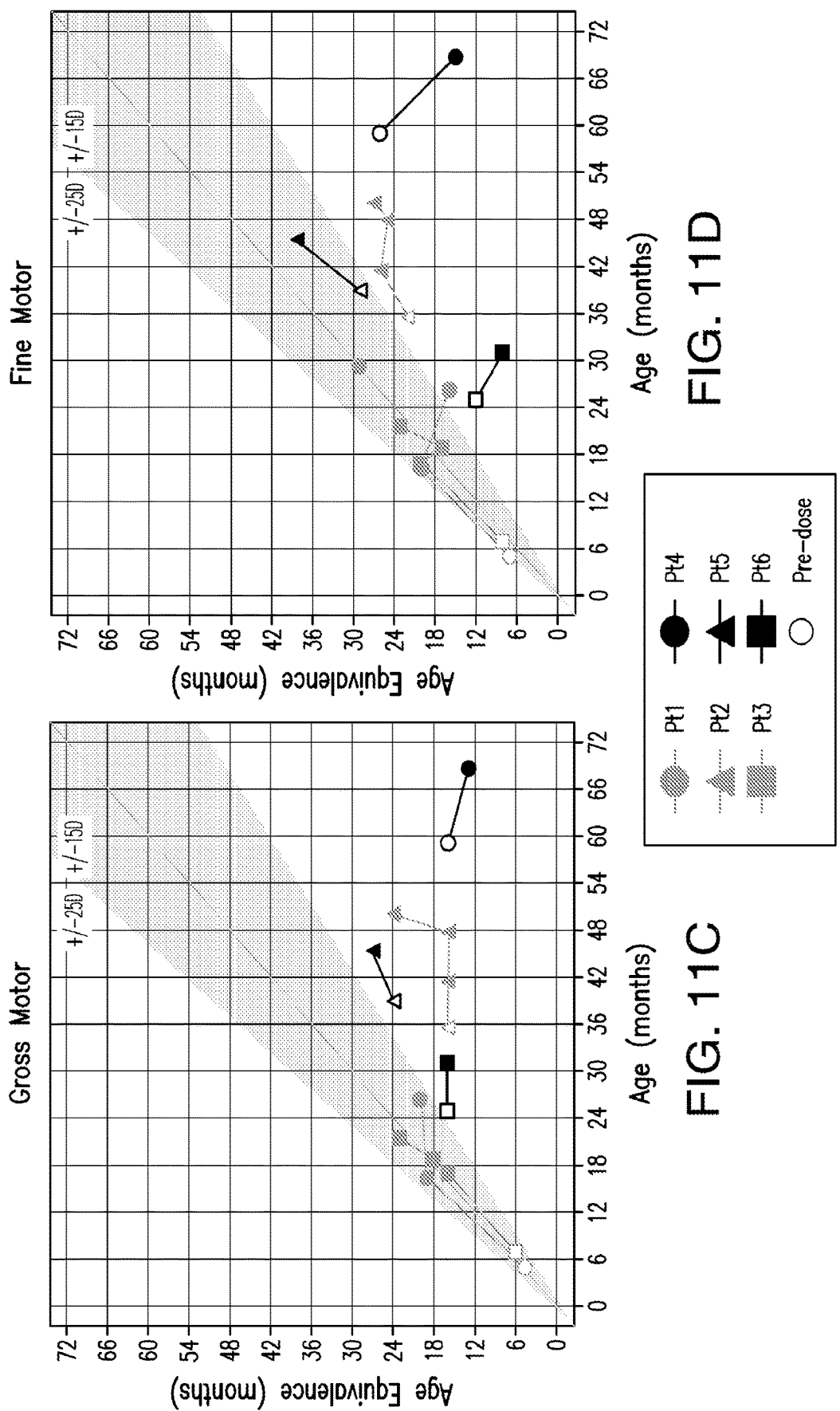

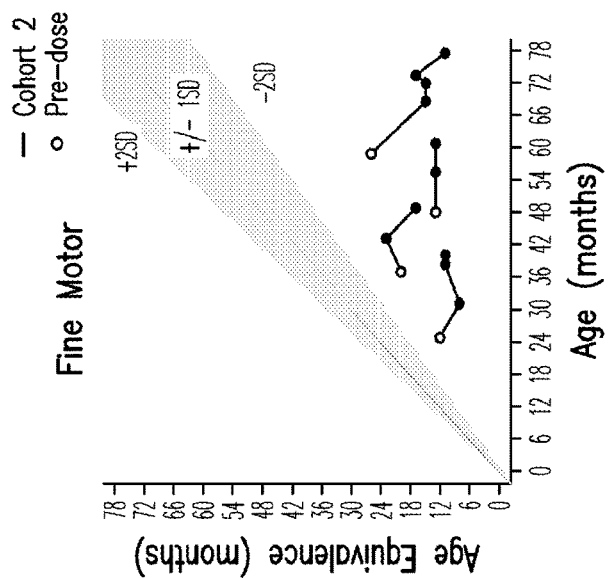
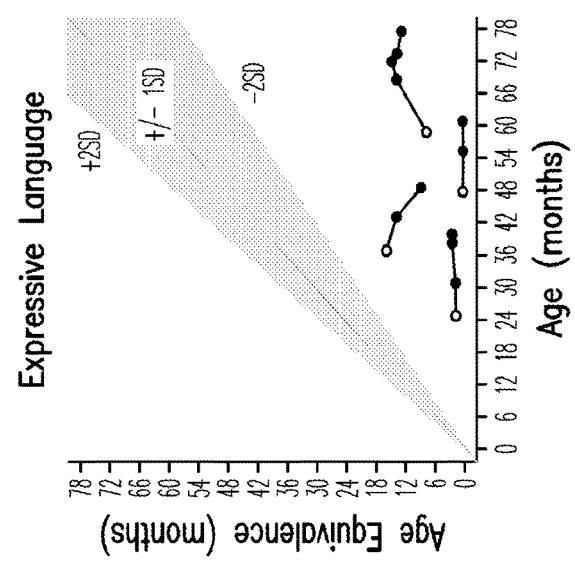
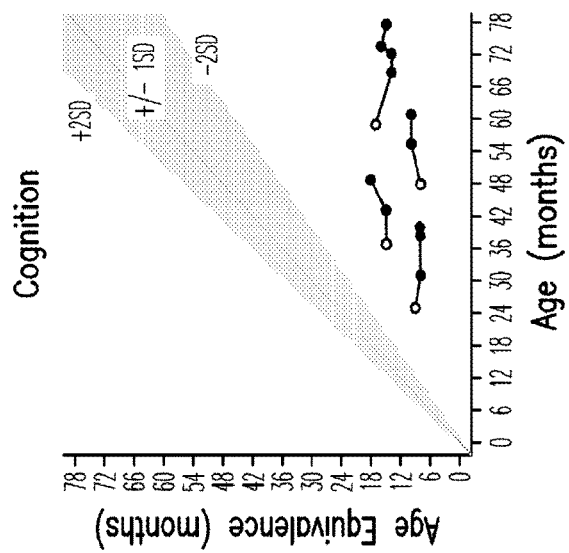
FIG. 27A    FIG. 27B    FIG. 27B

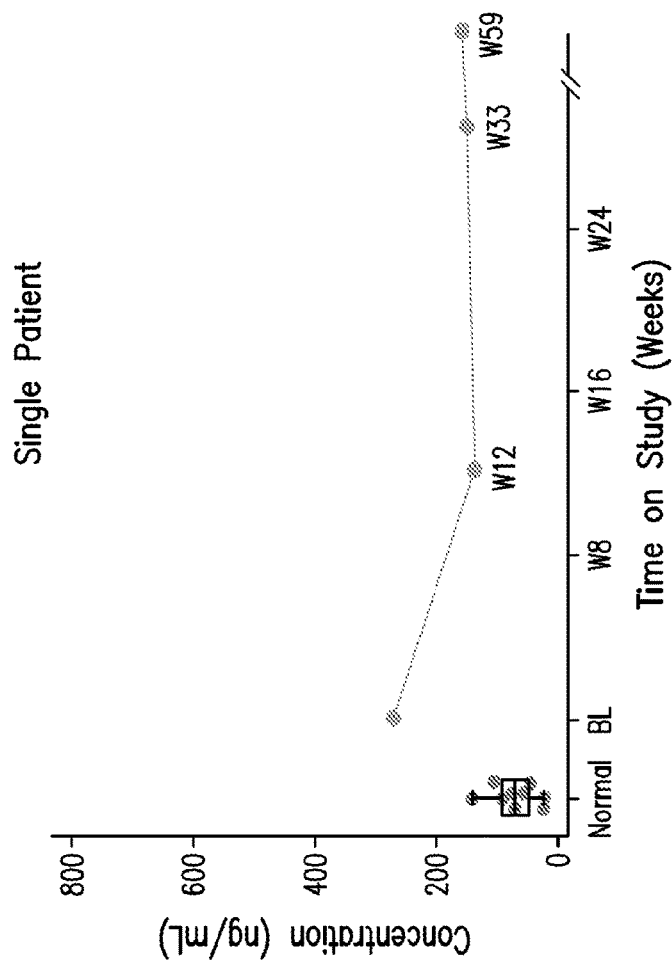
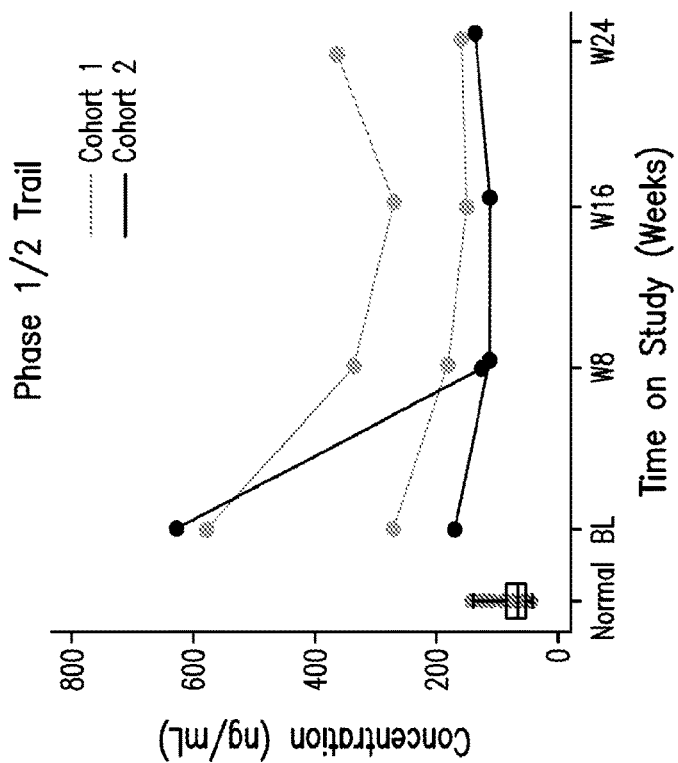
FIG. 31B
FIG. 31A

| VABS-III Age Equivalent Scores (year:month) | | |
| --- | --- | --- |
| | Baseline Chronological Age 13y | Week 52 Chronological Age 14y |
| Personal (dressing, feeding, toileting, and washing/hygiene) | 4:1 | 7:10 |
| Domestic | 7:7 | 6:7 |
| Community | 7:4 | 6:10 |
| Interpersonal Relationships | 5:10 | 7:4 |
| Play and Leisure | 8:1 | 8:1 |
| Coping Skill | 3:4 | 9:10 |
| Adaptive Behavior | 6:3 | 7:10 |
| Fine Motor | 5:7 | 6:4 |
| Gross Motor | 4:0 | 4:6 |

| WASI-II Full Scale Composite | | |
| --- | --- | --- |
| | Baseline Chronological Age 13y | Week 52 Chronological Age 14y |
| Mean 100 (SD 15) | 43 | 47 |

FIG. 34

TREATMENT OF MUCOPOLYSACCHARIDOSIS II WITH RECOMBINANT HUMAN IDURONATE-2-SULFATASE (IDS)

CROSS-REFERENCE TO RELATED APPLICATIONS

This application is a continuation of International Patent Application No. PCT/US2022/014526, filed Jan. 31, 2022, which claims the benefit of U.S. Provisional Application No. 63/148,093, filed Feb. 10, 2021, U.S. Provisional Application No. 63/180,361, filed Apr. 27, 2021, U.S. Provisional Application No. 63/210,610, filed Jun. 15, 2021, U.S. Provisional Application No. 63/242,250, filed Sep. 9, 2021, and U.S. Provisional Application No. 63/256,805, filed Oct. 18, 2021, the content of each of which is incorporated herein by reference in its entirety.

REFERENCE TO SEQUENCE LISTING SUBMITTED ELECTRONICALLY

This application contains a computer readable Substitute Sequence Listing which has been submitted in XML file format via Patent Center, the entire content of which is incorporated by reference herein in its entirety. The Substitute Sequence Listing XML file submitted via Patent Center is entitled "12656-196-999_SUB_SEQ_LISTING.xml", was created onFeb. 22, 2024 and is 92,767 bytes in size

1. INTRODUCTION

Compositions and methods are described for the delivery of recombinant human iduronate-2-sulfatase (IDS) produced by human neuronal or glial cells to the cerebrospinal fluid (CSF) of the central nervous system (CNS) of a human subject diagnosed with mucopolysaccharidosis II (MPS II).

2. BACKGROUND OF THE INVENTION

Hunter syndrome/MPS II is a rare X-linked recessive genetic disease occurring in 0.5 to 1.3 per 100,000 male live births. This progressive and devastating disease is caused by genetic mutation in the IDS gene leading to deficiency of the lysosomal storage enzyme iduronate-2-sulfatase, an enzyme required for the lysosomal catabolism of heparan sulfate and dermatan sulfate. With no or very little I2S, the protein is unable to perform its usual lysosomal exohydrolase function which leads to the accumulation of ubiquitous polysaccharides, called GAGs (glycosaminoglycans), in tissues and organs of MPS II patients resulting in the characteristic storage lesions and diverse disease sequelae. Morbidity and mortality are high in this patient population; death has been reported to occur at a mean age of 11.7 years in patients with the severe phenotype (characterized by neurocognitive deterioration) and 21.7 years in patients with a mild or attenuated phenotype. (Young et al., 1982, A clinical and genetic study of Hunter's syndrome. 2 Differences between the mild and severe forms. J. Medical Genetics 19:408-411). The majority (two-thirds) of patients are reported to have the severe form of this disease. (Wraith J E, et al., 2007, Enzyme replacement therapy in patients who have mucopolysaccharidosis I and are younger than 5 years: Results of a multinational study of recombinant human alpha-L-Iduronidase (Laronidase). Pediatrics 120(1):E37-E46). While the disease primarily affects boys, affected females have been reported as a result of non-random x-inactivation and/or mutation in both alleles of the gene. (Martin et al., 2008, Recognition and diagnosis of mucopolysaccharidosis II (Hunter Syndrome). Pediatrics 121:e377).

Patients with MPS II appear normal at birth, but signs and symptoms of disease typically present between the ages of 18 months and 4 years in the severe form and between the ages of 4 and 8 years in the attenuated form. Signs and symptoms common to all affected patients include short stature, coarse facial features, macrocephaly, macroglossia, hearing loss, hepato- and splenomegaly, dystosis multiplex, joint contractures, spinal stenosis and carpal tunnel syndrome. Frequent upper respiratory and ear infections occur in most patients and progressive airway obstruction is commonly found, leading to sleep apnea and often death. Cardiac disease is a major cause of death in this population and is characterized by valvular dysfunction leading to right and left ventricular hypertrophy and heart failure. Death is generally attributed to obstructive airway disease or cardiac failure.

In severe forms of the disease, early developmental milestones may be met, but developmental delay is readily apparent by 18-24 months. Some patients fail hearing screening tests in the first year and other milestones are delayed, including ability to sit unsupported, ability to walk, and speech. Developmental progression begins to plateau between 3 and 5 years of age, with regression reported to begin around 6.5 years. Of the ~50% of children with MPS II who become toilet trained, most, if not all, will lose this ability as the disease progresses. (Wraith et al., 2007, supra; Martin et al., 2008, supra).

Patients with significant neurologic involvement exhibit severe behavioral disturbances including hyperactivity, obstinacy, and aggression beginning in the second year of life and continuing until age 8-9, when neurodegeneration attenuates this behavior. (Muenzer, et al., 2009, Mucopolysaccharidosis I: Management and Treatment Guidelines, Pediatric 123(1): 19-29).

Seizures are reported in over half of severely affected patients who reach the age of 10, and by the time of death most patients with CNS involvement are severely mentally handicapped and require constant care. (Wraith et al., 2007, supra; Martin et al., 2008, supra). Although patients with attenuated disease exhibit normal intellectual functioning, MRI imaging reveals gross brain abnormalities in all patients with MPS II including white matter lesions, enlarged ventricles, and brain atrophy. (Muenzer, et al., 2009, supra).

Enzyme replacement therapy (ERT) with recombinant idursulfase produced by HT1080 (fibrosarcoma) cells (Elaprase®, Shire Human Genetic Therapies) is the only approved product for the treatment of Hunter syndrome and is administered as a weekly infusion. (ELAPRASE (idursulfase) injection [package insert]. Lexington, MA: Shire Human Genetic Therapies, Inc; 2013, available at http://pi.shirecontent.com/PI/PDFs/Elaprase_USA_ENG.pdf). While weekly treatment with intravenous (IV) ERT (recombinant idursulfase) has demonstrated improvement in the systemic manifestations of MPS II, patients and their caregivers have the added burden of living with these weekly ERT infusions through life thereby impacting patient quality of life.

ERT as currently administered does not cross the blood brain barrier and is therefore unable to address the unmet need in patients with severe disease, i.e., MPS II with CNS/neurocognitive and behavioral involvement. In a recent clinical trial designed to address this problem, idursulfase (Elaprase) formulated for intrathecal administration was administered once monthly to pediatric patients using an intrathecal drug delivery device implanted into the spine (insertion of the catheter at the level of L4/L5 with implantation of the access port via an incision on the lower ribs). The patients also received concurrent i.v. idursulfase once weekly. See Muenzer et al., 2016, Genetics in Med 18: 73-81, esp. p. 74; abstract available at https://www.ncbi.nlm.nih.gov/pubmed/25834948?dopt=Abstract). Device malfunction led to partial revision, total surgical revision, or removal in 6 of the 12 (50%) of the treated patients. Notably, 12 of 14 SAEs (serious adverse events) were device-related (complication of device insertion, device dislocation/connection issue, device breakage/malfunction/failure, implant site infection, procedural pain, and wound dehiscence). (Muenzer et al., 2016, p. 75, col. 2 and FIG. 1). Device breakage and catheter migration from the spinal canal was exacerbated by the high activity level of this pediatric population. (Muenzer et al., 2016 at p. 78 Discussion).

3. SUMMARY OF THE INVENTION

The invention involves the delivery of recombinant human iduronate-2-sulfatase (rhIDS) produced by human cells including but not limited to neuronal or glial cells to the cerebrospinal fluid (CSF) of the central nervous system (CNS), and cells of the liver for systemic distribution in a human subject diagnosed with mucopolysaccharidosis II (MPS II), including, but not limited to patients diagnosed with Hunter syndrome.

In a preferred embodiment, the treatment is accomplished via gene therapy—e.g., by administering a viral vector or other DNA expression construct encoding human IDS (hIDS), or a derivative of hIDS, to the CSF of a patient (human subject) diagnosed with MPS II, so that a permanent depot of (a) transduced neuronal and/or glial cells is generated that continuously supplies the transgene product to the CNS, and (b) transduced liver cells that supply the transgene product systemically. The rhIDS secreted from the neuronal/glial cell depot into the CSF, and from the liver depot systemically will be endocytosed by other CNS and liver cells, respectively, resulting in "cross-correction" of the enzymatic defect in the recipient cells. Moreover, it has been found, unexpectedly, that the administration of the viral vector to the CSF results in systemic delivery of the vector, and that the depot of transduced neural and glial cells in the CNS can deliver the recombinant enzyme to both the CNS and systemically, which may reduce or eliminate the need for systemic treatment, e.g., weekly i.v. injections of the enzyme.

In an alternative embodiment, the hIDS can be produced by human neuronal or glial cells in cell culture (e.g., bioreactors) and administered as an enzyme replacement therapy ("ERT"), e.g., by injecting the enzyme—into the CSF, directly into the CNS, and/or systemically. However, the gene therapy approach offers several advantages over ERT since systemic delivery of the enzyme will not result in treating the CNS because the enzyme cannot cross the blood brain barrier; and, unlike the gene therapy approach of the invention, direct delivery of the enzyme to the CSF and/or CNS would require repeat injections which are not only burdensome, but pose a risk of infection.

The hIDS encoded by the transgene can include, but is not limited to human IDS (hIDS) having the amino acid sequence of SEQ ID NO. 1 (as shown in FIG. 1), and derivatives of hIDS having amino acid substitutions, deletions, or additions, e.g., including but not limited to amino acid substitutions selected from corresponding non-conserved residues in orthologs of IDS shown in FIG. 2, with the proviso that such mutations do not include replacement of the cysteine residue at position 84 (C84) which is required for enzyme activity (Millat et al., 1997, Biochem J 326: 243-247); or a mutation that has been identified in severe, severe-intermediate, intermediate, or attenuated MPS II phenotypes e.g., as shown in FIG. 3, or as reported by Sukegawa-Hayasaka et al., 2006, J Inherit Metab Dis 29: 755-761 (reporting "attenuated" mutants R48P, A85T, W337R, and the truncated mutant Q531X; and "severe" mutants P86L, S333L, S349I, R468Q, R468L); Millat et al., 1998, BBA 1406: 214-218 (reporting "attenuated" mutants P480L and P480Q; and "severe" mutant P86L); and Bonucelli et al., 2001, BBA 1537:233-238, each of which is incorporated by reference herein in its entirety.

For example, amino acid substitutions at a particular position of hIDS can be selected from among corresponding non-conserved amino acid residues found at that position in the IDS orthologs aligned in FIG. 2, with the proviso that such substitutions do not include any of the deleterious mutations shown in FIG. 3 or as reported by Sukegawa-Hayasaka et al., 2006, supra; Millat et al., 1998, supra; or Bonucelli et al., 2001, supra, each of which is incorporated by reference herein in its entirety. The resulting transgene product can be tested using conventional assays in vitro, in cell culture or test animals to ensure that the mutation does not disrupt IDS function. Preferred amino acid substitutions, deletions or additions selected should be those that maintain or increase enzyme activity, stability or half-life of IDS, as tested by conventional assays in vitro, in cell culture or animal models for MPS II. For example, the enzyme activity of the transgene product can be assessed using a conventional enzyme assay with, for example, 4-Methylumbelliferyl α-L-idopyranosiduronic acid 2-sulfate or 4-methylumbelliferyl sulfate as the substrate (see, e.g., Lee et al., 2015, Clin. Biochem. 48(18):1350-1353, Dean et al., 2006, Clin. Chem. 52(4):643-649 for exemplary IDS enzyme assays that can be used, each of which is incorporated by reference herein in its entirety). The ability of the transgene product to correct MPS II phenotype can be assessed in cell culture; e.g., by transducing MPS II cells in culture with a viral vector or other DNA expression construct encoding hIDS or a derivative; by adding the transgene product or a derivative to MPS II cells in culture; or by co-culturing MPS II cells with human neuronal/glial host cells engineered to express and secrete rhIDS or a derivative, and determining correction of the defect in the MPS II cultured cells, e.g., by detecting IDS enzyme activity and/or reduction in GAG storage in the MPS II cells in culture (see, e.g., Stroncek et al., 1999, Transfusion 39(4):343-350, which is incorporated by reference herein in its entirety). In a preferred embodiment, the reduction in GAG storage is reduction in heparan sulfate (HS) storage. In another embodiment, the reduction in GAG storage is reduction in dermatan sulfate (DS) storage. In another embodiment, the reduction in GAG storage is reduction in both HS storage and DS storage.

Animal models for MPS II have been described that can be used to assess the therapeutics described herein. For example, a knockout mouse model (IDS-knockout) of MPS II was engineered by replacing exons 4 and 5 of the IDS gene with the neomycin resistance gene. (Garcia et al., 2007, J Inherit Metab Dis 30: 924-34). This IDS-knockout mouse exhibits many of the characteristics of MPS II, including skeletal abnormalities, hepatosplenomegaly, elevated urinary and tissue GAG, and brain storage lesions (Muenzer et al., 2001, Acta Paediatr Suppl 91:98-99) and was used to assess the effect of enzyme replacement therapy in MPS II in support of clinical trials for ERT. This mouse model, therefore, is a relevant model for studying the effects of gene therapy delivering rIDS produced by neuronal or glial cells as a treatment for MPS II (see, e.g., Polito and Cosma, 2009, Am. J. Hum. Genet. 85(2):296-301, which is incorporated by reference herein in its entirety).

Preferably, the hIDS transgene produced by the human neuronal/glial cells should be controlled by expression control elements that function in neurons and/or glial cells, e.g., the CB7 promoter (a chicken β-actin promoter and CMV enhancer), and can include other expression control elements that enhance expression of the transgene driven by the vector (e.g., chicken β-actin intron and rabbit β-globin poly A signal). The cDNA construct for the hIDS transgene should include a coding sequence for a signal peptide that ensures proper co- and post-translational processing (glycosylation and protein sulfation) by the transduced CNS cells. Such signal peptides used by CNS cells may include but are not limited to:

Oligodendrocyte-myelin glycoprotein (hOMG) signal peptide:

(SEQ ID NO: 2)
MEYQILKMSLCLFILLFLTPGILC

Cellular repressor of E1A-stimulated genes 2 (hCREG2) signal peptide:

(SEQ ID NO: 3)
MSVRRGRRPARPGTRLSWLLCCSALLSPAAG

V-set and transmembrane domain containing 2B (hVSTM2B) signal peptide:

(SEQ ID NO: 4)
MEQRNRLGALGYLPPLLLHALLLFVADA

Protocadherin alpha-1 (hPCADHA1) signal peptide:

(SEQ ID NO: 5)
MVFSRRGGLGARDLLLWLLLLAAWEVGSG

FAM19A1 (TAFA1) signal peptide:

(SEQ ID NO: 6)
MAMVSAMSWVLYLWISACA

Interleukin-2 signal peptide:

(SEQ ID NO: 14)
MYRMQLLSCIALILALVTNS

Signal peptides may also be referred to herein as leader sequences or leader peptides.

The recombinant vector used for delivering the transgene should have a tropism for cells in the CNS, including but limited to neurons and/or glial cells. Such vectors can include non-replicating recombinant adeno-associated virus vectors ("rAAV"), particularly those bearing an AAV9 or AAVrh10 capsid are preferred. AAV variant capsids can be used, including but not limited to those described by Wilson in U.S. Pat. No. 7,906,111 which is incorporated by reference herein in its entirety, with AAV/hu.31 and AAV/hu.32 being particularly preferred; as well as AAV variant capsids described by Chatterjee in U.S. Pat. Nos. 8,628,966, 8,927,514 and Smith et al., 2014, Mol Ther 22: 1625-1634, each of which is incorporated by reference herein in its entirety. However, other viral vectors may be used, including but not limited to lentiviral vectors, vaccinia viral vectors, or non-viral expression vectors referred to as "naked DNA" constructs.

In one embodiment, Construct 1 can be used for delivering the transgene. Construct 1 is a recombinant adeno-associated virus serotype 9 capsid containing human iduronate-2-sulfatase expression cassette wherein expression is driven by a hybrid of the cytomegalovirus (CMV) enhancer and the chicken beta actin promoter (CB7), wherein the IDS expression cassette is flanked by inverted terminal repeats (ITRs) and the transgene includes the chicken beta actin intron and a rabbit beta-globin polyadenylation (polyA) signal. In a preferred embodiment, the ITRs are AAV2 ITRs. In one embodiment, Construct 1 comprises a nucleic acid comprising the nucleotide sequence of SEQ ID NO:45.

Pharmaceutical compositions suitable for administration to the CSF comprise a suspension of the rhIDS vector in a formulation buffer comprising a physiologically compatible aqueous buffer, a surfactant and optional excipients. In certain embodiments, the pharmaceutical compositions are suitable for intrathecal administration. In certain embodiments, the pharmaceutical compositions are suitable for intracisternal administration (injection into the cisterna magna). In certain embodiments, the pharmaceutical compositions are suitable for injection into the subarachnoid space via a C1-2 puncture. In certain embodiments, the pharmaceutical compositions are suitable for intracerebroventricular administration. In certain embodiments, the pharmaceutical compositions are suitable for administration via lumbar puncture. In some embodiments, the pharmaceutical composition comprising the rAAV of the present disclosure comprises sodium chloride at a concentration of about 8.77 g/L, magnesium chloride 6-hydrate, at a concentration of about 0.244 g/L, potassium chloride at a concentration of about 0.224 g/L, calcium chloride dihydrate at a concentration of about 0.206 g/L, dextrose anhydrous at a concentration of about 0.793 g/L, poloxamer 188 at a concentration of about 0.001% (volume/volume), sodium phosphate monobasic monohydrate at a concentration of about 0.0278 g/L, and sodium phosphate dibasic anhydrous at a concentration of about 0.114 g/L.

Therapeutically effective doses of the recombinant vector should be administered to the CSF via intrathecal administration (i.e., injection into the subarachnoid space so that the recombinant vectors distribute through the CSF and transduce cells in the CNS). In some embodiments, the recombinant vector is administered in a solution comprising sodium chloride at a concentration of about 8.77 g/L, magnesium chloride 6-hydrate, at a concentration of about 0.244 g/L, potassium chloride at a concentration of about 0.224 g/L, calcium chloride dihydrate at a concentration of about 0.206 g/L, dextrose anhydrous at a concentration of about 0.793 g/L, poloxamer 188 at a concentration of about 0.001% (volume/volume), sodium phosphate monobasic monohydrate at a concentration of about 0.0278 g/L, and sodium phosphate dibasic anhydrous at a concentration of about 0.114 g/L. This can be accomplished in a number of ways—e.g., by intracranial (cisternal or ventricular) injection, or injection into the lumbar cistern. For example, intracisternal (IC) injection (into the cisterna magna) can be performed by CT-guided suboccipital puncture; or injection into the subarachnoid space can be performed via a C1-2 puncture when feasible for the patient; or lumbar puncture (typically diagnostic procedures performed in order to collect a sample of CSF) can be used to access the CSF. Alternatively, intracerebroventricular (ICV) administration (a more invasive technique used for the introduction of antiinfective or anticancer drugs that do not penetrate the blood-brain barrier) can be used to instill the recombinant vectors directly into the ventricles of the brain. Alternatively, intranasal administration may be used to deliver the recombinant vector to the CNS.

CSF concentrations can be monitored by directly measuring the concentration of rhIDS in the CSF fluid obtained from occipital or lumbar punctures, or estimated by extrapolation from concentrations of the rhIDS detected in the patient's serum.

In certain embodiments, the recombinant nucleotide expression vector is administered at a dose that is dependent on the human subject's brain mass, and wherein the brain mass is determined by brain magnetic resonance imaging (MRI) of the human subject's brain. In certain embodiments, the recombinant nucleotide expression vector is administered at a dose of about $1.3 \times 10^{10}$ GC/g brain mass as determined by MRI. In certain embodiments, the recombinant nucleotide expression vector is administered at a dose of about $1.9 \times 10^{10}$ GC/g brain mass as determined by MRI. In certain embodiments, the recombinant nucleotide expression vector is administered at a dose of about $9.6 \times 10^{10}$ GC/g brain mass as determined by MRI. In certain embodiments, the dose of the recombinant nucleotide expression vector is $1.3 \times 10^{10}$ GC/g brain mass (e.g., the brain mass is determined by MRI and the genome count is determined by a Poly-A PCR assay). In certain embodiments, the dose of the recombinant nucleotide expression vector is $1.9 \times 10^{10}$ GC/g brain mass (e.g., the brain mass is determined by MRI and the genome count is determined by a transgene-specific PCR assay). In certain embodiments, the dose of the recombinant nucleotide expression vector is $6.5 \times 10^{10}$ GC/g brain mass (e.g., the brain mass is determined by MRI and the genome count is determined by a Poly-A PCR assay). In certain embodiments, the dose of the recombinant nucleotide expression vector is $9.6 \times 10^{10}$ GC/g brain mass (e.g., the brain mass is determined by MRI and the genome count is determined by a transgene-specific PCR assay). In certain embodiments, the dose of the recombinant nucleotide expression vector is $2.0 \times 10^{11}$ GC/g brain mass (e.g., the brain mass is determined by MRI and the genome count is determined by a Poly-A PCR assay). In certain embodiments, the dose of the recombinant nucleotide expression vector is $2.9 \times 10^{11}$ GC/g brain mass (e.g., the brain mass is determined by MRI and the genome count is determined by a transgene-specific PCR assay). In certain embodiments, the recombinant nucleotide expression vector is administered at a dose of about $6.5 \times 10^{10}$ GC/g brain mass as determined by MRI. In certain embodiments, the recombinant nucleotide expression vector is administered at a dose of about $2.0 \times 10^{11}$ GC/g brain mass as determined by MRI. In certain embodiments, the recombinant nucleotide expression vector is administered at a dose of about $2.9 \times 10^{10}$ GC/g brain mass brain mass (e.g., as determined by MRI). In some embodiments, a transgene-specific assay or a PolyA-specific assay is used to calculate the dose of the recombinant nucleotide expression vector to be administered to a subject. In certain embodiments, the human subject's brain mass is converted from the human subject's brain volume by multiplying the human subject's brain volume in cm$^3$ by a factor of 1.046 g/cm$^3$, wherein the human subject's brain volume is obtained from the human subject's brain MRI.

By way of background, human IDS is translated as a 550 amino acid polypeptide that contains eight potential N-glycosylation sites ($N^{31}$, $N^{115}$, $N^{144}$, $N^{246}$, $N^{280}$, $N^{325}$, $N^{513}$ and $N^{537}$) depicted in FIG. 1 and includes a 25 amino acid signal sequence which is cleaved during processing. An initial 76 kDa intracellular precursor is converted into a phosphorylated 90 kDa precursor after modification of its oligosaccharide chains in the Golgi apparatus. This precursor is processed by glycosylation modifications and proteolytic cleavage through various intracellular intermediates to a major 55 kDa form. To summarize, after removal of the 25 aa signal sequence, proteolytic processing involves N-terminal proteolytic cleavage downstream of $N^{31}$ removing a propeptide of eight amino acids (residues 26-33), and C-terminal proteolytic cleavage upstream of $N^{513}$ which releases an 18 kDa polypeptide and produces a 62 kDa intermediate that is converted to a 55 kDa mature form. Further proteolytic cleavage yields a 45 kDa mature form located in the lysosomal compartment. (See FIG. 4 for diagram reproduced from Millat et al., 1997, Exp Cell Res 230: 362-367 ("Millat 1997"); Millat et al. 1997, Biochem J. 326: 243-247 ("Millat 1997a"); and Froissart et al., 1995, Biochem J. 309:425-430, each of which is incorporated by reference herein in its entirety).

A formylglycine modification of $C^{84}$ (shown in bold in FIG. 1) required for enzyme activity probably occurs as an early post-translational or co-translational event, most probably in the endoplasmic reticulum. (See, Millat 1997a, citing Schmidt et al., 1995, Cell 82: 271-278). Post-translational processing continues in the Golgi to include addition of complex sialic acid-containing glycans and acquisition of mannose-6-phosphate residues which tag the enzyme for delivery to the lysosomal compartment. (See, Clarke, 2008, Expert Opin Pharmacother 9: 311-317 for a concise review which is incorporated by reference herein in its entirety). While no single glycosylation site is essential for IDS stability, glycosylation at position $N^{280}$ is important for cellular internalization and lysosomal targeting via the mannose-6-phosphate (M6P) receptor. (Chung et al., 2014, Glycoconj J 31:309-315 at p. 310, first column). In the normal physiologic state, IDS is produced at very low levels and very little, if any, enzyme is secreted from the cell. (Clarke, 2008, supra).

The invention is based, in part, on the following principles:
(i) Neuronal and glial cells in the CNS are secretory cells that possess the cellular machinery for post-translational processing of secreted proteins—including glycosylation, mannose-6-phosphorylation, and tyrosine-O-sulfation—robust processes in the CNS. See, e.g., Sleat et al., 2005, Proteomics 5: 1520-1532, and Sleat 1996, J Biol Chem 271: 19191-98 which describes the human brain mannose-6-phosphate glycoproteome and notes that the brain contains more proteins with a much greater number of individual isoforms and mannose-6-phosphorylated proteins than found in other tissues; and Kanan et al., 2009, Exp. Eye Res. 89: 559-567 and Kanan & Al-Ubaidi, 2015, Exp. Eye Res. 133: 126-131 reporting the production of tyrosine-sulfated glycoproteins secreted by neuronal cells, each of which is incorporated by reference in its entirety for post-translational modifications made by human CNS cells.
(ii) The human brain produces multiple isoforms of natural/native IDS. In particular, N-terminal sequencing of human brain mannose-6-phosphorylated glycoproteins revealed that the N-terminal sequence of the mature 42 kDa chain of hIDS varies in the brain, starting at positions 34 or 36 as follows: T$^{34}$DALNVLLI (SEQ ID NO: 54); and A$^{36}$LNVLLIIV (SEQ ID NO: 55). (Sleat, 2005, Proteomics 5: 1520-1532, Table S2). Two of the eight N-linked glycosylation sites, namely N$^{280}$ and N$^{116}$, were found to be mannose-6-phophorylated in IDS obtained from human brain. (Sleat et al., 2006, Mol & Cell Proeomics 5.4: 686-701, reported at Table V).

(iii) During processing of hIDS, two polypeptides, 76 kDa and 90 kDa, are secreted by neural and glial cells, but only the 90 kDa polypeptide is mannose-6-phosphorylated, which is necessary for secreted forms of the enzyme to achieve cross correction. (See, Millat, 1997, FIG. 1 results for transduced lymphoblastoid cells, and Froissart 1995, FIG. 4 showing similar results for transduced fibroblasts—in culture medium, only the 90 kDa form is phosphorylated). Interestingly, it has been demonstrated that recombinant IDS produced by neuronal and glial cells may be endocytosed by recipient CNS cells more avidly than recombinant LDS produced by other cells such as kidney. Daniele 2002 (Biochimica et Biophysica Acta 1588(3):203-9) demonstrated M6P-receptor mediated endocytosis of recombinant IDS from conditioned media of transduced neuronal and glial cell cultures by a recipient population of non-transduced neuronal and glial cells which properly processed the precursor to the 45 kDa mature active form. Uptake of the recombinant IDS produced by the neuronal and glial cell lines (74% endocytosis) far exceeded uptake of the enzyme produced by a kidney cell line (5.6% endocytosis). In each case, uptake was inhibited by M6P, indicating that recombinant IDS uptake was M6P-receptor mediated. (See Daniele 2002, Tables 2 and 4 and accompanying description in Results at pp. 205-206 summarized in Table 1 below).

TABLE 1

Summary of Results Reported in Daniele 2002

| Cell Line Source of rIDS | Media Enzyme Units | Recipient Cells: Units Recovered | | % Endocytosis (mean value) |
|---|---|---|---|---|
| | | Neuronal | Glial | |
| Kidney *(transfected)* | 35 U | 1.7 U | 2.2 U | 5.6% |
| Neuronal *(Ad-transduced)* | 12 U | 8.8 U | 8.8 U | 74% |
| Glial *(Ad-transduced)* | 14 U | 10.5 U | 10.5 U | 74% |

(iv) The gene therapy approach described herein should result in the continuous secretion of an hIDS glycoprotein precursor of about 90 kDa as measured by polyacrylamide gel electrophoresis (depending on the assay used) that is enzymatically active. First, the enzyme responsible for the formylglycine modification of C$^{84}$ which is required for IDS activity—the FGly-Generating Enzyme (FGE, aka SUMF1)—is expressed in the cerebral cortex of the human brain (gene expression data for SUMF1 may be found, for example, at GeneCards, accessible at http://www.genecards.org). Second, the secreted glycosylated/phosphorylated rIDS produced by transduced neurons and glial cells in situ should be taken up and correctly processed by untransduced neural and glial cells in the CNS. Without being bound to any theory, it appears that the secreted rhIDS precursor produced in situ by gene therapy may be more avidly endocytosed by recipient cells in the CNS than would traditional recombinant enzymes used for ERT if administered to the CNS. For example, Elaprase® (made in HT1080, a fibrosarcoma cell line) is a purified protein reported to have a molecular weight of about 76 kDa—not the 90 kDa species secreted by neuronal and glial cells that appears to be more heavily phosphorylated. While the eight N-linked glycosylation sites are reported to be fully occupied in Elaprase® and contain two bis-mannose-6-phosphate terminated glycans as well as complex highly sialylated glycans, the post-translational modification of C$^{84}$ to FGly, which is an absolute requirement for enzyme activity, is only about 50%. (Clarke, 2008, Expert Opin Pharmacother 9:311-317; Elaprase® Full Prescribing Information and EMA filing). Another recombinant product, Hunterase® is made in CHO cells. While reported to have higher FGly and activity than Elaprase®, mannose-6-phosphorylation and uptake did not differ. (Chung, 2014, Glycoconj J 31:309-315).

(v) The extracellular IDS efficacy in vivo depends on uptake (cell and lysosome internalization) through M6P and its active site formylglycine (FGly), which is converted from C$^{84}$ through post-translational modification by formylglycine-generating enzyme. As shown above in Table 1, brain cells (neuronal and glial cells) show higher enzyme activities when incubated with IDS precursor media secreted by transduced neuronal and glial cells than with IDS precursor media secreted by genetically engineered kidney cells. The resultant five-fold increase in activity can likely be attributed to the efficient uptake of IDS (See Daniele 2002, Tables 2 and 4). Commercial forms of IDS, which are generated by CHO cells or HT-1080 cells, have a FGly content of about 50% to 70%, which determines the enzyme activity. However, neuronal and glial cells may improve upon this activity, due to improvement of IDS uptake.

(vi) The cellular and subcellular trafficking/uptake of lysosomal proteins, including IDS, is through M6P. IDS from brain cells may contain higher M6P content, as reported in Daniele 2002, and in Sleat, Proteomics, 2005 (indicating that the human brain contains more (in both a quantitative and qualitative sense) Man6-P glycoproteins than other tissues). It is possible to measure the M6P content of an IDS precursor, as done in Daniele 2002. In the presence of inhibitory M6P (e.g., 5 mM), the uptake of IDS precursor generated by non-neuronal or non-glial cells, such as the genetically engineered kidney cells of Daniele 2002, is predicted to decrease to levels close to that of the control cells, as was shown in Daniele 2002. While in the presence of inhibitory M6P, the uptake of IDS precursor generated by brain cells, such as neuronal and glial cells, is predicted to remain at a high level, as was shown in Daniele 2002, where the uptake was four times higher than control cells and comparable to the level of IDS activity (or uptake) of IDS precursor generated by genetically engineered kidney cells without the presence of inhibitory M6P. This assay allows for a way to predict the M6P content in IDS precursor generated by brain cells, and, in particular, to compare the M6P content in IDS precursors generated by different types of cells. The gene therapy approach described herein should result in the continuous secretion of an hIDS precursor that may be taken up into neuronal and glial cells at a high level in the presence of inhibitory M6P in such an assay.

(vii) The M6P content and uptake of IDS precursor may also be demonstrated by 90 kDa and 76 kDa gel bands (e.g., SDS-PAGE gel bands). The 90 kDa is reported to be highly glycosylated/phosphorylated and contains M6P, while 76 kDa is not. A very broad gel band with a range from 76 kDa to 95 kDa and with an average MW of 80-85 kDa, similar to the IDS precursor gel band generated from genetically engineered kidney cells (Daniele 2002, FIG. 1), may be contrasted with a gel band of IDS precursor generated from brain cells. In Daniele 2002, the gel band cannot be obtained due to unsuccessful immunoprecipitation of the IDS precursor. The gene therapy approach described herein should result in the continuous secretion of an hIDS precursor that differs from the IDS precursor gel band generated from genetically engineered kidney cells.

(viii) The M6P content of commercial IDS precursor is 2 to 2.5 mol/mol, majority of which is present in a form of di-phosphorylated glycans. Although in average, every IDS precursor is phosphorylated, a normal distribution of glycans will have some IDS precursor with 2, 1 and 0 of di-phosphorylated M6P glycans assuming multiple phosphorylation sites. Uptake rate should be significant higher with multiple phosphorylation.

(ix) The glycosylation of hIDS by human cells of the CNS will result in the addition of glycans that can improve stability, half-life and reduce unwanted aggregation of the transgene product. Significantly, the glycans that are added to hIDS of the invention include 2,6-sialic acid, incorporating Neu5Ac ("NANA") but not its hydroxylated derivative, NeuGc (N-Glycolylneuraminic acid, i.e., "NGNA" or "Neu5Gc"). Such glycans are not present in recombinant IDS products, such as Hunterase®, made in CHO cells because CHO cells do not have the 2,6-sialyltransferase required to make this post-translational modification; nor do CHO cells produce bisecting GlcNAc, although they do add Neu5Gc (NGNA) as sialic acid not typical (and potentially immunogenic) to humans instead of Neu5Ac (NANA). See, e.g., Dumont et al., 2016, Critical Rev in Biotech 36(6):1110-1122 (Early Online pp. 1-13 at p. 5); and Hague et al., 1998 Electrophor 19:2612-2630 ("[t]he CHO cell line is considered 'phenotypically restricted,' in terms of glycosylation, due to the lack of an α2,6-sialyl-transferase"). Moreover, CHO cells can also produce an immunogenic glycan, the α-Gal antigen, which reacts with anti-α-Gal antibodies present in most individuals, and at high concentrations can trigger anaphylaxis. See, e.g., Bosques, 2010, Nat Biotech 28: 1153-1156. The human glycosylation pattern of the rhIDS of the invention should reduce immunogenicity of the transgene product and improve efficacy.

(x) Immunogenicity of a transgene product could be induced by various factors, including the immune condition of the patient, the structure and characteristics of the infused protein drug, the administration route, and the duration of treatment. Process-related impurities, such as host cell protein (HCP), host cell DNA, and chemical residuals, and product-related impurities, such as protein degradants and structural characteristics, such as glycosylation, oxidation and aggregation (sub-visible particles), may also increase immunogenicity by serving as an adjuvant that enhances the immune response. The amounts of process-related and product-related impurities can be affected by the manufacturing process: cell culture, purification, formulation, storage and handling, which can affect commercially manufactured IDS products. In gene therapy, proteins are produced in vivo, such that process-related impurities are not present and protein products are not likely to contain product-related impurities/degradants associated with proteins produced by recombinant technologies, such as protein aggregation and protein oxidation. Aggregation, for example, is associated with protein production and storage due to high protein concentration, surface interaction with manufacturing equipment and containers, and the purification process with certain buffer systems. But these conditions that promote aggregation are not present when a transgene is expressed in vivo. Oxidation, such as methionine, tryptophan and histidine oxidation, is also associated with protein production and storage, caused, for example, by stressed cell culture conditions, metal and air contact, and impurities in buffers and excipients. The proteins expressed in vivo may also oxidize in a stressed condition, but humans, like many organisms, are equipped with an antioxidation defense system, which not only reduces the oxidation stress, but can also repairs and/or reverses the oxidation. Thus, proteins produced in vivo are not likely to be in an oxidized form. Both aggregation and oxidation could affect the potency, PK (clearance) and can increase immunogenicity concerns. The gene therapy approach described herein should result in the continuous secretion of an hIDS precursor with a reduced immunogenicity compared to commercially manufactured products.

(xi) In addition to the N-linked glycosylation sites, hIDS contains a tyrosine ("Y") sulfation site (PSSEKY$^{165}$ENTKTCRGPD (SEQ ID NO: 47)). (See, e.g., Yang et al., 2015, Molecules 20:2138-2164, esp. at p. 2154 which is incorporated by reference in its entirety for the analysis of amino acids surrounding tyrosine residues subjected to protein tyrosine sulfation. The "rules" can be summarized as follows: Y residues with E or D within +5 to −5 position of Y, and where position −1 of Y is a neutral or acidic charged amino acid—but not a basic amino acid, e.g., R, K, or H that abolishes sulfation). While not intending to be bound by any theory, sulfation of this site in hIDS may improve stability of the enzyme and binding affinity for substrate. Tyrosine-sulfation of hIDS—a robust post-translational process in human CNS cells—should result in improved processing and activity of transgene products. The significance of tyrosine-sulfation of lysosomal proteins has not been elucidated; but in other proteins it has been shown to increase avidity of protein-protein interactions (antibodies and receptors), and to promote proteolytic processing (peptide hormone). (See, Moore, 2003, J Biol. Chem. 278: 24243-46; and Bundegaard et al., 1995, The EMBO J 14: 3073-79). The tyrosylprotein sulfotransferase (TPST1) responsible for tyrosine-sulfation (which may occur as a final step in IDS processing) is apparently expressed at higher levels (based on mRNA) in the brain (gene expression data for TPST1 may be found, for example, at the EMBL-EBI Expression Atlas, accessible at http://www.ebi.ac.uk/gxa/home). Such post-translational modification, at best, is under-represented in CHO cell products. Unlike human CNS cells, CHO cells are not secretory cells and have a limited capacity for post-translational tyrosine-sulfation. (See, e.g., Mikkelsen & Ezban, 1991, Biochemistry 30: 1533-1537, esp. discussion at p. 1537).

For the foregoing reasons, the production of rhIDS by human neuronal and/or glial cells should result in a "biobetter" molecule for the treatment of MPS II accomplished via gene therapy—e.g., by administering a viral vector or other DNA expression construct encoding rhIDS to the CSF of a patient (human subject) diagnosed with an MPS II disease (including but not limited to Hunter) to create a permanent depot in the CNS that continuously supplies a fully human-glycosylated, mannose-6-phosphorylated, sulfated transgene product secreted by the transduced CNS cells. The hIDS transgene product secreted from the depot into the CSF will be endocytosed by cells in the CNS, resulting in "cross-correction" of the enzymatic defect in the MPS II recipient cells.

It is not essential that every rhIDS molecule produced either in the gene therapy or protein therapy approach be fully glycosylated, phosphorylated, and sulfated. Rather, the population of glycoproteins produced should have sufficient glycosylation (including 2,6-sialylation and mannose-6-phophorylation) and sulfation to demonstrate efficacy. The goal of gene therapy treatment of the invention is to slow or arrest the progression of disease. Efficacy may be monitored by measuring cognitive function (e.g., prevention or decrease in neurocognitive decline); reductions in biomarkers of disease (such as GAG) in CSF and or serum; and/or increase in IDS enzyme activity in CSF and/or serum. Signs of inflammation and other safety events may also be monitored.

As an alternative, or an additional treatment to gene therapy, the rhIDS glycoprotein can be produced in human neural or glial cell lines by recombinant DNA technology and the glycoprotein can be administered to patients diagnosed with MPS II systemically and/or into the CSF for ERT). Human cell lines that can be used for such recombinant glycoprotein production include but are not limited to HT-22, SK-N-MC, HCN-1A, HCN-2, NT2, SH-SY5y, hNSC11, or ReNcell VM (see, e.g., Dumont et al., 2016, Critical Rev in Biotech 36(6):1110-1122 "Human cell lines for biopharmaceutical manufacturing: history, status, and future perspectives" which is incorporated by reference in its entirety for a review of the human cell lines that could be used for the recombinant production of the rHuGlyIDS glycoprotein). To ensure complete glycosylation, especially sialylation, and tyrosine-sulfation, the cell line used for production can be enhanced by engineering the host cells to co-express α-2,6-sialyltransferase (or both α-2,3- and α-2,6-sialyltransferases) and/or TPST-1 and TPST-2 enzymes responsible for tyrosine-O-sulfation.

While the delivery of rhIDS should minimize immune reactions, the clearest potential source of toxicity related to CNS-directed gene therapy is generating immunity against the expressed rhIDS protein in human subjects who are genetically deficient for IDS and, therefore, potentially not tolerant of the protein and/or the vector used to deliver the transgene.

Thus, in a preferred embodiment, it is advisable to co-treat the patient with immune suppression therapy—especially when treating patients with severe disease who have close to zero levels of IDS. Immune suppression therapies involving a regimen of tacrolimus or rapamycin (sirolimus) in combination with mycophenolic acid, or other immune suppression regimens used in tissue transplantation procedures can be employed. Such immune suppression treatment may be administered during the course of gene therapy, and in certain embodiments, pre-treatment with immune suppression therapy may be preferred. Immune suppression therapy can be continued subsequent to the gene therapy treatment, based on the judgment of the treating physician, and may thereafter be withdrawn when immune tolerance is induced: e.g., after 180 days.

Combinations of delivery of the rhIDS to the CSF accompanied by delivery of other available treatments are encompassed by the methods of the invention. The additional treatments may be administered before, concurrently or subsequent to the gene therapy treatment. Available treatments for MPS II that could be combined with the gene therapy of the invention include but are not limited to enzyme replacement therapy using Elaprase® administered systemically or to the CSF; and/or HSCT therapy.

In one aspect, provided herein is a method for treating a human subject diagnosed with MPS II, comprising delivering to the CSF of the human subject a therapeutically effective amount of a glycosylated recombinant human IDS precursor produced by human neuronal or human glial cells, wherein the glycosylated recombinant human IDS precursor is delivered by administration of a recombinant nucleotide expression vector encoding human IDS, wherein the recombinant nucleotide expression vector is administered at a dose that is dependent on the human subject's brain mass, and wherein the brain mass is determined by brain MRI of the human subject's brain.

In another aspect, provided herein is a method for treating a human subject diagnosed with MPS II, comprising, in the following order: (a) delivering to the CSF of the human subject a therapeutically effective amount of a glycosylated recombinant human IDS precursor produced by human neuronal or human glial cells; (b) measuring level of heparan sulfate in the CSF of the human subject; and (c) comparing the level of heparan sulfate in the CSF of the human subject with level of heparan sulfatae in a reference population: wherein the glycosylated recombinant human IDS precursor is delivered by administration of a recombinant nucleotide expression vector encoding human IDS, wherein the recombinant nucleotide expression vector is administered at a dose that is dependent on the human subject's brain mass, and wherein the brain mass is determined by brain magnetic resonance imaging (MRI) of the human subject's brain. In certain embodiments, the reference population consists of: (a) at least 1, 2, 3, 4, 5, 10, 25, 50, 75, 100, 200, 250, 300, 400, 500, or 1000 individual healthy people without MPS II, preferably of similar age, weight, and/or of the same gender as the human subject.

In another aspect, provided herein is a method for treating a human subject diagnosed with MPS II, comprising, in the following order: (a) taking a first measurement of the level of heparan sulfate in the CSF of the human subject; (b) delivering to the CSF of the human subject a therapeutically effective amount of a glycosylated recombinant human IDS precursor produced by human neuronal or human glial cells; and (c) after a period of time, taking a second measurement of the level of heparan sulfate; wherein the glycosylated recombinant human IDS precursor is delivered by administration of a recombinant nucleotide expression vector encoding human IDS, wherein the recombinant nucleotide expression vector is administered at a dose that is dependent on the human subject's brain mass, and wherein the brain mass is determined by brain magnetic resonance imaging (MRI) of the human subject's brain. In certain embodiments, the period of time is about 1 day, 2 days, 3 days, 4 days, 5 days, 6 days, 1 week, 2 weeks, 3 weeks, 4 weeks, 2 months, 3 moths, 4 months, 5 months, 6 months, 7 months, 8 months, 11 months, or 1 year.

In certain embodiments of the method for treating described herein, the glycosylated recombinant human IDS precursor is delivered to lysosomes of cells in the CNS of the human subject.

In certain embodiments of the method for treating described herein, the human subject's brain mass is converted from the human subject's brain volume by multiplying the human subject's brain volume in cm$^3$ by a factor of 1.046 g/cm, wherein the human subject's brain volume is determined by brain MRI of the subject's brain.

In certain embodiments of the method for treating described herein, the recombinant nucleotide expression vector is administered at a dose of about $1.3 \times 10^{10}$ GC/g brain mass as determined by MRI, or about $6.5 \times 10^{11}$ GC/g brain mass as determined by MRI. In certain embodiments of the method for treating described herein, the recombinant nucleotide expression vector is administered at a dose of about $2.0 \times 10^{10}$ GC/g brain mass as determined by MRI. In certain embodiments of the method for treating described herein, the recombinant nucleotide expression vector is administered at a dose of about $1.9 \times 10^{10}$ GC/g brain mass as determined by MRI. In certain embodiments of the method for treating described herein, the recombinant nucleotide expression vector is administered at a dose of about $9.6 \times 10^{10}$ GC/g brain mass as determined by MRI. In certain embodiments of the method for treating described herein, the recombinant nucleotide expression vector is administered at a dose of about $2.0 \times 10^{11}$ GC/g brain mass (e.g., the brain mass is determined by MRI and the genome count is determined by a Poly-A-specific PCR assay). In certain embodiments of the method for treating described herein, the recombinant nucleotide expression vector is administered at a dose of about $2.9 \times 10^{11}$ GC/g brain mass as determined by MRI. In certain embodiments of the method for treating described herein, the recombinant nucleotide expression vector is administered at a dose of about $2.9 \times 10^{11}$ GC/g brain mass (e.g., the brain mass is determined by MRI and the genome count is determined by a transgene-specific PCR assay). In certain embodiments of the method for treating described herein, the recombinant nucleotide expression vector is administered at a dose of about $1.3 \times 10^{10}$ GC/g brain mass (e.g., the brain mass is determined by MRI and the genome count is determined by a Poly-A-specific PCR assay). In certain embodiments of the method for treating described herein, the recombinant nucleotide expression vector is administered at a dose of about $1.9 \times 10^{10}$ GC/g brain mass (e.g., the brain mass is determined by MRI and the genome count is determined by a transgene-specific PCR assay). In certain embodiments of the method for treating described herein, the recombinant nucleotide expression vector is administered at a dose of about $6.5 \times 10^{10}$ GC/g brain mass (e.g., the brain mass is determined by MRI and the genome count is determined by a Poly-A-specific PCR assay). In certain embodiments of the method for treating described herein, the recombinant nucleotide expression vector is administered at a dose of about $9.6 \times 10^{10}$ GC/g brain mass (e.g., the brain mass is determined by MRI and the genome count is determined by a transgene-specific PCR assay).

In various embodiments of the method for treating described herein, the human subject is 5 years old or older and less than 18 years old. In specific embodiments, the human subject is 5, 6, 7, 8, 9, 10, 11, 12, 13, 14, 15, 16, 17 or 18 years old. In specific embodiments, the human subject is about 5, 6, 7, 8, 9, 10, 11, 12, 13, 14, 15, 16, 17 or 18 years old. In specific embodiments, the human subject is 5-6, 6-7, 7-8, 8-9, 9-10, 10-11, 11-12, 12-13, 13-14, 14-15, 15-16, 16-17, 17-18 or 18-19 years old. In specific embodiments, the human subject is about 5-6, 6-7, 7-8, 8-9, 9-10, 10-11, 11-12, 12-13, 13-14, 14-15, 15-16, 16-17, 17-18 or 18-19 years old. In certain embodiments, the recombinant nucleotide expression vector is administered at a dose of about $6.5 \times 10^{10}$ GC/g brain mass as determined by MRI. In certain embodiments, the recombinant nucleotide expression vector is administered at a dose according to Table 7.

In various embodiments of the method for treating described herein, the human subject is 4 months old or older and less than 5 years old. In specific embodiments, the human subject is 4, 5, 6, 7, 8, 9, 10, or 11 months old. In specific embodiments, the human subject is about 4, 5, 6, 7, 8, 9, 10, or 11 months old. In specific embodiments, the human subject is 4-5, 5-6, 6-7, 7-8, 8-9, 9-10, 10-11, or 11-12 months old. In specific embodiments, the human subject is about 4-5, 5-6, 6-7, 7-8, 8-9, 9-10, 10-11, or 11-12 months old. In specific embodiments, the human subject is 1, 2, 3, 4, or 5 years old. In specific embodiments, the human subject is about 1, 2, 3, 4, or 5 years old. In specific embodiments, the human subject is 1-2, 2-3, 3-4, 4-5, or 5-6 years old. In specific embodiments, the human subject is about 1-2, 2-3, 3-4, 4-5, or 5-6 years old. In certain embodiments, the recombinant nucleotide expression vector is administered at a dose of about $1.3 \times 10^{10}$ GC/g brain mass as determined by MRI. In certain embodiments, the recombinant nucleotide expression vector is administered at a dose of about $6.5 \times 10^{10}$ GC/g brain mass as determined by MRI. In certain embodiments, the recombinant nucleotide expression vector is administered at a dose of about $1.9 \times 10^{10}$ GC/g brain mass as determined by MRI. In certain embodiments, the recombinant nucleotide expression vector is administered at a dose of about $9.6 \times 10^{10}$ GC/g brain mass as determined by MRI. In certain embodiments, the recombinant nucleotide expression vector is administered at a dose of about $2.0 \times 10^{11}$ GC/g brain mass as determined by MRI. In certain embodiments, the recombinant nucleotide expression vector is administered at a dose of about $2.9 \times 10^{11}$ GC/g brain mass as determined by MRI. In certain embodiments, the recombinant nucleotide expression vector is administered at a dose of about $2.0 \times 10^{11}$ GC/g brain mass (e.g., the brain mass is determined by MRI and the genome count is determined by a Poly-A-specific PCR assay). In certain embodiments, the recombinant nucleotide expression vector is administered at a dose of about $2.9 \times 10^{11}$ GC/g brain mass (e.g., the brain mass is determined by MRI and the genome count is determined by a transgene-specific PCR assay). In certain embodiments, the recombinant nucleotide expression vector is administered at a dose of about $1.3 \times 10^{10}$ GC/g brain mass (e.g., the brain mass is determined by MRI and the genome count is determined by a Poly-A-specific PCR assay). In certain embodiments, the recombinant nucleotide expression vector is administered at a dose of about $1.9 \times 10^{10}$ GC/g brain mass (e.g., the brain mass is determined by MRI and the genome count is determined by a transgene-specific PCR assay). In certain embodiments, the recombinant nucleotide expression vector is administered at a dose of about $6.5 \times 10^{10}$ GC/g brain mass (e.g., the brain mass is determined by MRI and the genome count is determined by a Poly-A-specific PCR assay). In certain embodiments, the recombinant nucleotide expression vector is administered at a dose of about $9.6 \times 10^{10}$ GC/g brain mass (e.g., the brain mass is determined by MRI and the genome count is determined by a transgene-specific PCR assay). In certain embodiments, the recombinant nucleotide expression vector is administered at a dose chosen from Dose 1 or Dose 2 according to Table 5. In certain embodiments, the recombinant nucleotide expression vector is administered at a dose according to Table 6.

In some embodiments of the method for treating described herein, the recombinant nucleotide expression vector is administered via intracisternal (IC) administration. In other embodiments of the method for treating described herein, the recombinant nucleotide expression vector is administered via intracerebroventricular (ICV) administration.

In certain embodiments of the method for treating described herein, the recombinant nucleotide expression vector is administered at a volume that does not exceed 10% of the total cerebrospinal fluid volume of the human subject.

In certain embodiments of the method for treating described herein, the glycosylated recombinant human IDS precursor is secreted at a detectable level.

In certain embodiments of the method for treating described herein, the human neuronal or human glial cells carry at least one mutation in the endogenous gene encoding human IDS precursor.

In certain embodiments of the method for treating described herein, the human neuronal or human glial cells are transduced with a recombinant adeno-associated virus vector (rAAV).

In a preferred embodiment, the recombinant nucleotide expression vector is an AAV9 or AAVrh10 vector.

In certain embodiments of the method for treating described herein, the glycosylated recombinant human IDS precursor is expressed under the control of a CB7 promoter.

In certain embodiments of the method for treating described herein, the glycosylated recombinant human IDS precursor is expressed from a cDNA encoding human IDS precursor.

In certain embodiments of the method for treating described herein, the glycosylated recombinant human IDS precursor is about 90 kDa as measured by polyacrylamide gel electrophoresis.

In certain embodiments of the method for treating described herein, the glycosylated recombinant human IDS precursor contains a formylglycine.

In certain embodiments of the method for treating described herein, the glycosylated recombinant human IDS precursor (a) is α2,6-sialylated; (b) does not contain detectable NeuGc; (c) does not contain detectable α-Gal antigen; (d) contains tyrosine-sulfation; and/or (e) is mannose-6-phosphorylated.

In certain embodiments of the method for treating described herein, the glycosylated recombinant human IDS precursor comprises the amino acid sequence of SEQ ID NO. 1.

In certain embodiments provided herein, the method further comprising administering an immune suppression therapy to the human subject before or concurrently with the human IDS precursor treatment and optionally continuing immune suppression therapy thereafter.

In some embodiments, the immune suppression therapy comprises administering one or more corticosteroids, sirolimus, and/or tacrolimus. In a specific embodiment, the one or more corticosteroids are methylprednisolone and/or prednisone.

In some embodiments, the method further comprises administering one or more antibiotics to the human subject before or concurrently with the immune suppression therapy. In a specific embodiment, the one or more antibiotics are trimethoprim, sulfamethoxazole, pentamidine, dapsone, and/or atovaquone.

In some embodiments, the method further comprises administering one or more antifungal therapies to the human subject before or concurrently with the immune suppression therapy.

In some embodiments, the method further comprises a step of measuring one or more of the following biomarkers after administration of the recombinant nucleotide expression vector: (a) level of glycosaminoglycans (GAGs) in CSF; (b) level of iduronate-2-sulfatase (I2S) in CSF; (c) level of GAGs in plasma; (d) level of I2S in plasma; (e) level of leukocyte I2S enzyme activity; and (f) level of GAGs in urine. In a specific embodiment, the GAGs in CSF comprise heparin sulfate in CSF. In another specific embodiment, the GAGs in CSF are heparin sulfate in CSF. In another specific embodiment, the GAGs in plasma comprise heparin sulfate in plasma. In another specific embodiment, the GAGs in plasma are heparin sulfate in plasma. In another specific embodiment, the GAGs in urine comprise heparin sulfate in urine. In another specific embodiment, the GAGs in urine are heparin sulfate in urine. In a specific embodiment, the step of measuring comprises mearing level of heparin sulfate in CSF. In another specific embodiment, the step of measuring comprises measuring level of leukocyte I2S enzyme activity In another aspect, provided herein is a method of treating a human subject diagnosed with MPS II, comprising: (a) administering a therapeutically effective amount of an rAAV encoding hIDS to the human subject, wherein the human subject was treated with ERT or is being treated with ERT; and (b) discontinuing ERT treatment in the human subject if the level of at least one biomarker in a biological sample from the human subject is lower than a reference, wherein the biological sample was obtained from the human subject after the administering, and wherein the at least one biomarker comprises D2S6, HS, and/or total GAG (e.g., as measured in urine). In some embodiments, the at least one biomarker is about or at least about 5%, 10%, 15%, 20%, 25%, 30%, 35%, 40%, 45%, 50%, 55%, 60%, 65%, 70%, 75%, 80%, 85%, 90%, 95% lower than the reference before ERT is discontinued. In some embodiments ERT is recombinant idursulfase. In some embodiments, the subject diagnosed with MPS II has hepatosplenomegaly.

In another aspect, provided herein is a method of treating a human subject diagnosed with MPS II, comprising: (a) administering a therapeutically effective amount of an rAAV encoding hIDS to the human subject, wherein the human subject was treated with ERT or is being treated with ERT; and (b) discontinuing ERT treatment in the human subject if the level of at least one biomarker in a biological sample from the human subject is higher than a reference, wherein the biological sample was obtained from the human subject before the administering, and wherein the at least one biomarker is an anti-IDS antibody. In some embodiments, the at least one biomarker is about or at least about 5%, 10%, 15%, 20%, 25%, 30%, 35%, 40%, 45%, 50%, 55%, 60%, 65%, 70%, 75%, 80%, 85%, 90%, 95%, 150%, 250%, 500%, 750%, or 1000% higher than the reference before ERT is discontinued. In some embodiments ERT is recombinant idursulfase. In some embodiments, the subject diagnosed with MPS II has hepatosplenomegaly.

In some embodiments, the reference is the level of the at least one biomarker in a biological sample obtained from the human subject prior to administration of the rAAV to the human subject. In some embodiments, the reference is the level of the at least one biomarker in a biological sample obtained from a subject diagnosed with MPS II but not receiving ERT. In some embodiments, the reference is a predetermined value. In some embodiments, ERT treatment is discontinued 52 weeks after the rAAV is administered to the human subject. In some embodiments, the biological sample is CSF, urine, plasma, or serum.

In another aspect, provided herein is a method of treating a human subject diagnosed with MPS II comprising: (a) discontinuing ERT treatment in the human subject, wherein the human subject was treated with ERT or is being treated with ERT; and (b) administering a therapeutically effective amount of an rAAV encoding hIDS to the human subject, wherein the administering is after ERT treatment is discontinued in the human subject. In some embodiments, the ERT treatment is discontinued about or at least about 1 year, 6 months, 5 months, 4 months, 3 months, 2 months, 1 month, 3 weeks, 2 weeks, 1 week, 10 days, 5 days, or one day before the rAAV encoding hIDS is administered to the human subject. In some embodiments, the ERT treatment is discontinued if the level of at least one biomarker is not detected in a biological sample from the human subject. In some embodiments, the at least one biomarker is an anti-AAV antibody. In some embodiments, the anti-AAV antibody is an anti-AAV9 antibody. In some embodiments, the biological sample is serum. In some embodiments, the human subject has hepatosplenomegaly. In some embodiments, the ERT is enzyme replacement therapy with recombinant idursulfase.

In another aspect, provided herein is a method of determining efficacy or monitoring efficacy of MPS II treatment in a human subject, comprising administering a therapeutically effective amount of an rAAV encoding hIDS to the human subject, wherein a decrease in the level of D2S6 in a biological sample from the human subject as compared to a reference is indicative of efficacy of the MPS II treatment in the human subject, wherein the biological sample was obtained from the human subject at about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 days, or 1, 2, 3, 4, 5, 6, 7, 8, 10, 16, 20, 24, 30, 35, 40, 45, 48, 50, 52, 56, 104 weeks, or 1, 2, 3, 4, 5, 6, 7, 8, 9, 10, 11, 12 months, or 1, 2, 3, 4, 5, 6, 7, 8, 9, or 10 years after the administering step. In some embodiments, the human subject was treated with ERT prior to the administration of the rAAV encoding hIDS to the human subject. In some embodiments, the human subject received ERT treatment after the administration of the rAAV encoding hIDS to the human subject. In some embodiments, the ERT is enzyme replacement therapy with recombinant idursulfase. In some embodiments, the biological sample is CSF. In some embodiments, the patient is a pediatric patient.

In some embodiments, efficacy of the treatment is demonstrated by a decrease in the level of D2S6 of about or at least about 5%, 10%, 15%, 20%, 25%, 30%, 35%, 40%, 45%, 50%, 55%, 60%, 65%, 70%, 75%, 80%, 85%, 90%, 95% as compared to the reference (eg, the D2S6 level in the same patient prior to the administering step). In some embodiments, the efficacy of MPS 11 treatment is an improvement in at least one subtest of the Bayley Scales of Infant and Toddler Development, 3rd Edition (BSID-III) as compared to a reference. In some embodiments, the at least one subtest is age equivalence score, cognitive developmental quotient (DQ), expressive language DQ, receptive language DQ, gross motor DQ, and/or fine motor DQ. In some embodiments, the improvement is an improvement in DQ of about or at least about 1, 2, 3, 4, 5, 6, 7, 8, 9, 10, 12, 15, 17, 20, 25, 30, 35, 40, 45, 50, 55, 60, 65, 70, 75, 80, 85, 90, 95, 100, or more than 100. In some embodiments, the age equivalence score is increased by about or at least about 1 month, 2 months, 3 months, 4 months, 5 months, 6 months, 7 months, 8 months, 9 months, 10 months, 11 months, 12 months, 18 months, 24 months, or more than 24 months. In some embodiments, the reference is the score of the at least one subtest of the BSID-III obtained prior to the administering. In some embodiments, the reference is an average score of the at least one subtest of the BSID-II obtained from human subjects with MPS II of the same age as the human subject. In some embodiments, the reference is the level of D2S6 in a biological sample obtained from the human subject prior to the administering.

In some embodiments, the rAAV is administered intrathecally to the human subject. In some embodiments, the rAAV is administered to the human subject in a solution comprising: (a) sodium chloride at a concentration of about 8.77 g/L, (b) magnesium chloride, at a concentration of about 0.244 g/L, (c) potassium chloride at a concentration of about 0.224 g/L, (d) calcium chloride at a concentration of about 0.206 g/L, (e) dextrose at a concentration of about 0.793 g/L, (f) poloxamer 188 at a concentration of about 0.001% (volume/volume), (g) sodium phosphate monobasic monohydrate at a concentration of about 0.0278 g/L, and (h) sodium phosphate dibasic anhydrous at a concentration of about 0.114 g/L.

In one aspect provided herein is a method of identifying or diagnosing a subject as having neuronopathic MPS II, wherein the method comprises: (a) determining the level of one or more heparan sulfate disaccharide(s) in a biological sample from the subject; (b) identifying or diagnosing the subject as having neuronopathic MPS II if the level of the one or more heparan sulfate disaccharide(s) is elevated as compared to a reference level; and (c) administering a therapeutically effective amount of an rAAV encoding hIDS to the subject identified or diagnosed as having neuronopathic MPS II. In some embodiments, the one or more heparan sulfate disaccharide(s) comprises one or more of D0A0, D0S0, D0A6, D2S6, or a combination thereof. In some embodiments, the one or more heparan sulfate disaccharide(s) is D2S6.

In one aspect provided herein is a method of identifying or diagnosing a subject as having neuronopathic MPS II, wherein the subject is identified or diagnosed as having neuronopathic MPS II if the level of D2S6 in a biological sample from the subject is elevated as compared to a reference level, and wherein a therapeutically effective amount of an rAAV encoding hIDS is administered to the subject identified or diagnosed as having neuronopathic MPS II.

In some embodiments, the biological sample is cerebrospinal fluid. In some embodiments, the subject is presymptomatic or has no visible or detectable MPS II symptom. In some embodiments, the subject has MPS II. In some embodiments, the reference level is the level of the at least one or more heparan sulfate disaccharide(s) in a biological sample from one or more healthy subjects and/or from one or more non-neuronopathic subjects. In some embodiments, the reference level is the level of D2S6 in a biological sample from one or more healthy subjects and/or from one or more non-neuronopathic subjects. In some embodiments, the biological sample from one or more healthy subjects and/or from one or more non-neuronopathic subjects is a CSF sample. In some embodiments, the reference level is a pre-determined level. In some embodiments, the level of D2S6 is about or at least about 12%, 13%, 14%, 15%, 16%, 17%, 18%, 19%, 20%, 25%, 30%, 35%, 40%, or higher than 40% of the total heparan sulfate disaccharides (HS) in the biological sample from the subject. In some embodiments, the level of D2S6 is about or at least about 20% of the total heparan sulfate disaccharides (HS) in the biological sample from the subject. In some embodiments, the level of one or more heparan sulfate disaccharide(s) or the level of D2S6 in the biological sample from the subject is about or at least about 50 ng/mL, 75 ng/mL, 80 ng/mL, 85 ng/mL, 90 ng/mL, 95 ng/mL, 100 ng/mL, 105 ng/mL, 110 ng/mL, 115 ng/mL, 120 ng/mL, 125 ng/mL, 130 ng/mL, 135 ng/mL, 140 ng/mL, 145 ng/mL, 150 ng/mL, 155 ng/mL, 160 ng/mL, 165 ng/mL, 170 ng/mL, 175 ng/mL, 180 ng/mL, 185 ng/mL, 190 ng/mL, 195 ng/mL, 200 ng/mL, 210 ng/mL, 220 ng/mL, 230 ng/mL, 240 ng/mL, 250 ng/mL, 260 ng/mL, 270 ng/mL, 280 ng/mL, 290 ng/mL, 300 ng/mL, 310 ng/mL, 320 ng/mL, 330 ng/mL, 340 ng/mL, 350 ng/mL, 360 ng/mL, 370 ng/mL, 380 ng/mL, 390 ng/mL, 400 ng/mL, or more than 400 ng/mL. In some embodiments, the level of one or more heparan sulfate disaccharide(s) or the level of D2S6 in the biological sample from the subject is about or at least about 100 ng/mL, 110 ng/mL, 120 ng/mL, 130 ng/mL, 140 ng/mL, 150 ng/mL, 160 ng/mL, 170 ng/mL, 180 ng/mL, 190 ng/mL, 200 ng/mL, or more than 200 ng/mL. In some embodiments, the level of the one or more heparan sulfate disaccharide(s) or the level of D2S6 in the biological sample from the subject is elevated by about or at least about 10 ng/mL, 20 ng/mL, 30 ng/mL, 40 ng/mL, 50 ng/mL, 60 ng/mL, 70 ng/mL, 80 ng/mL, 90 ng/mL, 100 ng/mL, 150 ng/mL, 160 ng/mL, 170 ng/mL, 180 ng/mL, 190 ng/mL, 200 ng/mL, 210 ng/mL, 220 ng/mL, 230 ng/mL, 240 ng/mL, 250 ng/mL, 260 ng/mL, 270 ng/mL, 280 ng/mL, 290 ng/mL, 300 ng/mL, 310 ng/mL, 320 ng/mL, 330 ng/mL, 340 ng/mL, 350 ng/mL, 360 ng/mL, 370 ng/mL, 380 ng/mL, 390 ng/mL, 400 ng/mL, 410 ng/mL, 420 ng/mL, 430 ng/mL, 440 ng/mL, 450 ng/mL, 460 ng/mL, 470 ng/mL, 480 ng/mL, 490 ng/mL, 500 ng/mL, or more than 500 ng/mL as compared to the reference level.

In one aspect provided herein is a method of determining efficacy or monitoring efficacy of MPS I treatment in a human subject, comprising administering a therapeutically effective amount of an rAAV encoding human IDUA to the human subject, wherein a decrease in the level of I0S6 in a biological sample from the human subject as compared to a reference is indicative of efficacy of the MPS I treatment in the human subject, wherein the biological sample was obtained from the human subject after the administering.

In some aspects, the biological sample is plasma. In some aspects, the human subject was treated with ERT prior to the administering and/or received ERT treatment after the administering. In some aspects, the ERT is enzyme replacement therapy with recombinant idursulfase. In some aspects, the decrease in the level of I0S6 is a decrease of about or at least about 5%, 10%, 15%, 20%, 25%, 30%, 35%, 40%, 45%, 50%, 55%, 60%, 65%, 70%, 75%, 80%, 85%, 90%, 95% as compared to the reference. In some aspects, the reference is the level of I0S6 in a biological sample obtained from the human subject prior to the administering. In some aspects, the reference is a predetermined value. In some aspects, the reference is the level of I0S6 in a biological sample obtained from another human subject diagnosed with MPS I or a population of human subjects diagnosed with MPS I. In some aspects, the efficacy of MPS I treatment is an improvement in at least one subtest of the Bayley Scales of Infant and Toddler Development, 3rd Edition (BSID-III) as compared to a reference. In some aspects, the at least one subtest is age equivalence score, cognitive developmental quotient (DQ), expressive language DQ, receptive language DQ, gross motor DQ, and/or fine motor DQ. In some aspects, the reference is the score of the at least one subtest of the BSID-III obtained from the human subject prior to the administering. In some aspects, the reference is an average score of the at least one subtest of the BSID-III obtained from human subjects with MPS I of the same age as the human subject.

In some aspects, the rAAV is administered to the human subject in a solution comprising: (a) sodium chloride at a concentration of about 8.77 g/L, (b) magnesium chloride, at a concentration of about 0.244 g/L, (c) potassium chloride at a concentration of about 0.224 g/L, (d) calcium chloride at a concentration of about 0.206 g/L, (e) dextrose at a concentration of about 0.793 g/L, (f) poloxamer 188 at a concentration of about 0.001% (volume/volume), (g) sodium phosphate monobasic monohydrate at a concentration of about 0.0278 g/L, and (h) sodium phosphate dibasic anhydrous at a concentration of about 0.114 g/L.

3.1 Illustrative Embodiments 3.1.1. Set 1

1. A method for treating a human subject diagnosed with mucopolysaccharidosis type II (MPS II), comprising delivering to the cerebrospinal fluid (CSF) of the human subject a therapeutically effective amount of a glycosylated recombinant human iduronate-2-sulfatase (IDS) precursor produced by human neuronal or human glial cells, wherein the glycosylated recombinant human IDS precursor is delivered by administration of a recombinant nucleotide expression vector encoding human IDS, wherein the recombinant nucleotide expression vector is administered at a dose that is dependent on the human subject's brain mass, and wherein the brain mass is determined by brain magnetic resonance imaging (MRI) of the human subject's brain.

2. The method of paragraph 1, wherein the glycosylated recombinant human IDS precursor is secreted at a detectable level.

3. The method of paragraph 1 or 2, wherein the human neuronal or human glial cells carry at least one mutation in the endogenous gene encoding human IDS precursor.

4. The method of any one of paragraphs 1-3, wherein the human neuronal or human glial cells are transduced with a recombinant adeno-associated virus vector (rAAV).

5. The method of any one of paragraphs 1-4, wherein the glycosylated recombinant human IDS precursor is expressed under the control of a CB7 promoter.

6. The method of any one of paragraphs 1-5, wherein the glycosylated recombinant human IDS precursor is expressed from a cDNA encoding human IDS precursor.

7. The method of any one of paragraphs 1-6, wherein the glycosylated recombinant human IDS precursor is about 90 kDa as measured by polyacrylamide gel electrophoresis.

8. The method of any one of paragraphs 1-7, wherein the glycosylated recombinant human IDS precursor contains a formylglycine.

9. The method of any one of paragraphs 1-8, wherein the glycosylated recombinant human IDS precursor (a) is α2,6-sialylated; (b) does not contain detectable NeuGc; (c) does not contain detectable α-Gal antigen; (d) contains tyrosine-sulfation; and/or (e) is mannose-6-phosphorylated.

10. The method of any one of paragraphs 1-9, in which the glycosylated recombinant human IDS precursor comprises the amino acid sequence of SEQ ID NO. 1.

11. The method of any one of paragraphs 1-10, wherein the recombinant nucleotide expression vector is an AAV9 or AAVrh10 vector.
12. The method of any one of paragraphs 1-11, wherein the human subject's brain mass is converted from the human subject's brain volume by multiplying the human subject's brain volume in cm$^3$ by a factor of 1.046 g/cm$^3$, wherein the human subject's brain volume is obtained from the human subject's brain MRI.
13. The method of any one of paragraphs 1-12, wherein the recombinant nucleotide expression vector is administered at a dose of about $1.3 \times 10^{10}$ GC/g brain mass as determined by MRI, or about $6.5 \times 10^{10}$ GC/g brain mass as determined by MRI.
14. The method of any one of paragraphs 1-13, wherein the recombinant nucleotide expression vector is administered via intracisternal (IC) administration.
15. The method of any one of paragraphs 1-13, wherein the recombinant nucleotide expression vector is administered via intracerebroventricular (ICV) administration.
16. The method of any one of paragraphs 1-15, wherein the recombinant nucleotide expression vector is administered at a volume that does not exceed 10% of the total cerebrospinal fluid volume of the human subject.
17. The method of any one of paragraphs 1-16, wherein the glycosylated recombinant human IDS precursor is delivered to lysosomes of cells in the CNS of the human subject.
18. The method of any one of paragraphs 1-17, further comprising administering an immune suppression therapy to the human subject before or concurrently with the human IDS precursor treatment and optionally continuing immune suppression therapy thereafter.
19. The method of paragraph 18, wherein the immune suppression therapy comprises administering one or more corticosteroids, sirolimus, and/or tacrolimus.
20. The method of paragraph 19, wherein the one or more corticosteroids are methylprednisolone and/or prednisone.
21. The method of any one of paragraphs 18-20, further comprising administering one or more antibiotics to the human subject before or concurrently with the immune suppression therapy.
22. The method of paragraph 21, wherein the one or more antibiotics are trimethoprim, sulfamethoxazole, pentamidine, dapsone, and/or atovaquone.
23. The method of any one of paragraphs 18-22, further comprising administering one or more antifungal therapies to the human subject before or concurrently with the immune suppression therapy.
24. The method of any one of paragraphs 1-23, further comprising a step of measuring one or more of the following biomarkers after administration of the recombinant nucleotide expression vector: (a) level of glycosaminoglycans (GAGs) in CSF; (b) level of iduronate-2-sulfatase (I2S) in CSF; (c) level of GAGs in plasma; (d) level of I2S in plasma; (e) level of leukocyte I2S enzyme activity; and (f) level of GAGs in urine.
25. The method of paragraph 24, wherein the GAGs in CSF comprise heparin sulfate in CSF.
26. The method of paragraph 24, wherein the GAGs in CSF are heparin sulfate in CSF.
27. The method of any one of paragraphs 24-26, wherein the GAGs in plasma comprise heparin sulfate in plasma.
28. The method of any one of paragraphs 24-26, wherein the GAGs in plasma are heparin sulfate in plasma.
29. The method of any one of paragraphs 24-28, wherein the GAGs in urine comprise heparin sulfate in urine.
30. The method of any one of paragraphs 24-28, wherein the GAGs in urine are heparin sulfate in urine.
31. The method of any one of paragraphs 24-30, wherein the step of measuring comprises mearing level of heparin sulfate in CSF.
32. The method of any one of paragraphs 24-31, wherein the step of measuring comprises measuring level of leukocyte I2S enzyme activity.

3.1.2. Set 2
1. A method for treating a human subject diagnosed with mucopolysaccharidosis type II (MPS 11), comprising delivering to the cerebrospinal fluid (CSF) of the human subject a therapeutically effective amount of a glycosylated recombinant human iduronate-2-sulfatase (IDS) precursor produced by human neuronal or human glial cells, wherein the glycosylated recombinant human IDS precursor is delivered by administration of a recombinant nucleotide expression vector encoding human IDS, wherein the recombinant nucleotide expression vector is administered at a dose that is dependent on the human subject's brain mass, and wherein the brain mass is determined by brain magnetic resonance imaging (MRI) of the human subject's brain.
2. The method of paragraph 1, wherein the glycosylated recombinant human IDS precursor is secreted at a detectable level.
3. The method of paragraph 1 or 2, wherein the human neuronal or human glial cells carry at least one mutation in the endogenous gene encoding human IDS precursor.
4. The method of any one of paragraphs 1-3, wherein the human neuronal or human glial cells are transduced with a recombinant adeno-associated virus vector (rAAV).
5. The method of any one of paragraphs 1-4, wherein the glycosylated recombinant human IDS precursor is expressed under the control of a CB7 promoter.
6. The method of any one of paragraphs 1-5, wherein the glycosylated recombinant human IDS precursor is expressed from a cDNA encoding human IDS precursor.
7. The method of any one of paragraphs 1-6, wherein the glycosylated recombinant human IDS precursor is about 90 kDa as measured by polyacrylamide gel electrophoresis.
8. The method of any one of paragraphs 1-7, wherein the glycosylated recombinant human IDS precursor contains a formylglycine.
9. The method of any one of paragraphs 1-8, wherein the glycosylated recombinant human IDS precursor (a) is α2,6-sialylated; (b) does not contain detectable NeuGc; (c) does not contain detectable α-Gal antigen; (d) contains tyrosine-sulfation; and/or (e) is mannose-6-phosphorylated.
10. The method of any one of paragraphs 1-9, in which the glycosylated recombinant human IDS precursor comprises the amino acid sequence of SEQ ID NO. 1.
11. The method of any one of paragraphs 1-10, wherein the recombinant nucleotide expression vector is an AAV9 or AAVrh10 vector.
12. The method of any one of paragraphs 1-11, wherein the human subject's brain mass is converted from the human subject's brain volume by multiplying the human subject's brain volume in cm$^3$ by a factor of 1.046 g/cm$^3$, wherein the human subject's brain volume is obtained from the human subject's brain MRI.

13. The method of any one of paragraphs 1-12, wherein the recombinant nucleotide expression vector is administered at a dose of about $1.3 \times 10^{10}$ GC/g brain mass as determined by MRI, or about $6.5 \times 10^{10}$ GC/g brain mass as determined by MRI.

14. The method of any one of paragraphs 1-12, wherein the recombinant nucleotide expression vector is administered at a dose of about $2.0 \times 10^{11}$ GC/g brain mass or about $2.9 \times 10^{11}$ GC/g brain mass as determined by MRI.

15. The method of any one of paragraphs 1-12, wherein the human subject is 5 years old or older and less than 18 years old.

16. The method of paragraph 15, wherein the recombinant nucleotide expression vector is administered at a dose of about $6.5 \times 10^{10}$ GC/g brain mass as determined by MRI.

17. The method of paragraph 15, wherein the recombinant nucleotide expression vector is administered at a dose according to the table below:

| Brain Mass (in g) | | Target Brain Mass (in g) | Dose: Total GC by Poly-A-specific PCR assay ($6.5 \times 10^{10}$ GC/g brain mass) |
|---|---|---|---|
| Min | Max | | |
| 801 | 900 | 850 | $5.5 \times 10^{13}$ |
| 901 | 1050 | 975 | $6.3 \times 10^{13}$ |
| 1051 | 1200 | 1125 | $7.3 \times 10^{13}$ |
| 1201 | — | 1300 | $8.5 \times 10^{13}$ |

18. The method of any one of paragraphs 1-12, wherein the human subject is 4 months old or older and less than 5 years old.

19. The method of paragraph 18, wherein the recombinant nucleotide expression vector is administered at a dose chosen from Dose 1 or Dose 2 according to the table below:

| Brain Mass (in g) | | | Dose Levels | |
|---|---|---|---|---|
| | | | Dose 1 Total GC by Poly-A specific PCR assay ($1.3 \times 10^{10}$ GC/g brain mass) | Dose 2 Total GC by Poly-A specific PCR assay ($6.5 \times 10^{10}$ GC/g brain mass) |
| Min | Max | Target | | |
| — | 700 | 650 | $8.5 \times 10^{12}$ | $4.2 \times 10^{13}$ |
| 701 | 800 | 750 | $9.8 \times 10^{12}$ | $4.9 \times 10^{13}$ |
| 801 | 900 | 850 | $1.1 \times 10^{13}$ | $5.5 \times 10^{13}$ |
| 901 | 1050 | 975 | $1.3 \times 10^{13}$ | $6.3 \times 10^{13}$ |
| 1051 | 1200 | 1125 | $1.5 \times 10^{13}$ | $7.3 \times 10^{13}$ |
| 1201 | — | 1300 | $1.7 \times 10^{13}$ | $8.5 \times 10^{13}$ |

20. The method of paragraph 18, wherein the recombinant nucleotide expression vector is administered at a dose according to the tables below;

| Brain Mass (in g) | | | Dose 3 Total GC by Poly-A-specific PCR assay ($2.0 \times 10^{11}$ GC/g brain mass) |
|---|---|---|---|
| Min | Max | Target | |
| — | 474 | 450 | $9.0 \times 10^{13}$ |
| 475 | 524 | 500 | $1.0 \times 10^{14}$ |
| 525 | 574 | 550 | $1.1 \times 10^{14}$ |
| 575 | 624 | 600 | $1.2 \times 10^{14}$ |
| 625 | 674 | 650 | $1.3 \times 10^{14}$ |
| 675 | 724 | 700 | $1.4 \times 10^{14}$ |
| 725 | 774 | 750 | $1.5 \times 10^{14}$ |
| 775 | 824 | 800 | $1.6 \times 10^{14}$ |
| 825 | 874 | 850 | $1.7 \times 10^{14}$ |
| 875 | 924 | 900 | $1.8 \times 10^{14}$ |
| 925 | 974 | 950 | $1.9 \times 10^{14}$ |
| 975 | 1024 | 1000 | $2.0 \times 10^{14}$ |
| 1025 | 1074 | 1050 | $2.1 \times 10^{14}$ |
| 1075 | 1124 | 1100 | $2.2 \times 10^{14}$ |
| 1125 | 1174 | 1150 | $2.3 \times 10^{14}$ |
| 1175 | 1224 | 1200 | $2.4 \times 10^{14}$ |
| 1225 | 1274 | 1250 | $2.5 \times 10^{14}$ |
| 1275 | >1300 | 1300 | $2.6 \times 10^{14}$ |

Total Dose Administered by Brain Mass Dose 3 EC

| Brain Mass (in g) | | | Dose 3 EC Total GC by Transgene PCR assay ($2.9 \times 10^{11}$ GC/g brain mass) |
|---|---|---|---|
| Min | Max | Target | |
| — | 474 | 450 | $1.3 \times 10^{14}$ |
| 475 | 524 | 500 | $1.5 \times 10^{14}$ |
| 525 | 574 | 550 | $1.6 \times 10^{14}$ |
| 575 | 624 | 600 | $1.8 \times 10^{14}$ |
| 625 | 674 | 650 | $1.9 \times 10^{14}$ |
| 675 | 724 | 700 | $2.1 \times 10^{14}$ |
| 725 | 774 | 750 | $2.2 \times 10^{14}$ |
| 775 | 824 | 800 | $2.4 \times 10^{14}$ |
| 825 | 874 | 850 | $2.4 \times 10^{14}$ |
| 875 | 924 | 900 | $2.6 \times 10^{14}$ |
| 925 | 974 | 950 | $2.8 \times 10^{14}$ |
| 975 | 1024 | 1000 | $2.9 \times 10^{14}$ |
| 1025 | 1074 | 1050 | $3.1 \times 10^{14}$ |
| 1075 | 1124 | 1100 | $3.2 \times 10^{14}$ |
| 1125 | 1174 | 1150 | $3.4 \times 10^{14}$ |
| 1175 | 1224 | 1200 | $3.5 \times 10^{14}$ |
| 1225 | 1274 | 1250 | $3.7 \times 10^{14}$ |
| 1275 | >1300 | 1300 | $3.8 \times 10^{14}$ |

21. The method of any one of paragraphs 1-20, wherein the recombinant nucleotide expression vector is administered via intracisternal (IC) administration.

22. The method of any one of paragraphs 1-20, wherein the recombinant nucleotide expression vector is administered via intracerebroventricular (ICV) administration.

23. The method of any one of paragraphs 1-22, wherein the recombinant nucleotide expression vector is administered at a volume that does not exceed 10% of the total cerebrospinal fluid volume of the human subject.

24. The method of any one of paragraphs 1-23, wherein the glycosylated recombinant human IDS precursor is delivered to lysosomes of cells in the CNS of the human subject.

25. The method of any one of paragraphs 1-24, further comprising administering an immune suppression therapy to the human subject before or concurrently with the human IDS precursor treatment and optionally continuing immune suppression therapy thereafter.

26. The method of paragraph 25, wherein the immune suppression therapy comprises administering one or more corticosteroids, sirolimus, and/or tacrolimus.

27. The method of paragraph 26, wherein the one or more corticosteroids are methylprednisolone and/or prednisone.

28. The method of any one of paragraphs 25-27, further comprising administering one or more antibiotics to the human subject before or concurrently with the immune suppression therapy.
29. The method of paragraph 28, wherein the one or more antibiotics are trimethoprim, sulfamethoxazole, pentamidine, dapsone, and/or atovaquone.
30. The method of any one of paragraphs 25-29, further comprising administering one or more antifungal therapies to the human subject before or concurrently with the immune suppression therapy.
31. The method of any one of paragraphs 1-30, further comprising a step of measuring one or more of the following biomarkers after administration of the recombinant nucleotide expression vector: (a) level of glycosaminoglycans (GAGs) in CSF; (b) level of iduronate-2-sulfatase (I2S) in CSF: (c) level of GAGs in plasma; (d) level of I2S in plasma: (e) level of leukocyte I2S enzyme activity; and (f) level of GAGs in urine.
32. The method of paragraph 31, wherein the GAGs in CSF comprise heparin sulfate in CSF.
33. The method of paragraph 31, wherein the GAGs in CSF are heparin sulfate in CSF.
34. The method of any one of paragraphs 31-33, wherein the GAGs in plasma comprise heparin sulfate in plasma.
35. The method of any one of paragraphs 31-33, wherein the GAGs in plasma are heparin sulfate in plasma.
36. The method of any one of paragraphs 31-35, wherein the GAGs in urine comprise heparin sulfate in urine.
37. The method of any one of paragraphs 31-35, wherein the GAGs in urine are heparin sulfate in urine.
38. The method of any one of paragraphs 31-37, wherein the step of measuring comprises mearing level of heparin sulfate in CSF.
39. The method of any one of paragraphs 31-38, wherein the step of measuring comprises measuring level of leukocyte I2S enzyme activity.

3.1.3. Set 3

1. A method for treating hepatosplenomegaly in a human subject diagnosed with mucopolysaccharidosis type II (MPS II), the method comprising administering to the cerebrospinal fluid (CSF) of the human subject in need of treatment a recombinant adeno-associated virus vector (rAAV) encoding human iduronate-2-sulfatase (hIDS).
2. A method for treating hepatosplenomegaly and central nervous system (CNS) symptoms in a human subject diagnosed with MPS II, the method comprising administering to the CSF of the human subject in need of treatment a single dose of an rAAV encoding hIDS, wherein no additional therapy for MPS II is administered outside the CNS.
3. The method of paragraph 2, wherein the CNS symptom is cognitive ability as measured by the Bayley Scale of Infant and Toddler Development, 3rd Edition (BSID-III).
4. The method of paragraph 2, wherein the CNS symptom is language as measured by the language domain of the BSID III.
5. The method of paragraph 2, wherein the CNS symptom is motor function as determined by the motor domain of the BSID-III.
6. A method of delivering to the liver and/or spleen of a human subject diagnosed with MPS II an rAAV encoding hIDS, the method comprising administering a single dose of the rAAV to the CSF of the human subject.
7. The method of any one of paragraphs 1-6, wherein the methods results in the size of the liver decreasing by about 10%, about 20%, or about 30% compared to the size of the liver prior to administration of the rAAV.
8. The method of any one of paragraphs 1-7, wherein the method results in the size of the spleen decreasing by about 10%, about 20%, or about 30% compared to the size of the spleen prior to administration of the rAAV.
9. A method for treating a human subject diagnosed with MPS II, the method comprising (i) administering to the CSF of the human subject a therapeutically effective amount of an rAAV encoding hIDS and (ii) measuring the levels of heparin sulfate (HS) D2S6 in the CSF of the subject.
10. The method of paragraph 9, wherein the reduction in HS D2S6 correlates with improved neurocognitive parameters in the human subject.
11. The method of paragraph 9 or 10, further comprising a step of determining whether an additional treatment is required.
12. The method of paragraph 11, further comprising a step of administering an additional treatment.
13. The method of paragraph 12, wherein the additional treatment is a second administration of the same rAAV as in step (i).
14. The method of paragraph 12, wherein the additional treatment is a second administration of the same rAAV as in step (i) at a higher dose.
15. The method of paragraph 12, wherein the additional treatment is enzyme replacement therapy with recombinant idursulfase.
16. The method of anyone of paragraphs 1-15, wherein the method results in a decrease in the levels of HS D2S6 in the CSF of the subject of about 10%, about 20%, about 30, about 40%, about 50%, about 60%, about 70%, about 80%, about 90%, or more than 95% compared to the levels of HS D2S6 in the CSF of the subject prior to administration of the rAAV.
17. The method of paragraph 16, wherein the levels of HS D2S6 are determined about 2 months, about 4 months, about 6 months, about 8 months, about 10 months, about 12 months, about 18 months, about 24 months, about 3 years, about 4 years, or about 5 years after administration of the rAAV.
18. The method of paragraph 16 or 17, wherein the decrease in levels of HS D2S6 is sustained for at least 6 months, at least 9 months, at last 12 months, at least 15 months, at least 18 months, at least 21 months, or at least 24 months after administration of the rAAV.
19. The method of any one of paragraphs 1-18, wherein the rAAV is administered at a dose of about $1.3 \times 10^{10}$ GC/g brain mass, about $6.5 \times 10^{10}$ GC/g brain mass, or about $2 \times 10^{11}$ GC/g brain mass, as determined by MRI.
20. The method of any one of paragraphs 1-19, wherein the human subject is 5 years old or older and less than 18 years old.
21. The method of any one of paragraphs 1-19, wherein the human subject is 4 months old or older and less than 5 years old.
22. The method of any one of paragraphs 1-21, wherein the human subject is receiving enzyme replacement therapy (ERT) at the time of the administration of the rAAV.

23. The method of paragraph 22, wherein the human subject is not responsive to ERT.
24. The method of paragraph 22 or 23, wherein the ERT is recombinant idursulfase.
25. The method of any one of paragraph 22-24, wherein the ERT is discontinued about 6 months, about 90 months, about 12 months, about 15 months, about 18 months, about 21 months, or about 24 months after the administration of the rAAV.
26. The method of any one of paragraphs 1-25, wherein the rAAV is administered via intracisternal (IC) administration.
27. The method of any one of paragraphs 1-25, wherein the rAAV is administered via intracerebroventricular (ICV) administration.
28. The method of any one of paragraphs 1-27, wherein the rAAV is administered at a volume that does not exceed 10% of the total cerebrospinal fluid volume of the human subject.
29. The method of any one of paragraphs 1-28, wherein the rAAV is a recombinant adeno-associated virus serotype 9
30. The method of paragraph 29, wherein the rAAV contains a human IDS expression cassette, wherein expression is driven by a hybrid of the cytomegalovirus (CMV) enhancer and the chicken beta actin promoter (CB7),
31. The method of paragraph 30, wherein the human IDS expression cassette comprises (i) an IDS transgene flanked by inverted terminal repeats (ITRs), (ii) the chicken beta actin intron, and (iii) a rabbit beta-globin polyadenylation (polyA) signal.
32. The method of paragraph 31, wherein the ITRs are AAV2 ITRs.
33. The method of any one of paragraphs 30-32, wherein the human IDS expression cassette comprises a nucleic acid comprising the nucleotide sequence of SEQ ID NO:45.
34. The method of any one of paragraphs 1-33, further comprising administering an immune suppression therapy to the human subject before or concurrently with the rAAV and optionally continuing immune suppression therapy thereafter.
35. The method of paragraph 34, wherein the immune suppression therapy comprises administering one or more corticosteroids, sirolimus, and/or tacrolimus.
36. The method of paragraph 35, wherein the one or more corticosteroids are methylprednisolone and/or prednisone.
37. The method of any one of paragraphs 1-36, further comprising administering one or more antibiotics to the human subject before or concurrently with the rAAV.
38. The method of paragraph 37, wherein the one or more antibiotics are trimethoprim, sulfamethoxazole, pentamidine, dapsone, and/or atovaquone.
39. The method of any one of paragraphs 1-38, further comprising administering one or more antifungal therapies to the human subject before or concurrently with rAAV
40. A method of treating a human subject diagnosed with MPS II, comprising:
(a) administering a therapeutically effective amount of an rAAV encoding hIDS to the human subject, wherein the human subject was treated with ERT or is being treated with ERT; and
(b) discontinuing ERT treatment in the human subject if the level of at least one biomarker in a biological sample from the human subject is lower than a reference, wherein the biological sample was obtained from the human subject after the administering, and wherein the at least one biomarker comprises D2S6, HS, and/or total GAG.
41. A method of treating a human subject diagnosed with MPS II, comprising:
(a) administering a therapeutically effective amount of an rAAV encoding hIDS to the human subject, wherein the human subject was treated with ERT or is being treated with ERT; and
(b) discontinuing ERT treatment in the human subject if the level of at least one biomarker in a biological sample from the human subject is higher than a reference, wherein the biological sample was obtained from the human subject before the administering, and wherein the at least one biomarker is an anti-IDS antibody.
42. The method of paragraph 40, wherein the at least one biomarker is D2S6.
43. The method of any one of paragraphs 40 or 42, wherein the at least one biomarker is about or at least about 5%, 10%, 15%, 20%, 25%, 30%, 35%, 40%, 45%, 50%, 55%, 60%, 65%, 70%, 75%, 80%, 85%, 90%, 95% lower than the reference before ERT is discontinued.
44. The method of paragraph 41, wherein the at least one biomarker is about or at least about 5%, 10%, 15%, 20%, 25%, 30%, 35%, 40%, 45%, 50%, 55%, 60%, 65%, 70%, 75%, 80%, 85%, 90%, 95% higher than the reference before ERT is discontinued.
45. The method of any one of paragraphs 40-44, wherein the reference is a predetermined value.
46. The method of any one of paragraphs 40-44, wherein the reference is the level of the at least one biomarker in a biological sample obtained from the human subject prior to administration of the rAAV to the human subject.
47. The method of any one of paragraphs 40-44, wherein the reference is the level of the at least one biomarker in a biological sample obtained from a subject diagnosed with MPS II but not receiving ERT.
48. The method of any one of paragraphs 40-47, wherein the ERT treatment is discontinued on the same day that the rAAV is administered to the human subject.
49. The method of any one of paragraphs 40 or 42-47, wherein the ERT treatment is discontinued 52 weeks after the rAAV is administered to the human subject.
50. The method of any one of paragraphs 40-49, wherein the biological sample is CSF, urine, plasma, or serum.
51. A method of treating a human subject diagnosed with MPS II comprising:
(a) discontinuing ERT treatment in the human subject, wherein the human subject was treated with ERT or is being treated with ERT; and
(b) administering a therapeutically effective amount of an rAAV encoding hIDS to the human subject, wherein the administering is after ERT treatment is discontinued in the human subject.
52. The method of paragraph 51, wherein the ERT treatment is discontinued about or at least about 1 year, 6 months, 5 months, 4 months, 3 months, 2 months, 1 month, 3 weeks, 2 weeks, 1 week, 10 days, 5 days, or one day before the administering.

53. The method of any one of paragraphs 51-52, wherein the level of at least one biomarker is not detected in a biological sample from the human subject prior to the discontinuing.
54. The method of paragraph 53, wherein the at least one biomarker is an anti-AAV antibody.
55. The method of paragraph 54, wherein the anti-AAV antibody is an anti-AAV9 antibody.
56. The method of any one of paragraphs 51-55, wherein the biological sample is serum.
57. A method of determining efficacy or monitoring efficacy of MPS II treatment in a human subject, comprising administering a therapeutically effective amount of an rAAV encoding hIDS to the human subject, wherein a decrease in the level of D2S6 in a biological sample from the human subject as compared to a reference is indicative of efficacy of the MPS II treatment in the human subject, wherein the biological sample was obtained from the human subject after the administering.
58. The method of any one of paragraphs 40-57, wherein the human subject has hepatosplenomegaly.
59. The method of paragraph 58, wherein the human subject was treated with ERT prior to the administering and/or received ERT treatment after the administering.
60. The method of any one of paragraphs 40-59, wherein the ERT is enzyme replacement therapy with recombinant idursulfase.
61. The method of any one of paragraphs 57-60, wherein the biological sample is CSF.
62. The method of any one of paragraphs 57-61, wherein the decrease in the level of D2S6 is a decrease of about or at least about 5%, 10%, 15%, 20%, 25%, 30%, 35%, 40%, 45%, 50%, 55%, 60%, 65%, 70%, 75%, 80%, 85%, 90%, 95% as compared to the reference.
63. The method of any one of paragraphs 57-62, wherein the efficacy of MPS II treatment is an improvement in at least one subtest of the Bayley Scales of Infant and Toddler Development, 3rd Edition (BSID-III) as compared to a reference.
64. The method of paragraph 63, wherein the at least one subtest is age equivalence score, cognitive developmental quotient (DQ), expressive language DQ, receptive language DQ, gross motor DQ, and/or fine motor DQ.
65. The method of paragraph 63 or 64, wherein the improvement is an improvement in DQ of about or at least about 1, 2, 3, 4, 5, 6, 7, 8, 9, 10, 12, 15, 17, 20, 25, 30, 35, 40, 45, 50, 55, 60, 65, 70, 75, 80, 85, 90, 95, 100, or more than 100.
66. The method of paragraph 64, wherein the age equivalence score is increased by about or at least about 1 month, 2 months, 3 months, 4 months, 5 months, 6 months, 7 months, 8 months, 9 months, 10 months, 11 months, 12 months, 18 months, 24 months, or more than 24 months.
67. The method of any one of paragraphs 63-66, wherein the reference is the score of the at least one subtest of the BSID-III obtained from the human subject prior to the administering.
68. The method of any one of paragraphs 63-66, wherein the reference is an average score of the at least one subtest of the BSID-III obtained from human subjects with MPS II of the same age as the human subject.
69. The method of any one of paragraphs 57-68, wherein the reference is the level of D2S6 in a biological sample obtained from the human subject prior to the administering.
70. The method of any one of paragraphs 57-69, wherein the biological sample was obtained from the human subject at about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 days, or 1, 2, 3, 4, 5, 6, 7, 8, 10, 16, 20, 24, 30, 35, 40, 45, 48, 50, 52, 56, 104 weeks, or 1, 2, 3, 4, 5, 6, 7, 8, 9, 10, 11, 12 months, or 1, 2, 3, 4, 5, 6, 7, 8, 9, or 10 years after the administering.
71. The method of any one of paragraphs 51-70, wherein the human subject is a pediatric subject.
72. The method of any one of paragraphs 57-71, wherein the efficacy of MPS II treatment is demonstrated by a decrease in the level of D2S6 of about or at least about 5%, 10%, 15%, 20%, 25%, 30%, 35%, 40%, 45%, 50%, 55%, 60%, 65%, 70%, 75%, 80%, 85%, 90%, 95% as compared to the level of D2S6 in the human subject prior to the administering.
73. The method of any one of paragraphs 1-72, wherein the rAAV is administered intrathecally to the human subject.
74. The method of any one of paragraphs 1-73, wherein the rAAV is administered to the human subject in a solution comprising:
(a) sodium chloride at a concentration of about 8.77 g/L,
(b) magnesium chloride, at a concentration of about 0.244 g/L,
(c) potassium chloride at a concentration of about 0.224 g/L,
(d) calcium chloride at a concentration of about 0.206 g/L,
(e) dextrose at a concentration of about 0.793 g/L,
(f) poloxamer 188 at a concentration of about 0.001% (volume/volume),
(g) sodium phosphate monobasic monohydrate at a concentration of about 0.0278 g/L, and
(h) sodium phosphate dibasic anhydrous at a concentration of about 0.114 g/L.
75. A method of identifying or diagnosing a subject as having neuronopathic MPS II, wherein the method comprises:
(a) determining the level of one or more heparan sulfate disaccharide(s) in a biological sample from the subject;
(b) identifying or diagnosing the subject as having neuronopathic MPS II if the level of the one or more heparan sulfate disaccharide(s) is elevated as compared to a reference level; and
(c) administering a therapeutically effective amount of an rAAV encoding hIDS to the subject identified or diagnosed as having neuronopathic MPS II.
76. The method of paragraph 75, wherein the one or more heparan sulfate disaccharide(s) comprises one or more of D0A0, D0S0, D0A6, D2S6, or a combination thereof.
77. The method of paragraph 76, wherein the one or more heparan sulfate disaccharide(s) is D2S6.
78. A method of identifying or diagnosing a subject as having neuronopathic MPS II, wherein the subject is identified or diagnosed as having neuronopathic MPS II if the level of D2S6 in a biological sample from the subject is elevated as compared to a reference level, and wherein a therapeutically effective amount of an rAAV encoding hIDS is administered to the subject identified or diagnosed as having neuronopathic MPS II.

79. The method of any one of paragraphs 75-78, wherein the biological sample is cerebrospinal fluid.

80. The method of any one of paragraphs 75-79, wherein the subject is presymptomatic or has no visible or detectable MPS II symptom.

81. The method of any one of paragraphs 75-80, wherein the subject has MPS II.

82. The method of any one of paragraphs 75-77 and 79-81, wherein the reference level is the level of the at least one or more heparan sulfate disaccharide(s) in a biological sample from one or more healthy subjects and/or from one or more non-neuronopathic subjects.

83. The method of any one of paragraphs 77-81, wherein the reference level is the level of D2S6 in a biological sample from one or more healthy subjects, and/or from one or more non-neuronopathic subjects.

84. The method of paragraph 82 or 83, wherein the biological sample from one or more healthy subjects and/or from one or more non-neuronopathic subjects is a CSF sample.

85. The method of any one of paragraphs 75-84, wherein the reference level is a pre-determined level.

86. The method of any one of paragraphs 77-85, wherein the level of D2S6 is about or at least about 12%, 13%, 14%, 15%, 16%, 17%, 18%, 19/o, 20%, 25%, 30%, 35%, 40%, or higher than 40% of the total heparan sulfate disaccharides (HS) in the biological sample from the subject.

87. The method of paragraph 86, wherein the level of D2S6 is about or at least about 20% of the total heparan sulfate disaccharides (HS) in the biological sample from the subject.

88. The method of any one of paragraphs 75-87, wherein the level of the one or more heparan sulfate disaccharide(s) or the level of D2S6 in the biological sample from the subject is about or at least about 50 ng/mL, 75 ng/mL, 80 ng/mL, 85 ng/mL, 90 ng/mL, 95 ng/mL, 100 ng/mL, 105 ng/mL, 110 ng/mL, 115 ng/mL, 120 ng/mL, 125 ng/mL, 130 ng/mL, 135 ng/mL, 140 ng/mL, 145 ng/mL, 150 ng/mL, 155 ng/mL, 160 ng/mL, 165 ng/mL, 170 ng/mL, 175 ng/mL, 180 ng/mL, 185 ng/mL, 190 ng/mL, 195 ng/mL, 200 ng/mL, 210 ng/mL, 220 ng/mL, 230 ng/mL, 240 ng/mL, 250 ng/mL, 260 ng/mL, 270 ng/mL, 280 ng/mL, 290 ng/mL, 300 ng/mL, 310 ng/mL, 320 ng/mL, 330 ng/mL, 340 ng/mL, 350 ng/mL, 360 ng/mL, 370 ng/mL, 380 ng/mL, 390 ng/mL, 400 ng/mL, or more than 400 ng/mL.

89. The method of any one of paragraphs 75-88, wherein the level of the one or more heparan sulfate disaccharide(s) or the level of D2S6 in the biological sample from the subject is about or at least about 100 ng/mL, 110 ng/mL, 120 ng/mL, 130 ng/mL, 140 ng/mL, 150 ng/mL, 160 ng/mL, 170 ng/mL, 180 ng/mL, 190 ng/mL, 200 ng/mL, or more than 200 ng/mL.

90. The method of any one of paragraphs 75-89, wherein the level of the one or more heparan sulfate disaccharide(s) or the level of D2S6 in the biological sample from the subject is elevated by about or at least about 10 ng/mL, 20 ng/mL, 30 ng/mL, 40 ng/mL, 50 ng/mL, 60 ng/mL, 70 ng/mL, 80 ng/mL, 90 ng/mL, 100 ng/mL, 150 ng/mL, 160 ng/mL, 170 ng/mL, 180 ng/mL, 190 ng/mL, 200 ng/mL, 210 ng/mL, 220 ng/mL, 230 ng/mL, 240 ng/mL, 250 ng/mL, 260 ng/mL, 270 ng/mL, 280 ng/mL, 290 ng/mL, 300 ng/mL, 310 ng/mL, 320 ng/mL, 330 ng/mL, 340 ng/mL, 350 ng/mL, 360 ng/mL, 370 ng/mL, 380 ng/mL, 390 ng/mL, 400 ng/mL, 410 ng/mL, 420 ng/mL, 430 ng/mL, 440 ng/mL, 450 ng/mL, 460 ng/mL, 470 ng/mL, 480 ng/mL, 490 ng/mL, 500 ng/mL, or more than 500 ng/mL as compared to the reference level.

91. A method of determining efficacy or monitoring efficacy of MPS I treatment in a human subject, comprising administering a therapeutically effective amount of an rAAV encoding human IDUA to the human subject, wherein a decrease in the level of I0S6 in a biological sample from the human subject as compared to a reference is indicative of efficacy of the MPS I treatment in the human subject, wherein the biological sample was obtained from the human subject after the administering.

92. The method of paragraph 91, wherein the biological sample is plasma.

93. The method of paragraph 90 or 91, wherein the human subject was treated with ERT prior to the administering and/or received ERT treatment after the administering.

94. The method of any one of paragraphs 91-93, wherein the ERT is enzyme replacement therapy with recombinant idursulfase.

95. The method of any one of paragraphs 91-94, wherein the decrease in the level of I0S6 is a decrease of about or at least about 5%, 10%, 15%, 20%, 25%, 30%, 35%, 40%, 45%, 50%, 55%, 60%, 65%, 70%, 75%, 80%, 85%, 90%, 95% as compared to the reference.

96. The method of any one of paragraphs 91-95, wherein the reference is the level of I0S6 in a biological sample obtained from the human subject prior to the administering.

97. The method of any one of paragraphs 91-95, wherein the reference is a predetermined value.

98. The method of any one of paragraphs 91-95, wherein the reference is the level of I0S6 in a biological sample obtained from another human subject diagnosed with MPS I or a population of human subjects diagnosed with MPS I.

99. The method of any one of paragraphs 91-98, wherein the efficacy of MPS I treatment is an improvement in at least one subtest of the Bayley Scales of Infant and Toddler Development, 3rd Edition (BSID-III) as compared to a reference.

100. The method of paragraph 99, wherein the at least one subtest is age equivalence score, cognitive developmental quotient (DQ), expressive language DQ, receptive language DQ, gross motor DQ, and/or fine motor DQ.

101. The method of paragraph 99 or 100, wherein the reference is the score of the at least one subtest of the BSID-III obtained from the human subject prior to the administering.

102. The method of any one of paragraphs 99-101, wherein the reference is an average score of the at least one subtest of the BSID-III obtained from human subjects with MPS I of the same age as the human subject.

103. The method of any one of paragraphs 91-102, wherein the rAAV is administered to the human subject in a solution comprising:
(a) sodium chloride at a concentration of about 8.77 g/L,
(b) magnesium chloride, at a concentration of about 0.244 g/L,
(c) potassium chloride at a concentration of about 0.224 g/L, (d) calcium chloride at a concentration of about 0.206 g/L,
(e) dextrose at a concentration of about 0.793 g/L,
(f) poloxamer 188 at a concentration of about 0.001% (volume/volume),
(g) sodium phosphate monobasic monohydrate at a concentration of about 0.0278 g/L, and
(h) sodium phosphate dibasic anhydrous at a concentration of about 0.114 g/L.

4. BRIEF DESCRIPTION OF THE DRAWINGS

FIG. 1. The amino acid sequence of human IDS (SEQ ID NO: 1). A post-translational formylglycine modification of $C^{84}$ (shown in bold in FIG. 1) is required for enzyme activity. Eight N linked glycosylation sites ($N^{31}$, $N^{115}$, $N^{144}$, $N^{246}$, $N^{280}$, $N^{325}$, $N^{513}$ and $N^{537}$) are bold and boxed. One tyrosine-O-sulfation site (Y) is bold and the full sulfation site sequence (PSSEKY$^{165}$ENTKTCRGPD (SEQ ID NO:47)) is boxed. The N-terminus of the mature 42 kDa and mature 14 kDa polypeptides are indicated by horizontal arrows. In the brain, the N-terminus of the mature 42 kDa form starts at positions 34 or 36 as follows: $T^{34}$DALNVLLI (SEQ ID NO: 54); and $A^{36}$LNVLLIIV (SEQ ID NO: 55) as indicated in FIG. 1. (See, Sleat, 2005, Proteomics 5: 1520-1532, Table S2). Two of the eight N-linked glycosylation sites, namely $N^{280}$ and $N^{116}$, are mannose-6-phophorylated in IDS obtained from human brain. (Sleat et al., 2006, Mol & Cell Procomics 5.4: 686-701, reported at Table V).

FIG. 2. Multiple sequence alignment of hIDS with known orthologs. The names of the species and protein IDs are as follows. SP|P22304|IDS_HUMAN [*Homo sapiens*]; TR|K6ZGI9_PANTR [Pan troglodytes (Chimpanzee)]; TR|K7BKV4_PANTR [Pan troglodytes (Chimpanzee)]; TR|H9FTX2_MACMU [*Macaca mulatta* (*Rhesus macaque*)]; TRF7EJG2_CALJA [*Callithrix jacchus* (White-tufted-ear marmoset)]; TR|U3DTL8_CALJA [*Callithrix jacchus* (White-tufted-ear marmoset)]; TRIG7NRX7_MACMU [*Macaca mulatta* (*Rhesus macaque*)]; TR|G7QIV9 MACFA [*Macaca fascicularis* (Crab-eating macaque; Cynomologous monkey)]; TR|H2PX10_PONAB [*Pongo abelii* (Sumatran orangutan)]; TR|A0A0D9R4D1_CHLSB [*Chlorocebus sabaeus* (Green monkey)]; TR|G1RST8|G1RST8_NOMLE [*Nomascus leucogenys* (Northern white-cheeked gibbon)]; UPI0000D9F625 [*Macaca mulatta* (*Rhesus macaque*)]; UPI000274358B [Pan paniscus (Pygmy chimpanzee; Bonobo)]; UPI00027F6FC5 [*Papio Anubis* (Olive baboon)]; UPI00027FAE03 [*Saimiri boliviensis* (Bolivian squirrel monkey)]; UPO0003ABBF28 [*Macaca fascicularis* (Crab-eating macaque; Cynomologous monkey)]; UPI000533297F [*Rhinopithecus roxellana* (Golden snub-nosed monkey; *Pygathrix roxellana*)]; UPI0005F40BD2 [*Colobus angolensis* palliates (Peters' Angolan *colobus*)] (SEQ ID NOs: 27-44).

FIG. 3. MPS 11 mutations in hIDS and corresponding disease phenotypes, mild, intermediate or severe. (from Uniprot).

FIG. 4. Human IDS processing as reported in Millat et al., 1997, Exp. Cell. Res. 230. 362-367, at FIG. 7.

Figure 5:
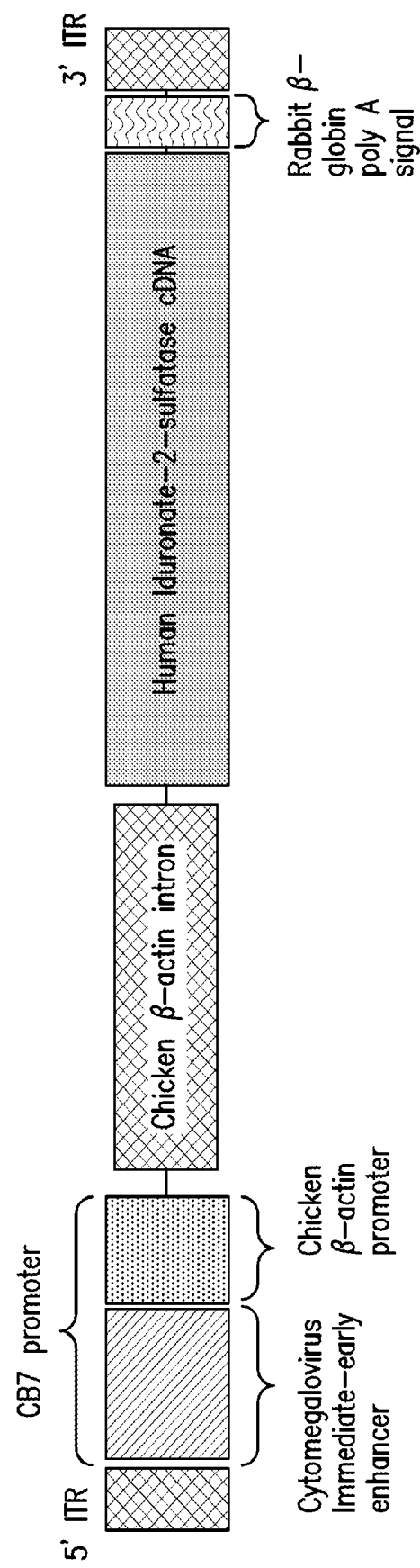

FIG. 5. Schematic Representation of Construct 1.

FIG. 6. Clustal Multiple Sequence Alignment of AAV capsids 1-9 (SEQ ID NOs: 16-26). Amino acid substitutions (shown in bold in the bottom rows) can be made to AAV9 and AAV8 capsids by "recruiting" amino acid residues from the corresponding position of other aligned AAV capsids. Sequence regions designated by "HVR"=hypervariable regions.

FIG. 7. Heparan Sulfate (HS) digestion with Heparinase.

Figure 8:
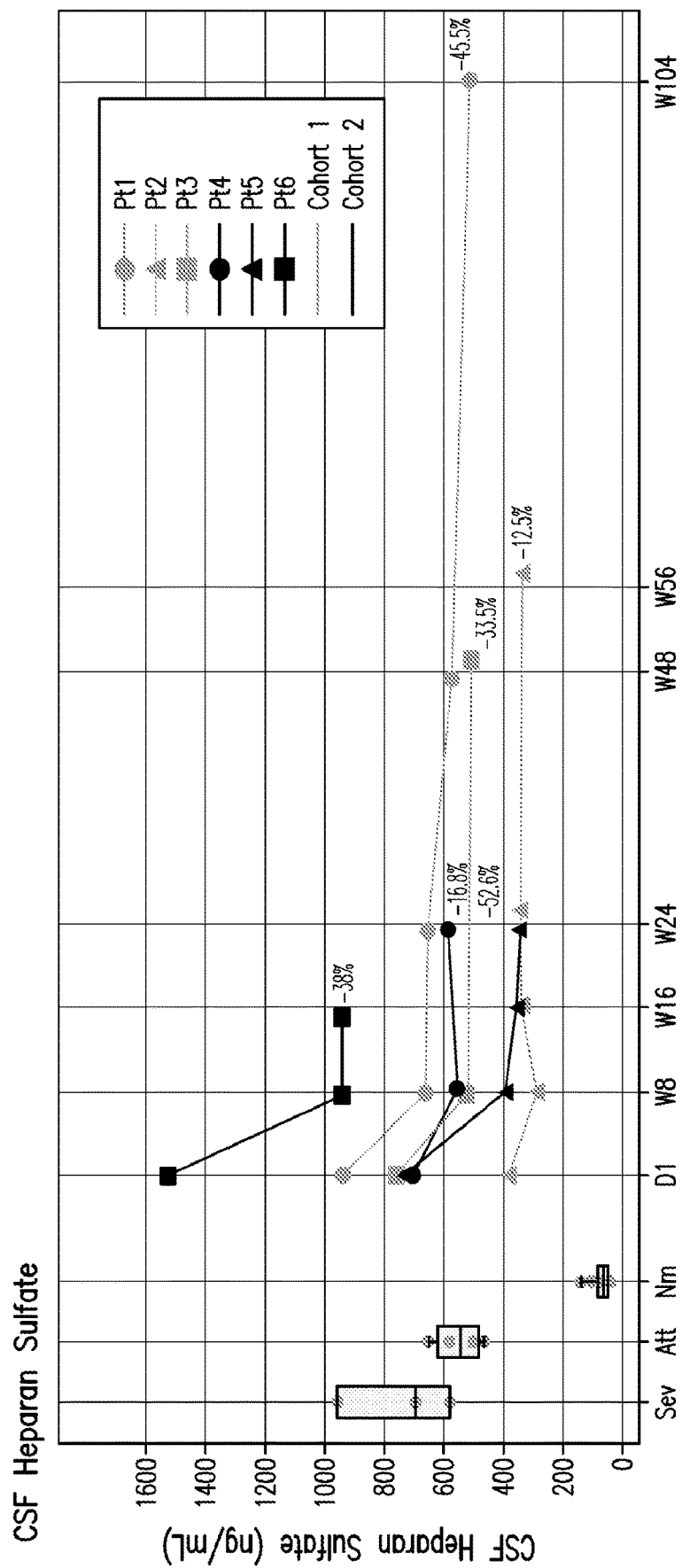

FIG. 8. Graph showing cerebral spinal fluid (CSF) heparan sulfate biomarker (ng/mL). Graph showed consistent HS decrease in the CSF after Construct 1 dosing. The median change from baseline at week 8 (N=6) was −30.3% (p-value=0.03 as measured by Wilcoxon signed rank test). The median change from baseline at the last available timepoint (N=6) was −35.8% (p-value=0.03 as measured by Wilcoxon signed rank test). The graph showed measurable CSF I2S enzyme concentration in cohort 2 after Construct 1 administration with a range of 1170-1940 pg/mL.

Figure 9:
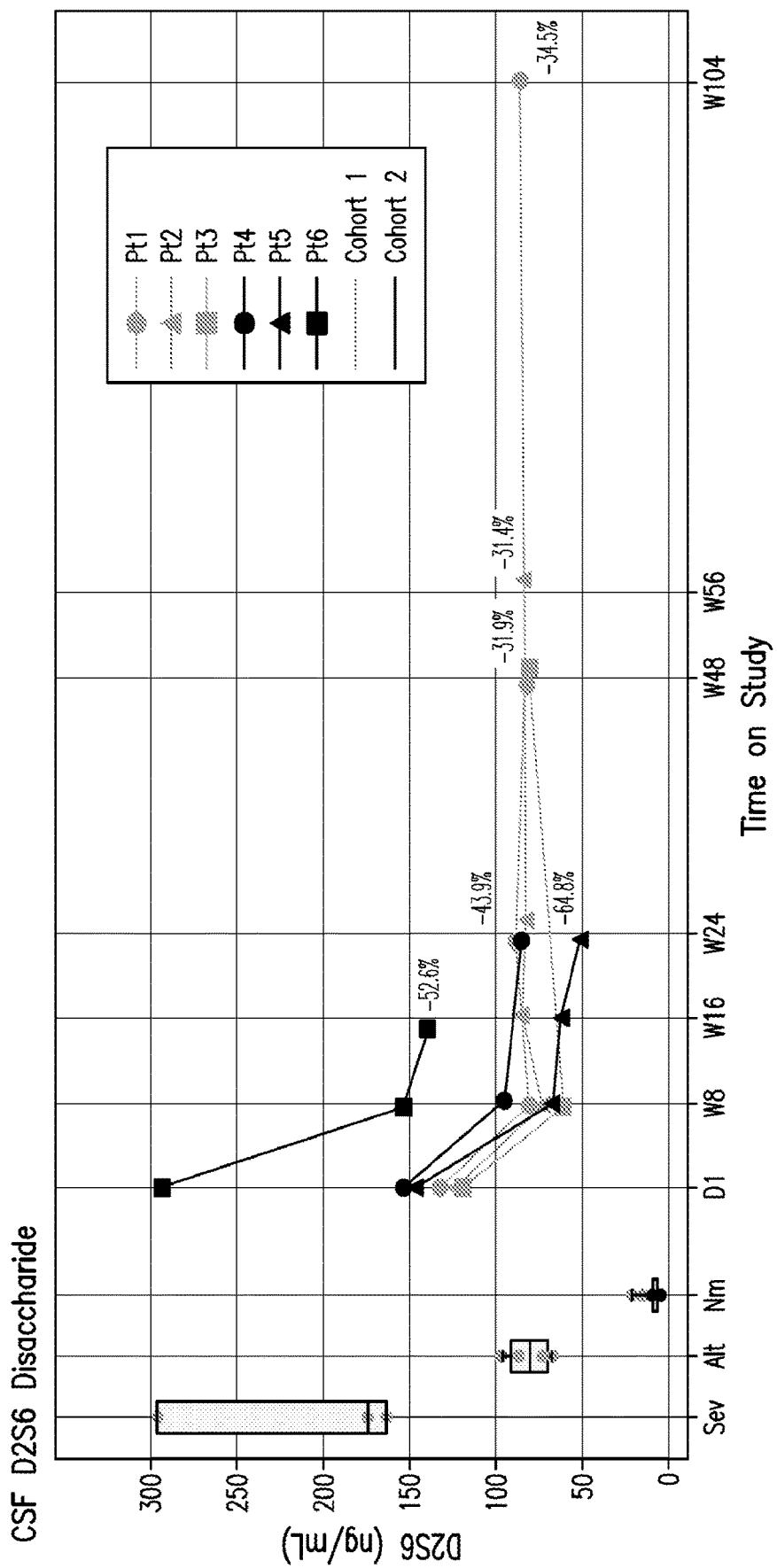

FIG. 9. Graph showing cerebral spinal fluid (CSF) D2S6 biomarker (ng/mL). The median change from baseline at week 8 (N=6) was −44.2% (p-value=0.03 as measured by Wilcoxon signed rank test). The median change from baseline at the last available timepoint (N=6) was −39.2% (p-value=0.03 as measured by Wilcoxon signed rank test).

Figure 10A:
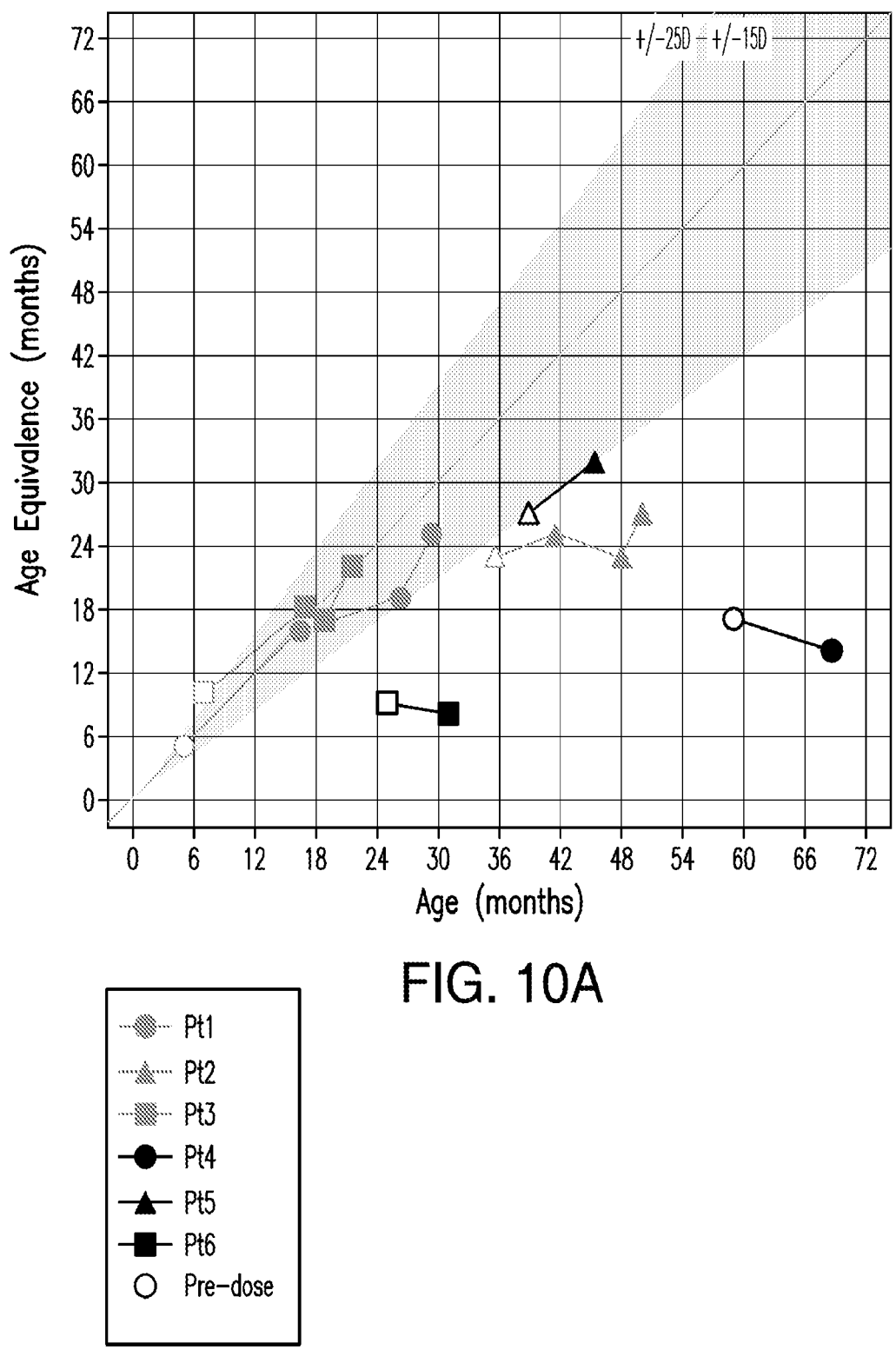
Figure 10B:
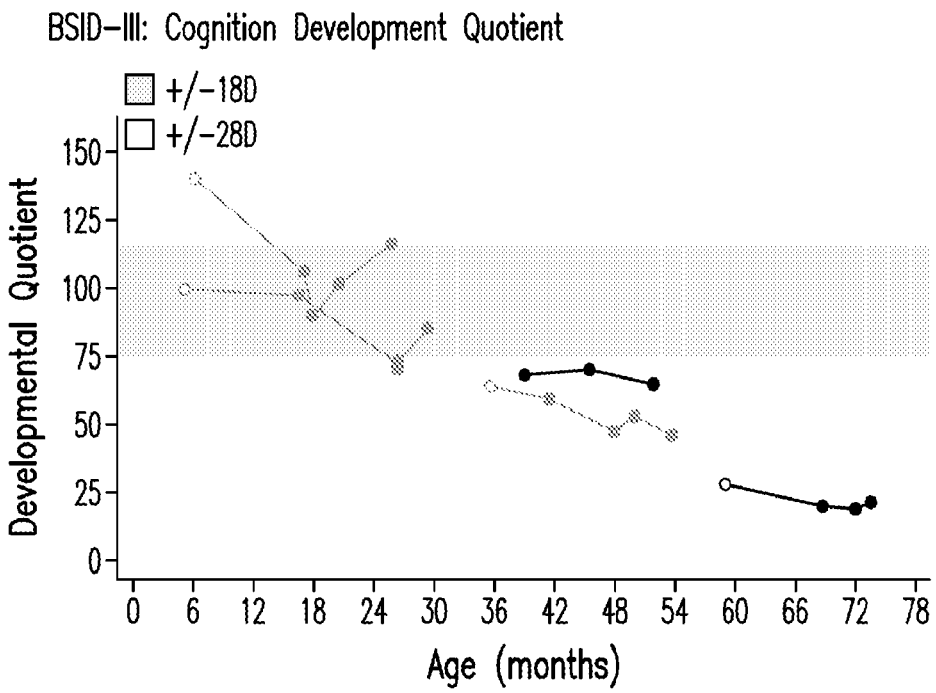
Figure 10C:
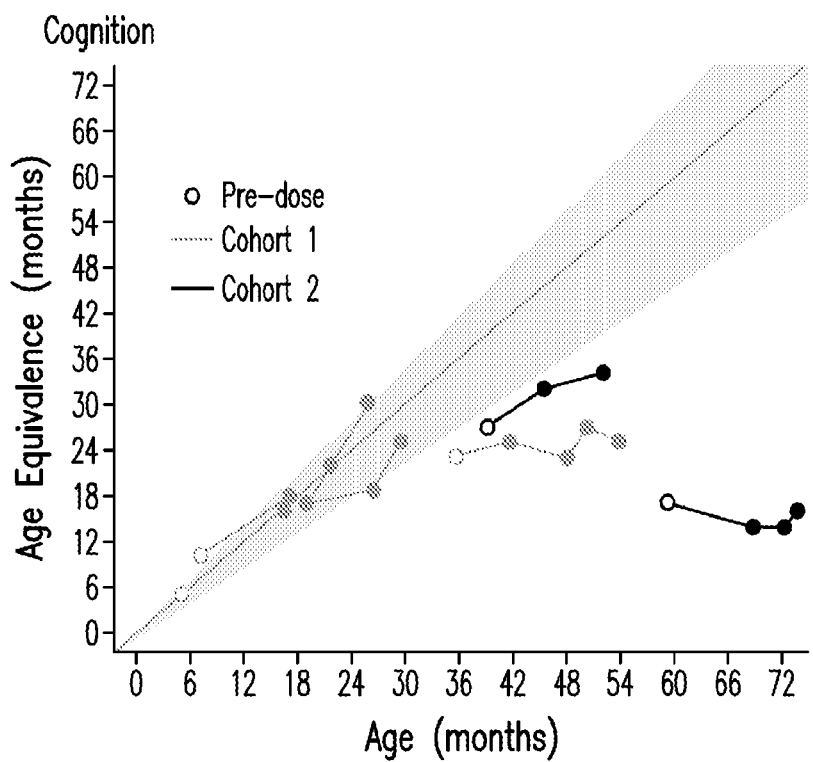

FIGS. 10A-10C. Graphs showing neurodevelopment function comparing age equivalence (months) and age (months). The Graph in FIG. 10A showed continued cognitive development in 4 of 5 patients with >6 months of follow-up. Patients 1, 3, and 5 demonstrated continued cognitive development within a normal range. Patients 2 and 4 presented with significant cognitive delay at baseline. Patient 2 has continued cognitive development. Patient 4 acquired expressive and receptive language skills. FIGS. 10B and 10C show cognitive developmental quotient and age equivalence quotient, respectively, of patients in Construct 1 gene therapy clinical trial. The graphs in FIGS. 10B and 10C show that 3 out of 4 patients who entered the study with cognitive skill above the −2SD of the normal range continued to stay above −2SD as of >6-month follow-up. One patient entered the study with significant delay in neurocognitive development at baseline but demonstrated relative stabilization following Construct 1 administration at an older age (59 months) and continued to acquire expressive and receptive language skills.

Figure 11A:
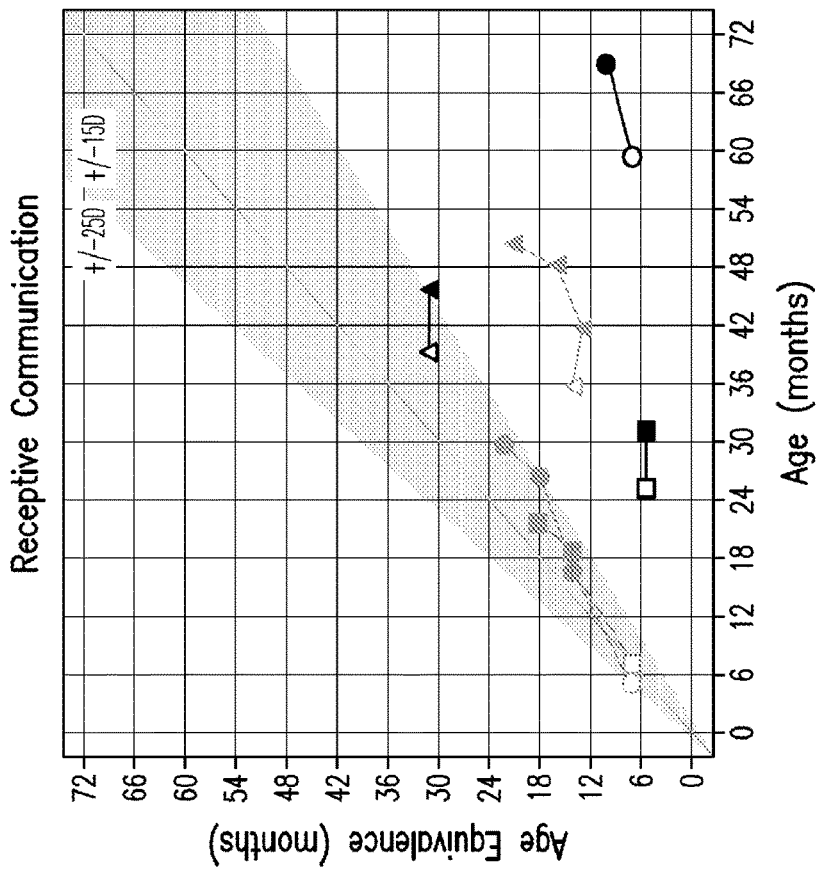
Figure 11B:
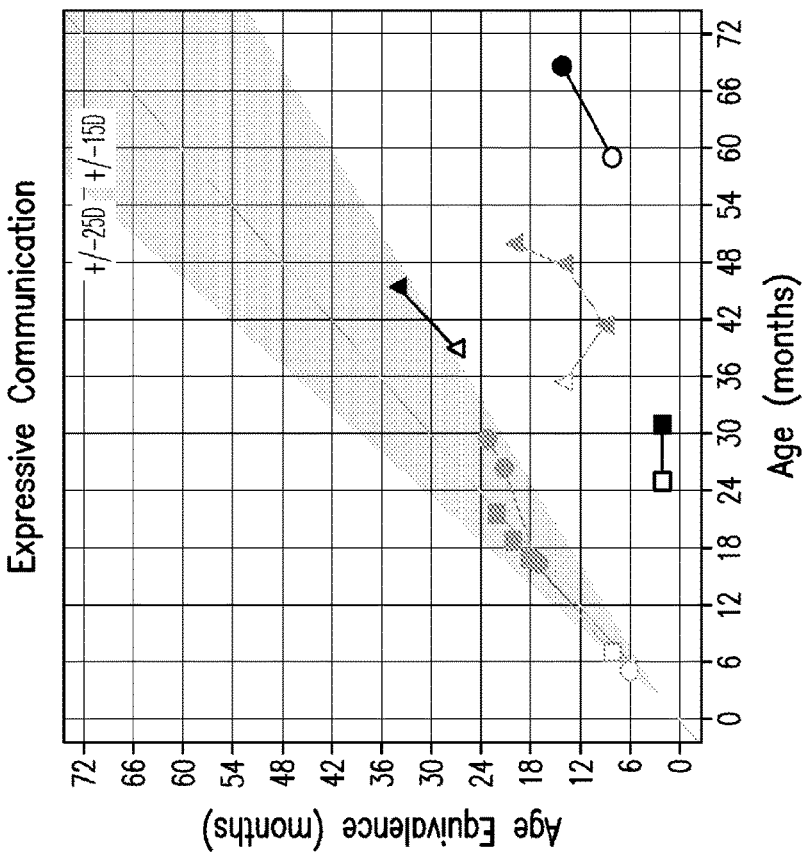

FIGS. 11A-11D. Graphs showing neurodevelopment function in terms of language and motor skills. FIG. 11A displays expressive communication; FIG. 11B displays receptive communication; FIG. 11C displays gross motor skills; and FIG. 11D displays fine motor skills. Graphs showed continued language and/or motor skills acquisition in patients with >6 months of follow-up.

Figure 12:
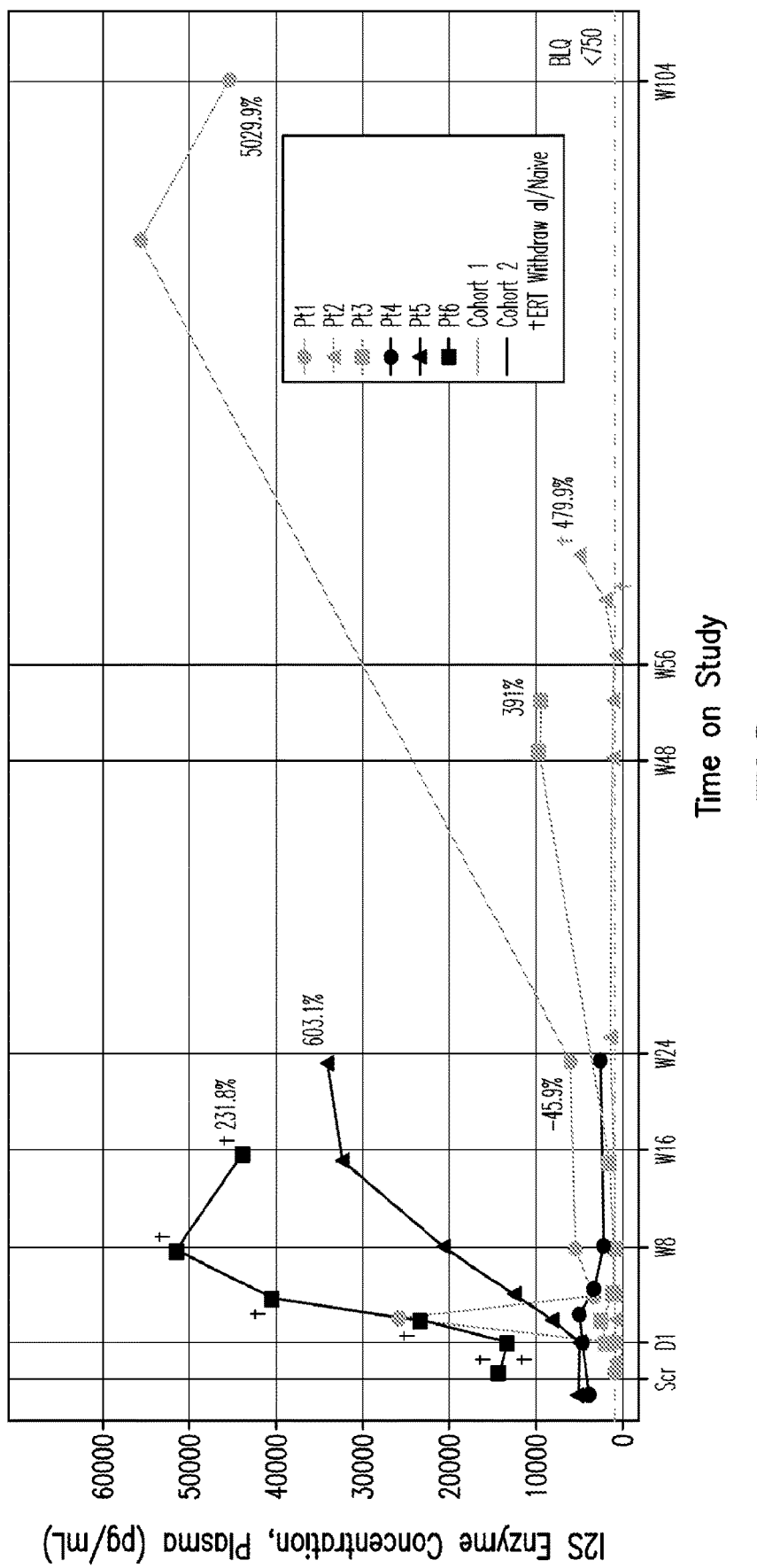

FIG. 12. Graph showing systemic efficacy by measuring plasma I2S protein concentration (μg/mL). The graph shows a general increase in plasma I2S enzyme levels in 5 out of 6 patients after Construct 1 administration (normal range (14,706 pg/mL~<100,000 pg/mL)).

Figure 13:
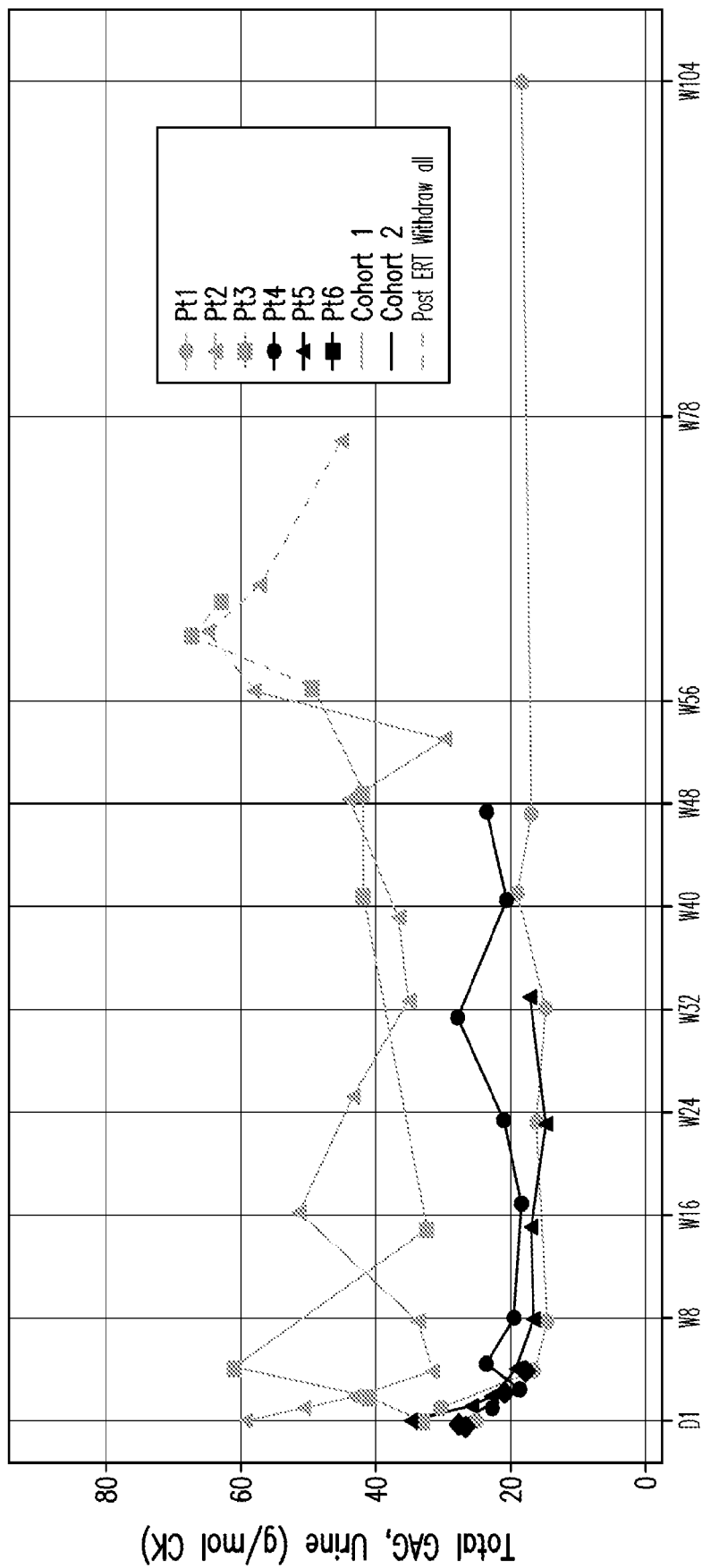

FIG. 13. Graph showing systemic efficacy by measuring urine total GAGs level (g/mol CK) in ERT-treated patients. Graph showed sustained decrease in urine GAG levels across all patients receiving ERT.

Figure 14:
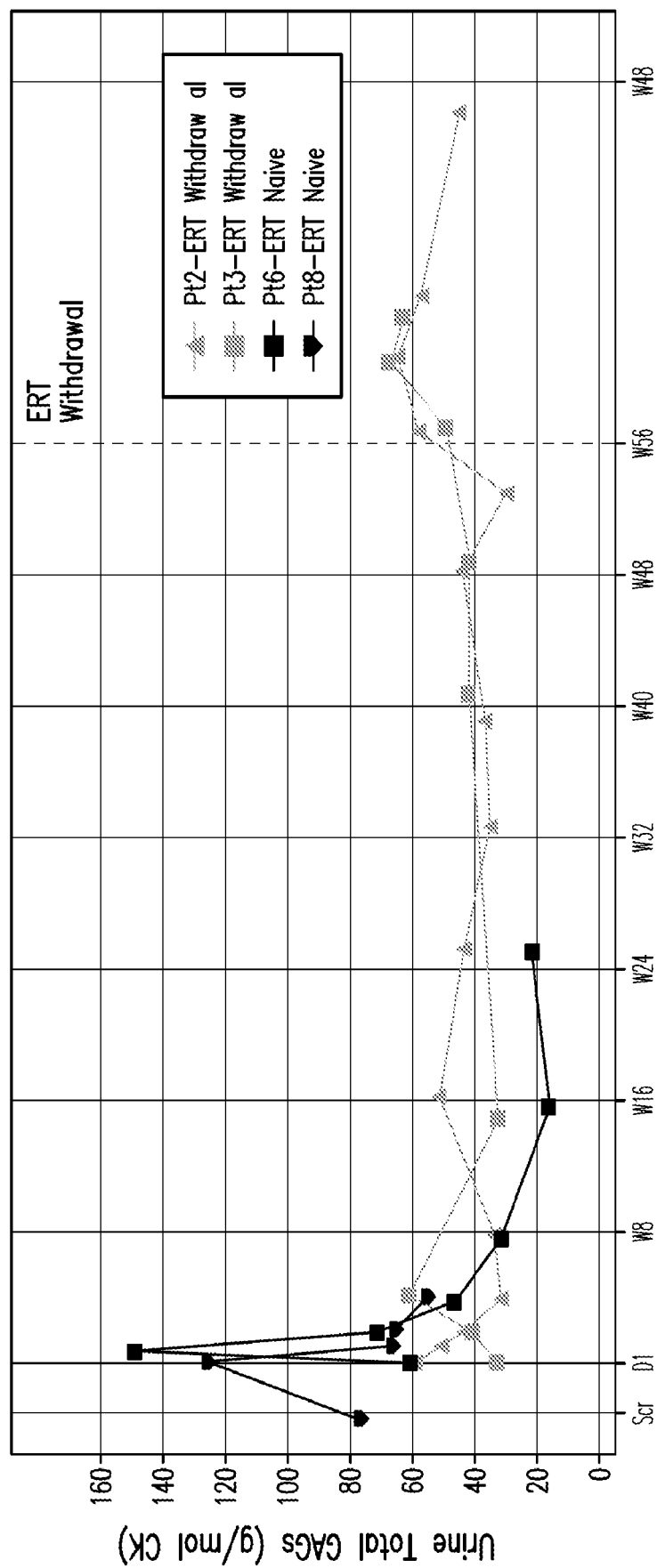

FIG. 14. Graph showing systemic efficacy by measuring urine total GAGs level (g/mol CK) in ERT naïve and ERT discontinued patients. Graphs showed a rapid decrease in urine GAGs in ERT-naïve patients after Construct 1 administration (absence of urine GAG rebound post ERT withdrawal).

Figure 15:
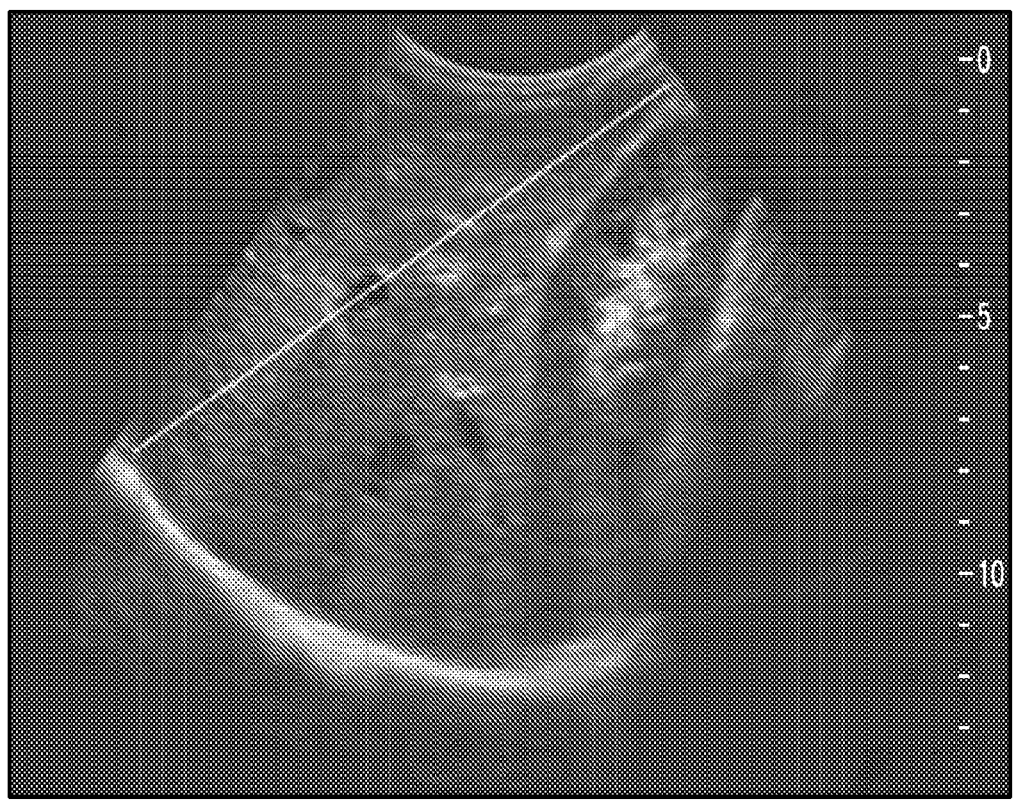

FIG. 15. Ultrasound of liver or spleen in ERT naïve patient. Liver and spleen dimensions in ERT-naïve patient decreased 24 weeks after Construct 1 administration.

Figure 16:
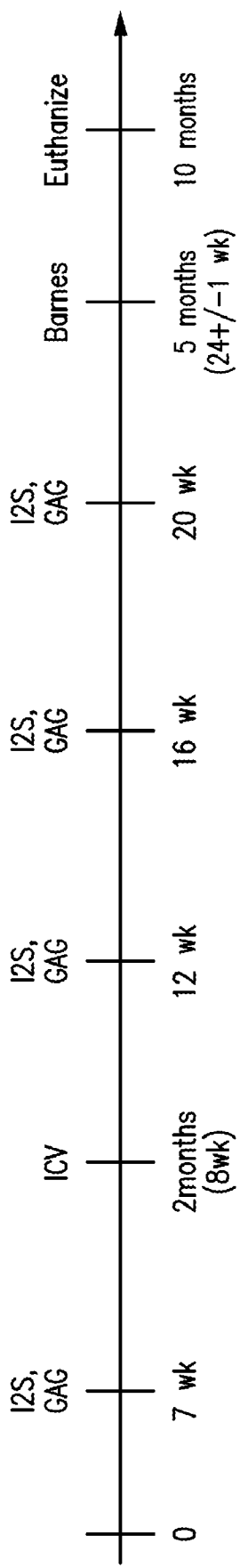

FIG. 16. Proof-of-concept Study Activities.

Figure 17:
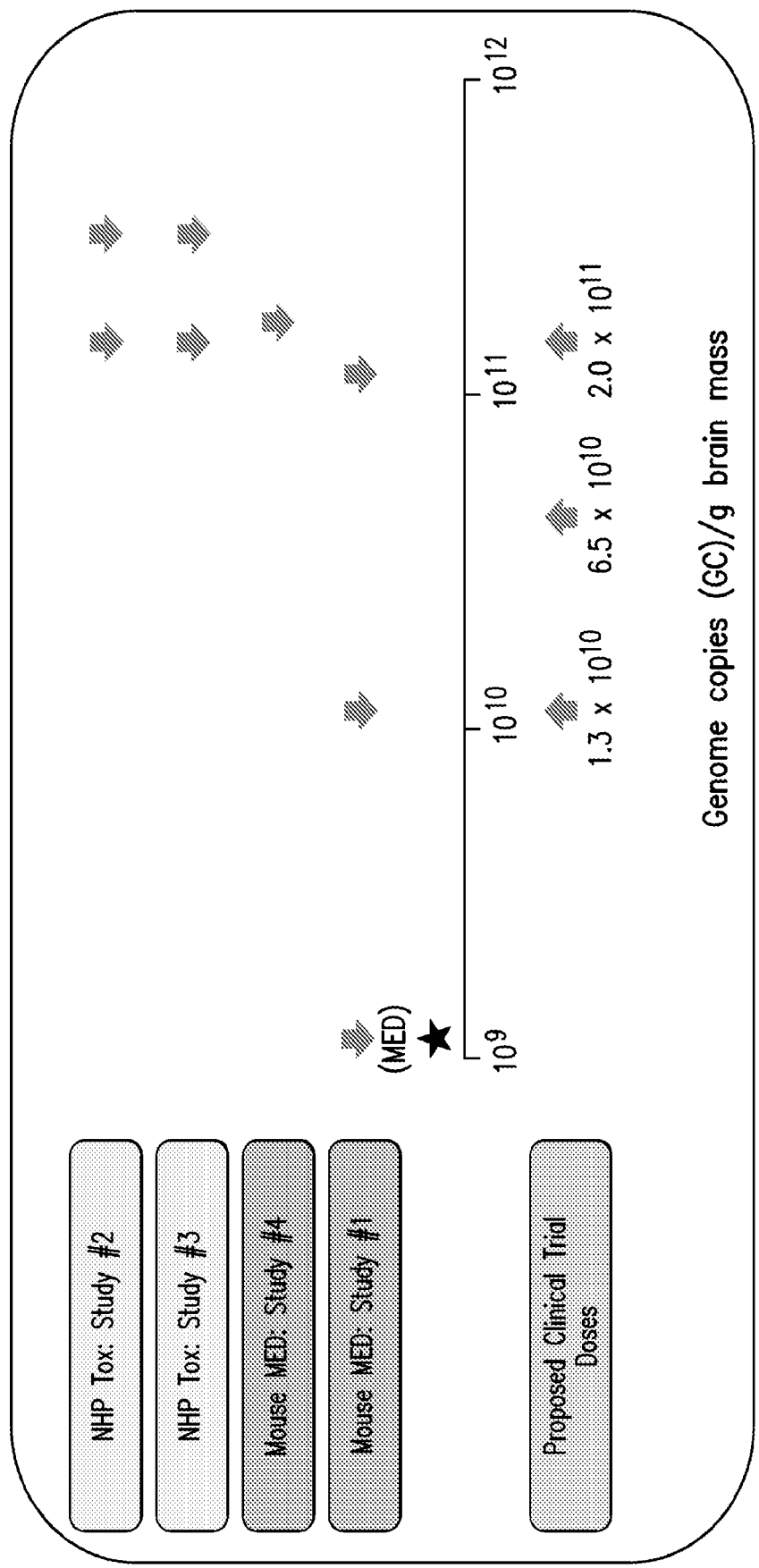

FIG. 17. Dose Rationale for the First-in-Human Clinical Trial.

Figure 18:
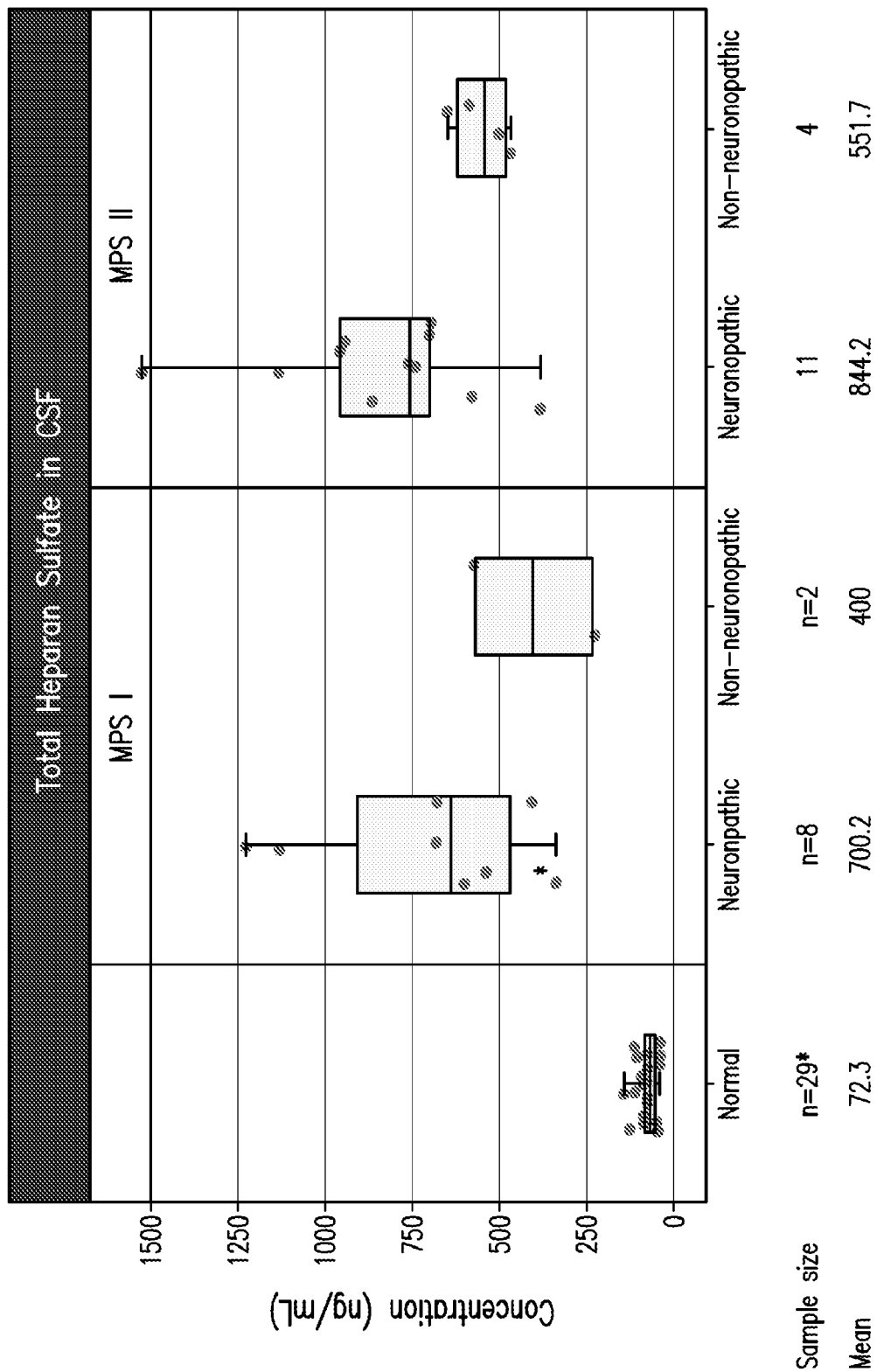

FIG. 18. Total heparan sulfate in CSF samples from healthy subjects, MPS I (neuronopathic and non-neuronopathic) subjects, and MPS II (neuronopathic and non-neuronopathic) subjects.

Figure 19B:
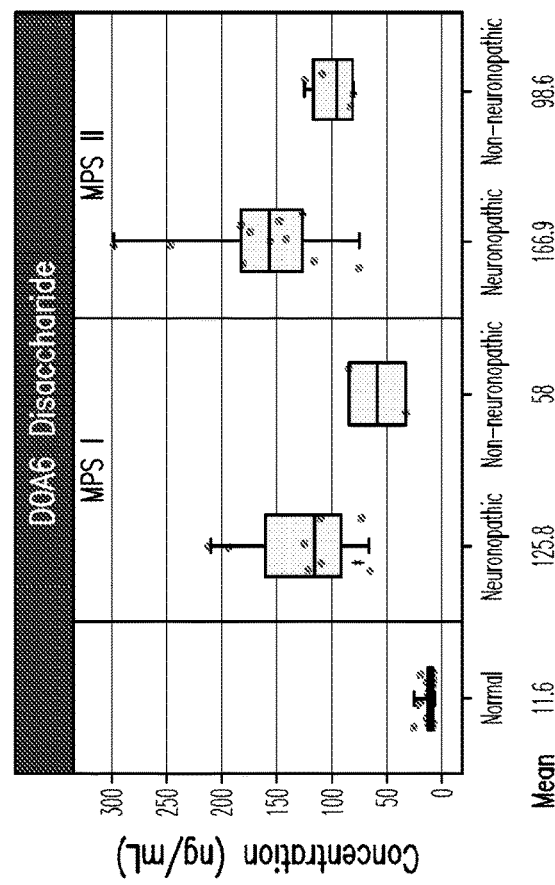
Figure 19A:
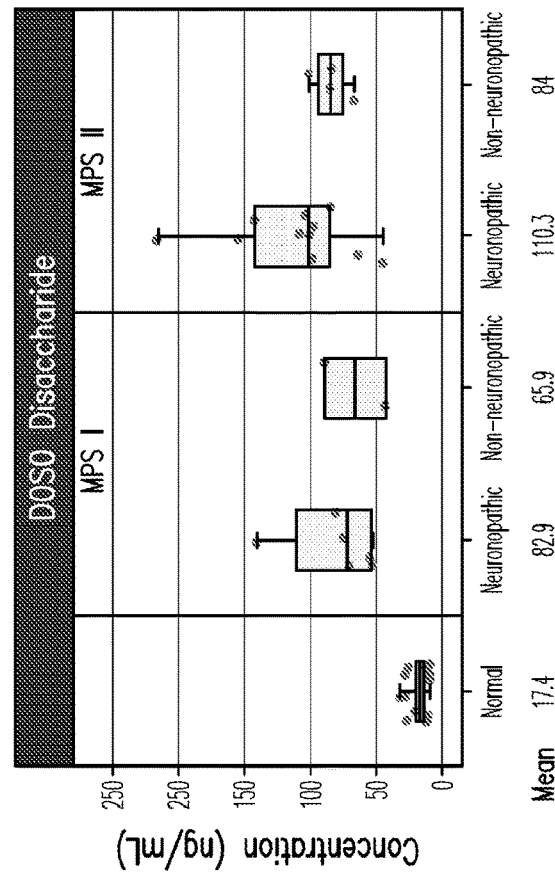
Figure 19C:
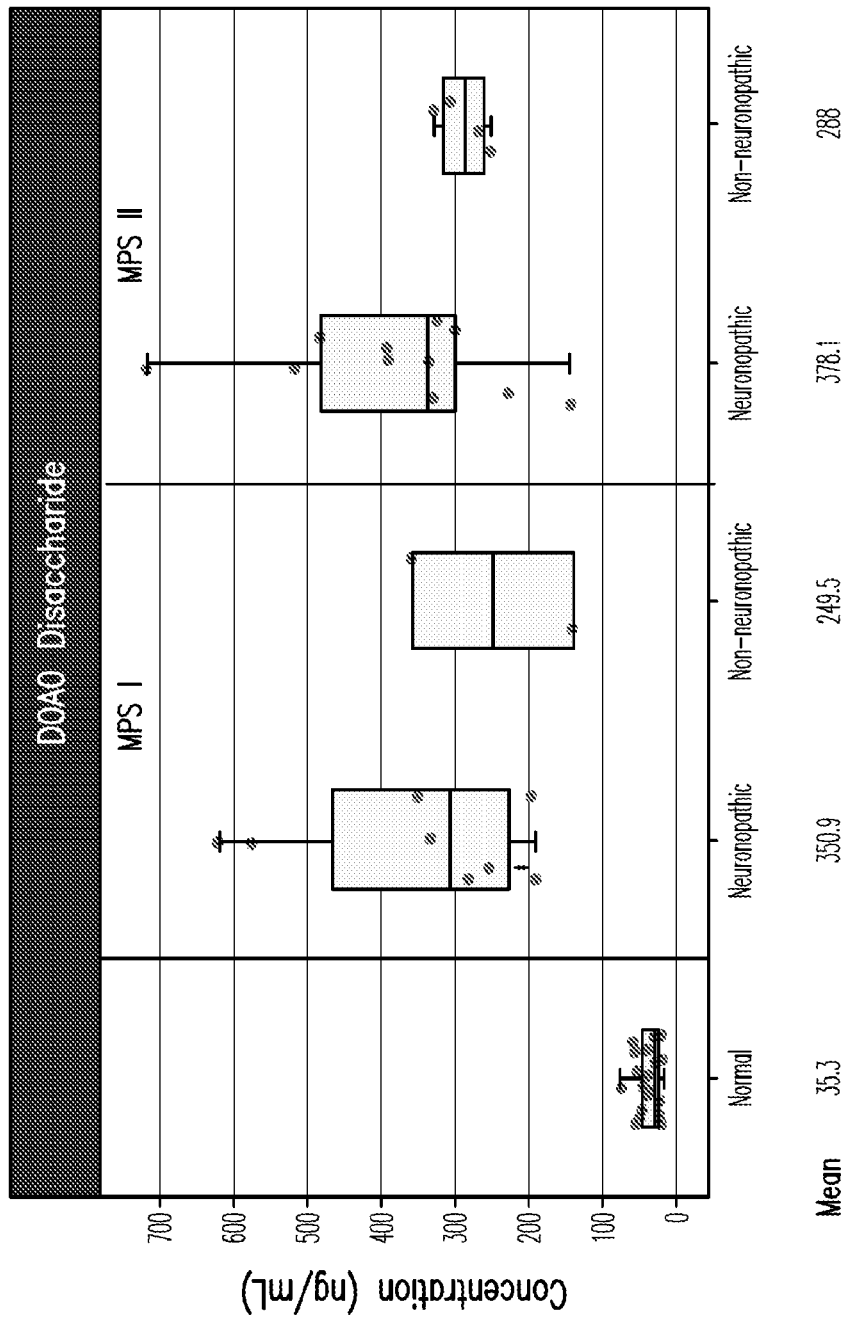

FIGS. 19A-19C. Graphs showing the level of D0S0 disaccharide (FIG. 19A), D0A6 disaccharide (FIG. 19B), and D0A0 (FIG. 19C) in healthy subjects, MPS I (neuronopathic and non-neuronopathic) subjects, and MPS II (neuronopathic and non-neuronopathic) subjects.

Figure 20:
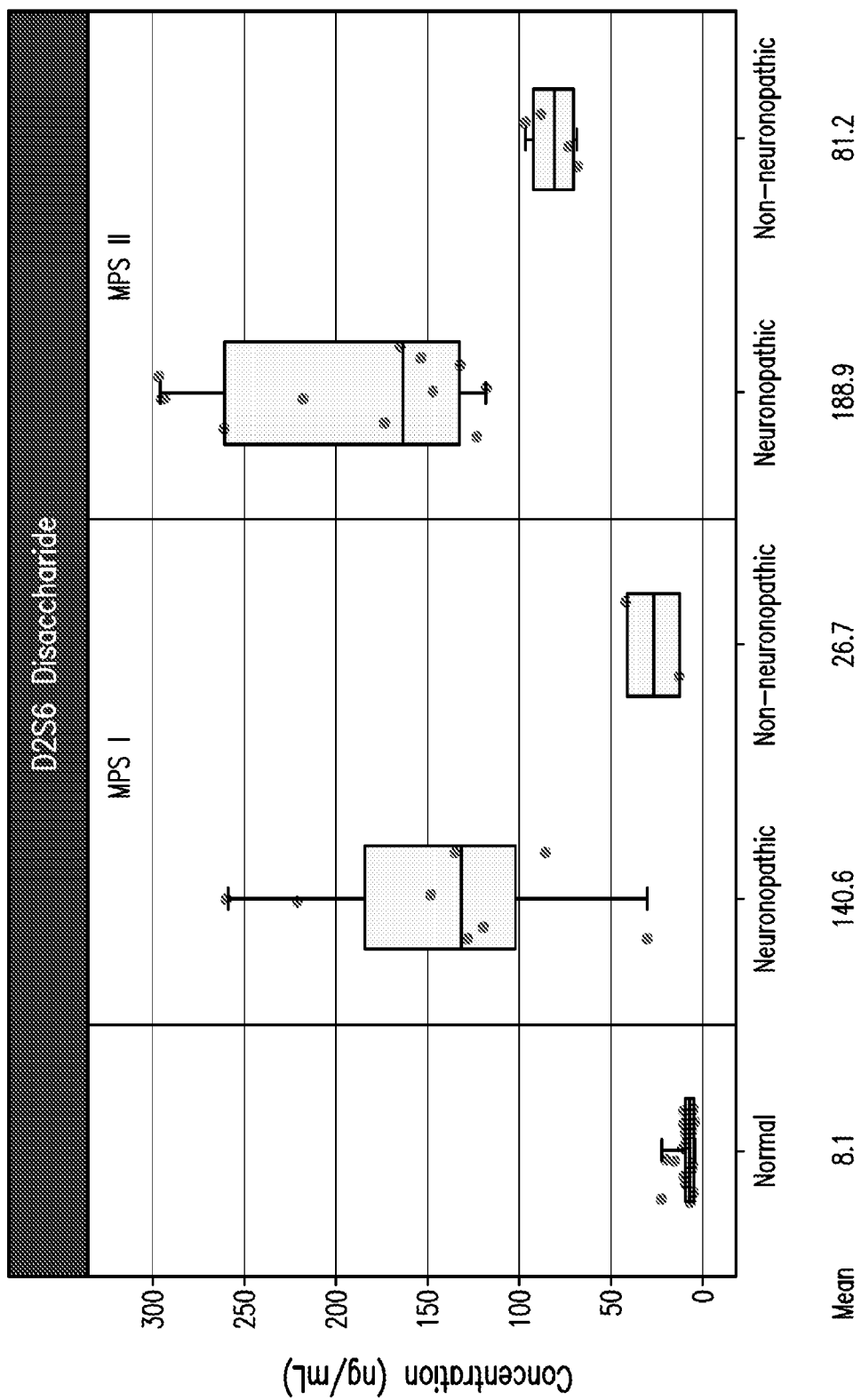

FIG. 20. Graph showing the level of D2S6 disaccharide in healthy subjects, MPS I (neuronopathic and non-neuronopathic) subjects, and MPS II (neuronopathic and non-neuronopathic) subjects.

Figure 21:
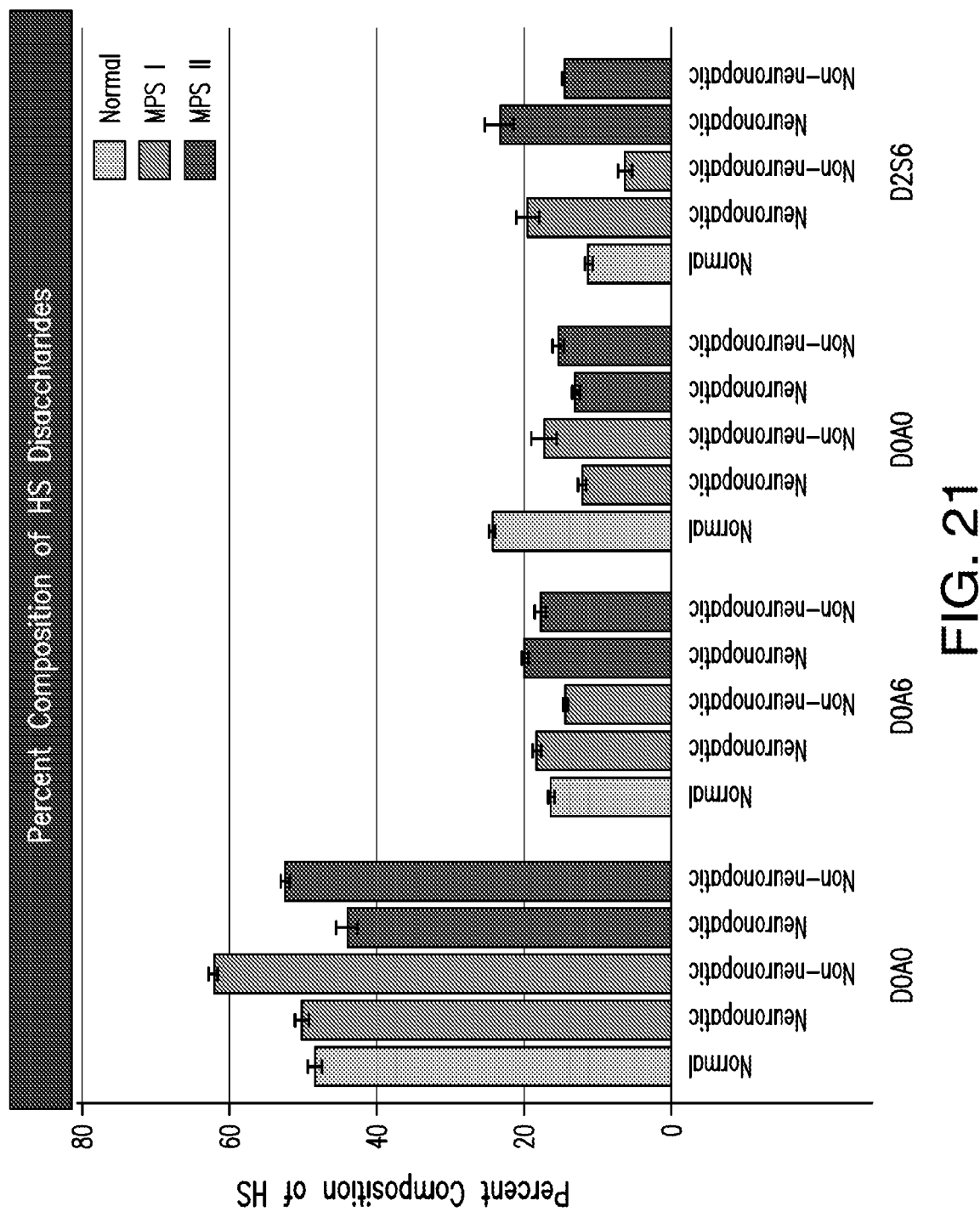

FIG. 21. Graph showing the percent composition of heparan sulfate disaccharides in healthy subjects, MPS I (neuronopathic and non-neuronopathic) subjects, and MPS II (neuronopathic and non-neuronopathic) subjects.

Figure 22:
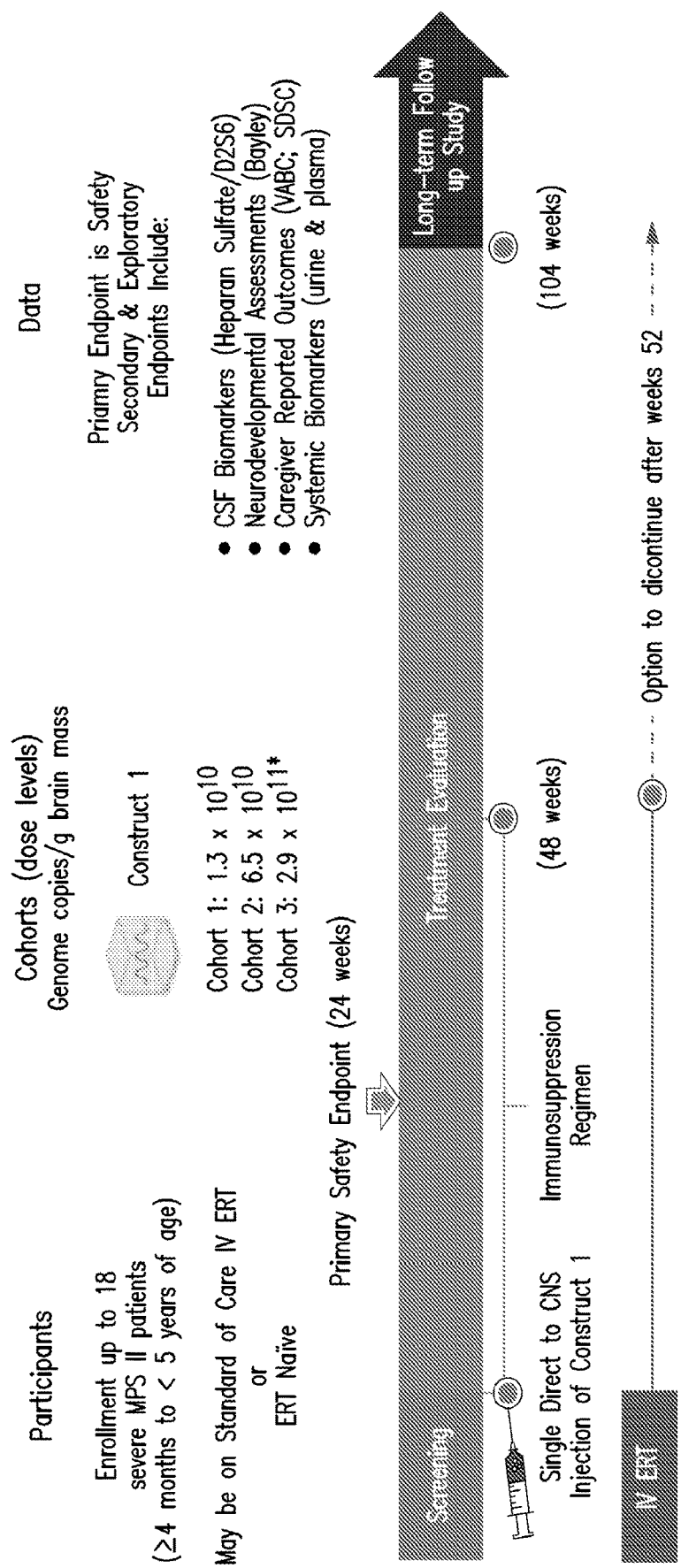

FIG. 22. Diagram showing MPS II phase 1/2 clinical study summary.

Figure 23:
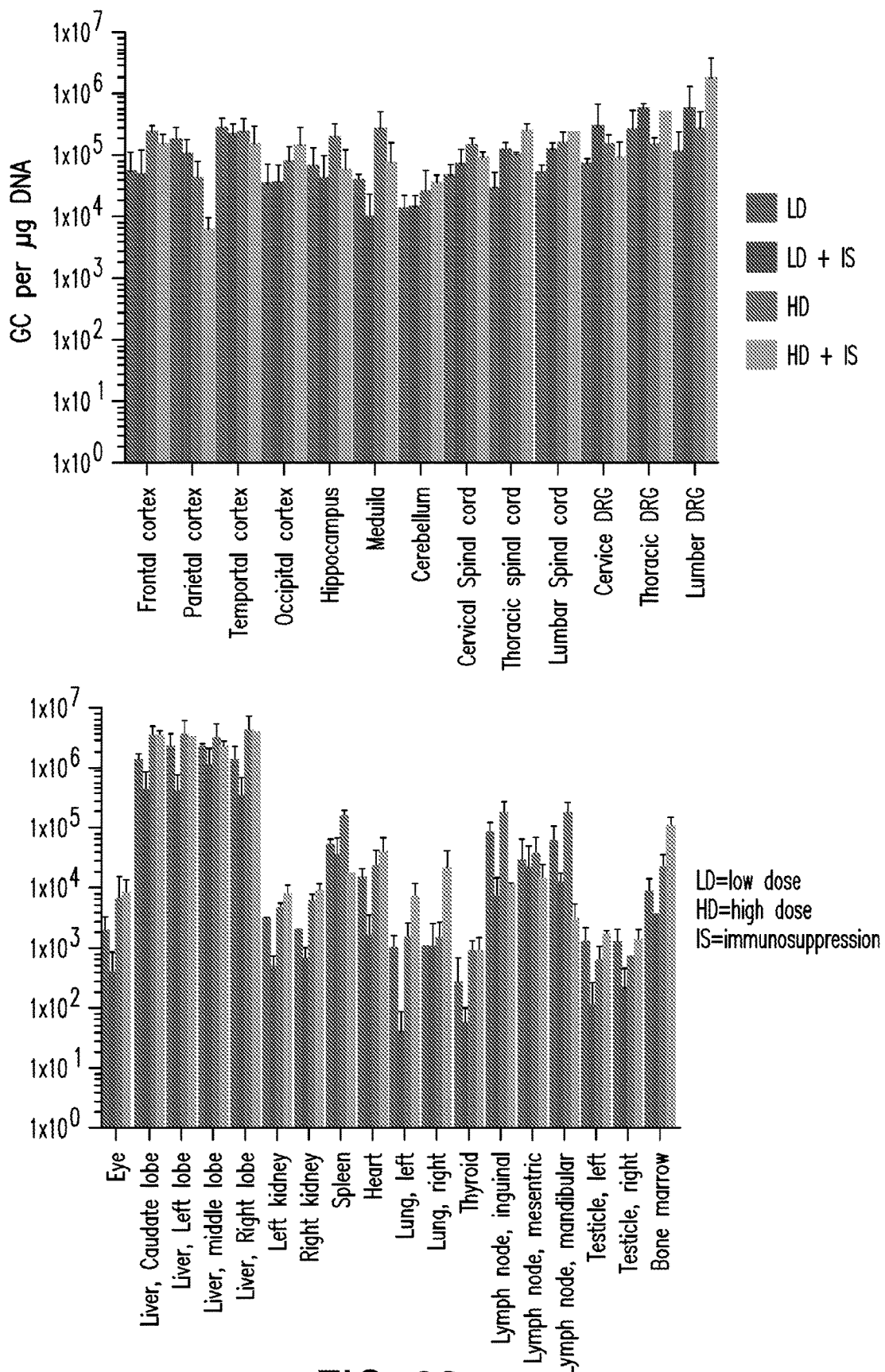

FIG. 23. Graphs showing widespread CNS and systemic biodistribution after Construct 1 IC administration in non-human. The term "LD" is low dose, "IS" is immunosuppression, and "HD" is high dose.

Figure 24A:
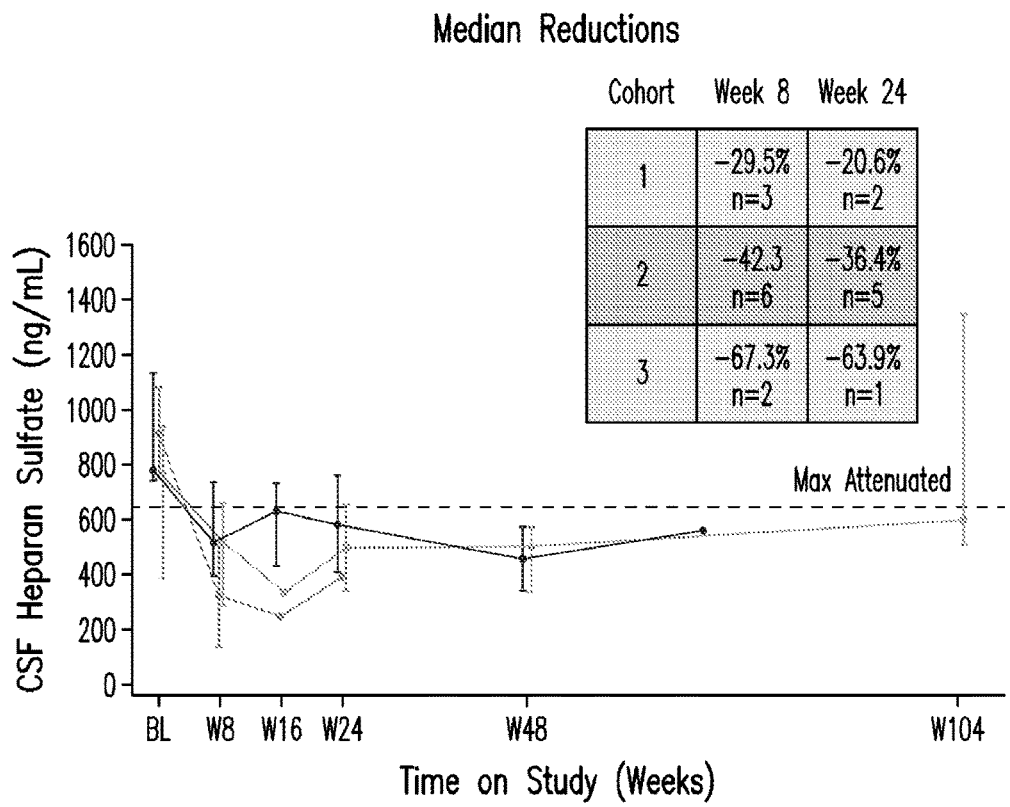
Figure 24B:
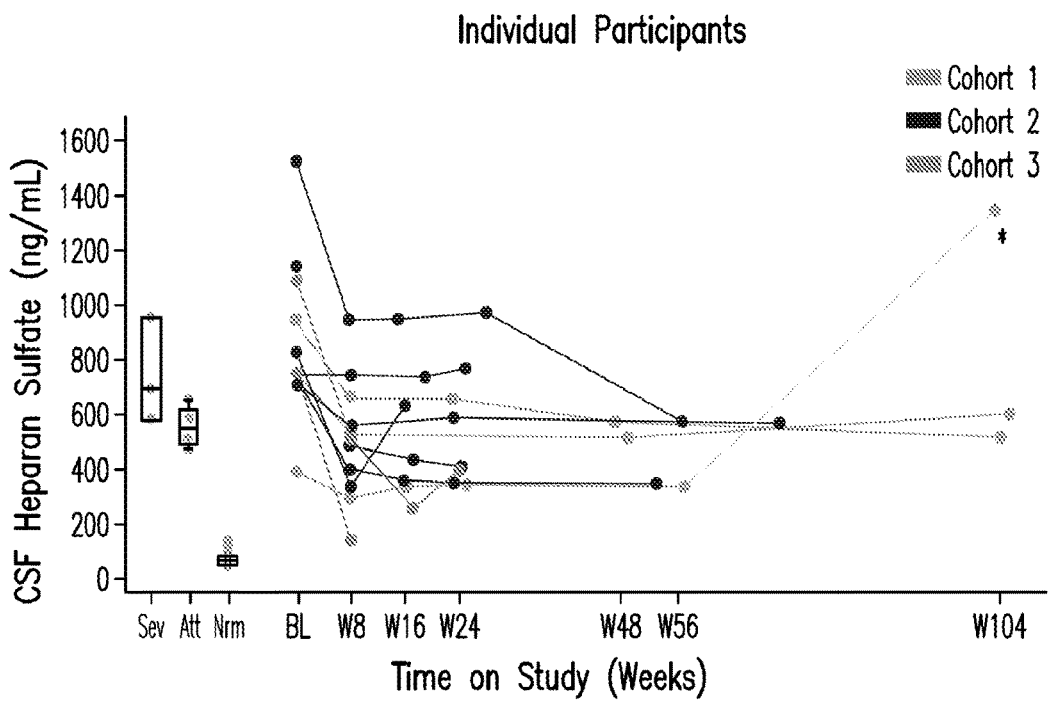

FIGS. 24A-24B. Graphs showing cerebral spinal fluid (CSF) Biomarker Heparan Sulfate (HS) in subjects in the Phase 1/2 study. CSF HS measurements showed dose-dependent reductions in Cohorts 1-3 at Weeks 8 and 24.

Figure 25A:
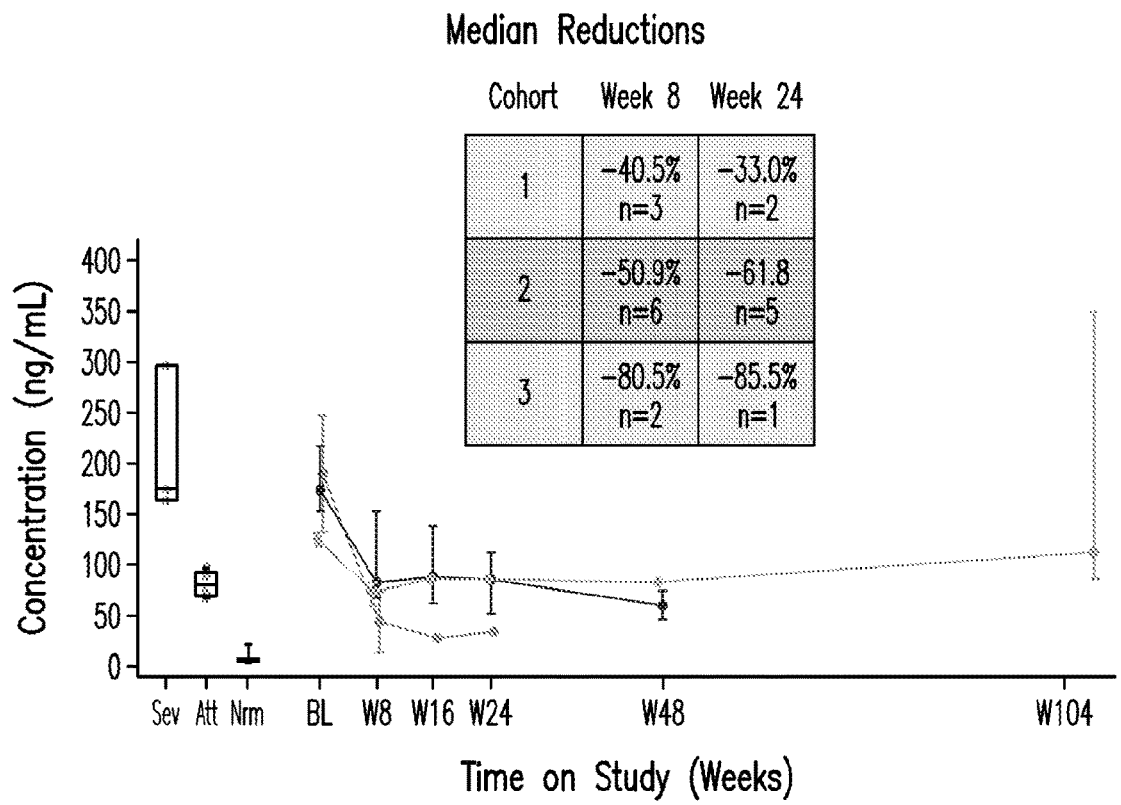
Figure 25B:
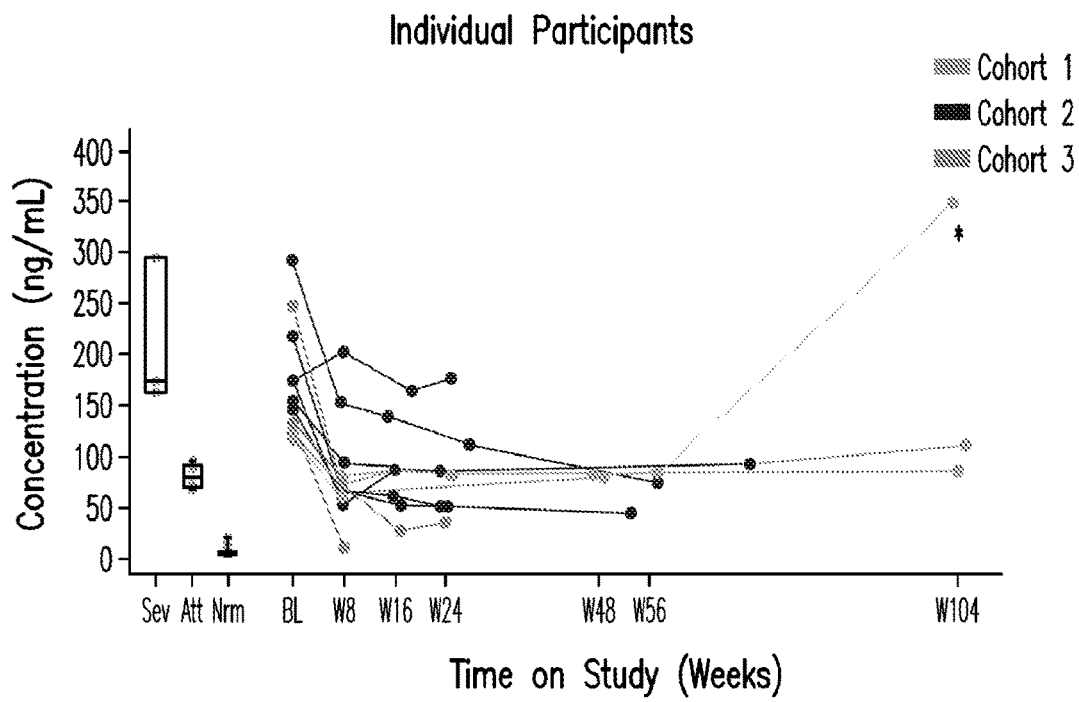

FIGS. 25A-25B. Graphs showing concentration of D2S6 in patients in Phase 1/2 study. CSF D2S6 measurement showed dose-dependent reductions in Cohorts 1-3 at Week 8 and 24, with Cohort 3 participants approaching normal levels.

Figures 26A, 26B, 26C:
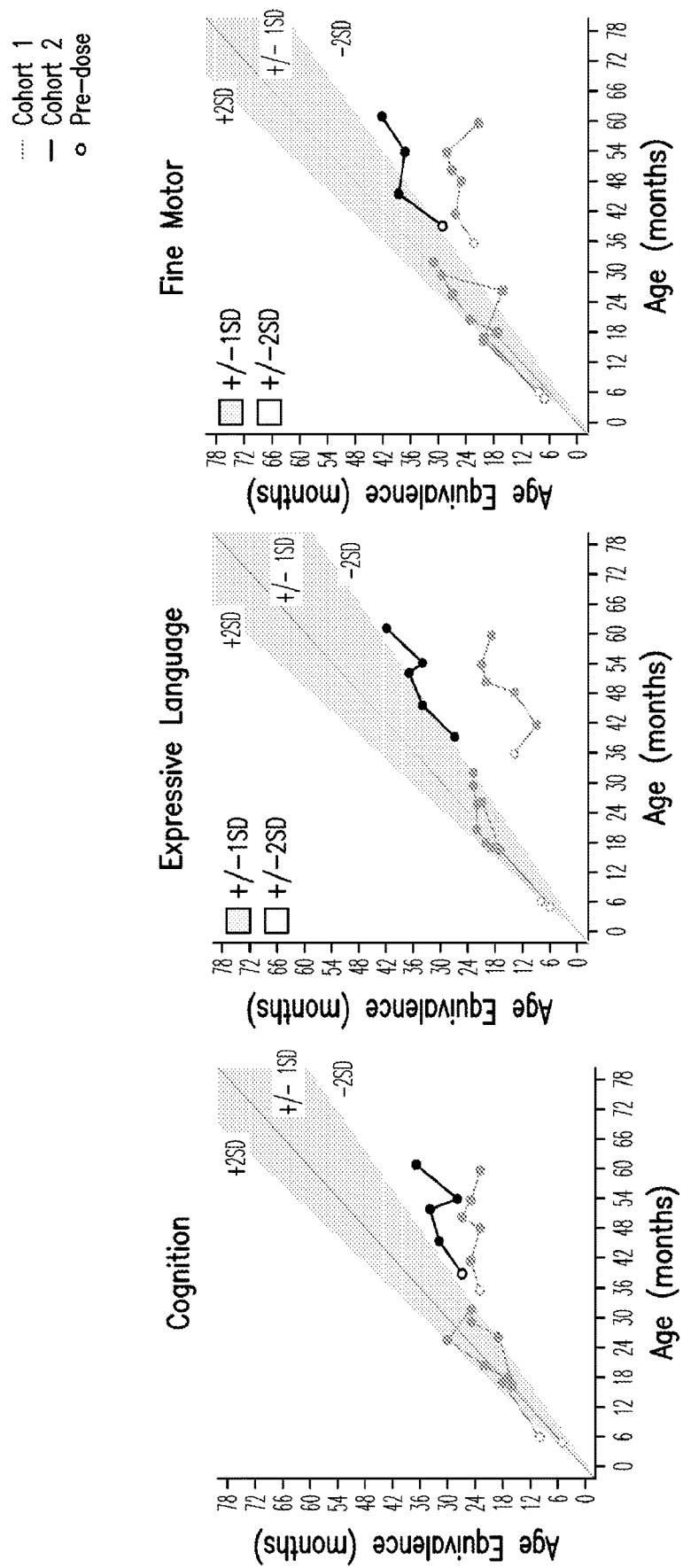

FIGS. 26A-26C. Graphs showing cognition, expressive language, and fine motor neurodevelopmental function for cohort 1 patients in Phase 1/2 study.

FIGS. 27A-27C. Graphs showing cognition, expressive language, and fine motor neurodevelopmental function for cohort 2 patients in Phase 1/2 study.

Figure 28A:
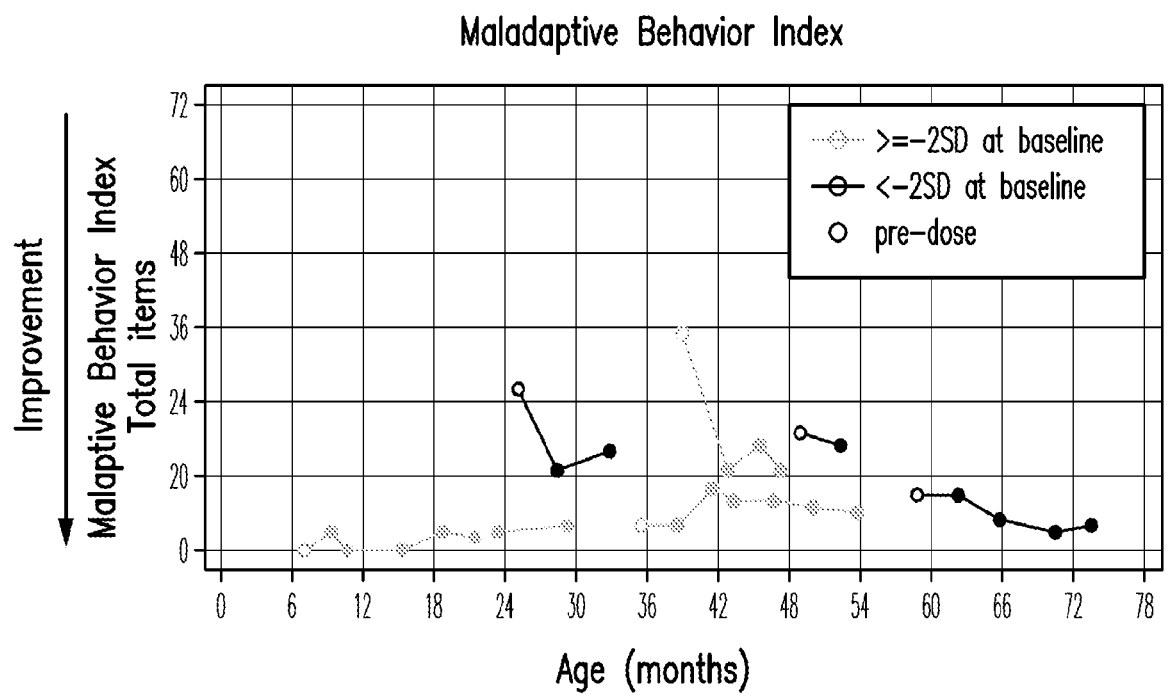
Figure 28B:
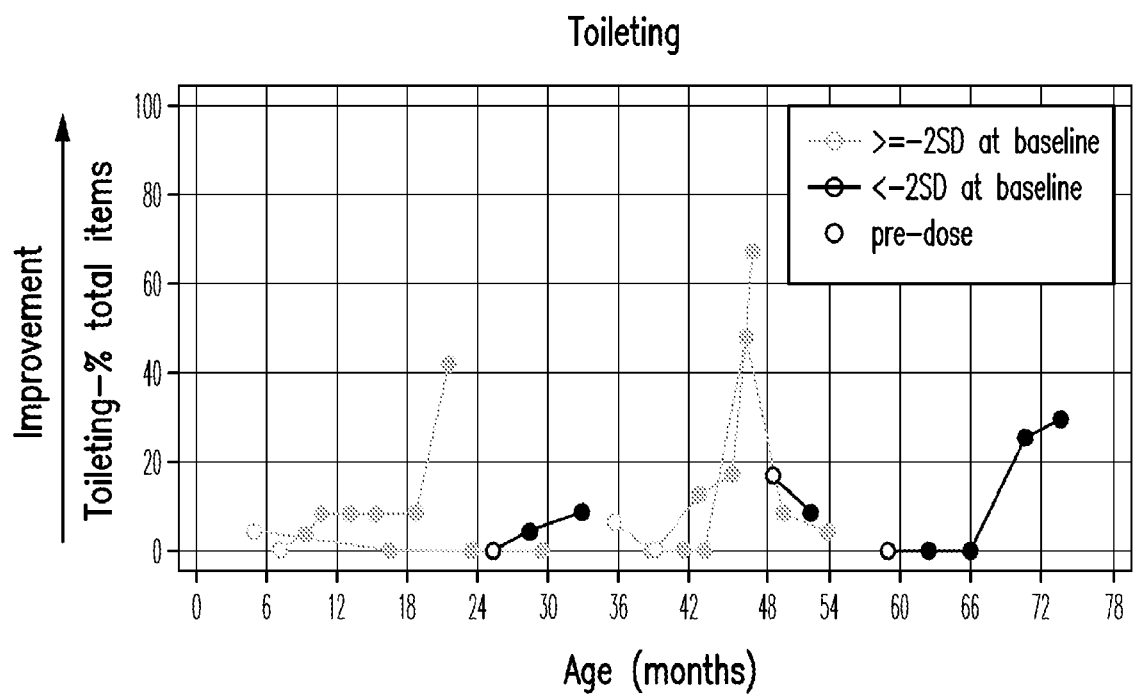

FIGS. 28A-28B. Graphs showing maladaptive behavior index and toileting skills for patients in Phase 1/2 study.

Figure 29A:
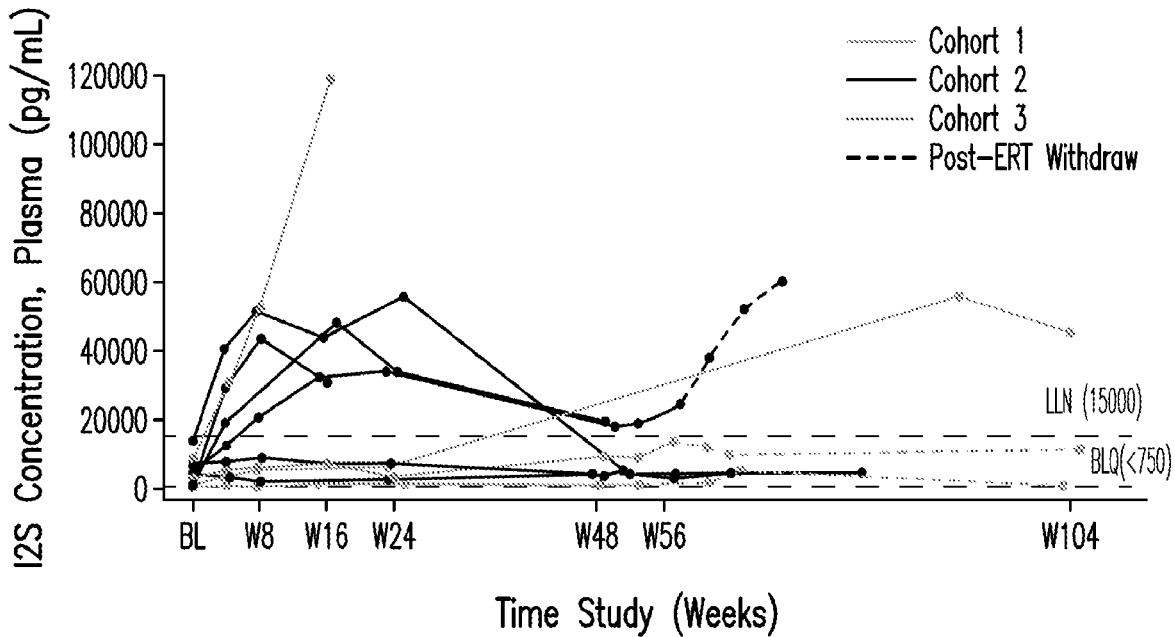
Figure 29B:
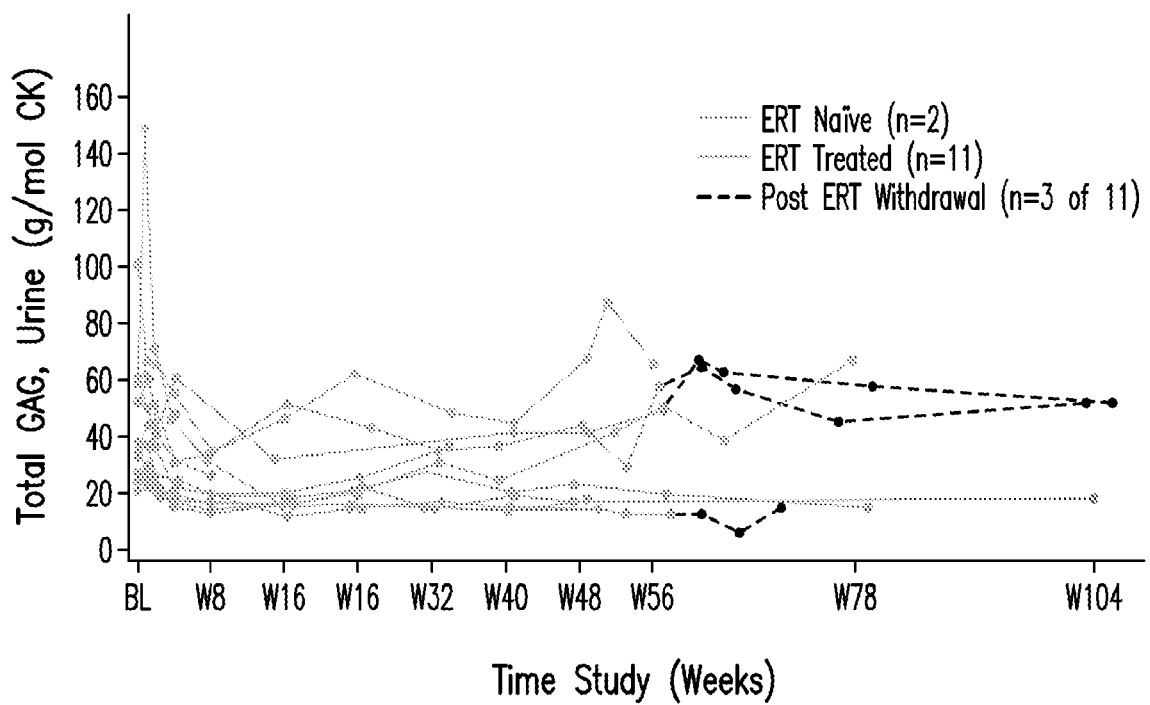

FIGS. 29A-29B. Graphs showing plasma I2S protein levels and urine GAG levels in patients in Phase 1/2 study.

Figure 30:
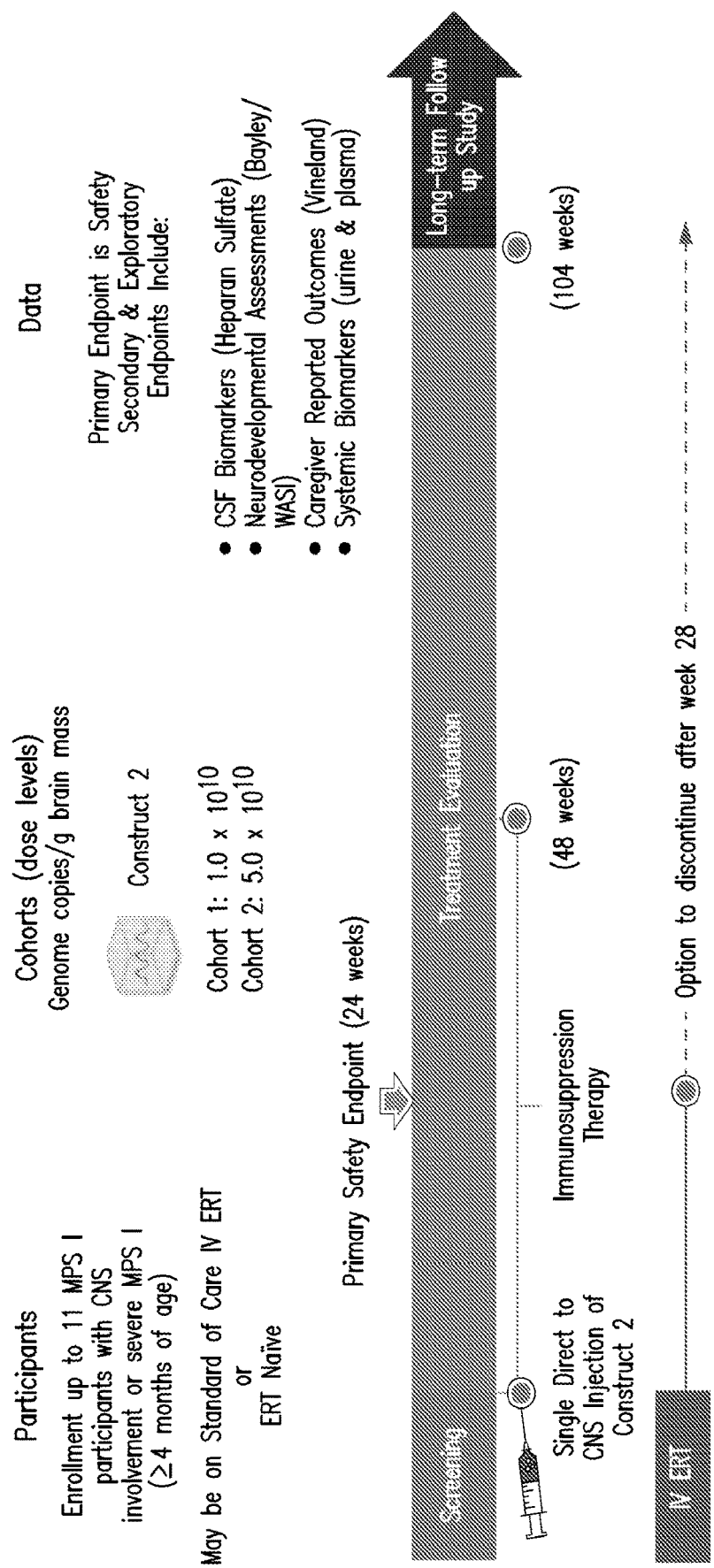
Figure 32C:
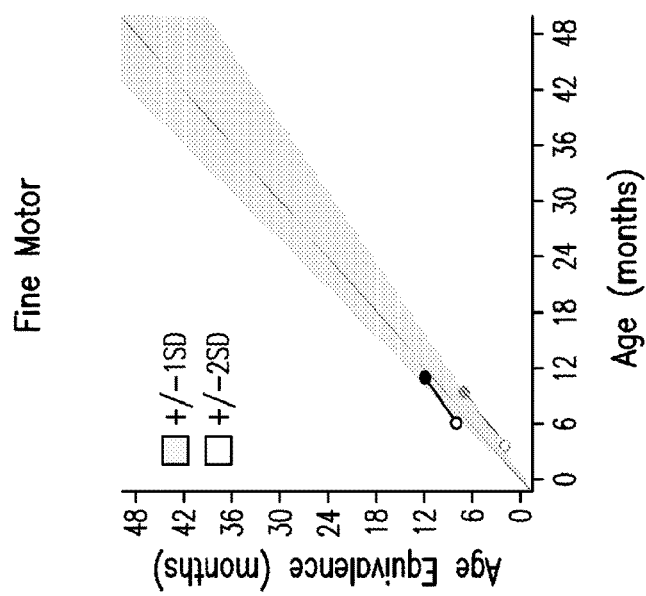
Figure 32B:
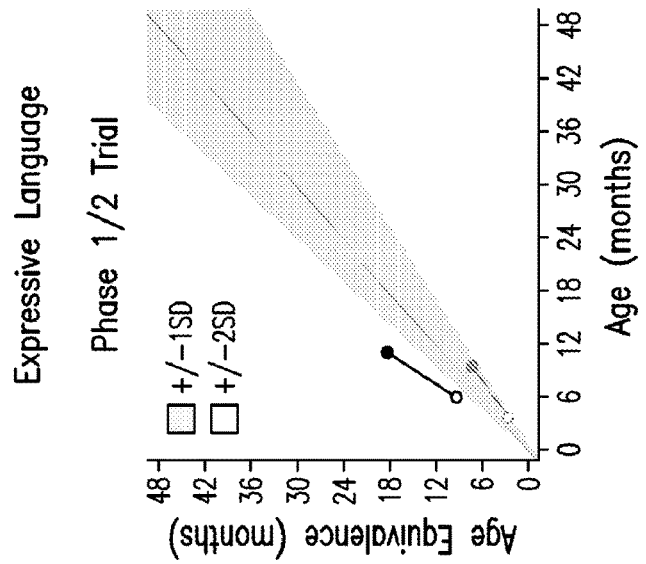
Figure 32A:
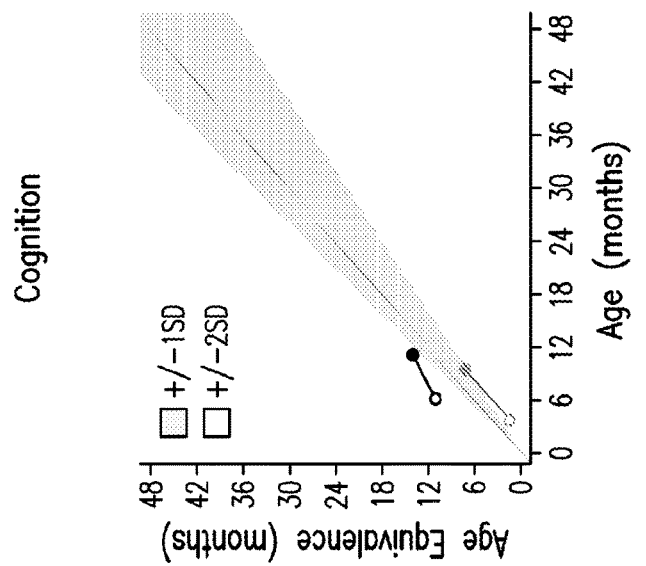
Figures 32D, 32E, 32F:
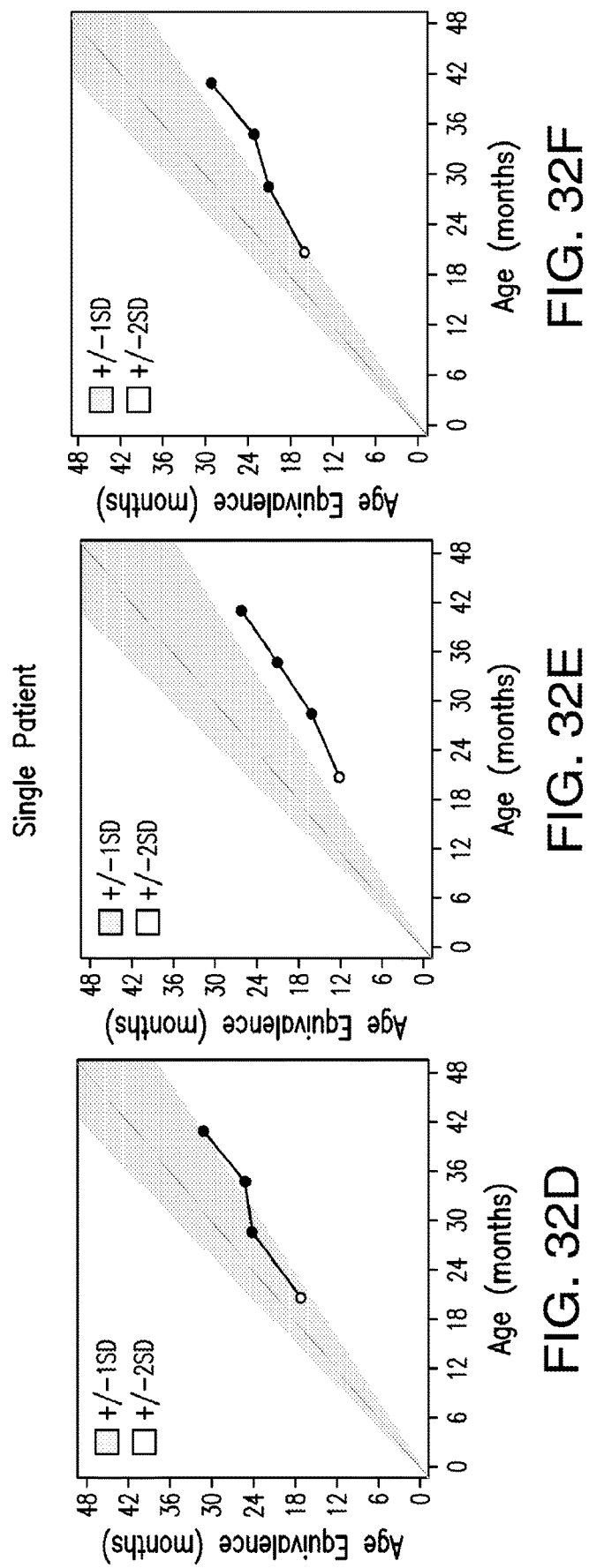

FIG. 30. Diagram showing MPS I phase 1/2 clinical study summary.

FIGS. 31A-31B. Graphs showing concentration of cerebral spinal fluid (CSF) biomarker and heparin sulfate in participants in the MPS I Phase 1/2 study (FIG. 31A) and in a single participant (FIG. 31B). Graphs show a decrease in CSF heparin sulfate in all participants through last time point available (e.g., week 24 for Phase 1/2 trial (FIG. 31A) and week 59 for the single participant (FIG. 31B). Study showed a measurable CSF IDUA enzyme activity in the majority of participants in the Phase 1/2 trial and in the single participant.

FIGS. 32A-32F. Graphs showing neurodevelopment function BSID-III as cognition, expressive language, and fine motor in MPS I Phase 1/2 study and the single participant study.

Figure 33:
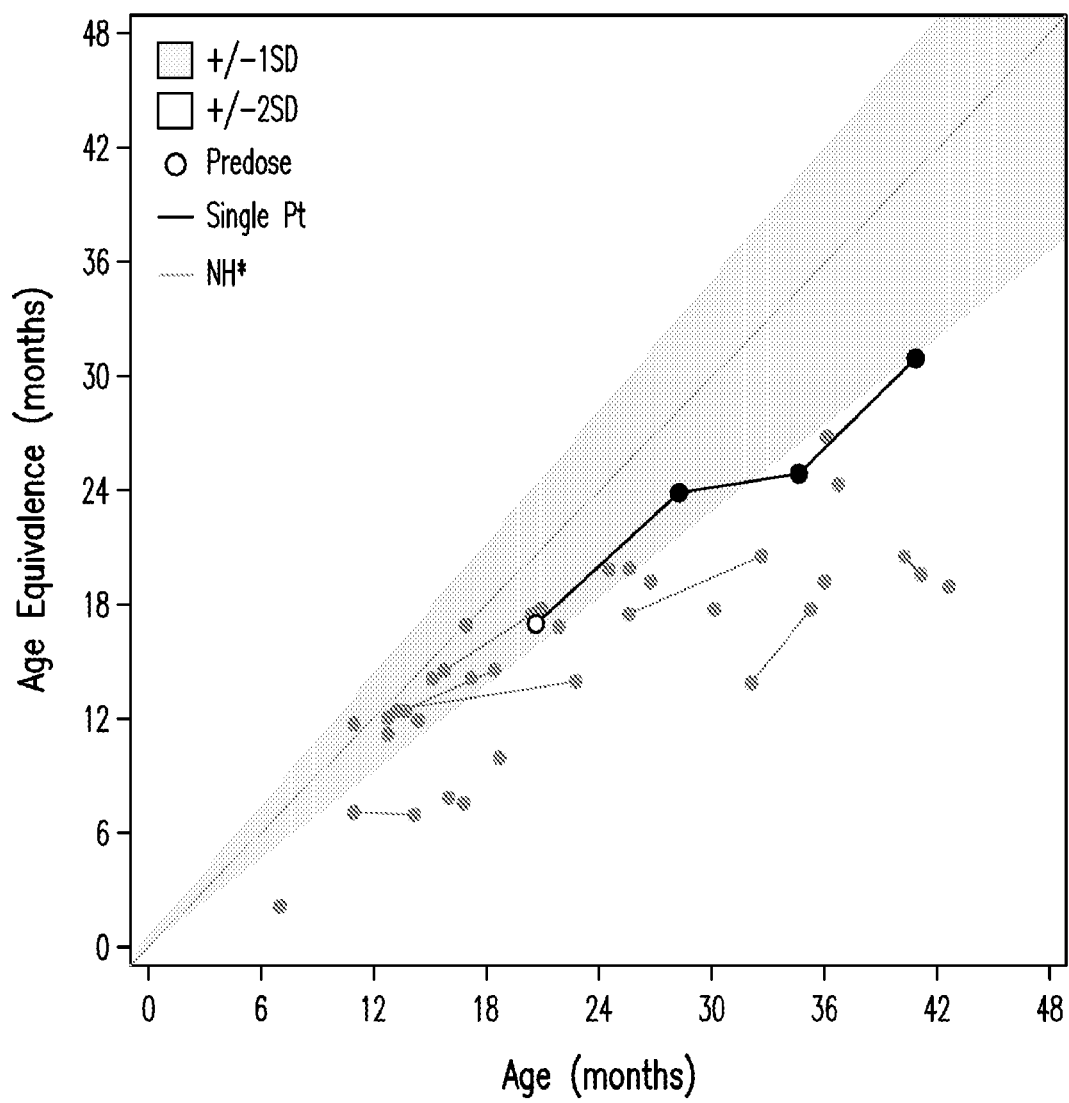

FIG. 33. Graph showing neurodevelopmental function BSID cognition in the MPS I single participant study.

FIG. 34. Tables showing the neurodevelopmental function (WASI-II and VABS-III) for a 13 year-old MPS I Phase 1/2 study participant.

Figures 35A, 35B:
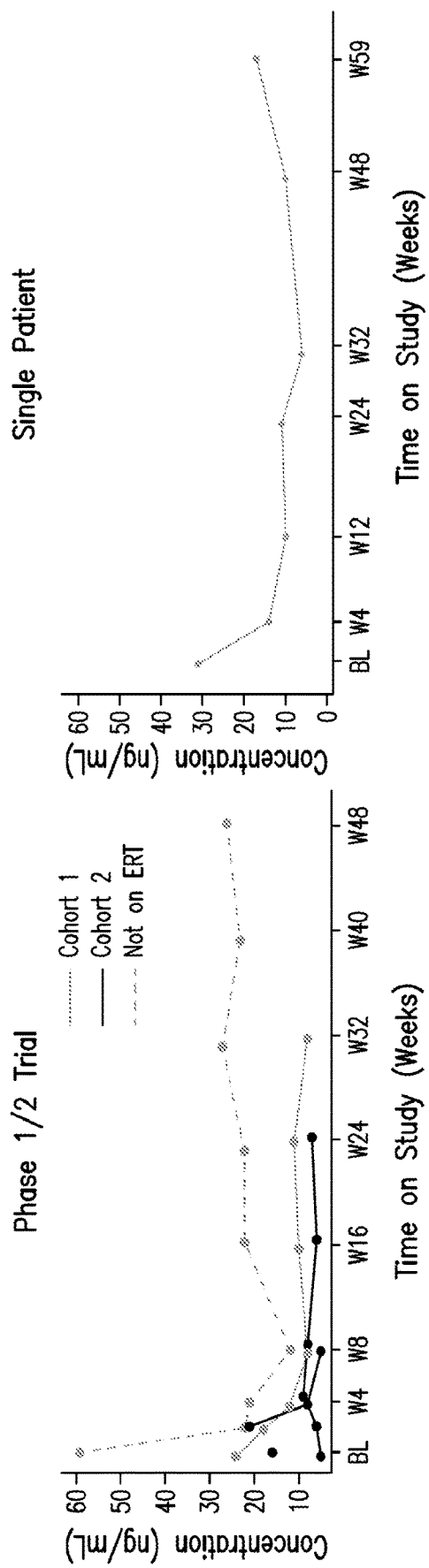

FIGS. 35A-35B. Graphs showing level of I0S6 in MPS I Phase 1/2 participants (FIG. 35A) and in the single participant study (FIG. 35B).

Figures 36A, 36B:
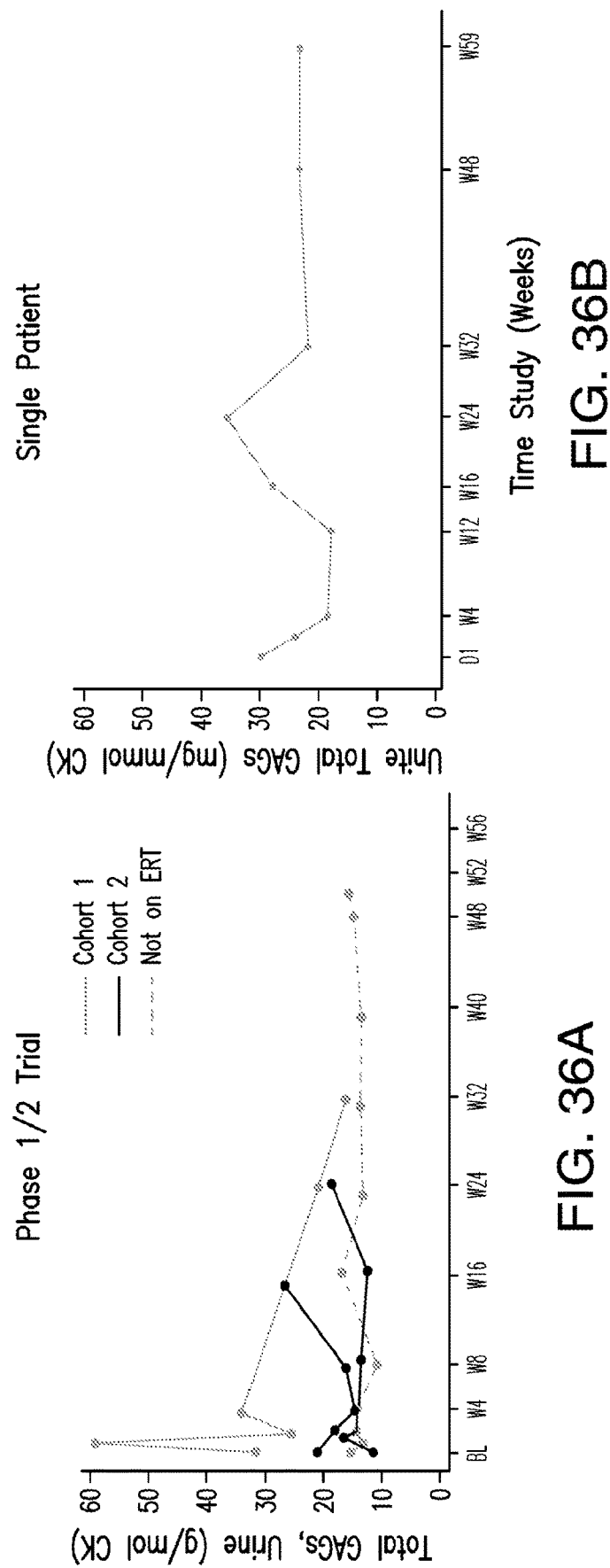

FIGS. 36A-36B. Graphs showing level of total urine GAGs in MPS I Phase 1/2 participants (FIG. 36A) and in the single participant study (FIG. 36B).

5. DETAILED DESCRIPTION OF THE INVENTION

The invention involves the delivery of recombinant human iduronate-2-sulfatase (rhIDS) produced by human neuronal or glial cells to the cerebrospinal fluid (CSF) of the central nervous system (CNS) of a human subject diagnosed with mucopolysaccharidosis II (MPS II), including, but not limited to patients diagnosed with Hunter syndrome. See, also, International Patent Application No. PCT/US2017/027770, filed Apr. 14, 2017 (published as WO/2017/181113 on Oct. 19, 2017), which is incorporated by reference herein in its entirety, for compositions and methods that can be used according to the invention described herein.

In a preferred embodiment, the treatment is accomplished via gene therapy—e.g., by administering a viral vector or other DNA expression construct encoding human IDS (hIDS), or a derivative of hIDS, to the CSF of a patient (human subject) diagnosed with MPS II, so that a permanent depot of transduced neuronal and/or glial cells is generated that continuously supplies the transgene product to the CNS. The rhIDS secreted from the neuronal/glial cell depot into the CSF will be endocytosed by cells in the CNS, resulting in "cross-correction" of the enzymatic defect in the recipient cells. Moreover, it has been found, unexpectedly, that the depot of transduced neural and glial cells in the CNS can deliver the recombinant enzyme to both the CNS and systemically, which may reduce or eliminate the need for systemic treatment, e.g., weekly i.v. injections of the enzyme. Also provided herein is the treatment of MPS I by administering a viral vector or other DNA expression construct encoding human IDUA to a subject (e.g., non-replicating recombinant AAV of serotype 9 capsid containing an hIDUA expression cassette; Construct 2; refer to PCT/US2021/014129; PCT/US2018/015910; and PCT/US2019/042205, each of which is incorporated by reference herein in its entirety).

In an alternative embodiment, the hIDS can be produced by human neuronal or glial cells in cell culture (e.g., bioreactors) and administered as an enzyme replacement therapy ("ERT"), e.g., by injecting the enzyme—into the CSF, directly into the CNS, and/or systemically. However, the gene therapy approach offers several advantages over ERT since systemic delivery of the enzyme will not result in treating the CNS because the enzyme cannot cross the blood brain barrier; and, unlike the gene therapy approach of the invention, direct delivery of the enzyme to the CSF and/or CNS would require repeat injections which are not only burdensome, but pose a risk of infection.

The hIDS encoded by the transgene can include, but is not limited to human IDS (hIDS) having the amino acid sequence of SEQ ID NO. 1 (as shown in FIG. 1), and derivatives of hIDS having amino acid substitutions, deletions, or additions, e.g., including but not limited to amino acid substitutions selected from corresponding non-conserved residues in orthologs of IDS shown in FIG. 2, with the proviso that such mutations do not include replacement of the cysteine residue at position 84 (C84) which is required for enzyme activity (Millat et al., 1997, Biochem J 326: 243-247); or a mutation that has been identified in severe, severe-intermediate, intermediate, or attenuated MPS II phenotypes e.g., as shown in FIG. 3, or as reported by Sukegawa-Hayasaka et al., 2006, J Inhert Metab Dis 29: 755-761

(reporting "attenuated" mutants R48P, A85T, W337R, and the truncated mutant Q531X; and "severe" mutants P86L, S333L, S349I, R468Q, R468L); Millat et al., 1998, BBA 1406: 214-218 (reporting "attenuated" mutants P480L and P480Q; and "severe" mutant P86L); and Bonucelli et al., 2001, BBA 1537:233-238, each of which is incorporated by reference herein in its entirety.

For example, amino acid substitutions at a particular position of hIDS can be selected from among corresponding non-conserved amino acid residues found at that position in the IDS orthologs aligned in FIG. 2, with the proviso that such substitutions do not include any of the deleterious mutations shown in FIG. 3 or as reported by Sukegawa-Hayasaka et al., 2006, supra; Millat et al., 1998, supra; or Bonucelli et al., 2001, supra, each of which is incorporated by reference herein in its entirety. The resulting transgene product can be tested using conventional assays in vitro, in cell culture or test animals to ensure that the mutation does not disrupt IDS function. Preferred amino acid substitutions, deletions or additions selected should be those that maintain or increase enzyme activity, stability or half-life of IDS, as tested by conventional assays in vitro, in cell culture or animal models for MPS II. For example, the enzyme activity of the transgene product can be assessed using a conventional enzyme assay with, for example, 4-Methylumbelliferyl α-L-idopyranosiduronic acid 2-sulfate or 4-methylumbelliferyl sulfate as the substrate (see, e.g., Lee et al., 2015, Clin. Biochem. 48(18):1350-1353, Dean et al., 2006, Clin. Chem. 52(4):643-649 for exemplary IDS enzyme assays that can be used, each of which is incorporated by reference herein in its entirety). The ability of the transgene product to correct MPS II phenotype can be assessed in cell culture; e.g., by transducing MPS II cells in culture with a viral vector or other DNA expression construct encoding hIDS or a derivative; by adding the transgene product or a derivative to MPS II cells in culture; or by co-culturing MPS II cells with human neuronal/glial host cells engineered to express and secrete rhIDS or a derivative, and determining correction of the defect in the MPS 11 cultured cells, e.g., by detecting IDS enzyme activity and/or reduction in GAG storage in the MPS II cells in culture (see, e.g., Stroncek et al., 1999, Transfusion 39(4):343-350, which is incorporated by reference herein in its entirety).

Animal models for MPS II have been described that can be used to assess the therapeutics described herein. For example, a knockout mouse model (IDS-knockout) of MPS II was engineered by replacing exons 4 and 5 of the IDS gene with the neomycin resistance gene. (Garcia et al., 2007, J Inherit Metab Dis 30: 924-34). This IDS-knockout mouse exhibits many of the characteristics of MPS IL, including skeletal abnormalities, hepatosplenomegaly, elevated urinary and tissue GAG, and brain storage lesions (Muenzer et al., 2001, Acta Paediatr Suppl 91:98-99) and was used to assess the effect of enzyme replacement therapy in MPS II in support of clinical trials for ERT. This mouse model, therefore, is a relevant model for studying the effects of gene therapy delivering rdDS produced by neuronal or glial cells as a treatment for MPS II (see, e.g., Polito and Cosma, 2009, Am. J. Hum. Genet. 85(2):296-301, which is incorporated by reference herein in its entirety).

Preferably, the hIDS transgene produced by the human neuronal/glial cells should be controlled by expression control elements that function in neurons and/or glial cells, e.g., the CB7 promoter (a chicken β-actin promoter and CMV enhancer), and can include other expression control elements that enhance expression of the transgene driven by the vector (e.g., chicken β-actin intron and rabbit β-globin poly A signal). The cDNA construct for the hIDS transgene should include a coding sequence for a signal peptide that ensures proper co- and post-translational processing (glycosylation and protein sulfation) by the transduced CNS cells. Such signal peptides used by CNS cells may include but are not limited to:

Oligodendrocyte-myelin glycoprotein (hOMG) signal peptide:

```
                                              (SEQ ID NO: 2)
           MEYQILKMSLCLFILLFLTPGILC
```

Cellular repressor of E1A-stimulated genes 2 (hCREG2) signal peptide:

```
                                              (SEQ ID NO: 3)
           MSVRRGRRPARPGTRLSWLLCCSALLSPAAG
```

V-set and transmembrane domain containing 2B (hVSTM2B) signal peptide:

```
                                              (SEQ ID NO: 4)
           MEQRNRLGALGYLPPLLLHALLLFVADA
```

Protocadherin alpha-1 (hPCADHA1) signal peptide:

```
                                              (SEQ ID NO: 5)
           MVFSRRGGLGARDLLLWLLLLAAWEVGSG
```

FAM19A1 (TAFA1) signal peptide:

```
                                              (SEQ ID NO: 6)
           MAMVSAMSWVLYLWISACA
```

Interleukin-2 signal peptide:

```
                                              (SEQ ID NO: 14)
           MYRMQLLSCIALILALVTNS
```

Signal peptides may also be referred to herein as leader sequences or leader peptides.

The recombinant vector used for delivering the transgene should have a tropism for cells in the CNS, including but limited to neurons and/or glial cells. Such vectors can include non-replicating recombinant adeno-associated virus vectors ("rAAV"), particularly those bearing an AAV9 or AAVrh10 capsid are preferred. AAV variant capsids can be used, including but not limited to those described by Wilson in U.S. Pat. No. 7,906,111 which is incorporated by reference herein in its entirety, with AAV/hu.31 and AAV/hu.32 being particularly preferred; as well as AAV variant capsids described by Chatterjee in U.S. Pat. Nos. 8,628,966, 8,927, 514 and Smith et al., 2014, Mol Ther 22: 1625-1634, each of which is incorporated by reference herein in its entirety. However, other viral vectors may be used, including but not limited to lentiviral vectors, vaccinia viral vectors, or non-viral expression vectors referred to as "naked DNA" constructs.

Pharmaceutical compositions suitable for administration to the CSF comprise a suspension of the rhIDS vector in a formulation buffer comprising a physiologically compatible aqueous buffer, a surfactant and optional excipients. In certain embodiments, the pharmaceutical compositions are suitable for intrathecal administration. In certain embodiments, the pharmaceutical compositions are suitable for intracisternal administration (injection into the cisterna magna). In certain embodiments, the pharmaceutical compositions are suitable for injection into the subarachnoid space via a C1-2 puncture. In certain embodiments, the pharmaceutical compositions are suitable for intracerebroventricular administration. In certain embodiments, the pharmaceutical compositions are suitable for administration via lumbar puncture. In some embodiments, the pharmaceutical composition comprising the rAAV of the present disclosure comprises sodium chloride at a concentration of about 8.77 g/L, magnesium chloride 6-hydrate, at a concentration of about 0.244 g/L, potassium chloride at a concentration of about 0.224 g/L, calcium chloride dihydrate at a concentration of about 0.206 g/L, dextrose anhydrous at a concentration of about 0.793 g/L, poloxamer 188 at a concentration of about 0.001% (volume/volume), sodium phosphate monobasic monohydrate at a concentration of about 0.0278 g/L, and sodium phosphate dibasic anhydrous at a concentration of about 0.114 g/L.

Therapeutically effective doses of the recombinant vector should be administered to the CSF via intrathecal administration (i.e., injection into the subarachnoid space so that the recombinant vectors distribute through the CSF and transduce cells in the CNS). In some embodiments, the recombinant vector is administered in a solution comprising sodium chloride at a concentration of about 8.77 g/L, magnesium chloride 6-hydrate, at a concentration of about 0.244 g/L, potassium chloride at a concentration of about 0.224 g/L, calcium chloride dihydrate at a concentration of about 0.206 g/L, dextrose anhydrous at a concentration of about 0.793 g/L, poloxamer 188 at a concentration of about 0.001% (volume/volume), sodium phosphate monobasic monohydrate at a concentration of about 0.0278 g/L, and sodium phosphate dibasic anhydrous at a concentration of about 0.114 g/L. This can be accomplished in a number of ways—e.g., by intracranial (cisternal or ventricular) injection, or injection into the lumbar cistern. For example intracisternal (IC) injection (into the cisterna magna) can be performed by CT-guided suboccipital puncture; or injection into the subarachnoid space can be performed via a C1-2 puncture when feasible for the patient; or lumbar puncture (typically diagnostic procedures performed in order to collect a sample of CSF) can be used to access the CSF. Alternatively, intracerebroventricular (ICV) administration (a more invasive technique used for the introduction of antiinfective or anticancer drugs that do not penetrate the blood-brain barrier) can be used to instill the recombinant vectors directly into the ventricles of the brain. Alternatively, intranasal administration may be used to deliver the recombinant vector to the CNS.

Because of the relatively rapid brain growth that occurs early in a developing child, the total dose of AAV9.hIDS administered IC depends on the assumed brain mass across different age strata, see, e.g., Table 2 below. For brain mass by age for the study subjects see, e.g., A S Dekaban, Ann Neurol, 1978 October; 4(4): 345-56.

TABLE 2

Total dose administered by age

| Subject Age | Assumed brain mass (g) | Dose 1 (total GC*) | Dose 2 (total GC*) |
|---|---|---|---|
| ≥4 to <9 months | 600 | $7.8 \times 10^{12}$ | $3.9 \times 10^{13}$ |
| ≥9 to <18 months | 1000 | $1.3 \times 10^{13}$ | $6.5 \times 10^{13}$ |
| ≥18 months to <3 years | 1100 | $1.4 \times 10^{13}$ | $7.2 \times 10^{13}$ |
| ≥3 years | 1300 | $1.7 \times 10^{13}$ | $8.5 \times 10^{13}$ |

*GC was determined using a Poly-A-specific PCR assay

CSF concentrations can be monitored by directly measuring the concentration of rhIDS in the CSF fluid obtained from occipital or lumbar punctures, or estimated by extrapolation from concentrations of the rhFDS detected in the patient's serum.

By way of background, human IDS is translated as a 550 amino acid polypeptide that contains eight potential N-glycosylation sites ($N^{31}$, $N^{115}$, $N^{144}$, $N^{246}$, $N^{280}$, $N^{325}$, $N^{513}$ and $N^{537}$) depicted in FIG. 1 and includes a 25 amino acid signal sequence which is cleaved during processing. An initial 76 kDa intracellular precursor is converted into a phosphorylated 90 kDa precursor after modification of its oligosaccharide chains in the Golgi apparatus. This precursor is processed by glycosylation modifications and proteolytic cleavage through various intracellular intermediates to a major 55 kDa form. To summarize, after removal of the 25 aa signal sequence, proteolytic processing involves N-terminal proteolytic cleavage downstream of $N^{31}$ removing a propeptide of eight amino acids (residues 26-33), and C-terminal proteolytic cleavage upstream of $N^{513}$ which releases an 18 kDa polypeptide and produces a 62 kDa intermediate that is converted to a 55 kDa mature form. Further proteolytic cleavage yields a 45 kDa mature form located in the lysosomal compartment. (See FIG. 4 for diagram reproduced from Millat et al., 1997, Exp Cell Res 230: 362-367 ("Millat 1997"); Millat et al. 1997, Biochem J. 326: 243-247 ("Millat 1997a"); and Froissart et al., 1995, Biochem J. 309:425-430, each of which is incorporated by reference herein in its entirety).

A formylglycine modification of $C^{84}$ (shown in bold in FIG. 1) required for enzyme activity probably occurs as an early post-translational or co-translational event, most probably in the endoplasmic reticulum. (See, Millat 1997a, citing Schmidt et al., 1995, Cell 82: 271-278). Post-translational processing continues in the Golgi to include addition of complex sialic acid-containing glycans and acquisition of mannose-6-phosphate residues which tag the enzyme for delivery to the lysosomal compartment. (See, Clarke, 2008, Expert Opin Pharmacother 9: 311-317 for a concise review which is incorporated by reference herein in its entirety). While no single glycosylation site is essential for IDS stability, glycosylation at position $N^{28}$ is important for cellular internalization and lysosomal targeting via the mannose-6-phosphate (M6P) receptor. (Chung et al., 2014, Glycoconj J 31:309-315 at p. 310, first column). In the normal physiologic state, IDS is produced at very low levels and very little, if any, enzyme is secreted from the cell. (Clarke, 2008, supra).

The invention is based, in part, on the following principles:

(i) Neuronal and glial cells in the CNS are secretory cells that possess the cellular machinery for post-translational processing of secreted proteins—including glycosylation, mannose-6-phosphorylation, and tyrosine-O-sulfation—robust processes in the CNS. See, e.g., Sleat et al., 2005, Proteomics 5: 1520-1532, and Sleat 1996, J Biol Chem 271: 19191-98 which describes the human brain mannose-6-phosphate glycoproteome and notes that the brain contains more proteins with a much greater number of individual isoforms and mannose-6-phosphorylated proteins than found in other tissues; and Kanan et al., 2009, Exp. Eye Res. 89: 559-567 and Kanan & Al-Ubaidi, 2015, Exp. Eye Res. 133: 126-131 reporting the production of tyrosine-sulfated glycoproteins secreted by neuronal cells, each of which is incorporated by reference in its entirety for post-translational modifications made by human CNS cells.

(ii) The human brain produces multiple isoforms of natural/native IDS. In particular, N-terminal sequencing of human brain mannose-6-phosphorylated glycoproteins revealed that the N-terminal sequence of the mature 42 kDa chain of hIDS varies in the brain, starting at positions 34 or 36 as follows: $T^{34}$DALNVLLI (SEQ ID NO: 54); and $A^{36}$LNVLLIIV (SEQ ID NO: 55). (Sleat, 2005, Proteomics 5: 1520-1532, Table S2). Two of the eight N-linked glycosylation sites, namely $N^{280}$ and $N^{116}$. were found to be mannose-6-phophorylated in IDS obtained from human brain. (Sleat et al., 2006, Mol & Cell Proeomics 5.4: 686-701, reported at Table V).

(iii) During processing of IDS, two polypeptides, 76 kDa and 90 kDa, are secreted by neural and glial cells, but only the 90 kDa polypeptide is mannose-6-phosphorylated, which is necessary for secreted forms of the enzyme to achieve cross correction. (See, Millat, 1997, FIG. 1 results for transduced lymphoblastoid cells, and Froissart 1995, FIG. 4 showing similar results for transduced fibroblasts—in culture medium, only the 90 kDa form is phosphorylated). Interestingly, it has been demonstrated that recombinant IDS produced by neuronal and glial cells may be endocytosed by recipient CNS cells more avidly than recombinant IDS produced by other cells such as kidney. Daniele 2002 demonstrated M6P-receptor mediated endocytosis of recombinant IDS from conditioned media of transduced neuronal and glial cell cultures by a recipient population of non-transduced neuronal and glial cells which properly processed the precursor to the 45 kDa mature active form. Uptake of the recombinant IDS produced by the neuronal and glial cell lines (74% endocytosis) far exceeded uptake of the enzyme produced by a kidney cell line (5.6% endocytosis). In each case, uptake was inhibited by M6P, indicating that recombinant IDS uptake was M6P-receptor mediated. (See Daniele 2002, Tables 2 and 4 and accompanying description in Results at pp. 205-206 summarized in Table 3 below).

TABLE 3

Summary of Results Reported in Daniele 2002

| Cell Line Source of rIDS | Media Enzyme Units | Recipient Cells: Units Recovered | | % Endocytosis (mean value) |
|---|---|---|---|---|
| | | Neuronal | Glial | |
| Kidney (transfected) | 35 U | 1.7 U | 2.2 U | 5.6% |
| Neuronal (Ad-transduced) | 12 U | 8.8 U | 8.8 U | 74% |
| Glial (Ad-transduced) | 14 U | 10.5 U | 10.5 U | 74% |

(iv) The gene therapy approach described herein should result in the continuous secretion of an hIDS glycoprotein precursor of about 90 kDa as measured by polyacrylamide gel electrophoresis (depending on the assay used) that is enzymatically active. First, the enzyme responsible for the formylglycine modification of $C^{84}$ which is required for IDS activity—the FGly-Generating Enzyme (FGE, aka SUMF1)—is expressed in the cerebral cortex of the human brain (gene expression data for SUMF1 may be found, for example, at GeneCards, accessible at http://www.genecards.org). Second, the secreted glycosylated/phosphorylated rIDS produced by transduced neurons and glial cells in situ should be taken up and correctly processed by untransduced neural and glial cells in the CNS. Without being bound to any theory, it appears that the secreted rhIDS precursor produced in situ by gene therapy may be more avidly endocytosed by recipient cells in the CNS than would traditional recombinant enzymes used for ERT if administered to the CNS. For example, Elaprase® (made in HT1080, a fibrosarcoma cell line) is a purified protein reported to have a molecular weight of about 76 kDa—not the 90 kDa species secreted by neuronal and glial cells that appears to be more heavily phosphorylated. While the eight N-linked glycosylation sites are reported to be fully occupied in Elaprase® and contain two bis-mannose-6-phosphate terminated glycans as well as complex highly sialylated glycans, the post-translational modification of $C^{84}$ to FGly, which is an absolute requirement for enzyme activity, is only about 50%. (Clarke, 2008, Expert Opin Pharmacother 9:311-317; Elaprase® Full Prescribing Information and EMA filing). Another recombinant product, Hunterase® is made in CHO cells. While reported to have higher FGly and activity than Elaprase®, mannose-6-phosphorylation and uptake did not differ. (Chung, 2014, Glycoconj J 31:309-315).

(v) The extracellular IDS efficacy in vivo depends on uptake (cell and lysosome internalization) through mannose-6-phosphate (M6P) and its active site formylglycine (FGly), which is converted from $C^{84}$ through post-translational modification by formylglycine-generating enzyme. As shown above in Table 3, brain cells (neuronal and glial cells) show higher enzyme activities when incubated with IDS precursor media secreted by transduced neuronal and glial cells than with IDS precursor media secreted by genetically engineered kidney cells. The resultant five-fold increase in activity can likely be attributed to the efficient uptake of IDS (See Daniele 2002, Tables 2 and 4). Commercial forms of IDS, which are generated by CHO cells or HT-1080 cells, have a FGly content of about 50% to 70%, which determines the enzyme activity. However, neuronal and glial cells may improve upon this activity, due to improvement of IDS uptake.

(vi) The cellular and subcellular trafficking/uptake of lysosomal proteins, including IDS, is through M6P. IDS from brain cells may contain higher M6P content, as reported in Daniele 2002, and in Sleat, Proteomics, 2005 (indicating that the human brain contains more (in both a quantitative and qualitative sense) Man6-P glycoproteins than other tissues). It is possible to measure the M6P content of an IDS precursor, as done in Daniele 2002. In the presence of inhibitory M6P (e.g., 5 mM), the uptake of IDS precursor generated by non-neuronal or non-glial cells, such as the genetically engineered kidney cells of Daniele 2002, is predicted to decrease to levels close to that of the control cells, as was shown in Daniele 2002. While in the presence of inhibitory M6P, the uptake of IDS precursor generated by brain cells, such as neuronal and glial cells, is predicted to remain at a high level, as was shown in Daniele 2002, where the uptake was four times higher than control cells and comparable to the level of IDS activity (or uptake) of IDS precursor generated by genetically engineered kidney cells without the presence of inhibitory M6P. This assay allows for a way to predict the M6P content in IDS precursor generated by brain cells, and, in particular, to compare the M6P content in IDS precursors generated by different types of cells. The gene therapy approach described herein should result in the continuous secretion of an hIDS precursor that may be taken up into neuronal and glial cells at a high level in the presence of inhibitory M6P in such an assay.

(vii) The M6P content and uptake of IDS precursor may also be demonstrated by 90 kDa and 76 kDa gel bands (e.g., SDS-PAGE gel bands). The 90 kDa is reported to be highly glycosylated/phosphorylated and contains M6P, while 76 kDa is not. A very broad gel band with a range from 76 kDa to 95 kDa and with an average MW of 80-85 kDa, similar to the IDS precursor gel band generated from genetically engineered kidney cells (Daniele 2002, FIG. 1), may be contrasted with a gel band of IDS precursor generated from brain cells. In Daniele 2002, the gel band cannot be obtained due to unsuccessful immunoprecipitation of the IDS precursor. The gene therapy approach described herein should result in the continuous secretion of an hIDS precursor that differs from the IDS precursor gel band generated from genetically engineered kidney cells.

(viii) The M6P content of commercial IDS precursor is 2 to 2.5 mol/mol, majority of which is present in a form of di-phosphorylated glycans. Although in average, every IDS precursor is phosphorylated, a normal distribution of glycans will have some IDS precursor with 2, 1 and 0 of di-phosphorylated M6P glycans assuming multiple phosphorylation sites. Uptake rate should be significant higher with multiple phosphorylation.

(ix) The glycosylation of hIDS by human cells of the CNS will result in the addition of glycans that can improve stability, half-life and reduce unwanted aggregation of the transgene product. Significantly, the glycans that are added to hIDS of the invention include 2,6-sialic acid, incorporating Neu5Ac ("NANA") but not its hydroxylated derivative, NeuGc (N-Glycolyl-neuraminic acid, i.e., "NGNA" or "Neu5Gc"). Such glycans are not present in recombinant IDS products, such as Hunterase®, made in CHO cells because CHO cells do not have the 2,6-sialyltransferase required to make this post-translational modification; nor do CHO cells produce bisecting GlcNAc, although they do add Neu5Gc (NGNA) as sialic acid not typical (and potentially immunogenic) to humans instead of Neu5Ac (NANA). See, e.g., Dumont et al., 2016, Critical Rev in Biotech 36(6):1110-1122 (Early Online pp. 1-13 at p. 5); and Hague et al., 1998 Electrophor 19:2612-2630 ("[t]he CHO cell line is considered 'phenotypically restricted,' in terms of glycosylation, due to the lack of an α2,6-sialyl-transferase"). Moreover, CHO cells can also produce an immunogenic glycan, the α-Gal antigen, which reacts with anti-α-Gal antibodies present in most individuals, and at high concentrations can trigger anaphylaxis. See, e.g., Bosques, 2010, Nat Biotech 28: 1153-1156. The human glycosylation pattern of the rhIDS of the invention should reduce immunogenicity of the transgene product and improve efficacy.

(x) Immunogenicity of a transgene product could be induced by various factors, including the immune condition of the patient, the structure and characteristics of the infused protein drug, the administration route, and the duration of treatment. Process-related impurities, such as host cell protein (HCP), host cell DNA, and chemical residuals, and product-related impurities, such as protein degradants and structural characteristics, such as glycosylation, oxidation and aggregation (sub-visible particles), may also increase immunogenicity by serving as an adjuvant that enhances the immune response. The amounts of process-related and product-related impurities can be affected by the manufacturing process: cell culture, purification, formulation, storage and handling, which can affect commercially manufactured IDS products. In gene therapy, proteins are produced in vivo, such that process-related impurities are not present and protein products are not likely to contain product-related impurities/degradants associated with proteins produced by recombinant technologies, such as protein aggregation and protein oxidation. Aggregation, for example, is associated with protein production and storage due to high protein concentration, surface interaction with manufacturing equipment and containers, and the purification process with certain buffer systems. But these conditions that promote aggregation are not present when a transgene is expressed in vivo. Oxidation, such as methionine, tryptophan and histidine oxidation, is also associated with protein production and storage, caused, for example, by stressed cell culture conditions, metal and air contact, and impurities in buffers and excipients. The proteins expressed in vivo may also oxidize in a stressed condition, but humans, like many organisms, are equipped with an antioxidation defense system, which not only reduces the oxidation stress, but can also repairs and/or reverses the oxidation. Thus, proteins produced in vivo are not likely to be in an oxidized form. Both aggregation and oxidation could affect the potency, pharmacokinetics (clearance) and can increase immunogenicity concerns. The gene therapy approach described herein should result in the continuous secretion of an hIDS precursor with a reduced immunogenicity compared to commercially manufactured products.

(xi) In addition to the N-linked glycosylation sites, hIDS contains a tyrosine ("Y") sulfation site (PSSEKY$^{165}$ENTKTCRGPD (SEQ ID NO: 47)). (See, e.g., Yang et al., 2015, Molecules 20:2138-2164, esp. at p. 2154 which is incorporated by reference in its entirety for the analysis of amino acids surrounding tyrosine residues subjected to protein tyrosine sulfation. The "rules" can be summarized as follows: Y residues with E or D within +5 to −5 position of Y, and where position −1 of Y is a neutral or acidic charged amino acid—but not a basic amino acid, e.g., R, K, or H that abolishes sulfation). While not intending to be bound by any theory, sulfation of this site in hIDS may improve stability of the enzyme and binding affinity for substrate. Tyrosine-sulfation of hIDS—a robust post-translational process in human CNS cells—should result in improved processing and activity of transgene products. The significance of tyrosine-sulfation of lysosomal proteins has not been elucidated; but in other proteins it has been shown to increase avidity of protein-protein interactions (antibodies and receptors), and to promote proteolytic processing (peptide hormone). (See, Moore, 2003, J Biol. Chem. 278: 24243-46; and Bundegaard et al., 1995, The EMBO J 14: 3073-79). The tyrosylprotein sulfotransferase (TPST1) responsible for tyrosine-sulfation (which may occur as a final step in IDS processing) is apparently expressed at higher levels (based on mRNA) in the brain (gene expression data for TPST1 may be found, for example, at the EMBL-EBI Expression Atlas, accessible at http://www.ebi.ac.uk/gxa/home). Such post-translational modification, at best, is under-represented in CHO cell products. Unlike human CNS cells, CHO cells are not secretory cells and have a limited capacity for post-translational tyrosine-sulfation. (See, e.g., Mikkelsen & Ezban, 1991, Biochemistry 30: 1533-1537, esp. discussion at p. 1537)

For the foregoing reasons, the production of rhIDS by human neuronal and/or glial cells should result in a "biobetter" molecule for the treatment of MPS II accomplished via gene therapy—e.g., by administering a viral vector or other DNA expression construct encoding rhIDS to the CSF of a patient (human subject) diagnosed with an MPS II disease (including but not limited to Hunter) to create a permanent depot in the CNS that continuously supplies a fully human-glycosylated, mannose-6-phosphorylated, sulfated transgene product secreted by the transduced CNS cells. The hIDS transgene product secreted from the depot into the CSF will be endocytosed by cells in the CNS, resulting in "cross-correction" of the enzymatic defect in the MPS II recipient cells.

It is not essential that every rhIDS molecule produced either in the gene therapy or protein therapy approach be fully glycosylated, phosphorylated, and sulfated. Rather, the population of glycoproteins produced should have sufficient glycosylation (including 2,6-sialylation and mannose-6-phosphorylation) and sulfation to demonstrate efficacy. The goal of gene therapy treatment of the invention is to slow or arrest the progression of disease. Efficacy may be monitored by measuring cognitive function (e.g., prevention or decrease in neurocognitive decline); reductions in biomarkers of disease (such as GAG) in CSF and or serum; and/or increase in IDS enzyme activity in CSF and/or serum. Signs of inflammation and other safety events may also be monitored.

As an alternative, or an additional treatment to gene therapy, the rhIDS glycoprotein can be produced in human neural or glial cell lines by recombinant DNA technology and the glycoprotein can be administered to patients diagnosed with MPS II systemically and/or into the CSF for ERT). Human cell lines that can be used for such recombinant glycoprotein production include but are not limited to HT-22, SK-N-MC, HCN-AA, HCN-2, NT2, SH-SY5y, hNSC11, or ReNcell VM (see, e.g., Dumont et al., 2016, Critical Rev in Biotech 36(6):1110-1122 "Human cell lines for biopharmaceutical manufacturing: history, status, and future perspectives" which is incorporated by reference in its entirety for a review of the human cell lines that could be used for the recombinant production of the rHuGlyIDS glycoprotein). To ensure complete glycosylation, especially sialylation, and tyrosine-sulfation, the cell line used for production can be enhanced by engineering the host cells to co-express α-2,6-sialyltransferase (or both α-2,3- and α-2, 6-sialyltransferases) and/or TPST-1 and TPST-2 enzymes responsible for tyrosine-O-sulfation.

While the delivery of rhIDS should minimize immune reactions, the clearest potential source of toxicity related to CNS-directed gene therapy is generating immunity against the expressed rhIDS protein in human subjects who are genetically deficient for IDS and, therefore, potentially not tolerant of the protein and/or the vector used to deliver the transgene.

Thus, in a preferred embodiment, it is advisable to cotreat the patient with immune suppression therapy—especially when treating patients with severe disease who have close to zero levels of IDS. Immune suppression therapies involving a regimen of tacrolimus or rapamycin (sirolimus) in combination with mycophenolic acid, or other immune suppression regimens used in tissue transplantation procedures can be employed. Such immune suppression treatment may be administered during the course of gene therapy, and in certain embodiments, pre-treatment with immune suppression therapy may be preferred. Immune suppression therapy can be continued subsequent to the gene therapy treatment, based on the judgment of the treating physician, and may thereafter be withdrawn when immune tolerance is induced; e.g., after 180 days.

Combinations of delivery of the rhIDS to the CSF accompanied by delivery of other available treatments are encompassed by the methods of the invention. The additional treatments may be administered before, concurrently or subsequent to the gene therapy treatment. Available treatments for MPS II that could be combined with the gene therapy of the invention include but are not limited to enzyme replacement therapy using Elaprase® administered systemically or to the CSF; and/or HSCT therapy.

In certain embodiments, described herein is a method for treating a human subject diagnosed with mucopolysaccharidosis type II (MPS II), comprising delivering to the cerebrospinal fluid (CSF) of said human subject a therapeutically effective amount of a recombinant human iduronate-2-sulfatase (IDS) precursor produced by human neuronal or human glial cells.

In certain embodiments, described herein is a method of treating a human subject diagnosed with mucopolysaccharidosis type II (MPS II), comprising delivering to the cerebrospinal fluid (CSF) of said human subject, a therapeutically effective amount of a recombinant human iduronate-2-sulfatase (IDS) glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, has a formylglycine residue at $C^{84}$ (FIG. 1), is α2,6-sialylated, does not contain detectable NeuGc, and is mannose-6-phosphorylated.

In certain embodiments, described herein is a method of treating a human subject diagnosed with mucopolysaccharidosis type II (MPS II), comprising delivering to the cerebrospinal fluid (CSF) of said human subject, a therapeutically effective amount of a recombinant human iduronate-2-sulfatase (IDS) glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, has a formylglycine residue at $C^4$ (FIG. 1), is α2,6-sialylated, does not contain detectable NeuGc and/or α-Gal antigen, and is mannose-6-phosphorylated.

In certain embodiments, the human IDS precursor is delivered to the CSF from a depot of cells in the central nervous system genetically engineered to secrete said IDS precursor into the CSF. In certain embodiments, the depot is formed in the subject's brain. In certain embodiments, the human subject is deficient in IDS activity. In certain embodiments, the human IDS comprises the amino acid sequence of SEQ ID NO. 1.

In certain embodiments, described herein is a method of treating a human subject diagnosed with mucopolysaccharidosis type II (MPS II), comprising administering to the cerebrospinal fluid (CSF) of said human subject a recombinant nucleotide expression vector encoding human iduronate-2-sulfatase (IDS), wherein said expression vector when used to transduce a primary human neuronal cell in culture directs the expression of a secreted human IDS glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, has a formylglycine residue at $C^{84}$ (FIG. 1), is α2,6-sialylated and mannose-6-phosphorylated.

In certain embodiments, described herein is a method of treating a human subject diagnosed with mucopolysaccharidosis type II (MPS II), comprising administering to the cerebrospinal fluid of the brain of said human subject, a therapeutically effective amount of a recombinant nucleotide expression vector encoding human IDS, so that a depot is formed in the subject's central nervous system that secretes a recombinant human IDS glycoprotein precursor that is α2,6-sialylated and mannose-6-phosphorylated.

In certain embodiments, secretion of said recombinant human IDS glycoprotein precursor that is α2,6-sialylated is confirmed by transducing a human neuronal cell line with said recombinant nucleotide expression vector in cell culture. In certain embodiments, secretion of said recombinant human IDS glycoprotein precursor that is mannose-6-phosphorylated is confirmed by transducing a human neuronal cell line with said recombinant nucleotide expression vector in cell culture. In certain embodiments, the secretion is confirmed in the presence and absence of mannose-6-phosphate.

In certain embodiments, described herein is a method of treating a human subject diagnosed with mucopolysaccharidosis type II (MPS II), comprising administering to the cerebrospinal fluid of the brain of said human subject, a therapeutically effective amount of a recombinant nucleotide expression vector encoding human IDS, so that a depot is formed that secretes a glycosylated IDS precursor containing a α2,6-sialylated glycan; wherein said recombinant vector, when used to transduce human neuronal cells in culture results in secretion of said glycosylated IDS precursor containing a α2,6-sialylated glycan in said cell culture.

In certain embodiments, described herein is a method of treating a human subject diagnosed with mucopolysaccharidosis type II (MPS II), comprising administering to the cerebrospinal fluid of the brain of said human subject, a therapeutically effective amount of a recombinant nucleotide expression vector encoding human IDS, so that a depot is formed that secretes a glycosylated IDS precursor that contains a mannose-6-phosphate; wherein said recombinant vector, when used to transduce human neuronal cells in culture results in secretion of said glycosylated IDS precursor that is mannose-6-phosphorylated in said cell culture.

In certain embodiments, described herein is a method of treating a human subject diagnosed with mucopolysaccharidosis type II (MPS II), comprising administering to the cerebrospinal fluid of the brain of said human subject, a therapeutically effective amount of a recombinant nucleotide expression vector encoding human IDS, so that a depot is formed that secretes a glycosylated IDS precursor that contains a formylglycine; wherein said recombinant vector, when used to transduce human neuronal cells in culture results in secretion of said glycosylated IDS precursor that contains a formylglycine in said cell culture.

In certain embodiments, the human IDS comprises the amino acid sequence of SEQ ID NO. 1. In certain embodiments, the IDS transgene encodes a leader peptide. In certain embodiments, the expression vector is a replication defective AAV vector. In certain embodiments, the expression vector is delivered to the CSF of the subject by intrathecal (e.g., intracisternal, C1-2 puncture if feasible for the patient, or lumbar puncture), intracerebroventricular, or intranasal administration. In certain embodiments, the human subject is deficient in IDS activity. In some embodiments, the expression vector is delivered to the CSF of the subject by intrathecal administration in a solution comprising sodium chloride at a concentration of about 8.77 g/L, magnesium chloride 6-hydrate, at a concentration of about 0.244 g/L, potassium chloride at a concentration of about 0.224 g/L, calcium chloride dihydrate at a concentration of about 0.206 g/L, dextrose anhydrous at a concentration of about 0.793 g/L, poloxamer 188 at a concentration of about 0.001% (volume/volume), sodium phosphate monobasic monohydrate at a concentration of about 0.0278 g/L, and sodium phosphate dibasic anhydrous at a concentration of about 0.114 g/L.

In preferred embodiments, the glycosylated IDS does not contain detectable NeuGc and/or α-Gal. The phrase "detectable NeuGc and/or α-Gal" used herein means NeuGc and/or α-Gal moieties detectable by standard assay methods known in the art. For example, NeuGc may be detected by HPLC according to Hara et al., 1989, "Highly Sensitive Determination of N-Acetyl- and N-Glycolylneuraminic Acids in Human Serum and Urine and Rat Serum by Reversed-Phase Liquid Chromatography with Fluorescence Detection." J. Chromatogr., B: Biomed. 377: 111-119, which is hereby incorporated by reference for the method of detecting NeuGc. Alternatively, NeuGc may be detected by mass spectrometry. The α-Gal may be detected using an ELISA, see, for example, Galili et al., 1998, "A sensitive assay for measuring alpha-Gal epitope expression on cells by a monoclonal anti-Gal antibody." Transplantation. 65(8): 1129-32, or by mass spectrometry, see, for example, Ayoub et al., 2013, "Correct primary structure assessment and extensive glyco-profiling of cetuximab by a combination of intact, middle-up, middle-down and bottom-up ESI and MALDI mass spectrometry techniques." Landes Bioscience. 5(5): 699-710. See also the references cited in Platts-Mills et al., 2015, "Anaphylaxis to the Carbohydrate Side-Chain Alpha-gal" Immunol Allergy Clin North Am. 35(2): 247-260.

In one aspect, provided herein is a method for treating a human subject diagnosed with MPS II, comprising delivering to the CSF of the human subject a therapeutically effective amount of a glycosylated recombinant human IDS precursor produced by human neuronal or human glial cells, wherein the glycosylated recombinant human IDS precursor is delivered by administration of a recombinant nucleotide expression vector encoding human IDS, wherein the recombinant nucleotide expression vector is administered at a dose that is dependent on the human subject's brain mass, and wherein the brain mass is determined by brain MRI of the human subject's brain.

In another aspect, provided herein is a method for treating a human subject diagnosed with MPS II, comprising determining the human subject's brain mass from the human subject's brain MRI, and subsequently delivering to the CSF of the human subject a therapeutically effective amount of a glycosylated recombinant human IDS precursor produced by human neuronal cells or human glial cells, wherein the glycosylated recombinant human IDS precursor is delivered by administration of a recombinant nucleotide expression vector encoding human IDS, and wherein the recombinant nucleotide expression vector is administered at a dose that is dependent on the human subject's brain mass.

In another aspect, provided herein is a method for treating a human subject diagnosed with MPS II, comprising (a) determining the human subject's brain mass from the human subject's brain MRI, (b) calculating the dose based on the human subject's brain mass, and (c) subsequently administrating to the CSF of the subject the dose of recombinant nucleotide expression vector encoding human IDS.

In another aspect, provided herein is a method for treating a human subject diagnosed with MPS II, comprising, in the following order: (a) delivering to the CSF of the human subject a therapeutically effective amount of a glycosylated recombinant human IDS precursor produced by human neuronal or human glial cells; (b) measuring level of heparan sulfate in the CSF of the human subject; and (c) comparing the level of heparan sulfate in the CSF of the human subject with level of heapran sulfatae in a reference population; wherein the glycosylated recombinant human IDS precursor is delivered by administration of a recombinant nucleotide expression vector encoding human IDS, wherein the recombinant nucleotide expression vector is administered at a dose that is dependent on the human subject's brain mass, and wherein the brain mass is determined by brain magnetic resonance imaging (MRI) of the human subject's brain. In certain embodiments, the reference population consists of: (a) at least 1, 2, 3, 4, 5, 10, 25, 50, 75, 100, 200, 250, 300, 400, 500, or 1000 individual healthy people without MPS II, preferably of similar age, weight, and/or of the same gender as the human subject.

In another aspect, provided herein is a method for treating a human subject diagnosed with MPS II, comprising, in the following order: (a) taking a first measurement of the level of heparan sulfate in the CSF of the human subject; (b) delivering to the CSF of the human subject a therapeutically effective amount of a glycosylated recombinant human IDS precursor produced by human neuronal or human glial cells; and (c) after a period of time, taking a second measurement of the level of heparan sulfate; wherein the glycosylated recombinant human IDS precursor is delivered by administration of a recombinant nucleotide expression vector encoding human IDS, wherein the recombinant nucleotide expression vector is administered at a dose that is dependent on the human subject's brain mass, and wherein the brain mass is determined by brain magnetic resonance imaging (MRI) of the human subject's brain. In certain embodiments, the period of time is about 1 day, 2 days, 3 days, 4 days, 5 days, 6 days, 1 week, 2 weeks, 3 weeks, 4 weeks, 2 months, 3 moths, 4 months, 5 months, 6 months, 7 months, 8 months, 11 months, or 1 year.

In a preferred embodiment, the glycosylated recombinant human IDS precursor will be endocytosed by cells in the CNS. In a preferred embodiment, the glycosylated recombinant human IDS precursor is delivered to lysosomes of cells in the CNS of the human subject.

In certain embodiments of the method for treating described herein, the human subject's brain mass is converted from the human subject's brain volume by multiplying the human subject's brain volume in $cm^3$ by a factor of 1.046 $g/cm^3$, wherein the human subject's brain volume is determined by brain MRI of the subject's brain.

In certain embodiments of the method for treating described herein, the recombinant nucleotide expression vector is administered at a dose of about $1.3\times10^{10}$ GC/g brain mass as determined by MRI, or about $6.5\times10^{10}$ GC/g brain mass as determined by MRI. In certain embodiments of the method for treating described herein, the recombinant nucleotide expression vector is administered at a dose of about $1.3\times10^{10}$ GC/g brain mass (e.g., the brain mass is determined by MRI and the genome count is determined by a Poly-A-specific PCR assay). In certain embodiments of the method for treating described herein, the recombinant nucleotide expression vector is administered at a dose of about $1.9\times10^{10}$ GC/g brain mass (e.g., the brain mass is determined by MRI and the genome count is determined by a transgene-specific PCR assay). In certain embodiments of the method for treating described herein, the recombinant nucleotide expression vector is administered at a dose of about $6.5\times10^{10}$ GC/g brain mass (e.g., the brain mass is determined by MRI and the genome count is determined by a Poly-A-specific PCR assay). In certain embodiments of the method for treating described herein, the recombinant nucleotide expression vector is administered at a dose of about $9.6\times10^{10}$ GC/g brain mass (e.g., the brain mass is determined by MRI and the genome count is determined by a transgene-specific PCR assay). In certain embodiments of the method for treating described herein, the recombinant nucleotide expression vector is administered at a dose of about $2.0\times10^{11}$ GC/g brain mass (e.g., the brain mass is determined by MRI and the genome count is determined by a Poly-A-specific PCR assay). In certain embodiments of the method for treating described herein, the recombinant nucleotide expression vector is administered at a dose of about $2.9\times10^{10}$ GC/g brain mass (e.g., the brain mass is determined by MRI and the genome count is determined by a transgene-specific PCR assay).

In various embodiments of the method for treating described herein, the human subject is 5 years old or older and less than 18 years old. In specific embodiments, the human subject is 5, 6, 7, 8, 9, 10, 11, 12, 13, 14, 15, 16, 17 or 18 years old. In specific embodiments, the human subject is about 5, 6, 7, 8, 9, 10, 11, 12, 13, 14, 15, 16, 17 or 18 years old. In specific embodiments, the human subject is 5-6, 6-7, 7-8, 8-9, 9-10, 10-11, 11-12, 12-13, 13-14, 14-15, 15-16, 16-17, 17-18 or 18-19 years old. In specific embodiments, the human subject is about 5-6, 6-7, 7-8, 8-9, 9-10, 10-11, 11-12, 12-13, 13-14, 14-15, 15-16, 16-17, 17-18 or 18-19 years old. In certain embodiments, the recombinant nucleotide expression vector is administered at a dose of about $6.5\times10^{10}$ GC/g brain mass as determined by MRI. In certain embodiments, the recombinant nucleotide expression vector is administered at a dose according to Table 7.

In various embodiments of the method for treating described herein, the human subject is 4 months old or older and less than 5 years old. In specific embodiments, the human subject is 4, 5, 6, 7, 8, 9, 10, or 11 months old. In specific embodiments, the human subject is about 4, 5, 6, 7, 8, 9, 10, or 11 months old. In specific embodiments, the human subject is 4-5, 5-6, 6-7, 7-8, 8-9, 9-10, 10-11, or 11-12 months old. In specific embodiments, the human subject is about 4-5, 5-6, 6-7, 7-8, 8-9, 9-10, 10-11, or 11-12 months old. In specific embodiments, the human subject is 1, 2, 3, 4, or 5 years old. In specific embodiments, the human subject is about 1, 2, 3, 4, or 5 years old. In specific embodiments, the human subject is 1-2, 2-3, 3-4, 4-5, or 5-6 years old. In specific embodiments, the human subject is about 1-2, 2-3, 3-4, 4-5, or 5-6 years old. In certain embodiments, the recombinant nucleotide expression vector is administered at a dose of about $1.3\times10^{10}$ GC/g brain mass as determined by MRI. In certain embodiments, the recombinant nucleotide expression vector is administered at a dose of about $6.5\times10^{10}$ GC/g brain mass as determined by MRI. In certain embodiments, the recombinant nucleotide expression vector is administered at a dose of about $2.0\times10^{10}$ GC/g brain mass as determined by MRI. In certain embodiments, the recombinant nucleotide expression vector is administered at a dose of about $2.9\times10^{10}$ GC/g brain mass as determined by MRI. In certain embodiments, the recombinant nucleotide expression vector is administered at a dose of about $1.9\times10^{10}$ GC/g brain mass as determined by MRI. In certain embodiments, the recombinant nucleotide expression vector is administered at a dose of about $9.6\times10^{10}$ GC/g brain mass as determined by MRI. In certain embodiments, the recombinant nucleotide expression vector is administered at a dose of about $2.0\times10^{10}$ GC/g brain mass (e.g., the brain mass is determined by MRI and the genome count is determined by a Poly-A-specific PCR assay). In certain embodiments, the recombinant nucleotide expression vector is administered at a dose of about $2.9 \times 10^{11}$ GC/g brain mass (e.g., the brain mass is determined by MRI and the genome count is determined by a transgene-specific PCR assay). In certain embodiments, the recombinant nucleotide expression vector is administered at a dose of about $1.3 \times 10^{10}$ GC/g brain mass (e.g., the brain mass is determined by MRI and the genome count is determined by a Poly-A-specific PCR assay). In certain embodiments, the recombinant nucleotide expression vector is administered at a dose of about $1.9 \times 10^{10}$ GC/g brain mass (e.g., the brain mass is determined by MRI and the genome count is determined by a transgene-specific PCR assay). In certain embodiments, the recombinant nucleotide expression vector is administered at a dose of about $6.5 \times 10^{10}$ GC/g brain mass (e.g., the brain mass is determined by MRI and the genome count is determined by a Poly-A-specific PCR assay). In certain embodiments, the recombinant nucleotide expression vector is administered at a dose of about $9.6 \times 10^{10}$ GC/g brain mass (e.g., the brain mass is determined by MRI and the genome count is determined by a transgene-specific PCR assay). In certain embodiments, the recombinant nucleotide expression vector is administered at a dose chosen from Dose 1 or Dose 2 according to Table 5. In certain embodiments, the recombinant nucleotide expression vector is administered at a dose according to Table 6.

In some embodiments of the method for treating described herein, the recombinant nucleotide expression vector is administered via intracisternal (IC) administration. In other embodiments of the method for treating described herein, the recombinant nucleotide expression vector is administered via intracerebroventricular (ICV) administration.

In certain embodiments of the method for treating described herein, the recombinant nucleotide expression vector is administered at a volume that does not exceed 10% of the total cerebrospinal fluid volume of the human subject.

In certain embodiments of the method for treating described herein, the glycosylated recombinant human IDS precursor is secreted at a detectable level.

In certain embodiments of the method for treating described herein, the human neuronal or human glial cells carry at least one mutation in the endogenous gene encoding human IDS precursor.

In certain embodiments of the method for treating described herein, the human neuronal or human glial cells are transduced with a recombinant adeno-associated virus vector (rAAV).

In a preferred embodiment, the recombinant nucleotide expression vector is an AAV9 or AAVrh10 vector.

In certain embodiments of the method for treating described herein, the glycosylated recombinant human IDS precursor is expressed under the control of a CB7 promoter.

In certain embodiments of the method for treating described herein, the glycosylated recombinant human IDS precursor is expressed from a cDNA encoding human IDS precursor.

In certain embodiments of the method for treating described herein, the glycosylated recombinant human IDS precursor is about 90 kDa as measured by polyacrylamide gel electrophoresis.

In certain embodiments of the method for treating described herein, the glycosylated recombinant human IDS precursor contains a formylglycine.

In certain embodiments of the method for treating described herein, the glycosylated recombinant human IDS precursor (a) is α2,6-sialylated; (b) does not contain detectable NeuGc; (c) does not contain detectable α-Gal antigen; (d) contains tyrosine-sulfation; and/or (e) is mannose-6-phosphorylated.

In certain embodiments of the method for treating described herein, the glycosylated recombinant human IDS precursor comprises the amino acid sequence of SEQ ID NO. 1.

In certain embodiments provided herein, the method further comprising administering an immune suppression therapy to the human subject before or concurrently with the human IDS precursor treatment and optionally continuing immune suppression therapy thereafter.

In some embodiments, the immune suppression therapy comprises administering one or more corticosteroids, sirolimus, and/or tacrolimus. In a specific embodiment, the one or more corticosteroids are methylprednisolone and/or prednisone.

In a specific embodiment, the immune suppression therapy comprises administering prednisone at a dose of about 0.10 mg/kg, 0.11 mg/kg, 0.12 mg/kg, 0.13 mg/kg, 0.14 mg/kg, 0.15 mg/kg, 0.16 mg/kg, 0.17 mg/kg, 0.18 mg/kg, 0.19 mg/kg, 0.20 mg/kg, 0.21 mg/kg, 0.22 mg/kg, 0.23 mg/kg, 0.24 mg/kg, 0.25 mg/kg, 0.26 mg/kg, 0.27 mg/kg, 0.28 mg/kg, 0.29 mg/kg, 0.30 mg/kg, 0.31 mg/kg, 0.32 mg/kg, 0.33 mg/kg, 0.34 mg/kg, 0.35 mg/kg, 0.36 mg/kg, 0.37 mg/kg, 0.38 mg/kg, 0.39 mg/kg, 0.40 mg/kg, 0.41 mg/kg, 0.42 mg/kg, 0.43 mg/kg, 0.44 mg/kg, 0.45 mg/kg, 0.46 mg/kg, 0.47 mg/kg, 0.48 mg/kg, 0.49 mg/kg, 0.5 mg/kg, 0.6 mg/kg, 0.7 mg/kg, 0.8 mg/kg, 0.9 mg/kg, or 1 mg/kg. In a specific embodiment, the immune suppression therapy comprises administering prednisone at a dose ranging from about 0.10 mg/kg to about 0.20 mg/kg. In a specific embodiment, the immune suppression therapy comprises administering prednisone at a dose ranging from about 0.20 mg/kg to about 0.30 mg/kg. In a specific embodiment, the immune suppression therapy comprises administering prednisone at a dose ranging from about 0.30 mg/kg to about 0.40 mg/kg. In a specific embodiment, the immune suppression therapy comprises administering prednisone at a dose ranging from about 0.40 mg/kg to about 0.50 mg/kg. In a specific embodiment, the immune suppression therapy comprises administering prednisone at a dose ranging from about 0.50 mg/kg to about 1 mg/kg. In a particular embodiment, the dose is administered daily. In a particular embodiment, the immune suppression therapy comprises administering prednisone at a dose of 0.5 mg/kg daily. In another particular embodiment, the immune suppression therapy comprises administering prednisone at a dose of 0.5 mg/kg daily with gradual tapering and discontinuation.

In a specific embodiment, the immune suppression therapy comprises administering methylprednisolone at a dose of about 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg. In a specific embodiment, the immune suppression therapy comprises administering methylprednisolone at a dose ranging from about 0.50 mg/kg to about 1.0 mg/kg. In a specific embodiment, the immune suppression therapy comprises administering methylprednisolone at a dose ranging from about 1.0 mg/kg to about 2.0 mg/kg. In a specific embodiment, the immune suppression therapy comprises administering methylprednisolone at a dose ranging from about 2.0 mg/kg to about 3.0 mg/kg. In a specific embodiment, the immune suppression therapy comprises administering methylprednisolone at a dose ranging from about 3.0 mg/kg to about 5.0 mg/kg. In a specific embodiment, the immune suppression therapy comprises administering methylprednisolone at a dose ranging from about 5.0 mg/kg to about 10.0 mg/kg. In a specific embodiment, the immune suppression therapy comprises administering methylprednisolone at a dose ranging from about 10.0 mg/kg to about 15.0 mg/kg. In a specific embodiment, the immune suppression therapy comprises administering methylprednisolone at a dose ranging from about 15.0 mg/kg to about 20.0 mg/kg. In a particular embodiment, the methylprednisolone is administered once. In a particular embodiment, the methylprednisolone is administered intravenously. In a particular embodiment, the methylprednisolone is administered for a maximum of 500 mg, In a particular embodiment, the methylprednisolone s administered over at least 30 minutes. In a particular embodiment, the immune suppression therapy comprises administering methylprednisolone at a dose of 10 mg/kg IV for maximum of 500 mg over at least 30 minutes.

In a specific embodiment, the immune suppression therapy comprises administering sirolimus at a dose to maintain a target blood level of 1-3 ng/mL. In a specific embodiment, the immune suppression therapy comprises administering sirolimus at a dose of about 0.25 mg/m$^2$/day, 0.3 mg/m$^2$/day, 0.4 mg/m$^2$/day, 0.5 mg/m$^2$/day, 0.6 mg/m$^2$/day, 0.7 mg/m$^2$/day, 0.8 mg/m$^2$/day, 0.9 mg/m$^2$/day, 1 mg/m$^2$/day, 1.25 mg/m$^2$/day, 1.5 mg/m$^2$/day, 1.75 mg/m$^2$/day, 2 mg/m$^2$/day, 2.25 mg/m$^2$/day, 2.5 mg/m$^2$/day, 2.75 mg/m$^2$/day, 3 mg/m$^2$/day, 3.25 mg/m$^2$/day, 3.5 mg/m$^2$/day, 3.75 mg/m$^2$/day, 4 mg/m$^2$/day, 4.25 mg/m$^2$/day, 4.5 mg/m$^2$/day, 4.75 mg/m$^2$/day, or 5 mg/m$^2$/day. In a specific embodiment, the immune suppression therapy comprises administering sirolimus at a dose ranging from about 0.25 mg/m$^2$/day to about 0.5 mg/m$^2$/day. In a specific embodiment, the immune suppression therapy comprises administering sirolimus at a dose ranging from about 0.50 mg/m$^2$/day to about 1.0 mg/m$^2$/day. In a specific embodiment, the immune suppression therapy comprises administering sirolimus at a dose ranging from about 1.0 mg/m$^2$/day to about 1.5 mg/m$^2$/day. In a specific embodiment, the immune suppression therapy comprises administering sirolimus at a dose ranging from about 1.5 mg/m$^2$/day to about 2 mg/m$^2$/day. In a specific embodiment, the immune suppression therapy comprises administering sirolimus at a dose ranging from about 2 mg/m$^2$/day to about 5 mg/m$^2$/day. In a particular embodiment, the dose is divided in BID dosing. In a particular embodiment, the immune suppression therapy comprises administering sirolimus at a dose of about 1 mg/m$^2$/day every 4 hours. In a particular embodiment, the immune suppression therapy comprises administering sirolimus at a dose of about 0.5 mg/m$^2$/day divided in BID dosing.

In a specific embodiment, the immune suppression therapy comprises administering tacrolimus at a dose to maintain a target blood level of 2-4 ng/mL. In a particular embodiment, the immune suppression therapy comprises administering tacrolimus at a dose of about 0.01 mg/kg, 0.02 mg/kg, 0.03 mg/kg 0.04 mg/kg 0.05 mg/kg, 0.06 mg/kg, 0.07 mg/kg, 0.08 mg/kg, 0.09 mg/kg, or 0.10 mg/kg. In a particular embodiment, the immune suppression therapy comprises administering tacrolimus at a dose ranging from 0.01 mg/kg to 0.02 mg/kg. In a particular embodiment, the immune suppression therapy comprises administering tacrolimus at a dose ranging from 0.02 mg/kg to 0.03 mg/kg. In a particular embodiment, the immune suppression therapy comprises administering tacrolimus at a dose ranging from 0.03 mg/kg to 0.05 mg/kg. In a particular embodiment, the immune suppression therapy comprises administering tacrolimus at a dose ranging from 0.05 mg/kg to 0.07 mg/kg. In a particular embodiment, the immune suppression therapy comprises administering tacrolimus at a dose ranging from 0.07 mg/kg to 0.10 mg/kg. In a particular embodiment, the dose is administered twice daily. In a particular embodiment, the immune suppression therapy comprises administering tacrolimus at a dose of about 0.05 mg/kg twice daily.

In some embodiments, the method further comprises administering one or more antibiotics to the human subject before or concurrently with the immune suppression therapy. In a specific embodiment, the one or more antibiotics are trimethoprim, sulfamethoxazole, pentamidine, dapsone, and/or atovaquone. In another specific embodiment, the one or more antibiotics are trimethoprim and/or sulfamethoxazole. In another specific embodiment, the one or more antibiotics are pentamidine, dapsone, and/or atovaquone. In specific embodiments, the one or more antibiotics are administered at a dose of about 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg. In specific embodiments, the one or more antibiotics are administered at a dose ranging from about 1 mg/kg to 2 mg/kg. In specific embodiments, the one or more antibiotics are administered at a dose ranging from about 2 mg/kg to 3 mg/kg. In specific embodiments, the one or more antibiotics are administered at a dose ranging from about 3 mg/kg to 5 mg/kg. In specific embodiments, the one or more antibiotics are administered at a dose ranging from about 5 mg/kg to 7 mg/kg. In specific embodiments, the one or more antibiotics are administered at a dose ranging from about 7 mg/kg to 10 mg/kg. In a specific embodiment, the one or more antibiotics are administered at a dose of about three times a week. In certain embodiments, the one or more antibiotics are administered to prevent *Pneumocystis carinii* pneumonia.

In some embodiments, the method further comprises administering one or more antifungal therapies to the human subject before or concurrently with the immune suppression therapy. In certain embodiments, the one or more antifungal therapies are initiated if the absolute neutrophil count is <500 mm$^3$.

In some embodiments, the method further comprises a step of measuring one or more of the following biomarkers after administration of the recombinant nucleotide expression vector: (a) level of glycosaminoglycans (GAGs) in CSF; (b) level of iduronate-2-sulfatase (I2S) in CSF; (c) level of GAGs in plasma; (d) level of I2S in plasma; (e) level of leukocyte I2S enzyme activity; and (f) level of GAGs in urine. In a specific embodiment, the GAGs in CSF comprise heparin sulfate in CSF. In another specific embodiment, the GAGs in CSF are heparin sulfate in CSF. In another specific embodiment, the GAGs in plasma comprise heparin sulfate in plasma. In another specific embodiment, the GAGs in plasma are heparin sulfate in plasma. In another specific embodiment, the GAGs in urine comprise heparin sulfate in urine. In another specific embodiment, the GAGs in urine are heparin sulfate in urine. In a specific embodiment, the step of measuring comprises mearing level of heparin sulfate in CSF. In another specific embodiment, the step of measuring comprises measuring level of leukocyte I2S enzyme activity.

In certain embodiments of the method for treating described herein, the recombinant nucleotide expression vector is a liquid composition. In certain embodiments of the method for treating described herein, the recombinant nucleotide expression vector is a frozen composition. In certain embodiments of the method for treating described herein, the recombinant nucleotide expression vector is a lyophilized composition or a reconstituted lyophilized composition. In certain embodiments of the method for treating described herein, the recombinant nucleotide expression vector provided herein may be formulated in various dosage forms for IC or ICV administration. In certain embodiments of the method for treating described herein, the recombinant nucleotide expression vector provided herein may be provided in a unit-dosage form or multiple-dosage form. A unit-dosage form, as used herein, refers to a physically discrete unit suitable for administration to human and animal subjects, and packaged individually as is known in the art. Each unit-dose contains a predetermined quantity of the said recombinant nucleotide expression vector and/or other ingredient(s) sufficient to produce the desired therapeutic effect, in association with the required pharmaceutical carriers or excipients. Examples of a unit-dosage form include an ampoule, a vial, a prefilled syringe, or a cartridge.

In certain embodiments of the method for treating described herein, a unit-dosage form may be administered in fractions or multiples thereof. In certain embodiments of the method for treating described herein, a multiple-dosage form is a plurality of identical unit-dosage forms packaged in a single container to be administered in segregated unit-dosage form. Examples of a multiple-dosage form include a vial, a prefilled syringe, or a cartridge. In certain embodiments, the prefilled syringe comprises $8.5 \times 10^{12}$ GC of the recombinant nucleotide expression vector In certain embodiments, the prefilled syringe comprises $9.8 \times 10^{12}$ GC of the recombinant nucleotide expression vector. In certain embodiments, the prefilled syringe comprises $1.1 \times 10^{13}$ GC of the recombinant nucleotide expression vector. In certain embodiments, the prefilled syringe comprises $1.3 \times 10^{13}$ GC of the recombinant nucleotide expression vector. In certain embodiments, the prefilled syringe comprises $1.5 \times 10^{11}$ GC of the recombinant nucleotide expression vector. In certain embodiments, the prefilled syringe comprises $1.7 \times 10^{13}$ GC of the recombinant nucleotide expression vector. In certain embodiments, the prefilled syringe comprises $4.2 \times 10^{11}$ GC of the recombinant nucleotide expression vector In certain embodiments, the prefilled syringe comprises $4.9 \times 10^{13}$ GC of the recombinant nucleotide expression vector. In certain embodiments, the prefilled syringe comprises $5.5 \times 10^{11}$ GC of the recombinant nucleotide expression vector. In certain embodiments, the prefilled syringe comprises $6.3 \times 10^{11}$ GC of the recombinant nucleotide expression vector. In certain embodiments, the prefilled syringe comprises $7.3 \times 10^{11}$ GC of the recombinant nucleotide expression vector. In certain embodiments, the prefilled syringe comprises $8.5 \times 10^{12}$ GC of the recombinant nucleotide expression vector. In certain embodiments, the prefilled syringe comprises $9.0 \times 10^{13}$ GC of the recombinant nucleotide expression vector. In certain embodiments, the prefilled syringe comprises $1.0 \times 10^{14}$ GC of the recombinant nucleotide expression vector. In certain embodiments, the prefilled syringe comprises $1.1 \times 10^{10}$ GC of the recombinant nucleotide expression vector. In certain embodiments, the prefilled syringe comprises $1.2 \times 10^{14}$ GC of the recombinant nucleotide expression vector. In certain embodiments, the prefilled syringe comprises $1.3 \times 10^{14}$ GC of the recombinant nucleotide expression vector. In certain embodiments, the prefilled syringe comprises $1.4 \times 10^{14}$ GC of the recombinant nucleotide expression vector. In certain embodiments, the prefilled syringe comprises $1.5 \times 10^{11}$ GC of the recombinant nucleotide expression vector. In certain embodiments, the prefilled syringe comprises $1.6 \times 10^{11}$ GC of the recombinant nucleotide expression vector. In certain embodiments, the prefilled syringe comprises $1.7 \times 10^{14}$ GC of the recombinant nucleotide expression vector. In certain embodiments, the prefilled syringe comprises $1.8 \times 10^{14}$ GC of the recombinant nucleotide expression vector. In certain embodiments, the prefilled syringe comprises $1.9 \times 10^{10}$ of the recombinant nucleotide expression vector. In certain embodiments, the prefilled syringe comprises $2.0 \times 10^{14}$ GC of the recombinant nucleotide expression vector. In certain embodiments, the prefilled syringe comprises $2.1 \times 10^{14}$ GC of the recombinant nucleotide expression vector. In certain embodiments, the prefilled syringe comprises $2.2 \times 10^{14}$ GC of the recombinant nucleotide expression vector. In certain embodiments, the prefilled syringe comprises $2.3 \times 10^{14}$ GC of the recombinant nucleotide expression vector. In certain embodiments, the prefilled syringe comprises $2.4 \times 10^{14}$ GC of the recombinant nucleotide expression vector. In certain embodiments, the prefilled syringe comprises $2.5 \times 10^{14}$ GC of the recombinant nucleotide expression vector. In certain embodiments, the prefilled syringe comprises $2.6 \times 10^{14}$ GC of the recombinant nucleotide expression vector. In certain embodiments, the prefilled syringe comprises $1.3 \times 10^{10}$ GC of the recombinant nucleotide expression vector. In certain embodiments, the prefilled syringe comprises $1.9 \times 10^{10}$ GC of the recombinant nucleotide expression vector. In certain embodiments, the prefilled syringe comprises $6.5 \times 10^{10}$ GC of the recombinant nucleotide expression vector. In certain embodiments, the prefilled syringe comprises $9.6 \times 10^{10}$ GC of the recombinant nucleotide expression vector. In certain embodiments, the prefilled syringe comprises $2.0 \times 10^{11}$ GC of the recombinant nucleotide expression vector. In certain embodiments, the prefilled syringe comprises $2.9 \times 10^{11}$ GC of the recombinant nucleotide expression vector.

As used herein, the term "about" means within plus or minus 10% of a given value or range. In certain embodiments, the term "about" means within plus or minus 1% of a given value or range, wherein the value is a dose that is dependent on the human subject's brain mass, and wherein the brain mass is determined by brain MRI of the human subject's brain. In certain embodiments, the term "about" means within plus or minus 2% of a given value or range, wherein the value is a dose that is determined by brain MRI of the subject's brain, and wherein the brain mass is determined by brain MRI of the human subject's brain. In certain embodiments, the term "about" means within plus or minus 5% of a given value or range, wherein the value is a dose that is dependent on the human subject's brain mass, and wherein the brain mass is determined by brain MRI of the human subject's brain. In certain embodiments, the term "about" means within plus or minus 7% of a given value or range, wherein the value is a dose that is dependent on the human subject's brain mass, and wherein the brain mass is determined by brain MRI of the human subject's brain. In certain embodiments, the term "about" means within plus or minus 10% c of a given value or range, wherein the value is a dose that is dependent on the human subject's brain mass, and wherein the brain mass is determined by brain MRI of the human subject's brain. However, it is to be understood that in this specification, the term "about" also affords support for recitation of the exact value with which the term is connected. For example, "about 10" also provides support for the number "10" exactly.

5.1 Processing, N-Glycosylation and Tyrosine Sulfation 5.1.1. Processing

Human IDS includes a 25 amino acid signal sequence which is cleaved during processing. An initial 76 kDa intracellular IDS precursor is converted into a phosphorylated 90 kDa IDS precursor after modification of its oligosaccharide chains in the Golgi apparatus. This precursor is processed by glycosylation modifications and proteolytic cleavage through various intracellular intermediates to a major 55 kDa form. To summarize, after removal of the 25 aa signal sequence, proteolytic processing involves N-terminal proteolytic cleavage downstream of $N^{31}$ removing a propeptide of eight amino acids (residues 26-33), and C-terminal proteolytic cleavage upstream of $N^{513}$ which releases an 18 kDa polypeptide and produces a 62 kDa intermediate that is converted to a 55 kDa mature form. Further proteolytic cleavage yields a 45 kDa mature form located in the lysosomal compartment. (See FIG. 4 for diagram reproduced from Millat et al., 1997, Exp Cell Res 230: 362-367 ("Millat 1997"); Millat et al. 1997, Biochem J. 326: 243-247 ("Millat 1997a"); and Froissart et al., 1995, Biochem J. 309:425-430, each of which is incorporated by reference herein in its entirety).

A formylglycine modification of $C^{84}$ (shown in bold in FIG. 1) required for enzyme activity probably occurs as an early post-translational or co-translational event, most probably in the endoplasmic reticulum. (See, Millat 1997a, citing Schmidt et al., 1995, Cell 82: 271-278). Post-translational processing continues in the Golgi to include addition of complex sialic acid-containing glycans and acquisition of mannose-6-phosphate residues which tag the enzyme for delivery to the lysosomal compartment. (See, Clarke, 2008, Expert Opin Pharmacother 9: 311-317 for a concise review which is incorporated by reference herein in its entirety).

In a specific embodiment, HuGlyIDS used in accordance with the methods described herein, when expressed in a neuronal or glial cell, in vivo or in vitro, can be the 90 kDa (e.g., 85 kDa, 86 kDa, 87 kDa, 88 kDa, 89 kDa, 90 kDa, 91 kDa, 92 kDa, 93 kDa, 94 kDa, or 95 kDa) mannose-6-phosphorylated form of the enzyme. IDS produced from neuronal and glial cells may contain higher M6P content, as reported in Daniele 2002, and in Sleat, Proteomics, 2005 (indicating that the human brain contains more (in both a quantitative and qualitative sense) M6P glycoproteins than other tissues). It is possible to measure the M6P content of an IDS precursor, as done in Daniele 2002.

Accordingly, in certain embodiments, HuGlyIDS used in accordance with the methods described herein, when expressed in a neuronal or glial cell, in vivo or in vitro, is mannose-6-phosphorylated at a higher level than IDS expressed in a non-neuronal or glial cell. In particular, HuGlyIDS used in accordance with the methods described herein, when expressed in a neuronal or glial cell, in vivo or in vitro, is mannose-6-phosphorylated at a higher level than IDS expressed in a HT1080 or CHO cell. In certain embodiments, the mannose-6-phosphorylation level of the expressed IDS is measured by uptake of the IDS by a human neuronal cell in the presence of M6P (e.g., 5 mM M6P). In certain embodiments, when expressed in a neuronal or glial cell, in vivo or in vitro, 10%-20%, 20%-30%, 30%-40%, 40%-50%, 50%-60%, 60%-70%, 70%-80%, 80%-90%, or 90%-100% of HuGlyIDS molecules used in accordance with the methods described herein are mannose-6-phosphorylated.

5.1.2. N-Glycosylation

Neuronal and glial cells in the CNS are secretory cells that possess the cellular machinery for post-translational processing of secreted proteins—including glycosylation and tyrosine-O-sulfation. hIDS has eight asparaginal ("N") glycosylation sites identified in FIG. 1 ($N^{31}$ST; $N^{115}$FS; $N^{144}$HT; $N^{246}$IT; $N^{280}$IS; $N^{325}$ST; $N^{513}$FS; $N^{537}$DS). Two of the eight N-linked glycosylation sites, namely $N^{280}$ and $N^{116}$, are mannose-6-phophorylated in IDS obtained from human brain. (Sleat et al., 2006, Mol & Cell Proeomics 5.4: 686-701, reported at Table V). While no single glycosylation site is essential for LDS stability, glycosylation at position $N^{280}$ is important for cellular internalization and lysosomal targeting via the mannose-6-phosphate (M6P) receptor. (Chung et al., 2014, Glycoconj J 31:309-315 at p. 310, first column). In the normal physiologic state, IDS is produced at very low levels and very little, if any, enzyme is secreted from the cell. (Clarke, 2008, supra).

It is not essential that every molecule produced either in the gene therapy or protein therapy approach be fully glycosylated and sulfated. Rather, the population of glycoproteins produced should have sufficient glycosylation and sulfation to demonstrate efficacy.

In a specific embodiment, HuGlyIDS used in accordance with the methods described herein, when expressed in a neuronal or glial cell, in vivo or in vitro, could be glycosylated at 100% of its N-glycosylation sites. However, one of skill in the art will appreciate that not every N-glycosylation site of HuGlyIDS need be N-glycosylated in order for benefits of glycosylation to be attained. Rather, benefits of glycosylation can be realized when only a percentage of N-glycosylation sites are glycosylated, and/or when only a percentage of expressed IDS molecules are glycosylated. Accordingly, in certain embodiments, HuGlyIDS used in accordance with the methods described herein, when expressed in a neuronal or glial cell, in vivo or in vitro, is glycosylated at 10%-20%, 20%-30%, 30%-40%, 40%-50%, 50%-60%, 60%-70%, 70%-80%, 80%-90°/%, or 90%-100% of its available N-glycosylation sites. In certain embodiments, when expressed in a neuronal or glial cell, in vivo or in vitro, 10%-20%, 20%-30%, 30%-40%, 40%-50%, 50%-60%, 60%-70%, 70%-80%, 80%-90%, or 90%-100% of HuGlyIDS molecules used in accordance with the methods described herein are glycosylated at least one of their available N-glycosylation sites.

In a specific embodiment, at least 10%, 20% 30%, 40%, 50%, 60%, 70%, 75%, 80%, 85%, 900, 95%, or 99% of the N-glycosylation sites present in HuGlyIDS used in accordance with the methods described herein are glycosylated at an Asn residue (or other relevant residue) present in an N-glycosylation site, when the HuGlyIDS is expressed in a neuronal or glial cell, in vivo or in vitro. That is, at least 50%, 60%, 70%, 75%, 80%, 85%, 90%, 95%, or 99% of the N-glycosylation sites of the resultant HuGlyIDS are glycosylated.

In another specific embodiment, at least 10%, 20% 30%, 40%, 50%, 60%, 70%, 75%, 80%, 85%, 90%, 95%, or 99% of the N-glycosylation sites present in a HuGlyIDS molecule used in accordance with the methods described herein are glycosylated with an identical attached glycan linked to the Asn residue (or other relevant residue) present in an N-glycosylation site, when the HuGlyIDS is expressed in a neuronal or glial cell, in vivo or in vitro. That is, at least 50%, 60%, 70%, 75%, 80%, 85%, 90%, 95%, or 99% of the N-glycosylation sites of the resultant HuGlyIDS have an identical attached glycan.

Importantly, when the IDS proteins used in accordance with the methods described herein are expressed in neuronal or glial cells, the need for in vitro production in prokaryotic host cells (e.g., E. coli) or eukaryotic host cells (e.g., CHO cells) is circumvented. Instead, as a result of the methods described herein (e.g., use of neuronal or glial cells to express IDS), N-glycosylation sites of the IDS proteins are advantageously decorated with glycans relevant to and beneficial to treatment of humans, and, in particular, at the target location of treatment. Such an advantage is unattainable when CHO cells or E. coli are utilized in protein production, because e.g., CHO cells (1) do not express 2,6 sialyltransferase and thus cannot add 2,6 sialic acid during N-glycosylation and (2) can add Neu5Gc as sialic acid instead of Neu5Ac; and because E. coli does not naturally contain components needed for N-glycosylation. Furthermore, such an advantage may be unattainable when human cells that are not neuronal or glial cells are utilized in protein production. Accordingly, in one embodiment, an IDS protein expressed in a neuronal or glial cell to give rise to a HuGlyIDS used in the methods of treatment described herein is glycosylated in the manner in which a protein is N-glycosylated in human neuronal or glial cells, but is not glycosylated in the manner in which proteins are glycosylated in CHO cells. In another embodiment, an IDS protein expressed in a neuronal or glial cell to give rise to a HuGlyIDS used in the methods of treatment described herein is glycosylated in the manner in which a protein is N-glycosylated in a neuronal or glial cells, wherein such glycosylation is not naturally possible using a prokaryotic host cell, e.g., using E. coli. In one embodiment, an IDS protein expressed in a human neuronal or glial cell to give rise to a HuGlyIDS used in the methods of treatment described herein is glycosylated in the manner in which a protein is N-glycosylated in human neuronal or glial cells, but is not glycosylated in the manner in which proteins are glycosylated in human cells which are not neuronal or glial cells.

Assays for determining the glycosylation pattern of proteins are known in the art. For example, hydrazinolysis can be used to analyze glycans. First, polysaccharides are released from their associated protein by incubation with hydrazine (the Ludger Liberate Hydrazinolysis Glycan Release Kit, Oxfordshire, UK can be used). The nucleophile hydrazine attacks the glycosidic bond between the polysaccharide and the carrier protein and allows release of the attached glycans. N-acetyl groups are lost during this treatment and have to be reconstituted by re-N-acetylation. The free glycans can be purified on carbon columns and subsequently labeled at the reducing end with the fluorophor 2-amino benzamide. The labeled polysaccharides can be separated on a GlycoSep-N column (GL Sciences) according to the HPLC protocol of Royle et al, Anal Biochem 2002, 304(1):70-90. The resulting fluorescence chromatogram indicates the polysaccharide length and number of repeating units. Structural information can be gathered by collecting individual peaks and subsequently performing MS/MS analysis. Thereby the monosaccharide composition and sequence of the repeating unit can be confirmed and additionally in homogeneity of the polysaccharide composition can be identified. Specific peaks of low molecular weight can be analyzed by MALDI-MS/MS and the result used to confirm the glycan sequence. Each peak corresponds to a polymer consisting of a certain number of repeat units and fragments thereof. The chromatogram thus allows measurement of the polymer length distribution. The elution time is an indication for polymer length, while fluorescence intensity correlates with molar abundance for the respective polymer.

Homogeneity of the glycan patterns associated with proteins, as it relates to both glycan length and numbers glycans present across glycosylation sites, can be assessed using methods known in the art, e.g., methods that measure glycan length and hydrodynamic radius. Size exclusion-HPLC allows the measurement of the hydrodynamic radius. Higher numbers of glycosylation sites in a protein lead to higher variation in hydrodynamic radius compared to a carrier with less glycosylation sites. However, when single glycan chains are analyzed, they may be more homogenous due to the more controlled length. Glycan length can measured by hydrazinolysis, SDS PAGE, and capillary gel electrophoresis. In addition, homogeneity can also mean that certain glycosylation site usage patterns change to a broader/narrower range. These factors can be measured by Glycopeptide LC-MS/MS.

N-glycosylation confers numerous benefits on the HuGlyIDS used in the methods described herein. Such benefits are unattainable by production of proteins in E. coli, because E. coli does not naturally possess components needed for N-glycosylation. Further, some benefits are unattainable through protein production in, e.g., CHO cells, because CHO cells lack components needed for addition of certain glycans (e.g., 2,6 sialic acid) and because CHO cells can add glycans, e.g., Neu5Gc not typical to humans, and the α-Gal antigen which is immunogenic in most individuals and at high concentrations can trigger anaphylaxis. Even further, some benefits are unattainable through protein production in human cells that are not neuronal or glial cells. Thus, the expression of IDS in human neuronal or glial cells results in the production of HuGlyIDS comprising beneficial glycans that otherwise would not be associated with the protein if produced in CHO cells, in E. coli, or in human cells which are not neuronal or glial cells.

5.1.3. Tyrosine Sulfation

In addition to the N-linked glycosylation sites, hIDS contains a tyrosine ("Y") sulfation site (PSSEKY$^{165}$ENTKTCRGPD (SEQ ID NO: 47)). (See, e.g., Yang et al., 2015, Molecules 20:2138-2164, esp. at p. 2154 which is incorporated by reference in its entirety for the analysis of amino acids surrounding tyrosine residues subjected to protein tyrosine sulfation. The "rules" can be summarized as follows: Y residues with E or D within +5 to −5 position of Y, and where position −1 of Y is a neutral or acidic charged amino acid—but not a basic amino acid, e.g., R, K, or H that abolishes sulfation).

Importantly, tyrosine-sulfated proteins cannot be produced in E. coli, which naturally does not possess the enzymes required for tyrosine-sulfation. Further, CHO cells are deficient for tyrosine sulfation-they are not secretory cells and have a limited capacity for post-translational tyrosine-sulfation. See, e.g., Mikkelsen & Ezban, 1991, Biochemistry 30: 1533-1537. Advantageously, the methods provided herein call for expression of IDS, e.g., HuGlyIDS, in neurons or glial cells, which are secretory and do have capacity for tyrosine sulfation. Assays for detection tyrosine sulfation are known in the art. See, e.g., Yang et al., 2015, Molecules 20:2138-2164.

Tyrosine-sulfation of hIDS—a robust post-translational process in human CNS cells—should result in improved processing and activity of transgene products. The significance of tyrosine-sulfation of lysosomal proteins has not been elucidated; but in other proteins it has been shown to increase avidity of protein-protein interactions (antibodies and receptors), and to promote proteolytic processing (peptide hormone). (See, Moore, 2003, J Biol. Chem. 278: 24243-46; and Bundegaard et al., 1995, The EMBO J 14: 3073-79). The tyrosylprotein sulfotransferase (TPST1) responsible for tyrosine-sulfation (which may occur as a final step in IDS processing) is apparently expressed at higher levels (based on mRNA) in the brain (gene expression data for TPST1 may be found, for example, at the EMBL-EBI Expression Atlas, accessible at http://www.ebi.ac.uk/gxa/home).

5.2 Constructs and Formulations

For use in the methods provided herein are viral vectors or other DNA expression constructs encoding iduronate-2- sulfatase (IDS), e.g., human IDS (hIDS). For use in the methods provided herein are viral vectors or other DNA expression constructs encoding glycosylated (HuGly) α-L-iduronidase (IDUA), e.g., human IDUA (hIDUA). The viral vectors and other DNA expression constructs provided herein include any suitable method for delivery of a transgene to the cerebrospinal fluid (CSF). The means of delivery of a transgene include viral vectors, liposomes, other lipid-containing complexes, other macromolecular complexes, synthetic modified mRNA, unmodified mRNA, small molecules, non-biologically active molecules (e.g., gold particles), polymerized molecules (e.g., dendrimers), naked DNA, plasmids, phages, transposons, cosmids, or episomes. In some embodiments, the vector is a targeted vector, e.g., a vector targeted to neuronal cells.

In some aspects, the disclosure provides for a nucleic acid for use, wherein the nucleic acid encodes an IDS, e.g., hIDS, operatively linked to a promoter selected from the group consisting of: cytomegalovirus (CMV) promoter, Rous sarcoma virus (RSV) promoter, MMT promoter, EF-1 alpha promoter, UB6 promoter, chicken beta-actin promoter, CAG promoter, RPE65 promoter and opsin promoter.

In certain embodiments, provided herein are recombinant vectors that comprise one or more nucleic acids (e.g. polynucleotides). The nucleic acids may comprise DNA, RNA, or a combination of DNA and RNA. In certain embodiments, the DNA comprises one or more of the sequences selected from the group consisting of promoter sequences, the sequence of the gene of interest (the transgene, e.g., IDS), untranslated regions, and termination sequences. In certain embodiments, viral vectors provided herein comprise a promoter operably linked to the gene of interest.

In certain embodiments, nucleic acids (e.g., polynucleotides) and nucleic acid sequences disclosed herein may be codon-optimized, for example, via any codon-optimization technique known to one of skill in the art (see, e.g., review by Quax et al., 2015, Mol Cell 59:149-161).

In another aspect, the disclosure provides for a formulation comprising a recombinant nucleotide expression vector encoding human IDS, wherein the formulation is suitable for administration to the cerebrospinal fluid of human brain, so that a depot is formed in the human central nervous system that secretes a recombinant human IDS glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain α-Gal antigen, and/or is mannose-6-phosphorylated. For example, the formulation may contain buffer (such as, a buffer having a particular pH, or a buffer containing a particular ingredient) that makes it suitable for administration to the cerebrospinal fluid of human brain, so that a depot is formed in the human central nervous system that secretes a recombinant human IDS glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain α-Gal antigen, and/or is mannose-6-phosphorylated. In a specific embodiment, the buffer comprises a physiologically compatible aqueous buffer, a surfactant and optional excipients.

In another aspect, the disclosure provides for a kit comprising a recombinant nucleotide expression vector encoding human IDS and a pharmaceutically acceptable carrier, wherein the recombinant nucleotide expression vector is suitable for administration to the cerebrospinal fluid (CSF) of human brain, so that a depot is formed in the human central nervous system that secretes a recombinant human IDS glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated. In another aspect, the disclosure provides for a kit comprising a formulation comprising a recombinant nucleotide expression vector encoding human IDS, wherein the formulation is suitable for administration to the CSF of human brain, so that a depot is formed in the human central nervous system that secretes a recombinant human IDS glycoprotein precursor that is about 90 kDa (e.g., 85 kDa, 86 kDa, 87 kDa, 88 kDa, 89 kDa, 90 kDa, 91 kDa, 92 kDa, 93 kDa, 94 kDa, or 95 kDa) as measured by polyacrylamide gel electrophoresis, contains a formylglycine, is α2,6-sialylated, does not contain detectable NeuGc, does not contain detectable α-Gal antigen, and/or is mannose-6-phosphorylated. A kit described herein comprises the recombinant nucleotide expression vector or the formulation in one or more containers. Optionally associated with such one or more containers can be a notice in the form prescribed by a governmental agency regulating the manufacture, use or sale of pharmaceuticals or biological products, which notice reflects approval by the agency of manufacture, use or sale for human administration.

The formulations and kits encompassed herein can be used in accordance with the methods for treating a human patient as provided in this disclosure.

5.2.1. mRNA

In certain embodiments, the vectors provided herein are modified mRNA encoding for the gene of interest (e.g., the transgene, for example, IDS). The synthesis of modified and unmodified mRNA for delivery of a transgene to the CSF is taught, for example, in Hocquemiller et al., 2016, Human Gene Therapy 27(7):478-496, which is incorporated by reference herein in its entirety. In certain embodiments, provided herein is a modified mRNA encoding for IDS, e.g., hIDS.

5.2.2. Viral Vectors

Viral vectors include adenovirus, adeno-associated virus (AAV, e.g., AAV9, AAVrh10), lentivirus, helper-dependent adenovirus, herpes simplex virus, poxvirus, hemagglutinin virus of Japan (HVJ), alphavirus, vaccinia virus, and retrovirus vectors. Retroviral vectors include murine leukemia virus (MLV)- and human immunodeficiency virus (HIV)-based vectors. Alphavirus vectors include semliki forest virus (SFV) and sindbis virus (SIN). In certain embodiments, the viral vectors provided herein are recombinant viral vectors. In certain embodiments, the viral vectors provided herein are altered such that they are replication-deficient in humans. In certain embodiments, the viral vectors are hybrid vectors, e.g., an AAV vector placed into a "helpless" adenoviral vector. In certain embodiments, provided herein are viral vectors comprising a viral capsid from a first virus and viral envelope proteins from a second virus. In specific embodiments, the second virus is vesicular stomatitus virus (VSV). In more specific embodiments, the envelope protein is VSV-G protein.

In certain embodiments, the viral vectors provided herein are HIV based viral vectors. In certain embodiments, HIV-based vectors provided herein comprise at least two polynucleotides, wherein the gag and pol genes are from an HIV genome and the env gene is from another virus.

In certain embodiments, the viral vectors provided herein are herpes simplex virus-based viral vectors. In certain embodiments, herpes simplex virus-based vectors provided herein are modified such that they do not comprise one or more immediately early (IE) genes, rendering them non-cytotoxic.

In certain embodiments, the viral vectors provided herein are MLV based viral vectors. In certain embodiments, MLV-based vectors provided herein comprise up to 8 kb of heterologous DNA in place of the viral genes.

In certain embodiments, the viral vectors provided herein are lentivirus-based viral vectors. In certain embodiments, lentiviral vectors provided herein are derived from human lentiviruses. In certain embodiments, lentiviral vectors provided herein are derived from non-human lentiviruses. In certain embodiments, lentiviral vectors provided herein are packaged into a lentiviral capsid. In certain embodiments, lentiviral vectors provided herein comprise one or more of the following elements: long terminal repeats, a primer binding site, a polypurine tract, att sites, and an encapsidation site.

In certain embodiments, the viral vectors provided herein are alphavirus-based viral vectors. In certain embodiments, alphavirus vectors provided herein are recombinant, replication-defective alphaviruses. In certain embodiments, alphavirus replicons in the alphavirus vectors provided herein are targeted to specific cell types by displaying a functional heterologous ligand on their virion surface.

In certain embodiments, the viral vectors provided herein are AAV based viral vectors. In preferred embodiments, the viral vectors provided herein are AAV9 or AAVrh10 based viral vectors. In certain embodiments, the AAV9 or AAVrh10 based viral vectors provided herein retain tropism for CNS cells. Multiple AAV serotypes have been identified. In certain embodiments, AAV-based vectors provided herein comprise components from one or more serotypes of AAV. In certain embodiments, AAV based vectors provided herein comprise components from one or more of AAV1, AAV2, AAV3, AAV4, AAV5, AAV6, AAV7, AAV8, AAV9, AAVrh10, AAV10 or AAV11. In preferred embodiments, AAV based vectors provided herein comprise components from one or more of AAV8, AAV9, AAVrh10, AAV10, or AAV11 serotypes. AAV9-based viral vectors are used in the methods described herein. Nucleic acid sequences of AAV based viral vectors and methods of making recombinant AAV and AAV capsids are taught, for example, in U.S. Pat. No. 7,282,199 B2, U.S. Pat. No. 7,790,449 B2, U.S. Pat. No. 8,318,480 B2, U.S. Pat. No. 8,962,332 B2 and International Patent Application No. PCT/EP2014/076466, each of which is incorporated herein by reference in its entirety. In one aspect, provided herein are AAV (e.g., AAV9 or AAVrh10)-based viral vectors encoding a transgene (e.g., IDS). In specific embodiments, provided herein are AAV9-based viral vectors encoding IDS. In more specific embodiments, provided herein are AAV9-based viral vectors encoding hIDS.

Provided in particular embodiments are AAV9 vectors comprising an artificial genome comprising (i) an expression cassette containing the transgene under the control of regulatory elements and flanked by ITRs; and (ii) a viral capsid that has the amino acid sequence of the AAV9 capsid protein or is at least 95%, 96%, 97%, 98%, 99% or 99.9% identical to the amino acid sequence of the AAV9 capsid protein (SEQ ID NO: 26) while retaining the biological function of the AAV9 capsid. In certain embodiments, the encoded AAV9 capsid has the sequence of SEQ ID NO: 26 with 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions and retaining the biological function of the AAV9 capsid. FIG. 6 provides a comparative alignment of the amino acid sequences of the capsid proteins of different AAV serotypes with potential amino acids that may be substituted at certain positions in the aligned sequences based upon the comparison in the row labeled SUBS. Accordingly, in specific embodiments, the AAV9 vector comprises an AAV9 capsid variant that has 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid substitutions identified in the SUBS row of FIG. 6 that are not present at that position in the native AAV9 sequence.

In certain embodiments, the AAV that is used in the methods described herein is Anc80 or Anc80L65, as described in Zinn et al., 2015, Cell Rep. 12(6): 1056-1068, which is incorporated by reference in its entirety. In certain embodiments, the AAV that is used in the methods described herein comprises one of the following amino acid insertions: LGETTRP (SEQ ID NO: 56) or LALGETTRP (SEQ ID NO: 57), as described in U.S. Pat. Nos. 9,193,956; 9,458,517; and 9,587,282 and US patent application publication no. 2016/0376323, each of which is incorporated herein by reference in its entirety. In certain embodiments, the AAV that is used in the methods described herein is AAV.7m8, as described in U.S. Pat. Nos. 9,193,956; 9,458,517; and 9,587,282 and US patent application publication no. 2016/0376323, each of which is incorporated herein by reference in its entirety. In certain embodiments, the AAV that is used in the methods described herein is any AAV disclosed in U.S. Pat. No. 9,585,971, such as AAV-PHP.B. In certain embodiments, the AAV that is used in the methods described herein is an AAV disclosed in any of the following patents and patent applications, each of which is incorporated herein by reference in its entirety: U.S. Pat. Nos. 7,906,111; 8,524,446; 8,999,678; 8,628,966; 8,927,514; 8,734,809; 9,284,357; 9,409,953; 9,169,299; 9,193,956; 9,458,517; and 9,587,282 US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335.

In certain embodiments, a single-stranded AAV (ssAAV) may be used supra. In certain embodiments, a self-complementary vector, e.g., scAAV, may be used (see, e.g., Wu, 2007, Human Gene Therapy, 18(2):171-82, McCarty et al, 2001, Gene Therapy, Vol 8, Number 16, Pages 1248-1254; and U.S. Pat. Nos. 6,596,535; 7,125,717; and 7,456,683, each of which is incorporated herein by reference in its entirety).

In certain embodiments, the viral vectors used in the methods described herein are adenovirus based viral vectors. A recombinant adenovirus vector may be used to transfer in the IDS. The recombinant adenovirus can be a first generation vector, with an E1 deletion, with or without an E3 deletion, and with the expression cassette inserted into either deleted region. The recombinant adenovirus can be a second generation vector, which contains full or partial deletions of the E2 and E4 regions. A helper-dependent adenovirus retains only the adenovirus inverted terminal repeats and the packaging signal (phi). The transgene is inserted between the packaging signal and the 3'ITR, with or without stuffer sequences to keep the artificial genome close to wild-type size of approx. 36 kb. An exemplary protocol for production of adenoviral vectors may be found in Alba et al., 2005, "Gutless adenovirus: last generation adenovirus for gene therapy," Gene Therapy 12:S18-S27, which is incorporated by reference herein in its entirety.

In certain embodiments, the viral vectors used in the methods described herein are lentivirus based viral vectors. A recombinant lentivirus vector may be used to transfer in the IDS. Four plasmids are used to make the construct: Gag/pol sequence containing plasmid, Rev sequence containing plasmids, Envelope protein containing plasmid (i.e. VSV-G), and Cis plasmid with the packaging elements and the IDS gene.

For lentiviral vector production, the four plasmids are co-transfected into cells (i.e., HEK293 based cells), whereby polyethylenimine or calcium phosphate can be used as transfection agents, among others. The lentivirus is then harvested in the supernatant (lentiviruses need to bud from the cells to be active, so no cell harvest needs/should be done). The supernatant is filtered (0.45 μm) and then magnesium chloride and benzonase added. Further downstream processes can vary widely, with using TFF and column chromatography being the most GMP compatible ones. Others use ultracentrifugation with/without column chromatography. Exemplary protocols for production of lentiviral vectors may be found in Lesch et al., 2011, "Production and purification of lentiviral vector generated in 293T suspension cells with baculoviral vectors," Gene Therapy 18:531-538, and Ausubel et al., 2012, "Production of CGMP-Grade Lentiviral Vectors," Bioprocess Int. 10(2):32-43, both of which are incorporated by reference herein in their entireties.

In a specific embodiment, a vector for use in the methods described herein is one that encodes an IDS (e.g., hIDS) such that, upon transduction of cells in the CNS, or a relevant cell (e.g., a neuronal cell in vivo or in vitro), a glycosylated variant of IDS is expressed by the transduced cell. In a specific embodiment, a vector for use in the methods described herein is one that encodes an IDS (e.g., hIDS) such that, upon transduction of a cell in the CNS, or a relevant cell (e.g., a neuronal cell in vivo or in vitro), a sulfated variant of IDS is expressed by the cell.

5.2.3. Promoters and Modifiers of Gene Expression

In certain embodiments, the vectors provided herein comprise components that modulate gene delivery or gene expression (e.g., "expression control elements"). In certain embodiments, the vectors provided herein comprise components that modulate gene expression. In certain embodiments, the vectors provided herein comprise components that influence binding or targeting to cells. In certain embodiments, the vectors provided herein comprise components that influence the localization of the polynucleotide (e.g., the transgene) within the cell after uptake. In certain embodiments, the vectors provided herein comprise components that can be used as detectable or selectable markers, e.g., to detect or select for cells that have taken up the polynucleotide.

In certain embodiments, the viral vectors provided herein comprise one or more promoters. In certain embodiments, the promoter is a constitutive promoter. In alternate embodiments, the promoter is an inducible promoter. The native IDS gene, like most housekeeping genes, primarily uses a GC-rich promoter. In a preferred embodiment, strong constitutive promoters that provide for sustained expression of hIDS are used. Such promoters include "CAG" synthetic promoters that contain: "C"—the cytomegalovirus (CMV) early enhancer element; "A"—the promoter as well as the first exon and intron of the chicken beta-actin gene; and "G"—the splice acceptor of the rabbit beta-globin gene (see, Miyazaki et al., 1989, Gene 79: 269-277; and Niwa et al., Gene 108: 193-199).

In certain embodiments, the promoter is a CB7 promoter (see Dinculescu et al., 2005, Hum Gene Ther 16: 649-663, incorporated by reference herein in its entirety). In some embodiments, the CB7 promoter includes other expression control elements that enhance expression of the transgene driven by the vector. In certain embodiments, the other expression control elements include chicken β-actin intron and/or rabbit β-globin polA signal. In certain embodiments, the promoter comprises a TATA box. In certain embodiments, the promoter comprises one or more elements. In certain embodiments, the one or more promoter elements may be inverted or moved relative to one another. In certain embodiments, the elements of the promoter are positioned to function cooperatively. In certain embodiments, the elements of the promoter are positioned to function independently. In certain embodiments, the viral vectors provided herein comprise one or more promoters selected from the group consisting of the human CMV immediate early gene promoter, the SV40 early promoter, the Rous sarcoma virus (RS) long terminal repeat, and rat insulin promoter. In certain embodiments, the vectors provided herein comprise one or more long terminal repeat (LTR) promoters selected from the group consisting of AAV, MLV, MMTV, SV40, RSV, HIV-1, and HIV-2 LTRs. In certain embodiments, the vectors provided herein comprise one or more tissue specific promoters (e.g., a neuronal cell-specific promoter).

In certain embodiments, the viral vectors provided herein comprise one or more regulatory elements other than a promoter. In certain embodiments, the viral vectors provided herein comprise an enhancer. In certain embodiments, the viral vectors provided herein comprise a repressor. In certain embodiments, the viral vectors provided herein comprise an intron or a chimeric intron. In certain embodiments, the viral vectors provided herein comprise a polyadenylation sequence.

5.2.4. Signal Peptides

In certain embodiments, the vectors provided herein comprise components that modulate protein delivery. In certain embodiments, the viral vectors provided herein comprise one or more signal peptides. In certain embodiments, the signal peptides allow for the transgene product (e.g., IDS) to achieve the proper packaging (e.g. glycosylation) in the cell. In certain embodiments, the signal peptides allow for the transgene product (e.g., IDS) to achieve the proper localization in the cell. In certain embodiments, the signal peptides allow for the transgene product (e.g., IDS) to achieve secretion from the cell. Examples of signal peptides to be used in connection with the vectors and transgenes provided herein may be found in Table 4. Signal peptides may also be referred to herein as leader sequences or leader peptides.

TABLE 4

Signal peptides for use with the vectors provided herein.

| SEQ ID NO. | Signal Peptide | Sequence |
|---|---|---|
| 2 | Oligodendrocyte-myelin glycoprotein (hOMG) signal peptide | MEYQILKMSLCLFILLFLTPGILC |

TABLE 4-continued

Signal peptides for use with the vectors provided herein.

| SEQ ID NO. | Signal Peptide | Sequence |
|---|---|---|
| 3 | Cellular repressor of E1A-stimulated genes 2 (hCREG2) signal peptide | MSVRRGRRPARPGTRLSWLLCCSALLSP AAG |
| 4 | V-set and transmembrane domain containing 2B (hVSTM2B) signal peptide | MEQRNRLGALGYLPPLLLHALLLFVADA |
| 5 | Protocadherin alpha-1 (hPCADHA1) signal peptide | MVFSRRGGLGARDLLLWLLLLAAWEVG SG |
| 6 | FAM19A1 (TAFA1) signal peptide | MAMVSAMSWVLYLWISACA |
| 7 | VEGF-A signal peptide | MNFLLSWVHW SLALLLYLHH AKWSQA |
| 8 | Fibulin-1 signal peptide | MERAAPSRRV PLPLLLLGGL ALLAAGVDA |
| 9 | Vitronectin signal peptide | MAPLRPLLIL ALLAWVALA |
| 10 | Complement Factor H signal peptide | MRLLAKIICLMLWAICVA |
| 11 | Opticin signal peptide | MRLLAFLSLL ALVLQETGT |
| 12 | Albumin signal peptide | MKWVTFISLLFLFSSAYS |
| 13 | Chymotrypsinogen signal peptide | MAFLWLLSCWALLGTTFG |
| 14 | Interleukin-2 signal peptide | MYRMQLLSCIALILALVTNS |
| 15 | Trypsinogen-2 signal peptide | MNLLLILTFVAAAVA |

5.2.5. Untranslated Regions

In certain embodiments, the viral vectors provided herein comprise one or more untranslated regions (UTRs), e.g., 3' and/or 5' UTRs. In certain embodiments, the UTRs are optimized for the desired level of protein expression. In certain embodiments, the UTRs are optimized for the mRNA half life of the transgene. In certain embodiments, the UTRs are optimized for the stability of the mRNA of the transgene. In certain embodiments, the UTRs are optimized for the secondary structure of the mRNA of the transgene.

5.2.6. Inverted Terminal Repeats

In certain embodiments, the viral vectors provided herein comprise one or more inverted terminal repeat (ITR) sequences. ITR sequences may be used for packaging the recombinant gene expression cassette into the virion of the viral vector. In certain embodiments, the ITR is from an AAV, e.g., AAV9 (see, e.g., Yan et al., 2005, J. Virol., 79(1):364-379; U.S. Pat. No. 7,282,199 B2, U.S. Pat. No. 7,790,449 B2, U.S. Pat. No. 8,318,480 B2, U.S. Pat. No. 8,962,332 B2 and International Patent Application No. PCT/EP2014/076466, each of which is incorporated herein by reference in its entirety).

5.2.7. Transgenes

In certain embodiments, the vectors provided herein encode an IDS transgene. In specific embodiments, the IDS is controlled by appropriate expression control elements for expression in neuronal cells: In certain embodiments, the IDS (e.g., hIDS) transgene comprises the amino acid sequence of SEQ ID NO: 1. In certain embodiments, the IDS (e.g., hIDS) transgene comprises an amino acid sequence that is at least 85%, 86%, 87%, 88%, 89%, 90%, 91%, 92%, 93%, 94%, 95%, 96%, 97%, 98% or 99% identical to the sequence set forth in SEQ ID NO: 1.

The HuGlyIDS encoded by the transgene can include, but is not limited to human IDS (hIDS) having the amino acid sequence of SEQ ID NO. 1 (as shown in FIG. 1), and derivatives of hIDS having amino acid substitutions, deletions, or additions, e.g., including but not limited to amino acid substitutions selected from corresponding non-conserved residues in orthologs of IDS shown in FIG. 2, with the proviso with the proviso that such mutations do not include replacement of the cysteine residue at position 84 (C84) which is required for enzyme activity (Millat et al., 1997, Biochem J 326: 243-247); or a mutation that has been identified in severe, severe-intermediate, intermediate, or attenuated MPS II phenotypes e.g., as shown in FIG. 3, or as reported by Sukegawa-Hayasaka et al., 2006, J Inhert Metab Dis 29: 755-761 (reporting "attenuated" mutants R48P, A85T, W337R, and the truncated mutant Q531X; and "severe" mutants P86L, S333L, S349I, R468Q, R468L); Millat et al., 1998, BBA 1406: 214-218 (reporting "attenuated" mutants P480L and P480Q; and "severe" mutant P86L): and Bonucelli et al., 2001, BBA 1537:233-238, each of which is incorporated by reference herein in its entirety.

For example, amino acid substitutions at a particular position of hIDS can be selected from among corresponding non-conserved amino acid residues found at that position in the IDS orthologs aligned in FIG. 2, with the proviso that such substitutions do not include any of the deleterious mutations shown in FIG. 3 or as reported by Sukegawa-Hayasaka et al., 2006, supra; Millat et al., 1998, supra; or Bonucelli et al., 2001, supra, each of which is incorporated by reference herein in its entirety. The resulting transgene product can be tested using conventional assays in vitro, in cell culture or test animals to ensure that the mutation does not disrupt IDS function. Preferred amino acid substitutions, deletions or additions selected should be those that maintain or increase enzyme activity, stability or half-life of IDS, as tested by conventional assays in vitro, in cell culture or animal models for MPS II. For example, the enzyme activity of the transgene product can be assessed using a conventional enzyme assay with, for example, 4-Methylumbelliferyl α-L-idopyranosiduronic acid 2-sulfate or 4-methylumbelliferyl sulfate as the substrate (see, e.g., Lee et al., 2015, Clin. Biochem. 48(18):1350-1353, Dean et al., 2006, Clin. Chem. 52(4):643-649 for exemplary IDS enzyme assays that can be used, each of which is incorporated by reference herein in its entirety). The ability of the transgene product to correct MPS II phenotype can be assessed in cell culture; e.g., by transducing MPS II cells in culture with a viral vector or other DNA expression construct encoding hIDS or a derivative; by adding the transgene product or a derivative to MPS II cells in culture; or by co-culturing MPS II cells with human neuronal/glial host cells engineered to express and secrete rhIDS or a derivative, and determining correction of the defect in the MPS II cultured cells, e.g., by detecting IDS enzyme activity and/or reduction in GAG storage in the MPS II cells in culture (see. e.g., Stroncek et al., 1999, Transfusion 39(4):343-350, which is incorporated by reference herein in its entirety).

In some embodiments, a dose of a recombinant AAV of the disclosure is determined using a PCR assay. In some embodiments, the PCR assay is a Poly-A PCR assay. In some embodiments, the PCR assay is a transgene-specific PCR assay. In some embodiments, the dose determined in one assay is different (e.g., higher or lower) than a dose determined in another assay. For example, a dose determined using a transgene-specific PCR assay is higher (e.g., about 50% higher) than a dose determined using a Poly-A-specific PCR assay. In some embodiments, a dose determined by a transgene-specific PCR assay is higher by about 5%, 10%, 15%, 20%, 25%, 30%, 35%, 40%, 45%, 50%, 55%, 60%, 65%, 70%, 75%, or higher than about 75% higher than a dose determined by a Poly-A-specific PCR assay. In some embodiments, a dose of $2.0 \times 10^{11}$ GC/g brain mass, where the number of genome copies is determined using a Poly-A-specific PCR assay is equivalent to a dose of $2.9 \times 10^{11}$ GC/g brain mass, where the number of genome copies is determined using a transgene-specific PCR assay. In some embodiments, the total dose administered to a subject accounts for the estimated brain mass of the subject, which can be determined using a magnetic resonance imaging (MRI) screening.

5.2.8. Constructs

In certain embodiments, the viral vectors provided herein comprise the following elements in the following order: a) a first ITR sequence, b) a first linker sequence, c) a promoter sequence, d) a second linker sequence, e) an intron sequence, f) a third linker sequence, g) a sequence encoding the transgene (e.g., IDS), h) a fourth linker sequence, i) a poly A sequence, j) a fifth linker sequence, and k) a second ITR sequence.

In certain embodiments, the viral vectors provided herein comprise the following elements in the following order: a) a promoter sequence, and b) a sequence encoding the transgene (e.g., IDS). In certain embodiments, the viral vectors provided herein comprise the following elements in the following order: a) a promoter sequence, and b) a sequence encoding the transgene (e.g., IDS), wherein the transgene comprises a signal peptide.

In certain embodiments, the viral vectors provided herein comprise the following elements in the following order: a) a first ITR sequence, b) a first linker sequence, c) a promoter sequence, d) a second linker sequence, e) an intron sequence, f) a third linker sequence, g) a first UTR sequence, h) a sequence encoding the transgene (e.g., IDS), i) a second UTR sequence, j) a fourth linker sequence, k) a poly A sequence, l) a fifth linker sequence, and m) a second ITR sequence.

In certain embodiments, the viral vectors provided herein comprise the following elements in the following order: a) a first ITR sequence, b) a first linker sequence, c) a promoter sequence, d) a second linker sequence, e) an intron sequence, f) a third linker sequence, g) a first UTR sequence, h) a sequence encoding the transgene (e.g., IDS), i) a second UTR sequence, j) a fourth linker sequence, k) a poly A sequence, l) a fifth linker sequence, and m) a second ITR sequence, wherein the transgene comprises a signal peptide, and wherein the transgene encodes hIDS.

In a specific embodiment, the viral vector described herein comprises the elements and in the order as illustrated in FIG. 5.

5.2.9. Manufacture and Testing of Vectors

The viral vectors provided herein may be manufactured using host cells. The viral vectors provided herein may be manufactured using mammalian host cells, for example, A549, WEHI, 10T1/2, BHK, MDCK, COS1, COS7, BSC 1, BSC 40, BMT 10, VERO, W138, HeLa, 293, Saos, C2C12, L, HT1080, HepG2, primary fibroblast, hepatocyte, and myoblast cells. The viral vectors provided herein may be manufactured using host cells from human, monkey, mouse, rat, rabbit, or hamster.

The host cells are stably transformed with the sequences encoding the transgene and associated elements (i.e., the vector genome), and the means of producing viruses in the host cells, for example, the replication and capsid genes (e.g., the rep and cap genes of AAV). For a method of producing recombinant AAV vectors with AAV8 capsids, see Section IV of the Detailed Description of U.S. Pat. No. 7,282,199 B2, which is incorporated herein by reference in its entirety. Genome copy titers of said vectors may be determined, for example, by TAQMAN® analysis. Virions may be recovered, for example, by $CsCl_2$ sedimentation.

In vitro assays, e.g., cell culture assays, can be used to measure transgene expression from a vector described herein, thus indicating, e.g., potency of the vector. For example, the HT-22, SK-N-MC, HCN-1A, HCN-2, NT2, SH-SY5y, hNSC11, or ReNcell VM cell lines, or other cell lines that are derived from neuronal or glial cells or progenitors of neuronal or glial cells can be used to assess transgene expression. Once expressed, characteristics of the expressed product (i.e., HuGlyIDS) can be determined, including determination of the glycosylation and tyrosine sulfation patterns associated with the HuGlyIDS.

5.2.10. Compositions

Compositions are described comprising a vector encoding a transgene described herein and a suitable carrier. A suitable carrier (e.g., for administration to the CSF, and, for example, to neuronal cells) would be readily selected by one of skill in the art.

5.3 Gene Therapy

Methods are described for the administration of a therapeutically effective amount of a transgene construct to human subjects having MPS II. More particularly, methods for administration of a therapeutically effective amount of a transgene construct to patients having MPS II, in particular, for administration to the CSF are described. In particular embodiments, such methods for administration to the CSF of a therapeutically effective amount of a transgene construct can be used to treat to patients having Hunter's syndrome.

5.3.1. Target Patient Populations

In certain embodiments, therapeutically effective doses of the recombinant vector are administered to patients diagnosed with MPS II. In specific embodiments, the patients have been diagnosed with mild MPS II. In specific embodiments, the patients have been diagnosed with severe MPS II. In specific embodiments, the patients have been diagnosed with Hunter's syndrome. In specific embodiments, the patients have been diagnosed with neuronopathic MPS II. In some embodiments, a patient has been diagnosed with hepatosplenomegaly, has a symptom associated with hepatosplenomegaly, is suspected of having hepatosplenomegaly, and/or has a predisposition to suffer from hepatosplenomegaly. Examples of symptoms associated with hepatosplenomegaly include, but are not limited to, brown urine, clay-colored bowel movements, enlarged or swollen abdomen, fever, itching, jaundice or yellowing of the eyes and skin, nausea, pain (e.g., I the upper right portion of the stomach), fatigue, and/or vomiting. In some embodiments, a patient diagnosed with MPS II has hepatosplenomegaly. In some embodiments, a patient is suffering from hepatosplenomegaly associated with MPS II. In some embodiments, a patient is being treated or has been treated with ERT.

In certain embodiments, therapeutically effective doses of the recombinant vector are administered to patients diagnosed with MPS II who have been identified as responsive to treatment with IDS, e.g., hIDS.

In certain embodiments, therapeutically effective doses of the recombinant vector are administered to pediatric patients. In certain embodiments, therapeutically effective doses of the recombinant vector are administered to patients that are less than three years old. In certain embodiments, therapeutically effective doses of the recombinant vector are administered to patients that are aged 2 to 4 years old. In certain embodiments, therapeutically effective doses of the recombinant vector are administered to patients that are 4 months old or older and less than 5 years old. In a specific embodiment, therapeutically effective doses of the recombinant vector are administered to patients that have severe MPS 11 and are 4 months old or older and less than 5 years old. In certain embodiments, therapeutically effective doses of the recombinant vector are administered to patients that are 5 years old or older and less than 18 years old. In a specific embodiment, therapeutically effective doses of the recombinant vector are administered to patients that have neuronopathic MPS II and are 5 years old or older and less than 18 years old. In certain embodiments, therapeutically effective doses of the recombinant vector are administered to patients that are 18 months old or older and 8 years old or younger. In a specific embodiment, therapeutically effective doses of the recombinant vector are administered to patients that are pediatric male patients and are 18 months old or older and 8 years old or younger. In certain embodiments, therapeutically effective doses of the recombinant vector are administered to patients that are aged 3 to 8 years old. In certain embodiments, therapeutically effective doses of the recombinant vector are administered to patients that are aged 8 to 16 years old. In certain embodiments, therapeutically effective doses of the recombinant vector are administered to patients that are aged 5 to 18 years old. In certain embodiments, therapeutically effective doses of the recombinant vector are administered to patients that are 10 years old or younger. In a specific embodiment, therapeutically effective doses of the recombinant vector are administered to patients that have severe MPS II and are 10 years old or younger. In certain embodiments, therapeutically effective doses of the recombinant vector are administered to patients that are 18 years old or younger. In certain embodiments, therapeutically effective doses of the recombinant vector are administered to patients that are more than 5 years old. In certain embodiments, therapeutically effective doses of the recombinant vector are administered to patients that are more than 10 years old.

In certain embodiments, therapeutically effective doses of the recombinant vector are administered to patients that are 4, 5, 6, 7, 8, 9, 10, or 11 months old. In certain embodiments, therapeutically effective doses of the recombinant vector are administered to patients that are about 4, 5, 6, 7, 8, 9, 10, or 11 months old. In certain embodiments, therapeutically effective doses of the recombinant vector are administered to patients that are 4-5, 5-6, 6-7, 7-8, 8-9, 9-10, 10-11, or 11-12 months old. In certain embodiments, therapeutically effective doses of the recombinant vector are administered to patients that are about 4-5, 5-6, 6-7, 7-8, 8-9, 9-10, 10-11, or 11-12 months old. In certain embodiments, therapeutically effective doses of the recombinant vector are administered to patients that are 1, 2, 3, 4, or 5 years old. In certain embodiments, therapeutically effective doses of the recombinant vector are administered to patients that are about 1, 2, 3, 4, or 5 years old. In certain embodiments, therapeutically effective doses of the recombinant vector are administered to patients that are 1-2, 2-3, 3-4, 4-5, or 5-6 years old. In certain embodiments, therapeutically effective doses of the recombinant vector are administered to patients that are about 1-2, 2-3, 3-4, 4-5, or 5-6 years old. In certain embodiments, therapeutically effective doses of the recombinant vector are administered to patients that are 5-6, 6-7, 7-8, 8-9, 9-10, 10-11, 11-12, 12-13, 13-14, 14-15, 15-16, 16-17, 17-18, or 18-19 years old. In certain embodiments, therapeutically effective doses of the recombinant vector are administered to patients that are about 5-6, 6-7, 7-8, 8-9, 9-10, 10-11, 11-12, 12-13, 13-14, 14-15, 15-16, 16-17, 17-18, or 18-19 years old.

In certain embodiments, therapeutically effective doses of the recombinant vector are administered to adolescent patients. In certain embodiments, therapeutically effective doses of the recombinant vector are administered to adult patients. In some embodiments, therapeutically effective doses of the recombinant vector are administered to male patients. In other embodiments, therapeutically effective doses of the recombinant vector are administered to female patients.

In certain embodiments, therapeutically effective doses of the recombinant vector are administered to patients diagnosed with MPS II who have been identified as responsive to treatment with IDS, e.g., hIDS, injected into the CSF prior to treatment with gene therapy.

5.3.2. Dosage and Mode of Administration

In certain embodiments, therapeutically effective doses of the recombinant vector are administered to the CSF via intrathecal administration (i.e., injection into the subarachnoid space so that the recombinant vectors distribute through the CSF and transduce cells in the CNS). This can be accomplished in a number of ways—e.g., by intracranial (cisternal or ventricular) injection, or injection into the lumbar cistern. In certain embodiments, intrathecal administration is performed via intracisternal (IC) injection (e.g., into the cisterna magna). In specific embodiments, intracisternal injection is performed by CT-guided suboccipital puncture. In specific embodiments, intrathecal injection is performed by lumbar puncture. In specific embodiments, injection into the subarachnoid space is performed by C1-2 puncture if feasible for the patient. Alternatively, intracerebroventricular (ICV) administration (a more invasive technique used for the introduction of antiinfective or anticancer drugs that do not penetrate the blood-brain barrier), for example, image-assisted ICV injection, can be used to instill the recombinant vectors directly into the ventricles of the brain. In a specific embodiment, the recombinant vector is administered via a single image-assisted ICV injection. In a further specific embodiment, the recombinant vector is administered via a single image-assisted ICV injection with immediate removal of the administration catheter. In certain embodiments, therapeutically effective doses of the recombinant vector are administered to the CNS via intranasal administration. In certain embodiments, therapeutically effective doses of the recombinant vector are administered to the CNS via intraparenchymal injection. In certain embodiments, intraparenchymal injection is targeted to the striatum. In certain embodiments, intraparenchymal injection is targeted to the white matter. In certain embodiments, therapeutically effective doses of the recombinant vector are administered to the CSF by any means known to the art, for example, by any means disclosed in Hocquemiller et al., 2016, Human Gene Therapy 27(7):478-496, which is hereby incorporated by reference in its entirety.

In preferred embodiments, for intrathecal administration (including IC and ICV administration), therapeutically effective doses of the recombinant vector are administered to the CSF in an injection volume that does not exceed 10% of the total CSF volume, which total CSF volume is about 50 mL in infants and about 150 mL in adults. A carrier suitable for intrathecal injection, such as Elliott's B Solution or a modified Elliott's B Solution, should be used as a vehicle for the recombinant vectors. Elliott's B Solution (generic name: sodium chloride, sodium bicarbonate, anhydrous dextrose, magnesium sulfate, potassium chloride, calcium chloride and sodium phosphate) is a sterile, nonpyrogenic, isotonic solution containing no bacteriostatic preservatives and is used as a diluent for intrathecal administration of chemotherapeutics. The modified Elliott's B solution includes 8.77 g/L sodium chloride, 0.244 g/L magnesium chloride, 0.0278 g/L sodium phosphate monobasic monohydrate, 0.114 g/L sodium phosphate dibasic anhydrous, 0.224 g/L potassium chloride, 0.206 g/L calcium chloride, 0.793 g/L dextrose, 0.001% poloxamer 188, pH 7.26. In some embodiments, the AAV or a composition comprising the AAV of the present disclosure is provided in a modified Elliott's B solution for intrathecal administration.

In one embodiment, a non-replicating recombinant AAV9 vector expressing human iduronate-2-sulfatase (IDS) is used for treatment. In certain embodiments, the IDS expression cassette is flanked by inverted terminal repeats (ITRs) and expression is driven by a hybrid of the cytomegalovirus (CMV) enhancer and the chicken beta actin promoter (CB7). In certain embodiments, the transgene includes the chicken beta actin intron and a rabbit beta-globin polyadenylation (polyA) signal.

In certain embodiments, the recombinant nucleotide expression vector is administered at a dose that is dependent on the human subject's brain mass. In preferred embodiments, the brain mass is determined by brain magnetic resonance imaging (MRI) of the human subject's brain. In certain embodiments, the human subject's brain mass is converted from the human subject's brain volume by multiplying the human subject's brain volume in $cm^3$ by a factor of 1.046 g/cm3, wherein the human subject's brain volume is obtained from the human subject's brain MRI. In some embodiments, a dose is the number of genome copies per weight of brain mass. In some embodiments, the number of genome copies in a dose (e.g., the dose of the recombinant nucleotide expression vector) is determined by a Poly-A-specific PCR assay. In some embodiments, the number genome copies in a dose (e.g., the dose of the recombinant nucleotide expression vector) is determined by a transgene-specific PCR assay. In some embodiments, the weight of brain mass is determined by MRI.

In certain embodiments, the rAAV9.hIDS is administered IC (by suboccipital injection) as a single flat dose ranging from $1.4 \times 10^{10}$ GC ($1.1 \times 10^{10}$ GC/g brain mass) to $7.0 \times 10^3$ GC ($5.6 \times 10^{10}$ GC/g brain mass) in a volume of about 5 to 20 ml. In the event the patient has neutralizing antibodies to AAV, doses at the high range may be used. In some embodiments, a single dose of an rAAV encoding hIDS is administered to the subject in the central nervous system (e.g., in the cerebrospinal fluid) and, surprisingly, treatment effects are observed outside of the CNS. For example, changes in organ sizes are observed outside of the CNS (e.g., spleen or liver) after the rAAV of the disclosure is administered to a subject in the CNS. In some embodiments, changes in biomarker levels (e.g., D2S6, HS, total GAG, and/or anti-IDS antibody) are detected outside of the CNS after administration of the rAAV of the disclosure in the cerebrospinal fluid (e.g., changes in biomarker levels detected in the liver, spleen, urine, plasma, or blood). In some embodiments, no additional therapy for MPS II is administered to the subject outside the CNS.

In certain embodiments, the recombinant vector described herein may be administered intrathecally as a single flat dose ranging from about $1.3 \times 10^{10}$ GC/g brain mass to about $6.5 \times 10^{10}$ GC/g brain mass (for example, when the human patient is 4 months old or older and less than 5 years old). In a specific embodiment, the recombinant vector described herein may be administered intrathecally as a single flat dose at about $1.3 \times 10^{10}$ GC/g brain mass (for example, when the human patient is 4 months old or older and less than 5 years old). In a specific embodiment, the recombinant vector described herein may be administered intrathecally as a single flat dose at about $1.9 \times 10^{10}$ GC/g brain mass (for example, when the human patient is 4 months old or older and less than 5 years old). In another specific embodiment, the recombinant vector described herein may be administered intrathecally as a single flat dose at about $6.5 \times 10^{10}$ GC/g brain mass (for example, when the human patient is 4 months old or older and less than 5 years old). In a specific embodiment, the recombinant vector described herein may be administered intrathecally as a single flat dose at about $9.6 \times 10^{10}$ GC/g brain mass (for example, when the human patient is 4 months old or older and less than 5 years old). In a specific embodiment, the recombinant vector described herein may be administered intrathecally as a single flat dose at about $2.0 \times 10^{10}$ GC/g brain mass (for example, when the human patient is 4 months old or older and less than 5 years old). In a specific embodiment, the recombinant vector described herein may be administered intrathecally as a single flat dose at about $2.9 \times 10^{11}$ GC/g brain mass (for example, when the human patient is 4 months old or older and less than 5 years old). In another specific embodiment, the recombinant vector described herein may be administered intrathecally as a single flat dose at Dose 1 or Dose 2 as listed in and according to Table 5 below (for example, when the human patient is 4 months old or older and less than 5 years old).

In certain embodiments, the recombinant vector described herein may be administered intrathecally as a single flat dose ranging from about $1.3 \times 10^{10}$ GC/g brain mass to about $2.0 \times 10^{11}$ GC/g brain mass (for example, when the human patient is 4 months old or older and less than 5 years old). In certain embodiments, the recombinant vector described herein may be administered intrathecally as a single flat dose ranging from about $1.3 \times 10^{10}$ GC/g brain mass to about $2.9 \times 10^{11}$ GC/g brain mass (for example, when the human patient is 4 months old or older and less than 5 years old). In a specific embodiment, the recombinant vector described herein may be administered intrathecally as a single flat dose at about $2.0 \times 10^{11}$ GC/g brain mass (for example, when the human patient is 4 months old or older and less than 5 years old). In a specific embodiment, the recombinant vector described herein may be administered intrathecally as a single flat dose at about $2.9 \times 10^{11}$ GC/g brain mass (for example, when the human patient is 4 months old or older and less than 5 years old). In another specific embodiment, the recombinant vector described herein may be administered intrathecally as a single flat dose at Dose 3 as listed in and according to Table 6 below (for example, when the human patient is 4 months old or older and less than 5 years old).

In certain embodiments, the recombinant vector described herein may be administered by IC administration as a single flat dose ranging from about $1.3 \times 10^{10}$ GC/g brain mass to about $6.5 \times 10^{10}$ GC/g brain mass (for example, when the human patient is 4 months old or older and less than 5 years old). In a specific embodiment, the recombinant vector described herein may be administered by IC administration as a single flat dose at about $1.3 \times 10^{10}$ GC/g brain mass (for example, when the human patient is 4 months old or older and less than 5 years old). In a specific embodiment, the recombinant vector described herein may be administered by IC administration as a single flat dose at about $1.9 \times 10^{10}$ GC/g brain mass (for example, when the human patient is 4 months old or older and less than 5 years old). In another specific embodiment, the recombinant vector described herein may be administered by IC administration as a single flat dose at about $6.5 \times 10^{10}$ GC/g brain mass (for example, when the human patient is 4 months old or older and less than 5 years old). In a specific embodiment, the recombinant vector described herein may be administered by IC administration as a single flat dose at about $9.6 \times 10^{10}$ GC/g brain mass (for example, when the human patient is 4 months old or older and less than 5 years old). In another specific embodiment, the recombinant vector described herein may be administered by IC administration as a single flat dose at Dose 1 or Dose 2 as listed in and according to Table 5 below (for example, when the human patient is 4 months old or older and less than 5 years old).

In certain embodiments, the recombinant vector described herein may be administered by IC administration as a single flat dose ranging from about $1.3 \times 10^{10}$ GC/g brain mass to about $2.0 \times 10^{11}$ GC/g brain mass (for example, when the human patient is 4 months old or older and less than 5 years old). In certain embodiments, the recombinant vector described herein may be administered by IC administration as a single flat dose ranging from about $1.3 \times 10^{10}$ GC/g brain mass to about $2.9 \times 10^{11}$ GC/g brain mass (for example, when the human patient is 4 months old or older and less than 5 years old). In a specific embodiment, the recombinant vector described herein may be administered by IC administration as a single flat dose at about $2.0 \times 10^{11}$ GC/g brain mass (for example, when the human patient is 4 months old or older and less than 5 years old). In a specific embodiment, the recombinant vector described herein may be administered by IC administration as a single flat dose at about $2.9 \times 10^{11}$ GC/g brain mass (for example, when the human patient is 4 months old or older and less than 5 years old). In another specific embodiment, the recombinant vector described herein may be administered by IC administration as a single flat dose at Dose 3 as listed in and according to Table 6 below (for example, when the human patient is 4 months old or older and less than 5 years old).

In certain embodiments, the recombinant vector described herein may be administered by ICV administration as a single flat dose ranging from about $1.3 \times 10^{10}$ GC/g brain mass to about $6.5 \times 10^{10}$ GC/g brain mass (for example, when the human patient is 4 months old or older and less than 5 years old). In a specific embodiment, the recombinant vector described herein may be administered by ICV administration as a single flat dose at about $1.3 \times 10^{10}$ GC/g brain mass (for example, when the human patient is 4 months old or older and less than 5 years old). In a specific embodiment, the recombinant vector described herein may be administered by ICV administration as a single flat dose at about $1.9 \times 10^{10}$ GC/g brain mass (for example, when the human patient is 4 months old or older and less than 5 years old). In another specific embodiment, the recombinant vector described herein may be administered by ICV administration as a single flat dose at about $6.5 \times 10^{10}$ GC/g brain mass (for example, when the human patient is 4 months old or older and less than 5 years old). In a specific embodiment, the recombinant vector described herein may be administered by ICV administration as a single flat dose at about $9.6 \times 10^{10}$ GC/g brain mass (for example, when the human patient is 4 months old or older and less than 5 years old). In another specific embodiment, the recombinant vector described herein may be administered by ICV administration as a single flat dose at Dose 1 or Dose 2 as listed in and according to Table 5 below (for example, when the human patient is 4 months old or older and less than 5 years old).

In certain embodiments, the recombinant vector described herein may be administered by ICV administration as a single flat dose ranging from about $1.3 \times 10^{10}$ GC/g brain mass to about $2.0 \times 10^{11}$ GC/g brain mass (for example, when the human patient is 4 months old or older and less than 5 years old). In certain embodiments, the recombinant vector described herein may be administered by ICV administration as a single flat dose ranging from about $1.3 \times 10^{10}$ GC/g brain mass to about $2.9 \times 10^{11}$ GC/g brain mass (for example, when the human patient is 4 months old or older and less than 5 years old). In a specific embodiment, the recombinant vector described herein may be administered by ICV administration as a single flat dose at about $2.0 \times 10^{11}$ GC/g brain mass (for example, when the human patient is 4 months old or older and less than 5 years old). In a specific embodiment, the recombinant vector described herein may be administered by ICV administration as a single flat dose at about $2.9 \times 10^{11}$ GC/g brain mass (for example, when the human patient is 4 months old or older and less than 5 years old). In another specific embodiment, the recombinant vector described herein may be administered by ICV administration as a single flat dose at Dose 3 as listed in and according to Table 6 below (for example, when the human patient is 4 months old or older and less than 5 years old).

TABLE 5

Total Dose Administered by Brain Mass (Dose 1 or Dose 2)

| Brain Mass (in g) | | | Dose Levels | |
|---|---|---|---|---|
| | | | Dose 1 Total GC* $(1.3 \times 10^{10}$ GC/g brain mass) | Dose 2 Total GC* $(6.5 \times 10^{10}$ GC/g brain mass) |
| Min | Max | Target | | |
| — | 700 | 650 | $8.5 \times 10^{12}$ | $4.2 \times 10^{13}$ |
| 701 | 800 | 750 | $9.8 \times 10^{12}$ | $4.9 \times 10^{13}$ |
| 801 | 900 | 850 | $1.1 \times 10^{13}$ | $5.5 \times 10^{13}$ |
| 901 | 1050 | 975 | $1.3 \times 10^{13}$ | $6.3 \times 10^{13}$ |
| 1051 | 1200 | 1125 | $1.5 \times 10^{13}$ | $7.3 \times 10^{13}$ |
| 1201 | — | 1300 | $1.7 \times 10^{13}$ | $8.5 \times 10^{13}$ |

*GC determined based on a Poly-A-specific PCR assay

TABLE 6

Total Dose Administered by Brain Mass (Dose 3)

| Brain Mass (in g) | | | Dose 3 Total GC determined by Poly-A-specific PCR assay $(2.0 \times 10^{11}$ GC/g brain mass) |
|---|---|---|---|
| Min | Max | Target | |
| — | 474 | 450 | $9.0 \times 10^{13}$ |
| 475 | 524 | 500 | $1.0 \times 10^{14}$ |
| 525 | 574 | 550 | $1.1 \times 10^{14}$ |

TABLE 6-continued

| 575 | 624 | 600 | $1.2 \times 10^{14}$ |
| 625 | 674 | 650 | $1.3 \times 10^{14}$ |
| 675 | 724 | 700 | $1.4 \times 10^{14}$ |
| 725 | 774 | 750 | $1.5 \times 10^{14}$ |
| 775 | 824 | 800 | $1.6 \times 10^{14}$ |
| 825 | 874 | 850 | $1.7 \times 10^{14}$ |
| 875 | 924 | 900 | $1.8 \times 10^{14}$ |
| 925 | 974 | 950 | $1.9 \times 10^{14}$ |
| 975 | 1024 | 1000 | $2.0 \times 10^{14}$ |
| 1025 | 1074 | 1050 | $2.1 \times 10^{14}$ |
| 1075 | 1124 | 1100 | $2.2 \times 10^{14}$ |
| 1125 | 1174 | 1150 | $2.3 \times 10^{14}$ |
| 1175 | 1224 | 1200 | $2.4 \times 10^{14}$ |
| 1225 | 1274 | 1250 | $2.5 \times 10^{14}$ |
| 1275 | >1300 | 1300 | $2.6 \times 10^{14}$ |

Total Dose Administered by Brain Mass Dose 3 EC

| Brain Mass (in g) | | | Dose 3 EC Total GC determined by Transgene PCR assay ($2.9 \times 10^{11}$ GC/g brain mass) |
|---|---|---|---|
| Min | Max | Target | |
| — | 474 | 450 | $1.3 \times 10^{14}$ |
| 475 | 524 | 500 | $1.5 \times 10^{14}$ |
| 525 | 574 | 550 | $1.6 \times 10^{14}$ |
| 575 | 624 | 600 | $1.8 \times 10^{14}$ |
| 625 | 674 | 650 | $1.9 \times 10^{14}$ |
| 675 | 724 | 700 | $2.1 \times 10^{14}$ |
| 725 | 774 | 750 | $2.2 \times 10^{14}$ |
| 775 | 824 | 800 | $2.4 \times 10^{14}$ |
| 825 | 874 | 850 | $2.4 \times 10^{14}$ |
| 875 | 924 | 900 | $2.6 \times 10^{14}$ |
| 925 | 974 | 950 | $2.8 \times 10^{14}$ |
| 975 | 1024 | 1000 | $2.9 \times 10^{14}$ |
| 1025 | 1074 | 1050 | $3.1 \times 10^{14}$ |
| 1075 | 1124 | 1100 | $3.2 \times 10^{14}$ |
| 1125 | 1174 | 1150 | $3.4 \times 10^{14}$ |
| 1175 | 1224 | 1200 | $3.5 \times 10^{14}$ |
| 1225 | 1274 | 1250 | $3.7 \times 10^{14}$ |
| 1275 | >1300 | 1300 | $3.8 \times 10^{14}$ |

In a specific embodiment, the recombinant vector described herein may be administered intrathecally as a single flat dose at about $6.5 \times 10^{10}$ GC/g brain mass (for example, when the human patient is 5 years old or older and less than 18 years old). In another specific embodiment, the recombinant vector described herein may be administered intrathecally as a single flat dose as listed in and according to Table 7 below (for example, when the human patient is 5 years old or older and less than 18 years old).

In a specific embodiment, the recombinant vector described herein may be administered by IC administration as a single flat dose at about $6.5 \times 10^{10}$ GC/g brain mass (for example, when the human patient is 5 years old or older and less than 18 years old). In another specific embodiment, the recombinant vector described herein may be administered by IC administration as a single flat dose as listed in and according to Table 7 below (for example, when the human patient is 5 years old or older and less than 18 years old).

In a specific embodiment, the recombinant vector described herein may be administered by ICV administration as a single flat dose at about $6.5 \times 10^{10}$ GC/g brain mass (for example, when the human patient is 5 years old or older and less than 18 years old). In another specific embodiment, the recombinant vector described herein may be administered by ICV administration as a single flat dose as listed in and according to Table 7 below (for example, when the human patient is 5 years old or older and less than 18 years old).

TABLE 7

Total Dose Administered by Brain Mass

| Brain Mass (in g) | | Target Brain Mass (in g) | Dose: Total GC determined by Poly-A-specific PCR assay ($6.5 \times 10^{10}$ GC/g brain mass) |
|---|---|---|---|
| Min | Max | | |
| 801 | 900 | 850 | $5.5 \times 10^{13}$ |
| 901 | 1050 | 975 | $6.3 \times 10^{13}$ |
| 1051 | 1200 | 1125 | $7.3 \times 10^{13}$ |
| 1201 | — | 1300 | $8.5 \times 10^{13}$ |

5.4 Combination Therapies

Combinations of administration of the HuGlyIDS to the CSF accompanied by administration of other available treatments are encompassed by the methods of the invention. The additional treatments may be administered before, concurrently or subsequent to the gene therapy treatment. Available treatments for MPS II that could be combined with the gene therapy of the invention include but are not limited to enzyme replacement therapy (ERT) using idursulfase administered systemically or to the CSF; and/or HSCT therapy. In another embodiment, ERT can be administered using the rHuGlyIDS glycoprotein produced in human neuronal and glial cell lines by recombinant DNA technology. Human neuronal and glial cell lines that can be used for such recombinant glycoprotein production include but are not limited to HT-22, SK-N-MC, HCN-1 A, HCN-2, NT2, SH-SY5y, hNSC11, or ReNcell VM to name a few. To ensure complete glycosylation, especially sialylation, and tyrosine-sulfation, the cell line used for production can be enhanced by engineering the host cells to co-express α-2,6-sialyltransferase (or both α-2,3- and α-2,6-sialyltransferases) and/or TPST-1 and TPST-2 enzymes responsible for tyrosine-O-sulfation.

5.5 Biomarkers/Sampling/Monitoring Efficacy

Efficacy may be monitored by measuring cognitive function (e.g., prevention or decrease in neurocognitive decline); reductions in biomarkers of disease (such as GAG, including heparan sulfate and dermatan sulfate) in CSF and or serum; and/or increase in IDS enzyme activity in CSF and/or serum. Signs of inflammation and other safety events may also be monitored.

In one aspect, provided herein is a method of monitoring efficacy by determining if a subject undergoing ERT treatment or a subject who has received ERT treatment can discontinue ERT treatment after administration of a gene therapy (e.g., rAAV encoding hIDS) of the disclosure. For example, provided herein is a method of treating and/or identifying a subject diagnosed with MPS II (e.g., a subject who is likely to be responsive to discontinuing treatment with ERT), comprising: (a) administering a therapeutically effective amount of a gene therapy (e.g., an rAAV encoding hIDS) of the disclosure to the subject, wherein the subject was treated with ERT or is being treated with ERT; (b) identifying the subject as being likely to be responsive to discontinuing ERT treatment, comprising: i. obtaining or having obtained a biological sample from the subject; ii. determining the level of at least one biomarker in the biological sample; and iii. identifying the subject as being likely to be responsive to discontinuing ERT treatment if the level of the biomarker in the biological sample is different (e.g., higher or lower) than a reference (e.g., reference level of the at least one biomarker); and (c) discontinuing ERT treatment in the subject. In some embodiments, a biomarker is D2S6, HS, total GAG, and/or anti-IDS antibody. In some embodiments, ERT is recombinant idursulfase. In some embodiments, the subject diagnosed with MPS II has hepatosplenomegaly.

In another aspect, provided herein is a method of selectively treating a human subject with MPS II, comprising administering to the subject a therapeutically effective amount of an rAAV encoding hIDS, wherein the subject was treated with ERT or is being treated with ERT, and wherein the subject has been determined likely to be responsive to discontinuing treatment with ERT according to a method comprising: (a) obtaining a biological sample from the subject; and (b) determining the level of at least one biomarker in the biological sample; wherein the subject is determined likely to be responsive to discontinuing treatment with ERT when the level of the at least one biomarker is different (e.g., higher or lower) than a reference. In some embodiments, a biomarker is D2S6, HS, total GAG, and/or anti-IDS antibody. In some embodiments, ERT is recombinant idursulfase. In some embodiments, the subject diagnosed with MPS II has hepatosplenomegaly.

In another aspect provided herein is a method of identifying or diagnosing a subject as having neuronopathic or non-neuronopathic MPS II or MPS I. In some embodiments, the method comprises determining the level of one or more disaccharides (e.g., D0A0, D0S0, D0A6, D2S6) in a biological sample from a subject. In some embodiments, the method comprises determining the level of undegraded glycosaminoglycans (GAGs) in a biological sample from a subject. In some embodiments, the subject is identified or diagnosed as having neuronopathic MPS II or MPS I if the level of one or more disaccharides (e.g., D0A0, D0S0, D0A6, and/or D2S6) is elevated as compared to a reference level. In some embodiments, the subject is identified or diagnosed as having neuronopathic MPS II or MPS I if the level of GAG heparan sulfate (HS) is elevated (e.g., in the brain) as compared to a reference level. In some embodiments, the total amount of heparin sulfate (t-HS) is the sum of four disaccharides (D2S6, D0A0, D0S0, D0A6) in cerebrospinal fluid (CSF) following enzymatic digestion (e.g., as determined based on a bioanalytical mass spectrometry method). In some embodiments, an elevated level of D2S6 in e.g., CSF of a subject (e.g., presymptomatic subject) is indicative of neuronopathic MPS II or MPS I. In some embodiments, the level of D2S6 is indicative of iduronate-2-sulfatase enzyme activity and can be used for therapy monitoring. In some embodiments, the one or more disaccharides comprises one or more of D0A0, D0S0, D0A6, D2S6, or a combination thereof. In another aspect provided herein is a method of identifying or diagnosing a subject as having neuronopathic or non-neuronopathic MPS II or MPS I, wherein the subject is identified or diagnosed as having neuronopathic MPS II if the level of one or more disaccharides (e.g., D0A0, D0S0, D0A6, and/or D2S6) in a biological sample from the subject is elevated as compared to a reference level. In some embodiments, the subject is presymptomatic or has no visible or detectable MPS II or MPS I symptom. In some embodiments, the subject has or has been diagnosed with MPS I or MPS II. In some embodiments, the reference level is the level of one or more disaccharides (e.g., D0A0, D0S0, D0A6, and/or D2S6) in a biological sample from one or more healthy subjects and/or from one or more non-neuronopathic subjects. In some embodiments, the reference level is the level of D2S6 in a biological sample (e.g., CSF sample) from one or more healthy subjects and/or from one or more non-neuronopathic subjects. In some embodiments, the reference level is a pre-determined level. In some embodiments, the level of one or more disaccharides (e.g., D0A0, D0S0, D0A6, D2S6) is about or at least about 12%, 13%, 14%, 15%, 16%, 17%, 18%, 19%, 20%, 25%, 30%, 35%, 40%, or higher than 40% of the total heparan sulfate disaccharides (HS) in a biological sample from a subject (e.g., a subject with MPS I or MPS II). In some embodiments, the level of one or more disaccharides (e.g., D0A0, D0S0, D0A6, and/or D2S6) is about or at least about 20% the total heparan sulfate disaccharides (HS) in a biological sample from a subject (e.g., a subject with MPS I or MPS II). In some embodiments, the level of one or more disaccharides (e.g., D0A0, D0S0, D0A6, and/or D2S6) in a biological sample from a subject (e.g., a subject with MPS I or MPS II) is about or at least about 5%, 10%, 115, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or more than 90°/% higher than the level of one or more disaccharides (e.g., D0A0, D0S0, D0A6, and/or D2S6) in a biological sample from a reference (e.g., a healthy subject). In some embodiments, the level of total heparin sulfate (e.g., D0A0, D0S0, D0A6, D2S6) is about or at least about 250 ng/mL, 275 ng/mL, 300 ng/mL, 325 ng/mL, 350 ng/mL, 375 ng/mL, 400 ng/mL, 425 ng/mL, 450 ng/mL, 475 ng/mL, 500 ng/mL, 525 ng/mL, 550 ng/mL, 575 ng/mL, 600 ng/mL, 625 ng/mL, 650 ng/mL, 675 ng/mL, 700 ng/mL, 725 ng/mL, 750 ng/mL, 775 ng/mL, 800 ng/mL, 825 ng/mL, 850 ng/mL, 875 ng/mL, 900 ng/mL, 925 ng/mL, 950 ng/mL, 975 ng/mL, 1000 ng/mL, or more than 1000 ng/mL. In some embodiments, the level of total heparin sulfate (e.g., D0A0, D0S0, D0A6, and/or D2S6) is about or at least about 500 ng/mL. In some embodiments, the level of total heparin sulfate (e.g., D0A0, D0S0, D0A6, and/or D2S6) is about or at least about 600 ng/mL. In some embodiments, the level of total heparin sulfate (e.g., D0A0, D0S0, D0A6, and/or D2S6) is about or at least about 700 ng/mL. In some embodiments, the level of total heparin sulfate (e.g., D0A0, D0S0, D0A6, and/or D2S6) is about or at least about 800 ng/mL. In some embodiments, the level of total heparin sulfate (e.g., D0A0, D0S0, D0A6, and/or D2S6) is between about 500 ng/mL to about 1000 ng/mL, about 300 ng/mL to about 1000 ng/mL, about 400 ng/mL to about 1000 ng/mL, about 550 ng/mL to about 1000 ng/mL about 600 ng/mL to about 1000 ng/mL, about 700 ng/mL to about 1000 ng/mL 500 ng/mL to about 900 ng/mL, about 300 ng/mL to about 900 ng/mL, about 400 ng/mL to about 900 ng/mL, about 550 ng/mL to about 900 ng/mL about 600 ng/mL to about 900 ng/mL, or about 700 ng/mL to about 900 ng/mL. In some embodiments, the level of at least one heparin sulfate (e.g., D0A0, D0S0, D0A6, and/or D2S6) is about or at least about 50 ng/mL, 75 ng/mL, 80 ng/mL, 85 ng/mL, 90 ng/mL, 95 ng/mL, 100 ng/mL, 105 ng/mL, 110 ng/mL, 115 ng/mL, 120 ng/mL, 125 ng/mL, 130 ng/mL, 135 ng/mL, 140 ng/mL, 145 ng/mL, 150 ng/mL, 155 ng/mL, 160 ng/mL, 165 ng/mL, 170 ng/mL, 175 ng/mL, 180 ng/mL, 185 ng/mL, 190 ng/mL, 195 ng/mL, 200 ng/mL, 210 ng/mL, 220 ng/mL, 230 ng/mL, 240 ng/mL, 250 ng/mL, 260 ng/mL, 270 ng/mL, 280 ng/mL, 290 ng/mL, 300 ng/mL, 310 ng/mL, 320 ng/mL, 330 ng/mL, 340 ng/mL, 350 ng/mL, 360 ng/mL, 370 ng/mL, 380 ng/mL, 390 ng/mL, 400 ng/mL, or more than 400 ng/mL. In some embodiments, the level of at least one heparin sulfate (e.g., D0A0, D0S0, D0A6, and/or D2S6) is about or at least about 50 ng/mL, 60 ng/mL, 70 ng/mL, 80 ng/mL, 90 ng/mL, 100 ng/mL, 110 ng/mL, 120 ng/mL, 130 ng/mL, 140 ng/mL, 150 ng/mL, 160 ng/mL, 170 ng/mL, 180 ng/mL, 190 ng/mL, 200 ng/mL, or more than 200 ng/mL. In some embodiments, the level of at least one heparin sulfate (e.g., D0A0, D0S0, D0A6, and/or D2S6) is about or at least about 80 ng/mL (e.g., for D0S0 or D0A6). In some embodiments, the level of at least one heparin sulfate (e.g., D0A0, D0S0, D0A6, and/or D2S6) is about or at least about 100 ng/mL (e.g., for D0S0, D0A6, or D2S6). In some embodiments, the level of at least one heparin sulfate (e.g., D0A0, D0S0, D0A6, and/or D2S6) is about or at least about 90 ng/mL (e.g., for D0S0, D0A6, or D2S6). In some embodiments, the level of at least one heparin sulfate (e.g., D0A0, D0S0, D0A6, and/or D2S6) is about or at least about 110 ng/mL (e.g., for D0S0, D0A6, or D2S6). In some embodiments, the level of at least one heparin sulfate (e.g., D0A0, D0S0, D0A6, and/or D2S6) is about or at least about 120 ng/mL (e.g., for D0S0, D0A6, or D2S6). In some embodiments, the level of at least one heparin sulfate (e.g., D0A0, D0S0, D0A6, and/or D2S6) is about or at least about 160 ng/mL (e.g., for D2S6 or D0A6). In some embodiments, the level of at least one heparin sulfate (e.g., D0A0, D0S0, D0A6, and/or D2S6) is about or at least about 250 ng/mL (e.g., for D2S6 or D0A0). In some embodiments, the level of at least one heparin sulfate (e.g., D0A0, D0S0, D0A6, and/or D2S6) is about or at least about 300 ng/mL (e.g., for D2S6 or D0A0). In some embodiments, the level of at least one heparin sulfate (e.g., D0A0, D0S0, D0A6, and/or D2S6) is about or at least about 350 ng/mL (e.g., for D2S6 or D0A0).). In some embodiments, the level of at least one heparin sulfate (e.g., D0A0, D0S0, D0A6, and/or D2S6) is about or at least about 150 ng/mL (e.g., for D2S6). In some embodiments, the level of at least one heparin sulfate (e.g., D0A0, D0S0, D0A6, and/or D2S6) is about or at least about 170 ng/mL (e.g., for D2S6). In some embodiments, the level of at least one heparin sulfate (e.g., D0A0, D0S0, D0A6, and/or D2S6) is about or at least about 180 ng/mL (e.g., for D2S6). In some embodiments, the level of at least one heparin sulfate (e.g., D0A0, D0S0, D0A6, and/or D2S6) is about or at least about 200 ng/mL (e.g., for D2S6). In some embodiments, the level of one or more heparan sulfate disaccharide(s) (e.g., D0A0, D0S0, D0A6, and/or D2S6) or the level of D2S6 in a biological sample from a subject is elevated by about or at least about 10 ng/mL, 20 ng/mL, 30 ng/mL, 40 ng/mL, 50 ng/mL, 60 ng/mL, 70 ng/mL, 80 ng/mL, 90 ng/mL, 100 ng/mL, 150 ng/mL, 160 ng/mL, 170 ng/mL, 180 ng/mL, 190 ng/mL, 200 ng/mL, 210 ng/mL, 220 ng/mL, 230 ng/mL, 240 ng/mL, 250 ng/mL, 260 ng/mL, 270 ng/mL, 280 ng/mL, 290 ng/mL, 300 ng/mL, 310 ng/mL, 320 ng/mL, 330 ng/mL, 340 ng/mL, 350 ng/mL, 360 ng/mL, 370 ng/mL, 380 ng/mL, 390 ng/mL, 400 ng/mL, 410 ng/mL, 420 ng/mL, 430 ng/mL, 440 ng/mL, 450 ng/mL, 460 ng/mL, 470 ng/mL, 480 ng/mL, 490 ng/mL, 500 ng/mL, or more than 500 ng/mL as compared to a reference level (e.g., level of one or more heparan sulfate disaccharide(s) (e.g., D0A0, D0S0, D0A6, and/or D2S6) or the level of D2S6 in a biological sample from one or more healthy subjects and/or from one or more non-neuronopathic subjects, or a pre-determined value). In some embodiments, the total level of heparan sulfate disaccharide(s) (e.g., D0A0, D0S0, D0A6, and/or D2S6) in a biological sample from a subject is elevated by about or at least about 10 ng/mL, 20 ng/mL, 30 ng/mL, 40 ng/mL, 50 ng/mL, 60 ng/mL, 70 ng/mL, 80 ng/mL, 90 ng/mL, 100 ng/mL, 150 ng/mL, 160 ng/mL, 170 ng/mL, 180 ng/mL, 190 ng/mL, 200 ng/mL, 210 ng/mL, 220 ng/mL, 230 ng/mL, 240 ng/mL, 250 ng/mL, 260 ng/mL, 270 ng/mL, 280 ng/mL, 290 ng/mL, 300 ng/mL, 310 ng/mL, 320 ng/mL, 330 ng/mL, 340 ng/mL, 350 ng/mL, 360 ng/mL, 370 ng/mL, 380 ng/mL, 390 ng/mL, 400 ng/mL, 410 ng/mL, 420 ng/mL, 430 ng/mL, 440 ng/mL, 450 ng/mL, 460 ng/mL, 470 ng/mL, 480 ng/mL, 490 ng/mL, 500 ng/mL, 510 ng/mL, 520 ng/mL, 530 ng/mL, 540 ng/mL, 550 ng/mL, 560 ng/mL, 570 ng/mL, 580 ng/mL, 590 ng/mL, 600 ng/mL, 610 ng/mL, 620 ng/mL, 630 ng/mL, 640 ng/mL, 650 ng/mL, 660 ng/mL, 670 ng/mL, 680 ng/mL, 690 ng/mL, 700 ng/mL, 710 ng/mL, 720 ng/mL, 730 ng/mL, 740 ng/mL, 750 ng/mL, 760 ng/mL, 770 ng/mL, 780 ng/mL, 790 ng/mL, 800 ng/mL, 850 ng/mL, 900 ng/mL, 950 ng/mL, 1000 ng/mL, or more than 1000 ng/mL as compared to a reference level (e.g., the total level of heparan sulfate disaccharides (e.g., D0A0, D0S0, D0A6, and D2S6) in a biological sample from one or more healthy subjects and/or from one or more non-neuronopathic subjects, or a pre-determined value).

In some embodiments, a subject is determined to be responsive to a treatment of the disclosure (e.g, rAAV9 encoding hIDUA for treating MPS I; Construct 2) based on the level of I0S6 in a biological sample from the subject. In some embodiments, an elevated level of I0S6 in a biological sample from the subject (e.g., subject with MPS I) as compared to a reference, is indicative that the subject is responsive to a treatment of the disclosure (or treatment with rAAV9 encoding hIDUA for MPS I). In some embodiments, the reference is a level of I0S6 in a biological sample from a healthy subject or a population of healthy subjects. In some embodiments, the reference is a level of I0S6 in a biological sample from a subject with MPS I or a population of subjects with MPS I. In some embodiments, the reference is a level of I0S6 in a biological sample from a subject who does not have MPS I or is not diagnosed with MPS I or a population of subjects not diagnosed with MPS I. In some embodiments, the reference is a level of IS06 in a biological sample from the same subject but taken at a different time point (e.g., obtained at an earlier time point). In some embodiments, the reference is a predetermined value.

5.5.1. Disease Markers

In certain embodiments, efficacy of treatment with the recombinant nucleotide expression vector is monitored by measuring the level of a disease biomarker in the patient. In certain embodiments, the level of the disease biomarker is measured in the CSF of the patient. In certain embodiments, the level of the disease biomarker is measured in the serum of the patient. In certain embodiments, the level of the disease biomarker is measured in the plasma of the patient. In certain embodiments, the level of the disease biomarker is measured in the urine of the patient. In certain embodiments, the disease biomarker is GAG. In some embodiments, the disease biomarker is I0S6. In preferred embodiments, the disease biomarker is heparan sulfate. In certain embodiments, the disease biomarker is D2S6. I2S enzyme cleaves sulfates from HS in the lysosome and absence of I2S causes long chains of fully sulfated D2S6 to accumulate. In some embodiments, quantitative measurement of D2S6 is reflective of I2S enzyme activity level and elevated levels of HS and D2S6 correlate closely with the neuronopathic phenotype of MPS II. In some embodiments, levels of D2S6 inversely correlate with neurocognitive development. In some embodiments, the disease biomarker is an anti-AAV antibody (e.g., anti-AAV9 antibody). In certain embodiments, the disease biomarker is dermatan sulfate. In certain embodiments, the disease biomarker is IDS enzyme activity. In certain embodiments, the disease biomarker is inflammation. In certain embodiments, the disease biomarker is a safety event.

In certain embodiments, efficacy of treatment with the recombinant nucleotide expression vector is monitored by measuring one or more of the following biomarkers in a sample from the patient: (a) level of GAGs in CSF; (b) level of I2S in CSF; (c) level of GAGs in plasma; (d) level of I2S in plasma; (e) level of leukocyte I2S enzyme activity; (f)

level of GAGs in urine, (g) level of heparan sulfate in CSF, and (h) level of dermatan sulfate in CSF. In certain embodiments, efficacy of treatment with the recombinant nucleotide expression vector is monitored by measuring I2S and/or GAGs in CSF, urine, and/or plasma. In certain embodiments, efficacy of treatment with the recombinant nucleotide expression vector is monitored by measuring heparan sulfate in CSF, plasma, and/or urine. In certain embodiments, efficacy of treatment with the recombinant nucleotide expression vector is monitored by measuring non-reducing heparan sulfate. In some embodiments, heparan sulfate measured in CSF is the primary endpoint for determining efficacy of treatment. In certain embodiments, efficacy of treatment with the recombinant nucleotide expression vector is monitored by measuring D2S6 in CSF. In some embodiments, D2S6 is measured using any detectable/available assay or biological sample used for detecting D2S6 (e.g., CSF, urine, and/or plasma). In certain embodiments, efficacy of treatment with the recombinant nucleotide expression vector is monitored by measuring total urine GAGs, urine HS and/or plasma I2S enzyme activity. In some embodiments, urine GAG is indicative of systemic effect and/or is independent of ERT treatment. In some embodiments, efficacy of a treatment of the disclosure is determined based on the level of I2S protein concentration in a sample from a subject (e.g., an increase in the level of I2S protein concentration is indicative of efficacy). In some embodiments, Heparan sulfate (HS) and D2S6 (glycosaminoglycans (GAGs) are measured in the cerebrospinal fluid (CSF) at baseline and/or after administration of the recombinant vector of the present disclosure. In some embodiments, determining or monitoring efficacy of MPS II treatment in a subject is determined by detecting a level of at least one biomarker (e.g., D2S6) in a biological sample from a subject obtained at about, at least about, or at most about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 days, or 1, 2, 3, 4, 5, 6, 7, 8, 10, 16, 20, 24, 30, 35, 40, 45, 48, 50, 52, 56, 104 weeks, or 1, 2, 3, 4, 5, 6, 7, 8, 9, 10, 11, 12 months, or 1, 2, 3, 4, 5, 6, 7, 8, 9, or 10 years after the the rAAV of the present disclosure is administered to the subject (e.g., and comparing the level with a reference). In some embodiments, determining or monitoring efficacy of MPS I treatment in a subject is determined by detecting a level of at least one biomarker (e.g., I0S6) in a biological sample from a subject obtained at about, at least about, or at most about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 days, or 1, 2, 3, 4, 5, 6, 7, 8, 10, 16, 20, 24, 30, 35, 40, 45, 48, 50, 52, 56, 104 weeks, or 1, 2, 3, 4, 5, 6, 7, 8, 9, 10, 11, 12 months, or 1, 2, 3, 4, 5, 6, 7, 8, 9, or 10 years after the the rAAV of the present disclosure is administered to the subject (e.g., and comparing the level with a reference).

In some embodiments, the level of HS and/or D2S6 is decreased in a subject after administration of a recombinant vector of the present disclosure as compared to a reference (e.g., compared to the level of HS and/or D2S6 in the subject before administration of a recombinant vector of the present disclosure, or as compared to baseline, or a predetermined value). In some embodiments, the level of HS is decreased by about or at least about 3%, 5%, 7%, 8%, 9%, 10%4, 12%, 15%, 17%, 20%, 22%, 25%, 27%, 30%, 32%, 35%, 37%, 40%, 42%, 45%, 47%, 50%, 52%, 55%, 57%, 60%, 62%, 65%, 67%, 70%, 72%, 75%, 77%, 80%, 88%, 85%, 87%, 90%, 92%, 95%, 97%, 100%, or more than 100% after administration of a recombinant vector of the present disclosure as compared to a reference, e.g., before ERT is discontinued, (e.g., compared to the level of HS in the subject before administration of a recombinant vector of the present disclosure). In some embodiments, the level of D2S6 is decreased by about or at least about 3%, 5%, 7%, 8%, 9%, 10%, 12%, 15%, 17%, 20%, 22%, 25%, 27%, 30%, 32%, 35%, 37%, 40%, 42%, 45%, 47%, 50%, 52%, 55%, 57%, 60%, 62%, 65%, 67%, 70%, 72%, 75%, 77%, 80%, 88%, 85%, 87%, 90%, 92%, 95%, 97%, 100%, or more than 100% after administration of a recombinant vector of the present disclosure as compared to a reference, e.g., before ERT is discontinued, (e.g., compared to the level of D2S6 in the subject before administration of a recombinant vector of the present disclosure). In some embodiments, the level of I0S6 is decreased in a subject after administration of a recombinant vector of the present disclosure as compared to a reference (e.g., compared to the level of I0S6 in the subject before administration of a recombinant vector of the present disclosure, or as compared to baseline, or a predetermined value). In some embodiments, the level of IS06 is decreased by about or at least about 3%, 5%, 7%, 8%, 9%, 10%, 12%, 15%, 17%, 20%, 22%, 25%, 27%, 30%, 32%, 35%, 37%, 40%, 42%, 45%, 47%, 50%, 52%, 55%, 57%, 60%, 62%, 65%, 67%, 70%, 72%, 75%, 77%, 80%, 88%, 85%, 87%, 90%, 92%, 95%, 97%, 100%, or more than 100% after administration of a recombinant vector of the present disclosure as compared to a reference, e.g., before ERT is discontinued, (e.g., compared to the level of I0S6 in the subject before administration of a recombinant vector of the present disclosure). In some embodiments, a biomarker (e.g., HS, D2S6, I0S6, total GAG, and/or I2S enzyme) is measured before administration of the recombinant vector of the present disclosure, on the same day as the administration of the recombinant vector of the present disclosure, on one day after the administration of the recombinant vector of the present disclosure, and/or after about 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 22 weeks, 24 weeks, 26 weeks, 30 weeks, 35 weeks, 40 weeks, 42 weeks, 44 weeks, 46 weeks, 48 weeks, 50 weeks, 52 weeks, 54 weeks, 56 weeks, 60 weeks, 65 weeks, 70 weeks, 75 weeks, 80 weeks, 85 weeks, 90 weeks, 95 weeks, 100 weeks, 104 weeks, 1 year, 2 years, or more than 2 years after the administration of the recombinant vector of the present disclosure. In some embodiments, a biomarker (e.g., HS, D2S6, I0S6, total GAG, and/or 2S enzyme) is measured before administration of the recombinant vector of the present disclosure, on the same day as the administration of the recombinant vector of the present disclosure, 8 weeks after, 16 weeks after, 24 weeks after, 32 weeks after, 40 weeks after, 48 weeks after, 56 weeks after, 72 weeks after, 104 weeks after, 1 year after, 2 years after, or more than 2 years after administration of the recombinant vector of the present disclosure. In some embodiments, HS and/or D2S6 is measured in CSF in ng/ml. In some embodiments, a biomarker (e.g., HS, I0S6, and/or D2S6) is decreased by about or at least about 5 ng/ml, 10 ng/ml, 15 ng/ml, 20 ng/ml, 25 ng/ml, 30 ng/ml, 35 mg/ml, 40 mg/ml, 45 ng/ml, 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml, 110 ng/ml, 120 ng/ml, 130 ng/ml, 140 ng/ml, 150 ng/ml, 160 ng/ml, 170 ng/ml, 180 ng/ml, 190 ng/ml, 200 ng/ml, 220 ng/ml, 250 ng/ml, 270 ng/ml, 300 ng/ml, or more than 300 ng/ml after the administration of the recombinant vector of the present disclosure as compared to a reference (e.g., as compared to the amount from baseline or the amount before treatment with the recombinant vector of the present disclosure). In some embodiments, total GAG (e.g., in urine) is measured in g/mol, CK. In some embodiments, a biomarker (e.g., total GAG) is decreased by about or at least about 5 g/mol, 10 g/mol, 15 g/mol, 20 g/mol, 25 g/mol, 30 g/mol, 35 mg/ml, 40 mg/ml, 45 g/mol, 50 g/mol, 55 g/mol, 60 g/mol, 65 g/mol, 70 g/mol, 75 g/mol, 80 g/mol, 85 g/mol, 90 g/mol, 95 g/mol, 100 g/mol, 110 g/mol, 120 g/mol, 130 g/mol, 140 g/mol, 150 g/mol, 160 g/mol, 170 g/mol, 200 g/mol, or more than 200 g/mol after the administration of the recombinant vector of the present disclosure as compared to a reference (e.g., as compared to the amount from baseline or the amount before treatment with the recombinant vector of the present disclosure). In some embodiments, a biomarker (e.g., HS, D2S6, I0S6, and/or total GAG) is decreased and/or hepatosplenomegaly is decreased by about or at least about 3%, 5%, 7%, 8%, 9%, 10%, 12%, 15%, 17%, 20%, 22%, 25%, 27%, 30%, 32%, 35%, 37%, 40%, 42%, 45%, 47%, 50%, 52%, 55%, 57%, 60%, 62%, 65%, 67%, 70%, 72%, 75%, 77%, 80%, 88%, 85%, 87%, 90%, 92%, 95%, 97%, 100%, or more than 100% after the administration of the recombinant vector of the present disclosure as compared to a reference, e.g., before ERT is discontinued, (e.g., as compared to the amount from baseline or the amount before treatment with the recombinant vector of the present disclosure). In some embodiments, determining that a biomarker is increased or decreased in a subject is determined before ERT is discontinued in the subject. In some embodiments, a biomarker (e.g., HS, I0S6, D2S6, and/or total GAG) is decreased and/or hepatosplenomegaly is decreased for about, after about, at least about, or up to about 2 days, 5 days, 1 week, 2 weeks, 3 weeks, 4 weeks, 5 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 22 weeks, 24 weeks, 26 weeks, 30 weeks, 35 weeks, 40 weeks, 42 weeks, 44 weeks, 46 weeks, 48 weeks, 50 weeks, 52 weeks, 54 weeks, 56 weeks, 60 weeks, 65 weeks, 70 weeks, 75 weeks, 80 weeks, 85 weeks, 90 weeks, 95 weeks, 100 weeks, 104 weeks, more than 104 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 40 months, 48 months, 50 months, 55 months, 60 months, 65 months, 70 months, 75 months, 80 months, 85 months, 90 months, 95 months, 100 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more than 10 years after the administration of the recombinant vector of the present disclosure as compared to a reference (e.g., compared to the level of a biomarker in the subject before administration of a recombinant vector of the present disclosure, or compared to a biomarker level from a previously obtained biological sample from the subject, or compared to baseline, or compared to the level of a biomarker in a healthy subject). For example, in some embodiments, a biomarker (e.g., HS, D2S6, I0S6, and/or total GAG) is decreased and/or hepatosplenomegaly is decreased by about or at least about 5%, 20%, 25%, 30%, 35%, 40% 45%, 50%, or more than 50% for about, at least about, or up to about 2 weeks, 4 weeks, 6 weeks, 8 weeks, 16 weeks, 24 weeks, 48 weeks, 56 weeks, 104 weeks, 2 years, or more than 2 years after the administration of the recombinant vector of the present disclosure (e.g., as compared to the level of the biomarker or hepatosplenomegaly from baseline or the level of the biomarker or hepatosplenomegaly before treatment with the recombinant vector of the present disclosure, or as compared to the level of a biomarker or hepatosplenomegaly obtained from the subject at an earlier time point). In some embodiments, a decrease in a biomarker (e.g., HS, D2S6, I0S6, and/or total GAG), a decrease in hepatosplenomegaly, and/or an increase in a biomarker (e.g., I2S) is sustained for about or at least about 2 days, 5 days, 1 week, 2 weeks, 3 weeks, 4 weeks, 5 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 22 weeks, 24 weeks, 26 weeks, 30 weeks, 35 weeks, 40 weeks, 42 weeks, 44 weeks, 46 weeks, 48 weeks, 50 weeks, 52 weeks, 54 weeks, 56 weeks, 60 weeks, 65 weeks, 70 weeks, 75 weeks, 80 weeks, 85 weeks, 90 weeks, 95 weeks, 100 weeks, 104 weeks, more than 104 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 40 months, 48 months, 50 months, 55 months, 60 months, 65 months, 70 months, 75 months, 80 months, 85 months, 90 months, 95 months, 100 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more than 10 years after the administration of the recombinant vector of the present disclosure.

In some embodiments, the level of a biomarker (e.g., I2S enzyme) is increased by about or at least about 3%, 5%, 7%, 8%, 9%, 10%, 12%, 15%, 17%, 20%, 22%, 25%, 27%, 30%, 32%, 35%, 37%, 40%, 42%, 45%, 47%, 50%, 52%, 55%, 57%, 60%, 62%, 65%, 67%, 70%, 72%, 75%, 77%, 80%, 88%, 85%, 87%, 90%, 92%, 95%, 97%, 100%, or more than 100% after the administration of the recombinant vector of the present disclosure as compared to a reference (e.g., compared to the level of the biomarker in the subject before administration of the recombinant vector of the present disclosure). In some embodiments, a biomarker (e.g., I2S enzyme) is increased for about, after about, at least about, or up to about 2 days, 5 days, 1 week, 2 weeks, 3 weeks, 4 weeks, 5 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 22 weeks, 24 weeks, 26 weeks, 30 weeks, 35 weeks, 40 weeks, 42 weeks, 44 weeks, 46 weeks, 48 weeks, 50 weeks, 52 weeks, 54 weeks, 56 weeks, 60 weeks, 65 weeks, 70 weeks, 75 weeks, 80 weeks, 85 weeks, 90 weeks, 95 weeks, 100 weeks, 104 weeks, more than 104 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 40 months, 48 months, 50 months, 55 months, 60 months, 65 months, 70 months, 75 months, 80 months, 85 months, 90 months, 95 months, 100 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more than 10 years after the administration of the recombinant vector of the present disclosure as compared to a reference (e.g., compared to the level of the biomarker in the subject before administration of the recombinant vector of the present disclosure). In some embodiments, a biomarker (e.g., I2S enzyme) is increased by about or at least about 5%, 20%, 25%, 30%, 35%, 40% 45%, 50%, or more than 50% at about, for about, at least about, or up to about 2 weeks, 4 weeks, 6 weeks, 8 weeks, 16 weeks, 24 weeks, 48 weeks, 56 weeks, 104 weeks, 2 years, or more than 2 years after the administration of the recombinant vector of the present disclosure (e.g., as compared to the amount from baseline or the amount before treatment with the recombinant vector of the present disclosure). In some embodiments, a biomarker (e.g., I2S enzyme) is increased by about or at least about 500 pg/ml, 1000 pg/ml, 1500 pg/ml, 10000 pg/ml, 15000 pg/ml, 20000 pg/ml, 25000 mg/ml, 30000 mg/ml, 35000 pg/ml, 40000 pg/ml, 45000 pg/ml, 50000 pg/ml, or more than 50000 pg/ml after the administration of the recombinant vector of the present disclosure (e.g., as compared to the amount from baseline or the amount before treatment with the recombinant vector of the present disclosure).

In some embodiments, heparan sulfate (HS) glycosaminoglycan (CAGs) in CSF is measured using a bioanalytical LC/MS. In some embodiments, heparan sulfate non-reducing ends and total heparan sulfate in CNS is measured using a bioanalytical LC/MS. In some embodiments, heparan sulfate non-reducing ends and total heparan sulfate CAGs in plasma is measured using a bioanalytical LC/MS. In some embodiments, HS CAGs in urine is measured using a bioanalytical LC/MS. In some embodiments, urine total CAGs concentration is measured using a colorimetric assay. In some embodiments, more details about the assays that can be used is provided in Section 6 of the disclosure.

In some embodiments, if a biomarker (e.g., D2S6, I0S6, HS, GAG (e.g., total GAG in urine)) and/or hepatosplenomegaly is increased and/or a biomarker (e.g., I2S) is decreased after a recombinant vector of the present disclosure is administered to the subject, another dose (e.g., same dose, lower dose, or higher dose as compared to previous dose) of the recombinant vector of the present disclosure is administered to the subject. In some embodiments, if a biomarker (e.g., D2S6, HS, GAG (e.g., total GAG in urine)) and/or hepatosplenomegaly is increased and/or a biomarker (e.g., I2S) is decreased after a recombinant vector of the present disclosure is administered to the subject, another therapy or treatment is administered to the the subject (e.g., a therapy or treatment that is used to treat MPS II, a therapy or treatment used to treat a symptom that the subject is suffering from, a therapy or treatment for hepatosplenomegaly, and/or a therapy or treatment used to treat or prevent a symptom from MPS II). In some embodiments, if a biomarker (e.g., I0S6)) and/or hepatosplenomegaly is increased and/or a biomarker (e.g., I2S) is decreased after a recombinant vector of the present disclosure is administered to the subject, another therapy or treatment is administered to the the subject (e.g., a therapy or treatment that is used to treat MPS 1, a therapy or treatment used to treat a symptom that the subject is suffering from, a therapy or treatment for hepatosplenomegaly, and/or a therapy or treatment used to treat or prevent a symptom from MPS I). For example, if a biomarker (e.g., D2S6, I0S6, HS, GAG (e.g., total GAG in urine)) and/or hepatosplenomegaly is increased and/or if a biomarker (e.g., I2S) is decreased by about or by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more than 100% as compared to a reference, another dose (e.g., same dose, lower dose, or higher dose as compared to previous dose) of the recombinant vector of the present disclosure is administered to the subject and/or another therapy or treatment is administered to the subject (e.g., ERT treatment). In some embodiments, a reference is a control. In some embodiments, a reference is the biomarker level and/or hepatosplenomegaly in a previous biological sample or from an image (e.g., ultrasound) obtained from the subject. In some embodiments, a reference is the biomarker level and/or hepatosplenomegaly from the subject at baseline (e.g., before the recombinant vector of the present disclosure is administered to the subject). In some embodiments, a reference is the biomarker level and/or hepatosplenomegaly in a healthy subject or in a subject who does not have or has not been diagnosed with MPS II. In some embodiments, a reference is the level of the at least one biomarker and/or hepatosplenomegaly in a biological sample obtained from a subject diagnosed with MPS II who never received ERT or is not receiving ERT. In some embodiments, a reference is the biomarker level and/or hepatosplenomegaly in a subject or group of subjects with MPS II. In some embodiments, if an increase in a biomarker (e.g., D2S6, I0S6, HS, GAG (e.g., total GAG in urine)) and/or an increase in hepatosplenomegaly and/or a decrease in a biomarker (e.g., I2S) is observed over a period of about, at least about, or up to about 1 week, 2 weeks, 3 weeks, 4 weeks, 5 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 22 weeks, 24 weeks, 26 weeks, 30 weeks, 35 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 65 weeks, 70 weeks, 75 weeks, 80 weeks, 85 weeks, 90 weeks, 95 weeks, 100 weeks, 104 weeks, more than 104 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 40 months, 48 months, 50 months, 55 months, 60 months, 65 months, 70 months, 75 months, 80 months, 85 months, 90 months, 95 months, 100 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more than 10 years after the administration of the recombinant vector of the present disclosure, another dose (e.g., same dose, lower dose, or higher dose as compared to previous dose) of the recombinant vector of the present disclosure is administered to the subject and/or another therapy or treatment is administered to the the subject.

In some embodiments, a subject is receiving or has received enzyme replacement therapy (ERT) prior to and/or continuously with the administration of a recombinant vector of the present disclosure. In some embodiments, ERT treatment is discontinued in a subject prior to the administration of a recombinant vector of the present disclosure. In some embodiments, ERT treatment is discontinued in a subject at about 52 weeks after a recombinant vector of the present disclosure is administered to a subject. In some embodiments, ERT treatment is discontinued in a subject at about 56 weeks after a recombinant vector of the present disclosure is administered to a subject. In some embodiments, ERT treatment is discontinued in a subject at about, before about, or after about 52 weeks after a recombinant vector of the present disclosure is administered to a subject (e.g., at about, before about, or after about one day, two days, three days, four days, five days, six days, 1 week, 2 weeks, 3 weeks, 4 weeks, 6 weeks, 8 weeks, 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, 58 weeks, 60 weeks, 65 weeks, 70 weeks, 75 weeks, 80 weeks, 85 weeks, 90 weeks, 95 weeks, 100 weeks, or more than 100 weeks after a recombinant vector of the present disclosure is administered to a subject). In some embodiments, determining the level of a biomarker and/or hepatosplenomegaly is used to determine if a patient can discontinue enzyme replacement therapy (ERT) treatment after a recombinant vector of the present disclosure is administered to a subject. In some embodiments, an increase in a biomarker (e.g., I2S) after a recombinant vector of the present disclosure is administered to a subject (e.g., as compared to baseline) is indicative that a subject can stop treatment with ERT. In some embodiments, an increase in a biomarker (e.g., I2S) over a period of time after a recombinant vector of the present disclosure is administered to a subject is indicative that a subject can stop treatment with ERT. In some embodiments, if a subject is negative for an anti-AAV antibody (e.g., a biological sample from the subject does not show a detectable level of anti-AAV9 antibodies), ERT treatment is discontinued before a recombinant vector of the present disclosure is administered to a subject. In some embodiments, ERT treatment is discontinued by about or at least about 1 year, 10 months, 8 months, 6 months, 5 months, 4 months, 3 months, 2 months, 1 month, 3 weeks, 2 weeks, 1 week, 10 days, 5 days, 4 days, 3 days, 2 days, or 1 day before a recombinant vector of the present disclosure is administered to a subject. In some embodiments, a decrease in a biomarker (e.g., D2S6, HS, GAG (e.g., total GAG in urine)) and/or a decrease in hepatosplenomegaly after a recombinant vector of the present disclosure is administered to a subject (e.g., as compared to baseline) is indicative that a subject can stop treatment with ERT. In some embodiments, a decrease in a biomarker (e.g., D2S6, I0S6, HS, GAG (e.g., total GAG in urine)) and/or decrease in hepatosplenomegaly over a period of time after a recombinant vector of the present disclosure is administered to a subject is indicative that a subject can stop treatment with ERT. In some embodiments, a decrease in a biomarker (e.g., D2S6, I0S6, HS, GAG (e.g., total GAG in urine)) and/or a decrease in hepatosplenomegaly and/or an increase in a biomarker (e.g., I2S) over a period of about, at least about, or up to about 1 week, 2 weeks, 3 weeks, 4 weeks, 5 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 22 weeks, 24 weeks, 26 weeks, 30 weeks, 35 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 65 weeks, 70 weeks, 75 weeks, 80 weeks, 85 weeks, 90 weeks, 95 weeks, 100 weeks, 104 weeks, more than 104 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 40 months, 48 months, 50 months, 55 months, 60 months, 65 months, 70 months, 75 months, 80 months, 85 months, 90 months, 95 months, 100 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more than 10 years after the administration of the recombinant vector of the present disclosure is indicative that the subject can discontinue or stop treatment with ERT. In some embodiments, if a biomarker level (e.g., D2S6, I0S6, HS, GAG (e.g., total GAG in urine)) decreased and/or hepatosplenomegaly is decreased and/or if a biomarker (e.g., I2S) is increased by about or by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more than 100% as compared to a reference level, ERT treatment is stopped or discontinued. In some embodiments, if a biomarker level (e.g., D2S6, I0S6, HS, GAG (e.g., total GAG in urine)) is decreased and/or hepatosplenomegaly is decreased and/or if a biomarker (e.g., I2S) is increased by about or by at least about 1-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, or more than 100-fold (e.g., after a recombinant vector of the present disclosure is administered) as compared to a reference level, ERT treatment is stopped or discontinued. In some embodiments, ERT is discontinued indefinitely. In some embodiments, ERT is discontinued or stopped for about, at least about, or at most about 1 day, 5 days, 7 days, 10 days, 2 weeks, 3 weeks, 4 weeks, 5 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 22 weeks, 24 weeks, 26 weeks, 30 weeks, 35 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 65 weeks, 70 weeks, 75 weeks, 80 weeks, 85 weeks, 90 weeks, 95 weeks, 100 weeks, 104 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 40 months, 48 months, 50 months, 55 months, 60 months, 65 months, 70 months, 75 months, 80 months, 85 months, 90 months, 95 months, 100 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more than 10 years. In some embodiments, ERT is stopped at about or at least about 52 weeks after the administration of the recombinant vector of the present disclosure.

In some embodiments, a biomarker (e.g., I2S, I0S6, D2S6, HS, GAG (e.g., total GAG in urine)) and/or hepatosplenomegaly is monitored after ERT treatment is discontinued. For example, in some embodiments, a biomarker (e.g., I2S, I0S6, D2S6, HS, GAG (e.g., total GAG in urine)) and/or hepatosplenomegaly (e.g., size of the liver or spleen) is measured at about, at least about, or every 2 days, 5 days, 7 days, 10 days, 2 weeks, 3 weeks, 4 weeks, 5 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 22 weeks, 24 weeks, 26 weeks, 30 weeks, 35 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 65 weeks, 70 weeks, 75 weeks, 80 weeks, 85 weeks, 90 weeks, 95 weeks, 100 weeks, 104 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 40 months, 48 months, 50 months, 55 months, 60 months, 65 months, 70 months, 75 months, 80 months, 85 months, 90 months, 95 months, 100 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more than 10 years after ERT treatment is stopped or discontinued and/or after the recombinant vector of the present disclosure is administered to the subject.

In some embodiments, if a biomarker (e.g., D2S6, I0S6, HS, GAG (e.g., total GAG in urine)) is increased and/or hepatosplenomegaly is increased and/or a biomarker (e.g., I2S) is decreased after ERT treatment is stopped or discontinued, ERT treatment is re-administered to the subject. For example, if a biomarker (e.g., D2S6, I0S6, HS, GAG (e.g., total GAG in urine)) is increased and/or hepatosplenomegaly is increased and/or if a biomarker (e.g., I2S) is decreased by about or by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more than 100% (e.g., after a recombinant vector of the present disclosure is administered to the subject) as compared to a reference, ERT treatment is re-administered to the subject (e.g., for a period of time until a biomarker (e.g., D2S6, I0S6, HS, GAG (e.g., total GAG in urine)) is reduced or controlled and/or hepatosplenomegaly is reduced or controlled and/or a biomarker (e.g., I2S) is increased or controlled. In some embodiments, a reference is a control. In some embodiments, a reference is the biomarker level and/or hepatosplenomegaly in a previous biological sample or from an image (e.g., ultrasound) obtained from the subject. In some embodiments, a reference is the biomarker level and/or hepatosplenomegaly from the subject at baseline (e.g., before the recombinant vector of the present disclosure is administered to the subject). In some embodiments, a reference is the biomarker level and/or hepatosplenomegaly in a healthy subject or in a subject who does not have or has not been diagnosed with MPS II. In some embodiments, a reference is the biomarker level and/or hepatosplenomegaly in a subject or group of subjects with MPS II. In some embodiments, a reference is the biomarker level and/or hepatosplenomegaly in a healthy subject or in a subject who does not have or has not been diagnosed with MPS 1. In some embodiments, a reference is the biomarker level and/or hepatosplenomegaly in a subject or group of subjects with MPS I. In some embodiments, a reference is the biomarker level and/or hepatosplenomegaly in a subject or group of subjects who is receiving or has received ERT treatment.

In some embodiments, ERT treatment is discontinued after administration of the recombinant vector of the present disclosure. For example, ERT treatment is stopped after the recombinant vector of the present disclosure is administered to a subject who has been treated with ERT and has anti-IDS Abs levels (e.g., anti-IDS Abs level as a result of ERT treatment). In some embodiments, a subject who has anti-IDS Abs levels has ERT treatment stopped as soon as or immediately after the recombinant vector of the present disclosure is administered to the subject. In some embodiments, anti-IDS Abs levels is determined in a biological sample from a subject (e.g., serum sample). In some embodiments, anti-IDS Abs levels is determined in a biological sample obtained from a subject before the recombinant vector of the present disclosure is administered to the subject. In some embodiments, anti-IDS Abs levels is monitored before and/or after the recombinant vector of the present disclosure is administered to the subject. In some embodiments, if anti-IDS Abs levels is higher than a reference level, ERT treatment is stopped or discontinued. In some embodiments, a reference level is a predetermined level. In some embodiments, a reference level is the anti-IDS Abs level in a previous biological sample obtained from the subject. In some embodiments, a reference level is the anti-IDS Abs level from the subject at baseline (e.g., before the recombinant vector of the present disclosure is administered to the subject). In some embodiments, a reference level is the anti-IDS Abs level in a healthy subject or in a subject who does not have or has not been diagnosed with MPS II. In some embodiments, a reference level is the anti-IDS Abs level in a subject or group of subjects with MPS II. In some embodiments, a reference level is the anti-IDS Abs level in a subject or group of subjects who is receiving or has received ERT treatment. In some embodiments, if the anti-IDS Abs level is higher or increased by about or by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 250%, 500%, 750%, 1000%, or more than 1000% as compared to a reference level then ERT treatment is discontinued. In some embodiments, if the anti-IDS Abs level is higher or increased by about or by at least about 1-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 150-fold, 250-fold, 500-fold, 750-fold, 1000-fold, or more than 1000-fold as compared to a reference level then ERT treatment is stopped or discontinued. In some embodiments, anti-IDS Abs level is measured at about, at least about, or every 1 day, 5 days, 7 days, 10 days, 2 weeks, 3 weeks, 4 weeks, 5 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 22 weeks, 24 weeks, 26 weeks, 30 weeks, 35 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 65 weeks, 70 weeks, 75 weeks, 80 weeks, 85 weeks, 90 weeks, 95 weeks, 100 weeks, 104 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 40 months, 48 months, 50 months, 55 months, 60 months, 65 months, 70 months, 75 months, 80 months, 85 months, 90 months, 95 months, 100 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more than 10 years after ERT treatment is administered to the subject, after ERT treatment is stopped or discontinued, before a recombinant vector of the present disclosure is administered to the subject and/or after a recombinant vector of the present disclosure is administered to the subject In some embodiments, efficacy of treatment or monitoring efficacy of treatment (e.g., with an rAAV9 encoding hIDUA) is based on the level of I0S6. In some embodiments, the level of I0S6 is determined from a biological sample from a subject. In some embodiments, the biological sample is plasma. In some embodiments, a decrease in the level of I0S6 after treatment with a recombinant vector of the disclosure (e.g., rAAV9 encoding hIDUA) in comparison with a reference, is indicative of efficacy of treatment. In some embodiments, the reference is a level of I0S6 in a biological sample from the subject obtained prior to administration of a recombinant AAV of the disclosure. In some embodiments, the reference is a predetermined value. In some embodiments, the reference is the level of I0S6 in a biological sample from another subject with MPS I or a population of subjects with MPS I. In some embodiments, the level of I0S6 is decreased after administration of a recombinant AAV of the disclosure as compared to before administration of the rAAV. In some embodiments, the subject was previously treated with ERT prior to rAAV administration and/or received ERT treatment after the rAAV administration. In some embodiments, the decrease in the level of I0S6 is a decrease of about or at least about 5%, 10%, 15%, 20%, 25%, 30%, 35%, 40%, 45%, 50%, 55%, 60%, 65%, 70%, 75%, 80%, 85%, 90%, 95% as compared to the reference. In some embodiments, efficacy of MPS I treatment is an improvement in at least one subtest of the Bayley Scales of Infant and Toddler Development, 3rd Edition (BSID-III) as compared to a reference. In some embodiments, the at least one subtest is age equivalence score, cognitive developmental quotient (DQ), expressive language DQ, receptive language DQ, gross motor DQ, and/or fine motor DQ. In some embodiments, efficacy of MPS I treatment is an improvement in WASI and/or VABS score. In some embodiments, the rAAV9 encoding hIDUA is administered to the human subject in a solution comprising: (a) sodium chloride at a concentration of about 8.77 g/L, (b) magnesium chloride, at a concentration of about 0.244 g/L, (c) potassium chloride at a concentration of about 0.224 g/L, (d) calcium chloride at a concentration of about 0.206 g/L, (e) dextrose at a concentration of about 0.793 g/L, (f) poloxamer 188 at a concentration of about 0.001% (volume/volume), (g) sodium phosphate monobasic monohydrate at a concentration of about 0.0278 g/L, and (h) sodium phosphate dibasic anhydrous at a concentration of about 0.114 g/L.

5.5.2. Hepatosplenomegaly

In some embodiments, a subject diagnosed with MPS II has hepatosplenomegaly or is experiencing a symptom associated with hepatosplenomegaly. In some embodiments, hepatosplenomegaly is diagnosed by a physical examination. For example, a physician or medical care professional can observe the area around the abdomen for signs of organ enlargement. In some embodiments, a physician or medical care professional feels or palpates the abdomen area of the subject for sensitivity or enlargement of the liver and/or spleen. In some embodiments, a diagnostic test is performed to detect hepatosplenomegaly. For example, hepatosplenomegaly can be detected using a blood test (e.g., liver function test, blood count, and/or tests for clotting factors). In some embodiments, hepatosplenomegaly is detected using an imaging scan such as a computed tomography (CT) scan or ultrasound. In some embodiments, hepatosplenomegaly is detected via a biopsy.

In some embodiments, hepatosplenomegaly is measured before, during, and/or after treatment with a recombinant vector of the present disclosure. In some embodiments, hepatosplenomegaly is measured at different time points before, during, and/or after treatment with a recombinant vector of the present disclosure. In some embodiments, a decrease in hepatosplenomegaly is indicative that the treatment is effective. In some embodiments, assessing or monitoring hepatosplenomegaly is used to determine dosage amount, if dosage is to be increased, if dosage is to be decreased, and/or to determine dosage frequency.

In some embodiments, hepatosplenomegaly is determined before the subject starts treatment with a therapy or treatment of the present disclosure and/or after the subject start treatment with a therapy or treatment of the present disclosure. In some embodiments, hepatosplenomegaly is determined between dosage administrations (e.g., between before the first dose (i.e., before treatment with the recombinant vector of the present disclosure commences) and after the first dose of the recombinant vector of the present disclosure is administered to the subject, between dose 0 and dose 2, between dose 0 and dose 3, between dose 1 and dose 2, between dose 1 and dose 3, and/or between dose 2 and dose 3). In some embodiments, hepatosplenomegaly is determined 1 day, 2 days, 3 days, 4 days, 5 days, 6 days, 7 days, 8 days, 9 days, 1 week, 2 weeks, 3 weeks, 4 weeks, 6 weeks, 8 weeks, 10 weeks, 12 weeks, 14 weeks, 16 weeks, 18 weeks, 20 weeks, 22 weeks, 24 weeks, 26 weeks, 28 weeks, 30 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 40 months, 48 months, 50 months, 55 months, 60 months, 65 months, 70 months, 75 months, 80 months, 85 months, 90 months, 95 months, 100 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more than 10 years after a dosage administration or after treatment commences (e.g., after a recombinant vector of the present disclosure is administered to the subject and/or after ERT treatment).

In some embodiments, hepatosplenomegaly (e.g., size of liver of spleen) is decreased by about or at least about 3%, 5%, 7%, 10%, 15%, 20%, 25%, 30%, 35%, 40%, 45%, 50%, 55%, 60%, 65%, 70%, 75%, 80%, 85%, 90%, 95%, 97%, 100%, 200%, or more than 200% after a recombinant vector of the present disclosure is administered to the subject. In some embodiments, hepatosplenomegaly is decreased by about or at least about 1.5-fold, 2-fold, 2.5-fold, 3-fold, 5-fold, 7-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 97-fold, 100-fold, 200-fold, or more than 200-fold after a recombinant vector of the present disclosure is administered to the subject. In some embodiments, a decrease in hepatosplenomegaly corresponds to a decrease in liver and/or spleen dimension. In some embodiments, a decrease in hepatosplenomegaly corresponds to a decrease in liver and/or spleen mass or diameter. In some embodiments, a decrease in hepatosplenomegaly corresponds to a decrease in liver and/or spleen size. In some embodiments, hepatosplenomegaly decreases a recombinant vector of the present disclosure is administered to the subject and/or between dosage administrations. In some embodiments, hepatosplenomegaly decreases after a recombinant vector of the present disclosure is administered to the subject and/or a dosage administration (e.g., after the first dose, after the second dose, after the third dose, after the fourth dose, after the fifth dose, or after several doses). In some embodiments, hepatosplenomegaly decreases at about, after about, for at least about, or for up to about 1 day, 3 days, 5 days, 7 days, one week, 2 weeks, 3 weeks, 4 weeks, 6 weeks, 8 weeks, 10 weeks, 12 weeks, 14 weeks, 16 weeks, 18 weeks, 20 weeks, 22 weeks, 24 weeks, 26 weeks, 28 weeks, 30 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 40 months, 48 months, 50 months, 55 months, 60 months, 65 months, 70 months, 75 months, 80 months, 85 months, 90 months, 95 months, 100 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more than 10 years, after a recombinant vector of the present disclosure is administered to the subject. In some embodiments, a decrease in hepatosplenomegaly is sustained for at least about or for about 1 day, 3 days, 5 days, 7 days, one week, 2 weeks, 3 weeks, 4 weeks, 6 weeks, 8 weeks, 10 weeks, 12 weeks, 14 weeks, 16 weeks, 18 weeks, 20 weeks, 22 weeks, 24 weeks, 26 weeks, 28 weeks, 30 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 40 months, 48 months, 50 months, 55 months, 60 months, 65 months, 70 months, 75 months, 80 months, 85 months, 90 months, 95 months, 100 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more than 10 years, after a recombinant vector of the present disclosure is administered to the subject. In some embodiments, the decrease in hepatosplenomegaly is greater in a subject undergoing a treatment of the present disclosure as compared to a decrease in hepatosplenomegaly if the subject was undergoing another treatment used for treating hepatosplenomegaly or MPS II. In some embodiments, the decrease in hepatosplenomegaly is greater in a subject who received treatment of a recombinant vector of the present disclosure as compared to a decrease in hepatosplenomegaly in a comparable subject having a comparable hepatosplenomegaly undergoing another treatment used for treating hepatosplenomegaly or MPS II. In some embodiments, a decrease in hepatosplenomegaly is greater by about or by at least about 3%, 5%, 7%, 10%, 15%, 20%, 25%, 30%, 35%, 40%, 45%, 50%, 55%, 60%, 65%, 70%, 75%, 80%, 85%, 90%, 95%, 97%, 100%, 200%, or more than 200% (e.g., as compared to the decrease in hepatosplenomegaly if the subject was undergoing another treatment used for treating hepatosplenomegaly or MPS II).

5.5.3. Tests for Neurocognitive and Neurodegeneration Function

In certain embodiments, efficacy of treatment with the recombinant vector is monitored by measuring the level of cognitive function in the patient. Cognitive function may be measured by any method known to one of skill in the art. In certain embodiments, cognitive function is measured via a validated instrument for measuring intelligence quotient (IQ). In specific embodiments, IQ is measured by Wechsler Abbreviated Scale of Intelligence, Second Edition (WASI-II). In some embodiments, neurocognition is determined by measuring intelligence quotient (IQ) as measured by Bayley's Infantile Development Scale. In some embodiments, developmental quotient (DQ) is measured using Bayley Scales of Infant Development (BSID-III). In some embodiments, Bayley Scales of Infant and Toddler Development is used to measure motor, cognitive, language, social-emotional, and/or adaptive behavior development in babies, young children, or in a patient of the present disclosure. In some embodiments, efficacy of a treatment of MPS II according to the methods of the present disclosure (e.g., by administering an rAAV encoding hIDS to a subject) is determined by analyzing at least one subtest of BSID-III. In some embodiments, efficacy of a treatment of MPS I according to the methods of the present disclosure (e.g., by administering an rAAV encoding hIDUA to a subject) is determined by analyzing at least one subtest of BSID-III. In some embodiments, efficacy of a treatment of MPS II or MPS I according to the methods of the present disclosure (e.g., by administering an rAAV encoding hIDS or an AAV encoding hIDUA to a subject) is determined by analyzing age equivalence score, cognitive developmental quotient (DQ), expressive language DQ, receptive language DQ, gross motor DQ, and/or fine motor DQ. In some embodiments, the efficacy of MPS II or MPS I treatment is an improvement in at least one subtest of the Bayley Scales of Infant and Toddler Development, 3rd Edition (BSID-III) as compared to a reference. In some embodiments, the at least one subtest is age equivalence score, cognitive developmental quotient (DQ), expressive language DQ, receptive language DQ, gross motor DQ, and/or fine motor DQ. In some embodiments, the improvement is an improvement in DQ of about or at least about 1, 2, 3, 4, 5, 6, 7, 8, 9, 10, 12, 15, 17, 20, 25, 30, 35, 40, 45, 50, 55, 60, 65, 70, 75, 80, 85, 90, 95, 100, or more than 100. In some embodiments, the age equivalence score is increased by about or at least about 1 month, 2 months, 3 months, 4 months, 5 months, 6 months, 7 months, 8 months, 9 months, 10 months, 11 months, 12 months, 18 months, 24 months, or more than 24 months as compared to a reference. In some embodiments, the reference is the score of the at least one subtest of the BSID-III obtained prior to administration of an rAAV of the present disclosure. In some embodiments, a reference is an average score of at least one subtest of BSID-III obtained from human subjects with MPS II of the same age as the human subject receiving an rAAV of the present disclosure. In some embodiments, a reference is an average score of at least one subtest of BSID-III obtained from human subjects with MPS I of the same age as the human subject receiving an rAAV of the present disclosure. In some embodiments, a level of a biomarker of the present disclosure is indicative of efficacy of an MPS II treatment. For example, in some embodiments, the level of D2S6 in a biological sample from a subject is inversely proportional to the efficacy of MPS II treatment. In some embodiments, a decrease in D2S6 level in a biological sample correlates with an improvement in at least one subtest of BSID-III. In some embodiments, a decrease in I0S6 level in a biological sample correlates with an improvement in at least one subtest of BSID-III. In some embodiments, a decrease in D2S6 level in a biological sample obtained from a subject after an rAAV encoding hIDS is administered to the subject (e.g., as compared to a reference or to the level of D2S6 prior to administration of the rAAV encoding hIDS), correlates with (or is indicative of) an improvement in the age equivalence score of a subject with MPS II. In some embodiments, a decrease in I0S6 level in a biological sample obtained from a subject after an rAAV encoding hIDUA is administered to the subject (e.g., as compared to a reference or to the level of I0S6 prior to administration of the rAAV encoding hIDUA), correlates with (or is indicative of) an improvement in the age equivalence score of a subject with MPS I. In some embodiments, a decrease in D2S6 level in a biological sample obtained from a subject after an rAAV encoding hIDS is administered to the subject (e.g., as compared to a reference or to the level of D2S6 prior to administration of the rAAV encoding hIDS), correlates with (or is indicative of) an improvement in cognitive developmental quotient (DQ), expressive language DQ, receptive language DQ, gross motor DQ, and/or fine motor DQ of a subject with MPS 11. In some embodiments, a decrease in I0S6 level in a biological sample obtained from a subject after an rAAV encoding hIDUA is administered to the subject (e.g., as compared to a reference or to the level of I0S6 prior to administration of the rAAV encoding hIDUA), correlates with (or is indicative of) an improvement in cognitive developmental quotient (DQ), expressive language DQ, receptive language DQ, gross motor DQ, and/or fine motor DQ of a subject with MPS I. In certain embodiments, cognitive function is measured via a validated instrument for measuring memory. In specific embodiments, memory is measured by Hopkins Verbal Learning Test (HVLT). In certain embodiments, cognitive function is measured via a validated instrument for measuring attention. In specific embodiments, attention is measured by Test Of Variables of Attention (TOVA). In certain embodiments, cognitive function is measured via a validated instrument for measuring one or more of IQ, memory, and attention.

In some embodiments, a decrease in a biomarker level (e.g., D2S6, I0S6, HS, GAG (e.g., total GAG in urine)) and/or a decrease in hepatosplenomegaly and/or an increase in a biomarker (e.g., I2S) level is indicative of improved or unchanged neurocognitive assessment (e.g., DQ, IQ, expressive communication, gross motor, receptive communication, and/or fine motor skills). In some embodiments, a decrease in a biomarker level (e.g., D2S6, I0S6, HS, GAG (e.g., total GAG in urine)) and/or a decrease in hepatosplenomegaly and/or an increase in a biomarker level (e.g., I2S) of about or at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more than 100% as compared to a reference, correlates with an increase (e.g., by about or at least about 1 point, 2 point, 3 points, 4 points, 5 points, 6 points, 7 points, 8 points, 9 points, 10 points, 15 points, 20 points, 25 points, 30 points 35 points, 40 points, 45 points, 50 points, or more than 50 points), an unchanged, or a decrease in neurocognitive assessment (e.g., DQ, expressive communication, gross motor, receptive communication, and/or fine motor skills) by no more than about 30 points, by no more than about 25 points, by no more than about 20 points, by no more than about 15 points, by no more than about 10 points, or by no more than about 5 points. In some embodiments, a decrease in a biomarker level (e.g., D2S6, I0S6, HS, GAG (e.g., total GAG in urine)) and/or a decrease in hepatosplenomegaly and/or an increase in a biomarker level (e.g., I2S) of about or at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more than 100% (e.g., after a recombinant vector of the present disclosure is administered to the subject) as compared to a reference, correlates with an increase (e.g., by about or at least about 1 month, 2 month, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 25 months, 30 months 35 months, 40 months, 45 months, 50 months, or more than 50 months), an unchanged, or a decrease in age equivalence by no more than about 30 months, by no more than about 25 months, by no more than about 20 months, by no more than about 18 months, by no more than about 15 months, by no more than about 14 months, by no more than about 13 months, by no more than about 12 months, by no more than about 11 months, by no more than about 10 months, by no more than about 9 months, by no more than about 8 months, by no more than about 7 months, by no more than about 6 months, by no more than about 5 months, by no more than about 4 months, by no more than about 3 months, by no more than about 2 months, or by no more than about 1 month.

A neurocognitive assessment instrument can be used to determine an indicator such as cognitive age equivalence (AEq) or cognitive developmental quotient (DQ). In some embodiments, the cognitive age equivalence (AEq) of the subject is unchanged or increases in comparison to the baseline level after treatment with a recombinant vector of the present disclosure. An increase relative to the baseline level of the subject can be 1 month, 2 months, 3 months, 4 months, 5 months, 6 months, 7 months, 8 months, 9 months, 10 months, 11 months, 12 months, 15 months 18 months, 20 months, 2 years, 2.5 years, 3 years, or more. In some embodiments, the chronological age of the subject at the time treatment is initiated or escalated is less than about or equal to about 3 months, 6 months, 9 months, 12 months, 18 months, 24 months, 30 months, 36 months, 42 months, 48 months, 60 months, 72 months, 84 months, 96 months, 108 months, 120 months, 5.5 years, 6 years, 6.5 years, 7 years, 7.5 years, 8 years, 8.5 years, 9 years, 9.5 years, 10 years, 10.5 years, 11 years, 11.5 years, 12 years, 12.5 years, 13 years, 14 years, 15 years, 16 years, 17 years, or higher. In some embodiments, the cognitive age equivalence (AEq) before the start of treatment with a recombinant vector of the present disclosure is lower than the baseline level by about, at least about or at most about 1 month, 2 months, 3 months, 4 months, 5 months, 6 months, 7 months, 8 months, months, 10 months, 12 months, or more than 12 months. In some embodiments, the cognitive age equivalence (AEq) after the start of treatment with a recombinant vector of the present disclosure is lower than the baseline level by about or at most about 1 month, 2 months, 3 months, 4 months, 5 months, 6 months, 7 months, 8 months, months, 10 months, 12 months, or more than 12 months.

In some embodiments, neurodevelopmental function (e.g., AEq or DQ) is determined based on expressive communication, gross motor, receptive communication, and/or fine motor skills. In some embodiments, any one of expressive communication, gross motor, receptive communication, and/or fine motor skills is indicative of AEq and/or DQ. In some embodiments, neurodevelopmental function (e.g., AEq, cognitive developmental quotient (DQ), IQ, expressive communication, gross motor, receptive communication, and/or fine motor skills) of a subject is measured at about, at least about, or every 1 day, 5 days, 7 days, 10 days, 2 weeks, 3 weeks, 4 weeks, 5 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 22 weeks, 24 weeks, 26 weeks, 30 weeks, 35 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 65 weeks, 70 weeks, 75 weeks, 80 weeks, 85 weeks, 90 weeks, 95 weeks, 100 weeks, 104 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 40 months, 48 months, 50 months, 55 months, 60 months, 65 months, 70 months, 75 months, 80 months, 85 months, 90 months, 95 months, 100 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more than 10 years after the recombinant vector is administered to the subject.

In some embodiments, treatment with a recombinant vector of the present disclosure (e.g., due to a decrease in a biomarker level (e.g., D2S6, I0S6, HS, GAG (e.g., total GAG in urine)) and/or a decrease in hepatosplenomegaly and/or an increase in a biomarker (e.g., I2S) level) results in an increase in neurocognitive developmental quotient (DQ), AEq, IQ, expressive communication, gross motor, receptive communication, and/or fine motor skills in a patient, e.g., as assessed using Bayley Scales of Infant Development. In some embodiments, treatment with a recombinant vector of the present disclosure (e.g., due to a decrease in a biomarker level (e.g., D2S6, I0S6, HS, GAG (e.g., total GAG in urine)) and/or a decrease in hepatosplenomegaly and/or an increase in a biomarker level (e.g., I2S)) results in unchanged neurocognitive developmental quotient (DQ), AEq, IQ, expressive communication, gross motor, receptive communication, and/or fine motor skills in a patient, e.g., as assessed using Bayley Scales of Infant Development. In some embodiments, the cognitive developmental quotient (DQ), AEq, IQ, expressive communication, gross motor, receptive communication, and/or fine motor skills of a subject is increased, remains unchanged, or is reduced by no more than 30 points, reduced by no more than 25 points, reduced by no more than 20 points, reduced by no more than 15 points, reduced by no more than 10 points, or reduced by no more than 5 points after treatment with a recombinant vector of the present disclosure. In some embodiments, treatment with a recombinant vector of the present disclosure results in an increase (e.g., by about or at least about 1 month, 2 month, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 25 months, 30 months 35 months, 40 months, 45 months, 50 months, or more than 50 months), unchanged, or a decrease in age equivalence (AEq) by no more than about 30 months, by no more than about 25 months, by no more than about 20 months, by no more than about 18 months, by no more than about 15 months, by no more than about 14 months, by no more than about 13 months, by no more than about 12 months, by no more than about 11 months, by no more than about 10 months, by no more than about 9 months, by no more than about 8 months, by no more than about 7 months, by no more than about 6 months, by no more than about 5 months, by no more than about 4 months, by no more than about 3 months, by no more than about 2 months, or by no more than about 1 month after a recombinant vector of the present disclosure is administered to the subject. In some embodiments, the cognitive developmental quotient (DQ), AEq, IQ, expressive communication, gross motor, receptive communication, and/or fine motor skills of a subject is increased by about or at least about 1 point, 2 point, 3 points, 4 points, 5 points, 6 points, 7 points, 8 points, 9 points, 10 points, 15 points, 20 points, 25 points, 30 points 35 points, 40 points, 45 points, 50 points, or more than 50 points after treatment with a recombinant vector of the present disclosure (e.g., due to a decrease in a biomarker level (e.g., D2S6, I0S6, HS, GAG (e.g., total GAG in urine)) and/or decrease in hepatosplenomegaly and/or an increase in a biomarker level (e.g., I2S)) as compared to the DQ, AEq, IQ, expressive communication, gross motor, receptive communication, and/or fine motor skills of the subject prior to start of treatment. In some embodiments, the cognitive developmental quotient (DQ), AEq, IQ, expressive communication, gross motor, receptive communication, and/or fine motor skills of a subject remains unchanged or is increased by about or by at least about 1 point, 2 point, 3 points, 4 points, 5 points, 6 points, 7 points, 8 points, 9 points, 10 points, 15 points, 20 points, 25 points, 30 points 35 points, 40 points, 45 points, 50 points, or more than 50 points after about, or after at least about 1 day, 5 days, 7 days, 10 days, 14 days, 21 days, 28 days, one week, 2 weeks, 3 weeks, 4 weeks, 5 weeks, 6 weeks, 7 weeks, 8 weeks, 1 month, 2 months, 3 months, 4 months, 5 months, 6 months, 7 months, 8 months, 9 months, 10 months, 11 months, 12 months, 15 months, 18 months, 21 months, 24 months, 30 months, 36 months, 40 months, 48 months, 50 months, 55 months, 60 months, 65 months, 70 months, 75 months, 80 months, 85 months, 90 months, 95 months, 100 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, or more than 10 years after treatment with a recombinant vector of the present disclosure (e.g., after a first dose of the rAAV of the present disclosure is administered to the subject, after several dosages of the rAAV of the present disclosure is administered to the subject, after a last dose of the rAAV of the present disclosure is administered to the subject, after treatment commences with the rAAV of the present disclosure, and/or after termination of treatment with the rAAV of the present disclosure).

In some embodiments, efficacy of treatment with the recombinant vector is monitored by analyzing maladaptive behavior, challenges with toilet training, and/or change in sleep disturbance scale. Maladaptive behaviors and challenges with toilet training are associated with neurodegeneration. As used herein, maladaptive behavior is a measure of an undesirable behavior that interferes with daily function (Sparrow S, Cichetti D, Balla D (2005) Vineland Adaptive Behavior Scales: 2nd Edition. Pearson, Bloomington, IN). In some embodiments, sleep disturbance is determined based on a subject's snoring pattern. In some embodiments, sleep disturbance is determined based on the level of difficulty of breathing during sleep. In some embodiments, a decrease in maladaptive behavior index is indicative of efficacy of treatment with the recombinant vector of the disclosure. In some embodiments, an improvement in toileting skills (e.g., bowel or bladder control) is indicative of efficacy of treatment with the recombinant vector of the disclosure. In some embodiments, an improvement in sleep patterns (e.g., less frequent snoring or improved breathing) is indicative of efficacy of treatment with the recombinant vector of the disclosure.

5.5.4. Physical Changes

In certain embodiments, efficacy of treatment with the recombinant vector is monitored by measuring physical characteristics associated with lysosomal storage deficiency in the patient. In certain embodiments, the physical characteristics are storage lesions. In certain embodiments, the physical characteristic is short stature. In certain embodiments, the physical characteristic is coarsened facial features. In certain embodiments, the physical characteristic is obstructive sleep apnea. In certain embodiments, the physical characteristic is hearing impairment. In certain embodiments, the physical characteristic is vision impairment. In specific embodiments, the visual impairment is due to corneal clouding. In certain embodiments, the physical characteristic is hydrocephalus. In certain embodiments, the physical characteristic is spinal cord compression. In certain embodiments, the physical characteristic is hepatosplenomegaly. In certain embodiments, the physical characteristics are bone and joint deformities. In certain embodiments, the physical characteristic is cardiac valve disease. In certain embodiments, the physical characteristics are recurrent upper respiratory infections. In certain embodiments, the physical characteristic is carpal tunnel syndrome. In certain embodiments, the physical characteristic is macroglossia (enlarged tongue). In certain embodiments, the physical characteristic is enlarged vocal cords and/or change in voice. Such physical characteristics may be measured by any method known to one of skill in the art.

TABLE OF SEQUENCES

| SEQ ID NO: | Description | Sequence |
|---|---|---|
| 1 | Human IDS amino acid sequence | MPPPRTGRGL LWLGLVLSSV CVALGSETQA NSTTDALNVL LIIVDDLRPS LGCYGDKLVR SPNIDQLASH SLLFQNAFAQ QAVCAPSRVS FLTGRRPDTT RLYDFNSYWR VHAGNFSTIP QYFKENGYVT MSVGKVFHPG ISSNHTDDSP YSWSFPPYHP SSEKYENTKT CRGPDGELHA NLLCPVDVLD VPEGTLPDKQ STEQAIQLLE KMKTSASPFF LAVGYHKPHI PFRYPKEFQK LYPLENITLA PDPEVPDGLP PVAYNPWMDI RQREDVQALN ISVPYGPIPV DFQRKIRQSY FASVSYLDTQ VGRLLSALDD LQLANSTIIA FTSDHGWALG EHGEWAKYSN FDVATHVPLI FYVPGRTASL PEAGEKLFPY LDPFDSASQL MEPGRQSMDL VELVSLFPTL AGLAGLQVPP RCPVPSFHVE LCREGKNLLK HFRFRDLEED PYLPGNPREL IAYSQYPRPS DIPQWNSDKP SLKDIKIMGY SIRTIDYRYT VWVGFNPDEF LANFSDIHAG ELYFVDSDPL QDHNMYNDSQ GGDLFQLLMP |
| 2 | Oligodendrocyte-myelin glycoprotein (hOMG) signal peptide | MEYQILKMSL CLFILLFLTP GILC |
| 3 | Cellular repressor of E1A-stimulated genes 2 (hCREG2) signal peptide | MSVRRGRRPA RPGTRLSWLL CCSALLSPAA G |
| 4 | V-set and transmembrane domain containing 2B (hVSTM2B) signal peptide | MEQRNRLGAL GYLPPLLLHA LLLFVADA |
| 5 | Protocadherin alpha-1 (hPCADHA1) signal peptide | MVFSRRGGLG ARDLLLWLLL LAAWEVGSG |
| 6 | FAM19A1 (TAFA1) signal peptide | MAMVSAMSWV LYLWISACA |
| 7 | VEGF-A signal peptide | MNFLLSWVHW SLALLLYLHH AKWSQA |
| 8 | Fibulin-1 signal peptide | MERAAPSRRV PLPLLLLGGL ALLAAGVDA |
| 9 | Vitronectin signal peptide | MAPLRPLLIL ALLAWVALA |
| 10 | Complement Factor H signal peptide | MRLLAKIICL MLWAICVA |
| 11 | Opticin signal peptide | MRLLAFLSLL ALVLQETGT |
| 12 | Albumin signal peptide | MKWVTFISLL FLFSSAYS |
| 13 | Chymotrypsinogen signal peptide | MAFLWLLSCW ALLGTTFG |
| 14 | Interleukin-2 signal peptide | MYRMQLLSCI ALILALVTNS |
| 15 | Trypsinogen-2 signal peptide | MNLLLILTFV AAAVA |
| 16 | AAV1 | MAADGYLPDWLEDNLSEGIREWWDLKPGAPKPKANQQKQDDG RGLVLPGYKYLGPFNGLDKGEPVNAADAAALEHDKAYDQQLK AGDNPYLRYNHADAEFQERLQEDTSFGGNLGRAVFQAKKRVL EPLGLVEEGAKTAPGKKRPVEQSPQEPDSSSGIGKTGQQPAK KRLNFGQTGDSESVPDPQPLGEPPATPAAVGPTTMASGGGAP MADNNEGADGVGNASGNWHCDSTWLGDRVITTSTRTWALPTY NNHLYKQISSASTGASNDNHYFGYSTPWGYFDFNRFHCHFSP RDWQRLINNNWGFRPKRLNFKLFNIQVKEVTTNDGVTTIANN LTSTVQVFSDSEYQLPYVLGSAHQGCLPPFPADVFMIPQYGY LTLNNGSQAVGRSSFYCLEYFPSQMLRTGNNFTFSYTFEEVP |

TABLE OF SEQUENCES

| SEQ ID NO: | Description | Sequence |
|---|---|---|
| | | FHSSYAHSQSLDRLMNPLIDQYLYYLNRTQNQSGSAQNKDLL FSRGSPAGMSVQPKNWLPGPCYRQQRVSKTKTDNNNSNFTWT GASKYNLNGRESIINPGTAMASHKDDEDKFFPMSGVMIFGKE SAGASNTALDNVMITDEEEIKATNPVATERFGTVAVNFQSSS TDPATGDVHAMGALPGMVWQDRDVYLQGPIWAKIPHTDGHFH PSPLMGGFGLKNPPPQILIKNTPVPANPPAEFSATKFASFIT QYSTGQVSVEIEWELQKENSKRWNPEVQYTSNYAKSANVDFT VDNNGLYTEPRPIGTRYLTRPL |
| 17 | AAV2 | MAADGYLPDWLEDTLSEGIRQWWKLKPGPPPPKPAERHKDDS RGLVLPGYKYLGPFNGLDKGEPVNEADAAALEHDKAYDRQLD SGDNPYLKYNHADAEFQERLKEDTSFGGNLGRAVFQAKKRVL EPLGLVEEPVKTAPGKKRPVEHSPVEPDSSSGTGKAGQQPAR KRLNFGQTGDADSVPDPQPLGQPPAAPSGLGTNTMATGSGAP MADNNEGADGVGNSSGNWHCDSTWMGDRVITTSTRTWALPTY NNHLYKQISSQSGASNDNHYFGYSTPWGYFDFNRFHCHFSPR DWQRLINNNWGFRPKRLNFKLFNIQVKEVTQNDGTTTIANNL TSTVQVFTDSEYQLPYVLGSAHQGCLPPFPADVFMVPQYGYL TLNNGSQAVGRSSFYCLEYFPSQMLRTGNNFTFSYTFEDVPF HSSYAHSQSLDRLMNPLIDQYLYYLSRTNTPSGTTTQSRLQF SQAGASDIRDQSRNWLPGPCYRQQRVSKTSADNNNSEYSWTG ATKYHLNGRDSLVNPGPAMASHKDDEEKFFPQSGVLIFGKQG SEKTNVDIEKVMITDEEEIRTTNPVATEQYGSVSTNLQRGNR QAATADVNTQGVLPGMVWQDRDVYLQGPIWAKIPHTDGHFHP SPLMGGFGLKHPPPQILIKNTPVPANPSTTFSAAKFASFITQ YSTGQVSVEIEWELQKENSKRWNPEIQYTSNYNKSVNVDFTV DTNGVYSEPRPIGTRYLTRNL |
| 18 | AAV3-3 | MAADGYLPDWLEDNLSEGIREWWALKPGVPQPKANQQHQDNR RGLVLPGYKYLGPGNGLDKGEPVNEADAAALEHDKAYDQQLK AGDNPYLKYNHADAEFQERLQEDTSFGGNLGRAVFQAKKRIL EPLGLVEEAAKTAPGKKGAVDQSPQEPDSSSGVGKSGKQPAR KRLNFGQTGDSESVPDPQPLGEPPAAPTSLGSNTMASGGGAP MADNNEGADGVGNSSGNWHCDSQWLGDRVITTSTRTWALPTY NNHLYKQISSQSGASNDNHYFGYSTPWGYFDFNRFHCHFSPR DWQRLINNNWGFRPKKLSFKLFNIQVRGVTQNDGTTTIANNL TSTVQVFTDSEYQLPYVLGSAHQGCLPPFPADVFMVPQYGYL TLNNGSQAVGRSSFYCLEYFPSQMLRTGNNFQFSYTFEDVPF HSSYAHSQSLDRLMNPLIDQYLYYLNRTQGTTSGTTNQSRLL FSQAGPQSMSLQARNWLPGPCYRQQRLSKTANDNNNSNFPWT AASKYHLNGRDSLVNPGPAMASHKDDEEKFFPMHGNLIFGKE GTTASNAELDNVMITDEEEIRTINPVATEQYGTVANNLQSSN TAPTTGTVNHQGALPGMVWQDRDVYLQGPIWAKIPHTDGHFH PSPLMGGFGLKHPPPQIMIKNTPVPANPPTTFSPAKFASFIT QYSTGQVSVEIEWELQKENSKRWNPEIQYTSNYNKSVNVDFT VDTNGVYSEPRPIGTRYLTRNL |
| 19 | AAV4-4 | MTDGYLPDWLEDNLSEGVREWWALQPGAPKPKANQQHQDNAR GLVLPGYKYLGPGNGLDKGEPVNAADAAALEHDKAYDQQLKA GDNPYLKYNHADAEFQQRLQGDTSFGGNLGRAVFQAKKRVLE PLGLVEQAGETAPGKKRPLIESPQQPDSSTGIGKKGKQPAKK KLVFEDETGAGDGPPEGSTSGAMSDDSEMRAAAGGAAVEGGQ GADGVGNASGDWHCDSTWSEGHVTTTSTRTWVLPTYNNHLYK RLGESLQSNTYNGFSTPWGYFDFNRFHCHFSPRDWQRLINNN WGMRPKAMRVKIFNIQVKEVTTSNGETTVANNLTSTVQIFAD SSYELPYVMDAGQEGSLPPFPNDVFMVPQYGYCGLVTGNTSQ QQTDRNAFYCLEYFPSQMLRTGNNFEITYSFEKVPFHSMYAH SQSLDRLMNPLIDQYLWGLQSTTTGTTLNAGTATTNFTKLRP TNFSNFKKNWLPGPSIKQQGFSKTANQNYKIPATGSDSLIKY ETHSTLDGRWSALTPGPPMATAGPADSKFSNSQLIFAGPKQN GNTATVPGTLIFTSEEELAATNATDTDMWGNLPGGDQSNSNL PTVDRLTALGAVPGMVWQNRDIYYQGPIWAKIPHTDGHFPS PLIGGFGLKHPPPQIFIKNTPVPANPATTFSSTPVNSFITQY STGQVSVQIDWEIQKERSKRWNPEVQFTSNYGQQNSLLWAPD AAGKYTEPRAIGTRYLTHHL |
| 20 | AAV5 | MSFVDHPPDWLEEVGEGLREFLGLEAGPPKPKPNQQHQDQAR GLVLPGYNYLGPGNGLDRGEPVNRADEVAREHDISYNEQLEA GDNPYLKYNHADAEFQEKLADDTSFGGNLGKAVFQAKKRVLE PFGLVEEGAKTAPTGKRIDDHFPKRKKARTEEDSKPSTSSDA EAGPSGSQQLQIPAQPASSLGADTMSAGGGGPLGDNNQGADG VGNASGDWHCDSTWMGDRVVTKSTRTWVLPSYNNHQYREIKS GSVDGSNANAYFGYSTPWGYFDFNRFHSHWSPRDWQRLINNY |

TABLE OF SEQUENCES

| SEQ ID NO: | Description | Sequence |
|---|---|---|
| | | WGFRPRSLRVKIFNIQVKEVTVQDSTTTIANNLTSTVQVFTD DDYQLPYVVGNGTEGCLPAFPPQVFTLPQYGYATLNRDNTEN PTERSSFFCLEYFPSKMLRTGNNFEFTYNFEEVPFHSSFAPS QNLFKLANPLVDQYLYRFVSTNNTGGVQFNKNLAGRYANTYK NWFPGPMGRTQGWNLGSGVNRASVSAFATTNRMELEGASYQV PPQPNGMTNNLQGSNTYALENTMIFNSQPANPGTTATYLEGN MLITSESETQPVNRVAYNVGGQMATNNQSSTTAPATGTYNLQ EIVPGSVWMERDVYLQGPIWAKIPETGAHFHPSPAMGGFGLK HPPPMMLIKNTPVPGNITSFSDVPVSSFITQYSTGQVTVEME WELKKENSKRWNPEIQYTNNYNDPQFVDFAPDSTGEYRTTRP IGTRYLTRPL |
| 21 | AAV6 | MAADGYLPDWLEDNLSEGIREWWDLKPGAPKPKANQQKQDDG RGLVLPGYKYLGPFNGLDKGEPVNAADAAALEHDKAYDQQLK AGDNPYLRYNHADAEFQERLQEDTSFGGNLGRAVFQAKKRVL EPFGLVEEGAKTAPGKKRPVEQSPQEPDSSSGIGKTGQQPAK KRLNFGQTGDSESVPDPQPLGEPPATPAAVGPTTMASGGGAP MADNNEGADGVGNASGNWHCDSTWLGDRVITTSTRTWALPTY NNHLYKQISSASTGASNDNHYFGYSTPWGYFDFNRFHCHFSP RDWQRLINNNWGFRPKRLNFKLFNIQVKEVTTNDGVTTIANN LTSTVQVFSDSEYQLPYVLGSAHQGCLPPFPADVFMIPQYGY LTLNNGSQAVGRSSFYCLEYFPSQMLRTGNNFTFSYTFEDVP FHSSYAHSQSLDRLMNPLIDQYLYYLNRTQNQSGSAQNKDLL FSRGSPAGMSVQPKNWLPGPCYRQQRVSKTKTDNNNSNFTWT GASKYNLNGRESIINPGTAMASHKDDKDKFFPMSGVMIFGKE SAGASNTALDNVMITDEEEIKATNPVATERFGTVAVNLQSSS TDPATGDVHVMGALPGMVWQDRDVYLQGPIWAKIPHTDGHFH PSPLMGGFGLKHPPPQILIKNTPVPANPPAEFSATKFASFIT QYSTGQVSVEIEWELQKENSKRWNPEVQYTSNYAKSANVDFT VDNNGLYTEPRPIGTRYLTRPL |
| 22 | AAV7 | MAADGYLPDWLEDNLSEGIREWWDLKPGAPKPKANQQKQDNG RGLVLPGYKYLGPFNGLDKGEPVNAADAAALEHDKAYDQQLK AGDNPYLRYNHADAEFQERLQEDTSFGGNLGRAVFQAKKRVL EPLGLVEEGAKTAPAKKRPVEPSPQRSPDSSTGIGKKGQQPA RKRLNFGQTGDSESVPDPQPLGEPPAAPSSVGSGTVAAGGGA PMADNNEGADGVGNASGNWHCDSTWLGDRVITTSTRTWALPT YNNHLYKQISSETAGSTNDNTYFGYSTPWGYFDFNRFHCHFS PRDWQRLINNNWGFRPKKLRFKLFNIQVKEVTTNDGVTTIAN NLTSTIQVFSDSEYQLPYVLGSAHQGCLPPFPADVFMIPQYG YLTLNNGSQSVGRSSFYCLEYFPSQMLRTGNNFEFSYSFEDV PFHSSYAHSQSLDRLMNPLIDQYLYYLARTQSNPGGTAGNRE LQFYQGGPSTMAEQAKNWLPGPCFRQQRVSKTLDQNNNSNFA WTGATKYHLNGRNSLVNPGVAMATHKDDEDRFFPSSGVLIFG KTGATNKTTLENVLMTNEEEIRPTNPVATEEYGIVSSNLQAA NTAAQTQVVNNQGALPGMVWQNRDVYLQGPIWAKIPHTDGNF HPSPLMGGFGLKHPPPQILIKNTPVPANPPEVFTPAKFASFI TQYSTGQVSVEIEWELQKENSKRWNPEIQYTSNFEKQTGVDF AVDSQGVYSEPRPIGTRYLTRNL |
| 23 | AAV8 | MAADGYLPDWLEDNLSEGIREWWALKPGAPKPKANQQKQDDG RGLVLPGYKYLGPFNGLDKGEPVNAADAAALEHDKAYDQQLQ AGDNPYLRYNHADAEFQERLQEDTSFGGNLGRAVFQAKKRVL EPLGLVEEGAKTAPGKKRPVEPSPQRSPDSSTGIGKKGQQPA RKRLNFGQTGDSESVPDPQPLGEPPAAPSGVGPNTMAAGGGA PMADNNEGADGVGSSSGNWHCDSTWLGDRVITTSTRTWALPT YNNHLYKQISNGTSGGATNDNTYFGYSTPWGYFDFNRFHCHF SPRDWQRLINNNWGFRPKRLSFKLFNIQVKEVTQNEGTKTIA NNLTSTIQVFTDSEYQLPYVLGSAHQGCLPPFPADVFMIPQY GYLTLNNGSQAVGRSSFYCLEYFPSQMLRTGNNFQFTYTFED VPFHSSYAHSQSLDRLMNPLIDQYLYYLSRTQTTGGTANTQT LGFSQGGPNTMANQAKNWLPGPCYRQQRVSTTTGQNNNSNFA WTAGTKYHLNGRNSLANPGIAMATHKDDEERFFPSNGILIFG KQNAARDNADYSDVMLTSEEEIKTTNPVATEEYGIVADNLQQ QNTAPQIGTVNSQGALPGMVWQNRDVYLQGPIWAKIPHTDGN FHPSPLMGGFGLKHPPPQILIKNTPVPADPPTTFNQSKLNSF ITQYSTGQVSVEIEWELQKENSKRWNPEIQYTSNYYKSTSVD FAVNTEGVYSEPRPIGTRYLTRNL |
| 24 | hu31 | MAADGYLPDWLEDTLSEGIRQWWKLKPGPPPPKPAERHKDDS RGLVLPGYKYLGPNGLDKGEPVNAADAAALEHDKAYDQQLK AGDNPYLKYNHADAEFQERLKEDTSFGGNLGRAVFQAKKRLL EPLGLVEEAAKTAPGKKRPVEQSPQEPDSSAGIGKSGSQPAK |

| SEQ ID NO: | Description | Sequence |
|---|---|---|
| | | KKLNFGQTGDTESVPDPQPIGEPPAAPSGVGSLTMASGGGAP VADNNEGADGVGSSSGNWHCDSQWLGDRVITTSTRTWALPTY NNHLYKQISNSTSGGSSNDNAYFGYSTPWGYFDFNRFHCHFS PRDWQRLINNNWGFRPKRLNFKLFNIQVKEVTDNNGVKTIAN NLTSTVQVFTDSDYQLPYVLGSAHEGCLPPFPADVFMIPQYG YLTLNDGGQAVGRSSFYCLEYFPSQMLRTGNNFQFSYEFENV PFHSSYAHSQSLDRLMNPLIDQYLYYLSKTINGSGQNQQTLK FSVAGPSNMAVQGRNYIPGPSYRQQRVSTTVTQNNNSEFAWP GASSWALNGRNSLMNPGPAMASHKEGEDRFFPLSGSLIFGKQ GTGRDNVDADKVMITNEEEIKTTNPVATESYGQVATNHQSAQ AQAQTGWVQNQGILPGMVWQDRDVYLQGPIWAKIPHTDGNFH PSPLMGGFGMKHPPPQILIKNTPVPADPPTAFNKDKLNSFIT QYSTGQVSVEIEWELQKENSKRWNPEIQYTSNYYKSNNVEFA VSTEGVYSEPRPIGTRYLTRNL |
| 25 | hu32 | MAADGYLPDWLEDTLSEGIRQWWKLKPGPPPPKPAERHKDDS RGLVLPGYKYLGPGNGLDKGEPVNAADAAALEHDKAYDQQLK AGDNPYLKYNHADAEFQERLKEDTSFGGNLGRAVFQAKKRLL EPLGLVEEAAKTAPGKKRPVEQSPQEPDSSAGIGKSGSQPAK KKLNFGQTGDTESVPDPQPIGEPPAAPSGVGSLTMASGGGAP VADNNEGADGVGSSSGNWHCDSQWLGDRVITTSTRTWALPTY NNHLYKQISNSTSGGSSNDNAYFGYSTPWGYFDFNRFHCHFS PRDWQRLINNNWGFRPKRLNFKLFNIQVKEVTDNNGVKTIAN NLTSTVQVFTDSDYQLPYVLGSAHEGCLPPFPADVFMIPQYG YLTLNDGSQAVGRSSFYCLEYFPSQMLRTGNNFQFSYEFENV PFHSSYAHSQSLDRLMNPLIDQYLYYLSKTINGSGWNQQTLK FSVAGPSNMAVQGRNYIPGPSYRQQRVSTTVTQNNNSEFAWP GASSWALNGRNSLMNPGPAMASHKEGEDRFFPLSGSLIFGKQ GTGRDNVDADKVMITNEEEIKTTNPVATESYGQVATNHQSAQ AQAQTGWVQNQGILPGMVWQDRDVYLQGPIWAKIPHTDGNFH PSPLMGGFGMKHPPPQILIKNTPVPADPPTAFNKDKLNSFIT QYSTGQVSVEIEWELQKENSKRWNPEIQYTSNYYKSNNVEFA VNTEGVYSEPRPIGTRYLTRNL |
| 26 | AAV9 | MAADGYLPDWLEDNLSEGIREWWALKPGAPQPKANQQHQDNA RGLVLPGYKYLGPGNGLDKGEPVNAADAAALEHDKAYDQQLK AGDNPYLKYNHADAEFQERLKEDTSFGGNLGRAVFQAKKRLL EPLGLVEEAAKTAPGKKRPVEQSPQEPDSSAGIGKSGAQPAK KRLNFGQTGDTESVPDPQPIGEPPAAPSGVGSLTMASGGGAP VADNNEGADGVGSSSGNWHCDSQWLGDRVITTSTRTWALPTY NNHLYKQISNSTSGGSSNDNAYFGYSTPWGYFDFNRFHCHFS PRDWQRLINNNWGFRPKRLNFKLFNIQVKEVTDNNGVKTIAN NLTSTVQVFTDSDYQLPYVLGSAHEGCLPPFPADVFMIPQYG YLTLNDGSQAVGRSSFYCLEYFPSQMLRTGNNFQFSYEFENV PFHSSYAHSQSLDRLMNPLIDQYLYYLSKTINGSGQNQQTLK FSVAGPSNMAVQGRNYIPGPSYRQQRVSTTVTQNNNSEFAWP GASSWALNGRNSLMNPGPAMASHKEGEDRFFPLSGSLIFGKQ GTGRDNVDADKVMITNEEEIKTTNPVATESYGQVATNHQSAQ AQAQTGWVQNQGILPGMVWQDRDVYLQGPIWAKIPHTDGNFH PSPLMGGFGMKHPPPQILIKNTPVPADPPTAFNKDKLNSFIT QYSTGQVSVEIEWELQKENSKRWNPEIQYTSNYYKSNNVEFA VNTEGVYSEPRPIGTRYLTRNL |
| 27 | SP\|P22304\|IDS HUMAN [Homo sapiens] | MPPPRTGRGLLWLGLVLSSVCVALGSETQANSTTDALNVLLI IVDDLRPSLGCYGDKLVRSPNIDQLASHSLLFQNAFAQQAVC APSRVSFLTGRRPDTTRLYDFNSYWRVAGNFSTIPQYFKEN GYVTMSVGKVFHPGISSNHTDDSPYSWSFPPYHPSSEKYENT KTCRGPDGELHANLLCPVDVLDVPEGTLPDKQSTEQAIQLLE KMKTSASPFFLAVGYHKPHIPFRYPKEFQKLYPLENITLAPD PEVPDGLPPVAYNPWMDIRQREDVQALNISVPYGPIPVDFQR KIRQSYFASVSYLDTQVGRLLSALDDLQLANSTIIAFTSDHG WALGEHGEWAKYSNFDVATHVPLIFYVPGRTASLPEAGEKLF PYLDPFDSASQLMEPGRQSMDLVELVSLFPTLAGLAGLQVPP RCPVPSFHVELCREGKNLLKHFRFRDLEEDPYLGNPRELIA YSQYPRPSDIPQWNSDKPSLKDIKIMGYSIRTIDYRYTVWVG FNPDEFLANFSDIHAGELYFVDSDPLQDHNMYNDSQGGDLFQ LLMP |
| 28 | TR\|K6ZGI9_PANTR [Pan troglodytes (Chimpanzee)] | MPPPRTGRGLPWLGLVLSSVCVALGSETQANSTTDALNVLLI IVDDLRPSLGCYGDKLVRSPNIDQLASHSLLFQNAFAQQAVC APSRVSFLTGRRPDPTRLYDFNSYWRVAGNFSTIPQYFKEN GYVTMSVGKVFHPGISSNHTDDSPYSWSFPPYHPSSEKYENT KTCRGPDGELHANLLCPVDVLDVPEGTLPDKQSTEQAIQLLE |

| SEQ ID NO: | Description | Sequence |
|---|---|---|
| | | KMKTSASPFFLAVGYHKPHIPFRYPKEFQKLYPLENITLAPD PEVPDGLPPVAYNPWMDIRQREDVQALNISVPYGPIPVDFQR KIRQSYFASVSYLDTQVGRLLSALDDLQLANSTIIAFTSDHG WALGEHGEWAKYSNFDVATHVPLMFYVPGRTASLPEAGEKLF PYLDPFDSASQLMEPGRQSMDLVELVSLFPTLAGLAGLQAPP RCPVPSFHVELCREGKNLLKHFRFRDLEEDPYLPGNPRELIA YSQYPRPSDIPQWNSDKPSLKDIKIMGYSIRTIDYRYTVWIG FNPDEFLANFSDIHAGELYFVDSDPLQDHNMYNDSQGGDLFQ LLMP |
| 29 | TR\|K7BKV4_PANTR [Pan troglodytes (Chimpanzee)] | MPPPRTGRGLPWLGLVLSSVCVALGSETQANSTTDALNVLLI IVDDLRPSLGCYGDKLVRSPNIDQLASHSLLFQNAFAQQAVC APSRVSFLTGRRPDTTRLYDFNSYWRVHAGNFSTIPQYFKEN GYVTMSVGKVFHPGISSNHTDDSPYSWSFPPYHPSSEKYENT KTCRGPDGELHANLLCPVDVLDVPEGTLPDKQSTEQAIQLLE KMKTSASPFFLAVGYHKPHIPFRYPKEFQKLYPLENITLAPD PEVPDGLPPVAYNPWMDIRQREDVQALNISVPYGPIPVDFQR KIRQSYFASVSYLDTQVGRLLSALDDLQLANSTIIAFTSDHG WALGEHGEWAKYSNFDVATHVPLMFYVPGRTASLPEAGEKLF PYLDPFDSASQLMEPGRQSMDLVELVSLFPTLAGLAGLQAPP RCPVPSFHVELCREGKNLLKHFRFRDLEEDPYLPGNPRELIA YSQYPRPSDIPQWNSDKPSLKDIKIMGYSIRTIDYRYTVWIG FNPDEFLANFSDIHAGELYFVDSDPLQDHNMYNDSQGGDLFQ LLMP |
| 30 | TR\|H9FTX2_MACMU [Macaca mulatta (Rhesus macaque)] | MPTPGSGRGFLWLGLVLSSVCVALGCETQANSTTDALNILLI IVDDLRPSLGCYGDKLVRSPNIDQLASHSLLFQNAFAQQAVC APSRVSFLTGRRPDTTRLYDFNSYWRVHAGNFSTIPQYFKEN GYVTMSVGKVFHPGITSNHTDDSPYSWSFPPYHPSSEKYENT KTCRGPDGELHANLLCPVDVVDVPEGTLPDKQSTEQAIQLLE KMKTSASPFFLAVGYHKPHIPFRYPKEFQKLYPLENITLAPD SEVPDGLPPVAYNPWMDIRQREDVQALNISVPYGPIPVEFQR KIRQSYFASVSYLDTQVGRLLSALDDLQLANSTIVAFTSDHG WALGEHGEWAKYSNFDVATHVPLMFYVPGRTASLPEAGEKLF PYLDPFDSASELMEPGRQSMDLVELVSLFPTLAGLAGLQVPP RCPVPSFHVELCREGKNLLKHFRFRDLEEDPYLPGNPRELIA YSQYPRPADFPQWNSDKPSLKDIKIMGYSIRTIDYRYTVWVG FNPDEFLANFSDIHAGELYFVDSDPLQDHNMYNDSQGGDLFQ LLMP |
| 31 | TR\|F7EJG2_CALJA [Callithrix jacchus (White-tufted-ear marmoset)] | MPPPRTSRCLLLLGLVLGSVCVTLGSQAQASSTTDALNVLLI IVDDLRPSLGCYGDKLVRSPNIDQLASHSLLFQNAFAQQAVC APSRVSFLTGRRPDTTRLYDFNSYWRVHAGNFSTIPQYFKDN GYVTMSVGKVFHPGISSNHSDDSPYSWSFPPYHPSSEKYENT KTCRGPDGELHANLLCPVDVVDVPEGTLPDKQSTEEAIRLLE KMKTSASPFFLAVGYHKPHIPFRYPKEFQKLYPLENITLAPD PEVPDGLPPVAYNPWMDIRQREDVQALNISVPYGPIPVDFQR KIRQSYFASVSYLDTQVGHLLSALDDLQLANSTIVAFTSDHG WALGEHGEWAKYSNFDVATRVPLMFYVPGRTASLPEADEKLF PYVDPFHSASELMEPGRQSMDLVELVSLFPTLAGLAGLQVPP RCPVPSFHVELCREGKSLLKHFRFHGLEEDPYLPGNPRELIA YSQYPRPADFPQWNSDKPSLKYIKIMGYSIRTVDYRYTVWVG FNPDEFLANFSDIHAGELYFVDSDPLQDHNMYNDSQGGELFQ SLMP |
| 32 | TR\|U3DTL8_CALJA [Callithrix jacchus (White-tufted-ear marmoset)] | MPPPRPSRCLLLLGLVLGSVCVTLGSQAQASSTTDALNVLLI IVDDLRPSLGCYGDKLVRSPNIDQLASHSLLFQNAFAQQAVC APSRVSFLTGRRPDTTRLYDFNSYWRVHAGNFSTIPQYFKDN GYVTMSVGKVFHPGISSNHSDDSPYSWSFPPYHPSSEKYENT KTCRGPDGELHANLLCPVDVVDVPEGTLPDKQSTEEAIRLLE KMKTSASPFFLAVGYHKPHIPFRYPKEFQKLYPLENITLAPD PEVPDGLPPVAYNPWMDIRQREDVQALNISVPYGPIPVDFQR KIRQSYFASVSYLDTQVGHLLSALDDLQLANSTIVAFTSDHG WALGEHGEWAKYSNFDVATRVPLMFYVPGRTASLPEADEKLF PYVDPFHSASELMEPGRQSMDLVELVSLFPTLAGLAGLQVPP RCPVPSFHVELCREGKSLLKHFRFHGLEEDPYLPGNPRELIA YSQYPRPADFPQWNSDKPSLKYIKIMGYSIRTVDYRYTVWVG FNPDEFLANFSDIHAGELYFVDSDPLQDHNMYNDSQGGELFQ SLMP |

-continued

| TABLE OF SEQUENCES | | |
|---|---|---|
| SEQ ID NO: | Description | Sequence |
| 33 | TR\|G7NRX7_MAC MU [*Macaca mulatta* (Rhesus macaque)] | MPTPGSGRGFLWLGLVLSSVCVALGCETQANSTTDALNILLI IVDDLRPSLGCYGDKLVRSPNIDQLASHSLLFQNAFAQQAVC APSRVSFLTGRRPDTTRLYDFNSYWRVHAGNFSTIPQYFKEN GYVTMSVGKVFHPGITSNHTDDSPYSWSFPPYHPSSEKYENT KTCRGPDGELHANLLCPVDVVDVPEGTLPDKQSTEQAIQLLE KMKTSASPFFLAVGYHKPHIPFRYPKEFQKLYPLENITLAPD SEVPDGLPPVAYNPWMDIRQREDVQALNISVPYGPIPVEFQR KIRQSYFASVSYLDTQVGRLLSALDDLQLANSTIVAFTSDHG WALGEHGEWAKYSNFDVATHVPLMFYVPGRTASLPEAGEKLF PYLDPFDSASELMEPGRQSMDLVELVSLFPTLAGLAGLQVPP RCPVPSFHVELCREGKNLLKHFRFRDLEEDPYLPGNPRELIA YSQYPRPADFPQWNSDKPSLKDIKIMGYSIRTIDYRYTVWVG FNPDEFLANFSDIHAGELYFVDSDPLQDHNMYNDSQGGDLLQ LLMP |
| 34 | TR\|G7Q1V9_MAC FA [*Macaca fascicularis* (Crab-eating macaque; Cynomologous monkey)] | MPTPGSGRGFLWLGLVLSSVCVALGCETQANSTTDALNILLI IVDDLRPSLGCYGDKLVRSPNIDQLASHSLLFQNAFAQQAVC APSRVSFLTGRRPDTTRLYDFNSYWRVHAGNFSTIPQYFKEN GYVTMSVGKVFHPGITSNHTDDSPYSWSFPPYHPSSEKYENT KTCRGPDGELHANLLCPVDVVDVPEGTLPDKQSTEQAIQLLE KMKTSASPFFLAVGYHKPHIPFRYPKEFQKLYPLENITLAPD SEVPDGLPPVAYNPWMDIRQREDVQALNISVPYGPIPVEFQR KIRQSYFASVSYLDTQVGHLLSALDDLQLANSTIVAFTSDHG WALGEHGEWAKYSNFDVATHVPLMFYVPGRTASLPEAGEKLF PYLDPFDSASELMEPGRQSMDLVELVSLFPTLAGLAGLQVPP RCPVPSFHVELCREGKNLLKHFRFRDLEEDPYLPGNPRELIA YSQYPRPADFPQWNSDKPSLKDIKIMGYSIRTIDYRYTVWVG FNPDEFLANFSDIHAGELYFVDSDPLQDHNMYNDSQGGDLFQ LLMP |
| 35 | TR\|H2PX10_PONA B [*Pongo abelii* (Sumatran orangutan)] | MPPPRTGRGLLWLGLVLSSVCVALGSETQADSTTDGLNVLLI IVDDLRPSLGCYGDKLVRSPNIDQLASHSLLFQNAFAQQAVC APSRVSFLTGRRPDTTRLYDFNSYWRVHAGNFSTIPQYFKEN GYVTMSVGKVFHPGISSNHTDDSPYSWSFPPYHPSSEKYENT KTCRGPDGELHANLIAKKMCWMFPRAPCCDKQSTEQAIQLLE KMKTSASPFFLAVGYHKPHIPFRYPKEFQKLYPLENITLAPD PEVPDGLPPVAYNPWMDIRQREDVQALNISVPYGPIPVDFQQ KIRQSYFASVSYLDTQVGRLLSTLDDLQLANSTIIAFTSDHG WALGEHGEWAKYSNFDVATHVPLMFYVPGRTASLPEAGEKLF PYLDPFDSASELMEPGRQSMDLVELVSLFPTLAGLAGLQVPP RCPVPSFHVELCREGKNLLKHFRFRDLEEDPYLPGNPRELIA YSQYPRPADIPQWNSDKPSLKDIKIMGYSIRTIDYRYTVWVG FNPDEFLANFSDIHAGELYFVDSDPLQDHNMYNDSQGGDLFQ LLMP |
| 36 | TR\|A0A0D9R4D1_ CHLSB [*Chlorocebus sabaeus* (Green monkey)] | MPTPGSGRGFLWLGLVLSSVCVALGSETQANSTTDALNILLI IVDDLRPSLGCYGDKLVRSPNIDQLASHSLLFQNAFAQQAVC APSRVSFLTGRRPDTTRLHFNSYWRVHAGNFSTIPQYFKEN GYVTMSVGKVFHPGITSNHTDDSPYSWSFPPYHPSSEKYENT KTCRGPDGELHANLLCPVDVVDVPEGTLPDKQSTEQAIQLLE KMKTSASPFFLAVGYHKPHIPFRYPKEFQKLYPLENITLAPD SEVPDGLPPVAYNPWMDIRQREDVQALNISVPYGPIPVEFQR KIRQSYFASVSYLDTQVGRLLSALDDLQLANSTIVAFTSDHG WALGEHGEWAKYSNFDVATHVPLMFYVPGRTASLPEAGEKLF PYLDPFDSASELMEPGRQSMDLVELVSLFPTLAGLAGLQVPP RCPVPSFHVELCREGKNLLKHFRFRDLEEDPYLPGNPRELIA YSQYPRPADFPQWNSDKPNLKDIKIMGYSIRTIDYRYTVWVG FNPDEFLANFSDIHAGELYFVDSDPLQDHNMYNDSQGGDLFQ LLMP |
| 37 | TR\|G1RST8\|G1RST 8_NOMLE [*Nomascus leucogenys* (Northern white-cheeked gibbon)] | MSPPRTGQGLLWLGVVLSSVCVAXVTSPKPPSFVDALNVLLI IVDDLRPSLGCYGDKLVRSPNIDQLASHSLLFQNAFAQQAVC APSRVSFLTGRRPDTTRLYDFNSYWRVHAGNFSTIPQYFKEN GYVTMSVGKVFHPGISSNHTDDSPYSWSFPPYHPSSXXXXXX KTCRGPDGELHANLLCPVDVLDVPEGTLPDKQSTEQAIQLLE KMKTSASPFFLAVGYHKPHIPFRYPKEFQKLYPLENITLAPD PEVPDGLPPVAYNPWMDIRQREDVQALNISVPYGPIPVDFQR KIRQSYFASVSYLDTQVGRLLSALDDLQLANSTIIAFTSDHG WALGEHGEWAKYSNFDVATHVPLMFYVPGRTASLPEAGEKLF PYLDPFDSASELMEPGRQSMDLVELVSLFPTLAGLAGLQVPP RCPVPSFHVELCREGKNLLKHFRFRDLEEDPYLPGNPRELIA YSQYPRPADIPQWNSDKPSLKDIKIMGYSIRTIDYRYTVWVG |

TABLE OF SEQUENCES

| SEQ ID NO: | Description | Sequence |
|---|---|---|
| | | FSPDEFLANFSDIHAGELYFVDSDPLQDHNMYNDSQGGDLFQ LLMP |
| 38 | UPI0000D9F625 [*Macaca mulatta* (Rhesus macaque)] | MPTPGSGRGFLWLGLVLSSVCVALGCETQANSTTDALNILLI IVDDLRPSLGCYGDKLVRSPNIDQLASHSLLFQNAFAQQAVC APSRVSFLTGRRPDTTRLYDFNSYWRVHAGNFSTIPQYFKEN GYVTMSVGKVFHPGITSNHTDDSPYSWSFPPYHPSSEKYENT KTCRGPDGELHANLLCPVDVVDVPEGTLPDKQSTEQAIQLLE KMKTSASPFFLAVGYHKPHIPFRYPKEFQKLYPLENITLAPD SEVPDGLPPVAYNPWMDIRQREDVQALNISVPYGPIPVEFQR KIRQSYFASVSYLDTQVGHLLSALDDLQLANSTIVAFTSDHG WALGEHGEWAKYSNFDVATHVPLMFYVPGRTASLPEAGEKLF PYLDPFDSASELMEPGRQSMDLVELVSLFPTLAGLAGLQVPP RCPVPSFHVELCREGKNLLKHFRFRDLEEDPYLPGNPRELIA YSQYPRPADFPQWNSDKPSLKDIKIMGYSIRTIDYRYTVWVG FNPDEFLANFSDIHAGELYFVDSDPLQDHNMYNDSQGGDLLQ LLMP |
| 39 | UPI000274358B [*Pan paniscus* (Pygmy chimpanzee; Bonobo)] | MPPPRTGRGLLWLGLVLSSVCVALGSETQANSTTDALNVLLI IVDDLRPSLGCYGDKLVRSPNIDQLASHSLLFQNAFAQQAVC APSRVSFLTGRRPDTTRLYDFNSYWRVHAGNFSTIPQYFKEN GYVTMSVGKVFHPGISSNHTDDSPYSWSFPPYHPSSEKYENT KTCRGPDGELHANLLCPVDVLDVPEGTLPDKQSTEQAIRLLE KMKTSASPFFLAVGYHKPHIPFRYPKEFQKLYPLENITLAPD PEVPDGLPPVAYNPWMDIRQREDVQALNISVPYGPIPVDFQR KIRQSYFASVSYLDTQVGRLLSALDDLQLANSTIIAFTSDHG WALGEHGEWAKYSNFDVATHVPLMFYVPGRTASLPEAGEKLF PYLDPFDSASQLMEPGRQSMDLVELVSLFPTLAGLAGLQVPP RCPVPSFHVELCREGKNLLKHFRFRDLEEDPYLPGNPRELIA YSQYPRPSDIPQWNSDKPSLKDIKIMGYSIRTIDYRYTVWVG FNPDEFLANFSDIHAGELYFVDSDPLQDHNMYNDSQGGDLFQ LLMP |
| 40 | UPI00027F6FC5 [*Papio Anubis* (Olive baboon)] | MPTPGSGRGFLWLGLVLSSVCVALGCEMQANSTTDALNILLI IVDDLRPSLGCYGDKLVRSPNIDQLASHSLLFQNAFAQQAVC APSRVSFLTGRRPDTTRLYDFNSYWRVHAGNFSTIPQYFKEN GYVTMSVGKVFHPGITSNHTDDSPYSWSFPPYHPSSEKYENT KTCRGPDGELHANLLCPVDVVDVPEGTLPDKQSTEQAIQLLE KMKTSASPFFLAVGYHKPHIPFRYPKEFQKLYPLENITLAPD SEVPDGLPPVAYNPWMDIRQREDVQALNISVPYGPIPVEFQR KIRQSYFASVSYLDTQVGRLLSALDDLQLANSTIVAFTSDHG WALGEHGEWAKYSNFDVATHVPLMFYVPGRTASLPEAGEKLF PYLDPFDSASELMEPGRQSMDLVELVSLFPTLAGLAGLQVPP RCPVPSFHVELCREGKNLLKHFRFRDLEEDPYLPGNPRELIA YSQYPRPADFPQWNSDKPSLKDIKIMGYSIRTIDYRYTVWVG FNPDEFLANFSDIHAGELYFVDSDPLQDHNMYNDSQGGDLFQ LLMP |
| 41 | UPI00027FAE03 [*Saimiri boliviensis* (Bolivian squirrel monkey)] | MPPPRTGLCLLLLGLVLGSVCVTLGSQAQANSTTDALNVLLI IVDDLRPSLGCYGDKLVRSPNIDQLASHSLLFQNAFVQQAVC APSRVSFLTGRRPDTTRLYDFNSYWRVHAGNFSTIPQYFKDN GYVTMSVGKVFHPGISSNHSDDSPYSWSFPPYHPSSEKYENT KTCRGPDGELHANLLCPVDVVDVPEGTLPDKQSTEEAIRLLK KMKTSASPFFLAVGYHKPHIPFRYPKEFQKLYPLENITLAPD PEVPDGLPPVAYNPWMDIRQREDVQALNISVPYGPIPVDFQR KIRQSYFASVSYLDTQVGHLLSALDDLHLANSTIVAFTSDHG WALGEHGEWAKYSNFDVATRVPLMFYVPGRTASLPETGEKLF PYVDPFHSASELMEPGRQSTDLVELVSLFPTLAGLAGLQVPP RCPVPSFHIELCREGKNLLKHFRFHGLEEDPYLPGNPRELIA YSQYPRPADFPQQNSDKPSLKYIKIMGYSIRTVDYRYTVWVG FNPDEFLANFSDIHAGELYFVDSDPLQDHNMYNDSQGGELFQ SLMP |
| 42 | UPI0003ABBF28 [*Macaca fascicularis* (Crab-eating macaque; Cynomologous monkey)] | MPTPGSGRGFLWLGLVLSSVCVALGCETQANSTTDALNILLI IVDDLRPSLGCYGDKLVRSPNIDQLASHSLLFQNAFAQEAVC APSRVSFLTGRRPDTTRLYDFNSYWRVHAGNFSTIPQYFKEN GYVTMSVGKVFHPGITSNHTDDSPYSWSFPPYHPSSEKYENT KTCRGPDGELHANLLCPVDVVDVPEGTLPDKQSTEQAIQLLE KMKTSASPFFLAVGYHKPHIPFRYPKEFQKLYPLENITLAPD SEVPDGLPPVAYNPWMDIRQREDVQALNISVPYGPIPVEFQR KIRQSYFASVSYLDTQVGRLLSALDDLQLANSTIVAFTSDHG WALGEHGEWAKYSNFDVATHVPLMFYVPGRTASLPEAGEKLF PYLDPFDSASELMEPGRQSMDLVELVSLFPTLAGLAGLQVPP |

TABLE OF SEQUENCES

| SEQ ID NO: | Description | Sequence |
|---|---|---|
| | | RCPVPSFHVELCREGKNLLKHFRFRDLEEDPYLPGNPRELIA YSQYPRPADFPQWNSDKPSLKDIKIMGYSIRTIDYRYTVWVG FNPDEFLANFSDIHAGELYFVDSDPLQDHNMYNDSQGGDLFQ LLMP |
| 43 | UPI000533297F [*Rhinopithecus roxellana* (Golden snub-nosed monkey; *Pygathrix roxellana*)] | MPTPASGRGFLWLGLVLSSVCVALGSETQANSTTDALNILLI IVDDLRPSLGCYGDKLVRSPNIDQLASHSLLFQNAFAQQAVC APSRVSFLTGRRPDTTRLYDFNSYWRVHAGNFSTIPQYFKEN GYVTMSVGKVFHPGITSNHTDDSPYSWSFPPYHPSSEKYENT KTCRGPDGELHANLLCPVDVVDVPEGTLPDKQSTEQAVQLLE KMKTSASPFFLAVGYHKPHIPFRYPKEFQKLYPLENITLAPD SEVPDGLPPVAYNPWMDIRQREDVQALNISVPYGPIPVDFQR KIRQSYFASVSYLDTQVGHLLSALDDLQLANSTIVAFTSDHG WALGEHGEWAKYSNFDVATHVPLMFYVPGRTASLPEAGEKLF PYLDPFDSASELMEPGRQSMDLVELVSLFPTLAGLAGLQVPP RCPVPSFHVELCREGKNLLKHFRFRDLEEDPYLPGNPRELIA YSQYPRPADFPQWNSDKPSLKDIKIMGYSIRTIDYRYTVWVG FNPDEFLANFSDIHAGELYFVDSDPFQDHNMYNDSQGGDLFQ LLMP |
| 44 | UPI0005F40BD2 [*Colobus angolensis palliates* (Peters' Angolan colobus)] | MPTPASGRGFLWLGLVLRSVCVALGSETQANSTTDALNILLI IVDDLRPSLGCYGDKLVRSPNIDQLASHSLLFQNAFAQQAVC TPSHVSFLTGRRPDTTRLYDFNSYWRVHAGNFSTIPQYFKEN GYVTMSVGKVFHPGITSNHTDDSPYSWSFPPYHPSSEKYENT KTCRGPDGELHANLLCPVDVVDVPEGTLPDKQSTEQAIQLLE KMKTSASPFFLAVGYHKPHIPFRYPKEFQKLYPLENITLAPD SEVPDGLPPVAYNPWMDIRQREDVQALNISVPYGPIPVDFQR KIRQSYFASVSYLDTQVGHLLSALDDLQLANSTIVAFTSDHG WALGEHGEWAKYSNFDVATHVPLMFYVPGRTASLPEAGEKLF PYLDPFDSASELMEPGRQSMDLVELVSLFPTLAGLAGLQVPP RCPVPSFHVELCREGKNLLKHFRFRDLEEDPYLPGNPRELIA YSQYPRPADFPQWNSDKPSLKDIKIMGYSIRTIDYRYTVWVG FNPDEFLANFSDIHAGELYFVDSDPLQDHNMYNDSQGGDLFQ LLMP |
| 45 | CB7.CI.hIDS.RBG | gctgcgcgct cgctcgctca ctgaggccgc ccgggcaaag cccgggcgtc gggcgacctt 60 |
| | (2) . . . (131) 5' ITR | tggtcgcccg gcctcagtga gcgagcgagc gcgcagagag ggagtggcca actccatcac 120 |
| | (199) . . . (580) CMV IE promoter | tagggggttcc ttgtagttaa tgattaaccc gccatgctac ttatctacca gggtaatggg 180 |
| | (583) . . . (864) CB promoter | gatcctctag aactatagct agtcgacatt gattattgac tagttattaa tagtaatcaa 240 |
| | | ttacggggtc attagttcat agcccatata tggagttccg cgttacataa cttacggtaa 300 |
| | (837) . . . (840) TATA_signal | atggcccgcc tggctgaccg cccaacgacc cccgcccatt gacgtcaata atgacgtatg 360 |
| | (959) . . . (1930) chicken beta-actin intron | ttcccatagt aacgccaata gggactttcc attgacgtca atgggtggac tatttacggt 420 |
| | | aaactgccca cttggcagta catcaagtgt atcatatgcc aagtacgccc cctattgacg 480 |
| | (1937) . . . (3589) hIDS | tcaatgacgg taaatggccc gcctggcatt atgcccagta catgacctta tgggactttc 540 |

| TABLE OF SEQUENCES | |
|---|---|
| SEQ ID NO: Description | Sequence |
| | ctacttggca gtacatctac gtattagtca tcgctattac catggtcgag gtgagcccca 600 |
| (3623) . . . (3749) rabbit globin polyA | cgttctgctt cactctcccc atctcccccc cctccccacc cccaattttg tatttattta 660 |
| (3838) . . . (3967) 3' ITR | ttttttaatt attttgtgca gcgatggggg cggggggggg ggggggcgc gcgccaggcg 720 |
| | ggggggggcg gggcgagggg cggggcgggg cgaggcggag aggtgcggcg gcagccaatc 780 |
| | agagcggcgc gctccgaaag tttccttta tggcgaggcg gcggcggcgg cggccctata 840 |
| | aaaagcgaag cgcgcggcgg gcgggagtc gctgcgacgc tgccttcgcc ccgtgccccg 900 |
| | ctccgccgcc gcctcgcgcc gcccgcccg gctctgactg accgcgttac tcccacaggt 960 |
| | gagcgggcgg gacggccctt ctcctccggg ctgtaattag cgcttggttt aatgacggct 1020 |
| | tgtttctttt ctgtggctgc gtgaaagcct tgaggggctc cgggagggcc ctttgtgcgg 1080 |
| | ggggagcggc tcggggggtg cgtgcgtgtg tgtgtgcgtg gggagcgccg cgtgcggctc 1140 |
| | cgcgctgccc ggcggctgtg agcgctgcgg gcgcggcgcg gggctttgtg cgctccgcag 1200 |
| | tgtgcgcgag gggagcgcgg ccggggggcgg tgcccgcgg tgcgggggg gctgcgaggg 1260 |
| | gaacaaaggc tgcgtgcggg gtgtgtgcgt gggggggtga gcagggggtg tgggcgcgtc 1320 |
| | ggtcgggctg caacccccc tgcacccccc tccccgagtt gctgagcacg gcccggcttc 1380 |
| | gggtgcgggg ctccgtacgg ggcgtggcgc ggggctcgcc gtgccgggcg gggggtggcg 1440 |
| | gcaggtgggg gtgccgggcg gggcggggcc gcctcgggcc gggagggct cggggagggg 1500 |
| | gcgcggcggc ccccggagcg ccggcggctg tcgaggcgcg gcgagccgca gccattgcct 1560 |
| | tttatggtaa tcgtgcgaga gggcgcaggg acttcctttg tcccaaatct gtgcggagcc 1620 |

TABLE OF SEQUENCES

| SEQ ID NO: Description | Sequence |
|---|---|
| | gaaatctggg aggcgccgcc gcaccccctc tagcgggcgc ggggcgaagc ggtgcggcgc 1680 |
| | cggcaggaag gaaatgggcg gggagggcct tcgtgcgtcg ccgcgccgcc gtccccttct 1740 |
| | ccctctccag cctcgggget gtccgcgggg ggacggctgc cttcgggggg gacggggcag 1800 |
| | ggcggggttc ggcttctggc gtgtgaccgg cggctctaga gcctctgcta accatgttca 1860 |
| | tgccttcttc ttttcctac agctcctggg caacgtgctg gttattgtgc tgtctcatca 1920 |
| | ttttggcaaa gaattcatgc cgccaccccg gaccggccga ggccttctct ggctgggtct 1980 |
| | ggttctgagc tccgtctgcg tcgccctcgg atccgaaacg caggccaact cgaccacaga 2040 |
| | tgctctgaac gttcttctca tcatcgtgga tgacctgcgc ccctccctgg gctgttatgg 2100 |
| | ggataagctg gtgaggtccc caaatattga ccaactggca tcccacagcc tcctcttcca 2160 |
| | gaatgccttt gcgcagcaag cagtgtgcgc cccgagccgc gtttctttcc tcactggcag 2220 |
| | gagacctgac accacccgcc tgtacgactt caactcctac tggagggtgc acgctggaaa 2280 |
| | cttctccacc atcccccagt acttcaagga gaatggctat gtgaccatgt cggtgggaaa 2340 |
| | agtctttcac cctgggatat cttctaacca taccgatgat tctccgtata gctggtcttt 2400 |
| | tccaccttat catccttcct ctgagaagta tgaaaacact aagacatgtc gagggccaga 2460 |
| | tggagaactc catgccaacc tgctttgccc tgtggatgtg ctggatgttc ccgagggcac 2520 |
| | cttgcctgac aaacagagca ctgagcaagc catacagttg ttggaaaaga tgaaaacgtc 2580 |
| | agccagtcct ttcttcctgg ccgttgggta tcataagcca cacatcccct tcagataccc 2640 |
| | caaggaattt cagaagttgt atccccttgga gaacatcacc ctggccccg atcccgaggt 2700 |

TABLE OF SEQUENCES

| SEQ ID NO: Description | Sequence |
|---|---|
| | ccctgatggc ctacccctg tggcctacaa ccctggatg gacatcaggc aacgggaaga 2760 |
| | cgtccaagcc ttaaacatca gtgtgccgta tggtccaatt cctgtggact ttcagcggaa 2820 |
| | aatccgccag agctactttg cctctgtgtc atatttggat acacaggtcg gccgcctctt 2880 |
| | gagtgctttg gacgatcttc agctggccaa cagcaccatc attgcattta cctcggatca 2940 |
| | tgggtgggct ctaggtgaac atggagaatg ggccaaatac agcaattttg atgttgctac 3000 |
| | ccatgttccc ctgatattct atgttcctgg aaggacggct tcacttccgg aggcaggcga 3060 |
| | gaagcttttc ccttacctcg acccttttga ttccgcctca cagttgatgg agccaggcag 3120 |
| | gcaatccatg gaccttgtgg aacttgtgtc tcttttccc acgctggctg gacttgcagg 3180 |
| | actgcaggtt ccacctcgct gccccgttcc ttcatttcac gttgagctgt gcagagaagg 3240 |
| | caagaacctt ctgaagcatt ttcgattccg tgacttggaa gaggatccgt acctccctgg 3300 |
| | taatccccgt gaactgattg cctatagcca gtatccccgg ccttcagaca tccctcagtg 3360 |
| | gaattctgac aagccgagtt taaaagatat aaagatcatg ggctattcca tacgcaccat 3420 |
| | agactatagg tatactgtgt gggttggctt caatcctgat gaatttctag ctaactttc 3480 |
| | tgacatccat gcagggggaac tgtattttgt ggattctgac ccattgcagg atcacaatat 3540 |
| | gtataatgat tcccaaggtg gagatctttt ccagttgttg atgccttgac tcgaggacgg 3600 |
| | ggtgaactac gcctgaggat ccgatctttt tccctctgcc aaaaattatg gggacatcat 3660 |
| | gaagccccctt gagcatctga cttctggcta ataaaggaaa tttatttca ttgcaatagt 3720 |
| | gtgttggaat tttttgtgtc tctcactcgg aagcaattcg ttgatctgaa tttcgaccac 3780 |

TABLE OF SEQUENCES

| SEQ ID NO: | Description | Sequence |
|---|---|---|
| | | ccataatacc cattaccctg gtagataagt<br>agcatggcgg gttaatcatt aactacaagg 3840<br><br>aacccctagt gatggagttg gccactccct<br>ctctgcgcgc tcgctcgctc actgaggccg 3900<br><br>ggcgaccaaa ggtcgcccga cgcccgggct<br>ttgcccgggc ggcctcagtg agcgagcgag 3960<br><br>cgcgcag 3967 |

6. EXAMPLES

6.1 Example 1: hIDS cDNA

A hIDS cDNA-based vector is constructed comprising a transgene comprising hIDS (SEQ ID NO:1). The transgene also comprises nucleic acids comprising a signal peptide chosen from the group listed in Table 4. Optionally, the vector additionally comprises a promoter.

6.2 Example 2: Substituted hIDS cDNAs

A hIDS cDNA-based vector is constructed comprising a transgene comprising hIDS having amino acid substitutions, deletions, or additions compared to the hIDS sequence of SEQ ID NO:1, e.g., including but not limited to amino acid substitutions selected from corresponding non-conserved residues in orthologs of IDS shown in FIG. 2, with the proviso that such mutations do not include replacement of the cysteine residue at position 84 (C84) which is required for enzyme activity (Millat et al., 1997, Biochem J 326: 243-247); or a mutation that has been identified in severe, severe-intermediate, intermediate, or attenuated MPS II phenotypes e.g., as shown in FIG. 3, or as reported by Sukegawa-Hayasaka et al., 2006, J Inherit Metab Dis 29: 755-761 (reporting "attenuated" mutants R48P, A85T, W337R, and the truncated mutant Q531X; and "severe" mutants P86L, S333L, S349I, R468Q, R468L); Millat et al., 1998, BBA 1406: 214-218 (reporting "attenuated" mutants P480L and P480Q; and "severe" mutant P86L); and Bonucelli et al., 2001, BBA 1537:233-238, each of which is incorporated by reference herein in its entirety. The transgene also comprises nucleic acids comprising a signal peptide chosen from the group listed in Table 4. Optionally, the vector additionally comprises a promoter.

6.3 Example 3: Treatment of MPS II in Animals Models with hIDS or Substituted hIDS An hIDS cDNA-based vector is deemed useful for treatment of MPS II when expressed as a transgene. An animal model for MPS II, for example a mouse model described in Garcia et al., 2007, J Inherit Metab Dis 30: 924-34 or Muenzer et al., 2001, Acta Paediatr Suppl 91:98-99 is administered a recombinant vector that encodes hIDS intrathecally at a dose sufficient to deliver and maintain a therapeutically effective concentration of the transgene product in the CSF of the animal. Following treatment, the animal is evaluated for improvement in symptoms consistent with the disease in the particular animal model.

6.4 Example 4: Treatment of MPS II with hIDS or Substituted hIDS

An hIDS cDNA-based vector is deemed useful for treatment of MPS II when expressed as a transgene. A subject presenting with MPS II is administered a cDNA-based vector that encodes hIDS (e.g., such as Construct 1 (see below) intrathecally at a dose sufficient to deliver and maintain a therapeutic concentration of the transgene product in the CSF. Following treatment, the subject is evaluated for improvement in symptoms of MPS II.

6.5 Example 5: A Phase 1/1I Multicenter, Open-Label Study to Evaluate the Safety, Tolerability, and Pharmacodynamics of Construct 1 in Pediatric Subjects with MPS 11 (Hunter Syndrome)

6.5.1. Synopsis

Investigational Product, Dose, and Route of Administration

Construct 1: AAV9.CB7.hIDS (recombinant adeno-associated virus serotype 9 capsid containing human iduronate-2-sulfatase expression cassette). See FIG. 5.

Product will be delivered as a single intracisternal (IC) dose.

Three dose levels will be evaluated, $1.3 \times 10^{10}$ genome copies (GC)/g brain mass (Dose 1), $6.5 \times 10^{10}$ GC/g brain mass (Dose 2), $2.0 \times 10^{10}$ GC/g brain mass (Dose 3), or $2.9 \times 10^{11}$ GC/g brain mass (Dose 3 Expanded Cohort (EC)). The Dose 3 Cohort receives $2.0 \times 10^{11}$ GC/g brain mass (the number of genome copies as determined by a Poly-A-specific PCR assay) or $2.9 \times 10^{11}$ GC/g brain mass (the number of genome copies as determined by a transgene-specific PCR assay). Total dose administered will account for estimated brain size of study subjects based on their age. Total volume of product administered will not exceed 5 mL.

Objectives

Primary Objective:
To evaluate the safety and tolerability of Construct 1 through 24 weeks following a single IC dose administered to pediatric subjects who have severe MPS II
Secondary Objectives:
To evaluate the long-term safety and tolerability of Construct 1
To evaluate the effect of Construct 1 on biomarkers in cerebrospinal fluid (CSF), plasma, and urine
To evaluate the effect of Construct 1 on neurodevelopmental parameters of cognitive, behavioral, and adaptive function
To evaluate vector shedding in CSF, plasma, and urine
Exploratory Objectives:
To evaluate immunogenicity of Construct 1
To explore the effect of Construct 1 on physical changes to the CNS
To explore the effect of Construct 1 on systemic manifestations of disease
To explore the effect of Construct 1 on auditory capacity
To explore the effect of Construct 1 on biomarkers in plasma and urine in subjects who temporarily discontinue IV ERT (ELAPRASE®)
To explore the effect of Construct 1 on quality of life (QOL) and sleep measures.
Study Design and Methodology This is a Phase I/II, first-in-human, multicenter, open-label, single arm dose escalation study of Construct 1. No control group is included. Approximately 6 pediatric subjects who have severe MPS II could be enrolled into 2 dose cohorts, $1.3\times10^{10}$ GC/g brain mass (Dose 1) or $6.5\times10^{10}$ GC/g brain mass (Dose 2) and will receive a single dose of Construct 1 administered by IC injection. Safety will be the primary focus for the initial 24 weeks after treatment (primary study period). Following completion of the primary study period, subjects will continue to be assessed (safety and efficacy) for up to a total of 104 weeks following treatment with Construct 1. At the end of the study, subjects are invited to participate in a long-term follow-up study.

The first 3 eligible subjects will be enrolled into the Dose 1 cohort ($1.3\times10^{10}$ GC/g brain mass). After Construct 1 administration to the first subject, there will be an 8-week observation period for safety. The Internal Safety Committee (ISC) will review the safety data obtained during the first 8 weeks (including data obtained during the Week 8 visit) for this subject, and if there are no safety concerns, the $2^{nd}$ subject may be enrolled. The same process will be used to enroll the $3^{rd}$ subject. If no safety review trigger (SRT) event is observed, all available safety data for the Dose 1 cohort obtained up to and including the Week 8 visit for the $3^{rd}$ subject will be evaluated by the Independent Data Monitoring Committee (IDMC). If the decision is to proceed to the second dose ($6.5\times10^{10}$ GC/g brain mass), the subsequent 2 subjects will follow the same dosing scheme as the initial dose cohort with dosing of each subsequent subject occurring after all safety data obtained during the first 8 weeks (including data obtained during the Week 8 visit) for the last dosed subject have been reviewed. The ISC will review all subject safety data obtained up to and including the Week 2 visit of the $2^{nd}$ subject and may determine that it is safe to proceed with dosing of the $3^{rd}$ subject immediately after this assessment. All available safety data for the Dose 2 cohort will be evaluated by the IDMC after the Week 8 visit for the 3' subject in the Dose 2 cohort.

Potential subjects will be screened up to 35 days prior to dosing to determine eligibility for the study. Those subjects who meet the eligibility criteria will be admitted to the hospital between Day −2 and the morning of Day 1 (according to institutional practice), and baseline assessments will be performed pre-dose. Subjects will receive a single IC dose of Construct 1 on Day 1 and will remain in the hospital for approximately 30-36 hours after dosing for observation. Subsequent assessments in the primary study period (i.e., through Week 24) will be performed weekly through Week 4 and at Weeks 8, 12, 16, 20, and 24. After the primary study period, visits will be at Weeks 28, 32, 40, 48, 52, 56, 64, 78, and 104. The Week 12, 40, and 64 visits may be performed by a home health nurse. The Week 20 and 28 assessments will be limited to evaluation of AEs and concomitant therapies by telephone contact.

All subjects will initially receive immune suppression (IS) in the study based on findings of potential immunogenicity in the nonclinical safety/toxicology study conducted in animals and will include corticosteroids (methylprednisolone 10 mg/kg intravenously [IV] once on Day 1 predose and oral prednisone starting at 0.5 mg/kg/day on Day 2 with gradual tapering and discontinuation by Week 12), tacrolimus (1 mg twice daily [BID] by mouth [PO] Day 2 to Week 24 with target blood level of 4-8 ng/mL and tapering over 8 weeks between Week 24 and 32) and sirolimus (a loading dose of 1 mg/m$^2$ every 4 hours×3 doses on Day −2 and then from Day −1: sirolimus 0.5 mg/m$^2$/day divided in BID dosing with target blood level of 4-8 ng/ml until Week 48). Neurologic assessments and tacrolimus/sirolimus blood level monitoring will be conducted. The doses of sirolimus and tacrolimus will be adjusted to maintain blood levels in the target range.

No IS therapy is planned after Week 48. If IS is required after Week 48 to control a clinically-relevant immune response, the appropriate immunosuppressive regimen will be determined by the principal investigator (PI), in discussion with the Medical Monitor and Sponsor, as clinically indicated.

Efficacy assessments will include neurocognitive function, auditory capacity, brain MRI, liver and spleen size, and measurements of levels of pharmacodynamic (PD) biomarkers in CSF, plasma, and urine. Neurocognitive or adaptive scales performed as part of subjects' standard of care while participating in the trial may also be collected, as determined by the study sponsor after discussing with the site.

Endpoints
Primary Endpoints:
Safety through Week 24: AEs and serious adverse events (SAEs)
Secondary Endpoints:
Safety through Week 104: AE reporting, laboratory evaluations, vital signs, ECGs, physical examinations, and neurologic assessments
Biomarkers in CSF (GAGs, I2S activity), plasma (GAGs, I2S activity), and urine (GAGs)
Neurodevelopmental parameters of cognitive, behavioral, and adaptive function:
Bayley Scales of Infant and Toddler Development, $3^{rd}$ Edition (BSID-III) (Bayley, 2005, Scales of Infant and Toddler Development, 3rd Ed., Springer, New York, NY) or Kaufman Assessment Battery for Children, $2^{nd}$ Edition (KABC-1I) (Kaufman, 2004, Kaufman Assessment Battery for Children, 2nd Ed.)

Vineland Adaptive Behavior Scales, 2nd Edition, Comprehensive Interview Form (VABS-II)(Sparrow et al., 2005, Vineland Adaptive Behavior Scales, 2nd Ed.)

Vector concentration in CSF, plasma, and urine by quantitative polymerase chain reaction (PCR) to Construct 1 deoxyribonucleic acid (DNA)

Exploratory Endpoints:

Immunogenicity measurements
- Neutralizing antibody titers to AAV9 and binding antibody titers to I2S in CSF and serum
- Enzyme-linked immunospot (ELISPOT) assay: T-cell response to AAV9 and I2S
- Flow cytometry: AAV- and I2S-specific regulatory T cells CNS structural abnormalities assessed by magnetic resonance imaging (MRI) of the brain Liver and spleen size assessed by MRI and ultrasound of the abdomen Auditory capacity changes measured by auditory brainstem response (ABR) testing Plasma and urinary GAGs in subjects who temporarily discontinue IV ERT (ELAPRASE®)

PedsQL (Version 4)

Global impression of sleep scale

The total duration of the study may be 104 weeks post-dose with a primary safety evaluation time point of 24 weeks. Screening may take up to 35 days.

Diagnosis and Criteria for Inclusion and Exclusion

To be eligible to participate in this study, a subject must meet all the following inclusion criteria:

1. The subject's legal guardian(s) is(are) willing and able to provide written, signed informed consent after the nature of the study has been explained, and prior to any research-related procedures.
2. Is a male
3. Meets one of the following criteria:
   a. Has a documented diagnosis of MPS II AND is ≥4 months to <5 years of age AND a has a neurocognitive testing score>55 and ≤77 (BSID-III or KABC-II), OR
   b. Has a documented diagnosis of MPS II AND is ≥4 months and <5 years of age AND has a decline of ≥1 standard deviation on sequential neurocognitive testing (BSID-III or KABC-II) and a testing score>55, OR
   c. Has a relative diagnosed with severe MPS 11 who has the same IDS mutation as the subject AND in the opinion of a geneticist has inherited a severe form of MPS II
4. Has sufficient auditory and visual capacity, with or without aids, to complete the required protocol testing, and be compliant with wearing the aid, if applicable, on testing days Subjects who meet any of the following exclusion criteria will not be eligible to participate in the study:

1. Has a contraindication for an IC injection, including any of the following.
   a. Review of baseline MRI testing by the team of neuroradiologists/neurosurgeons participating in study (1 per site) shows a contraindication for an IC injection
   b. History of prior head/neck surgery, which resulted in a contraindication to IC injection, based on review of available information by the team of neuroradiologists/neurosurgeons participating in study
   c. Has any contraindication to computed tomography (CT), contrast agent, or to general anesthesia
   d. Has any contraindication to MRJ or gadolinium
   e. Has estimated glomerular filtration rate (eGFR)<30 mL/min/1.73 m$^2$
2. Has any condition that would contraindicate treatment with prednisone, tacrolimus or sirolimus
3. Has any neurocognitive deficit not attributable to MPS II or diagnosis of a neuropsychiatric condition that may in the opinion of the PI confound interpretation of study results
4. Has any contraindication to lumbar puncture
5. Has a ventricular shunt
6. Has undergone hematopoietic stem cell transplantation (HSCT)
7. Has had prior treatment with an AAV-based gene therapy product
8. Has received idursulfase [ELAPRASE®] via intrathecal (IT) administration
9. Has received idursulfase [ELAPRASE®] IV and experienced a serious hypersensitivity reaction, including anaphylaxis, deemed related to IV idursulfase [ELAPRASE®] administration.
10. Has received any investigational product within 30 days of Day 1 or 5 half-lives before signing of the Informed Consent Form (ICF), whichever is longer
11. Has any history of lymphoma or history of another cancer, other than squamous cell or basal cell carcinoma of the skin, that has not been in full remission for at least 3 months before screening
12. Has a platelet count<100,000 per microliter (µL)
13. Has aminotransferase (ALT) or aspartate aminotransferase (AST)>3×ULN or total bilirubin>1.5×ULN at screening unless the subject has a previously known history of Gilbert's syndrome and a fractionated bilirubin that shows conjugated bilirubin<35% of total bilirubin
14. Uncontrolled hypertension (systolic blood pressure [BP]>180 mmHg, diastolic BP>100 mmHg) despite maximal medical treatment
15. Has a history of human immunodeficiency virus (HIV) or hepatitis B or hepatitis C virus infection, or positive screening tests for hepatitis B surface antigen or hepatitis B core antibody, or hepatitis C or HIV antibodies
16. Is a first-degree family member of a clinical site employee or any other individual involved with the conduct of the study or is a clinical site employee or other individual involved with the conduct of the study
17. Has a clinically significant ECG abnormality that, in the opinion of the PI, would compromise the subject's safety
18. Has a serious or unstable medical or psychological condition that, in the opinion of the PI, would compromise the subject's safety or successful participation in the study or interpretation of study results
19. Has uncontrolled seizures that in opinion of the PI would put the subject at undue risk Exclusion criteria related to immunosuppressive therapy:

20. Has a history of a hypersensitivity reaction to tacrolimus, sirolimus, or prednisone
21. Has a history of a primary immunodeficiency (e.g., common variable immunodeficiency syndrome), splenectomy, or any underlying condition that predisposes the subject to infection
22. Has herpes zoster (VZV), cytomegalovirus (CMV), or Epstein-Barr virus (EBV) infection that has not completely resolved at least 12 weeks prior to screening 23. Has any infection requiring hospitalization or treatment with parenteral anti-infectives not resolved at least 8 weeks prior to Visit 2
24. Has any active infection requiring oral anti-infectives (including antivirals) within 10 days prior to Visit 2
25. Has a history of active tuberculosis (TB) or a positive Quantiferon-TB Gold test during screening
26. Has any live vaccine within 8 weeks prior to signing the ICF
27. Had major surgery within 8 weeks before signing the ICF or major surgery planned during the study period
28. Anticipate the need for adenoidectomy or tonsillectomy within 6 months of enrollment
29. Has an absolute neutrophil count<$1.3 \times 10^3/\mu L$
30. Has any condition or laboratory abnormality that the PI believes would not be appropriate for immunosuppressive therapy Statistical Methods All data will be presented in subject data listings. Categorical variables will be summarized using frequencies and percentages, and continuous variables will be summarized using descriptive statistics (n, mean, standard deviation, median, minimum, and maximum). Graphical displays will be presented as appropriate. Safety and PD endpoints will be reported by dose group and may also be reported for the 2 dose groups combined.

Sample Size and Power Calculation: No formal calculation was performed to determine sample size.

6.5.2. Abbreviations and Terms

TABLE 8

Abbreviations and Specialist Terms

| Abbreviation | Term |
| --- | --- |
| AAV | Adeno-associated virus |
| AAV9 | AAV vector of serotype 9 |
| AE(s) | Adverse event(s) |
| ALP | Alkaline phosphatase |
| ALT | Alanine aminotransferase |
| AST | Aspartate aminotransferase |
| BBB | Blood-brain barrier |
| BID | Twice a day |
| BP | Blood pressure |
| BSID | Bayley Scales of Infant and Toddler Development |
| BSL | Biosafety level |
| CB7 | Hybrid C4 and CB (chicken beta actin promoter) |
| CBC | Complete blood count |
| cDNA | Consensus DNA |
| CFR | Code of Federal Regulations |
| CI | Confidence interval |
| CMV | Cytomegalovirus |
| CNS | Central nervous system |
| CoA | Certificate of analysis |
| CRF | Case Report Form |
| CSF | Cerebrospinal fluid |
| CT | Computed tomography |
| CTA | Clinical Trial Agreement |
| CTCAE | Common Terminology Criteria for Adverse Events |
| CZ | Crystal Zenith ® |
| DLT(s) | Dose-limiting toxicity(ies) |
| DNA | Deoxyribonucleic acid |
| DRG | Dorsal root ganglia |
| EBV | Epstein-Barr virus |
| ECG | Electrocardiogram |
| EDC | Electronic Data Capture |
| eGFR | Estimated glomerular filtration rate |
| ELISA | Enzyme-Linked Immunosorbent Assay |
| ELISPOT | Enzyme-linked immunospot |
| EOS | End of Study |
| ERT | Enzyme replacement therapy |
| ET | Early Termination |
| FDA | US Food and Drug Administration |

TABLE 8-continued

Abbreviations and Specialist Terms

| Abbreviation | Term |
| --- | --- |
| GAG(s) | Glycosaminoglycan(s) |
| GAN | Giant Axonal Neuropathy |
| GC | Genome copies |
| GCP | Good Clinical Practice |
| GLP | Good Laboratory Practice |
| GM3 | Monosialodihexosylganglioside |
| HDL | High-density lipoprotein |
| Hep | hepatitis |
| Hex | Hexosaminidase |
| hIDS | Human iduronate-2-sulfatase |
| HIPAA | Health Insurance Portability and Accounting Act |
| HIV | Human immunodeficiency virus |
| HSCT | Hematopoietic stem cell transplantation |
| I2S | Iduronate-2-sulfatase |
| IB | Investigator's Brochure |
| IC | Intracisternal(ly) |
| ICF | Informed Consent Form |
| ICH | International Council for Harmonisation |
| ICV | Intracerebroventricular |
| IDMC | Independent Data Monitoring Committee |
| IDS | Iduronate-2-sulfatase gene |
| IEC(s) | Independent Ethics Committee(s) |
| IgG | Immunoglobulin G |
| IND | Investigation New Drug |
| IP | Investigational product |
| IQ | Intelligence quotient |
| IRB | Institutional Review Board |
| IS | immune suppression/immunosuppression |
| IT | Intrathecal(ly) |
| ITR(s) | Inverted terminal repeat(s) |
| IV | Intravenous(ly) |
| KABC | Kaufman Assessment Battery for Children |
| KIDS | Kinder Infant Development Scale |
| KSPD | Kyoto Scale of Psychological Development |
| LDL | Low-density lipoprotein |
| LIMP2 | Lysosomal membrane protein |
| MED | Minimum effective dose |
| MedDRA | Medical Dictionary of Regulatory Activities |
| MMF | Mycophenolate mofetil |
| MPS I | Mucopolysaccharidosis type I |
| MPS II | Mucopolysaccharidosis type II |
| MPS III | Sanfilippo syndrome |
| MPS VII | Mucopolysaccharidosis type VII |
| MRI | Magnetic resonance imaging |
| MTD | Maximum tolerated dose |
| mTORC1 | Mammalian/mechanistic target of rapamycin complex 1 |
| N | Number in sample |
| NAB | Neutralizing antibody |
| NCI | National Cancer Institute |
| NHP(s) | Non-human primate(s) |
| NIH | National Institutes of Health |
| NOAEL | No-observable-adverse-effect level |
| PBMC(s) | Peripheral blood mononuclear cell(s) |
| PCR | Polymerase chain reaction |
| PD | Pharmacodynamic(s) |
| PgP | P-glycoprotein |
| PI | Principal Investigator |
| PML | Progressive multifocal leukoencephalopathy |
| PO | By mouth/orally |
| PT | Prothrombin time or Preferred Term |
| PTT | Partial thromboplastin time |
| PVAN | Polyoma virus-associated nephropathy |
| QD | Daily |
| qPCR | Quantitative polymerase chain reaction |
| RBC | Red blood cell |
| RG1 | Risk Group 1 |
| Construct 1 | Recombinant adeno-associated virus serotype 9 capsid containing human iduronate-2-sulfatase expression cassette |
| SAE(s) | Serious adverse event(s) |
| SAP | Statistical analysis plan |
| SDV | Source document verification |
| SMA | Spinal Muscular Atrophy |
| SOC | System Organ Class |
| SRT | Safety review trigger |

TABLE 8-continued

Abbreviations and Specialist Terms

| Abbreviation | Term |
| --- | --- |
| TB | Tuberculosis |
| TEAE(s) | Treatment-emergent adverse event(s) |
| Treg | Regulatory T cell |
| ULN | Upper limit of normal |
| U.S. | United States |
| US | Ultrasound |
| USMs | Urgent safety measures |
| VZV | Varicella zoster virus |
| WBC | White blood cell (count) |
| WHO | World Health Organization |

6.2.3. Investigational Plan

Endpoints

Primary Endpoints

Safety through Week 24: AEs and SAEs

Secondary Endpoints

Safety through Week 104: AE reporting, laboratory evaluations, vital signs, electrocardiograms (ECGs), physical examinations, and neurologic assessments Biomarkers in CSF (GAGs, I2S activity), plasma (GAGs, I2S activity), and urine (GAGs)

Neurodevelopmental parameters of cognitive, behavioral, and adaptive function:
  Bayley Scales of Infant and Toddler Development, 3rd Edition (BSID-III) (Bayley, 2005, Scales of Infant and Toddler Development, 3rd Ed.) or Kaufman Assessment Battery for Children, 2nd Edition (KABC-II) (Kaufman, 2004, Kaufman Assessment Battery for Children, 2nd Ed.)
  Vineland Adaptive Behavior Scales, 2nd Edition, Comprehensive Interview Form (VABS-II)(Sparrow et al., 2005, Vineland Adaptive Behavior Scales, 2nd Ed.)

Vector concentration in CSF, plasma, and urine by quantitative polymerase chain reaction (PCR) to Construct 1 DNA Exploratory Endpoints Immunogenicity measurements
  Neutralizing antibody titers to AAV9 and binding antibody titers to I2S in CSF and serum
  Enzyme-linked immunospot (ELISPOT) assay: T-cell response to AAV9 and I2S
  Flow cytometry: AAV- and I2S-specific regulatory T cells CNS structural abnormalities assessed by MRI of the brain Liver and spleen size assessed by MRI of the abdomen Auditory capacity changes measured by auditory brainstem response (ABR) testing Plasma and urinary GAGss in subjects who temporarily discontinue IV ERT (ELAPRASE®)

PedsQL (Version 4)

Global impression of sleep scale

Study Design

This is a Phase I/II, first-in-human, multicenter, open-label, single arm dose escalation study of Construct 1. Approximately 6 pediatric subjects with severe MPS II could be enrolled into 2 dose cohorts, $1.3 \times 10^{10}$ GC/g brain mass (Dose 1) or $6.5 \cdot 10^{10}$ GC/g brain mass (Dose 2), and will receive a single dose of Construct 1 administered by IC injection. Safety will be the primary focus for the initial 24 weeks after treatment (primary study period). Following completion of the primary study period, subjects will continue to be assessed (safety and efficacy) for up to a total of 104 weeks following treatment with Construct 1. At the end of the study, all subjects will be invited to participate in a long-term follow-up study.

Potential subjects will be screened up to 35 days prior to dosing to determine eligibility for the study. Those subjects who meet the eligibility criteria will be admitted to the hospital between Day −2 and the morning of Day 1 (according to institutional practice), and baseline assessments will be performed pre-dose. Subjects will receive a single IC dose of Construct 1 on Day 1 and will remain in the hospital for approximately 30 to 36 hours after dosing for observation. Subsequent assessments in the primary study period (i.e., through Week 24) will be performed weekly through Week 4 and at Weeks 8, 12, 16, 20, and 24. After the primary study period, visits will be at Weeks 28, 32, 40, 48, 52, 56, 64, 78, and 104. The Week 12, 40, and 64 visits may be performed by a home health nurse. The Week 20 and 28 assessments will be limited to evaluation of AEs and concomitant therapies by telephone contact.

All subjects will initially receive IS in the study based on findings in the nonclinical studies. IS therapy will include corticosteroids (methylprednisolone 10 mg/kg IV once on Day 1 predose and oral prednisone starting at 0.5 mg/kg/day on Day 2 with gradual tapering and discontinuation by Week 12), tacrolimus (1 mg twice daily [BID] by mouth [PO] Day 2 to Week 24 with target blood level of 4-8 ng/mL and tapering over 8 weeks between Week 24 and 32), and sirolimus (a loading dose of 1 mg/m² every 4 hours×3 doses on Day −2 and then from Day −1: sirolimus 0.5 mg/m²/day divided in twice a day dosing with target blood level of 4-8 ng/ml until Week 48). Neurologic assessments and tacrolimus/sirolimus blood level monitoring will be conducted. The doses of sirolimus and tacrolimus will be adjusted to maintain blood levels in the target range.

No IS therapy is planned after Week 48. If IS is required after Week 48 to control a clinically relevant immune response, the appropriate immunosuppressive regimen will be determined by the principal investigator (PI), in discussion with the Medical Monitor and Sponsor, as clinically indicated.

The safety and tolerability of Construct 1 will be monitored through assessment of AEs and serious adverse events (SAEs), chemistry, hematology, urinalysis, markers of CSF inflammation, immunogenicity, vector shedding (vector concentration), vital signs, electrocardiograms (ECGs), and physical examinations including neurological assessments.

Efficacy assessments will include neurocognitive and adaptive function, auditory capacity, brain MRI, liver and spleen size, measurements of levels of PD biomarkers in CSF, plasma, and urine.

6.5.4. Subject Population and Selection

Selection of Study Population

Approximately 6 pediatric subjects ages≥4 months to <5 years who have documented neurocognitive deficits due to MPS II or who have a genotype and family history consistent with an inherited form of severe MPS II will be treated with investigational product (IP).

Inclusion Criteria

To be eligible to participate in this study, a subject must meet all the following criteria:
  1. The subject's legal guardian is (are) willing and able to provide written, signed informed consent after the nature of the study has been explained, and prior to any research-related procedures.

2. Is a male 3. Meets one of the following criteria:
   a. Has a documented diagnosis of MPS II AND is ≥4 months to <5 years of age AND a has a neurocognitive testing score>55 and ≤77 (BSID-III or KABC-II), OR
   b. Has a documented diagnosis of MPS II AND is ≥4 months and <5 years of age AND has a decline of ≥1 standard deviation on sequential neurocognitive testing (BSID-III or KABC-II) and a testing score>55, OR
   c. Has relative diagnosed with severe MPS II carrying the same/DS mutation as the subject AND in the opinion of a geneticist has inherited a severe form of MPS II
4. Has sufficient auditory and visual capacity, with or without aids, to complete the required protocol testing, and be compliant with wearing the aid, if applicable, on testing days.

Exclusion Criteria

A subject who meets any of the following exclusion criteria will not be eligible to participate in the study:

1. Has a contraindication for an IC injection, including any of the following:
   a. Review of baseline MRI testing by the team of neuroradiologists/neurosurgeons participating in study (1 per site) shows a contraindication for an IC injection
   b. History of prior head/neck surgery, which resulted in a contraindication to IC injection, based on review of available information by the team of neuroradiologists/neurosurgeons participating in study
   c. Has any contraindication to computed tomography (CT), contrast agent or general anesthesia
   d. Has any contraindication to MRI or gadolinium
   e. Has estimated glomerular filtration rate (eGFR)<30 mL/min/1.73 m²
2. Has any condition that would contraindicate treatment with prednisone, tacrolimus, or sirolimus.
3. Has any neurocognitive deficit not attributable to MPS II or diagnosis of a neuropsychiatric condition that may in the opinion of the PI confound interpretation of study results.
4. Has any contraindication to lumbar puncture
5. Has a ventricular shunt
6. Has undergone hematopoietic stem cell transplantation (HSCT).
7. Has had prior treatment with an AAV-based gene therapy product.
8. Has received idursulfase via intrathecal (IT) administration
9. Has received IV idursulfase [ELAPRASE®] and experienced a serious hypersensitivity reaction, including anaphylaxis, deemed related to IV idursulfase [ELAPRASE®] administration.
10. Has received any investigational product within 30 days of Day 1 or 5 half-lives before signing of the Informed Consent Form (ICF), whichever is longer
11. Has any history of lymphoma or history of another cancer, other than squamous cell or basal cell carcinoma of the skin, that has not been in full remission for at least 3 months before screening.
12. Platelet count<100,000 per microliter (µL)
13. Has aminotransferase (ALT) or aspartate aminotransferase (AST)>3×ULN or total bilirubin>1.5×/ULN at screening unless the subject has a previously known history of Gilbert's syndrome and a fractionated bilirubin that shows conjugated bilirubin<35% of total bilirubin.
14. Uncontrolled hypertension (systolic blood pressure [BP]>180 mmHg, diastolic BP>100 mmHg) despite maximal medical treatment.
15. Has a history of human immunodeficiency virus (HIV) or hepatitis B or hepatitis C virus infection, or positive screening tests for hepatitis B surface antigen or hepatitis B core antibody, or hepatitis C or HIV antibodies.
16. Is a first-degree family member of a clinical site employee or any other individual involved with the conduct of the study or is a clinical site employee or other individual involved with the conduct of the study.
17. Has a clinically significant ECG abnormality that, in the opinion of the PI, would compromise the subject's safety.
18. Has a serious or unstable medical or psychological condition that, in the opinion of the PI, would compromise the subject's safety or successful participation in the study or interpretation of study results.
19. Has uncontrolled seizures that in opinion of the PI would put the subject at undue risk.

Exclusion Criteria Related to Immunosuppressive Therapy:

20. A history of a hypersensitivity reaction to tacrolimus, sirolimus, or prednisone
21. A history of a primary immunodeficiency (e.g., common variable immunodeficiency syndrome), splenectomy, or any underlying condition that predisposes the subject to infection
22. Herpes zoster (VZV), cytomegalovirus (CMV), or Epstein-Barr virus (EBV) infection that has not completely resolved at least 12 weeks prior to screening
23. Any infection requiring hospitalization or treatment with parenteral anti-infectives not resolved at least 8 weeks prior to Visit 2
24. Any active infection requiring oral anti-infectives (including antivirals) within 10 days prior to Visit 2
25. History of active tuberculosis (TB) or a positive Quantiferon-TB Gold test during screening
26. Any live vaccine within 8 weeks prior to signing the ICF
27. Major surgery within 8 weeks before signing the ICF or major surgery planned during the study period
28. Anticipate the need for adenoidectomy or tonsillectomy within 6 months of enrollment
29. Absolute neutrophil count<1.3×10³/µL
30. Any condition or laboratory abnormality that the PI believes would not be appropriate for immunosuppressive therapy 6.5.5. Treatments Treatments Administered The investigational product (IP), Construct 1 (see FIG. 5), will be given as a single dose IC administration. Two dose levels: $1.3 \times 10^{10}$ GC/g brain mass (Dose 1) or $6.5 \times 10^{10}$ GC/g brain mass (Dose 2). Total dose administered (total GC) will be adjusted to account for differences in brain size by age. Total volume of product administered will not exceed 5 mL.

No reference therapy will be administered during this study. IS therapy will be given in addition to IP, as described below.

Investigational Product

Construct 1 is a non-replicating recombinant AAV of serotype 9 capsid containing an hIDS expression cassette.

| Product | Construct 1 |
|---|---|
| Gene | hIDS |
| Control Elements: | CB7 promoter, chicken beta actin intron, rabbit beta-globin polyadenylation signal |
| AAV | 9 |

AAV = adeno-associated virus;
CB = chicken beta-actin;
hIDS = human iduronate-2-sulfatase Construct 1 is a non-replicating recombinant AAV9 vector that allows for efficient expression of the human iduronate-2-sulfatase (hIDS) product in the central nervous system (CNS) following intrathecal (IT) administration. The vector genome contains an hIDS expression cassette flanked by AAV2 inverted terminal repeats (ITRs). Expression from the cassette is driven by a CB7 promoter, a hybrid between a cytomegalovirus (CMV) immediate-early enhancer and the chicken β-actin promoter. Transcription from this promoter is enhanced by the presence of the chicken β-actin intron (CI). The polyadenylation signal for the expression cassette is from the rabbit β-globin (RBG) gene. A schematic representation of Construct 1 is illustrated in FIG. 5.

The final IP is supplied as a frozen solution of the AAV vector active ingredient (AAV9.CB7.hIDS) in modified Elliott's B® solution with 0.001% Pluronic® F68, filled into 2-mL in CRYSTAL ZENITH® (CZ) vials, and sealed with a latex-free rubber stopper and aluminum flip-off seal. In some embodiments, the AAV vector active ingredient (AAV9.CB7.hIDS) is supplied in a solution containing 8.77 g/L sodium chloride, 0.244 g/L magnesium chloride, 0.0278 g/L sodium phosphate monobasic monohydrate, 0.114 g/L sodium phosphate dibasic anhydrous, 0.224 g/L potassium chloride, 0.206 g/L calcium chloride, 0.793 g/L dextrose, 0.001% poloxamer 188, pH 7.26. Vials should be stored at ≤−60° C. The concentration (in GC/mL) of each IP lot will be reported in the Certificate of Analysis (CoA). Detailed dosing instructions, based on the product concentration, will be provided in the Administration Manual.

Immunosuppressive Therapy

Corticosteroids

In the morning of vector administration (Day 1 predose), subjects will receive methylprednisolone 10 mg/kg IV (maximum of 500 mg) over at least 30 minutes. The methylprednisolone should be administered before the lumbar puncture and IC injection of IP. Premedication with acetaminophen and an antihistamine is optional and at the discretion of the investigator.

On Day 2, oral prednisone will be started with the goal to discontinue prednisone by Week 12. The dose of prednisone will be as follows:

Day 2 to the end of Week 2: 0.5 mg/kg/day
Week 3 and 4: 0.35 mg/kg/day
Week 5-8: 0.2 mg/kg/day
Week 9-12: 0.1 mg/kg Prednisone will be discontinued after Week 12. The exact dose of prednisone can be adjusted to the next higher clinically practical dose.

Sirolimus 2 days prior to vector administration (Day −2): a loading dose of sirolimus 1 mg/m² every 4 hours×3 doses will be administered From Day −1: sirolimus 0.5 mg/m²/day divided in twice a day dosing with target blood level of 4-8 ng/ml Sirolimus will be discontinued after the Week 48 visit.

Tacrolimus

Tacrolimus will be started on Day 2 (the day following IP administration) at a dose of 1 mg twice daily and adjusted to achieve a blood level 4-8 ng/mL for 24 Weeks.

Starting at Week 24 visit, tacrolimus will be tapered off over 8 weeks. At Week 24 the dose will be decreased by approximately 50%. At Week 28 the dose will be further decreased by approximately 50%. Tacrolimus will be discontinued at Week 32.

Tacrolimus and sirolimus blood level monitoring will be conducted. Dosing adjustments are discussed in the disclosure.

Method of Assigning Subjects to Treatment

Eligible subjects will be enrolled and assigned sequentially to a dose cohort with the initial 3 subjects assigned to get $1.3 \times 10^{10}$ GC/g brain mass; the subsequent 3 subjects will be assigned to get $6.5 \times 10^{10}$ GC/g brain mass pending review of safety data by the IDMC.

Dosing Considerations

Investigational Product

A description of the plan to sequentially dose subjects, including review of safety data between individual subjects and after each cohort has been dosed at any dose level is disclosed in the disclosure (e.g., [00237] to [00265]; [00175] to [00186]).

Immunosuppressive Therapy

Prednisone dosing will start at 0.5 mg/kg/day and will be gradually tapered off by the Week 12 visit.

Tacrolimus dose adjustments will be made to maintain whole blood trough concentrations within 4 to 8 ng/mL for the first 24 Weeks. At Week 24 the dose will be decreased by approximately 50%. At Week 28 the dose will be further decreased by approximately 50%. Tacrolimus will be discontinued at Week 32. Sirolimus dose adjustments will be made to maintain whole blood trough concentrations within 4 to 8 ng/mL. In most subjects, dose adjustments can be based on the equation: new dose=current dose×(target concentration/current concentration). Subjects should continue on the new maintenance dose for at least 7 to 14 days before further dosage adjustment with concentration monitoring.

The following medications and procedures are prohibited:

No IT ERT is allowed within 6 months of screening.

Any investigational product within the 30 days or 5 half-lives, whichever is longer, prior to signing the ICF or at any time during the study (through Week 104)

Live vaccines should be avoided while on sirolimus and/or tacrolimus

Strong inhibitors of CYP3A4 and/or P-glycoprotein (PgP) (such as ketoconazole, voriconazole, itraconazole, posaconazole, erythromycin, telithromycin or clarithromycin) or strong inducers of CYP3A4 and or Pgp (such as rifampin or rifabutin) should be avoided while on sirolimus and/or tacrolimus Grapefruit juice inhibits CYP3A-enzymes resulting in increased tacrolimus and sirolimus whole blood trough concentrations. Subjects should avoid eating grapefruit or drinking grapefruit juice with tacrolimus and/or sirolimus.

Permitted Medications and Procedures

Subjects will be permitted to remain on a stable regimen of IV ERT as well as any supportive measures (e.g., physical therapy). According to local hospital standard of care, subjects will be permitted to receive medication to prevent claustrophobia during MRI and receive general anesthesia for lumbar puncture, MRI, and neuroconduction studies (ABRs or sensory evoked potentials).

Medications other than that described above, which are considered necessary for the subject's safety and wellbeing (e.g., for hypertension), may be given at the discretion of the Investigator in accordance with local standard of care and recorded in the appropriate sections of the CRF.

6.6 Example 6: A Phase I/II Multicenter, Open-Label Study to Evaluate the Safety, Tolerability, and Pharmacodynamics of Construct 1 in Pediatric Subjects with MPS II (Hunter Syndrome)

As described above, Construct 1 is AAV9.CB7.hIDS (recombinant adeno-associated virus serotype 9 capsid containing human iduronate-2-sulfatase expression cassette). See FIG. 5, and Example 5.

Construct 1 will be delivered as a single intracisternal (IC) or intracerebroventricular (ICV) dose.

Two dose levels will be evaluated, $1.3\times10^{10}$ genome copies (GC)/g brain mass (Dose 1) and $6.5\times10^{10}$ GC/g brain mass (Dose 2). Total dose administered will account for estimated brain mass of study subjects based on their screening magnetic resonance imaging (MRI). The total volume of product administered will not exceed 10% of the total CSF volume (estimated to be ~50 mL in infant brain and ~150 mL in adult brain).

6.6.1. Objectives:
Primary Objective
To evaluate the safety and tolerability of Construct 1 through 24 weeks following a single IC, or ICV if IC is contraindicated, dose administered to pediatric subjects who have severe MPS II
Secondary Objectives:
To evaluate the long-term safety and tolerability of Construct 1
To evaluate the effect of Construct 1 on biomarkers in cerebrospinal fluid (CSF), plasma, and urine
To evaluate the effect of Construct 1 on neurodevelopmental parameters of cognitive, behavioral, and adaptive function
To evaluate vector shedding in CSF, serum, and urine
Exploratory Objectives:
To evaluate immunogenicity of Construct 1
To explore the effect of Construct 1 on CNS imaging
To explore the effect of Construct 1 on systemic manifestations of disease
To explore the effect of Construct 1 on auditory capacity
To explore the effect of Construct 1 on biomarkers in plasma and urine in subjects who temporarily discontinue intravenous (IV) ERT (ELAPRASE®)
To explore the effect of Construct 1 on quality of life (QOL)
To explore the effect of Construct 1 on sleep measures
To explore the effect of Construct 1 on clinician reported outcome
To explore the effect of Construct I on caregiver reported outcome 6.6.2. Study Design and Methodology
This is a Phase I/II, first-in-human, multicenter, open-label, single arm dose escalation study of Construct 1. No control group is included. Approximately 6 pediatric subjects who have severe MPS II could be enrolled into 2 dose cohorts, $1.3\times10^{10}$ GC/g brain mass (Dose 1) or $6.5\times10^{10}$ GC/g brain mass (Dose 2) and will receive a single dose of Construct 1 administered by IC or ICV injection. Safety will be the primary focus for the initial 24 weeks after treatment (primary study period). Following completion of the primary study period, subjects will continue to be assessed (safety and efficacy) for up to a total of 104 weeks following treatment with Construct 1. At the end of the study, subjects will be invited to participate in a long-term follow-up study.

The first 3 eligible subjects will be enrolled into the Dose 1 cohort ($1.3\times10^{10}$ GC/g brain mass). After Construct 1 administration to the first subject, there will be an 8-week observation period for safety. The Internal Safety Committee (ISC) will review the safety data obtained during the first 8 weeks of the study according to the ISC Charter (including data obtained during the Week 8 visit) for this subject, and if there are no safety concerns, the 2nd subject may be enrolled. The same process will be used to enroll the 3rd subject. Informed consent and screening activities for the next subject may proceed during the observation period for the preceding subject.

If no safety review trigger (SRT) event is observed, all available safety data for the Dose 1 cohort obtained up to and including the Week 8 visit for the 3rd subject will be evaluated by the Independent Data Monitoring Committee (IDMC). If the decision is to proceed to the second dose cohort ($6.5\times10^{10}$ GC/g brain mass), the subsequent 2 subjects will follow the same dosing scheme as the initial dose cohort. The ISC will review all subject safety data obtained up to and including the Week 2 visit of the 2nd subject in the Dose 2 cohort and may determine that it is safe to proceed with dosing of the 3rd subject immediately after this assessment. All available safety data for the Dose 2 cohort will be evaluated by the IDMC after the Week 8 visit for the 3rd subject in the Dose 2 cohort. With approval of the IDMC, additional subjects may be dosed in a Dose 2 Expanded Cohort as long as study drug is available, and there is Sponsor approval and no safety event that warrants suspension of enrollment as per either the ISC or the IDMC. Each subject in the Expanded Cohort will be dosed in a staggered fashion at intervals of at least 2 weeks.

At any given IDMC meeting, whether planned at the conclusion of a dose cohort or called for by an SRT, the IDMC may recommend stopping the trial, dose additional subjects at the current dose, proceed to the next dose cohort, or proceed at a lower dose. Once 8 weeks of data are available from the last Dose 2 cohort subject, and if none of the Dose 2 cohort subjects had an SRT event, then enrollment in the study will be considered completed: enrollment into the Expanded Cohort may continue as stipulated above. Once the last subject enrolled in the Expanded Cohort completes the Week 2 visit, all safety data for the Expanded Cohort including data from the last subject's Week 2 visit will be evaluated by the IDMC.

If any event meets the criteria of a Stopping Rule, dosing of any new subjects will be suspended until a complete review of all safety data by REGENXBIO and the external IDMC has been performed.

Potential subjects will be screened up to 35 days prior to dosing to determine eligibility for the study; screening assessments performed after signing the Informed Consent Form (ICF) but outside of this window may be acceptable as determined by the principal investigator and approved by the Medical Monitor. Assessments performed outside the screening window will be repeated as deemed necessary by the Medical Monitor. Subjects may be rescreened for the study one time if initially failing to enroll; Sponsor approval to rescreen the subject will be required. Rescreening can occur after at least 3 months have elapsed from the time of the subject's initial screen failure.

Those subjects who meet the eligibility criteria will be admitted to the hospital between Day −2 and the morning of Day 1 (according to institutional practice), and baseline assessments will be performed pre-dose. Subjects will receive a single IC or ICV dose of Construct 1 on Day 1 and will remain in the hospital overnight and for approximately 1-2 days after dosing for observation. Subjects will be discharged after the principal investigator concludes that prolongation of hospitalization beyond two overnight stays is not necessary. Subsequent assessments in the primary study period (i.e., through Week 24) will be performed weekly through Week 4 and at Weeks 8, 12, 16, 20, and 24. After the primary study period, visits will be at Weeks 28, 32, 40, 48, 52, 56, 60, 64, 78, and 104. The Week 64 visit will be performed only for subjects who discontinue IV ERT. The Week 20 and 28 assessments will be limited to evaluation of adverse events (AEs) and concomitant therapies by telephone contact.

All subjects will initially receive immune suppression (IS) in the study to minimize the risk of any immune mediated reaction against tissues expressing the transgene as well as minimize any risk associated with the formation or increase of antibodies to IDS which may decrease efficacy. The IS regimen will include corticosteroids (methylprednisolone 10 mg/kg IV once on Day 1 predose and oral prednisone starting at 0.5 mg/kg/day on Day 2 with gradual tapering and discontinuation by Week 12), tacrolimus (0.05 mg/kg twice daily [BID] by mouth [PO] Day 2 to Week 24 with dose adjustments made to obtain a target blood level of 2-4 ng/ml and tapering over 8 weeks between Week 24 and 32) and sirolimus (a loading dose of 1 mg/m$^2$ every 4 hours×3 doses on Day −2 and then from Day −1: sirolimus 0.5 mg/m$^2$/day divided in BID dosing with target blood level of 1-3 ng/ml until Week 48). Neurologic assessments and tacrolimus/sirolimus blood level monitoring will be conducted. The doses of sirolimus and tacrolimus will be adjusted to maintain blood levels in the target range.

No IS therapy is planned after Week 48. If IS were required after Week 48 to control a clinically-relevant immune response, the appropriate immunosuppressive regimen will be determined by the principal investigator (PI), in discussion with the Medical Monitor and Sponsor, as clinically indicated.

Given the histopathological findings in the dorsal root ganglia and associated axonopathy observed in the nonclinical safety/toxicology studies and the potential safety risks with the IC administration procedure, close neurological monitoring, including focused neurological assessments and somatosensory evoked potential (SSEP) testing will be employed.

Since animal data suggest that there may be systemic benefits of IC and ICV Construct 1 administration, subjects who are on IV idursulfase (ELAPRASE®) may be offered the option to discontinue ERT after the Week 52 visit. The decision to discontinue ERT will be at the clinical judgement of the PI and as agreed with the study sponsor. Additional information that may be useful for the decision to stop ERT are trough measurements (based on ERT dosing) of plasma I2S and plasma and urine GAGs up to the Week 52 visit, and measurement of the liver and spleen size by ultrasound. The Week 52, 56, 60, 64 and 78 visits will include additional monitoring of the subject's plasma I2S and plasma and urine GAGs levels in subjects who elect to discontinue ERT. Subjects who discontinue IV ERT will have an additional abdominal ultrasound at Week 64 to perform measurement of the liver and spleen size. IV ERT will be restarted if any of following criteria are met: increase in urinary GAGs levels 2 times above the level measured at the Week 52 visit, or an increase of liver diameter>20% above the Week 52 value, or any change in other safety parameters deemed by the internal safety committee and/or the IDMC to warrant a restart of IV ERT. However, subjects may restart ERT at any time, if deemed necessary by the PI.

The safety and tolerability of Construct 1 will be monitored through assessment of AEs and serious adverse events (SAEs), chemistry, hematology, urinalysis, markers of CSF inflammation, immunogenicity, vector shedding (vector concentration), vital signs, electrocardiograms (ECGs), SSEP testing, and physical examinations including neurological assessments. Serial PCR (polymerase chain reaction) for detection of circulating viral genomes (EBV and CMV) will also be performed while subjects are receiving IS.

Efficacy assessments will include measurements of levels of pharmacodynamic (PD) biomarkers (GAGs and I2S in CSF and plasma, leukocyte I2S enzyme activity, and GAGs in urine), as well as on neurocognitive function, auditory capacity, brain MRI, liver and spleen size, and cardiac evaluation by echocardiogram. Neurocognitive or adaptive assessments performed as part of subjects' standard of care while participating in the trial may also be collected, as determined by the study sponsor after discussing with the site.

6.6.3. Endpoints
Primary Endpoints:
Safety through Week 24: AEs and SAEs
Secondary Endpoints:
Safety through Week 104: AE reporting, laboratory evaluations, vital signs, ECGs, physical examinations, and neurologic assessments
Biomarkers in CSF (GAGs, I2S), plasma (GAGs, I2S), and urine (GAGs)
Neurodevelopmental parameters of cognitive, behavioral, and adaptive function:
  Bayley Scales of Infant and Toddler Development, 3rd Edition (BSID-III) (Bayley, 2005, Scales of Infant and Toddler Development, 3rd Ed.) or Kaufman Assessment Battery for Children, 2nd Edition (KABC-II) (Kaufman, 2004, Kaufman Assessment Battery for Children, 2nd Ed.)
  Vineland Adaptive Behavior Scales, 2nd Edition, Expanded Interview Form (VABS-II) (Sparrow et al., 2005, Vineland Adaptive Behavior Scales, 2nd Ed.)
Vector concentration in CSF, serum, and urine by quantitative polymerase chain reaction (PCR) to Construct 1 deoxyribonucleic acid (DNA)
Exploratory Endpoints:
Immunogenicity Measurements
  Neutralizing antibody titers to AAV9 and binding antibody titers to I2S in CSF and serum
  Enzyme-linked immunospot (ELISPOT) assay: T-cell response to AAV9 and I2S
  Flow cytometry: AAV- and I2S-specific regulatory T cells
CNS structural abnormalities assessed by MRI of the brain
Liver and spleen size assessed by ultrasound of the abdomen
Cardiac evaluation by echocardiogram for valvular disease and left ventricular mass index
Auditory capacity changes measured by auditory brainstem response (ABR) testing or behavioral audiometry and otoacoustic emissions testing Plasma and urinary GAGs in subjects who temporarily discontinue IV ERT (ELAPRASE@)

PedsQL

Sleep assessment (Ferreira et al., 2009, Sleep Medicine; 10(4):457-463)

Clinical Assessment of Disease

Caregiver Assessment of Disease

Activities of Daily Living (Tanjuakio et al. 2015, Mol Genet Metab, 114(2):161-169; Kato et al., 2007, Brain Dev, 29(5): 298-305)

Burden of Illness

6.6.4. Number of Subjects Planned and Study Duration

Up to 12 subjects will be enrolled.

3 subjects in Dose 1 cohort 3 subjects in Dose 2 cohort

Up to 6 subjects in Dose 2 Expanded Cohort

The IDMC may recommend adding additional subjects.

The total duration of the study will be 104 weeks post-dose with a primary safety evaluation time point of 24 weeks. Screening may take up to 35 days.

6.6.5. Diagnosis and Criteria for Inclusion and Exclusion:

The following information about the affected relative will be collected, if available, after relative informed consent has been obtained:

Demographics (age, sex)

Medical and surgical histories (e.g., cardiac disease, carpal tunnel syndrome, hip dysplasia or subluxation, etc.)

Age at diagnosis of severe MPS II and how diagnosis was made

Genotyping results

Results of neurodevelopmental testing, including cognition, speech and language, fine motor and gross motor (if available and diagnosis of severe MPS II was done through neurodevelopmental testing)

Results of brain MRI

Treatment for MPS II, including ERT or HSCT

Current concomitant medications

Subjects may be rescreened for the study one time if initially failing to enroll; Sponsor approval to rescreen the subject will be required. Rescreening can occur after at least 3 months have elapsed from the time of the subject's initial screen failure. Participants who are rescreened are required to sign a new ICF. All screening procedures will be repeated, with the exception of MRI, for which retesting will be decided by the neuroradiologist/neurosurgeon.

To be eligible to participate in this study, a subject must meet all the following inclusion criteria:

1. The subject's legal guardian(s) is (are) willing and able to provide written, signed informed consent after the nature of the study has been explained, and prior to any research-related procedures.
2. Is a male≥4 months to <5 years of age
3. Meets any of the following criteria:
   a. Has a documented diagnosis of MPS II AND has a neurocognitive testing score≤77 (BSID-III or KABC-II), OR
   b. Has a documented diagnosis of MPS II AND has a decline of ≥1 standard deviation on serial neurocognitive testing administered between 3 to 36 months apart (BSID-III or KABC-II), OR
   c. Has a relative clinically diagnosed with severe MPS II who has the same IDS mutation as the subject AND the subject in the opinion of a geneticist has inherited a severe form of MPS II, OR
   d. Has documented mutation(s) in IDS that in the opinion of a geneticist is always known to result in a neuronopathic phenotype [e.g., a complete deletion or large deletion (e.g., spanning≥1 exon), or recombination] AND in the opinion of a clinician has a severe form of MPS II
4. Has sufficient auditory and visual capacity, with or without aids, to complete the required protocol testing, and be compliant with wearing the aid, if applicable, on testing days Subjects who meet any of the following exclusion criteria will not be eligible to participate in the study:

1. Has a contraindication for an IC or ICV injection, including any of the following:
   a. Review of baseline MRI testing by the team of neuroradiologists/neurosurgeons participating in study (1 neuroradiologist or neurosurgeon per site) shows a contraindication for an IC or an ICV injection
   b. History of prior head/neck surgery, which resulted in a contraindication to both IC and ICV injection, based on review of available information by the team of neuroradiologists/neurosurgeons participating in study
   c. Has any contraindication to computed tomography, contrast agent, or to general anesthesia
   d. Has any contraindication to MRI or gadolinium
   e. Has renal insufficiency as determined by an estimated glomerular filtration rate (eGFR)<30 mL/min/1.73 m$^2$, based on creatinine. If laboratory determines that creatinine is less than the lower limit of assay validation or detection then the lowest limit cutoff value will be used to estimate eGFR
   f. Has previously experienced a clinically significant intracranial bleed that, in the opinion of the investigator and team of neuroradiologists/neurosurgeons, is a contraindication to IC and ICV injection
2. Has any condition that would contraindicate treatment with prednisone, tacrolimus or sirolimus
3. Has any neurocognitive deficit not attributable to MPS II or diagnosis of a neuropsychiatric condition that may in the opinion of the PI confound interpretation of study results
4. Has any contraindication to lumbar puncture
5. Has a (cerebral) ventricular shunt that in the opinion of the site neuroradiologist/neurosurgeon and through discussion with the Medical Monitor, may impact the administration and proper dosing of the subject
6. Has undergone HSCT
7. Has had prior treatment with an AAV-based gene therapy product a 8. Has received idursulfase (ELAPRASE®) via intrathecal (IT) administration within 4 months of signing the ICF
9. Has received idursulfase (ELAPRASE®) IV and experienced a serious hypersensitivity reaction, including anaphylaxis, deemed related to IV idursulfase (ELAPRASE®) administration. If currently receiving IV idursulfase and has had dose interruptions or a dose regimen different than weekly, then discussion with REGENXBIO Medical Monitor is needed.
10. Has received any investigational product within 30 days of Day 1 or 5 half-lives before signing of the ICF, whichever is longer
11. Has any history of lymphoma or history of another cancer, other than squamous cell or basal cell carcinoma of the skin, that has not been in full remission for at least 1 year before screening
12. Has a platelet count<100,000 per microliter (µL)
13. Has aminotransferase (ALT) or aspartate aminotransferase (AST)>3×ULN or total bilirubin>1.5×ULN at screening unless the subject has a previously known history of Gilbert's syndrome
14. Uncontrolled hypertension despite medical treatment, defined for children≤17 years of age to be systolic blood pressure or diastolic blood pressure>99th percentile plus 5 mmHg based on normative standards for age, sex, and height
15. Has a history of human immunodeficiency virus (HIV) or hepatitis B or hepatitis C virus infection, or positive screening tests for hepatitis B surface antigen or hepatitis B core antibody, or hepatitis C or HIV antibodies
16. Is a first-degree family member of a clinical site employee or any other individual involved with the conduct of the study or is a clinical site employee or other individual involved with the conduct of the study
17. Has a clinically significant ECG abnormality that, in the opinion of the PI, would compromise the subject's safety
18. Has a serious or unstable medical or psychological condition that, in the opinion of the PI, would compromise the subject's safety or successful participation in the study or interpretation of study results
19. Has uncontrolled seizures that in opinion of the PI would put the subject at undue risk Exclusion Criteria Related to Immunosuppressive Therapy:
20. Has a history of a hypersensitivity reaction to tacrolimus, sirolimus, or prednisone
21. Has a history of a primary immunodeficiency (e.g., common variable immunodeficiency syndrome), splenectomy, or any underlying condition that predisposes the subject to infection
22. Has herpes zoster (VZV), cytomegalovirus (CMV), or Epstein Barr virus (EBV) infection that has not completely resolved at least 12 weeks prior to screening
23. Has any infection requiring hospitalization or treatment with parenteral anti-infectives not resolved at least 8 weeks prior to Visit 2
24. Has any active infection requiring oral anti-infectives (including antivirals) within 10 days prior to Visit 2
25. Has a history of active tuberculosis (TB) or a positive Quantiferon-TB Gold test during screening
26. Has received any live vaccine within 4 weeks prior to Day −2
27. Had major surgery within 8 weeks before signing the ICF or major surgery planned during the study period
28. Anticipate the need for adenoidectomy or tonsillectomy within 6 months of enrollment. If adenoidectomy or tonsillectomy is anticipated it should be performed prior to screening.
29. Has an absolute neutrophil count<1.0×10³/μL
30. Has any condition or laboratory abnormality that the PI believes would not be appropriate for immunosuppressive therapy 6.6.6. Proposed Dose Construct 1 will be preferentially administered as a single IC injection, or as a single ICV injection should IC administration prove difficult or potentially unsafe, to allow direct delivery of the vector to the target tissue within the confined CSF compartment. Although cervical puncture (C1-C2) is a routine clinical procedure used for contrast administration for myelography, image-assisted suboccipital puncture is proposed as the IC clinical route of administration. This replicates the route of administration used in the nonclinical studies and is considered advantageous over the C1-C2 puncture in the intended patient population because patients with MPS II have a high incidence of abnormal narrowing of the C1-C2 IT space, which substantially increases the risks associated with a C1-C2 puncture. Prior to the procedure, each subject will have a magnetic resonance imaging (MRI) of the area reviewed by a team of neuroradiologists/neurosurgeons participating in the study. If it is not considered safe to proceed with an IC injection, then the subject will be considered for ICV injection. ICV injection is a commonly used route for ventriculoperitoneal shunt placement in pediatric and adult individuals and, more recently, CNS drug administration (Drake et al., 2000, Childs Nerv Syst. 16(10-11):800-804; Cohen et al., 2017, Pediatric Neurology, 67:23-25; Slavc et al., 2018, Mol Genetics and Metabolism, 124:184-188). Image-assisted single ICV injection, as proposed in this protocol, is comparable to stereotactic brain biopsy, which has also become a routine neurosurgical intervention with the advent of precise MRI and computed tomography (CT) technology.

From pharmacology studies conducted in MPS II mice with Construct 1, it has been shown that the biodistribution and transgene expression profiles of AAV9 vector-based products are comparable for ICV and IC routes, supporting the use of ICV as an alternative route of administration should IC administration prove difficult or potentially unsafe. Further details of the IC and ICV procedures are outlined in their respective Administration Manual.

The total volume of product administered will not exceed 10% of the total CSF volume (estimated to be ~50 mL in infant brain and ~150 mL in adult brain).

Because of the relatively rapid brain growth that occurs early in a developing child, the total dose of Construct 1 administered IC or ICV depends on the estimated brain mass derived from the study subject's screening MRI. The study subject's estimated brain volume from their MRI will be converted to brain mass and used to calculate the exact dose to be administered, as presented in Table 5, Section 5.3.2.

6.6.7. Immunosuppressive Therapy

Corticosteroids

In the morning of vector administration (Day 1 predose), subjects will receive methylprednisolone 10 mg/kg IV (maximum of 500 mg) over at least 30 minutes. The methylprednisolone should be administered before the lumbar puncture and IC or ICV injection of IP. Premedication with acetaminophen and an antihistamine is optional and at the discretion of the investigator.

On Day 2, oral prednisone will be started with the goal to discontinue prednisone by Week 12. The dose of prednisone will be as follows:
Day 2 to the end of Week 2: 0.5 mg/kg/day
Week 3 and 4: 0.35 mg/kg/day
Week 5-8: 0.2 mg/kg/day
Week 9-12: 0.1 mg/kg
Prednisone will be discontinued after Week 12. The exact dose of prednisone can be adjusted to the next higher clinically practical dose.

Sirolimus
2 days prior to vector administration (Day −2): a loading dose of sirolimus 1 mg/m² every 4 hours×3 doses will be administered
From Day −1: sirolimus 0.5 mg/m²/day divided in twice a day dosing with target blood level of 1-3 ng/ml
Sirolimus will be discontinued after the Week 48 visit.

Tacrolimus
Tacrolimus will be started on Day 2 (the day following IP administration) at a dose of 0.05 mg/kg twice daily and adjusted to achieve a blood level 2-4 ng/mL for 24 Weeks.

Starting at Week 24 visit, tacrolimus will be tapered off over 8 weeks. At Week 24, the dose will be decreased by approximately 50%. At Week 28, the dose will be further decreased by approximately 50%. Tacrolimus will be discontinued at Week 32.

Tacrolimus and sirolimus blood level monitoring will be conducted.

Dosing Adjustments

Prednisone dosing will start at 0.5 mg/kg/day and will be gradually tapered off by the Week 12 visit.

Tacrolimus dose adjustments will be made to maintain whole blood trough concentrations within 2-4 ng/mL for the first 24 Weeks. At Week 24, the dose will be decreased by approximately 50%. At Week 28, the dose will be further decreased by approximately 50%. Tacrolimus will be discontinued at Week 32. Sirolimus dose adjustments will be made to maintain whole blood trough concentrations within 1-3 ng/mL. Dose adjustments should be performed by a clinical pharmacist. Subjects should continue on the new maintenance dose for at least 7 to 14 days before further dosage adjustment with concentration monitoring.

*Pneumocystis carinii* pneumonia (PCP) prophylaxis with trimethoprim/sulfamethoxazole (Bactrim™; BACTRIM™ USPI, 2013) will be given three times a week (example dosing schedule; Monday, Wednesday, Friday) at a dose of 5 mg/kg beginning on Day −2 and continuing until Week 48. Refer to the prescribing information for risks associated with trimethoprim/sulfamethoxazole use (BACTRIM™ USPI, 2013). For patients with sulfa allergies, alternative medications can include pentamidine, dapsone, and atovaquone.

Antifungal prophylaxis is to be initiated if the ANC is <500 mm$^3$. The treatment regimen will be determined through local site standard of care in consultation with appropriate subspecialists.

The concomitant use of Rapamune with a calcineurin inhibitor may increase the risk of calcineurin inhibitor-induced thrombotic microangiopathies. Thrombotic microangiopathies (TMA) are a group of disorders characterized by thrombocytopenia, microangiopathic hemolytic anemia, and variable organ system involvement.

This may present severe thrombocytopenia (<30×10$^9$/L), microangiopathic hemolytic anemia characterized by schistocytes on the blood smear, increased reticulocyte count (>120×10$^9$/L), elevated lactate dehydrogenase level (LDH), and signs of skin and mucosal hemorrhage, weakness, and dyspnea. Treatment includes discontinuation of tacrolimus and possible initiation of plasma exchange.

If rising CMV or EBV viral genomes are detected during serial testing, the decision to decrease IS or begin antiviral therapy will be determined through local site standard of care in consultation with appropriate subspecialists.

6.6.8. Prohibited Medications and Procedures

The following medications and procedures are prohibited:

No IT ERT is allowed within 4 months of signing the ICF.

Any investigational product within the 30 days or 5 half-lives, whichever is longer, prior to signing the ICF or at any time during the study (through Week 104)

Live vaccines should be avoided while on sirolimus and/or tacrolimus

Strong inhibitors of CYP3A4 and/or P-glycoprotein (PgP) (such as ketoconazole, voriconazole, itraconazole, posaconazole, erythromycin, telithromycin or clarithromycin) or strong inducers of CYP3A4 and Pgp (such as rifampin or rifabutin) should be avoided while on sirolimus and/or tacrolimus Grapefruit juice inhibits CYP3A-enzymes resulting in increased tacrolimus and sirolimus whole blood trough concentrations. Subjects should avoid eating grapefruit or drinking grapefruit juice with tacrolimus and/or sirolimus.

6.6.9. Permitted Medications and Procedures

Subjects will be permitted to remain on a stable regimen of IV ERT as well as any supportive measures (e.g., physical therapy). According to local hospital standard of care, subjects will be permitted to receive medication to prevent claustrophobia during MRI and receive general anesthesia for lumbar puncture, MRI, and neuroconduction studies (ABRs or SSEP).

Medications other than that described above, which are considered necessary for the subject's safety and wellbeing (e.g., for hypertension), may be given at the discretion of the Investigator in accordance with local standard of care and recorded in the appropriate sections of the CRF.

6.6.10. Efficacy Assessments

Biomarkers

CSF: GAGs, I2S

Plasma: GAGs, I2S. For subjects treated with weekly IV ERT, plasma biomarkers are to be collected at trough, defined as at least 96 hours after ERT infusion up until the start of the subsequent infusion Leukocyte I2S enzyme activity. For subjects treated with weekly IV ERT, whole blood is to be collected at trough, defined as at least 96 hours after ERT infusion up until the start of the subsequent infusion Urine: GAGs. For subjects treated with weekly IV ERT, urine GAGs are to be collected at trough, defined as at least 96 hours after ERT infusion up until the start of the subsequent infusion Neurodevelopmental parameters of cognitive, behavioral, and adaptive function:

Bayley Scales of Infant and Toddler Development, 3rd Edition (BSID-III) or Kaufman Assessment Battery for Children, 2nd Edition (KABC-II)

Vineland Adaptive Behavior Scales, 2nd Edition, Expanded Interview Form (VABS-II)

Other neurocognitive or adaptive assessments performed as part of subjects' standard of care while participating in the trial may also be collected, as determined by the study sponsor after discussing with the site Imaging Assessments MRI of the brain will be performed at certain visits. Estimated glomerular filtration rate (eGFR) must be documented prior to the screening MRI with gadolinium. The investigator must consult with the Medical Monitor before proceeding with the screening MRI if the eGFR is <30 mL/min/1.73 m$^2$ Abdominal ultrasounds will be performed at certain visits to document craniocaudal liver diameter at the mid-clavicular line (Kratzer et al., 2003, J. Ultrasound Med. 22:1155-1161) and spleen volume calculated using the prolate ellipsoid formula (0.52×length×anteroposterior dimension×width)

2-D echocardiogram will be performed at certain visits to evaluate for valvular disease and left ventricular mass index.

Auditory capacity changes will be measured by behavioral audiometry and otoacoustic emissions testing; if behavioral audiometry is not feasible, then ABR testing will be completed. Auditory capacity will be assessed at certain visits; an additional assessment is permitted at the Week 24 visit if deemed clinically necessary by the investigator.
QOL assessments using PedsQL
Sleep assessment
Clinical Assessment of Disease
Caregiver Assessment of Disease
ADL
Burden of Illness 6.6.11. Clinical Laboratory Tests The following CSF safety laboratory and antibody tests will be assessed:
  Markers of CSF inflammation: CSF pressure, erythrocyte cell count, WBC count with differential, total protein, and glucose
  Immune Response Monitoring: neutralizing antibodies to AAV9 and binding antibodies to I2S
  Vector concentration (gPCR): Construct 1 concentrations
The following clinical laboratory tests will be assessed:
  Chemistry: glucose, blood urea nitrogen, creatinine, sodium, potassium, chloride, carbon dioxide, calcium, magnesium, phosphorus, total protein, albumin, total bilirubin, direct bilirubin, alkaline phosphatase (ALP), ALT, AST, gamma glutamyl-transferase, and creatine kinase
  Lipid panel: total cholesterol, low-density lipoprotein (LDL) cholesterol, high-density lipoprotein (HDL) cholesterol, and triglycerides
  Hematology: CBC with differential and platelet count, including hematocrit, hemoglobin, red blood cell (RBC), WBC, platelet, neutrophil, lymphocyte, monocyte, eosinophil, and basophil counts
  Coagulation: prothrombin time (PT) and partial thromboplastin time (PTT)
  Urinalysis: dipstick for glucose, ketones, protein, and blood (if warranted, a microscopic evaluation will be completed)
  Immunogenicity measurements: neutralizing antibodies to AAV9 and binding antibodies to I2S; ELISPOT assay: T-cell response to AAV9 and I2S; flow cytometry for AAV and I2S specific regulatory T cells
  Vector concentration (qPCR): Construct 1 concentrations in serum and urine
  Viral testing for serology and genome detection:
    VZV: Ab titer (baseline)
    EBV and CMV: PCR testing for viral genome (baseline and serially)
    Hepatitis B surface antigen, hepatitis B core antibody, anti-hepatitis C, and HIV: only for screening purposes
  Quantiferon-Gold_TB Plus: only for screening purposes.
  Plasma biomarkers
  Urine biomarkers Laboratory reports will be made available to the PI in a timely manner to ensure appropriate clinical review. The PI is responsible for reviewing and signing all laboratory reports.

6.6.12. Vital Signs and Electrocardiogram

Assessment of vital signs (systolic/diastolic BP, pulse rate, temperature, and respiratory rate), head circumference, height, weight, and ECGs will be obtained/performed at visits.

6.6.13. Neurologic Assessments

Neurologic assessments should include the following:
Level of consciousness
Cranial nerve testing
Motor function
Sensory function
Coordination and gait SSEP testing will also be performed at selected time points. Additional details on protocol requirements for SSEP testing can be found in the SSEP Manual.

6.7 Example 7: MPS II Murine Model Study

MPS II or Hunter syndrome is caused by a deficiency of iduronate-2-sulfatase (I2S) leading to an accumulation of glycosaminoglycans (GAGs) in tissues. Severe MPS II results in irreversible neurocognitive decline and behavioral symptoms that are not addressed by intravenously administered enzyme replacement therapy with recombinant I2S enzyme. Construct 1 is a recombinant adeno-associated virus serotype 9 capsid (AAV9) containing a human iduronate-2-sulfatase expression cassette (AAV9.CB7.hIDS). In an MPS II murine model, Construct 1 administered into the cerebrospinal fluid (CSF) demonstrated dose-dependent I2S activity, reduced GAG levels, amelioration of storage pathology in the central nervous system and improved neurobehavioral function. Vector distribution and reduced GAG levels were observed in peripheral organs, as well as normalization of liver size and weight.

6.8 Example 8: A Phase 1/2, First-In-Human, Multicenter, Open-Label. Dose Escalation Trial Mucopolysaccharidosis Type II (MPS II) is a rare, X-linked recessive disease caused by a deficiency in the lysosomal enzyme iduronate-2-sulfatase (I2S) leading to an accumulation of glycosaminoglycans (GAGs), including heparin sulfate (HS) in tissues which ultimately results in cell, tissue, and organ dysfunction. In severe forms of the disease, early developmental milestones may be met, but developmental delay is readily apparent by 18 to 24 months. Patients with MPS II continue to have significant difficulties despite the availability of systemic enzyme replacement therapy which does not address manifestations of the disease in the central nervous system (CNS) such as impaired cognitive development. Specific treatment to address the neurological manifestations of MPS II and prevent or stabilize cognitive decline remains a significant unmet medical need. Key biomarkers of I2S enzymatic activity in MPS I1 patients include its substrate HS, which has been shown to correlate with neurocognitive manifestations of the disorder.

In an ongoing phase 1/2, first-in-human, multicenter, open-label, dose escalation trial, Construct 1 has been administered as a one-time injection using a single intracisternal injection into the cisterna magna of participants with severe MPS II ages 4 months to 5 years. Construct 1 is designed to deliver the gene that encodes the I2S enzyme direct to the CNS using the AAV9 vector, aimed to provide a permanent source of secreted I2S beyond the blood-brain barrier, allowing for long-term cross correction of cells throughout the CNS.

Patients must have met any of the following inclusion criteria: a) a documented diagnosis of MPS II and a neurocognitive testing score≤77 (Bayley or Kaufman); b) a documented diagnosis of MPS II and a decline of ≥1 standard deviation on serial neurocognitive testing administered between 3 to 36 months apart (Bayley or Kaufman); c) a relative clinically diagnosed with severe MPS II who has the same IDS mutation as the subject and in the opinion of a geneticist has inherited a severe form of MPS II; or d) a documented mutation(s) in IDS that in the opinion of a geneticist is always known to result in a neuronopathic phenotype and in the opinion of a clinician has a severe form of MPS II. Patient must be ≥4 months to <5 years of age.

Exclusion criteria included: patient having contraindications for intracisternal injection, intracerebroventricular injection, or lumbar puncture; contraindications for immunosuppressive therapy; neurocognitive deficit not attributable to MPS II or diagnosis of a neuropsychiatric condition; patients having a (cerebral) ventricular shunt that may impact the proper dosing of the subject; subjects that received hematopoietic stem cell transplantation; subjects that had prior treatment with an AAV-based gene therapy product; subjects that received ELAPRASE® via intrathecal (IT) administration within 4 months of signing the ICF or experienced a serious hypersensitivity reaction to ELAPRASE®; subjects that received any investigational product within 30 days of Day 1 or 5 half-lives before signing the ICF, whichever is longer; subjects that have a platelet count<100,000 per microliter (μL), absolute neutrophil count<$1.3 \times 10^3$/μL, or aminotransferase (ALT) or aspartate aminotransferase (AST)>3×upper limit of normal (ULN) or total bilirubin>1.5×ULN at screening unless the subject has a previously known history of Gilbert's syndrome.

Assessments included safety and tolerability up to 104 weeks; CSF, plasma and urine biomarkers; immunogenicity; neurodevelopmental scales (Bayley Scales of Infant and Toddler Development or Kaufman Assessment Battery for Children, and Vineland Adaptive Behavior Scales); audiometry; imaging of the brain, liver and spleen; and clinician- and patient-reported outcome measures.

A total of 8 patients have been dosed with either $1.3 \times 10^{10}$ genome copies per gram (GC/g) of brain mass (Cohort 1) or $6.5 \times 10^{10}$ GC/g of brain mass (Cohort 2). The ages of the patients range from 5 months to 59 months. At least 3 patients completed immunosuppression regimen in Cohort 1 with 64, 78, and 104 follow-up weeks and at least 1 patient completed immunosuppression regimen in Cohort 2 with 56 follow up weeks as presented in Table 9. Mutations among the patients included 3 missense, 2 gene inversion, and 3 frameshift. In Cohort 1 and Cohort 2 of the Phase 1/2 study, eight patients were dosed intracistermally at ages ranging from 5 months to 59 months with 3 patients dosed at $1.3 \times 10^{10}$ genome copies per gram (GC/g) of brain mass and 4 patients dosed at $6.5 \times 10^{10}$ genome copies per gram (GC/g) of brain mass. Cohort 3 of the Phase 1/2 study also includes Cohort 3 with patients dosed at $2.0 \times 10^{11}$ genome copies per gram (GC/g) of brain mass. In some cases, Cohort 3 of the Phase 1/2 study can also include another Cohort with patients dosed at $2.9 \times 10^{11}$ genome copies per gram (GC/g) of brain mass. The number of genome copies in the dose of $2.0 \times 10^{11}$ GC/g brain mass was determined based on a Poly-A-specific PCR assay and the weight of brain mass was determined by MRI. The number of genome copies in the dose of $2.9 \times 10^{11}$ GC/g brain mass was determined based on a transgene-specific PCR assay and the weight of brain mass was determined by MRI. Construct 1 administration has been well tolerated in all six patients in Cohort 1 and Cohort 2, with no drug-related serious adverse events (SAEs) reported. Per protocol, patients received a 48 week immunosuppression regimen to minimize the potential for immune-mediated reactions with 4 patients (3 from Cohort 1 and 1 from Cohort 2) completing the immunosuppression regimen.

TABLE 9

Cohort 1 and Cohort 2 Overview

| Patient | Dose (GC/g brain mass) | Follow-Up (weeks) | Immunosuppression Regimen Status | ERT (IV) status[†] |
|---|---|---|---|---|
| 1 | $1.3 \times 10^{10}$ | 104 | Complete | Weekly |
| 2 | $1.3 \times 10^{10}$ | 78 | Complete | Discontinued |
| 3 | $1.3 \times 10^{10}$ | 64 | Complete | Discontinued |
| 4 | $6.5 \times 10^{10}$ | 56 | Complete | Weekly |
| 5 | $6.5 \times 10^{10}$ | 32 | Tapering | Weekly |
| 6 | $6.5 \times 10^{10}$ | 24 | Tapering | Naive |
| 7 | $6.5 \times 10^{10}$ | 8 | Active | Weekly |
| 8 | $6.5 \times 10^{10}$ | 4 | Active | Naïve |

[†]ERT can be discontinued after week 52

A total of 13 patients participated in a Phase 1/2 trial (FIG. 22). Previous studies found that a widespread CNS and systemic biodistribution was observed in non-human primates after IC administration of Construct 1 (FIG. 23). Patients (3 patients) in cohort 1 were dosed with $1.3 \times 10^{10}$ genome copies per gram (GC/g) of brain mass of Construct 1, patients (7 patients) in cohort 2 were dosed with $6.5 \times 10^{10}$ GC/g of brain mass of Construct 1, and patients (3 patients) in cohort 3 were dosed with $2.9 \times 10^{11}$ GC/g of brain mass of Construct 1 (cohort 3 was previously reported as $2.0 \times 10^{10}$ GC/g of brain mass based on a Poly-A-specific PCR assay, which is equivalent to $2.9 \times 10^{11}$ GC/g of brain mass using a transgene-specific PCR assay). Participant ages at dosing ranged from 5 months to 59 months. IDS mutations among severe MIPS II trial participants included missense, gene inversion, and frameshift. Follow-up included 104 weeks for participants in cohort 1, 8-104 weeks for participants in cohort 2, and 8-36 weeks for participants in cohort 3.

Immunosuppression discontinued (e.g., after 52 weeks) in all eligible participants (n=8) as follows: three participants completed immunosuppression regimen in cohort 1; 5 participants completed immunosuppression regimen in cohort 2 (while 2 are active); and 3 participants in cohort 3 are active for immunosuppression regimen. The ERT (IV) status were as follows: 1 weekly and 2 discontinued for cohort 1; 4 weekly, 1 discontinued, and 2 naïve for cohort 2; and 3 weekly for cohort 3. Results showed that no SAEs related to the study has been identified. CSF HS levels were determined at different time points and results showed dose-dependent reductions in Cohorts 1-3 at Weeks 8 and 24 (FIGS. 24A-24B). Further, the majority of participants in all three cohorts demonstrated decreased CSF HS at last time point available. The HS D2S6 disaccharide level was determined at different time points and results showed dose-dependent reductions in Cohorts 1-3 at Week 8 and 24, with Cohort 3 participants approaching normal levels (FIGS. 25A-25B). Results showed that the majority of participants in all three cohorts demonstrated decreased CSF D2S6 at last time point available. Further, samples from the subjects showed measurable CSF I2S protein concentration in cohort 2 and 3 participants after Construct 1 administration (range 834-4830 pg/mL).

Patients were evaluated for safety, tolerability, and efficacy for 104 weeks after dosing. Assessments include biomarkers in the CSF, plasma and urine: neurodevelopmental scales (Bayley Scales of Infant and Toddler Development—BSID, Vineland Adaptive Behavior Scales—VABS): audiometry; imaging of the brain, liver and spleen; immune response assays; and clinician- and patient-reported outcome measures. Participants were assessed using the BSID-III cognitive, expressive and receptive language, and fine and gross motor subtests (e.g., FIG. 26A and FIG. 27A (cohort 1 and cohort 2 respectively) show data for BSID-III cognitive subtest, FIG. 26B and FIG. 27B (cohort 1 and cohort 2 respectively) show data for expressive language subtest, and FIG. 26C and FIG. 27C (cohort 1 and cohort 2 respectively) show data for fine motor subtest). It was observed that for cohort 1, 3 participants with cognitive function above −2 standard deviations (SD) at baseline remained within 2 SD at the last assessment on the cognition, expressive language and fine motor subtests, and that another participant acquired skills on the expressive language subtest. For cohort 2, minimal skill acquisition was demonstrated in cognition for 2 participants (AEq increase of 2-3 months) and in expressive language for another participant (AEq increase of 5 months). The participants were also tested for maladaptive behavior (undesirable behaviors that interfere with daily function) and toileting skills using Vineland Adaptive Behavior Scales-II (VABS-II). Maladaptive behaviors and challenges with toilet training are associated with neurodegeneration. Results showed that 4 participants (3 with cognitive function<−2SD at baseline) showed a reduction in maladaptive behaviors (FIG. 28A), and 4 participants (2 with cognitive function below <−2SD at baseline) showed an improvement in toileting skills (FIG. 28B). Further, participants were subjected to a sleep breathing subtest and it was found that 10 of 11 participants (5 with cognitive function<−2SD) showed improved sleep breathing following Construct 1 administration. The sleep breathing subtest detects sleep disturbances in children, such as snoring and difficulty breathing during sleep, which can be due to airway abnormalities, respiratory mechanisms and CNS involvement. To analyze systemic effects, plasma I2S protein concentration and urine total GAGs were determined at different timepoints. It was found that increased plasma I2S protein concentration was demonstrated in the majority of participants after Construct 1 administration (FIG. 29A). It was also found that urine GAG levels showed evidence of systemic effect of Construct 1 independent of ERT treatment (FIG. 29B). For example, for ERT Naïve participants, a notable decline was demonstrated in urine GAGs in one of two participants through last time point available; for ERT withdrawal, total urine GAGs following ERT withdrawal remained relatively consistent with total urine GAGs prior to ERT withdrawal; and for ERT continuation, total urine GAGs decreased in all participants at the last time point available (FIG. 29B).

The primary outcome for the Phase 1/2 study include safety measures to determine the number of patients with treatment-related adverse events and serious adverse events with the time frame of 24 weeks.

The secondary outcome include safety measures to determine the number of patients with treatment-related adverse events and serious adverse events with the time frame of 104 weeks; biomarker measurement to determine change from baseline in Glycosaminoglycan levels (ng/mL) measured at baseline, Week 2, Week 4, Week 8, Week 24, Week 48, Week 56, Week 104; biomarker measurement to determine change from baseline in iduronate-2-sulfatase activity measured at baseline Week 1, Week 2, Week 4, Week 8, Week 24, Week 32, Week 48, Week 56, Week 104; change from baseline in neurodevelopment parameters of cognitive, behavioral and adaptive function as measured by the Bayley Scales of Infant and Toddler Development, 3rd Edition (BSID-III) or Kaufman Assessment Battery for Children, 2nd Edition (KABC-II). Based on their mean age equivalence score on the Vineland Adaptive Behavior Scales (outcome #7), the child will be assessed using either the BSID-III (for scores of <36 months or </=42 months and unable to complete the KABC-II) OR the KABC-II (for scores of >/=36 months) measured at baseline, Week 48, Week 78, Week 104; change from baseline in neurodevelopment parameters of cognitive, behavioral and adaptive function as measured by the Mullen Scales of Early Learning (MSEL) measured at baseline, Week 48, Week 78, Week 104; and change from baseline in neurodevelopment parameters of cognitive, behavioral and adaptive function as measured by the Vineland Adaptive Behavior Scales, 2nd Edition (VABS-II), Comprehensive Interview Form measured at baseline, Week 48, Week 78, Week 104.

Data and safety summary: Construct 1 is well-tolerated with no drug-related serious adverse events (SAEs) as observed in eight patients. Time of post-administration follow-up ranges from four weeks to two years. All four patients that reached 48-weeks of follow-up completed the immunosuppression regimen, per study protocol. Six of the patients were receiving weekly, intravenous enzyme replacement therapy (ERT) at the time of enrollment; two of these patients have since discontinued ERT.

CNS biomarker data: in MPS II patients, high amounts of HS accumulate in the CNS, closely correlating with neurocognitive decline. Biomarker data from patients in Cohort 1 and Cohort 2 showed signals of I2S enzyme activity in the CNS following one-time administration of Construct 1. Heparan sulfate (HS) and D2S6, a component of HS, are glycosaminoglycans (GAGs) that are key biomarkers of I2S enzyme activity and were measured in the cerebrospinal fluid (CSF) at baseline and after administration of Construct 1. I2S enzyme cleaves sulfates from HS in the lysosome and absence of I2S causes long chains of fully sulfated D2S6 to accumulate in HS. As such, quantitative measurement of D2S6 is reflective of I2S enzyme activity level. I2S6 and D2S6 are products of heparinase digestion as illustrated in FIG. 7. Elevated levels of HS and D2S6 correlate closely with the neuronopathic phenotype of MPS II. HS levels in the first six patients in Cohorts 1 and 2 demonstrated consistent reductions in the CSF up to 2 years following Construct 1 administration, with median reductions from baseline of 30.3% at Week 8 and 35.8% at the last timepoint available for each patient (p-value is 0.03 obtained from Wilcoxon signed rank test) (see FIG. 8). Similarly, these patients demonstrated consistent reductions of D2S6 up to 2 years following Construct 1 administration, with median reductions from baseline of 44.2% at Week 8 and 39.2% at the last timepoint available for each patient. In addition, I2S enzyme concentration in the CSF, which was undetectable in all patients prior to dosing, was measurable in patients from Cohort 2 after Construct 1 administration (range 1170-1940 pg/mL) (see FIG. 8). Change in CSF HS disaccharide D2S6 in Cohort 1 and Cohort 2 patients was determined (see FIG. 9). The median change from baseline at week 8 (N=6) was 44.2% and the p-value was 0.03 and the median change from baseline at the last available timepoint (N=6) was 39.2% as determined by Wilcoxon signed rank test (see FIG. 9). The D2S6 disaccharide clearly differentiated between severe, attenuated and normal patients; study patients showed consistent decrease in CSF D2S6 into the attenuated range.

Neurocognitive development data: patients in Cohorts 1 and 2 demonstrated continued neurocognitive development up to two years after Construct 1 administration. Five patients in Cohorts 1 and 2 reached at least 6 months of follow-up since Construct 1 administration, and of those five patients, three continued to demonstrate neurocognitive development within a normal range, according to the Bayley Scales1 (see FIGS. 10A-10C).). Further, data interpretation from the firt in human (FIH) trial of Construct 1 using DQ and AEq were shown to be consistent (FIGS. 10B-10C), indicating that 75% of the patients who started treatment before the onset of development decline continued to demonstrate neurocognitive development above −2SD of normal as of >6-month follow-up and the cognitively declined patient at baseline demonstrated relative stabilized and continued to acquire expressive and receptive language skills. In brief, mock data were generated from raw, standard and AEq scores in the BSID-III manual for subjects between 4 and 42 months of age with normal, below and above 1SD (1 standard deviation) from normal, and below and above 2SD (2 standard deviations) from normal developmental status. Raw score, AEq, and DQ were derived to correspond to a mean scale score, and 1 and 2 SDs from the mean. The scores were fitted with a quadratic or linear regression line to approximate the range of the normal distribution. The fitted±1SD and ±2SD lines using the data from the BSID-III manual for cognitive domain were then applied to Construct 1 longitudinal BSID-III data to track change over time and to evaluate treatment efficacy. Two patients entered the study with significant delay in neurocognitive development at baseline. After Construct 1 administration, one of these patients demonstrated ongoing neurocognitive development, and both patients continued to acquire expressive and receptive language skills based on the Bayley Scales. Continued language and/or motor skills acquisition was observed in all patients with greater than 6 months follow-up (see FIGS. 11A-li D).

Systemic biomarker data and clinical efficacy: patients in Cohorts 1 and 2 demonstrated evidence of I2S enzyme activity in plasma and urine following administration of Construct 1. Five of six patients demonstrated increased I2S enzyme concentration levels in plasma over time (see FIG. 12). Six of eight patients dosed with Construct 1 were receiving ERT at the time of enrollment in the study. All six of these patients showed decreased total GAG levels in urine up to two years following Construct 1 administration (see FIG. 13). Notably, two patients in Cohort 2 who were naïve to ERT demonstrated rapid reductions in urine total GAG levels following Construct 1 administration (see FIG. 14). One patient who never received ERT, demonstrated clear reduction in liver and spleen dimensions 24 weeks after receiving Construct 1 (see Table 10). Dimensions of liver and spleen can be measured using ultrasound (see FIG. 15). A decrease in liver diameter (10%) and spleen volume (77%) in patient 6 who is ERT naïve was observed by abdominal ultrasound 24 weeks after Construct 1 administration (see Table 10).

TABLE 10

Liver and Spleen Dimensions

| Patient | Follow-Up (weeks) | Liver Diameter (cm) | Spleen Length (cm) | Spleen Height (cm) | Spleen Width (cm) |
|---|---|---|---|---|---|
| Patient 6 (Cohort 2) | Screening | 12.0 | 9.0 | 6.0 | 7.7 |
| Patient 6 (Cohort 2) | 24 | 10.8 | 7.6 | 4.0 | 3.2 |

Conclusion: Construct 1 has been well-tolerated in patients with MPS I1 following one-time intracisternal administration (8 patients showed no SAE related to Construct 1); immunosuppression discontinued in 4 patients according to protocol; treatment with Construct 1 resulted in a consistent and sustained reduction in CSF levels of heparan sulfate, a key biomarker of I2S enzyme activity in MPS II, as consistent reductions in HS in the CSF was observed up to 2 years; CSF I2S enzyme concentration was measurable in all Cohort 2 patients; continued cognitive development was observed in 4 of 5 patients with >6 months of follow-up; continued language and/or motor skills acquisition was observed in patients with >6 months of follow-up; continued acquisition of cognitive and/or language skills was observed in patients with cognitive delay prior to dosing; plasma I2S enzyme levels increased in 5 of 6 patients; rapid urine GAG reduction was observed in ERT naïve patients; decreased liver and spleen dimensions was observed in ERT naïve patient; absence of urine GAG rebound in the 2 patients who have discontinued ERT; and improvement in neurocognitive parameters correlate with decline in D2S6 marker.

6.9 Example 9: A Phase 1/II Multicenter, Open-Label Study to Evaluate the Safety, Tolerability, and Pharmacodynamics of Construct 1 in Children 5 Years of Age and Older with MPS II (Hunter Syndrome)

6.9.1. Synopsis

Study Design

This is a Phase I/II, multicenter, open-label, single arm study of Construct 1. No control group is included. Approximately 6 children (≥5 years to <18 years of age) who have severe (neuronopathic) MPS II could be enrolled into a single dose cohort of $6.5 \times 10^{10}$ GC/g brain mass and will receive a single dose of Construct 1 administered by IC or ICV injection.

Primary Objectives

To evaluate the safety and tolerability of Construct 1 through 24 weeks following a single IC dose, or ICV dose if the IC route is contraindicated, administered to older (≥5 years) children who have neuronopathic MPS II Secondary Objectives To evaluate immunogenicity of Construct 1

To explore the effect of Construct 1 on CNS imaging

To explore the effect of Construct 1 on systemic manifestations of disease

To explore the effect of Construct 1 on biomarkers in plasma and urine in participants who discontinue IV ERT (ELAPRASE®)

To explore the effect of Construct 1 on quality of life (QOL)

To explore the effect of Construct 1 on sleep measures

To explore the effect of Construct 1 on clinician reported outcome

To explore the effect of Construct 1 on caregiver reported outcome

To use video recording to capture everyday function

To explore the effect of Construct 1 on fine motor dexterity

Diagnosis and Main Criteria for Inclusion:

To be eligible to participate in this study, a participant must be a male≥5 years to <18 years of age with:

a documented diagnosis of MPS II with neurocognitive decline, or a documented mutation(s) in IDS known to result in a neuronopathic form of MPS II, or a documented mutation(s) in IDS identical to that of a relative with neuronopathic MPS II.

In addition, the participant must be able to safely receive an IC or ICV injection and immunosuppression.

Investigational Product, Dosage and Mode of Administration

Construct 1: AAV9.CB7.hIDS (recombinant adeno-associated virus serotype 9 capsid containing human iduronate-2-sulfatase expression cassette). See FIG. 5.

Product will be delivered as a single IC or ICV dose.

One dose level will be evaluated, $6.5 \times 10^{10}$ GC/g brain mass. Total dose administered will account for estimated brain size of study participants based on their screening MRI. Total volume of product administered will not exceed 10% of estimated CSF volume.

6.9.2. Criteria for Evaluation Safety and Efficacy

Primary Endpoints

Safety through Week 24: AEs and SAEs

Secondary Endpoints

Safety through Week 104: AEs and SAEs

Biomarkers in CSF (GAGs, I2S), plasma (GAGs, I2S), and urine (GAGs)

Neurodevelopmental parameters of cognitive, behavioral, and adaptive function:

Bayley Scales of Infant and Toddler Development, 3rd Edition (BSID-III) (Bayley, 2005, Scales of Infant and Toddler Development, 3rd Ed.)

Mullen Scales of Early Learning (MSEL) (Mullen, Circle Pines, MN: American Guidance Service Inc.; 1995)

Vineland Adaptive Behavior Scales, 2nd Edition, Expanded Interview Form (VABS-II) (Sparrow et al., 2005, Vineland Adaptive Behavior Scales, 2nd Ed.)

Exploratory Endpoints

Immunogenicity measurements

Neutralizing antibody titers to AAV9 and binding antibody titers to I2S in CSF and serum Enzyme-linked immunospot (ELISPOT) assay: T-cell response to AAV9 and I2S CNS structural abnormalities assessed by MRI of the brain Liver and spleen size assessed by ultrasound of the abdomen Cardiac evaluation by echocardiogram for valvular disease and left ventricular mass index Median nerve motor and sensory distal conduction velocity and latency Plasma and urinary GAGs in participants who discontinue IV ERT (ELAPRASE®)

PedsQL

Sleep assessment (Sleep Disturbance Scale for Children—SDSC) (Ferreira et al., 2009, Sleep Medicine; 10(4):457-463)

Clinician Global Impression of Severity and Clinician Global Impression of Change Caregiver Global Impression of Severity and Caregiver Global Impression of Change Activities of Daily Living (Tanjuakio et al. 2015, Mol Genet Metab, 114(2):161-169; Kato et al., 2007, Brain Dev, 29(5): 298-305)

Pediatric Evaluation of Disability Inventory Computer Adaptive Test (PEDI CAT)

9-Hole Peg Test

Functional performance as captured by video

Statistical Methods

All data will be analyzed using descriptive statistics. Categorical variables will be summarized using frequencies and percentages. Continuous variables will be summarized using number of non-missing observations, mean, standard deviation, median, minimum, and maximum). Graphical displays will be presented as appropriate. Participant data listings will also be presented.

Sample Size and Power Calculation

No formal calculation was performed to determine sample size.

6.9.3. List of Abbreviations and Definitions of Terms

TABLE 11

Abbreviations and Specialist Terms

| Abbreviation or Specialist Term | Explanation |
|---|---|
| AAV | Adeno-associated virus |
| AAV9 | Adeno-associated virus serotype 9 |
| ABR | Auditory brainstem response (s) |
| ADL | Activities of Daily Living |
| AE | Adverse event |
| AESI | Adverse event of special interest |
| ALP | Alkaline phosphatase |
| ALT | Alanine aminotransferase |
| ANC | Absolute neutrophil count |
| APB | Abductor pollicis brevis |
| AST | Aspartate aminotransferase |
| BBB | Blood-brain barrier |
| BID | Twice a day |
| BP | Blood Pressure |
| BSID | Bayley Scales of Infant and Toddler Development |
| BSL | Biosafety level |
| BUN | Blood urea nitrogen |
| CB7 | Hybrid C4 and CB (chicken beta actin promoter) |
| CBC | Complete blood count |
| CFR | Code of Federal Regulations |
| CGI-C | Clinician Global Impression Scale for change |
| CGI-S | Clinician Global Impression Scale for severity |
| CI | Confidence Interval |
| CIOMS | Council for International Organizations of Medical Sciences |
| CMV | Cytomegalovirus |
| CNS | Central nervous system |
| CoA | Certificate of Analysis |
| CRF | Case report form |
| CRO | Contract research organization |
| CSF | Cerebrospinal fluid |
| CT | Computed tomography |
| CTA | Clinical Trial Agreement |
| CTCAE | Common Terminology Criteria for Adverse Events |
| CZ | Crystal Zenith ® |
| DLT | Dose-limiting toxicity |
| DNA | Deoxyribonucleic acid |
| DRG | Dorsal root ganglia |
| DS | Dermatan sulfate |
| ECG | Electrocardiogram |
| ED | Early discontinuation (visit) |
| EDC | Electronic data capture |
| eGFR | Estimated glomerular filtration rate |
| ELISA | Enzyme-Linked Immunosorbent Assay |
| ELISPOT | Enzyme-Linked immunospot |
| EOS | End of Study |
| ERT | Enzyme Replacement Therapy |
| EU | European Union |
| FDA | Food and Drug Administration |
| FIM | Family Impact Module |
| G | gram |
| GAG(s) | Glycosaminoglycan(s) |
| GC | Genome copies |
| GCP | Good Clinical Practice |
| GLP | Good Laboratory Practice |
| HBsAg | Hepatitis B surface antigen |
| HCV | Hepatitis C virus |
| Hep | Hepatitis |
| hIDS | Human iduronate-2-sulfatase gene |
| HIPAA | Health Insurance Portability and Accounting Act |
| HIV | Human immunodeficiency virus |
| HS | Heparan Sulfate |
| HSCT | Hematopoietic stem cell transplantation |
| IB | Investigator's brochure |
| IC | Intracisternal |
| ICF | Informed consent form |

TABLE 11-continued

Abbreviations and Specialist Terms

| Abbreviation or Specialist Term | Explanation |
|---|---|
| ICH | International Conference on Harmonisation |
| ICV | Intracerebroventricular |
| IDMC | Independent Data Monitoring Committee |
| IDS | Iduronate-2-sulfatase gene |
| IEC | Independent Ethics Committee (s) |
| IgG | Immunoglobulin G |
| IMP | Investigational medicinal product |
| IND | Investigational New Drug |
| INR | International normalized ratio |
| IP | Investigational Product |
| IRB/IEC | Institutional review board/independent ethics committee |
| IS | Immune Suppression |
| ISC | Internal Safety Committee |
| IT | Intrathecal(ly) |
| ITRs | Inverted terminal repeats |
| IV | Intravenous(ly) |
| LDH | Lactate dehydrogenase level |
| LDL | Low-density lipoprotein |
| LFT | Liver function tests |
| MED | Minimum effective dose |
| MedDRA | Medical Dictionary for Regulatory Activities |
| mL | Milliliter |
| MPS I | Mucopolysaccharidosis type II |
| MPS VII | Mucopolysaccharidosis type VII |
| MRI | Magnetic resonance imaging |
| MSEL | Mullen Scales of Early Learning |
| MTD | Maximum tolerated dose |
| NAb | Neutralizing antibody |
| NHP | Non-human primates |
| NIH | National Institutes of Health |
| NIMP | Non-investigational medicinal product |
| OAE | Otoacoustic emission |
| PBMC | Peripheral blood mononuclear cell |
| PCP | Pneumocystis carinii pneumonia |
| PCR | Polymerase chain reaction |
| PD | Pharmacodynamic |
| PEDI-CAT | Pediatric Evaluation of Disability Inventory Computer Adaptive Test |
| PHI | Protected health information |
| PI | Principal Investigator |
| PML | Progressive multifocal leukoencephalopathy |
| PK | Pharmacokinetic |
| PO | By mouth/orally |
| PT | Prothrombin time, (MedDRA) preferred term |
| PTT | Partial thromboplastin time |
| PVAN | Polyoma virus-associated nephropathy |
| QD | Daily |
| QOL | Quality of Life |
| qPCR | Quantitative polymerase chain reaction |
| RBC | Red blood cell |
| Construct 1 | Recombinant adeno-associated virus serotype 9 capsid containing human iduronate-2-sulfatase expression cassette |
| RNA | Ribonucleic acid |
| SAE | Serious adverse event |
| SAP | Statistical Analysis Plan |
| SD | Standard deviation |
| SDSC | Sleep Disturbance Scale for Children |
| SDV | Source data verification |
| SNAP | Sensory nerve action potential |
| SOC | (MedDRA) System Organ Class |
| SRT | Safety Review Trigger |
| SSEP | Somatosensory evoked potential |
| SUSAR | Suspected unexpected serious adverse reaction |
| TB | Tuberculosis |
| TEAE | Treatment-emergent adverse event |
| TMA | Thrombotic microangiopathies |
| Treg | Regulatory T cell |
| ULN | Upper limit of normal |
| US | United States |
| VABS | Vineland Adaptive Behavior Scales |
| VAS | Visual Analog Scale |
| VZV | Varicella zoster virus |
| WBC | White blood cell |
| WHO | World Health Organization |

6.9.4. Overall Study Design

This is a Phase I/II, multicenter, open-label, single arm study of Construct 1. No control group is included. Approximately 6 children ($\geq 5$ years to <18 years of age) who have severe (neuronopathic) MPS II could be enrolled into a single dose cohort of $6.5 \times 10^{10}$ GC/g brain mass and will receive a single dose of Construct 1 administered by IC or ICV injection. Safety will be the primary focus for the initial 24 weeks after treatment (primary study period). Following completion of the primary study period, participants continue to be assessed (safety and efficacy) for up to a total of 104 weeks following treatment with Construct 1 (FIG. 10A). At the end of the study, participants will be invited to participate in a long-term follow-up study.

The first 2 eligible participants will be enrolled in a staggered fashion. After Construct 1 administration to the first participant, there will be an 8-week observation period for safety. The Internal Safety Committee (ISC) will review the safety data obtained during the first 8 weeks of the study according to the ISC Charter (including data obtained during the Week 8 visit) for this participant, and if there are no safety concerns, the $2^{nd}$ participant may be dosed. Informed consent and screening activities for the $2^{nd}$ participant may proceed during the observation period for the first participant.

If no safety review trigger (SRT) event is observed, all available safety data for the first 2 participants obtained up to and including the Week 8 visit for the $2^{nd}$ participant will be evaluated by the Independent Data Monitoring Committee (IDMC). If the decision is to proceed, the next 4 participants may be enrolled.

All available safety data will be evaluated by the IDMC after the Week 8 visit for the $6^{th}$ participant and at intervals stipulated within the study-specific IDMC Charter.

At any given IDMC meeting, whether planned or called for by an SRT, the IDMC may recommend stopping the trial, delaying the dosing of additional participants, or proceeding at a lower dose. Once 8 weeks of data are available from the $6^{th}$ participant, then enrollment in the study will be completed.

If any event meets the criteria of a prespecified Stopping Rule, dosing of any new participants will be suspended until a complete review of all safety data by REGENXBIO and the external IDMC has been performed.

Those participants who meet the eligibility criteria will be admitted to the hospital between Day −2 and the morning of Day 1 (according to institutional practice), and baseline assessments will be performed pre-dose. Participants will receive a single IC or ICV dose of Construct 1 on Day 1 and will remain in the hospital overnight after dosing for observation. Participants will be discharged after the principal investigator concludes that the participant is ready for discharge and prolongation of hospitalization is not necessary. Subsequent assessments in the primary study period (i.e., through Week 24) will be performed at Weeks 1, 2, 3, 4, 12, and 24. The Weeks 8 and 16 assessments will be limited to evaluation of adverse events (AEs) and concomitant therapies by telephone contact. After the primary study period, visits will be at Weeks 38, 52, 64, 78, and 104. The Week 30 visit will be performed only for participants who discontinue IV ERT starting at Week 24.

Because of the brain growth that occurs in children and differences in brain growth that may occur in MPS II, the total dose of Construct 1 administered IC or ICV will be calculated from the estimated brain mass derived from the study participant's screening MRI. The study participant's estimated brain volume from their MRI will be converted to brain mass and used to calculate the exact dose to be administered, as presented in Table 12.

TABLE 12

Total Dose Administered by Brain Mass

| Brain Mass (in g) | | Target Brain Mass | Dose: Total GC |
|---|---|---|---|
| Min | Max | (in g) | ($6.5 \times 10^{10}$ GC/g brain mass) |
| 801 | 900 | 850 | $5.5 \times 10^{13}$ |
| 901 | 1050 | 975 | $6.3 \times 10^{13}$ |
| 1051 | 1200 | 1125 | $7.3 \times 10^{13}$ |
| 1201 | — | 1300 | $8.5 \times 10^{13}$ |

1. Obtain participant brain volume in $cm^3$ from screening MRI.
2. Convert participant's MRI brain volume to brain mass: brain mass=(brain volume in $cm^3$)×1.046 $g/cm^3$ (brain density taken from (Hasgall et al, 2018, Tissue Properties, Density. [cited 4 Nov. 2019]. In: IT'IS Database for Thermal and Electromagnetic Parameters of Biological Tissues, Version 4.0, 15 May 2018 [Internet]. Zurich: IT'IS Foundation. c2010).
3. Identify appropriate dose in Table 12 above.

Construct 1 is intended for investigational use only by selected investigators familiar with the information in the investigator's brochure for Construct 1 and experienced in conducting clinical trials. Construct 1 may only be administered to human participants enrolled in clinical trials sponsored/approved by the Sponsor and who have provided formal written consent.

6.9.5. Inclusion Criteria

Participants are eligible to be included in the study only if all of the following criteria apply:

1. The participant's legal guardian(s) is (are) willing and able to provide written, signed informed consent after the nature of the study has been explained, and prior to any research-related procedures.
2. Is a male≥5 years to <18 years of age
3. Meets any of the following criteria:
   a. Has a documented diagnosis of MPS II AND a neurocognitive testing score≤1½ standard deviation (SD) from the test normative mean (BSID-III: 77 and MSEL Visual Reception: 35), OR
   b. Has a documented diagnosis of MPS II AND has a decline of ≥1 standard deviation on serial neurocognitive testing administered between 3 to 36 months apart (BSID-III Cognitive or MSEL Visual Reception), OR
   c. Has a relative clinically diagnosed with neuronopathic MPS II who has the same IDS mutation as the participant AND the participant in the opinion of a geneticist has inherited a neuronopathic form of MPS IL, OR
   d. Has documented mutation(s) in IDS that in the opinion of a geneticist is known to result in a neuronopathic phenotype AND in the opinion of a clinician has a neuronopathic form of MPS II 6.9.6. Exclusion Criteria Participants are excluded from the study if any of the following criteria apply:

1. Has a contraindication for an IC and ICV injection, including any of the following:
   a. Review of baseline MRI testing by the team of neuroradiologists/neurosurgeons participating in study shows a contraindication for an IC and an ICV injection
   b. History of prior head/neck surgery, which resulted in a contraindication to both IC and ICV injection, based on review of available information by the team of neuroradiologists/neurosurgeons participating in study
   c. Has any contraindication to general anesthesia
   d. Has any contraindication to MRI or gadolinium
   e. Has renal insufficiency as determined by an estimated glomerular filtration rate (eGFR)<30 mL/min/ 1.73 $m^2$, based on creatinine. If laboratory determines that creatinine is less than the lower limit of assay validation or detection then the lowest limit cutoff value will be used to estimate eGFR.
   f. Has previously experienced a clinically significant intracranial bleed that, in the opinion of the investigator and team of neuroradiologists/neurosurgeons, is a contraindication to IC and ICV injection
   g. Has an elevated intracranial pressure (≥30 cm $H_2O$)
2. Has any condition that would contraindicate treatment with prednisone, tacrolimus or sirolimus
3. Has any neurocognitive deficit not attributable to MPS II or diagnosis of a neuropsychiatric condition that may in the opinion of the PI confound interpretation of study results
4. Has any contraindication to lumbar puncture
5. Has a (cerebral) ventricular shunt that in the opinion of the site neuroradiologist/neurosurgeon and through discussion with the Medical Monitor, may impact the administration and proper dosing of the participant
6. Has had prior treatment with an AAV-based gene therapy product
7. Is receiving idursulfase (ELAPRASE®) via intrathecal (IT) administration at the time of ICF. The participant must agree to discontinue IT idursulfase for the duration of the study, starting immediately after signing the ICF
8. Has received idursulfase (ELAPRASE®) IV and experienced a serious hypersensitivity reaction, including anaphylaxis, deemed related to IV idursulfase (ELAPRASE®) administration
9. Is failing to respond to idursulfase (ELAPRASE®) IV due to neutralizing anti-IDS antibodies, documented as increasing urine GAG levels; the participant may enroll if he has received immune modulation and is currently responsive to IV idursulfase (ELAPRASE®)
10. Has received any investigational product within 30 days of Day 1 or 5 half-lives before signing of the ICF, whichever is longer
11. Has any history of lymphoma or history of another cancer, other than squamous cell or basal cell carcinoma of the skin, that has not been in full remission for at least 1 year before screening
12. Has a platelet count<100,000 per microliter (µL)
13. Has aminotransferase (ALT) or aspartate aminotransferase (AST)>3×ULN or total bilirubin>1.5×ULN at screening unless the participant has a previously known history of Gilbert's syndrome
14. Has a history of human immunodeficiency virus (HIV) or hepatitis B or hepatitis C virus infection, or positive screening tests for hepatitis B surface antigen or hepatitis B core antibody, or hepatitis C or HIV antibodies
15. Is a first-degree family member of a clinical site employee or any other individual involved with the conduct of the study or is a clinical site employee or other individual involved with the conduct of the study
16. Has a clinically significant ECG abnormality that, in the opinion of the PI, would compromise the participant's safety
17. Has a serious or unstable medical or psychological condition that, in the opinion of the PI, would compromise the participant's safety in the study
18. Has uncontrolled seizures that in opinion of the PI would put the participant at undue risk
19. Has a history of a hypersensitivity reaction to tacrolimus, sirolimus, or prednisone
20. Has a history of a primary immunodeficiency (e.g., common variable immunodeficiency syndrome), splenectomy, or any underlying condition that predisposes the participant to infection
21. Has herpes zoster (VZV), cytomegalovirus (CMV), or Epstein-Barr virus (EBV) infection that has not completely resolved at least 12 weeks prior to screening
22. Has any infection requiring hospitalization or treatment with parenteral anti-infectives not resolved at least 8 weeks prior to Visit 2
23. Has any active infection requiring oral anti-infectives (including antivirals) within 10 days prior to Visit 2
24. Has a history of active tuberculosis (TB) or a positive Quantiferon-TB Gold test during screening
25. Has any live vaccine within 4 weeks prior to Day −2
26. Had major surgery within 8 weeks before signing the ICF or major surgery planned during the study period
27. Anticipate the need for adenoidectomy or tonsillectomy within 6 months of enrollment. If adenoidectomy or tonsillectomy is anticipated, it should be performed prior to screening.
28. Has an absolute neutrophil count<$1.0\times10^3/\mu L$
29. Has any condition or laboratory abnormality that the PI believes would not be appropriate for immunosuppressive therapy.

6.9.7. Immunosuppressive Therapy
Corticosteroids
In the morning of vector administration (Day 1 pre-dose), participants will receive methylprednisolone 10 mg/kg IV (maximum of 500 mg) over at least 30 minutes. The methylprednisolone should be administered before the lumbar puncture and IC injection of IP. Premedication with acetaminophen and an antihistamine is optional and at the discretion of the investigator.
On Day 2, oral prednisolone will be started with the goal to discontinue prednisolone by Week 12. The dose of prednisolone will be as follows:
Day 2 to the end of Week 2: 0.5 mg/kg/day
Week 3 and 4: 0.35 mg/kg/day
Week 5-8: 0.2 mg/kg/day
Week 9-12: 0.1 mg/kg
Prednisolone will be discontinued after Week 12. The exact dose of prednisolone can be adjusted to the next higher clinically practical dose.

Sirolimus
2 days prior to vector administration (Day −2): a loading dose of sirolimus 1 mg/m$^2$ every 4 hours×3 doses will be administered
From Day −1: sirolimus 0.5 mg/m$^2$/day divided in twice a day dosing with target blood level of 1-3 ng/ml
Sirolimus will be discontinued after the Week 48 visit.
Tacrolimus
Tacrolimus will be started on Day 2 (the day following IP administration) at a dose of 0.05 mg/kg twice daily and adjusted to achieve a blood level 2-4 ng/mL for 24 Weeks.
Starting at Week 24 visit, tacrolimus will be tapered off over 8 weeks. At Week 24 the dose will be decreased by approximately 50%. At Week 28 the dose will be further decreased by approximately 50%. Tacrolimus will be discontinued at Week 32.
Tacrolimus and sirolimus blood level monitoring will be conducted.
Tacrolimus dose adjustments will be made to maintain whole blood trough concentrations within 2-4 ng/mL for the first 24 Weeks. At Week 24 the dose will be decreased by approximately 50%. At Week 28 the dose will be further decreased by approximately 50%. Tacrolimus will be discontinued at Week 32. Sirolimus dose adjustments will be made to maintain whole blood trough concentrations within 1-3 ng/mL. Dose adjustments should be performed by a clinical pharmacist. Participants should continue on the new maintenance dose for at least 7 to 14 days before further dosage adjustment with concentration monitoring.
Immunosuppressant drug accountability, IS dispensation, sirolimus and tacrolimus whole blood trough concentrations will be completed by the investigator during routine study visits.
No IS therapy is planned after Week 48. If IS were required after Week 48 to control a clinically-relevant immune response, the appropriate immunosuppressive regimen will be determined by the PI, in discussion with the Medical Monitor and Sponsor, as clinically indicated.
*Pneumocystis carinii* pneumonia (PCP) prophylaxis with trimethoprim/sulfamethoxazole (Septra®; Bactrim™) (SEPTRA® USPI, 2018; BACTRIM™ USPI, 2013) will be given three times a week (example dosing schedule; Monday, Wednesday, Friday) at a dose of 5 mg/kg beginning on Day −2 and continuing until Week 48. Refer to the prescribing information for risks associated with trimethoprim/sulfamethoxazole use (BACTRIM™ USPI, 2013). For patients with sulfa allergies, alternative medications can include pentamidine, dapsone, and atovaquone.
Antifungal prophylaxis is to be initiated if the ANC is <500 mm$^3$. The treatment regimen will be determined through local site standard of care in consultation with appropriate subspecialists.
The concomitant use of Rapamune with a calcineurin inhibitor may increase the risk of calcineurin inhibitor-induced thrombotic microangiopathies. Thrombotic microangiopathies (TMA) are a group of disorders characterized by thrombocytopenia, microangiopathic hemolytic anemia, and variable organ system involvement.
This may present severe thrombocytopenia (<$30\times10^9$/L), microangiopathic hemolytic anemia characterized by schistocytes on the blood smear, increased reticulocyte count (>$120\times10^9$/L), elevated lactate dehydrogenase level (LDH), and signs of skin and mucosal hemorrhage, weakness, and dyspnea. Treatment includes discontinuation of tacrolimus and possible initiation of plasma exchange.
If rising CMV or EBV viral genomes are detected during serial testing, the decision to decrease IS or begin antiviral therapy will be determined through local site standard of care in consultation with appropriate subspecialists.

6.10 Example 10: A Phase I/II Multicenter, Open-Label Study to Evaluate the Safety, Tolerability, and Pharmacodynamics of Construct 1 in Pediatric Subjects with NIPS II (Hunter Syndrome)

6.10.1. Synopsis

Study Design

This is a Phase I/II, first-in-human, multicenter, open-label, single arm dose escalation study of Construct 1. No control group is included. Approximately 12 or 18 pediatric subjects (or up to 18 pediatric subjects) who have severe MPS II could be enrolled into 3 dose cohorts, $1.3 \times 10^{10}$ GC/g brain mass (Dose 1), $6.5 \times 10^{10}$ GC/g brain mass (Dose 2), $2.0 \times 10^{11}$ GC/g brain mass (Dose 3; the number of genome copies was determined based on a Poly-A assay), or $2.9 \times 10^{11}$ GC/g brain mass (Dose 3 EC; the number of genome copies was determined based on a transgene specific assay) and will receive a single dose of Construct 1 administered by IC or ICV injection. The Dose 3 Expanded Cohort (EC) receives $2.9 \times 10^{11}$ GC/g brain mass (dose calculated using a transgene-specific assay), a dose equivalent to Dose 3, which was estimated using a PolyA-specific assay. In some cases, the effective dose for both Dose 3 and Dose 3 EC are the same. Safety will be the primary focus for the initial 24 weeks after treatment (primary study period). Following completion of the primary study period, subjects continue to be assessed (safety and efficacy) for up to a total of 104 weeks following treatment with Construct 1. At the end of the study, subjects will be invited to participate in a long-term follow-up study.

The first 3 eligible subjects will be enrolled into the Dose 1 cohort ($1.3 \times 10^{10}$ GC/g brain mass). After Construct 1 administration to the first subject, there will be an 8-week observation period for safety. The Internal Safety Committee (ISC) will review the safety data obtained during the first 8 weeks of the study according to the ISC Charter (including data obtained during the Week 8 visit) for this subject, and if there are no safety concerns, the 2nd subject may be enrolled. The same process will be used to enroll the 3rd subject. Informed consent and screening activities for the next subject may proceed during the observation period for the preceding subject.

If no safety review trigger (SRT) event is observed, all available safety data for the Dose 1 cohort obtained up to and including the Week 8 visit for the 3rd subject will be evaluated by the Independent Data Monitoring Committee (IDMC). If the decision is to proceed to the second dose cohort ($6.5 \times 10^{10}$ GC/g brain mass), the subsequent 2 subjects will follow the same dosing scheme as the initial dose cohort. The ISC will review all subject safety data obtained up to and including the Week 2 visit of the 2nd subject in the Dose 2 cohort and may determine that it is safe to proceed with dosing of the 3rd subject immediately after this assessment. All available safety data for the Dose 2 cohort will be evaluated by the IDMC after the Week 8 visit for the 3rd subject in the Dose 2 cohort.

With approval of the IDMC, up to 6 subjects may be dosed in a Dose 2 Expanded Cohort as long as study drug is available, and there is Sponsor approval and no safety event that warrants suspension of enrollment as per either the ISC or the IDMC.

If no safety review trigger (SRT) event is observed and the IDMC provides approval, a third dose cohort ($2.0 \times 10^{11}$ GC/g brain mass) will begin enrollment. In some cases, an additional Dose 3 Expanded Cohort (EC) receives $2.9 \times 10^{11}$ GC/g brain mass. The ISC will review all available safety data for the first subject dosed up to and including the Week 8 visit. If there are no safety concerns, the second subject will be dosed. The ISC will review all subject safety data obtained up to and including the Week 2 visit of the $2^{nd}$ subject in the Dose 3 cohort and may determine that it is safe to proceed with dosing of the $3^{rd}$ subject immediately after this assessment.

At any given IDMC meeting, whether planned at the conclusion of a dose cohort or called for by an SRT, the IDMC may recommend stopping the trial, dose additional subjects at the current dose, proceed to the next dose cohort, or proceed at a lower dose. Once 8 weeks of data are available from the subject of Dose 3 cohort, all safety data up to and including the $3^{rd}$ subject's Week 8 visit will be evaluated by the IDMC. With approval of the IDMC, up to 3 additional subjects may be dosed in Dose 3 EC in a similarly staggered fashion: 8-week observation period with ISC review after first subject dosed, 2-week observation period after second subject dosed, IDMC review after data from the Week 8 visit of $3^d$ subject becomes available.

If any event meets the criteria of a Stopping Rule (refer to the table below), dosing of any new subjects will be suspended until a complete review of all safety data has been performed.

| Safety Review Trigger Event | Safety Review Action |
|---|---|
| Any of the following Stopping Rules is met | Dosing of any new subjects is suspended until a complete review of all safety data has been performed. |
| Any death | |
| Any Grade 4 or 5 AE, regardless of relationship to treatment | The IDMC provides a recommendation on whether to enroll additional subjects. |
| Two or more Grade 3 AEs in the same subject considered possibly or probably related to Construct 1, the administration procedure or IS (by the PI) | |
| ALT or AST ≥3 × ULN and total bilirubin ≥2 × ULN and no other reason can be found to explain the changes observed | |
| Any event of CNS hemorrhage, stroke, or acute paralysis that the PI considers to be related to either Construct 1 or the injection procedure | |
| Any Grade 3 AE Any report by the PI of technical issues with the Construct I administration procedure that may warrant modifications to the procedure or instruments | An Internal Safety Committee (ISC) reviews all available safety data. If safety concerns arise while a cohort is enrolling, they may ask the IDMC to review and make a recommendation on whether to keep enrolling subjects in that cohort. |

The subjects who meet the eligibility criteria are admitted to the hospital between Day 2 and the morning of Day 1 (according to institutional practice), and baseline assessments are performed pre-dose. Subjects receive a single IC or ICV dose of Construct 1 on Day 1 and remain in the hospital overnight and for approximately 1-2 days after dosing for observation. Subjects are discharged after the principal investigator (PI) concludes that prolongation of hospitalization beyond two overnight stays is not necessary. Subsequent assessments in the primary study period (i.e., through Week 24) are performed weekly through Week 4 and at Weeks 8, 12, 16, 20, and 24. After the primary study period, visits are at Weeks 28, 32, 40, 48, 52, 56, 60, 64, 78, and 104. The Week 64 visit are performed only for subjects who discontinue IV ERT. The Week 20 and 28 assessments are limited to evaluation of adverse events (AEs) and concomitant therapies by telephone contact.

Findings in non-human primates (NHPs) showed histological findings of dorsal root ganglion neuronopathy and associated axonopathy which were partially immune mediated as demonstrated by the presence of inflammatory cells in the DRG and partial attenuation of axonopathy by immunosuppression (IS). For these reasons, all subjects initially receive immune suppression (IS) in the study to minimize the risk of any immune mediated reaction against tissues expressing the transgene as well as minimize any risk associated with the formation or increase of antibodies to IDS which may decrease efficacy. The IS regimen include corticosteroids (methylprednisolone 10 mg/kg IV once on Day 1 predose and oral prednisone starting at 0.5 mg/kg/day on Day 2 with gradual tapering and discontinuation by Week 12), tacrolimus (0.05 mg/kg twice daily [BID] by mouth [PO] Day 2 to Week 24 with dose adjustments made to obtain a target blood level of 2-4 ng/ml and tapering over 8 weeks between Week 24 and 32) and sirolimus (a loading dose of 1 mg/m$^2$ every 4 hours×3 doses on Day 2 and then from Day 1: sirolimus 0.5 mg/m$^2$/day divided in BID dosing with target blood level of 1-3 ng/ml until Week 48). Neurologic assessments and tacrolimus/sirolimus blood level monitoring are conducted as per Table A. The doses of sirolimus and tacrolimus are adjusted to maintain blood levels in the target range No IS therapy is planned after Week 48. If IS were required after Week 48 to control a clinically relevant immune response, the appropriate immunosuppressive regimen is determined by the principal investigator (PI), in discussion with the Medical Monitor and Sponsor, as clinically indicated.

Given the histopathological findings in the dorsal root ganglia and associated axonopathy observed in the nonclinical safety/toxicology studies and the potential safety risks with the IC administration procedure, close neurological monitoring, including focused neurological assessments and somatosensory evoked potential (SSEP) testing is employed as listed in Table A.

If treatment with Construct 1 shows IDS activity in plasma, as suggested in animal studies, subjects who are on IV idursulfase (Elaprase®) may be offered the option to discontinue ERT after the Week 24 visit. The decision to discontinue ERT is at the clinical judgement of the PI and as agreed with the study sponsor. Additional information that may be useful for the decision to stop ERT are trough measurements (based on ERT dosing) of plasma I2S and plasma and urine GAGs up to the Week 24 visit, and measurement of the liver and spleen size by ultrasound. The Week 52, 56, 60, 64 and 78 visits include additional monitoring of the subject's plasma I2S and plasma and urine GAGs levels in subjects who elect to discontinue ERT. Subjects who discontinue IV ERT have an additional abdominal ultrasound at Weeks 32 and 64 to perform measurement of the liver and spleen size. IV ERT restarted if any of following criteria are met: increase in urinary GAGs levels 2 times above the level measured at the Week 24 visit, or an increase of liver diameter>20% above the Week 24 value, or any change in other safety parameters deemed by the internal safety committee and/or the IDMC to warrant a restart of IV ERT. However, subjects may restart ERT at any time, if deemed necessary by the PI.

The safety and tolerability of Construct 1 is monitored through assessment of AEs and serious adverse events (SAEs), chemistry, hematology, urinalysis, markers of CSF inflammation, immunogenicity, vector shedding (vector concentration), vital signs, electrocardiograms (ECGs), SSEP testing, and physical examinations including neurological assessments. Serial PCR (polymerase chain reaction) for detection of circulating viral genomes (EBV and CMV) is performed while subjects are receiving IS according to the schedule in Table A.

Efficacy assessments include measurements of levels of pharmacodynamic (PD) biomarkers (GAGs and I2S in CSF and plasma, and GAGs in urine), as well as on neurocognitive function, auditory capacity, brain MRI, liver and spleen size, and cardiac evaluation by echocardiogram. Neurocognitive or adaptive assessments performed as part of subjects' standard of care while participating in the trial may also be collected, as determined by the study sponsor after discussing with the site.

Primary Objectives

To evaluate the safety and tolerability of Construct 1 through 24 weeks following a single IC, or ICV if IC is contraindicated, dose administered to pediatric subjects who have severe MPS II. AEs and SAEs are determined trough week 24.

Secondary Objectives

To evaluate the long-term safety and tolerability of Construct 1. Safety through Week 104: AE reporting, laboratory evaluations, vital signs, ECGs, physical examinations, and neurologic assessments.

To evaluate the effect of Construct 1 on biomarkers in CSF (GAGs, I2S), plasma (GAGs, I2S), and urine (GAGs)

To evaluate the effect of Construct 1 on neurodevelopmental parameters of cognitive, behavioral, and adaptive function Bayley Scales of Infant and Toddler Development, 3rd Edition (BSID-III) (Bayley, 2005) or Kaufman Assessment Battery for Children, 2nd Edition (KABC-II) (Kaufman, 2004)

Vineland Adaptive Behavior Scales, 2nd Edition, Expanded Interview Form (VABS-II) (Sparrow et al., 2005)

To evaluate vector shedding in CSF, serum, and urine (e.g., by quantitative polymerase chain reaction (PCR) to Construct 1 deoxyribonucleic acid (DNA)).

Exploratory Objectives

To evaluate immunogenicity of Construct 1 (e.g., by determining antibody titers to AAV9 and I2S in CSF and serum; and/or by using enzyme-linked immunospot (ELISPOT) assay: T-cell response to AAV9 and I2S)

To explore the effect of Construct 1 on CNS imaging. CNS structural abnormalities assessed by MRI of the brain Liver and spleen size assessed by ultrasound of the abdomen Cardiac evaluation by echocardiogram for valvular disease and left ventricular mass index To explore the effect of Construct 1 on systemic manifestations of disease To explore the effect of Construct 1 on auditory capacity. Auditory capacity changes measured by auditory brainstem response (ABR) and, if feasible, by behavioral audiometry. Tympanometry accompany both BAUD and ABR assessments To explore the effect of Construct 1 on biomarkers in plasma and urine in subjects who temporarily discontinue IV ERT (ELAPRASE®)

To explore the effect of Construct 1 on quality of life (QOL)

To explore the effect of Construct 1 on sleep measures (Ferreira et al., 2009)

To explore the effect of Construct 1 on clinician reported outcome

To explore the effect of Construct 1 on caregiver reported outcome

Activities of Daily Living (Tanjuakio J., 2015; Kato et al., 2007)

Burden of Illness

Number of Subjects Planned and Study Duration:

Up to 18 subjects are enrolled. For example, 3 subjects in Dose 1 cohort; 3 subjects in Dose 2 cohort and up to 6 subjects in Dose 2 Expanded Cohort; 3 subjects in Dose 3 cohort and up to 3 subjects in Dose 3 Expanded Cohort. Total dose administered (total GC) is adjusted to account for differences in brain mass as estimated from each subject's screening MRI. A transgene-specific PCR assay for vector quantification of Construct 1 results in a different number of genome copies than a Poly-A PCR assay for the same dose (refer to Table B). In some cases, a transgene specific PCR assay is implemented to quantify the product concentration and dose. When testing the same Construct 1 samples, the transgene-specific PCR assay results in values approximately 50% higher than the dose obtained from a Poly-A PCR assay. Therefore, a dose of $2.0 \times 10^{11}$ GC/g using the Poly-A PCR assay for calculating the number of genome copies is equivalent to a dose of $2.9 \times 10^{11}$ GC/g using the transgene specific PCR assay for calculating the number of genome copies. The total volume of product administered does not exceed 10% of the total CSF volume (estimated to be ~50 mL in infant brain and ~150 mL in adult brain). The IDMC may recommend adding additional subjects in any dose cohort. In some cases, the total duration of the study is 104 weeks post-dose with a primary safety evaluation time point of 24 weeks. Screening may take up to 35 days.

TABLE B

| Construct 1 Dose Cohorts (Total GC/g brain mass) | | |
|---|---|---|
| Dose level | Poly-A PCR Assay | Transgene-Specific PCR Assay |
| 1 | $1.3 \times 10^{10}$ | $1.9 \times 10^{10}$ |
| 2 | $6.5 \times 10^{10}$ | $9.6 \times 10^{10}$ |
| 3 | $2.0 \times 10^{11}$ | $2.9 \times 10^{11}$ |

Diagnosis and Main Criteria for Inclusion:

To be eligible to participate in this study, a subject must meet all the following inclusion criteria:

1. The subject's legal guardian(s) is (are) willing and able to provide written, signed informed consent after the nature of the study has been explained, and prior to any research-related procedures.
2. Is a male≥4 months to <5 years of age
3. Meets any of the following criteria:
   a) Has a documented diagnosis of MPS II AND has a neurocognitive testing score≤77 (BSID-III or KABC-II), OR
   b) Has a documented diagnosis of MPS II AND has a decline of ≥1 standard deviation on serial neurocognitive testing administered between 3 to 36 months apart (BSID-III or KABC-II), OR
   c) Has a relative clinically diagnosed with severe MPS II who has the same IDS mutation as the subject AND the subject in the opinion of a geneticist has inherited a severe form of MPS II, OR
   d) Has documented mutation(s) in IDS that in the opinion of a geneticist is always known to result in a neuronopathic phenotype [e.g., a complete deletion or large deletion (e.g., spanning≥1 exon), or recombination] AND in the opinion of a clinician has a severe form of MPS II
4. Has sufficient auditory and visual capacity, with or without aids, to complete the required protocol testing, and be compliant with wearing the aid, if applicable, on testing days Diagnosis and Main Criteria for Exclusion:

Subjects who meet any of the following exclusion criteria will not be eligible to participate in the study:

1. Has a contraindication for an IC or ICV injection, including any of the following:
   a) Review of baseline MRI testing by the team of neuroradiologists/neurosurgeons participating in study (1 neuroradiologist or neurosurgeon per site) shows a contraindication for an IC or an ICV injection
   b) History of prior head/neck surgery, which resulted in a contraindication to both IC and ICV injection, based on review of available information by the team of neuroradiologists/neurosurgeons participating in study
   c) Has any contraindication to computed tomography, contrast agent, or to general anesthesia
   d) Has any contraindication to MRI or gadolinium
   e) Has renal insufficiency as determined by an estimated glomerular filtration rate (eGFR)<30 mL/min/1.73 m2, based on creatinine. If laboratory determines that creatinine is less than the lower limit of assay validation or detection then the lowest limit cutoff value will be used to estimate eGFR
   f) Has previously experienced a clinically significant intracranial bleed that, in the opinion of the investigator and team of neuroradiologists/neurosurgeons, is a contraindication to IC and ICV injection
2. Has any condition that would contraindicate treatment with prednisone, tacrolimus or sirolimus
3. Has any neurocognitive deficit not attributable to MPS II or diagnosis of a neuropsychiatric condition that may in the opinion of the PI confound interpretation of study results
4. Has any contraindication to lumbar puncture
5. Has a (cerebral) ventricular shunt that in the opinion of the site neuroradiologist/neurosurgeon and through discussion with the Medical Monitor, may impact the administration and proper dosing of the subject
6. Has undergone HSCT
7. Has had prior treatment with an AAV-based gene therapy product
8. Has received idursulfase (ELAPRASE®) via intrathecal (IT) administration within 4 months of signing the ICF
9. Has received idursulfase (ELAPRASE®) IV and experienced a serious hypersensitivity reaction, including anaphylaxis, deemed related to IV idursulfase (ELAPRASE®) administration. If currently receiving IV idursulfase and has had dose interruptions or a dose regimen different than weekly, then discussion with REGENXBIO Medical Monitor is needed.

10. Has received any investigational product within 30 days of Day 1 or 5 half-lives before signing of the ICF, whichever is longer
11. Has any history of lymphoma or history of another cancer, other than squamous cell or basal cell carcinoma of the skin, that has not been in full remission for at least 1 year before screening
12. Has a platelet count<100,000 per microliter (µL)
13. Has aminotransferase (ALT) or aspartate aminotransferase (AST)>3×ULN or total bilirubin>1.5×ULN at screening unless the subject has a previously known history of Gilbert's syndrome
14. Uncontrolled hypertension despite medical treatment, defined for children≤17 years of age to be systolic blood pressure or diastolic blood pressure>99th percentile plus 5 mmHg based on normative standards for age, sex, and height
15. Has a history of human immunodeficiency virus (HIV) or hepatitis B or hepatitis C virus infection, or positive screening tests for hepatitis B surface antigen or hepatitis B core antibody, or hepatitis C or HIV antibodies
16. Is a first-degree family member of a clinical site employee or any other individual involved with the conduct of the study or is a clinical site employee or other individual involved with the conduct of the study
17. Has a clinically significant ECG abnormality that, in the opinion of the PI, would compromise the subject's safety
18. Has a serious or unstable medical or psychological condition that, in the opinion of the PI, would compromise the subject's safety or successful participation in the study or interpretation of study results
19. Has uncontrolled seizures that in opinion of the PI would put the subject at undue risk Exclusion Criteria Related to Immunosuppressive Therapy:
20. Has a history of a hypersensitivity reaction to tacrolimus, sirolimus, or prednisone
21. Has a history of a primary immunodeficiency (e.g., common variable immunodeficiency syndrome), splenectomy, or any underlying condition that predisposes the subject to infection
22. Has herpes zoster (VZV), cytomegalovirus (CMV), or Epstein-Barr virus (EBV) infection that has not completely resolved at least 12 weeks prior to screening
23. Has any infection requiring hospitalization or treatment with parenteral anti-infectives not resolved at least 8 weeks prior to Visit 2
24. Has any active infection requiring oral anti-infectives (including antivirals) within 10 days prior to Visit 2
25. Has a history of active tuberculosis (TB) or a positive Quantiferon-TB Gold test during screening
26. Has received any live vaccine within 4 weeks prior to Day 2
27. Had major surgery within 8 weeks before signing the ICF or major surgery planned during the study period
28. Anticipate the need for adenoidectomy or tonsillectomy within 6 months of enrollment. If adenoidectomy or tonsillectomy is anticipated it should be performed prior to screening.
29. Has an absolute neutrophil count<$1.0 \times 10^1$/µL
30. Has any condition or laboratory abnormality that the PI believes would not be appropriate for immunosuppressive therapy Size and Power Calculation Three to nine subjects at each dose cohort and up to 18 subjects are enrolled to assess the safety and tolerability of Construct 1 and explore the effect of Consruct 1 across 3 dose levels on biomarkers and clinical efficacy endpoints.

TABLE A

Study Flow Chart: Schedule of Events

| Study Interval | Screening | Gene Therapy Inpatient Administration | | | | Visits (Weeks) | | | | | | | | | | | | | | | | | | | EOS/22 | ET[b] | Uns[c] |
|---|---|---|---|---|---|---|---|---|---|---|---|---|---|---|---|---|---|---|---|---|---|---|---|---|---|---|---|
| Study Visit Number | 1 | 2[a] | | | | 3 | 4 | 5 | 6 | 7 | 8 | 9 | 10 | 11 | 12 | 13 | 14 | 15 | 16 | 17 | 18 | 19 | 20 | 21 | EOS/22 | ET | Uns |
| Study Visit Window (Days) | D −35 to −2 | D −2 | D1 (Pre) | D1 (Post)[d] | D2[e] | ±3 | ±3 | ±3 | ±3 | ±3 | ±3 | ±3 | ±7 | ±7 | ±7 | ±7 | ±7 | ±7 | ±7 | ±7 | ±14 | ±14 | ±14 | ±14 | ±14 | | |
| Study Day or Week | | | | | | 1 | 2 | 3 | 4 | 8 | 12 | 16 | 20[f] | 24 | 28[g] | 32 | 40 | 48 | 52 | 56 | 60 | 64[f] | 78 | 104 | | | |
| General Procedures and Assessments | | | | | | | | | | | | | | | | | | | | | | | | | | | |
| Informed Consent | X[v] | | | | | | | | | | | | | | | | | | | | | | | | | | |
| Confirm Eligibility | X | X | | | | | | | | | | | | | | | | | | | | | | | | | |
| Medical History | X | X | | | | | | | | | | | | | | | | | | | | | | | | | |
| Concomitant Medications | X | X | | X | X | X | X | X | X | X | X | X | X | X | X | X | X | X | X | X | X | X | X | X | X | X | |
| Physical Examination[h] | X | X | | | X | | X | | | | | | | | | | | | | | | | | | | | |
| Targeted Physical Examination[h] | | | X | X | | | | | | | | | | | | | | | | | | | | | | | |
| Neurologic Assessment[h] | X | | X | X | | X | | | | | | | | | | | | | | | | | | | | | |
| Anesthesiologist Examination[i] | X | | | | | | | | | | | | | | | | | | | | | | | | | | |
| Somatosensory Evoked Potentials[k] | | X | | | | | | | | | | | | | | | | | | | | | | | | | |
| Vital Signs | X | X | | X | X | X | X | X | X | X | X | X | X | X | X | X | X | X | X | X | X | X | X | X | X | X | X[i] |
| Height, Weight, and Head Circumference | X | X | | | | | | | | | | | | | | | | | | | | | | | | | |
| ECG | X | X | | | | | | | | | | | | | | | | | | | | | | | | X | |
| Renal Function[k] | X | | | | | | | | | | | | | | | | | | | | | | | | | | |
| IC/ICV Administration Evaluation[l] | X | X | | | | | | | | | | | | | | | | | | | | | | | | | |
| Head/Neck MRI[m] | X | | | | | | | | | | | | | | | | | X | | | | | | X | | | |
| Abdominal ultrasound[p] | X | | | | | | | | | | | | X[p] | | | | | | | | | | X[p] | | | | |
| 2-D Echocardiogram | X | | | | | | | | | | | | | | | | | | | X | | | | X | | | |
| Adverse Events | X | X | | X | X | X | X | X | X | X | X | X | X | X | X | X | X | X | X | X | X | X | X | X | X | X | X[i] |
| Genetic testing[n] | X | | | | | | | | | | | | | X | | | | | | | | | | X | | | |
| Auditory capacity testing[m] | X | | | | | | | | | | | | | | | | | | | | | | | | | | |
| Clinical Laboratory Assessments | | | | | | | | | | | | | | | | | | | | | | | | | | | |
| Hematology | X | X | | X | X | | X | | X | X | X | X | X | X | X | X | | X | X | X | | X | X | X | X | X | X[i] |
| Chemistry | X | X | | X | X | | X | | X | X | X | X | X | X | X | X | X | X | X | X | X | X | X | X | X | X | X |
| Lipid Panel | X | X | | | | | | | | | | | | | | | | | | | | | | | X | X | |
| QuantiFERO N-TB Gold | X | X | | | | | | | | | | | | | | | | | | | | | | | | | |
| Urinalysis | X | X | | X | | X | | | | | | | | X | | | | X | | | | | | | X | X | X |
| PT/PT/INR | X | X | | X | | | | | | | | | | | | | | | | | | | | | | | |
| Hep B sAg/Hep B Core Antibody/Hep C/HIV | X | | | | | | | | | | | | | | | | | | | | | | | | | | |
| ELISPOT Assay; T-Cell Response to AAV9 | X | | | X | | | X | X | X | X | X | X | X | X | X | X | X | X | X | | | | | X | X | X | |
| Vector and 12S | | | | | | | | | | | | | | | | | | | | | | | | | | | |
| Plasma Biomarkers[o] | X | | | X | | | X | X | X | X | X | X | X | X | X | X | X | X[p] | X[p] | X[p] | X[p] | X[p] | X | X | X | X | |
| Serum Immune Response Monitoring[q] | | | | | | | | | | | | | | | X | X | | | X | | X | | | X | X | X | |
| Urine Biomarkers[j] | X | X | | X | | | X | X | X | X | X | X | X | X | X | X | | X[p] | X[p] | X[p] | X[p] | X[p] | | X | X | X | |
| Viral testing[z] | X | | | | | | | | | | | | | | | | | | | | | | | | X | X | |
| Vector Concentration (qPCR to Construct 1 DNA) in Serum and Urine | | | | X | | X | | | | | | | | | | | | | | | | | | | X | X | X |

TABLE A-continued

Study Flow Chart: Schedule of Events

| Study Interval | Screening | Gene Therapy Inpatient Administration | | | | Visits (Weeks) | | | | | | | | | | | | | | | | | | | |
|---|---|---|---|---|---|---|---|---|---|---|---|---|---|---|---|---|---|---|---|---|---|---|---|---|---|
| Study Visit Number | 1 | 2[a] | | | | 3 | 4 | 5 | 6 | 7 | 8 | 9 | 10 | 11 | 12 | 13 | 15 | 16 | 17 | 18 | 19 | 20 | 21 | EOS/22 | ET[b] | Uns[c] |
| Study Visit Window (Days) | D −35 to −2 | D −2 | D1 (Pre) | D1 (Post)[d] | D2[e] | ±3 | ±3 | ±3 | ±3 | ±3 | ±3 | ±7 | ±7 | ±7 | ±7 | ±7 | ±7 | ±7 | ±7 | ±14 | ±14 | ±14 | ±14 | ±14 | | |
| Study Day or Week | | | | | 1 | 2 | 3 | 4 | 8 | 12 | 16 | 20[g] | 24 | 28[g] | 32 | 40 | 48 | 52 | 56 | 60 | 64[f] | 78 | 104 | | |
| Future Use Research Sample | X | | | | | | | | | X | | X | X | X | X | X | X | X | | | | X | | X | | |
| Construct 1 Administration (CT-Guided) | | X | | | | | | | | | | | | | | | | | | | | | | | | |
| Construct 1 Administration[s] | | | | | | | | | | | | | | | | | | | | | | | | | | |
| Immunosuppression Therapy[t] | | | | | | | | | | | | | | | | | | | | | | | | | | |
| Dispense Prednisone (QD PO Day 2 to Week 12 Visits) | | | | | X | | | | | | | | | | | | | | | | | | | | | |
| Methylprednisolone (IV Day | | | X | | | | | | | | | | | | | | | | | | | | | | | |
| Dispense Tacrolimus (PO BID Day 2 to Week 24 Visits) | | | | | X | | | | | | X | | X | | | | | | | | | | | | | |
| Dispense Sirolimus (Day −2 until Week 48 Visits) | X | | | | X | | | | | X | | X | X | X | X | X | | | | | | | | | | |
| Dispense Sulfamethoxazole/Trimethoprim (Day −2 until Week 48 Visits) | X | | | | X | | | | | X | | X | X | X | X | X | | | | | | | | | | |
| Immunosuppressant Drug Accountability | | | | | X | | | | X | X | X | X | X | X | X | X | X | | | | | | | | | |
| Tacrolimus Whole Blood Levels | | | | | X | X | X | X | X | X | X | X | X | X | X | X | | | | | | | | | | |
| Sirolimus Whole Blood Levels | | | | | X | X | X | X | X | X | X | X | X | X | X | X | X | | | | | | | | | |
| CSF Laboratory Assessments | | | | | | | | | | | | | | | X | X | | | | | | | | | | |
| Lumbar Puncture | X[u] | X[u] | | | | | | | | | | | | | | | X | | | | | | | X | | |
| CSF Biomarkers[v] | X | X | | | | | | | | | | | | | | | X | | | | | | | X | X | |
| CSF Safety Laboratory[w] | X | X | | | | | | | | | | | | | | | X | | | | | | | X | X | |
| CSF Immune Response Monitoring[q] | X | X | | | | | | | | | | | | | | | X | | | | | | | X | X | |
| Vector Concentration (qPCR to Construct 1 DNA) in CSF | X | | | | | | | | | | | | | | | | X | | | | | | | | | |
| Neurocognitive Assessments | | | | | | | | | | | | | | | | | | | | | | | | | | |
| Cognitive Testing[k] | X | | | | | | | | X | | | | X | | X | | X | X | | X | X | X | X | X | X | X |
| Adaptive & Behavioral Function Testing[x,aa] | X | | | | | | | | X | | | | X | | X | | X | X | | X | X | X | X | X | X | X |
| Clinical Assessment of Disease[bb] | X | X | | | | | | | X | | X | | X | | X | | X | X | X | X | X | X | X | X | X | X |
| Caregiver Assessment of Disease[aa] | X | | | | | | | | X | | | | X | | X | | X | X | | X | | X | X | X | X | X |
| PedsQL[aa] | X | | | | | | | | X | | | | X | | X | | X | X | | | X | X | X | X | X | X |
| Sleep Assessment[aa] | X | | | | | | | | | | | | X | | X | | X | X | | | | X | X | X | X | X |
| Activities of Daily Living[aa] | X | | | | | | | | | | | | X | | X | | X | X | | | | X | X | X | X | X |
| Burden of Illness Survey[aa] | X | | | | | | | | | | | | X | | X | | X | X | | | | X | X | X | X | X |

AAV9 = Adeno-associated virus vector of serotype 9;
ABR = auditory brainstem response;
CSF = cerebrospinal fluid;
CT = computed tomography;
DNA = deoxyribonucleic acid;

TABLE A-continued

Study Flow Chart: Schedule of Events

| Study Interval | Screening | Gene Therapy Inpatient Administration | | | | Visits (Weeks) | | | | | | | | | | | | | | | | |
|---|---|---|---|---|---|---|---|---|---|---|---|---|---|---|---|---|---|---|---|---|---|---|
| Study Visit Number | 1 | 2[a] | | | | 3 | 4 | 5 | 6 | 7 | 8 | 9 | 10 | 11 | 12 | 13 | 15 | 16 | 17 | 18 | 19 | 20 | 21 | EOS/22 | ET[b] | Uns[c] |
| Study Visit Window (Days) | | | | | | ±3 | ±3 | ±3 | ±3 | ±3 | ±3 | ±7 | ±7 | ±7 | ±7 | ±7 | ±7 | ±7 | ±14 | ±14 | ±14 | ±14 | ±14 | ±14 | | |
| Study Day or Week | D −35 to −2 | D −2 | D1 (Pre) | D1 (Post)[d] | D2[e] | 1 | 2 | 3 | 4 | 8 | 12 | 16 | 20[g] | 24 | 28[g] | 32 | 40 | 48 | 52 | 56 | 60 | 64[f] | 78 | 104 | | |

ECG = electrocardiogram;
ELISPOT = enzyme-linked immunospot;
EOS = end of study;
ERT = enzyme replacement therapy;
ET = early termination;
GAG = glycosaminoglycan;
Hep = hepatitis;
HIV = human immunodeficiency virus;
IC = intracisternal;
ICV = intracerebroventricular;
INR = International Normalized Ratio;
IQ = intelligence quotient;
IT = intrathecally;
IV = intravenous;
MRI = magnetic resonance imaging;
PI = principal investigator;
PO = orally;
PT = prothrombin time;
PTT = partial thromboplastin time;
QD = once daily;
qPCR = quantitative polymerase chain reaction;
sAg = surface antigen;
T cell = T lymphocyte.
Visit 14 is deliberately omitted from the visit numbering scheme.
Construct 1 = Recombinant adeno-associated virus serotype 9 capsid containing human iduronate-2-sulfatase expression cassette;

[a]Sites can admit the subject between Day −2 and the morning of Day 1. Therefore, some of the pre-dose testing can be done on Day −2 or on Day −1, as per institution's standards.
[b]For an ET visit, lumbar puncture (and CSF assessments) is performed only if withdrawal occurs before Week 56 and cognitive function assessment is performed only if withdrawal occurs before Week 48.
[c]The Investigator, in consultation with the Medical Monitor, should determine which assessments need to be performed at an unscheduled visit.
[d]Vital signs and neurologic assessments are monitored frequently, including assessments every 45 ± 10 minutes for 3 hours starting in the post-anesthesia care unit, then hourly ±15 minutes for the next 4 hours, and then every 4 hours ±30 minutes for the remainder of the 24-hour period immediately post-dose.
[e]Subjects can be discharged home approximately 1-2 days after dosing if deemed appropriate by the PI. Subjects/caregivers are to receive instructions on neurologic function monitoring.
[f]Week 64 visit is to be performed only for subjects who discontinue IV ERT.
[g]Week 20 and 28 assessments, italicized in the table, will be limited to evaluation of adverse events and concomitant therapies by telephone contact.
[h]Pre-dose neurologic assessment can be performed any time from Day −2 to Day 1.
[i]If clinically indicated.
[j]Performed according to each institution's standards and may be performed prior to Day 1.
[k]Results should be assessed or reviewed by a neurologist.
[l]Estimated glomerular filtration rate (eGFR) based on creatinine must be measured prior to screening MRI with gadolinium. If laboratory determines that creatinine is less than the lower limit of assay validation or detection then the lowest limit cutoff value will be used to estimate eGFR. The investigator must consult with the Medical Monitor before proceeding with MRI if the eGFR is <30 mL/min/1.73 m².
Assessments to evaluate contraindication to IC or ICV injection is performed according to the appropriate Administration Manual and be completed prior to Day −2. Approval to proceed with the IC or ICV injection has to be documented before starting IS on Day −2.
[m]MRI with gadolinium is performed as a screening assessment only. All attempts should be made to perform MRI following confirmation of neurocognitive scores. If an MRI under sedation occurs prior to neurocognitive testing, then there must be at least 24 hours between the time of the MRI and when the neurocognitive testing can be performed.
[n]Genetic confirmation of MPS type 2. Genetic test done prior to the study is acceptable with adequate documentation. Subject with no prior genetic testing can have it done during screening.

TABLE A-continued

Study Flow Chart: Schedule of Events

| Study Interval | Screening | Gene Therapy Inpatient Administration | | | Visits (Weeks) | | | | | | | | | | | | | | | | | |
|---|---|---|---|---|---|---|---|---|---|---|---|---|---|---|---|---|---|---|---|---|---|---|
| Study Visit Number | 1 | 2[a] | | | 3 | 4 | 5 | 6 | 7 | 8 | 9 | 10 | 11 | 12 | 13 | 15 | 16 | 17 | 18 | 19 | 20 | 21 | EOS/22 | ET[b] | Uns[c] |
| Study Visit Window (Days) | | | | | ±3 | ±3 | ±3 | ±3 | ±3 | ±3 | ±7 | ±7 | ±7 | ±7 | ±7 | ±7 | ±7 | ±14 | ±14 | ±14 | ±14 | ±14 | ±14 | ±14 |
| Study Day or Week | D −35 to −2 | D −2 | D1 (Pre) | D1 (Post)[d] | D2[e] | 1 | 2 | 3 | 4 | 8 | 12 | 16 | 20[g] | 24 | 28[g] | 32 | 40 | 48 | 52 | 56 | 60 | 64[f] | 78 | 104 |

[a]Auditory capacity changes are measured by auditory brainstem response (ABR) and, if possible, behavioral audiometry (BAUD). Tympanometry is done at the time BAUD and/or ABR assessments are completed. Auditory capacity are assessed at visits specified in this Schedule of Events; an additional assessment is permitted at the Week 24 visit if deemed clinically necessary by the investigator.
[o]Plasma biomarkers: samples are taken for GAGs and I2S. All attempts should be made to perform I2S assessments at trough in relation to IV ERT, defined as at least 96 hours after ERT infusion up until the start of the subsequent infusion.
[p]Abdominal ultrasound are done to assess the size of the liver and spleen. For subjects who have ERT withdrawn after Week 24, plasma and urine biomarkers are to be drawn. The abdominal ultrasound is performed at the same facility for every timepoint.
[q]Antibodies to AAV9 and I2S.
[r]Urine biomarkers: samples are taken for GAGs. All attempts should be made to collect urine GAGs at trough in relation to IV ERT, defined as at least 96 hours after ERT infusion up until the start of the subsequent infusion.
[s]IC or ICV injection are performed according to the appropriate Administration Manual.
[t]Tacrolimus: dose adjustments are made to maintain whole blood trough concentrations within 2-4 ng/ml Sirolimus: dose adjustments are made to maintain whole blood trough concentrations within 1-3 ng/mL. Subjects should continue the new maintenance dose for at least 7-14 days before further dosage adjustment with concentration monitoring. The methylprednisolone should be administered before the lumbar puncture and IC or ICV injection of the investigational product. Pre-medication with acetaminophen and an antihistamine is optional, at the discretion of the investigator.
[u]The screening (Day −35 to Day −2) lumbar puncture is for assessment of CSF pressure and biomarkers only. Following the Day 1 pre-dose lumbar puncture, iodinated myelographic contrast are administered IT (see Administration Manual).
[v]CSF biomarkers: samples are taken for GAGs and I2S, and future use sample testing are only conducted from remnants of study samples, if available.
[w]CSF safety laboratory tests: CSF pressure, erythrocyte cell count, white blood cell count with differential, total protein, and glucose.
[x]Cognition is assessed using BSID-III or KABC-II; adaptive function using VABS-II. If an MRI under sedation occurs prior to neurocognitive testing, then there must be at least 24 hours between the time of the MRI and when the neurocognitive testing can be performed.
[y]For VZV: Ab titer at baseline. For EBV and CMV: Viral genome PCR at baseline and serial testing as described in able X. If positive at any timepoint then more frequent testing can be performed as per site standard of care.
[z]If a subject has a relative with the same MPS II mutation, separate informed consent to review appropriate relative documentation is provided.
[aa]To be completed by same caregiver throughout study if possible.
[bb]To be completed by same clinician throughout study if possible.

Investigational Product

Construct 1: AAV9.CB7.hIDS (recombinant adeno-associated virus serotype 9 capsid containing human iduronate-2-sulfatase expression cassette). See FIG. 5.

Dose

Construct 1 will be preferentially administered as a single IC injection, or as a single ICV injection should IC administration prove difficult or potentially unsafe, to allow direct delivery of the vector to the target tissue within the confined CSF compartment. Although cervical puncture (C1-C2) is a routine clinical procedure used for contrast administration for myelography, image-assisted suboccipital puncture is proposed as the IC clinical route of administration. This replicates the route of administration used in the nonclinical studies and is considered advantageous over the C1-C2 puncture in the intended patient population because patients with MPS II have a high incidence of abnormal narrowing of the C1-C2 IT space, which substantially increases the risks associated with a C1-C2 puncture. Prior to the procedure, each subject will have a magnetic resonance imaging (MRI) of the area reviewed by a team of neuroradiologists/neurosurgeons participating in the study. If it is not considered safe to proceed with an IC injection, then the subject will be considered for ICV injection.

TABLE 13

Total Dose Administered by Brain Mass

| Brain Mass (in g) | | | Dose 1 Total GC by Poly-A-specific PCR (1.3 × 10^10 GC/g brain mass) | Dose 2 Total GC by Poly-A-specific PCR (6.5 × 10^10 GC/g brain mass) |
|---|---|---|---|---|
| Min | Max | Target | | |
| — | 700 | 650 | $8.5 \times 10^{12}$ | $4.2 \times 10^{13}$ |
| 701 | 800 | 750 | $9.8 \times 10^{12}$ | $4.9 \times 10^{13}$ |
| 801 | 900 | 850 | $1.1 \times 10^{13}$ | $5.5 \times 10^{13}$ |
| 901 | 1050 | 975 | $1.3 \times 10^{13}$ | $6.3 \times 10^{13}$ |
| 1051 | 1200 | 1125 | $1.5 \times 10^{13}$ | $7.3 \times 10^{13}$ |
| 1201 | — | 1300 | $1.7 \times 10^{13}$ | $8.5 \times 10^{13}$ |

Total Dose Administered by Brain Mass Dose 3

| Brain Mass (in g) | | | Dose 3 Total GC by Poly-A-specific PCR (2.0 × 10^11 GC/g brain mass) |
|---|---|---|---|
| Min | Max | Target | |
| — | 474 | 450 | $9.0 \times 10^{13}$ |
| 475 | 524 | 500 | $1.0 \times 10^{14}$ |
| 525 | 574 | 550 | $1.1 \times 10^{14}$ |
| 575 | 624 | 600 | $1.2 \times 10^{14}$ |
| 625 | 674 | 650 | $1.3 \times 10^{14}$ |
| 675 | 724 | 700 | $1.4 \times 10^{14}$ |
| 725 | 774 | 750 | $1.5 \times 10^{14}$ |
| 775 | 824 | 800 | $1.6 \times 10^{14}$ |
| 825 | 874 | 850 | $1.7 \times 10^{14}$ |
| 875 | 924 | 900 | $1.8 \times 10^{14}$ |
| 925 | 974 | 950 | $1.9 \times 10^{14}$ |
| 975 | 1024 | 1000 | $2.0 \times 10^{14}$ |
| 1025 | 1074 | 1050 | $2.1 \times 10^{14}$ |
| 1075 | 1124 | 1100 | $2.2 \times 10^{14}$ |
| 1125 | 1174 | 1150 | $2.3 \times 10^{14}$ |
| 1175 | 1224 | 1200 | $2.4 \times 10^{14}$ |
| 1225 | 1274 | 1250 | $2.5 \times 10^{14}$ |
| 1275 | >1300 | 1300 | $2.6 \times 10^{14}$ |

TABLE 13-continued

Total Dose Administered by Brain Mass

Total Dose Administered by Brain Mass Dose 3 EC

| Brain Mass (in g) | | | Dose 3 EC Total GC by Transgene ddPCR (Conversion factor: Transgene ddPCR = Poly-A ddPCR × 1.48) |
|---|---|---|---|
| Min | Max | Target | ($2.9 \times 10^{11}$ GC/g brain mass) |
| — | 474 | 450 | $1.3 \times 10^{14}$ |
| 475 | 524 | 500 | $1.5 \times 10^{14}$ |
| 525 | 574 | 550 | $1.6 \times 10^{14}$ |
| 575 | 624 | 600 | $1.8 \times 10^{14}$ |
| 625 | 674 | 650 | $1.9 \times 10^{14}$ |
| 675 | 724 | 700 | $2.1 \times 10^{14}$ |
| 725 | 774 | 750 | $2.2 \times 10^{14}$ |
| 775 | 824 | 800 | $2.4 \times 10^{14}$ |
| 825 | 874 | 850 | $2.4 \times 10^{14}$ |
| 875 | 924 | 900 | $2.6 \times 10^{14}$ |
| 925 | 974 | 950 | $2.8 \times 10^{14}$ |
| 975 | 1024 | 1000 | $2.9 \times 10^{14}$ |
| 1025 | 1074 | 1050 | $3.1 \times 10^{14}$ |
| 1075 | 1124 | 1100 | $3.2 \times 10^{14}$ |
| 1125 | 1174 | 1150 | $3.4 \times 10^{14}$ |
| 1175 | 1224 | 1200 | $3.5 \times 10^{14}$ |
| 1225 | 1274 | 1250 | $3.7 \times 10^{14}$ |
| 1275 | >1300 | 1300 | $3.8 \times 10^{14}$ |

1. Obtain subject brain volume in cm3 from screening MRI.
2. Convert subject's MRI brain volume to brain mass:
3. brain mass=(brain volume in cm$^3$)×1.046 g/cm$^3$ (brain density taken from Hasgall et al, 2018, Tissue Properties, Density. [cited 4 Nov. 2019]. In: IT'IS Database for Thermal and Electromagnetic Parameters of Biological Tissues, Version 4.0, 15 May 2018 [Internet]. Zurich: IT'IS Foundation. c2010).
4. Identify appropriate dose in Table 13 above.

Construct 1 is intended for investigational use only by selected investigators familiar with the information in the investigator brochure for Construct 1 and experienced in conducting clinical trials. Construct 1 may only be administered to human subjects participating in clinical trials sponsored/approved by the Sponsor and who have provided formal written consent.

6.10.2. Criteria for Evaluation Safety and Efficacy
Primary Endpoints
Safety through Week 24: AEs and SAEs
Secondary Endpoints
Safety through Week 104: AEs and SAEs
Biomarkers in CSF (GAGs, I2S), plasma (GAGs, I2S), and urine (GAGs)
Neurodevelopmental parameters of cognitive, behavioral, and adaptive function:
  Bayley Scales of Infant and Toddler Development, 3rd Edition (BSID-III) (Bayley, 2005, Scales of Infant and Toddler Development, 3rd Ed.)
  Vineland Adaptive Behavior Scales, 2nd Edition, Expanded Interview Form (VABS-II) (Sparrow et al., 2005, Vineland Adaptive Behavior Scales, 2nd Ed.)
Vector concentration in CSF, serum, and urine by quantitative polymerase chain reaction (PCR) to Construct 1 DNA
Exploratory Endpoints
Immunogenicity measurements
Neutralizing antibody titers to AAV9 and binding antibody titers to I2S in CSF and serum
Enzyme-linked immunospot (ELISPOT) assay: T-cell response to AAV9 and I2S Flow cytometry: AAV9 and I2S-specific regulatory T cells
CNS structural abnormalities assessed by MRI of the brain
Liver and spleen size assessed by ultrasound of the abdomen
Cardiac evaluation by echocardiogram for valvular disease and left ventricular mass index
Auditory capacity changes measured by auditory brainstem response (ABR) testing or behavioral audiometry and otoacoustic emissions testing
Plasma and urinary GAGs in subjects who temporarily discontinue IV ERT (ELAPRASE®)
PedsQL
Sleep assessment (Ferreira et al., 2009, Sleep Medicine; 10(4):457-463)
Clinical Assessment of Disease
Caregiver Assessment of Disease
Activities of Daily Living (ADL) (Tanjuakio et al. 2015, Mol Genet Metab, 114(2):161-169: Kato et al., 2007, Brain Dev, 29(5): 298-305)
Burden of Illness 6.10.3. List of Abbreviations and Definitions of Terms

TABLE 14

Abbreviations and Specialist Terms

| Abbreviation | Term |
| --- | --- |
| AAV | Adeno-associated virus |
| AAV9 | AAV vector of serotype 9 |
| ABR | Auditory brainstem response(s) |
| ADL | Activities of Daily Living |
| AE(s) | Adverse event(s) |
| AESI | Adverse Event(s) of Special Interest |
| ALP | Alkaline phosphatase |
| ALT | Alanine aminotransferase |
| ANC | Absolute neutrophil count |
| AST | Aspartate aminotransferase |
| BBB | Blood-brain barrier |
| BID | Twice a day |
| BP | Blood pressure |
| BSID | Bayley Scales of Infant and Toddler Development |
| BSL | Biosafety level |
| CB7 | Hybrid C4 and CB (chicken beta actin promoter) |
| CBC | Complete blood count |
| cDNA | Consensus DNA |
| CFC | Contextual fear conditioning |
| CFR | Code of Federal Regulations |
| CI | Confidence interval |
| CMV | Cytomegalovirus |
| CNS | Central nervous system |
| CoA | Certificate of analysis |
| CRF | Case Report Form |
| CSF | Cerebrospinal fluid |
| CT | Computed tomography |
| CTA | Clinical Trial Agreement |
| CTCAE | Common Terminology Criteria for Adverse Events |
| CZ | Crystal Zenith ® |
| ddPCR | Digital droplet polymerase chain reaction |
| DLT(s) | Dose-limiting toxicity(ies) |
| DNA | Deoxyribonucleic acid |
| DRG | Dorsal root ganglia |
| DS | Dermatan sulfate |
| EBV | Epstein-Barr virus |
| ECG | Electrocardiogram |
| EDC | Electronic Data Capture |
| eGFR | Estimated glomerular filtration rate |
| ELISA | Enzyme-Linked Immunosorbent Assay |
| ELISPOT | Enzyme-linked immunospot |
| EOS | End of Study |
| ERT | Enzyme replacement therapy |
| ET | Early Termination |
| FDA | US Food and Drug Administration |
| g | gram |

TABLE 14-continued

Abbreviations and Specialist Terms

| Abbreviation | Term |
| --- | --- |
| GAG(s) | Glycosaminoglycan(s) |
| GAN | Giant Axonal Neuropathy |
| GC | Genome copies |
| GCP | Good Clinical Practice |
| GLP | Good Laboratory Practice |
| GM3 | Monosialodihexosylganglioside |
| HD | High dose |
| HDL | High-density lipoprotein |
| Hep | Hepatitis |
| Hex | Hexosaminidase |
| hIDS | Human iduronate-2-sulfatase |
| HIPAA | Health Insurance Portability and Accounting Act |
| HIV | Human immunodeficiency virus |
| HS | Heparan sulfate |
| HSCT | Hematopoietic stem cell transplantation |
| I2S | Iduronate-2-sulfatase |
| IB | Investigator's Brochure |
| IC | Intracisternal(ly) |
| ICF | Informed Consent Form |
| ICH | International Council for Harmonisation |
| ICV | Intracerebroventricular |
| IDMC | Independent Data Monitoring Committee |
| IDS | Iduronate-2-sulfatase gene |
| IEC(s) | Independent Ethics Committee(s) |
| IgG | Immunoglobulin G |
| IND | Investigation New Drug |
| IP | Investigational product |
| IQ | Intelligence quotient |
| IRB | Institutional Review Board |
| IS | Immune suppression/immunosuppression |
| ISC | Internal Safety Committee |
| IT | Intrathecal(ly) |
| ITR(s) | Inverted terminal repeat(s) |
| IV | Intravenous(ly) |
| KABC | Kaufman Assessment Battery for Children |
| KIDS | Kinder Infant Development Scale |
| KSPD | Kyoto Scale of Psychological Development |
| LD | Low dose |
| LDH | Lactate dehydrogenase |
| LDL | Low-density lipoprotein |
| LIMP2 | Lysosomal membrane protein |
| MED | Minimum effective dose |
| MedDRA | Medical Dictionary of Regulatory Activities |
| mL | milliliter |
| MMF | Mycophenolate mofetil |
| MPS I | Mucopolysaccharidosis type I |
| MPS II | Mucopolysaccharidosis type II |
| MPS III | Sanfilippo syndrome |
| MPS VII | Mucopolysaccharidosis type VII |
| MRI | Magnetic resonance imaging |
| MTD | Maximum tolerated dose |
| mTORC1 | Mammalian/mechanistic target of rapamycin complex 1 |
| N | Number in sample |
| NAb | Neutralizing antibody |
| NAGLU | N-acetyl-alpha-glucosaminidase |
| NCI | National Cancer Institute |
| NHP(s) | Non-human primate(s) |
| NIH | National Institutes of Health |
| NOAEL | No-observable-adverse-effect level |
| NOR | Novel object recognition |
| PBMC(s) | Peripheral blood mononuclear cell(s) |
| PCR | Polymerase chain reaction |
| PCP | Pneumocystis carinii pneumonia |
| PD | Pharmacodynamic(s) |
| PgP | P-glycoprotein |
| PI | Principal Investigator |
| PML | Progressive multifocal leukoencephalopathy |
| PNS | Peripheral nervous system |
| PO | By mouth/orally |
| PT | Prothrombin time or Preferred Term |
| PTT | Partial thromboplastin time |
| PVAN | Polyoma virus-associated nephropathy |
| QD | Daily |
| QOL | Quality of Life |
| qPCR | Quantitative polymerase chain reaction |
| RBC | Red blood cell |

TABLE 14-continued

Abbreviations and Specialist Terms

| Abbreviation | Term |
|---|---|
| RG1 | Risk Group 1 |
| Construct 1 | Recombinant adeno-associated virus serotype 9 capsid containing human iduronate-2-sulfatase expression cassette |
| SAE(s) | Serious adverse event(s) |
| SAP | Statistical analysis plan |
| SDV | Source document verification |
| SMA | Spinal Muscular Atrophy |
| SOC | System Organ Class |
| SRT | Safety review trigger |
| SSEP | Somatosensory evoked potential |
| TB | Tuberculosis |
| TEAE(s) | Treatment-emergent adverse event(s) |
| TMA | Thrombotic microangiopathy |
| TPP | Thrombocytopenia purpura |
| Treg | Regulatory T cell |
| ULN | Upper limit of normal |
| US | United States |
| USMs | Urgent safety measures |
| VABS | Vineland Adaptive Behavior Scales |
| VZV | Varicella zoster virus |
| WBC | White blood cell (count) |
| WHO | World Health Organization |

6.10.4. Immunosuppressive Therapy

Corticosteroids

In the morning of vector administration (Day 1 pre-dose), participants will receive methylprednisolone 10 mg/kg IV (maximum of 500 mg) over at least 30 minutes. The methylprednisolone should be administered before the lumbar puncture and IC injection of IP. Premedication with acetaminophen and an antihistamine is optional and at the discretion of the investigator.

On Day 2, oral prednisolone will be started with the goal to discontinue prednisolone by Week 12. The dose of prednisolone will be as follows:

Day 2 to the end of Week 2: 0.5 mg/kg/day

Week 3 and 4: 0.35 mg/kg/day

Week 5-8: 0.2 mg/kg/day

Week 9-12: 0.1 mg/kg

Prednisolone will be discontinued after Week 12. The exact dose of prednisolone can be adjusted to the next higher clinically practical dose.

Note: Prednisolone may be substituted for prednisone in a 1:1 conversion rate, at the discretion of the investigator.

Sirolimus 2 days prior to vector administration (Day −2): a loading dose of sirolimus 1 mg/m$^2$ every 4 hours×3 doses will be administered From Day −1: sirolimus 0.5 mg/m$^2$/day divided in twice a day dosing with target blood level of 1-3 ng/ml Sirolimus will be discontinued after the Week 48 visit.

Tacrolimus

Tacrolimus will be started on Day 2 (the day following IP administration) at a dose of 0.05 mg/kg twice daily and adjusted to achieve a blood level 2-4 ng/mL for 24 Weeks.

Starting at Week 24 visit, tacrolimus will be tapered off over 8 weeks. At Week 24 the dose will be decreased by approximately 50%. At Week 28 the dose will be further decreased by approximately 50%. Tacrolimus will be discontinued at Week 32.

Tacrolimus and sirolimus blood level monitoring will be conducted.

Prednisone dosing will start at 0.5 mg/kg/day and will be gradually tapered off by the Week 12 visit.

Tacrolimus dose adjustments will be made to maintain whole blood trough concentrations within 2-4 ng/mL for the first 24 Weeks. At Week 24, the dose will be decreased by approximately 50%. At Week 28, the dose will be further decreased by approximately 50%. Tacrolimus will be discontinued at Week 32. Sirolimus dose adjustments will be made to maintain whole blood trough concentrations within 1-3 ng/mL. Dose adjustments should be performed by a clinical pharmacist. Subjects should continue on the new maintenance dose for at least 7 to 14 days before further dosage adjustment with concentration monitoring.

*Pneumocystis carinii* pneumonia (PCP) prophylaxis with trimethoprim/sulfamethoxazole (Bactrim™; BACTRIM™ USPI, 2013) will be given three times a week (example dosing schedule; Monday, Wednesday, Friday) at a dose of 5 mg/kg beginning on Day −2 and continuing until Week 48. Refer to the prescribing information for risks associated with trimethoprim/sulfamethoxazole use (BACTRIM™ USPI, 2013). For patients with sulfa allergies, alternative medications can include pentamidine, dapsone, and atovaquone.

Antifungal prophylaxis is to be initiated if the ANC is <500 mm$^3$. The treatment regimen will be determined through local site standard of care in consultation with appropriate subspecialists.

The concomitant use of Rapamune with a calcineurin inhibitor may increase the risk of calcineurin inhibitor-induced thrombotic microangiopathies. Thrombotic microangiopathies (TMA) are a group of disorders characterized by thrombocytopenia, microangiopathic hemolytic anemia, and variable organ system involvement.

This may present severe thrombocytopenia (<30-109/L), microangiopathic hemolytic anemia characterized by schistocytes on the blood smear, increased reticulocyte count (>120×10$^9$/L), elevated lactate dehydrogenase level (LDH), and signs of skin and mucosal hemorrhage, weakness, and dyspnea. Treatment includes discontinuation of tacrolimus and possible initiation of plasma exchange.

If rising CMV or EBV viral genomes are detected during serial testing, the decision to decrease IS or begin antiviral therapy will be determined through local site standard of care in consultation with appropriate subspecialists.

6.11 Example 11: Pharmacology Studies in MPS II Mice

Minimum Effective Dose Study (Study #1): This study was designed to determine the minimum effective dose (MED) of Construct 1 (AAV9.CB7.CI.hIDS.rBG) administered through the ICV route as a single dose with a 3 months post-injection (pi) observation period, in a murine model of MPS 11. Limited safety assessments were also included (evaluation of the humoral immune response to the transgene and brain histopathology).

Construct 1 was administered ICV to 2-3 month old C57BL/6 IDS γ/− (MPS II) mice (16 males/group) at doses of 1.3×10$^9$, 1.3×10$^{10}$, or 1.3×10$^{11}$ GC/g brain mass (calculated based on a conversation factor to ddPCR titering from original method presented in study report) on Day 0. At Day 21, 8 mice from each of the treated dose groups were euthanized and necropsied for evaluation of CNS I2S activity, biodistribution and anti-hI2S immunogenicity. Between Days 60 and 89, wildtype mice and untreated MPS II mice were evaluated in a series of neurobehavioral assays (open field, Y-maze, contextual fear conditioning and novel object recognition) to characterize effect of the disease state on these endpoints. Based on the results of these initial assays, remaining treated mice were evaluated in the two assays that evaluated long term memory (contextual fear conditioning and novel object recognition).

Approximately 3 months after ICV dosing of Construct 1, all the remaining mice were euthanized and necropsied. Serum and CSF were evaluated for 2S activity as well as serum for anti-I2S antibodies. Liver and heart were evaluated for GAG tissue content. Brain overall lysosomal storage (both primary GAG storage and secondary ganglioside storage) was assessed by immunohistochemical staining of LIMP2 and GM3. Tissue hexosaminidase levels have been shown to be higher in MPS II mice and MPS II patients, and to be a biomarker of lysosomal homeostasis disruption. Tissue hexosaminidase enzymatic activity was thus measured as a biomarker of lysosomal function secondary to Construct 1 administration. Histopathology of the brain was evaluated to investigate both efficacy and safety.

ICV administration of Construct 1 to C57BL/6 IDS γ/− (MPS II) mice at up to $1.3 \times 10^{10}$ GC/g brain mass (using conversion factor to ddPCR method) was well tolerated, with no clinical signs or mortality, and resulted in distribution to the CNS as well as to peripheral tissues, particularly liver, thus demonstrating partial redistribution of injected viral particles from the CSF to the peripheral blood.

Corresponding to the presence of vector, there was evidence of IDS gene expression based on dose dependent increases in I2S activity in the brain at Day 21 and in the CSF 3 months post-injection, with enzymatic activity close to wildtype level at the highest dose (brain tissue) and comparable to or higher than wildtype at the mid and high doses (CSF). There was dose dependent normalization of the lysosomal compartment, as shown by reductions in LIMP2 and GM3 staining in the CNS at all doses 3 months post injection. In H&E stained brain sections, dose dependent reductions in the amount and frequency of glial vacuolation and neuronal accumulation of amphophilic material, indicators of MPS II CNS phenotype, were also observed. Corresponding to the changes in CNS lysosomal content and improvements in disease-related morphology in the H&E stained sections, there were improvements in one measure of long term memory (novel object recognition, NOR) but not in the other, contextual fear conditioning (CFC). No clear dose response was apparent in the improvement in NOR.

Dose dependent increases in serum I2S activity were also observed 3 months post-injection, with enzymatic activity comparable to or higher than wild type at the mid and high doses. Reflecting the normalization of I2S activity in serum, the treated MPS II mice had dose dependent decreases in hexosaminidase activity and GAG content in the liver and heart. Hepatic hexosaminidase and GAG levels were normalized at all dose levels in liver and at the mid and high doses in the heart. The highly transduced liver (1 to 10 GC per diploid genome) may have acted as a depot organ for the secretion of I2S into the serum, contributing to the reduction in GAGs seen in the heart at the higher doses.

Construct 1 and injection procedure were well tolerated. No clinical abnormality was noted in the mice and they all survived up to the scheduled euthanasia. There was no evidence of Construct 1 related toxicity in the brain on histopathology, although changes related to the ICV administration procedure itself were observed in some mice. Humoral immune response to the transgene was minor, observed only in some mid- and high-dose animals without impact on the health or brain histopathology of those animals.

In conclusion, Construct 1 was well tolerated in MPS II mice at all dose levels and resulted in dose-dependent increases in I2S levels (enzymatic activity) that were associated with improvements in both CNS and peripheral parameters of MPS II. The lowest dose administered, $1.3 \times 10^9$ GC/g brain mass (conversion factor to ddPCR method), was the minimum effective dose in this study.

GLP Toxicology and Biodistribution Studies in Non-Human Primates (Safety of Two Dose Levels of Construct 1; Study #2): This study evaluated the safety, biodistribution, and pharmacology of two dose levels of Construct 1 for up to 90 days after administration by image-guided suboccipital puncture in adult male rhesus macaques. Control article (Elliott's B®+0.001% Pluronic® F68 buffer) was administered via suboccipital puncture to a single macaque in Group 1. Construct 1 in the same buffer was administered via suboccipital puncture to 6 male rhesus macaques randomized to Groups 2-3. Macaques in Group 2 (n=3) received Construct 1 at a high dose (HD) of $5.6 \times 10^{10}$ GC/g brain mass ($5 \times 10^{13}$ GC total); macaques in Group 3 (n=3) received Construct 1 administered at a low dose (LD) of $1.9 \times 10^{11}$ GC/g brain mass ($1.7 \times 10^{13}$ GC total). Blood and cerebrospinal fluid (CSF) were collected as part of a general safety panel at baseline, Day 7, 14, 21, 30, 45, 60, and 90. Humoral response to the transgene product hI2S and to the AAV9 capsid, and hI2S enzymatic activity were analyzed in serum and CSF at the same timepoints. T-cell responses to the transgene product hI2S and to the AAV9 capsid were evaluated at baseline, Day 14, 30, 60, and 90 in the blood, and at Day 90 in spleen and bone marrow. Vector genomes were quantified in the total blood and CSF at baseline, Day 7, 14, 21, 30, 45, 60, and 90, and in urine and feces (shedding) at baseline, Day 5, 30, and 90. Following completion of the in-life phase of the study at 90±3 days post-vector administration, macaques were necropsied and tissues harvested for further evaluation. Histopathologic evaluation and biodistribution of the vector genome were done in a comprehensive list of tissues from the central nervous system (CNS), peripheral nervous system (PNS) and peripheral organs.

There were no adverse events (AEs) associated with the administration procedure, and no treatment-related abnormalities on clinical general observations, body weight change, serum chemistry, or coagulation parameters. Treatment-related transient modifications of complete blood count (CBC), namely lymphocytosis, monocytosis, and basophilia, were observed around Day 7 and around Day 30. Increases were moderate, less than 3-fold over the baseline, and were in general less pronounced in LD animals compared to HD animals. A dose-dependent CSF mild lymphocytic pleocytosis (less than 20 cells per µL) was observed in ⅔ HD animals between Day 21 and Day 45 and in ⅓ LD animal on Day 30. All but one animal (RA2203, HD) had normalized values by Day 90.

A dose-dependent humoral immune response to the transgene-expressed hI2S was present in the serum of 3/3 HD and 2/3 LD, and in the CSF of 2/3 HD and 1/3 LD animals. Only one Construct 1 treated animal (LD) developed a peripheral blood T-cell immune response to the protein hI2S.

All treated animals developed a dose-dependent anti-AAV9 neutralizing antibody (NAb) response from Day 7 in the serum. Anti-AAV9 NAb levels were lower in the CSF, did not appear until Day 45, and stayed negative throughout the study in one animal. No animal had a detectable T-cell response to AAV9 capsid in the blood, spleen, or bone marrow.

Dose dependent treatment-related histologic findings were predominately found within the dorsal root ganglia (DRG) (minimal to mild neuronal degeneration with mononuclear cell infiltration) and within the corresponding dorsal white matter tracts of the spinal cord (minimal to mild dorsal axonopathy). Both incidence and severity were reduced at the low dose compared to the high dose. Inflammatory cells in the DRG were mostly CD3+ T cells with the inconsistent presence of fewer CD20+ B cells. These histological findings were not associated with any observed clinical abnormalities.

High levels of AAV vector genomes were detected throughout the brain, spinal cord, and DRG of all Construct 1-treated animals yielding an average across all CNS and DRG samples of $8.30 \times 10^4$ GC/μg DNA in the LD group, and $1.51 \times 10^5$ GC/μg DNA in the HD group. Significant vector biodistribution was also found in the periphery, especially in the liver at levels about 10 times higher than in the CNS. The least transduced organs were eye, kidney, testicle, lung and thyroid gland with levels about $10^3$ GC/μg DNA, representing 1% of those measured in the CNS.

Vector was cleared from the CSF between Day 30 and Day 90 in all animals, whereas it declined over time but persisted at low levels in the whole blood at the final Day 90 time point. At the earliest time point, Day 7, vector DNA was more abundant in the blood than in the CSF, showing rapid transfer from the intrathecal compartment to the systemic circulation. Vector shedding occurred through biliary clearance mostly, with higher genome copy values detected in the feces than in the urine. Shedding was also more durable in the feces (up to Day 30-90) than in the urine (up to Day 5).

I2S activity rapidly increased over the baseline in all animals in the serum and CSF. Activity levels fell below the baseline level in the serum between Day 21 and Day 60 in all but one animal (LD). There was a correlation between the onset of anti-hI2S antibodies, and the decrease of serum activity. In the CSF, humoral immune response was less pronounced and the I2S activity was more variable but stayed above the baseline level in all but one animal (HD). There was no clear dose response in either serum or CSF.

Based on the observation of a dose-dependent minimal to mild dorsal axonopathy, a no observable adverse effect level (NOAEL) could not be defined in *rhesus* macaques injected IT with Construct 1, a vector expressing human I2S.

Safety of Consruct 1 with Immunosuppression (Study #3): To further investigate the histopathological findings, an additional 90-day exploratory NHP GLP study was conducted at the same dose levels ($1.9 \times 10^{11}$ and $5.6 \times 10^{11}$ GC/g brain mass) with immunosuppression (IS). The IS regimen consisted of rapamycin and mycophenolate mofetil (MMF) with withdrawal of the latter at 60 days post-injection. Trough drug levels were measured and doses were adjusted as needed to maintain effective drug levels.

There were no AEs associated with the administration procedure, and no Construct 1-related abnormalities on clinical general observations, body weight change, organ weights, CBC, serum chemistry, or coagulation parameters. IS procedure caused intestinal signs with increase of some inflammation parameters and anemia that were not related to Construct 1 administration. Only one animal from the LD group (RA2233) had a lymphocytic CSF pleocytosis (23 cells per μL) on the necropsy day.

High levels of AAV vector genomes were detected throughout the brain, spinal cord, and dorsal root ganglia of all Construct 1-treated animals. Significant vector biodistribution was also found in the periphery, especially in the liver that had levels about 10 times higher than in the CNS for the HD animals and equivalent to the CNS for the LD animals. The least transduced organs were eye, kidney, testicle, and thyroid gland.

One animal had pre-existing AAV9 NAb (baseline titer 1:40) that completely inhibited the transduction of liver, eye, heart, lung, testicles, and thyroid (undetected genome copies), whereas the CNS and PNS vector biodistribution was not affected. Corresponding to the presence of vector genome copies in the CNS, PNS, and peripheral organs, I2S activity rapidly increased over the baseline in all but one animal in the serum and in all animals in the CSF, showing that Construct 1 expresses functional I2S enzyme that is present both in the CSF and in the serum of intrathecally treated animals.

Humoral immune response to hI2S was absent or reduced to a minimal response. There was no T cell response to hI2S in IS animals and minimal to moderate response to AAV9 in the LD group only. No rebound immune response was seen following the withdrawal of MMF on Day 60.

There was a mild AAV9 NAb response following vector administration that was more obvious in the LD animals than in the HD animals. IS had no clear effect on AAV9 NAb response of the LD animals (low in both IS and non-IS animals) but seemed efficient in modulating the AAV9 NAb response of the HD animals. IS completely prevented CSF AAV9 NAb response in both HD and LD animals treated with Construct 1.

Treatment-related histopathologic findings were observed in both low- and high-dose groups. These findings consisted of minimal to mild neuronal cell body degeneration with mononuclear cell infiltration in the trigeminal ganglia and in dorsal root ganglia, that project in the dorsal white matter tracts, including minimal to mild axonopathy of the spinal cord dorsal white matter tracts and sciatic nerve. Immunohistochemistry of the DRG identified infiltrates of CD3+ cells in both groups, with occasional CD20+ cells also observed at the low-dose. These findings were generally qualitatively similar to those observed in Study #2 and therefore were not prevented by IS in this NHP study. However, there were some differences between the two studies with respect to histopathology. In Study #2, there was an apparent dose response between the low- and high-dose groups with respect to incidence and severity of findings. No dose response was observed in Study #3. The severity of axonopathy at the high-dose appear to be lower in Study #3 as compared to Study #2, whereas at the low dose IS in Study #3 did not decrease the findings. The histopathological findings may have been partially ameliorated (but not prevented) by the IS protocol in high-dose treated animals. No inflammation was seen within the brain or spinal cord, despite the presence of high vector copy number, likely reflecting the anatomic specificity of dorsal root ganglia that are highly vascularized and lack a protective blood brain-barrier unlike CNS.

Proof-of-Concept Study (Study #4): The purpose of this proof-of-concept study was to evaluate the effectiveness of ICV administered Construct 1 in correcting IDS deficiency and preventing neurologic deficit in MPS II mice.

Eight-week old MPS II male mice (C57BL/6 IDS-/0; n=13) were anesthetized with ketamine/xylazine and Construct 1 was administered into the right lateral cerebral ventricle at $2.15 \times 10^{11}$ GC/g brain mass in 5 μL. Fifteen untreated MPS II mice and 15 wild type mice served as comparators. An additional three animals were used separately for biodistribution The timeline for study data collection is illustrated in FIG. 16. Blood for plasma I2S activity assessment was collected every 4 weeks for 28 weeks post dose. At 6 months of age, wild type, treated and untreated mice were evaluated for performance in the Barnes maze, a circular maze with holes around the perimeter permitting the rodent subject to escape the platform. This maze is used to assess spatial learning and memory in mice that is thought to involve hippocampal function; untreated MPS II mice are significantly slower than wild type littermates at escaping the platform even after 6 days of trials (average latency to escape of 71 seconds versus 30 seconds in WT animals; p≤0.05). At the end of the study (when the mice were 40 weeks old), urine was collected for evaluation of creatinine and glycosaminoglycan (GAG) content and mice were euthanized. Selected tissues were collected and weighed at necropsy and tissue homogenates of brain, spinal cord, heart, lung, liver, spleen and kidney were prepared and evaluated for I2S activity and GAG content. DNA was isolated from the same tissue homogenates and evaluated for vector biodistribution by qPCR.

Treated mice exhibited increased ability to perform in the Barnes maze on the fifth and sixth day of trials, with no significant difference in performance between treated animals and wild type littermates (p>0.05).

Vector distributed well through the CNS of treated mice, except for one animal which was attributed to a failed injection. One to 10 vector copies per genome equivalent were observed in most areas of the brain except the right hippocampus, where 49 vector copies/genome equivalent were detected.

Vector also distributed to peripheral organs of treated mice, though generally at a slightly lower level (less than one vector copy per genome equivalent) in heart, lung, spleen and kidney, on average. The exception was the liver, which contained an average of 60 vector copies per genome equivalent.

CNS tissue I2S activity levels in treated mice were 9 to 28% of wild type levels in the 12 regions of the brain, except the olfactory bulb (58%) and spinal cord (7%). Peripheral tissue I2S activity levels were 11-, 270-, 5- and 3-fold higher than in wild type mice (heart, liver, spleen and kidney, respectively). Lung I2S activity levels were 34% of wild type mice. Plasma I2S activity in treated mice was 160-fold higher than in wild type mice. Untreated MPS II mice had no detectable plasma I2S activity.

Urine GAG levels in treated MPS II mice, normalized to urine protein, were comparable to those of wild type mice and significantly lower than untreated MPS II mice. GAG content in the sections of CNS tissues and peripheral organs was significantly lower in treated MPS II mice compared to untreated MPS II controls (mean 12.53 versus 30.58; p<0.01) and was not significantly different from wild type mice (mean 12.53 versus 10.11; p>0.05). Reduction in liver GAG content correlated with a reduction in liver weight in treated animals compared to untreated MPS 11 mice. Liver weight in treated MPS 11 mice was comparable to wild type mice.

In conclusion, Construct 1 at a dose of $2.15 \times 10^{11}$ GC/g brain was well tolerated in MPS II mice and resulted in distribution of vector within both the CNS and periphery, increased CNS and peripheral organ I2S activity, and improvements in both CNS function and peripheral parameters of MPS II.

From pharmacology studies conducted in MPS II mice with Construct 1, it has been shown that the biodistribution and transgene expression profiles of AAV9 vector-based products are comparable for ICV and IC routes, supporting the use of ICV as an alternative route of administration should IC administration prove difficult or potentially unsafe (Study #2, Study #4). The FDA recommended that dose scaling from animals to humans should be based on the volume of the targeted compartment. Therefore, the calculated human equivalent of the animal doses is based on the relative size of the CNS compartment by age (using brain mass as a measure because accurate data are available for brain mass in most species).

Therefore, the initial dose level proposed has been scaled from the mouse pharmacology study into humans. The proposed starting dose in humans, $1.3 \times 10^{10}$ GC/g brain mass (Dose 1), is based on observations in the MPS II mouse model (Study #1). As shown in FIG. 17, the starting dose represents the middle dose evaluated in Study #1 and is 10-fold higher than the observed MED in mice. It is also approximately 14-fold lower than the lowest dose evaluated in the Safety/Toxicology studies conducted in NHPs ($1.9 \times 10^{10}$ GC/g brain mass: Study #2, Study #3). Dose 2 is $6.5 \times 10^{10}$ GC/g brain mass (i.e., 5-fold greater than the low dose) and is 3-fold lower than the lowest dose evaluated in the NHP toxicology studies (i.e., $1.9 \times 10^{11}$ GC/g brain mass). Dose 3 and Dose 3 Expanded Cohort (EC) is $2.0 \times 10^{11}$ GC/g brain mass (Poly-A assay) or $2.9 \times 10^{11}$ GC/g brain mass (transgene-specific assay), which is a 3-fold increase from Dose 2, and equivalent to the lowest dose used in the NHP studies. The analytical assay used to determine the number of genomic copies (GC) in drug product for Dose 3 EC has been updated to be more specific to the Construct 1 transgene. When testing the same lot, the updated assay reports a 1.48-fold higher number of GC than the assay used in prior dose cohorts (e.g., Poly-A PCR assay and transgene-specific assay). However, the effective dose (the dose that the subject experiences) remains unchanged.

While there were no treatment-related clinical adverse events or findings in any NHP, dose-dependent treatment-related histologic findings occurred within the dorsal root ganglia (DRG) and their corresponding dorsal white matter tracts of the spinal cord. Both incidence and severity were reduced at the $1.9 \times 10^{11}$ GC/g brain mass dose compared to the high dose of $5.6 \times 10^{11}$ GC/g brain mass. The total volume of product administered does not exceed 10% of the total CSF volume (estimated to be ~50 mL in infant brain and ~150 mL in adult brain).

TABLE 15

Tabular Summary of Nonclinical Studies with Construct 1

| Species | Study Type | Doses (GC/g brain mass)† | Key Results |
|---|---|---|---|
| MPS II Mouse (Study #1) | MED Pilot biodistribution | $1.3 \times 10^9$<br>$1.3 \times 10^{10}$<br>$1.3 \times 10^{11}$ | Comparable biodistribution to brain and liver, which was greater than other organs<br>Dose-dependent increase in brain I2S activity<br>Dose-dependent reduction in LIMP2 and GM3 staining<br>Dose-dependent decreases in hepatic and cardiac hexosaminidase activity and GAG content<br>Improvement in preference for novel object indicating improvement of long term memory; no dose-dependence was observed<br>Identified MED of $1.3 \times 10^9$ GC/g brain mass |
| MPS II Mouse (Study #4) | Proof-of-Concept study | $2.15 \times 10^{11}$ | At 6 months post-dose, treated MPS II mice outperformed untreated MPS II mice in the Barnes maze<br>Comparable biodistribution to brain and liver<br>CNS I2S levels were 9-28% of wild type<br>Plasma and peripheral tissue I2S levels were higher than wild type<br>GAG content in CNS and peripheral organs was comparable to wild type mice and correlated with lower liver weight in treated MPS II mice compared to untreated MPS II mice<br>Urinary GAG excretion in treated MPS II mice was comparable to wild type mice and significantly lower than in untreated MPS II mice |
| Rhesus macaque (Study #2) | Safety, toxicology, and biodistribution | $1.9 \times 10^{11}$<br>$5.6 \times 10^{11}$ | No abnormal clinical observations<br>No administration procedure-related adverse events<br>No treatment-related abnormalities on clinical observations, body weight, serum chemistry, coagulation; no unscheduled deaths<br>High levels of vector genome detected through brain, SC and DRG; highest concentrations were in liver; less in other peripheral organs.<br>Transient moderate (<3-fold baseline) lymphocytosis, monocytosis, and basophilia around D 7 and D 30. Generally normalized by D 90.<br>CSF: Dose-dependent mild lymphocytic pleocytosis (less than 20 cells per μL) in 2/3 HD animals D 21-D 45 and 1/3 LD animal D 30. All but 1 HD animals normalized by D 90.<br>Humoral immune response to hIDS: dose-dependent anti-hIDS response in serum of 3/3 HD and 2/3 LD; and CSF of 2/3 HD and 1/3 LD.<br>T-cell response to hIDS: 1 LD animal had a peripheral blood T-cell immune response to the protein hIDS; no T-cell response identified in spleen or bone marrow.<br>Dose-dependent treatment-related findings in DRG and SC. DRG: Minimal to mild neuronal degeneration with mononuclear cell infiltrates (mostly CD3+ cells); corresponding axonopathy in SC dorsal WM.<br>A NOAEL was not identified |
| Rhesus macaque (Study #3) | Exploratory safety, toxicology, and biodistribution of Construct 1 in combination with immunosuppression (MMF and sirolimus/ rapamycin) | $1.9 \times 10^{11}$<br>$5.6 \times 10^{11}$ | There were no AEs associated with the administration procedure, and no Construct 1-related abnormalities on clinical general observations, body weight change, organ weights, CBC, serum chemistry, or coagulation parameters.<br>No unscheduled deaths; no abnormal clinical observations<br>IS procedure caused intestinal signs with increase of some inflammation parameters and anemia that were not related to Consruct I administration.<br>Humoral immune response to hIDS was prevented by IS and was absent or reduced to a minimal (close to background) response in other animals. There was no T cell response to hIDS in IS animals and minimal to moderate response to AAV9 in the LD group only.<br>No rebound immune response was seen following the withdrawal of MMF on Day 60.<br>Both high and low dose groups had minimal neuronal cell body degeneration with mononuclear cell infiltration in the dorsal root ganglia, that project in |

TABLE 15-continued

Tabular Summary of Nonclinical Studies with Construct 1

| Species | Study Type | Doses (GC/g brain mass)[†] | Key Results |
|---|---|---|---|
| | | | the dorsal white matter tracts, and trigeminal ganglia, associated with minimal to mild axonopathy of the spinal cord dorsal white matter tracts and sciatic nerve. These findings were generally similar to Study #2 No inflammation was seen within the brain or spinal cord, despite the presence of high vector copy number High levels of AAV vector genomes were detected throughout the brain, spinal cord, and dorsal root ganglia. Significant vector biodistribution was also found in the periphery, especially in the liver |

[†]Doses presented on a per gram basis were estimated from total dose administered by assuming a mouse brain size of 0.4 grams and NHP brain size of 90 grams. Dose levels in mouse pharmacology studies (Study #1, Study #4) were also converted to the ddPCR doses based on bridging studies to account for differences in assay titer between nonclinical studies and using a standard conversion factor based on comparability studies. The corrected doses are included in this document for consistency with the toxicology study vector dose (Study #2, Study #3), as well as the proposed clinical doses.

6.12 Example 12: Identification of a Biomarker that Differentiates Neuronopathic Forms of MPS I and MPS II In this study, cerebrospinal fluid (CSF) samples from healthy controls (n=31; age range from 1 month to 89 years), MPS I (Neuronopathic n=7, Non-neuronopathic n=2; age range from 1 to 28 years) and MPS II (Neuronopathic n=14, Non-neuronopathic n=4; age range from 4 to 29 years) patients were used to determine total amount of heparan sulfate (t-HS) and GAG heparan sulfate (HS). MPS patients were classified as neuronopathic or non-neuronopathic based on an IQ of less than or equal to 70 or less than 70, respectively. Further, total HS was calculated as the sum of the 4 disaccharides (FIG. 18). In brief, a bioanalytical mass spectrometry method was developed and validated to quantify the total amount of heparan sulfate (t-HS) as the sum of four disaccharides (D2S6, D0A0, D0S0, D0A6) in cerebrospinal fluid (CSF) following enzymatic digestion. LC-MS/MS assay was used for the determination of HS disaccharides D0A0, D0S0, D0A6, and D2S6 in human cerebrospinal fluid (CSF) using isotope-labelled disaccharide derivative as internal standards. HS polysaccharides are digested by enzymes (Heparinase I, II and III) into disaccharides, which are derivatized before being analyzed with LC-MS. Separation of the disaccharides was achieved by reversed-phase HPLC and disaccharides were detected using MS/MS.

Results showed that HS composition revealed differential disaccharide concentrations in MPS I and MPS II compared to normal controls (FIGS. 19A-C). In addition, D2S6 concentrations were elevated in neuronopathic compared to non-neuronopathic MPS I and MPS II and to healthy controls (FIG. 20). Thus, the concentration of D2S6 in CSF samples separated patients with neuronopathic from patients with non-neuronopathic MPS I and MPS II (FIG. 20). Accordingly, CSF D2S6 can provide a diagnostic biomarker to differentiate neuronopathic and non-neuronopathic MPS II in presymptomatic patients. Additionally, D2S6 is a direct substrate of the deficient iduronate-2-sulfatase enzyme in MPS II and provides a direct estimate of enzyme activity with potential utility in monitoring therapy. The percent composition of HS disaccharides (e.g., D0A0, D0A6, D0S0, and D2S6) in normal, neuronopathic MPS I, non-neuronopathic MPS I, neuronopathic MPS II, and non-neuronopathic MPS II from this study is shown in FIG. 21. FIG. 21 shows that an increase in the four disaccharides (e.g., D0A0, D0A6, D0S0, and D2S6) was observed in MPS I and MPS II CSF samples compared to healthy controls. HS composition analysis showed that D2S6 constituted 21% and 23.3% of CSF HS in neuronopathic MPS I and MPS II, respectively, but only 11.2% of CSF HS in healthy controls.

6.13 Example 13: Phase I/II Study for MPS I Using Construct 2 (rAAV9 Encoding Human IDUA (hIDUA))

A Phase I/II study was performed in which participants in cohort 1 received a dose of $1.0 \times 10^{10}$ genome copies per gram of brain mass and participants in cohort 2 received a dose of $5.0 \times 10^{10}$ genome copies per gram of brain mass of Construct 2 (FIG. 30 shows a representation of the Phase I/II study). Construct 2 is a non-replicating recombinant AAV of serotype 9 capsid containing an hIDUA expression cassette (refer to PCT/US2021/014129; PCT/US2018/015910; and PCT/US2019/042205, each of which is incorporated by reference herein in its entirety). The primary endpoint was safety and the secondary endpoints included: CSF biomarkers (heparin sulfate), neurodevelopmental assessments (Bayley/WASI), caregiver reported outcomes (Vineland), and systemic biomarkers (urine and plasma). Participants' ages (total of 6 participants) at dosing ranged from 4 months to 13 years in Phase 1/2 study and 20 months in a single patient study. The IDUA mutations among participants in the Phase 1/2 trial and the single patient study included nonsense/frameshift, nonsense/null variant splice site, and missense. No SAE related to the studies were observed and immunosuppression was discontinued after week 28. Table 16 summarizes the Phase I/II study and the single participant study (FIGS. 31A-31B). It was observed that CSF heparan sulfate decreased in all participants through the last time point available and that measurable CSF IDUA enzyme activity was observed in 3 of 4 participants in the Phase 1/2 trial and the single patient IND participant.

TABLE 16

Phase I/II and single patient trial

| Cohort | N | Dose (GC/g Brain Mass) | Follow-up (weeks) | Prior treatment at dosing | Immuno-suppression regimen status | ERT (IV) status |
|---|---|---|---|---|---|---|
| 1 | 2 | $1.0 \times 10^{10}$ | 40-46 | 1 prior HSCT + ERT<br>1 ERT | 1 completed<br>1 active | 1 not on ERT<br>1 weekly |
| 2 | 3 | $5.0 \times 10^{10}$ | 3-32 | 1 HSCT + ERT<br>1 ERT<br>1 ERT naïve | 3 active | 2 weekly<br>1 ERT Naïve |
| Single Patient | 1 | $1.0 \times 10^{10}$* | 87 | ERT | completed | weekly |

*Previously reported as $1.3 \times 10^{10}$ from initial calculations for brain mass Neurodevelopmental assessments included Bayley Scale of Infant and Toddler Development, Third Edition (BSID-III) for chronological or developmental ages 0 to 42 months; Wechsler Abbreviated Scale of Intelligence (WASI-II) for chronological and development age>6 years; and Vineland Adaptive Behavior Scale, Third Edition (VABS-III). Results for the cognition, expressive language, and fine motor tests for participants in cohorts 1 and 2 are provided in FIGS. 32A-32F. All participants showed continued skill acquisition within 2 SD of normative mean on the cognition, expressive language and fine motor subtests at last assessment (FIGS. 32A-32F). The neurodevelopmental function BSID cognition of the single patient study was compared to MPS I natural history. It was found that cognitive function remains within 2 SD of normative range at the last assessment, 20 months after Construct 2 administration (FIG. 33). BSID cognition in participant approaching 42 months of age demonstrated higher age equivalent scores than available natural history data (FIG. 33). Further, a 13 year old Phase 1/2 study participant demonstrated improvements in WASI composite and the majority of components of the VABS 52 weeks after Construct 2 administration (FIG. 34). Systemic effect was also determined by measuring plasma I0S6 levels (FIGS. 35A-35B) and urine total GAGs (FIGS. 36A-36B) in the participants. I0S6 is a non-reducing end (NRE) disaccharide of glycosaminoglycans shown to be elevated in plasma, urine and CSF of MPS I patients. It was observed that participants with elevated I0S6 at baseline showed a decrease in I0S6 following Construct 2 administration and that in general, I0S6 levels were lower in participants after Construct 2 administration. Total urinary GAGs remained below 30 g/mol in all participants at the last time point available (FIGS. 36A-36B).

EQUIVALENTS

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties.

```
                          SEQUENCE LISTING

Sequence total quantity: 57
SEQ ID NO: 1             moltype = AA  length = 550
FEATURE                  Location/Qualifiers
source                   1..550
                         mol_type = protein
                         note = Human IDS amino acid sequence
                         organism = Homo sapiens
SEQUENCE: 1
MPPPRTGRGL LWLGLVLSSV CVALGSETQA NSTTDALNVL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ISSNHTDDSP YSWSFPPYHP SSEKYENTKT CRGPDGELHA   180
NLLCPVDVLD VPEGTLPDKQ STEQAIQLLE KMKTSASPFF LAVGYHKPHI PFRYPKEFQK   240
LYPLENITLA PDPEVPDGLP PVAYNPWMDI RQREDVQALN ISVPYGPIPV DFQRKIRQSY   300
FASVSYLDTQ VGRLLSALDD LQLANSTIIA FTSDHGWALG EHGEWAKYSN FDVATHVPLI   360
FYVPGRTASL PEAGEKLFPY LDPFDSASQL MEPGRQSMDL VELVSLFPTL AGLAGLQVPP   420
RCPVPSFHVE LCREGKNLLK HFRFRDLEED PYLPGNPREL IAYSQYPRPS DIPQWNSDKP   480
SLKDIKIMGY SIRTIDYRYT VWVGFNPDEF LANFSDIHAG ELYFVDSDPL QDHNMYNDSQ   540
GGDLFQLLMP                                                         550

SEQ ID NO: 2             moltype = AA  length = 24
FEATURE                  Location/Qualifiers
source                   1..24
                         mol_type = protein
                         note = Oligodendrocyte-myelin glycoprotein (hOMG) signal
                          peptide
                         organism = synthetic construct
SEQUENCE: 2
MEYQILKMSL CLFILLFLTP GILC                                           24

SEQ ID NO: 3             moltype = AA  length = 31
FEATURE                  Location/Qualifiers
```

```
source                   1..31
                         mol_type = protein
                         note = Cellular repressor of E1A-stimulated genes 2(hCREG2)
                          signal peptide
                         organism = synthetic construct
SEQUENCE: 3
MSVRRGRRPA RPGTRLSWLL CCSALLSPAA G                                             31

SEQ ID NO: 4             moltype = AA   length = 28
FEATURE                  Location/Qualifiers
source                   1..28
                         mol_type = protein
                         note = V-set and transmembrane domain containing
                          2B(hVSTM2B) signal peptide
                         organism = synthetic construct
SEQUENCE: 4
MEQRNRLGAL GYLPPLLLHA LLLFVADA                                                 28

SEQ ID NO: 5             moltype = AA   length = 29
FEATURE                  Location/Qualifiers
source                   1..29
                         mol_type = protein
                         note = Protocadherin alpha-1 (hPCADHA1) signal peptide
                         organism = synthetic construct
SEQUENCE: 5
MVFSRRGGLG ARDLLLWLLL LAAWEVGSG                                                29

SEQ ID NO: 6             moltype = AA   length = 19
FEATURE                  Location/Qualifiers
source                   1..19
                         mol_type = protein
                         note = FAM19A1 (TAFA1) signal peptide
                         organism = synthetic construct
SEQUENCE: 6
MAMVSAMSWV LYLWISACA                                                           19

SEQ ID NO: 7             moltype = AA   length = 26
FEATURE                  Location/Qualifiers
source                   1..26
                         mol_type = protein
                         note = VEGF-A signal peptide
                         organism = synthetic construct
SEQUENCE: 7
MNFLLSWVHW SLALLLYLHH AKWSQA                                                   26

SEQ ID NO: 8             moltype = AA   length = 29
FEATURE                  Location/Qualifiers
source                   1..29
                         mol_type = protein
                         note = Fibulin-1 signal peptide
                         organism = synthetic construct
SEQUENCE: 8
MERAAPSRRV PLPLLLLGGL ALLAAGVDA                                                29

SEQ ID NO: 9             moltype = AA   length = 19
FEATURE                  Location/Qualifiers
REGION                   1..19
                         note = Vitronectin signal peptide
source                   1..19
                         mol_type = protein
                         note = Vitronectin signal peptide
                         organism = synthetic construct
SEQUENCE: 9
MAPLRPLLIL ALLAWVALA                                                           19

SEQ ID NO: 10            moltype = AA   length = 18
FEATURE                  Location/Qualifiers
source                   1..18
                         mol_type = protein
                         note = Complement Factor H signal peptide
                         organism = synthetic construct
SEQUENCE: 10
MRLLAKIICL MLWAICVA                                                            18

SEQ ID NO: 11            moltype = AA   length = 19
FEATURE                  Location/Qualifiers
source                   1..19
                         mol_type = protein
                         note = Opticin signal peptide
```

-continued

```
SEQUENCE: 11
MRLLAFLSLL ALVLQETGT                                               19

SEQ ID NO: 12            moltype = AA   length = 18
FEATURE                  Location/Qualifiers
source                   1..18
                         mol_type = protein
                         note = Albumin signal peptide
                         organism = synthetic construct
SEQUENCE: 12
MKWVTFISLL FLFSSAYS                                                18

SEQ ID NO: 13            moltype = AA   length = 18
FEATURE                  Location/Qualifiers
source                   1..18
                         mol_type = protein
                         note = Chymotrypsinogen signal peptide
                         organism = synthetic construct
SEQUENCE: 13
MAFLWLLSCW ALLGTTFG                                                18

SEQ ID NO: 14            moltype = AA   length = 20
FEATURE                  Location/Qualifiers
source                   1..20
                         mol_type = protein
                         note = Interleukin-2 signal peptide
                         organism = synthetic construct
SEQUENCE: 14
MYRMQLLSCI ALILALVTNS                                              20

SEQ ID NO: 15            moltype = AA   length = 15
FEATURE                  Location/Qualifiers
source                   1..15
                         mol_type = protein
                         note = Trypsinogen-2 signal peptide
                         organism = synthetic construct
SEQUENCE: 15
MNLLLILTFV AAAVA                                                   15

SEQ ID NO: 16            moltype = AA   length = 736
FEATURE                  Location/Qualifiers
source                   1..736
                         mol_type = protein
                         note = AAV1
                         organism = synthetic construct
SEQUENCE: 16
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KTGQQPAKKR LNFGQTGDSE   180
SVPDPQPLGE PPATPAAVGP TTMASGGGAP MADNNEGADG VGNASGNWHC DSTWLGDRVI   240
TTSTRTWALP TYNNHLYKQI SSASTGASND NHYFGYSTPW GYFDFNRFHC HFSPRDWQRL   300
INNNWGFRPK RLNFKLFNIQ VKEVTTNDGV TTIANNLTST VQVFSDSEYQ LPYVLGSAHQ   360
GCLPPFPADV FMIPQYGYLT LNNGSQAVGR SSFYCLEYFP SQMLRTGNNF TFSYTFEEVP   420
FHSSYAHSQS LDRLMNPLID QYLYYLNRTQ NQSGSAQNKD LLFSRGSPAG MSVQPKNWLP   480
GPCYRQQRVS KTKTDNNNSN FTWTGASKYN LNGRESIINP GTAMASHKDD EDKFFPMSGV   540
MIFGKESAGA SNTALDNVMI TDEEEIKATN PVATERFGTV AVNFQSSSTD PATGDVHAMG   600
ALPGMVWQDR DVYLQGPIWA KIPHTDGHFH PSPLMGGFGL KNPPPQILIK NTPVPANPPA   660
EFSATKFASF ITQYSTGQVS VEIEWELQKE NSKRWNPEVQ YTSNYAKSAN VDFTVDNNGL   720
YTEPRPIGTR YLTRPL                                                  736

SEQ ID NO: 17            moltype = AA   length = 735
FEATURE                  Location/Qualifiers
source                   1..735
                         mol_type = protein
                         note = AAV2
                         organism = synthetic construct
SEQUENCE: 17
MAADGYLPDW LEDTLSEGIR QWWKLKPGPP PKPAERHKD DSRGLVLPGY KYLGPFNGLD    60
KGEPVNEADA AALEHDKAYD RQLDSGDNPY LKYNHADAEF QERLKEDTSF GGNLGRAVFQ   120
AKKRVLEPLG LVEEPVKTAP GKKRPVEHSP VEPDSSSGTG KAGQQPARKR LNFGQTGDAD   180
SVPDPQPLGQ PPAAPSGLGT NTMATGSGAP MADNNEGADG VGNSSGNWHC DSTWMGDRVI   240
TTSTRTWALP TYNNHLYKQI SSQSGASNDN HYFGYSTPWG YFDFNRFHCH FSPRDWQRLI   300
NNNWGFRPKR LNFKLFNIQV KEVTQNDGTT TIANNLTSTV QVFTDSEYQL PYVLGSAHQG   360
CLPPFPADVF MVPQYGYLTL NNGSQAVGRS SFYCLEYFPS QMLRTGNNFT FSYTFEDVPF   420
HSSYAHSQSL DRLMNPLIDQ YLYYLSRTNT PSGTTTQSRL QFSQAGASDI RDQSRNWLPG   480
PCYRQQRVSK TSADNNNSEY SWTGATKYHL NGRDSLVNPG PAMASHKDDE EKFFPQSGVL   540
IFGKQGSEKT NVDIEKVMIT DEEEIRTTNP VATEQYGSVS TNLQRGNRQA ATADVNTQGV   600
LPGMVWQDRD VYLQGPIWAK IPHTDGHFHP SPLMGGFGLK HPPPQILIKN TPVPANPSTT   660
```

```
FSAAKFASFI TQYSTGQVSV EIEWELQKEN SKRWNPEIQY TSNYNKSVNV DFTVDTNGVY  720
SEPRPIGTRY LTRNL                                                  735

SEQ ID NO: 18           moltype = AA  length = 736
FEATURE                 Location/Qualifiers
source                  1..736
                        mol_type = protein
                        note = AAV3-3
                        organism = synthetic construct
SEQUENCE: 18
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKGAVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGASNDN HYFGYSTPWG YFDFNRFHCH FSPRDWQRLI  300
NNNWGFRPKK LSFKLFNIQV RGVTQNDGTT TIANNLTSTV QVFTDSEYQL PYVLGSAHQG  360
CLPPFPADVF MVPQYGYLTL NNGSQAVGRS SFYCLEYFPS QMLRTGNNFQ FSYTFEDVPF  420
HSSYAHSQSL DRLMNPLIDQ YLYYLNRTQG TTSGTTNQSR LLFSQAGPQS MSLQARNWLP  480
GPCYRQQRLS KTANDNNNSN FPWTAASKYH LNGRDSLVNP GPAMASHKDD EEKFFPMHGN  540
LIFGKEGTTA SNAELDNVMI TDEEEIRTTN PVATEQYGTV ANNLQSSNTA PTTGTVNHQG  600
ALPGMVWQDR DVYLQGPIWA KIPHTDGHFH PSPLMGGFGL KHPPPQIMIK NTPVANPPT   660
TFSPAKFASF ITQYSTGQVS VEIEWELQKE NSKRWNPEIQ YTSNYNKSVN VDFTVDTNGV  720
YSEPRPIGTR YLTRNL                                                 736

SEQ ID NO: 19           moltype = AA  length = 734
FEATURE                 Location/Qualifiers
source                  1..734
                        mol_type = protein
                        note = AAV4-4
                        organism = synthetic construct
SEQUENCE: 19
MTDGYLPDWL EDNLSEGVRE WWALQPGAPK PKANQQHQDN ARGLVLPGYK YLGPGNGLDK  60
GEPVNAADAA ALEHDKAYDQ QLKAGDNPYL KYNHADAEFQ QRLQGDTSFG GNLGRAVFQA  120
KKRVLEPLGL VEQAGETAPG KKRPLIESPQ QPDSSTGIGK KGKQPAKKKL VFEDETGAGD  180
GPPEGSTSGA MSDDSEMRAA AGGAAVEGGQ GADGVGNASG DWHCDSTWSE GHVTTTSTRT  240
WVLPTYNNHL YKRLGESLQS NTYNGFSTPW GYFDFNRFHC HFSPRDWQRL INNNWGMRPK  300
AMRVKIFNIQ VKEVTTSNGE TTVANNLTST VQIFADSSYE LPYVMDAGQE GSLPPFPNDV  360
FMVPQYGYCG LVTGNTSQQQ TDRNAFYCLE YFPSQMLRTG NNFEITYSFE KVPFHSMYAH  420
SQSLDRLMNP LIDQYLWGLQ STTTGTTLNA GTATTNFTKL RPTNFSNFKK NWLPGPSIKQ  480
QGFSKTANQN YKIPATGSDS LIKYETHSTL DGRWSALTPG PPMATAGPAD SKFSNSQLIF  540
AGPKQNGNTA TVPGTLIFTS EEELAATNAT DTDMWGNLPG GDQSNSNLPT VDRLTALGAV  600
PGMVWQNRDI YYQGPIWAKI PHTDGHFHPS PLIGGFGLKH PPPQIFIKNT PVANPATTF   660
SSTPVNSFIT QYSTGQVSVQ IDWEIQKERS KRWNPEVQFT SNYGQQNSLL WAPDAAGKYT  720
EPRAIGTRYL THHL                                                   734

SEQ ID NO: 20           moltype = AA  length = 724
FEATURE                 Location/Qualifiers
source                  1..724
                        mol_type = protein
                        note = AAV5
                        organism = synthetic construct
SEQUENCE: 20
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVV TKSTRTWVLP  240
SYNNHQYREI KSGSVDGSNA NAYFGYSTPW GYFDFNRFHS HWSPRDWQRL INNYWGFRPR  300
SLRVKIFNIQ VKEVTVQDST TTIANNLTST QVFTDDDYQ LPYVVGNGTE GCLPAFPPQV  360
FTLPQYGYAT LNRDNTENPT ERSSFFCLEY FPSKMLRTGN NFEFTYNFEE VPFHSSFAPS  420
QNLFKLANPL VDQYLYRFVS TNNTGGVQFN KNLAGRYANT YKNWFPGPMG RTQGWNLGSG  480
VNRASVSAFA TTNRMELEGA SYQVPPQPNG MTNNLQGSNT YALENTMIFN SQPANPGTTA  540
TYLEGNMLIT SESETQPVNR VAYNVGGQMA TNNQSSTTAP ATGTYNLQEI VPGSVWMERD  600
VYLQGPIWAK IPETGAHFHP SPAMGGFGLK HPPPMMLIKN TPVPGNITSF SDVPVSSFIT  660
QYSTGQVTVE MEWELKKENS KRWNPEIQYT NNYNDPQFVD FAPDSTGEYR TTRPIGTRYL  720
TRPL                                                              724

SEQ ID NO: 21           moltype = AA  length = 736
FEATURE                 Location/Qualifiers
source                  1..736
                        mol_type = protein
                        note = AAV6
                        organism = synthetic construct
SEQUENCE: 21
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPFG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
```

```
GCLPPFPADV FMIPQYGYLT LNNGSQAVGR SSFYCLEYFP SQMLRTGNNF TFSYTFEDVP    420
FHSSYAHSQS LDRLMNPLID QYLYYLNRTQ NQSGSAQNKD LLFSRGSPAG MSVQPKNWLP    480
GPCYRQQRVS KTKTDNNNSN FTWTGASKYN LNGRESIINP GTAMASHKDD KDKFFPMSGV    540
MIFGKESAGA SNTALDNVMI TDEEEIKATN PVATERFGTV AVNLQSSSTD PATGDVHVMG    600
ALPGMVWQDR DVYLQGPIWA KIPHTDGHFH PSPLMGGFGL KHPPPQILIK NTPVPANPPA    660
EFSATKFASF ITQYSTGQVS VEIEWELQKE NSKRWNPEVQ YTSNYAKSAN VDFTVDNNGL    720
YTEPRPIGTR YLTRPL                                                   736

SEQ ID NO: 22           moltype = AA   length = 737
FEATURE                 Location/Qualifiers
source                  1..737
                        mol_type = protein
                        note = AAV7
                        organism = synthetic construct
SEQUENCE: 22
MAADGYLPDW LEDNLSEGIR EWWDLKPGAP KPKANQQKQD NGRGLVLPGY KYLGPFNGLD     60
KGEPVNAADA AALEHDKAYD QQLKAGDNPY LRYNHADAEF QERLQEDTSF GGNLGRAVFQ    120
AKKRVLEPLG LVEEGAKTAP AKKRPVEPSP QRSPDSSTGI GKKGQQPARK RLNFGQTGDS    180
ESVPDPQPLG EPPAAPSSVG SGTVAAGGGA PMADNNEGAD GVGNASGNWH CDSTWLGDRV    240
ITTSTRTWAL PTYNNHLYKQ ISSETAGSTN DNTYFGYSTP WGYFDFNRFH CHFSPRDWQR    300
LINNNWGFRP KKLRFKLFNI QVKEVTTNDG VTTIANNLTS TIQVFSDSEY QLPYVLGSAH    360
QGCLPPFPPA VFMIPQYGYL TLNNGSQSVG RSSFYCLEYF PSQMLRTGNN FEFSYSFEDV    420
PFHSSYAHSQ SLDRLMNPLI DQYLYYLART QSNPGGTAGN RELQFYQGGP STMAEQAKNW    480
LPGPCFRQQR VSKTLDQNNN SNFAWTGATK YHLNGRNSLV NPGVAMATHK DDEDRFFPSS    540
GVLIFGKTGA TNKTTLENVL MTNEEEIRPT NPVATEEYGI VSSNLQAANT AAQTQVVNNQ    600
GALPGMVWQN RDVYLQGPIW AKIPHTDGNF HPSPLMGGFG LKHPPPQILI KNTPVPANPP    660
EVFTPAKFAS FITQYSTGQV SVEIEWELQK ENSKRWNPEI QYTSNFEKQT GVDFAVDSQG    720
VYSEPRPIGT RYLTRNL                                                  737

SEQ ID NO: 23           moltype = AA   length = 738
FEATURE                 Location/Qualifiers
source                  1..738
                        mol_type = protein
                        note = AAV8
                        organism = synthetic construct
SEQUENCE: 23
MAADGYLPDW LEDNLSEGIR EWWALKPGAP KPKANQQKQD DGRGLVLPGY KYLGPFNGLD     60
KGEPVNAADA AALEHDKAYD QQLQAGDNPY LRYNHADAEF QERLQEDTSF GGNLGRAVFQ    120
AKKRVLEPLG LVEEGAKTAP GKKRPVEPSP QRSPDSSTGI GKKGQQPARK RLNFGQTGDS    180
ESVPDPQPLG EPPAAPSGVG PNTMAAGGGA PMADNNEGAD GVGSSSGNWH CDSTWLGDRV    240
ITTSTRTWAL PTYNNHLYKQ ISNGTSGGAT NDNTYFGYST PWGYFDFNRF HCHFSPRDWQ    300
RLINNNWGFR PKRLSFKLFN IQVKEVTQNE GTKTIANNLT STIQVFTDSE YQLPYVLGSA    360
HQGCLPPFPA DVFMIPQYGY LTLNNGSQAV GRSSFYCLEY FPSQMLRTGN NFQFTYTFED    420
VPFHSSYAHS QSLDRLMNPL IDQYLYYLSR TQTTGGTANT QTLGFSQGGP NTMANQAKNW    480
LPGPCYQQR VSTTTGQNNN SNFAWTAGTK YHLNGRNSLA NPGIAMATHK DDEERFFPSN    540
GILIFGKQNA ARDNADYSDV MLTSEEEIKT TNPVATEEYG IVADNLQQQN TAPQIGTVNS    600
QGALPGMVWQ NRDVYLQGPI WAKIPHTDGN FHPSPLMGGF GLKHPPPQIL IKNTPVPADP    660
PTTFNQSKLN SFITQYSTGQ VSVEIEWELQ KENSKRWNPE IQYTSNYYKS TSVDFAVNTE    720
GVYSEPRPIG TRYLTRNL                                                 738

SEQ ID NO: 24           moltype = AA   length = 736
FEATURE                 Location/Qualifiers
source                  1..736
                        mol_type = protein
                        note = hu31
                        organism = synthetic construct
SEQUENCE: 24
MAADGYLPDW LEDTLSEGIR QWWKLKPGPP PPKPAERHKD DSRGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGSQPAKKK LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TDSDY QLPYVLGSAH         360
EGCLPPFPAD VFMIPQYGYL TLNDGGQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVSTEGV    720
YSEPRPIGTR YLTRNL                                                   736

SEQ ID NO: 25           moltype = AA   length = 736
FEATURE                 Location/Qualifiers
source                  1..736
                        mol_type = protein
                        note = hu32
                        organism = synthetic construct
SEQUENCE: 25
MAADGYLPDW LEDTLSEGIR QWWKLKPGPP PPKPAERHKD DSRGLVLPGY KYLGPGNGLD     60
```

```
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGSQPAKKK LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 26           moltype = AA  length = 736
FEATURE                 Location/Qualifiers
source                  1..736
                        mol_type = protein
                        note = AAV9
                        organism = synthetic construct
SEQUENCE: 26
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQGRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQNQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                   736

SEQ ID NO: 27           moltype = AA  length = 550
FEATURE                 Location/Qualifiers
source                  1..550
                        mol_type = protein
                        note = SP/P22304/IDS_human
                        organism = Homo sapiens
SEQUENCE: 27
MPPPRTGRGL LWLGLVLSSV CVALGSETQA NSTTDALNVL LIIVDDLRPS LGCYGDKLVR     60
SPNIDQLASH SLLFQNAFAQ QAVCAPSRVS FLTGRRPDTT RLYDFNSYWR VHAGNFSTIP    120
QYFKENGYVT MSVGKVFHPG ISSNHTDDSP YSWSFPPYHP SSEKYENTKT CRGPDGELHA    180
NLLCPVDVLD VPEGTLPDKQ STEQAIQLLE KMKTSASPFF LAVGYHKPHI PFRYPKEFQK    240
LYPLENITLA PDPEVPDGLP PVAYNPWMDI RQREDVQALN ISVPYGIPPV DFQRKIRQSY    300
FASVSYLDTQ VGRLLSALDD LQLANSTIIA FTSDHGWALG EHGEWAKYSN FDVATHVPLI    360
FYVPGRTASL PEAGEKLFPY LDPFDSASQL MEPGRQSMDL VELVSLFPTL AGLAGLQVPP    420
RCPVPSFHVE LCREGKNLLK HFRFRDLEED PYLPGNPREL IAYSQYPRPS DIPQWNSDKP    480
SLKDIKIMGY SIRTIDYRYT VWVGFNPDEF LANFSDIHAG ELYFVDSDPL QDHNMYNDSQ    540
GGDLFQLLMP                                                          550

SEQ ID NO: 28           moltype = AA  length = 550
FEATURE                 Location/Qualifiers
REGION                  1..550
                        note = TR/K6ZGI9_PANTR
source                  1..550
                        mol_type = protein
                        note = Chimpanzee
                        note = TR/K6ZGI9_PANTR
                        organism = Pan troglodytes
SEQUENCE: 28
MPPPRTGRGL PWLGLVLSSV CVALGSETQA NSTTDALNVL LIIVDDLRPS LGCYGDKLVR     60
SPNIDQLASH SLLFQNAFAQ QAVCAPSRVS FLTGRRPDPT RLYDFNSYWR VHAGNFSTIP    120
QYFKENGYVT MSVGKVFHPG ISSNHTDDSP YSWSFPPYHP SSEKYENTKT CRGPDGELHA    180
NLLCPVDVLD VPEGTLPDKQ STEQAIQLLE KMKTSASPFF LAVGYHKPHI PFRYPKEFQK    240
LYPLENITLA PDPEVPDGLP PVAYNPWMDI RQREDVQALN ISVPYGIPPV DFQRKIRQSY    300
FASVSYLDTQ VGRLLSALDD LQLANSTIIA FTSDHGWALG EHGEWAKYSN FDVATHVPLM    360
FYVPGRTASL PEAGEKLFPY LDPFDSASQL MEPGRQSMDL VELVSLFPTL AGLAGLQAPP    420
RCPVPSFHVE LCREGKNLLK HFRFRDLEED PYLPGNPREL IAYSQYPRPS DIPQWNSDKP    480
SLKDIKIMGY SIRTIDYRYT VWIGFNPDEF LANFSDIHAG ELYFVDSDPL QDHNMYNDSQ    540
GGDLFQLLMP                                                          550

SEQ ID NO: 29           moltype = AA  length = 550
FEATURE                 Location/Qualifiers
source                  1..550
                        mol_type = protein
                        note = Chimpanzee
                        note = TR/K7BKV4_PANTR
```

```
                        organism = Pan troglodytes
SEQUENCE: 29
MPPPRTGRGL PWLGLVLSSV CVALGSETQA NSTTDALNVL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ISSNHTDDSP YSWSFPYHP  SSEKYENTKT CRGPDGELHA   180
NLLCPVDVLD VPEGTLPDKQ STEQAIQLLE KMKTSASPFF LAVGYHKPHI PFRYPKEFQK   240
LYPLENITLA PDPEVPDGLP PVAYNPWMDI RQREDVQALN ISVPYGPIPV DFQRKIRQSY   300
FASVSYLDTQ VGRLLSALDD LQLANSTIIA FTSDHGWALG EHGEWAKYSN FDVATHVPLM   360
FYVPGRTASL PEAGEKLFPY LDPFDSASQL MEPGRQSMDL VELVSLFPTL AGLAGLQAPP   420
RCPVPSFHVE LCREGKNLLK HFRFRDLEED PYLPGNPREL IAYSQYPRPS DIPQWNSDKP   480
SLKDIKIMGY SIRTIDYRYT VWIGFNPDEF LANFSDIHAG ELYFVDSDPL QDHNMYNDSQ   540
GGDLFQLLMP                                                          550

SEQ ID NO: 30           moltype = AA   length = 550
FEATURE                 Location/Qualifiers
source                  1..550
                        mol_type = protein
                        note = TR/H9FTX2_MACMU
                        note = Rhesus macaque
                        organism = Macaca mulatta
SEQUENCE: 30
MPTPGSGRGF LWLGLVLSSV CVALGCETQA NSTTDALNIL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ITSNHTDDSP YSWSFPPYHP SSEKYENTKT CRGPDGELHA   180
NLLCPVDVVD VPEGTLPDKQ STEQAIQLLE KMKTSASPFF LAVGYHKPHI PFRYPKEFQK   240
LYPLENITLA PDSEVPDGLP PVAYNPWMDI RQREDVQALN ISVPYGPIPV EFQRKIRQSY   300
FASVSYLDTQ VGRLLSALDD LQLANSTIVA FTSDHGWALG EHGEWAKYSN FDVATHVPLM   360
FYVPGRTASL PEAGEKLFPY LDPFDSASEL MEPGRQSMDL VELVSLFPTL AGLAGLQVPP   420
RCPVPSFHVE LCREGKNLLK HFRFRDLEED PYLPGNPREL IAYSQYPRPA DFPQWNSDKP   480
SLKDIKIMGY SIRTIDYRYT VWVGFNPDEF LANFSDIHAG ELYFVDSDPL QDHNMYNDSQ   540
GGDLFQLLMP                                                          550

SEQ ID NO: 31           moltype = AA   length = 550
FEATURE                 Location/Qualifiers
REGION                  1..550
                        note = TRF7EJG2_CALJA
source                  1..550
                        mol_type = protein
                        note = TRF7EJG2_CALJA
                        note = White-tufted-ear marmoset
                        organism = Callithrix jacchus
SEQUENCE: 31
MPPPRTSRCL LLLGLVLGSV CVTLGSQAQA SSTTDALNVL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKDNGYVT MSVGKVFHPG ISSNHSDDSP YSWSFPPYHP SSEKYENTKT CRGPDGELHA   180
NLLCPVDVVD VPEGTLPDKQ STEEAIRLLE KMKTSASPFF LAVGYHKPHI PFRYPKEFQK   240
LYPLENITLA PDPEVPDGLP PVAYNPWMDI RQREDVQALN ISVPYGPIPV DFQRKIRQSY   300
FASVSYLDTQ VGHLLSALDD LQLANSTIVA FTSDHGWALG EHGEWAKYSN FDVATRVPLM   360
FYVPGRTASL PEADEKLFPY VDPFHSASEL MEPGRQSMDL VELVSLFPTL AGLAGLQVPP   420
RCPVPSFHVE LCREGKSLLK HFRFHGLEED PYLPGNPREL IAYSQYPRPA DFPQWNSDKP   480
SLKYIKIMGY SIRTVDYRYT VWVGFNPDEF LANFSDIHAG ELYFVDSDPL QDHNMYNDSQ   540
GGELFQSLMP                                                          550

SEQ ID NO: 32           moltype = AA   length = 550
FEATURE                 Location/Qualifiers
source                  1..550
                        mol_type = protein
                        note = TR/U3DTL8_CALJA
                        note = White-tufted-ear marmoset
                        organism = Callithrix jacchus
SEQUENCE: 32
MPPPRPSRCL LLLGLVLGSV CVTLGSQAQA SSTTDALNVL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKDNGYVT MSVGKVFHPG ISSNHSDDSP YSWSFPPYHP SSEKYENTKT CRGPDGELHA   180
NLLCPVDVVD VPEGTLPDKQ STEEAIRLLE KMKTSASPFF LAVGYHKPHI PFRYPKEFQK   240
LYPLENITLA PDPEVPDGLP PVAYNPWMDI RQREDVQALN ISVPYGPIPV DFQRKIRQSY   300
FASVSYLDTQ VGHLLSALDD LQLANSTIVA FTSDHGWALG EHGEWAKYSN FDVATRVPLM   360
FYVPGRTASL PEADEKLFPY VDPFHSASEL MEPGRQSMDL VELVSLFPTL AGLAGLQVPP   420
RCPVPSFHVE LCREGKSLLK HFRFHGLEED PYLPGNPREL IAYSQYPRPA DFPQWNSDKP   480
SLKYIKIMGY SIRTVDYRYT VWVGFNPDEF LANFSDIHAG ELYFVDSDPL QDHNMYNDSQ   540
GGELFQSLMP                                                          550

SEQ ID NO: 33           moltype = AA   length = 550
FEATURE                 Location/Qualifiers
source                  1..550
                        mol_type = protein
                        note = Rhesus macaque
                        note = TR/G7NRX7_MACMU
                        organism = Macaca mulatta
```

```
SEQUENCE: 33
MPTPGSGRGF LWLGLVLSSV CVALGCETQA NSTTDALNIL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ITSNHTDDSP YSWSFPPYHP SSEKYENTKT CRGPDGELHA   180
NLLCPVDVVD VPEGTLPDKQ STEQAIQLLE KMKTSASPFF LAVGYHKPHI PFRYPKEFQK   240
LYPLENITLA PDSEVPDGLP PVAYNPWMDI RQREDVQALN ISVPYGPIPV EFQRKIRQSY   300
FASVSYLDTQ VGRLLSALDD LQLANSTIVA FTSDHGWALG EHGEWAKYSN FDVATHVPLM   360
FYVPGRTASL PEAGEKLFPY LDPFDSASEL MEPGRQSMDL VELVSLFPTL AGLAGLQVPP   420
RCPVPSFHVE LCREGKNLLK HFRFRDLEED PYLPGNPREL IAYSQYPRPA DFPQWNSDKP   480
SLKDIKIMGY SIRTIDYRYT VWVGFNPDEF LANFSDIHAG ELYFVDSDPL QDHNMYNDSQ   540
GGDLLQLLMP                                                         550

SEQ ID NO: 34          moltype = AA   length = 550
FEATURE                Location/Qualifiers
source                 1..550
                       mol_type = protein
                       note = Crab-eating macaque; Cynomologous monkey
                       note = RT/G7Q1V9_MACFA
                       organism = Macaca fascicularis
SEQUENCE: 34
MPTPGSGRGF LWLGLVLSSV CVALGCETQA NSTTDALNIL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ITSNHTDDSP YSWSFPPYHP SSEKYENTKT CRGPDGELHA   180
NLLCPVDVVD VPEGTLPDKQ STEQAIQLLE KMKTSASPFF LAVGYHKPHI PFRYPKEFQK   240
LYPLENITLA PDSEVPDGLP PVAYNPWMDI RQREDVQALN ISVPYGPIPV EFQRKIRQSY   300
FASVSYLDTQ VGHLLSALDD LQLANSTIVA FTSDHGWALG EHGEWAKYSN FDVATHVPLM   360
FYVPGRTASL PEAGEKLFPY LDPFDSASEL MEPGRQSMDL VELVSLFPTL AGLAGLQVPP   420
RCPVPSFHVE LCREGKNLLK HFRFRDLEED PYLPGNPREL IAYSQYPRPA DFPQWNSDKP   480
SLKDIKIMGY SIRTIDYRYT VWVGFNPDEF LANFSDIHAG ELYFVDSDPL QDHNMYNDSQ   540
GGDLFQLLMP                                                         550

SEQ ID NO: 35          moltype = AA   length = 550
FEATURE                Location/Qualifiers
source                 1..550
                       mol_type = protein
                       note = TR/H2PX10_PONAB
                       note = Sumatran orangutan
                       organism = Pongo abelii
SEQUENCE: 35
MPPPRTGRGL LWLGLVLSSV CVALGSETQA DSTTDGLNVL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ISSNHTDDSP YSWSFPPYHP SSEKYENTKT CRGPDGELHA   180
NLIAKKMCWM FPRAPCCDKQ STEQAIQLLE KMKTSASPFF LAVGYHKPHI PFRYPKEFQK   240
LYPLENITLA PDPEVPDGLP PVAYNPWMDI RQREDVQALN ISVPYGPIPV DFQQKIRQSY   300
FASVSYLDTQ VGRLLSTLDD LQLANSTIIA FTSDHGWALG EHGEWAKYSN FDVATHVPLM   360
FYVPGRTASL PEAGEKLFPY LDPFDSASEL MEPGRQSMDL VELVSLFPTL AGLAGLQVPP   420
RCPVPSFHVE LCREGKNLLK HFRFRDLEED PYLPGNPREL IAYSQYPRPA DIPQWNSDKP   480
SLKDIKIMGY SIRTIDYRYT VWVGFNPDEF LANFSDIHAG ELYFVDSDPL QDHNMYNDSQ   540
GGDLFQLLMP                                                         550

SEQ ID NO: 36          moltype = AA   length = 550
FEATURE                Location/Qualifiers
source                 1..550
                       mol_type = protein
                       note = Green monkey
                       note = TR/A0A0D9R4D1_CHLSB
                       organism = Chlorocebus sabaeus
SEQUENCE: 36
MPTPGSGRGF LWLGLVLSSV CVALGSETQA NSTTDALNIL LIIVDDLRPS LGCYGDKLVR    60
SPNIDQLASH SLLFQNAFAQ QAVCAPSRVS FLTGRRPDTT RLHNFNSYWR VHAGNFSTIP   120
QYFKENGYVT MSVGKVFHPG ITSNHTDDSP YSWSFPPYHP SSEKYENTKT CRGPDGELHA   180
NLLCPVDVVD VPEGTLPDKQ STEQAIQLLE KMKTSASPFF LAVGYHKPHI PFRYPKEFQK   240
LYPLENITLA PDSEVPDGLP PVAYNPWMDI RQREDVQALN ISVPYGPIPV EFQRKIRQSY   300
FASVSYLDTQ VGRLLSALDD LQLANSTIVA FTSDHGWALG EHGEWAKYSN FDVATHVPLM   360
FYVPGRTASL PEAGEKLFPY LDPFDSASEL MEPGRQSMDL VELVSLFPTL AGLAGLQVPP   420
RCPVPSFHVE LCREGKNLLK HFRFRDLEED PYLPGNPREL IAYSQYPRPA DFPQWNSDKP   480
NLKDIKIMGY SIRTIDYRYT VWVGFNPDEF LANFSDIHAG ELYFVDSDPL QDHNMYNDSQ   540
GGDLFQLLMP                                                         550

SEQ ID NO: 37          moltype = AA   length = 550
FEATURE                Location/Qualifiers
VARIANT                24
                       note = Xaa can be any naturally occurring amino acid
VARIANT                163..168
                       note = Xaa can be any naturally occurring amino acid
source                 1..550
                       mol_type = protein
                       note = TR/G1RST8/G1RST8_NOMLE
                       note = Northern white-cheeked gibbon
```

```
                        organism = Nomascus leucogenys
SEQUENCE: 37
MSPPRTGQGL LWLGVVLSSV CVAXVTSPKP PSFVDALNVL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ISSNHTDDSP YSWSFPPYHP SSXXXXXXKT CRGPDGELHA   180
NLLCPVDVLD VPEGTLPDKQ STEQAIQLLE KMKTSASPFF LAVGYHKPHI PFRYPKEFQK   240
LYPLENITLA PDPEVPDGLP PVAYNPWMDI RQREDVQALN ISVPYGPIPV DFQRKIRQSY   300
FASVSYLDTQ VGRLLSALDD LQLANSTIIA FTSDHGWALG EHGEWAKYSN FDVATHVPLM   360
FYVPGRTASL PEAGEKLFPY LDPFDSASEL MEPGRQSMDL VELVSLFPTL AGLAGLQVPP   420
RCPVPSFHVE LCREGKNLLK HFRFRDLEED PYLPGNPREL IAYSQYPRPA DIPQWNSDKP   480
SLKDIKIMGY SIRTIDYRYT VWVGFSPDEF LANFSDIHAG ELYFVDSDPL QDHNMYNDSQ   540
GGDLFQLLMP                                                         550

SEQ ID NO: 38           moltype = AA   length = 550
FEATURE                 Location/Qualifiers
source                  1..550
                        mol_type = protein
                        note = UPI0000D9F625
                        note = Rhesus macaque
                        organism = Macaca mulatta
SEQUENCE: 38
MPTPGSGRGF LWLGLVLSSV CVALGCETQA NSTTDALNIL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ITSNHTDDSP YSWSFPPYHP SSEKYENTKT CRGPDGELHA   180
NLLCPVDVVD VPEGTLPDKQ STEQAIQLLE KMKTSASPFF LAVGYHKPHI PFRYPKEFQK   240
LYPLENITLA PDSEVPDGLP PVAYNPWMDI RQREDVQALN ISVPYGPIPV EFQRKIRQSY   300
FASVSYLDTQ VGHLLSALDD LQLANSTIVA FTSDHGWALG EHGEWAKYSN FDVATHVPLM   360
FYVPGRTASL PEAGEKLFPY LDPFDSASEL MEPGRQSMDL VELVSLFPTL AGLAGLQVPP   420
RCPVPSFHVE LCREGKNLLK HFRFRDLEED PYLPGNPREL IAYSQYPRPA DFPQWNSDKP   480
SLKDIKIMGY SIRTIDYRYT VWVGFNPDEF LANFSDIHAG ELYFVDSDPL QDHNMYNDSQ   540
GGDLLQLLMP                                                         550

SEQ ID NO: 39           moltype = AA   length = 550
FEATURE                 Location/Qualifiers
source                  1..550
                        mol_type = protein
                        note = Pygmy chimpanzee; Bonobo
                        note = UPI0000274358B
                        organism = Pan paniscus
SEQUENCE: 39
MPPPRTGRGL LWLGLVLSSV CVALGSETQA NSTTDALNVL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ISSNHTDDSP YSWSFPPYHP SSEKYENTKT CRGPDGELHA   180
NLLCPVDVLD VPEGTLPDKQ STEQAIRLLE KMKTSASPFF LAVGYHKPHI PFRYPKEFQK   240
LYPLENITLA PDPEVPDGLP PVAYNPWMDI RQREDVQALN ISVPYGPIPV DFQRKIRQSY   300
FASVSYLDTQ VGRLLSALDD LQLANSTIIA FTSDHGWALG EHGEWAKYSN FDVATHVPLM   360
FYVPGRTASL PEAGEKLFPY LDPFDSASQL MEPGRQSMDL VELVSLFPTL AGLAGLQVPP   420
RCPVPSFHVE LCREGKNLLK HFRFRDLEED PYLPGNPREL IAYSQYPRPS DIPQWNSDKP   480
SLKDIKIMGY SIRTIDYRYT VWVGFNPDEF LANFSDIHAG ELYFVDSDPL QDHNMYNDSQ   540
GGDLFQLLMP                                                         550

SEQ ID NO: 40           moltype = AA   length = 550
FEATURE                 Location/Qualifiers
source                  1..550
                        mol_type = protein
                        note = UPI00027F6FC5
                        note = Olive baboon
                        organism = Papio anubis
SEQUENCE: 40
MPTPGSGRGF LWLGLVLSSV CVALGCEMQA NSTTDALNIL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ITSNHTDDSP YSWSFPPYHP SSEKYENTKT CRGPDGELHA   180
NLLCPVDVVD VPEGTLPDKQ STEQAIQLLE KMKTSASPFF LAVGYHKPHI PFRYPKEFQK   240
LYPLENITLA PDSEVPDGLP PVAYNPWMDI RQREDVQALN ISVPYGPIPV EFQRKIRQSY   300
FASVSYLDTQ VGRLLSALDD LQLANSTIVA FTSDHGWALG EHGEWAKYSN FDVATHVPLM   360
FYVPGRTASL PEAGEKLFPY LDPFDSASEL MEPGRQSMDL VELVSLFPTL AGLAGLQVPP   420
RCPVPSFHVE LCREGKNLLK HFRFRDLEED PYLPGNPREL IAYSQYPRPA DIPQWNSDKP   480
SLKDIKIMGY SIRTIDYRYT VWVGFNPDEF LANFSDIHAG ELYFVDSDPL QDHNMYNDSQ   540
GGDLFQLLMP                                                         550

SEQ ID NO: 41           moltype = AA   length = 550
FEATURE                 Location/Qualifiers
source                  1..550
                        mol_type = protein
                        note = UPI00027FAE03
                        note = Bolivian squirrel monkey
                        organism = Saimiri boliviensis
SEQUENCE: 41
MPPPRTGLCL LLLGLVLGSV CVTLGSQAQA NSTTDALNVL LIIVDDLRPS LGCYGDKLVR    60
```

```
SPNIDQLASH SLLFQNAFVQ QAVCAPSRVS FLTGRRPDTT RLYDFNSYWR VHAGNFSTIP    120
QYFKDNGYVT MSVGKVFHPG ISSNHSDDSP YSWSFPPYHP SSEKYENTKT CRGPDGELHA    180
NLLCPVDVVD VPEGTLPDKQ STEEAIRLLK KMKTSASPFF LAVGYHKPHI PFRYPKEFQK    240
LYPLENITLA PDPEVPDGLP PVAYNPWMDI RQREDVQALN ISVPYGPIPV DFQRKIRQSY    300
FASVSYLDTQ VGHLLSALDD LHLANSTIVA FTSDHGWALG EHGEWAKYSN FDVATRVPLM    360
FYVPGRTASL PETGEKLFPY VDPFHSASEL MEPGRQSTDL VELVSLFPTL AGLAGLQVPP    420
RCPVPSFHIE LCREGKNLLK HFRFHGLEED PYLPGNPREL IAYSQYPRPA DFPQQNSDKP    480
SLKYIKIMGY SIRTVDYRYT VWVGFNPDEF LANFSDIHAG ELYFVDSDPL QDHNMYNDSQ    540
GGELFQSLMP                                                          550

SEQ ID NO: 42           moltype = AA  length = 550
FEATURE                 Location/Qualifiers
source                  1..550
                        mol_type = protein
                        note = UPI0003ABBF28
                        note = Crab-eating macaque; Cynomologous monkey
                        organism = Macaca fascicularis
SEQUENCE: 42
MPTPGSGRGF LWLGLVLSSV CVALGCETQA NSTTDALNIL LIIVDDLRPS LGCYGDKLVR     60
SPNIDQLASH SLLFQNAFAQ EAVCAPSRVS FLTGRRPDTT RLYDFNSYWR VHAGNFSTIP    120
QYFKENGYVT MSVGKVFHPG ITSNHTDDSP YSWSFPPYHP SSEKYENTKT CRGPDGELHA    180
NLLCPVDVVD VPEGTLPDKQ STEQAIQLLE KMKTSASPFF LAVGYHKPHI PFRYPKEFQK    240
LYPLENITLA PDSEVPDGLP PVAYNPWMDI RQREDVQALN ISVPYGPIPV EFQRKIRQSY    300
FASVSYLDTQ VGRLLSALDD LQLANSTIVA FTSDHGWALG EHGEWAKYSN FDVATHVPLM    360
FYVPGRTASL PEAGEKLFPY LDPFDSASEL MEPGRQSMDL VELVSLFPTL AGLAGLQVPP    420
RCPVPSFHVE LCREGKNLLK HFRFRDLEED PYLPGNPREL IAYSQYPRPA DFPQWNSDKP    480
SLKDIKIMGY SIRTIDYRYT VWVGFNPDEF LANFSDIHAG ELYFVDSDPL QDHNMYNDSQ    540
GGDLFQLLMP                                                          550

SEQ ID NO: 43           moltype = AA  length = 550
FEATURE                 Location/Qualifiers
source                  1..550
                        mol_type = protein
                        note = UPI000533297F
                        note = Golden snub-nosed monkey
                        organism = Rhinopithecus roxellana
SEQUENCE: 43
MPTPASGRGF LWLGLVLSSV CVALGSETQA NSTTDALNIL LIIVDDLRPS LGCYGDKLVR     60
SPNIDQLASH SLLFQNAFAQ QAVCAPSRVS FLTGRRPDTT RLYDFNSYWR VHAGNFSTIP    120
QYFKENGYVT MSVGKVFHPG ITSNHTDDSP YSWSFPPYHP SSEKYENTKT CRGPDGELHA    180
NLLCPVDVVD VPEGTLPDKQ STEQAVQLLE KMKTSASPFF LAVGYHKPHI PFRYPKEFQK    240
LYPLENITLA PDSEVPDGLP PVAYNPWMDI RQREDVQALN ISVPYGPIPV DFQRKIRQSY    300
FASVSYLDTQ VGHLLSALDD LQLANSTIVA FTSDHGWALG EHGEWAKYSN FDVATHVPLM    360
FYVPGRTASL PEAGEKLFPY LDPFDSASEL MEPGRQSMDL VELVSLFPTL AGLAGLQVPP    420
RCPVPSFHVE LCREGKNLLK HFRFRDLEED PYLPGNPREL IAYSQYPRPA DFPQWNSDKP    480
SLKDIKIMGY SIRTIDYRYT VWVGFNPDEF LANFSDIHAG ELYFVDSDPF QDHNMYNDSQ    540
GGDLFQLLMP                                                          550

SEQ ID NO: 44           moltype = AA  length = 550
FEATURE                 Location/Qualifiers
source                  1..550
                        mol_type = protein
                        note = UPI0005F40BD2
                        note = Peters Angolan colobus
                        organism = Colobus angolensis
SEQUENCE: 44
MPTPASGRGF LWLGLVLRSV CVALGSETQA NSTTDALNIL LIIVDDLRPS LGCYGDKLVR     60
SPNIDQLASH SLLFQNAFAQ QAVCTPSHVS FLTGRRPDTT RLYDFNSYWR VHAGNFSTIP    120
QYFKENGYVT MSVGKVFHPG ITSNHTDDSP YSWSFPPYHP SSEKYENTKT CRGPDGELHA    180
NLLCPVDVVD VPEGTLPDKQ STEQAIQLLE KMKTSASPFF LAVGYHKPHI PFRYPKEFQK    240
LYPLENITLA PDSEVPDGLP PVAYNPWMDI RQREDVQALN ISVPYGPIPV DFQRKIRQSY    300
FASVSYLDTQ VGHLLSALDD LQLANSTIVA FTSDHGWALG EHGEWAKYSN FDVATHVPLM    360
FYVPGRTASL PEAGEKLFPY LDPFDSASEL MEPGRQSMDL VELVSLFPTL AGLAGLQVPP    420
RCPVPSFHVE LCREGKNLLK HFRFRDLEED PYLPGNPREL IAYSQYPRPA DFPQWNSDKP    480
SLKDIKIMGY SIRTIDYRYT VWVGFNPDEF LANFSDIHAG ELYFVDSDPL QDHNMYNDSQ    540
GGDLFQLLMP                                                          550

SEQ ID NO: 45           moltype = DNA  length = 3967
FEATURE                 Location/Qualifiers
source                  1..3967
                        mol_type = other DNA
                        note = CB7.CI.hIDS.RBG
                        organism = synthetic construct
SEQUENCE: 45
gctgcgcgct cgctcgctca ctgaggccgc ccgggcaaag cccgggcgtc gggcgacctt     60
tggtcgcccg gcctcagtga gcgagcgagc gcgcagagag ggagtggcca actccatcac    120
tagggggttcc ttagttaa tgattaaccc gccatgctac ttatctacca gggtaatggg    180
gatcctctag aactatagct agtcgacatt gattattgac tagttattaa tagtaatcaa    240
ttacggggtc attagttcat agcccatata tggagttccg cgttacataa cttacggtaa    300
```

```
atggcccgcc tggctgaccg cccaacgacc cccgcccatt gacgtcaata atgacgtatg    360
ttcccatagt aacgccaata gggactttcc attgacgtca atgggtggac tatttacggt    420
aaactgccca cttggcagta catcaagtgt atcatatgcc aagtacgccc cctattgacg    480
tcaatgacgg taaatggccc gcctggcatt atgcccagta catgacctta tgggactttc    540
ctacttggca gtacatctac gtattagtca tcgctattac catggtcgag gtgagcccca    600
cgttctgctt cactctcccc atctcccccc cctcccacc cccaattttg tatttattta    660
tttttaatt attttgtgca gcgatggggg cggggggggg gggggggcgc gcgcaggcg    720
gggcggggcg gggcgagggg cggggcgggg cgaggcggag aggtgcggcg gcagccaatc    780
agagcggcgc gctccgaaag tttcctttta tggcgaggcg cggcggcgg cggccctata    840
aaaagcgaag cgcgcgacgg gcgggagtc gctgcgcacg tgccttcgcc ccgtgcccg    900
ctccgccgcc gcctcgcgcc gccgccccg gctctgactg accgcgttac tcccacaggt    960
gagcgggcgg gacggccctt ctcctccggg ctgtaattag cgcttggttt aatgacggct   1020
tgtttctttt ctgtggctgc gtgaaagcct tgaggggctc cggagggcc ctttgtgcgg   1080
gggagcggc tcgggggtg cgtgcgtgtg tgtgtgcgtg gggagcgccg cgtgcggctc   1140
cgcgctgccc ggcggctgtg agcgctgcgg gcgcggcgcg gggctttgtg cgctccgcag   1200
tgtgcgcgag gggagcgcgg ccggggcgg tgccccgcgg tgcgggggg gctgcgaggg   1260
gaacaaaggc tgcgtgcggg gtgtgtgcgt gggggggtga gcaggggtg tgggcgcgtc   1320
ggtcgggctg caacccccc tgcaccccc tccccgaggt gctgagcacg gcccggcttc   1380
gggtgcgggg ctccgtacgg ggcgtggcgc ggggctcgcc gtgccgggcg ggggtggcg   1440
gcaggtgggg gtgccgggcg gggcggggcc gcctcgggcc ggggagggct cggggggagg   1500
gcgcggcggc ccccggagcg ccggcggctg tcgaggcgcg gcgagccgca gccattgcct   1560
tttatggtaa tcgtgcgaga gggcgcaggg acttccttg tcccaaatct gtgcggagcc   1620
gaaatctggg aggcgccgcc gcaccccctc tagcgggcgc ggggcgaagc ggtgcggcgc   1680
cggcaggaag gaaatgggcg gggagggcct tcgtgcgtcg ccgcgccgcc gtccccttct   1740
ccctctccag cctcggggct gtccgcgggg ggacggctgc cttcgggggg gacggggcag   1800
ggcggggttc ggcttctggc gtgtgaccgg cggctctaga gcctctgcta accatgttca   1860
tgccttcttc tttttcctac agctcctggg caacgtgctg gttattgtgc tgtctcatca   1920
ttttggcaaa gaattcatgc cgccaccccg gaccggccga ggccttctct ggctgggtct   1980
ggttctgagc tccgtctgcg tcgccctcgg atccgaaacg caggcaaact cgaccacaga   2040
tgctctgaac gttcttctca tcatcgtgga tgacctgcgc cccctccctg gctgttatgg   2100
ggataagctg gtgaggtccc caaatattga ccaactggca tcccacagcc tcctcttcca   2160
gaatgccttt gcgcagcaag cagtgtgcgc cccgagccgc gtttctttcc tcactggcag   2220
gagacctgac accacccgcc tgtacgactt caactcctac tggagggtgc acgctggaaa   2280
cttctccacc atccccagt acttcaagga gaatgctat gtgaccatgt cggtgggaaa   2340
agtcttcac cctgggatat cttctaacca taccgatgat tctccgtata gctggtcttt   2400
tccaccttat catccttcct ctgagaagta tgaaaacact aagacatgtc gagggccaga   2460
tggagaactc catgccaacc tgctttgccc tgtggatgtg ctggatgttc ccgagggcac   2520
cttgcctgac aaacagagca ctgagcaagc catacagttg ttggaaaaga tgaaaacgtc   2580
agccagtcct ttcttcctgg ccgttgggta tcataagcca cacatcccct tcagatacc   2640
caaggaattt cagaagttgt atccttgga gaacatcacc ctggccccg atcccgaggt   2700
ccctgatggc ctaccccctg tggcctacaa ccccctggatg gacatcaggc aacgggaaga   2760
cgtccaagcc ttaaacatca gtgtgccgta tggtccaatt cctgtggact ttcagcggaa   2820
aatccgcag agctactttg cctctgtgtc atatttggat acacaggtcg ggcgcctgtt   2880
gagtgctttg gacgatcttc agctggccaa cagcaccatc attgcattta cctcggatca   2940
tgggtgggct ctaggtgaac atggagaatg ggccaaatac agcaattttg atgttgctac   3000
ccatgttccc ctgatattct atgttcctgg aaggacggct tcacttccgg aggcaggcga   3060
gaagcttttc ccttacctcg acccttttga ttccgcctca cagttgatgg agccaggcag   3120
gcaatccatg gaccttgtgg aacttgtgtc tcttttttccc acgctggctg gacttgcagg   3180
actgcaggtt ccacctcgct gccccgttcc ttcatttcac gttgagctgt gcagagaagg   3240
caagaacctt ctgaagcatt ttcgattccg tgacttggaa gaggatccgt acctccctgg   3300
taatccccgt gaactgattg cctatagcca gtatccccg ccttcagaca tccctcagtg   3360
gaattctgac aagccgagtt taaaagatat aaagatcatg gctattcca tacgcaccat   3420
agactatagg tatactgtgt gggttggctt caatcctgat gaatttctag ctaactttc   3480
tgacatccca gcagggggaac tgtatttgt ggattctgac ccattgcagg atcacaatat   3540
gtataatgat tcccaaggtg gagatctttt ccagttgttg atgccttgac tcgaggacgg   3600
ggtgaactac gcctgaggat ccgatctttt tccctctgcc aaaaattatg gggacatcat   3660
gaagcccctt gagcatctga cttctggcta ataaggaaa tttatttttca ttgcaatagt   3720
gtgttggaat tttttgtgtc tctcactcgg aagcaattcg ttgatctgaa tttcgaccac   3780
ccataatacc cattaccctg gtagataagt agcatgcgg gttaatcatt aactacaagg   3840
aaccctagt gatggagttg gccactccct ctctgcgcgc tcgctcgctc actgaggccg   3900
ggcgaccaaa ggtcgcccga cgcccgggct tgcccgggc ggcctcagtg agcgagcgag   3960
cgcgcag                                                             3967
```

SEQ ID NO: 46          moltype = AA  length = 25
FEATURE                Location/Qualifiers
source                 1..25
                       mol_type = protein
                       note = Signal sequence
                       organism = Homo sapiens
SEQUENCE: 46
MPPPRTGRGL LWLGLVLSSV CVALG                                          25

SEQ ID NO: 47          moltype = AA  length = 16
FEATURE                Location/Qualifiers
source                 1..16
                       mol_type = protein
                       note = Y-sulfation site
                       organism = Homo sapiens
SEQUENCE: 47

```
PSSEKYENTK TCRGPD                                                                 16

SEQ ID NO: 48           moltype = AA  length = 736
FEATURE                 Location/Qualifiers
source                  1..736
                        mol_type = protein
                        note = Exemplary AAV variant
                        organism = synthetic construct
SEQUENCE: 48
MSTVDHPPDW LEETVGEGVR QFLKLQAGPP KPKPAERKKD DGRGLVLPGY NYLGPFNGLD   60
RGEPVNEADE VAREHDISYN EQLDSGDNPY LRYNHADAEF QQKLQDDTSF GGNLGKAVFQ  120
AKKRVLEPFG LVEQGGETAP TGKGIDDHFP VSPDSSSGTG KKKQARTREK SVPEDETGAG  180
DGPSSQLQQ TSGTMASLDP NEVRAAAGGA MGEGGQGADG VGNASGDWHC DSTWMEGHVT  240
TKSTRTWVLP SYNNHQYRRL GSGSQSDATQ ANTYFGYSTP WGYFDFNRFH SHWSPRDWQR  300
LINNNWGMRP RAMRVKIFNI QVKEVTVQDS TTTIANNLTS TIQIFSDDEY ELPYVMDAGQ  360
QGSLPAFPPQ VFTLPQYGYC GLVNDGNPTD RNAFFCLEYF PSQMLRTGNN FEITYTFEDV  420
PFHSMFAHSQ SLDRLANPLV DQYLWGFNRT QTNTSAGTKR TQFTQGSAAT FSNFAKNWLP  480
GPCIKTQGWN LGSGVNTGSD SLIKYETHST LDGASYQVPP QTPGMTAGLQ GSNTYAMENT  540
MFANPKQNTN TATVPGTLIF TSESETQPVN ATDYDMWGNL PGGDQRNSNL PTVDRLTALE  600
AVPGSVWMER DIYLQGPIWA KIPETGAHFH PSPAIGGFGL KNPPPMMMIK NTPVPGDIAA  660
EFSDVPVSSF ITQYSTGQVS VQMDWEIKKE RSKRWNPEVQ YTSNYGQQVS LLWTPDAAGK  720
YRTTRAIGTR YLTHPL                                                  736

SEQ ID NO: 49           moltype = AA  length = 736
FEATURE                 Location/Qualifiers
source                  1..736
                        mol_type = protein
                        note = Exemplary AAV variant
                        organism = synthetic construct
SEQUENCE: 49
MMFDGYLPDW LEDNLSEGLR EWWDLEPGVP PPKANQQHQD QSRGLVLPGY KYLGPGNGLD   60
KGEPVNRADA AALEHDKAYD RQLEAGDNPY LKYNHADAEF QERLAGDTSF GGNLGRAVFQ  120
AKKRILEPLG LVEEPVKTAP AKKRALIPSP QQPDSSTGVG KTGKQPAEKD LKFSTSSDSD  180
AVPDPQPEGS PAQPATAVGA GTMSTGSGAP LVDNNEGADG VGSSSGNWHC DSQWSGDRVV  240
TTSTRTWALP TYNNHLYKEI KNAATTEGLN SNHYFGYSTP WGYFDFNRFH CHFSPRDWQR  300
LINNNWGFRP KKLSFKLFNI QVKEVTQSEG EKTIANNLTS TVQVFADSSY QLPYVLGSAT  360
EGCLPPFPND VFMVPQYGYA TLNTGQQQVE RSSFYCLEYF PSQMLRTGNN FTFSYSFEEV  420
PFHSSYAHSQ SLDRLMNPLI DQYLYYLQST NSTPTTQNSD VNFNKNLPQG YRDTPRNYFP  480
GPMGRQQRFS KTANDNRASN YTFATTNRME LEGRDSALTP GVNMASNNPA DEKFSPQHQL  540
IIFGSESAEA SKAALENMLM TDEEEIRATN RVATNVFGTM SNNLQASNTA AAIADYHTMG  600
VLPGMVWQNR DVYLQGPIWA KIPHTDGNFH PSPLMGGFGM KHPPPQIFIK NTPVPADPSE  660
TFTAAKFASF ITQYSTGQVS VEIEWELQKE NSKRWNPEIQ YTSNYNDPQF VDFAVSSNGE  720
YTEPRPIGTR YLTRHL                                                  736

SEQ ID NO: 50           moltype = AA  length = 736
FEATURE                 Location/Qualifiers
source                  1..736
                        mol_type = protein
                        note = Exemplary AAV variant
                        organism = synthetic construct
SEQUENCE: 50
MAADGYLPDW LEDNLSEGIR EWWGLKPGAP QPKANQQHQD NRRGLVLPGY KYLGPGNGLD   60
KGEPVNAADA AALEHDKAYD QQLQAGDNPY LKYNHADAEF QERLKEDTSF GGNLGRAVFQ  120
AKKRLLEPLG LVEEAAKTAP GKKRPVEESP QEPDSSAGIG KAGSQPAKKR LNFGQTGDTE  180
SVPDPQPIGI PPAAPSGVGD TTMASGGGAP AADNNEGADG VGSSSGNWHC DSQWLGDRVI  240
TTSTRTWALP TYNNHLYKQI SNSGSVGSSN DNAYFGYSTP WGYFDFNRFH CHFSPRDWQR  300
LINNNWGFRP KSLNFKLFNI QVKEVTDNNG VKTIANNLTS TVQVFTDSDY QLPYVLGSAH  360
EGCLPPFPAD VFMIPQYGYL TLNRGEQSVG RSSFYCLEYF PSQMLRTGNN FQFSYNFEKV  420
PFHSSYAHSQ SLDRLMNPLI DQYLYYLVKT TGGQGQTQAE LLFYRLRPTR IALQKRNYIP  480
GPSFRQQRLS TTKAQNNNSV FPWTAGSKYN LNGRWSIINP GIAMASHKDD KDRFFPNNGV  540
LIFGKTPSAK DNKTYDKVML TNEEEIATTN PVATEQGGIV AVNNQQGTRD AQTQTVNHQG  600
ILPGMVWQDR DVYLQGPIWA KIPHTDGNFH PSPLMGGFGM KHPPPQILIK NTPVPADPPT  660
SFNPTKLNSF ITQYSTGQVS VEIEWELQKE NSKRWNPEIQ YTSNYAKSTG VEFAVNNQGL  720
YSEPRPIGTR YLTRNL                                                  736

SEQ ID NO: 51           moltype = AA  length = 736
FEATURE                 Location/Qualifiers
source                  1..736
                        mol_type = protein
                        note = Exemplary AAV variant
                        organism = synthetic construct
SEQUENCE: 51
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KRGAQPAKKR LNFGQTGDTE  180
SVPDPQPIGE PPAAPSGVGT DTMASGGGAP VADNNEGADG VGSSSGNWHC DSQWLGDRVI  240
TTSTRTWALP TYNNHLYKQI SNSESAGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
```

```
PFHSSYAHSQ SLDRLMNPLI DQYLYYLAKT INGSGQNRG  LGFSVAGPGS MAEQYRNYIP    480
GPSYRQQRVS TTLDQNNNSE FSWPGASSWH LNGRESLANP GPAMASHKEG EDRFFPSSGI    540
LIFGKQNTGR DNVEIDKVMI TNEEEIKTTN PVATEEYGSV ASNFQSQQAQ AQTGVVQLQG    600
ILPGMVWQDR DVYLQGPIWA KIPHTDGNFH PSPLMGGFGM KHPPPQILIK NTPVPADPPT    660
VFNQSKLNSF ITQYSTGQVS VEIEWELQKE NSKRWNPEIQ YTSNYEKSAN VEFAVNTTGV    720
YSEPRPIGTR YLTRNL                                                    736

SEQ ID NO: 52           moltype = AA  length = 736
FEATURE                 Location/Qualifiers
source                  1..736
                        mol_type = protein
                        note = Exemplary AAV variant
                        organism = synthetic construct
SEQUENCE: 52
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS STMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPND MAVQSRNYIP    480
GPSYRQQRVS TTTTQNNNSE FAWPGASSWA LNGRNSLMNP GPAMASHKEG EDRFFPLSGN    540
LIFGKQGTGR DNVYADKVMI TNEEEIKTTN PVATERYGQV ADNHQSAQAQ AQTGWVQVQG    600
ILPGMVWQDR DVYLQGPIWA KIPHTDGNFH PSPLMGGFGM KHPPPQILIK NTPVPADPPT    660
AFNSDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 53           moltype = AA  length = 736
FEATURE                 Location/Qualifiers
source                  1..736
                        mol_type = protein
                        note = Exemplary AAV variant
                        organism = synthetic construct
SEQUENCE: 53
MAADGYLPDW LEDNLSEGIR EWWALKPGAP QPKANQQHQD NARGLVLPGY KYLGPGNGLD     60
KGEPVNAADA AALEHDKAYD QQLKAGDNPY LKYNHADAEF QERLKEDTSF GGNLGRAVFQ    120
AKKRLLEPLG LVEEAAKTAP GKKRPVEQSP QEPDSSAGIG KSGAQPAKKR LNFGQTGDTE    180
SVPDPQPIGE PPAAPSGVGS LTMASGGGAP VADNNEGADG VGSSSGNWHC DSQWLGDRVI    240
TTSTRTWALP TYNNHLYKQI SNSTSGGSSN DNAYFGYSTP WGYFDFNRFH CHFSPRDWQR    300
LINNNWGFRP KRLNFKLFNI QVKEVTDNNG VKTIANNLTS TVQVFTDSDY QLPYVLGSAH    360
EGCLPPFPAD VFMIPQYGYL TLNDGSQAVG RSSFYCLEYF PSQMLRTGNN FQFSYEFENV    420
PFHSSYAHSQ SLDRLMNPLI DQYLYYLSKT INGSGQNQQT LKFSVAGPSN MAVQSRNYIP    480
GPSYRQQRVS TTVTQNNNSE FAWPGASSWA LNGRNSLMNP GPAMASHKEG EDRFFPLSGS    540
LIFGKQGTGR DNVDADKVMI TNEEEIKTTN PVATESYGQV ATNHQSAQAQ AQTGWVQSQG    600
ILPGMVWQDR DVYLQGPIWA KIPHTDGNFH PSPLMGGFGM KHPPPQILIK NTPVPADPPT    660
AFNKDKLNSF ITQYSTGQVS VEIEWELQKE NSKRWNPEIQ YTSNYYKSNN VEFAVNTEGV    720
YSEPRPIGTR YLTRNL                                                    736

SEQ ID NO: 54           moltype = AA  length = 9
FEATURE                 Location/Qualifiers
source                  1..9
                        mol_type = protein
                        note = Portion of a sequence from human IDS
                        organism = Homo sapiens
SEQUENCE: 54
TDALNVLLI                                                              9

SEQ ID NO: 55           moltype = AA  length = 9
FEATURE                 Location/Qualifiers
source                  1..9
                        mol_type = protein
                        note = Portion of a sequence from human IDS
                        organism = Homo sapiens
SEQUENCE: 55
ALNVLLIIV                                                              9

SEQ ID NO: 56           moltype = AA  length = 7
FEATURE                 Location/Qualifiers
source                  1..7
                        mol_type = protein
                        note = Exemplary amino acid insertion
                        organism = Homo sapiens
SEQUENCE: 56
LGETTRP                                                                7

SEQ ID NO: 57           moltype = AA  length = 9
FEATURE                 Location/Qualifiers
source                  1..9
```

```
                mol_type = protein
                note = Exemplary amino acid insertion
                organism = Homo sapiens
SEQUENCE: 57
LALGETTRP                                                                9
```

What is claimed is:

1. A method of treating mucopolysaccharidosis II (MPS II) in a human subject, the method comprising:
   a) measuring the level of D2S6 present in a biological sample obtained from the human subject;
   b) diagnosing the human subject with MPS II when the level of D2S6 in the biological sample is higher than a reference; and
   c) delivering an effective amount of an active human iduronate-2-sulfatase (hIDS) to the central nervous system (CNS) of the human subject diagnosed with MPS II, wherein the method further comprises calculating a ratio of D2S6 to total heparan sulfate disaccharides (HS) in the biological sample, wherein the total HS comprises disaccharides D2S6, D0A0, D0S0, and D0A6.

2. The method of claim 1, wherein the human subject is determined to be responsive to the active hIDS treatment if the D2S6 level is at least 20% of the total HS.

3. The method of claim 1, wherein the active hIDS is delivered to the CNS by administering an adeno-associated virus (AAV) vector comprising a nucleotide sequence encoding hIDS to the human subject.

4. The method of claim 1, wherein the active hIDS is delivered to the CNS by administering an enzyme replacement therapy with recombinant hIDS to the human subject.

5. The method of claim 1, wherein the delivering step c is performed via a viral vector, liposome, a lipid-containing complex, a macromolecular complex, a synthetic modified mRNA, an unmodified mRNA, a small molecule, a non-biologically active molecule, a polymerized molecule, a naked DNA, a plasmid, a phage, a transposon, a cosmid, or an episome.

6. The method of claim 1, wherein the active hIDS is delivered to the CNS via intrathecal, intracisternal (IC), intravenous, or intracerebroventricular (ICV) administration.

7. The method of claim 1, wherein the biological sample is obtained from the cerebrospinal fluid (CSF) of the human subject.

8. The method of claim 1, wherein the reference is the level of D2S6 in a CSF sample obtained from a human subject with attenuated MPS II.

9. The method of claim 1, wherein the method further comprises monitoring the level of D2S6 present in a biological sample obtained from the human subject after the delivering step c, wherein a decrease in the level of D2S6 compared to the level of D2S6 measured in step a is indicative of treatment.

10. The method of claim 9, wherein the biological sample obtained after the delivering step c is obtained from the human subject after about 1, 2, 3, 4, 5, 6, 7, 8, 10, 16, 20, 24, 30, 35, 40, 45, 48, 50, 52, or 56 weeks, or 1, 2, 3, 4, 5, or 6 months after the delivering step c.

11. The method of claim 9, wherein the decrease in the level of D2S6 after delivering step c is about or at least about 5%, 10%, 15%, 20%, 25%, 30%, 35%, 40%, 45%, 50%, 55%, 60%, 65%, 70%, 75%, 80%, 85%, or 90%, as compared to the level of D2S6 measured in step a.

12. The method of claim 1, wherein the level of D2S6 is higher by about or at least about 5%, 10%, 15%, 20%, 25%, 30%, 35%, 40%, 45%, 50%, 55%, 60%, 65%, 70%, 75%, 80%, 85%, 90%, or 95% than the reference.

13. A method of treating mucopolysaccharidosis II (MPS II) in a human subject, the method comprising delivering an effective amount of an active human iduronate-2-sulfatase (hIDS) to the central nervous system (CNS) of the human subject diagnosed with MPS II and measuring the level of D2S6 present in a biological sample obtained from the human subject after the active hIDS has been delivered to the CNS of the human subject.

14. The method of claim 13, wherein the active hIDS is delivered to the CNS by administering an adeno-associated virus (AAV) vector comprising a nucleotide sequence encoding hIDS to the human subject.

15. The method of claim 14, wherein the active hIDS is delivered to the CNS via intracisternal (IC) or intracerebroventricular (ICV) administration.

16. The method of claim 14, wherein the active hIDS is delivered to the CNS via intravenous, intracisternal (IC), or intracerebroventricular (ICV) administration.

17. The method of claim 13, wherein the active hIDS is delivered to the CNS by administering an enzyme replacement therapy with recombinant hIDS to the human subject.

18. The method of claim 17, wherein the active hIDS is delivered to the CNS via intrathecal, intracisternal (IC), intracerebroventricular (ICV), or intravenous administration.

19. The method of claim 13, wherein the biological sample is obtained from the cerebrospinal fluid (CSF) of the human subject.

20. The method of claim 13, wherein the human subject has neuronopathic MPS II.

21. The method of claim 20, wherein the level of D2S6 in the human subject after treatment with the active hIDS is in the attenuated range.

22. The method of claim 13, wherein the method further comprises monitoring the level of D2S6 present in a biological sample obtained from the human subject at more than one time after delivering the active hIDS to the human subject, wherein a decrease in the level of D2S6 over time is indicative of treatment.

23. The method of claim 22, wherein the level of D2S6 in the human subject after treatment with the active hIDS is decreased into the attenuated range.

24. The method of claim 22, wherein the biological sample is obtained from the human subject after about 1, 2, 3, 4, 5, 6, 7, 8, 10, 16, 20, 24, 30, 35, 40, 45, 48, 50, 52, or 56 weeks, or 1, 2, 3, 4, 5, or 6 months after delivering the active hIDS to the human subject.

25. A method of treating mucopolysaccharidosis II (MPS II) in a human subject, the method comprising delivering an effective amount of an active human iduronate-2-sulfatase (hIDS) to the central nervous system (CNS) of the human subject diagnosed with MPS II and measuring the level of D2S6 present in a biological sample obtained from the human subject, wherein the method comprises measuring the level of D2S6 present in a first biological sample obtained from the human subject before delivering the active hIDS to the human subject and measuring the level of D2S6 present in a second biological sample obtained from the human subject after delivering the active hIDS to the human subject, and wherein the first and second biological samples are obtained from the cerebrospinal fluid (CSF) of the human subject.

26. The method of claim 13, wherein the human subject is an adult human subject.

27. The method of claim 13, wherein the human subject is younger than 18 years old.

28. The method of claim 13, wherein the human subject is 5 years old or older and younger than 18 years old.

29. The method of claim 13, wherein the human subject is 4 months old or older and younger than 5 years old.

30. The method of claim 25, wherein the decrease in the level of D2S6 after delivering the active hIDS to the human subject is about or at least about 5%, 10%, 15%, 20%, 25%, 30%, 35%, 40%, 45%, 50%, 55%, 60%, 65%, 70%, 75%, 80%, 85%, or 90%, as compared to the first level of D2S6.

* * * * *